US006986892B1

(12) United States Patent
Coit et al.

(10) Patent No.: US 6,986,892 B1
(45) Date of Patent: Jan. 17, 2006

(54) IMMUNOGENIC HEPATITIS C VIRUS NON-STRUCTURAL POLYPEPTIDES

(75) Inventors: Doris Coit, Petaluma, CA (US); Angelica Medina-Selby, San Francisco, CA (US); Mark Selby, San Francisco, CA (US); Michael Houghton, Berkeley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/721,479

(22) Filed: Nov. 22, 2000

Related U.S. Application Data

(60) Provisional application No. 60/167,502, filed on Nov. 24, 1999.

(51) Int. Cl.
*A61K 39/29* (2006.01)
*A61K 39/12* (2006.01)

(52) U.S. Cl. .............................. 424/228.1; 424/185.1; 424/186.1; 424/189.1; 424/204.1; 530/300; 530/350

(58) Field of Classification Search ................ 530/300, 530/350; 424/185.1, 186.1, 189.1, 228.1, 424/204.1
See application file for complete search history.

(56) References Cited

U.S. PATENT DOCUMENTS

| | | | | |
|---|---|---|---|---|
| 5,371,017 A | | 12/1994 | Houghton et al. | 435/320.1 |
| 5,372,928 A | * | 12/1994 | Miyamura et al. | 435/5 |
| 5,843,752 A | | 12/1998 | Dasmahapatra et al. | 435/219 |
| 6,333,186 B1 | | 12/2001 | Wittekind et al. | 435/219 |
| 6,800,456 B2 | | 10/2004 | Wittekind et al. | 435/69.1 |

FOREIGN PATENT DOCUMENTS

EP 0693687 * 1/1996

OTHER PUBLICATIONS

Bartenschlager et al., Nonstructural Protein 3 of the Hepatitis C Virus Encodes a Serine-Type Proteinase Required for Cleavage at the NS3/4 and NS4/5 Junctions, J. Virology, Jul. 1993, vol. 67, pp. 3835-3844.*

Botarelli et al., "T-Lymphocyte Response to Hepatitis C Virus in Different Clinical Courses of Infection," *Gastroenterology 104*:580-587 (1993).

Cooper et al. "Analysis of a Successful Immune Response Against Hepatitis C Virus," *Immunity 10*:439-449 (1999).

Diepolder et al., "Possible Mechanism Involving T-lymphocyte Response to Non-structural Protein 3 in Viral Clearance in Acute Hepatitis C Virus Inf ction," *Lancet 346*:1006-1007(1995).

Diepolder et al., "Immunodominant $CD4^+$ T-Cell Epitope Within Nonstructural Protein 3 in Acute Hepatitis C Virus Infection," *Journal of Virology 71*:6011-6019 (1997).

Farrari et al., "T-Cell Response to Structural and Nonstructural Hepatitis C Virus Antigens in Persistent and Self-Limited Hepatitis C Virus Infections," *Hepatology 19*: 286-295 (1994).

Hoffman et al., "Mapping of Immunodominant $CD4^+$ T Lymphocyte Epitopes of Hepatitis C Virus Antigens and Their Relevance During the Course of Chronic Infection," *Hepatology 21*:632-638 (1995).

Iwata et al., "Interferon Gamma Production by Peripheral Blood Lymphocytes to Hepatitis C Virus Core Protein in Chronic Hepatitis C Infection," *Hepatology 22*:1057-1064 (1995).

Minutello et al., "Compartmentalization of T Lymphocytes to the Site of Disease: Intrahepatic $CD4^+$ T Cells Specific for the Protein NS4 of Hepatitis C Virus in Patients with Chronic Hepatitis C," *J. Exp. Med. 178*:17-25 (1993).

Missale et al., "Different Clinical Behaviors of Acute Hepatitis C Virus Infection are Associated with Different Vigor of the Anti-viral Cell-mediated Immune Response," *J. Clin. Invest. 98*:706-714 (1996).

Tsai et al., "Detection of Type 2-Like T-Helper Cells in Hepatitis C Virus Infection: Implications for Hepatitis C Virus Chronicity," *Hepatology 25*:449-458 (1997).

Tsai et al., "Cellular Immune Responses in Patients With Dual Infection of Hepatitis B and C Viruses: Dominant Role of Hepatitis C Virus," *Hepatology 21*:908-912 (1995).

Chen et al., "Human and murine antibody recognition is focused on the ATPase/helicase, but not the protease domain of the hepatitis C virus nonstructural 3 protein," *Hepatology*28(1):219-224, 1998.

* cited by examiner

*Primary Examiner*—James Housel
*Assistant Examiner*—Stacy B. Chen
(74) *Attorney, Agent, or Firm*—Roberta L. Robins; Michael J. Moran; Alisa A. Alexander

(57) ABSTRACT

Polypeptides comprising a mutant non-structural Hepatitis C virus useful in diagnostic and/or immunogenic compositions are disclosed, in which the mutant is an N-terminal mutation that functionally disrupt the catalytic domain of NS3. Polynucleotides encoding these polypeptides, host cells transformed with polynucleotides and methods of using the polypeptides and polynucleotides are also disclosed.

19 Claims, 119 Drawing Sheets pCMV-NS35

```
  1  TCGCGCGTTT CGGTGATGAC GGTGAAAACC TCTGACACAT GCAGCTCCCG GAGACGGTCA CAGCTTGTCT GTAAGCGGAT
     AGCGCGCAAA GCCACTACTG CCACTTTTGG AGACTGTGTA CGTCGAGGGC CTCTGCCAGT GTCGAACAGA CATTCGCCTA

 81  GCCGGGAGCA GACAAGCCCG TCAGGGCGCG TCAGCGGGTG TTGGCGGGTG TCGGGGCTGG CTTAACTATG CGGCATCAGA
     CGGCCCTCGT CTGTTCGGGC AGTCCCGCGC AGTCGCCCAC AACCGCCCAC AGCCCCGACC GAATTGATAC GCCGTAGTCT

                                                     StuI
                                                   -------
161  GCAGATTGTA CTGAGAGTGC ACCATATGAA GCTTTTTGCA AAAGCCTAGG CCTCCAAAAA AGCCTCCTCA CTACTTCTGG
     CGTCTAACAT GACTCTCACG TGGTATACTT CGAAAAACGT TTTCGGATCC GGAGGTTTTT TCGGAGGAGT GATGAAGACC

241  AATAGCTCAG AGGCCGAGGC GGCCTCGGCC TCTGCATAAA TAAAAAAAAT TAGTCAGCCA TGGGGCGGAG AATGGGCGGA
     TTATCGAGTC TCCGGCTCCG CCGGAGCCGG AGACGTATTT ATTTTTTTTA ATCAGTCGGT ACCCCGCCTC TTACCCGCCT

321  ACTGGGCGGG GAGGGAATTA TTGGCTATTG GCCATTGCAT ACGTTGTATC TATATCATAA TATGTACATT TATATTGGCT
     TGACCCGCCC CTCCCTTAAT AACCGATAAC CGGTAACGTA TGCAACATAG ATATAGTATT ATACATGTAA ATATAACCGA

401  CATGTCCAAT ATGACCGCCA TGTTGACATT GATTATTGAC TAGTTATTAA TAGTAATCAA TTACGGGGTC ATTAGTTCAT
     GTACAGGTTA TACTGGCGGT ACAACTGTAA CTAATAACTG ATCAATAATT ATCATTAGTT AATGCCCCAG TAATCAAGTA

481  AGCCCATATA TGGAGTTCCG CGTTACATAA CTTACGGTAA ATGGCCCGCC TGGCTGACCG CCCAACGACC CCCGCCCATT
     TCGGGTATAT ACCTCAAGGC GCAATGTATT GAATGCCATT TACCGGGCGG ACCGACTGGC GGGTTGCTGG GGGCGGGTAA

561  GACGTCAATA ATGACGTATG TTCCCATAGT AACGCCAATA GGGACTTTCC ATTGACGTCA ATGGGTGGAG TATTTACGGT
     CTGCAGTTAT TACTGCATAC AAGGGTATCA TTGCGGTTAT CCCTGAAAGG TAACTGCAGT TACCCACCTC ATAAATGCCA

641  AAACTGCCCA CTTGGCAGTA CATCAAGTGT ATCATATGCC AAGTCCGCCC CCTATTGACG TCAATGACGG TAAATGGCCC
     TTTGACGGGT GAACCGTCAT GTAGTTCACA TAGTATACGG TTCAGGCGGG GGATAACTGC AGTTACTGCC ATTTACCGGG
```

FIG. 3A pCMV-NS35

721 GCCTGGCATT ATGCCCAGTA CATGACCTTA CGGGACTTTC CTACTTGGCA GTACATCTAC GTATTAGTCA TCGCTATTAC
CGGACCGTAA TACGGGTCAT GTACTGGAAT GCCCTGAAAG GATGAACCGT CATGTAGATG CATAATCAGT AGCGATAATG

801 CATGGTGATG CGGTTTTGGC AGTACACCAA TGGGCGTGGA TAGCGGTTTG ACTCACGGGG ATTTCCAAGT CTCCACCCCA
GTACCACTAC GCCAAAACCG TCATGTGGTT ACCCGCACCT ATCGCCAAAC TGAGTGCCCC TAAAGGTTCA GAGGTGGGGT

881 TTGACGTCAA TGGGAGTTTG TTTTGGCACC AAAATCAACG GGACTTTCCA AAATGTCGTA ATAACCCCGC CCCGTTGACG
AACTGCAGTT ACCCTCAAAC AAAACCGTGG TTTTAGTTGC CCTGAAAGGT TTTACAGCAT TATTGGGGCG GGGCAACTGC

961 CAAATGGGCG GTAGGCGTGT ACGGTGGGAG GTCTATATAA GCAGAGCTCG TTTAGTGAAC CGTCAGATCG CCTGGAGACG
GTTTACCCGC CATCCGCACA TGCCACCCTC CAGATATATT CGTCTCGAGC AAATCACTTG GCAGTCTAGC GGACCTCTGC

1041 CCATCCACGC TGTTTTGACC TCCATAGAAG ACACCGGGAC CGATCCAGCC TCCGCGGCCG GGAACGGTGC ATTGGAACGC
GGTAGGTGCG ACAAAACTGG AGGTATCTTC TGTGGCCCTG GCTAGGTCGG AGGCGCCGGC CCTTGCCACG TAACCTTGCG

1121 GGATTCCCCG TGCCAAGAGT GACGTAAGTA CCGCCTATAG ACTCTATAGG CACACCCCTT TGGCTCTTAT GCATGCTATA
CCTAAGGGGC ACGGTTCTCA CTGCATTCAT GGCGGATATC TGAGATATCC GTGTGGGGAA ACCGAGAATA CGTACGATAT

1201 CTGTTTTTGG CTTGGGGCCT ATACACCCCC GCTCCTTATG CTATAGGTGA TGGTATAGCT TAGCCTATAG GTGTGGGTTA
GACAAAAACC GAACCCCGGA TATGTGGGGG CGAGGAATAC GATATCCACT ACCATATCGA ATCGGATATC CACACCCAAT

1281 TTGACCATTA TTGACCACTC CCCTATTGGT GACGATACTT TCCATTACTA ATCCATAACA TGGCTCTTTG CCACAACTAT
AACTGGTAAT AACTGGTGAG GGGATAACCA CTGCTATGAA AGGTAATGAT TAGGTATTGT ACCGAGAAAC GGTGTTGATA

1361 CTCTATTGGC TATATGCCAA TACTCTGTCC TTCAGAGACT GACACGGACT CTGTATTTTT ACAGGATGGG GTCCATTTAT
GAGATAACCG ATATACGGTT ATGAGACAGG AAGTCTCTGA CTGTGCCTGA GACATAAAAA TGTCCTACCC CAGGTAAATA

FIG. 3B pCMV-NS35

```
1441  TATTTACAAA TTCACATATA CAACAACGCC GTCCCCCGTG CCCGCAGTTT TTATTAAACA TAGCGTGGGA TCTCCGACAT
      ATAAATGTTT AAGTGTATAT GTTGTTGCGG CAGGGGGCAC GGGCGTCAAA AATAATTTGT ATCGCACCCT AGAGGCTGTA

1521  CTCGGGTACG TGTTCCGGAC ATGGGCTCTT CTCCGGTAGC GGCGGAGCTT CCACATCCGA GCCCTGGTCC CATCCGTCCA
      GAGCCCATGC ACAAGGCCTG TACCCGAGAA GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA CTTAGGCACA GCACAATGCC CACCACCACC
      CGCCGAGTAC CAGCGAGCCG TCGAGGAACG AGGATTGTCA CCTCCGGTCT GAATCCGTGT CGTGTTACGG GTGGTGGTGG

1681  AGTGTGCCGC ACAAGGCCGT GGCGGTAGGG TATGTGTCTG AAAATGAGCT CGGAGATTGG GCTCGCACCT GGACGCAGAT
      TCACACGGCG TGTTCCGGCA CCGCCATCCC ATACACAGAC TTTTACTCGA GCCTCTAACC CGAGCGTGGA CCTGCGTCTA

1761  GGAAGACTTA AGGCAGCGGC AGAAGAAGAT GCAGGCAGCT GAGTTGTTGT ATTCTGATAA GAGTCAGAGG TAACTCCCGT
      CCTTCTGAAT TCCGTCGCCG TCTTCTTCTA CGTCCGTCGA CTCAACAACA TAAGACTATT CTCAGTCTCC ATTGAGGGCA

1841  TGCGGTGCTG TTAACGGTGG AGGGCAGTGT AGTCTGAGCA GTACTCGTTG CTGCCGCGCG CGCCACCAGA CATAATAGCT
      ACGCCACGAC AATTGCCACC TCCCGTCACA TCAGACTCGT CATGAGCAAC GACGGCGCGC GCGGTGGTCT GTATTATCGA

  +2                                                                                M  A  A
                                                                      EcoRI
                                                                     ------
1921  GACAGACTAA CAGACTGTTC CTTTCCATGG GTCTTTTCTG CAGTCACCGT CGTCGACCTA AGAATTCACC ATGGCTGCAT
      CTGTCTGATT GTCTGACAAG GAAAGGTACC CAGAAAAGAC GTCAGTGGCA GCAGCTGGAT TCTTAAGTGG TACCGACGTA

  +2  Y  A  A  Q   G  Y  K   V  L  V  L   N  P  S   V  A  A   T  L  G  F   G  A  Y   M  S  K
2001  ATGCAGCTCA GGGCTATAAG GTGCTAGTAC TCAACCCCTC TGTTGCTGCA ACACTGGGCT TTGGTGCTTA CATGTCCAAG
      TACGTCGAGT CCCGATATTC CACGATCATG AGTTGGGGAG ACAACGACGT TGTGACCCGA AACCACGAAT GTACAGGTTC
```

FIG. 3C pCMV-NS35

```
  +2 A  H  G  I   D  P  N   I  R  T   G  V  R  T   I  T  T   G  S  P   I  T  Y  S   T  Y  G
2081  GCTCATGGGA TCGATCCTAA CATCAGGACC GGGGTGAGAA CAATTACCAC TGGCAGCCCC ATCACGTACT CCACCTACGG
      CGAGTACCCT AGCTAGGATT GTAGTCCTGG CCCCACTCTT GTTAATGGTG ACCGTCGGGG TAGTGCATGA GGTGGATGCC

  +2  K  F  L   A  D  G  G   C  S  G   G  A  Y   D  I  I  I   C  D  E   C  H  S   T  D  A
2161  CAAGTTCCTT GCCGACGGCG GGTGCTCGGG GGGCGCTTAT GACATAATAA TTTGTGACGA GTGCCACTCC ACGGATGCCA
      GTTCAAGGAA CGGCTGCCGC CCACGAGCCC CCCGCGAATA CTGTATTATT AAACACTGCT CACGGTGAGG TGCCTACGGT

  +2 T  S  I  L   G  I  G   T  V  L  D   Q  A  E   T  A  G   A  R  L  V   V  L  A   T  A  T
2241  CATCCATCTT GGGCATTGGC ACTGTCCTTG ACCAAGCAGA GACTGCGGGG GCGAGACTGG TTGTGCTCGC CACCGCCACC
      GTAGGTAGAA CCCGTAACCG TGACAGGAAC TGGTTCGTCT CTGACGCCCC CGCTCTGACC AACACGAGCG GTGGCGGTGG

  +2  P  P  G  S   V  T  V   P  H  P   N  I  E  E   V  A  L   S  T  T   G  E  I  P   F  Y  G
2321  CCTCCGGGCT CCGTCACTGT GCCCCATCCC AACATCGAGG AGGTTGCTCT GTCCACCACC GGAGAGATCC CTTTTTACGG
      GGAGGCCCGA GGCAGTGACA CGGGGTAGGG TTGTAGCTCC TCCAACGAGA CAGGTGGTGG CCTCTCTAGG GAAAAATGCC

  +2  K  A  I   P  L  E  V   I  K  G   G  R  H   L  I  F  C   H  S  K   K  K  C   D  E  L
2401  CAAGGCTATC CCCCTCGAAG TAATCAAGGG GGGGAGACAT CTCATCTTCT GTCATTCAAA GAAGAAGTGC GACGAACTCG
      GTTCCGATAG GGGGAGCTTC ATTAGTTCCC CCCCTCTGTA GAGTAGAAGA CAGTAAGTTT CTTCTTCACG CTGCTTGAGC

  +2 A  A  K  L   V  A  L   G  I  N  A   V  A  Y   Y  R  G   L  D  V  S   V  I  P   T  S  G
2481  CCGCAAAGCT GGTCGCATTG GGCATCAATG CCGTGGCCTA CTACCGCGGT CTTGACGTGT CCGTCATCCC GACCAGCGGC
      GGCGTTTCGA CCAGCGTAAC CCGTAGTTAC GGCACCGGAT GATGGCGCCA GAACTGCACA GGCAGTAGGG CTGGTCGCCG

  +2  D  V  V  V   V  A  T   D  A  L   M  T  G  Y   T  G  D   F  D  S   V  I  D  C   N  T  C
2561  GATGTTGTCG TCGTGGCAAC CGATGCCCTC ATGACCGGCT ATACCGGCGA CTTCGACTCG GTGATAGACT GCAATACGTG
      CTACAACAGC AGCACCGTTG GCTACGGGAG TACTGGCCGA TATGGCCGCT GAAGCTGAGC CACTATCTGA CGTTATGCAC
```

FIG. 3D pCMV-NS35

```
  +2  V  T  Q   T  V  D  F   S  L  D   P  T  F   T  I  E  T   I  T  L   P  Q  D   A  V  S
2641  TGTCACCCAG ACAGTCGATT TCAGCCTTGA CCCTACCTTC ACCATTGAGA CAATCACGCT CCCCCAAGAT GCTGTCTCCC
      ACAGTGGGTC TGTCAGCTAA AGTCGGAACT GGGATGGAAG TGGTAACTCT GTTAGTGCGA GGGGGTTCTA CGACAGAGGG
-------------------------------------------------------------------------------------------
  +2 R  T  Q  R   R  G  R   T  G  R  G   K  P  G   I  Y  R   F  V  A  P   G  E  R   P  S  G
2721  GCACTCAACG TCGGGGCAGG ACTGGCAGGG GGAAGCCAGG CATCTACAGA TTTGTGGCAC CGGGGGAGCG CCCCTCCGGC
      CGTGAGTTGC AGCCCCGTCC TGACCGTCCC CCTTCGGTCC GTAGATGTCT AAACACCGTG GCCCCCTCGC GGGGAGGCCG
-------------------------------------------------------------------------------------------
  +2  M  F  D  S   S  V  L   C  E  C   Y  D  A  G   C  A  W   Y  E  L   T  P  A  E   T  T  V
2801  ATGTTCGACT CGTCCGTCCT CTGTGAGTGC TATGACGCAG GCTGTGCTTG GTATGAGCTC ACGCCCGCCG AGACTACAGT
      TACAAGCTGA GCAGGCAGGA GACACTCACG ATACTGCGTC CGACACGAAC CATACTCGAG TGCGGGCGGC TCTGATGTCA
-------------------------------------------------------------------------------------------
  +2   R  L  R   A  Y  M  N   T  P  G   L  P  V   C  Q  D  H   L  E  F   W  E  G   V  F  T
                                                                                       StuI
                                                                                         --
2881  TAGGCTACGA GCGTACATGA ACACCCCGGG GCTTCCCGTG TGCCAGGACC ATCTTGAATT TTGGGAGGGC GTCTTTACAG
      ATCCGATGCT CGCATGTACT TGTGGGGCCC CGAAGGGCAC ACGGTCCTGG TAGAACTTAA AACCCTCCCG CAGAAATGTC
-------------------------------------------------------------------------------------------
  +2 G  L  T  H   I  D  A   H  F  L  S   Q  T  K   Q  S  G   E  N  L  P   Y  L  V   A  Y  Q
     StuI
     ----
2961  GCCTCACTCA TATAGATGCC CACTTTCTAT CCCAGACAAA GCAGAGTGGG GAGAACCTTC CTTACCTGGT AGCGTACCAA
      CGGAGTGAGT ATATCTACGG GTGAAAGATA GGGTCTGTTT CGTCTCACCC CTCTTGGAAG GAATGGACCA TCGCATGGTT
-------------------------------------------------------------------------------------------
  +2  A  T  V  C   A  R  A   Q  A  P   P  P  S  W   D  Q  M   W  K  C   L  I  R  L   K  P  T
3041  GCCACCGTGT GCGCTAGGGC TCAAGCCCCT CCCCCATCGT GGGACCAGAT GTGGAAGTGT TTGATTCGCC TCAAGCCCAC
      CGGTGGCACA CGCGATCCCG AGTTCGGGGA GGGGGTAGCA CCCTGGTCTA CACCTTCACA AACTAAGCGG AGTTCGGGTG
-------------------------------------------------------------------------------------------
```

FIG. 3E pCMV-NS35

```
  +2   L  H  G   P  T  P  L   L  Y  R   L  G  A   V  Q  N  E   I  T  L   T  H  P   V  T  K
3121  CCTCCATGGG CCAACACCCC TGCTATACAG ACTGGGCGCT GTTCAGAATG AAATCACCCT GACGCACCCA GTCACCAAAT
      GGAGGTACCC GGTTGTGGGG ACGATATGTC TGACCCGCGA CAAGTCTTAC TTTAGTGGGA CTGCGTGGGT CAGTGGTTTA

  +2 Y  I  M  T   C  M  S   A  D  L  E   V  V  T   S  T  W   V  L  V  G   G  V  L   A  A  L
3201  ACATCATGAC ATGCATGTCG GCCGACCTGG AGGTCGTCAC GAGCACCTGG GTGCTCGTTG GCGGCGTCCT GGCTGCTTTG
      TGTAGTACTG TACGTACAGC CGGCTGGACC TCCAGCAGTG CTCGTGGACC CACGAGCAAC CGCCGCAGGA CCGACGAAAC

  +2  A  A  Y  C   L  S  T   G  C  V   V  I  V  G   R  V  V   L  S  G   K  P  A  I   I  P  D
3281  GCCGCGTATT GCCTGTCAAC AGGCTGCGTG GTCATAGTGG GCAGGGTCGT CTTGTCCGGG AAGCCGGCAA TCATACCTGA
      CGGCGCATAA CGGACAGTTG TCCGACGCAC CAGTATCACC CGTCCCAGCA GAACAGGCCC TTCGGCCGTT AGTATGGACT

  +2   R  E  V   L  Y  R  E   F  D  E   M  E  E   C  S  Q  H   L  P  Y   I  E  Q   G  M  M
3361  CAGGGAAGTC CTCTACCGAG AGTTCGATGA GATGGAAGAG TGCTCTCAGC ACTTACCGTA CATCGAGCAA GGGATGATGC
      GTCCCTTCAG GAGATGGCTC TCAAGCTACT CTACCTTCTC ACGAGAGTCG TGAATGGCAT GTAGCTCGTT CCCTACTACG

  +2 L  A  E  Q   F  K  Q   K  A  L  G   L  L  Q   T  A  S   R  Q  A  E   V  I  A   P  A  V
3441  TCGCCGAGCA GTTCAAGCAG AAGGCCCTCG GCCTCCTGCA GACCGCGTCC CGTCAGGCAG AGGTTATCGC CCCTGCTGTC
      AGCGGCTCGT CAAGTTCGTC TTCCGGGAGC CGGAGGACGT CTGGCGCAGG GCAGTCCGTC TCCAATAGCG GGGACGACAG

  +2  Q  T  N  W   Q  K  L   E  T  F   W  A  K  H   M  W  N   F  I  S   G  I  Q  Y   L  A  G
3521  CAGACCAACT GGCAAAAACT CGAGACCTTC TGGGCGAAGC ATATGTGGAA CTTCATCAGT GGGATACAAT ACTTGGCGGG
      GTCTGGTTGA CCGTTTTTGA GCTCTGGAAG ACCCGCTTCG TATACACCTT GAAGTAGTCA CCCTATGTTA TGAACCGCCC

  +2   L  S  T   L  P  G  N   P  A  I   A  S  L   M  A  F  T   A  A  V   T  S  P   L  T  T
3601  CTTGTCAACG CTGCCTGGTA ACCCCGCCAT TGCTTCATTG ATGGCTTTTA CAGCTGCTGT CACCAGCCCA CTAACCACTA
      GAACAGTTGC GACGGACCAT TGGGGCGGTA ACGAAGTAAC TACCGAAAAT GTCGACGACA GTGGTCGGGT GATTGGTGAT
```

FIG. 3F pCMV-NS35

```
  +2 S  Q  T  L   L  F  N   I  L  G  G   W  V  A   A  Q  L   A  A  P  G   A  A  T   A  F  V
3681  GCCAAACCCT CCTCTTCAAC ATATTGGGGG GGTGGGTGGC TGCCCAGCTC GCCGCCCCCG GTGCCGCTAC TGCCTTTGTG
      CGGTTTGGGA GGAGAAGTTG TATAACCCCC CCACCCACCG ACGGGTCGAG CGGCGGGGGC CACGGCGATG ACGGAAACAC

  +2  G  A  G  L   A  G  A   A  I  G   S  V  G  L   G  K  V   L  I  D   I  L  A  G   Y  G  A
3761  GGCGCTGGCT TAGCTGGCGC CGCCATCGGC AGTGTTGGAC TGGGGAAGGT CCTCATAGAC ATCCTTGCAG GGTATGGCGC
      CCGCGACCGA ATCGACCGCG GCGGTAGCCG TCACAACCTG ACCCCTTCCA GGAGTATCTG TAGGAACGTC CCATACCGCG

  +2  G  V  A   G  A  L  V   A  F  K   I  M  S   G  E  V  P   S  T  E   D  L  V   N  L  L
3841  GGGCGTGGCG GGAGCTCTTG TGGCATTCAA GATCATGAGC GGTGAGGTCC CCTCCACGGA GGACCTGGTC AATCTACTGC
      CCCGCACCGC CCTCGAGAAC ACCGTAAGTT CTAGTACTCG CCACTCCAGG GGAGGTGCCT CCTGGACCAG TTAGATGACG

  +2 P  A  I  L   S  P  G   A  L  V  V   G  V  V   C  A  A   I  L  R  R   H  V  G   P  G  E
3921  CCGCCATCCT CTCGCCCGGA GCCCTCGTAG TCGGCGTGGT CTGTGCAGCA ATACTGCGCC GGCACGTTGG CCCGGGCGAG
      GGCGGTAGGA GAGCGGGCCT CGGGAGCATC AGCCGCACCA GACACGTCGT TATGACGCGG CCGTGCAACC GGGCCCGCTC

  +2  G  A  V  Q   W  M  N   R  L  I   A  F  A  S   R  G  N   H  V  S   P  T  H  Y   V  P  E
4001  GGGGCAGTGC AGTGGATGAA CCGGCTGATA GCCTTCGCCT CCCGGGGGAA CCATGTTTCC CCCACGCACT ACGTGCCGGA
      CCCCGTCACG TCACCTACTT GGCCGACTAT CGGAAGCGGA GGGCCCCCTT GGTACAAAGG GGGTGCGTGA TGCACGGCCT

  +2  S  D  A   A  A  R  V   T  A  I   L  S  S   L  T  V  T   Q  L  L   R  R  L   H  Q  W
4081  GAGCGATGCA GCTGCCCGCG TCACTGCCAT ACTCAGCAGC CTCACTGTAA CCCAGCTCCT GAGGCGACTG CACCAGTGGA
      CTCGCTACGT CGACGGGCGC AGTGACGGTA TGAGTCGTCG GAGTGACATT GGGTCGAGGA CTCCGCTGAC GTGGTCACCT

  +2 I  S  S  E   C  T  T   P  C  S  G   S  W  L   R  D  I   W  D  W  I   C  E  V   L  S  D
4161  TAAGCTCGGA GTGTACCACT CCATGCTCCG GTTCCTGGCT AAGGGACATC TGGGACTGGA TATGCGAGGT GTTGAGCGAC
      ATTCGAGCCT CACATGGTGA GGTACGAGGC CAAGGACCGA TTCCCTGTAG ACCCTGACCT ATACGCTCCA CAACTCGCTG
```

FIG. 3G pCMV-NS35

```
  +2  F  K  T  W   L  K  A   K  L  M   P  Q  L  P   G  I  P   F  V  S   C  Q  R  G   Y  K  G
                                                     BamHI
                                                    -------
4241  TTTAAGACCT GGCTAAAAGC TAAGCTCATG CCACAGCTGC CTGGGATCCC CTTTGTGTCC TGCCAGCGCG GGTATAAGGG
      AAATTCTGGA CCGATTTTCG ATTCGAGTAC GGTGTCGACG GACCCTAGGG GAAACACAGG ACGGTCGCGC CCATATTCCC

  +2   V  W  R   G  D  G  I   M  H  T   R  C  H   C  G  A  E   I  T  G   H  V  K   N  G  T
4321  GGTCTGGCGA GGGGACGGCA TCATGCACAC TCGCTGCCAC TGTGGAGCTG AGATCACTGG ACATGTCAAA AACGGGACGA
      CCAGACCGCT CCCCTGCCGT AGTACGTGTG AGCGACGGTG ACACCTCGAC TCTAGTGACC TGTACAGTTT TTGCCCTGCT

  +2 M  R  I  V   G  P  R   T  C  R  N   M  W  S   G  T  F   P  I  N  A   Y  T  T   G  P  C
4401  TGAGGATCGT CGGTCCTAGG ACCTGCAGGA ACATGTGGAG TGGGACCTTC CCCATTAATG CCTACACCAC GGGCCCCTGT
      ACTCCTAGCA GCCAGGATCC TGGACGTCCT TGTACACCTC ACCCTGGAAG GGGTAATTAC GGATGTGGTG CCCGGGGACA

  +2  T  P  L  P   A  P  N   Y  T  F   A  L  W  R   V  S  A   E  E  Y   V  E  I  R   Q  V  G
4481  ACCCCCCTTC CTGCGCCGAA CTACACGTTC GCGCTATGGA GGGTGTCTGC AGAGGAATAC GTGGAGATAA GGCAGGTGGG
      TGGGGGGAAG GACGCGGCTT GATGTGCAAG CGCGATACCT CCCACAGACG TCTCCTTATG CACCTCTATT CCGTCCACCC

  +2   D  F  H   Y  V  T  G   M  T  T   D  N  L   K  C  P  C   Q  V  P   S  P  E   F  F  T
4561  GGACTTCCAC TACGTGACGG GTATGACTAC TGACAATCTT AAATGCCCGT GCCAGGTCCC ATCGCCCGAA TTTTTCACAG
      CCTGAAGGTG ATGCACTGCC CATACTGATG ACTGTTAGAA TTTACGGGCA CGGTCCAGGG TAGCGGGCTT AAAAAGTGTC

  +2 E  L  D  G   V  R  L   H  R  F  A   P  P  C   K  P  L   L  R  E  E   V  S  F   R  V  G
4641  AATTGGACGG GGTGCGCCTA CATAGGTTTG CGCCCCCCTG CAAGCCCTTG CTGCGGGAGG AGGTATCATT CAGAGTAGGA
      TTAACCTGCC CCACGCGGAT GTATCCAAAC GCGGGGGGAC GTTCGGGAAC GACGCCCTCC TCCATAGTAA GTCTCATCCT

  +2  L  H  E  Y   P  V  G   S  Q  L   P  C  E  P   E  P  D   V  A  V   L  T  S  M   L  T  D
4721  CTCCACGAAT ACCCGGTAGG GTCGCAATTA CCTTGCGAGC CCGAACCGGA CGTGGCCGTG TTGACGTCCA TGCTCACTGA
      GAGGTGCTTA TGGGCCATCC CAGCGTTAAT GGAACGCTCG GGCTTGGCCT GCACCGGCAC AACTGCAGGT ACGAGTGACT
```

FIG. 3H pCMV-NS35

```
+2     P  S  H    I  T  A    E  A  A    G  R  R    L  A  R    G  S  P    P  S  V    A  S  S    S  A
4801  TCCCTCCCAT ATAACAGCAG AGGCGGCCGG GCGAAGGTTG GCGAGGGGAT CACCCCCCTC TGTGGCCAGC TCCTCGGCTA
      AGGGAGGGTA TATTGTCGTC TCCGCCGGCC CGCTTCCAAC CGCTCCCCTA GTGGGGGGAG ACACCGGTCG AGGAGCCGAT

+2    S  Q  L  S    A  P  S    L  K  A  T    C  T  A    N  H  D    S  P  D  A    E  L  I    E  A  N
4881  GCCAGCTATC CGCTCCATCT CTCAAGGCAA CTTGCACCGC TAACCATGAC TCCCCTGATG CTGAGCTCAT AGAGGCCAAC
      CGGTCGATAG GCGAGGTAGA GAGTTCCGTT GAACGTGGCG ATTGGTACTG AGGGGACTAC GACTCGAGTA TCTCCGGTTG

+2     L  L  W  R    Q  E  M    G  G  N    I  T  R  V    E  S  E    N  K  V    V  I  L  D    S  F  D
4961  CTCCTATGGA GGCAGGAGAT GGGCGGCAAC ATCACCAGGG TTGAGTCAGA AAACAAAGTG GTGATTCTGG ACTCCTTCGA
      GAGGATACCT CCGTCCTCTA CCCGCCGTTG TAGTGGTCCC AACTCAGTCT TTTGTTTCAC CACTAAGACC TGAGGAAGCT

+2     P  L  V    A  E  E  D    E  R  E    I  S  V    P  A  E  I    L  R  K    S  R  R    F  A  Q
5041  TCCGCTTGTG GCGGAGGAGG ACGAGCGGGA GATCTCCGTA CCCGCAGAAA TCCTGCGGAA GTCTCGGAGA TTCGCCCAGG
      AGGCGAACAC CGCCTCCTCC TGCTCGCCCT CTAGAGGCAT GGGCGTCTTT AGGACGCCTT CAGAGCCTCT AAGCGGGTCC

+2    A  L  P  V    W  A  R    P  D  Y  N    P  P  L    V  E  T    W  K  K  P    D  Y  E    P  P  V
5121  CCCTGCCCGT TTGGGCGCGG CCGGACTATA ACCCCCCGCT AGTGGAGACG TGGAAAAAGC CCGACTACGA ACCACCTGTG
      GGGACGGGCA AACCCGCGCC GGCCTGATAT TGGGGGGCGA TCACCTCTGC ACCTTTTTCG GGCTGATGCT TGGTGGACAC

+2     V  H  G  C    P  L  P    P  P  K    S  P  P  V    P  P  P    R  K  K    R  T  V  V    L  T  E
5201  GTCCATGGCT GCCCGCTTCC ACCTCCAAAG TCCCCTCCTG TGCCTCCGCC TCGGAAGAAG CGGACGGTGG TCCTCACTGA
      CAGGTACCGA CGGGCGAAGG TGGAGGTTTC AGGGGAGGAC ACGGAGGCGG AGCCTTCTTC GCCTGCCACC AGGAGTGACT

+2     S  T  L    S  T  A  L    A  E  L    A  T  R    S  F  G  S    S  S  T    S  G  I    T  G  D
5281  ATCAACCCTA TCTACTGCCT TGGCCGAGCT CGCCACCAGA AGCTTTGGCA GCTCCTCAAC TTCCGGCATT ACGGGCGACA
      TAGTTGGGAT AGATGACGGA ACCGGCTCGA GCGGTGGTCT TCGAAACCGT CGAGGAGTTG AAGGCCGTAA TGCCCGCTGT
```

FIG. 3I pCMV-NS35

```
  +2  N  T  T  T   S  S  E   P  A  P  S   G  C  P   P  D  S   D  A  E  S   Y  S  S   M  P  P
5361  ATACGACAAC ATCCTCTGAG CCCGCCCCTT CTGGCTGCCC CCCCGACTCC GACGCTGAGT CCTATTCCTC CATGCCCCCC
      TATGCTGTTG TAGGAGACTC GGGCGGGGAA GACCGACGGG GGGGCTGAGG CTGCGACTCA GGATAAGGAG GTACGGGGGG

  +2  L  E  G  E   P  G  D   P  D  L   S  D  G  S   W  S  T   V  S  S   E  A  N  A   E  D  V
                     BamHI
                    -------
5441  CTGGAGGGGG AGCCTGGGGA TCCGGATCTT AGCGACGGGT CATGGTCAAC GGTCAGTAGT GAGGCCAACG CGGAGGATGT
      GACCTCCCCC TCGGACCCCT AGGCCTAGAA TCGCTGCCCA GTACCAGTTG CCAGTCATCA CTCCGGTTGC GCCTCCTACA

  +2   V  C  C   S  M  S  Y   S  W  T   G  A  L   V  T  P  C   A  A  E   E  Q  K   L  P  I
5521  CGTGTGCTGC TCAATGTCTT ACTCTTGGAC AGGCGCACTC GTCACCCCGT GCGCCGCGGA AGAACAGAAA CTGCCCATCA
      GCACACGACG AGTTACAGAA TGAGAACCTG TCCGCGTGAG CAGTGGGGCA CGCGGCGCCT TCTTGTCTTT GACGGGTAGT

  +2  N  A  L  S   N  S  L   L  R  H  H   N  L  V   Y  S  T   T  S  R  S   A  C  Q   R  Q  K
5601  ATGCACTAAG CAACTCGTTG CTACGTCACC ACAATTTGGT GTATTCCACC ACCTCACGCA GTGCTTGCCA AAGGCAGAAG
      TACGTGATTC GTTGAGCAAC GATGCAGTGG TGTTAAACCA CATAAGGTGG TGGAGTGCGT CACGAACGGT TTCCGTCTTC

  +2  K  V  T  F   D  R  L   Q  V  L   D  S  H  Y   Q  D  V   L  K  E   V  K  A  A   A  S  K
5681  AAAGTCACAT TTGACAGACT GCAAGTTCTG GACAGCCATT ACCAGGACGT ACTCAAGGAG GTTAAAGCAG CGGCGTCAAA
      TTTCAGTGTA AACTGTCTGA CGTTCAAGAC CTGTCGGTAA TGGTCCTGCA TGAGTTCCTC CAATTTCGTC GCCGCAGTTT

  +2   V  K  A   N  L  L  S   V  E  E   A  C  S   L  T  P  P   H  S  A   K  S  K   F  G  Y
5761  AGTGAAGGCT AACTTGCTAT CCGTAGAGGA AGCTTGCAGC CTGACGCCCC CACACTCAGC CAAATCCAAG TTTGGTTATG
      TCACTTCCGA TTGAACGATA GGCATCTCCT TCGAACGTCG GACTGCGGGG GTGTGAGTCG GTTTAGGTTC AAACCAATAC
```

FIG. 3J pCMV-NS35

```
+2   G  A  K  D   V  R  C   H  A  R  K   A  V  T   H  I  N   S  V  W  K   D  L  L   E  D  N
5841 GGGCAAAAGA CGTCCGTTGC CATGCCAGAA AGGCCGTAAC CCACATCAAC TCCGTGTGGA AAGACCTTCT GGAAGACAAT
     CCCGTTTTCT GCAGGCAACG GTACGGTCTT TCCGGCATTG GGTGTAGTTG AGGCACACCT TTCTGGAAGA CCTTCTGTTA

+2   V  T  P  I   D  T  T   I  M  A   K  N  E  V   F  C  V   Q  P  E   K  G  G  R   K  P  A
5921 GTAACACCAA TAGACACTAC CATCATGGCT AAGAACGAGG TTTTCTGCGT TCAGCCTGAG AAGGGGGGTC GTAAGCCAGC
     CATTGTGGTT ATCTGTGATG GTAGTACCGA TTCTTGCTCC AAAAGACGCA AGTCGGACTC TTCCCCCCAG CATTCGGTCG

+2   R  L  I   V  F  P  D   L  G  V   R  V  C   E  K  M  A   L  Y  D   V  V  T   K  L  P
6001 TCGTCTCATC GTGTTCCCCG ATCTGGGCGT GCGCGTGTGC GAAAAGATGG CTTTGTACGA CGTGGTTACA AAGCTCCCCT
     AGCAGAGTAG CACAAGGGGC TAGACCCGCA CGCGCACACG CTTTTCTACC GAAACATGCT GCACCAATGT TTCGAGGGGA

+2   L  A  V  M   G  S  S   Y  G  F  Q   Y  S  P   G  Q  R   V  E  F  L   V  Q  A   W  K  S
                                                                  EcoRI
                                                                 ------
6081 TGGCCGTGAT GGGAAGCTCC TACGGATTCC AATACTCACC AGGACAGCGG GTTGAATTCC TCGTGCAAGC GTGGAAGTCC
     ACCGGCACTA CCCTTCGAGG ATGCCTAAGG TTATGAGTGG TCCTGTCGCC CAACTTAAGG AGCACGTTCG CACCTTCAGG

+2   K  K  T  P   M  G  F   S  Y  D   T  R  C  F   D  S  T   V  T  E   S  D  I  R   T  E  E
6161 AAGAAAACCC CAATGGGGTT CTCGTATGAT ACCCGCTGCT TTGACTCCAC AGTCACTGAG AGCGACATCC GTACGGAGGA
     TTCTTTTGGG GTTACCCCAA GAGCATACTA TGGGCGACGA AACTGAGGTG TCAGTGACTC TCGCTGTAGG CATGCCTCCT

+2   A  I  Y   Q  C  C  D   L  D  P   Q  A  R   V  A  I  K   S  L  T   E  R  L   Y  V  G
6241 GGCAATCTAC CAATGTTGTG ACCTCGACCC CCAAGCCCGC GTGGCCATCA AGTCCCTCAC CGAGAGGCTT TATGTTGGGG
     CCGTTAGATG GTTACAACAC TGGAGCTGGG GGTTCGGGCG CACCGGTAGT TCAGGGAGTG GCTCTCCGAA ATACAACCCC

+2   G  P  L  T   N  S  R   G  E  N  C   G  Y  R   R  C  R   A  S  G  V   L  T  T   S  C  G
6321 GCCCTCTTAC CAATTCAAGG GGGGAGAACT GCGGCTATCG CAGGTGCCGC GCGAGCGGCG TACTGACAAC TAGCTGTGGT
     CGGGAGAATG GTTAAGTTCC CCCCTCTTGA CGCCGATAGC GTCCACGGCG CGCTCGCCGC ATGACTGTTG ATCGACACCA
```

FIG. 3K pCMV-NS35

```
  +2 N  T  L  T   C  Y  I   K  A  R   A  A  C  R   A  A  G   L  Q  D   C  T  M  L   V  C  G
6401 AACACCCTCA CTTGCTACAT CAAGGCCCGG GCAGCCTGTC GAGCCGCAGG GCTCCAGGAC TGCACCATGC TCGTGTGTGG
     TTGTGGGAGT GAACGATGTA GTTCCGGGCC CGTCGGACAG CTCGGCGTCC CGAGGTCCTG ACGTGGTACG AGCACACACC

  +2  D  D  L   V  V  I  C   E  S  A   G  V  Q   E  D  A  A   S  L  R   A  F  T   E  A  M
6481 CGACGACTTA GTCGTTATCT GTGAAAGCGC GGGGGTCCAG GAGGACGCGG CGAGCCTGAG AGCCTTCACG GAGGCTATGA
     GCTGCTGAAT CAGCAATAGA CACTTTCGCG CCCCCAGGTC CTCCTGCGCC GCTCGGACTC TCGGAAGTGC CTCCGATACT

  +2 T  R  Y  S   A  P  P   G  D  P  P   Q  P  E   Y  D  L   E  L  I  T   S  C  S   S  N  V
6561 CCAGGTACTC CGCCCCCCCT GGGGACCCCC CACAACCAGA ATACGACTTG GAGCTCATAA CATCATGCTC CTCCAACGTG
     GGTCCATGAG GCGGGGGGGA CCCCTGGGGG GTGTTGGTCT TATGCTGAAC CTCGAGTATT GTAGTACGAG GAGGTTGCAC

  +2  S  V  A  H   D  G  A   G  K  R   V  Y  Y  L   T  R  D   P  T  T   P  L  A  R   A  A  W
6641 TCAGTCGCCC ACGACGGCGC TGGAAAGAGG GTCTACTACC TCACCCGTGA CCCTACAACC CCCCTCGCGA GAGCTGCGTG
     AGTCAGCGGG TGCTGCCGCG ACCTTTCTCC CAGATGATGG AGTGGGCACT GGGATGTTGG GGGGAGCGCT CTCGACGCAC

  +2  E  T  A   R  H  T  P   V  N  S   W  L  G   N  I  I  M   F  A  P   T  L  W   A  R  M
6721 GGAGACAGCA AGACACACTC CAGTCAATTC CTGGCTAGGC AACATAATCA TGTTTGCCCC CACACTGTGG GCGAGGATGA
     CCTCTGTCGT TCTGTGTGAG GTCAGTTAAG GACCGATCCG TTGTATTAGT ACAAACGGGG GTGTGACACC CGCTCCTACT

  +2 I  L  M  T   H  F  F   S  V  L  I   A  R  D   Q  L  E   Q  A  L  D   C  E  I   Y  G  A
6801 TACTGATGAC CCATTTCTTT AGCGTCCTTA TAGCCAGGGA CCAGCTTGAA CAGGCCCTCG ATTGCGAGAT CTACGGGGCC
     ATGACTACTG GGTAAAGAAA TCGCAGGAAT ATCGGTCCCT GGTCGAACTT GTCCGGGAGC TAACGCTCTA GATGCCCCGG

  +2  C  Y  S  I   E  P  L   D  L  P   P  I  I  Q   R  L  H   G  L  S   A  F  S  L   H  S  Y
6881 TGCTACTCCA TAGAACCACT GGATCTACCT CCAATCATTC AAAGACTCCA TGGCCTCAGC GCATTTTCAC TCCACAGTTA
     ACGATGAGGT ATCTTGGTGA CCTAGATGGA GGTTAGTAAG TTTCTGAGGT ACCGGAGTCG CGTAAAAGTG AGGTGTCAAT
```

FIG. 3L pCMV-NS35

```
  +2   S  P  G   E  I  N  R   V  A  A   C  L  R   K  L  G  V   P  P  L   R  A  W   R  H  R
6961  CTCTCCAGGT GAAATCAATA GGGTGGCCGC ATGCCTCAGA AAACTTGGGG TACCGCCCTT GCGAGCTTGG AGACACCGGG
      GAGAGGTCCA CTTTAGTTAT CCCACCGGCG TACGGAGTCT TTTGAACCCC ATGGCGGGAA CGCTCGAACC TCTGTGGCCC

  +2 A  R  S  V   R  A  R   L  L  A  R   G  G  R   A  A  I   C  G  K  Y   L  F  N   W  A  V
7041  CCCGGAGCGT CCGCGCTAGG CTTCTGGCCA GAGGAGGCAG GGCTGCCATA TGTGGCAAGT ACCTCTTCAA CTGGGCAGTA
      GGGCCTCGCA GGCGCGATCC GAAGACCGGT CTCCTCCGTC CCGACGGTAT ACACCGTTCA TGGAGAAGTT GACCCGTCAT

  +2  R  T  K  L   K  L  T   P  I  A   A  A  G  Q   L  D  L   S  G  W   F  T  A  G   Y  S  G
7121  AGAACAAAGC TCAAACTCAC TCCAATAGCG GCCGCTGGCC AGCTGGACTT GTCCGGCTGG TTCACGGCTG GCTACAGCGG
      TCTTGTTTCG AGTTTGAGTG AGGTTATCGC CGGCGACCGG TCGACCTGAA CAGGCCGACC AAGTGCCGAC CGATGTCGCC

  +2   G  D  I   Y  H  S  V   S  H  A   R  P  R   W  I  W  F   C  L  L   L  L  A   A  G  V
7201  GGGAGACATT TATCACAGCG TGTCTCATGC CCGGCCCCGC TGGATCTGGT TTTGCCTACT CCTGCTTGCT GCAGGGGTAG
      CCCTCTGTAA ATAGTGTCGC ACAGAGTACG GGCCGGGGCG ACCTAGACCA AAACGGATGA GGACGAACGA CGTCCCCATC

  +2 G  I  Y  L   L  P  N   R
7281  GCATCTACCT CCTCCCCAAC CGATGAAGGT TGGGGTAAAC ACTCCGGCCT AAAAAAAAAA AAAAATCTAG AAAGGCGCGC
      CGTAGATGGA GGAGGGGTTG GCTACTTCCA ACCCCATTTG TGAGGCCGGA TTTTTTTTTT TTTTTAGATC TTTCCGCGCG

                  BAMHI      MluI
                 ------     ------
7361  CAAGATATCA AGGATCCACT ACGCGTTAGA GCTCGCTGAT CAGCCTCGAC TGTGCCTTCT AGTTGCCAGC CATCTGTTGT
      GTTCTATAGT TCCTAGGTGA TGCGCAATCT CGAGCGACTA GTCGGAGCTG ACACGGAAGA TCAACGGTCG GTAGACAACA

7441  TTGCCCCTCC CCCGTGCCTT CCTTGACCCT GGAAGGTGCC ACTCCCACTG TCCTTTCCTA ATAAAATGAG GAAATTGCAT
      AACGGGGAGG GGGCACGGAA GGAACTGGGA CCTTCCACGG TGAGGGTGAC AGGAAAGGAT TATTTTACTC CTTTAACGTA
```

FIG. 3M pCMV-NS35

```
7521  CGCATTGTCT GAGTAGGTGT CATTCTATTC TGGGGGGTGG GGTGGGGCAG GACAGCAAGG GGGAGGATTG GGAAGACAAT
      GCGTAACAGA CTCATCCACA GTAAGATAAG ACCCCCCACC CCACCCCGTC CTGTCGTTCC CCCTCCTAAC CCTTCTGTTA

7601  AGCAGGCATG CTGGGGAGCT CTTCCGCTTC CTCGCTCACT GACTCGCTGC GCTCGGTCGT TCGGCTGCGG CGAGCGGTAT
      TCGTCCGTAC GACCCCTCGA GAAGGCGAAG GAGCGAGTGA CTGAGCGACG CGAGCCAGCA AGCCGACGCC GCTCGCCATA

7681  CAGCTCACTC AAAGGCGGTA ATACGGTTAT CCACAGAATC AGGGGATAAC GCAGGAAAGA ACATGTGAGC AAAAGGCCAG
      GTCGAGTGAG TTTCCGCCAT TATGCCAATA GGTGTCTTAG TCCCCTATTG CGTCCTTTCT TGTACACTCG TTTTCCGGTC

7761  CAAAAGGCCA GGAACCGTAA AAAGGCCGCG TTGCTGGCGT TTTTCCATAG GCTCCGCCCC CCTGACGAGC ATCACAAAAA
      GTTTTCCGGT CCTTGGCATT TTTCCGGCGC AACGACCGCA AAAAGGTATC CGAGGCGGGG GGACTGCTCG TAGTGTTTTT

7841  TCGACGCTCA AGTCAGAGGT GGCGAAACCC GACAGGACTA TAAAGATACC AGGCGTTTCC CCCTGGAAGC TCCCTCGTGC
      AGCTGCGAGT TCAGTCTCCA CCGCTTTGGG CTGTCCTGAT ATTTCTATGG TCCGCAAAGG GGGACCTTCG AGGGAGCACG

7921  GCTCTCCTGT TCCGACCCTG CCGCTTACCG GATACCTGTC CGCCTTTCTC CCTTCGGGAA GCGTGGCGCT TTCTCAATGC
      CGAGAGGACA AGGCTGGGAC GGCGAATGGC CTATGGACAG GCGGAAAGAG GGAAGCCCTT CGCACCGCGA AAGAGTTACG

8001  TCACGCTGTA GGTATCTCAG TTCGGTGTAG GTCGTTCGCT CCAAGCTGGG CTGTGTGCAC GAACCCCCCG TTCAGCCCGA
      AGTGCGACAT CCATAGAGTC AAGCCACATC CAGCAAGCGA GGTTCGACCC GACACACGTG CTTGGGGGGC AAGTCGGGCT

8081  CCGCTGCGCC TTATCCGGTA ACTATCGTCT TGAGTCCAAC CCGGTAAGAC ACGACTTATC GCCACTGGCA GCAGCCACTG
      GGCGACGCGG AATAGGCCAT TGATAGCAGA ACTCAGGTTG GGCCATTCTG TGCTGAATAG CGGTGACCGT CGTCGGTGAC

8161  GTAACAGGAT TAGCAGAGCG AGGTATGTAG GCGGTGCTAC AGAGTTCTTG AAGTGGTGGC CTAACTACGG CTACACTAGA
      CATTGTCCTA ATCGTCTCGC TCCATACATC CGCCACGATG TCTCAAGAAC TTCACCACCG GATTGATGCC GATGTGATCT
```

FIG. 3N pCMV-NS35

8241 AGGACAGTAT TTGGTATCTG CGCTCTGCTG AAGCCAGTTA CCTTCGGAAA AAGAGTTGGT AGCTCTTGAT CCGGCAAACA
TCCTGTCATA AACCATAGAC GCGAGACGAC TTCGGTCAAT GGAAGCCTTT TTCTCAACCA TCGAGAACTA GGCCGTTTGT

8321 AACCACCGCT GGTAGCGGTG GTTTTTTTGT TTGCAAGCAG CAGATTACGC GCAGAAAAAA AGGATCTCAA GAAGATCCTT
TTGGTGGCGA CCATCGCCAC CAAAAAAACA AACGTTCGTC GTCTAATGCG CGTCTTTTTT TCCTAGAGTT CTTCTAGGAA

8401 TGATCTTTTC TACGGGGTCT GACGCTCAGT GGAACGAAAA CTCACGTTAA GGGATTTTGG TCATGAGATT ATCAAAAAGG
ACTAGAAAAG ATGCCCCAGA CTGCGAGTCA CCTTGCTTTT GAGTGCAATT CCCTAAAACC AGTACTCTAA TAGTTTTTCC

8481 ATCTTCACCT AGATCCTTTT AAATTAAAAA TGAAGTTTTA AATCAATCTA AAGTATATAT GAGTAAACTT GGTCTGACAG
TAGAAGTGGA TCTAGGAAAA TTTAATTTTT ACTTCAAAAT TTAGTTAGAT TTCATATATA CTCATTTGAA CCAGACTGTC

8561 TTACCAATGC TTAATCAGTG AGGCACCTAT CTCAGCGATC TGTCTATTTC GTTCATCCAT AGTTGCCTGA CTCCCCGTCG
AATGGTTACG AATTAGTCAC TCCGTGGATA GAGTCGCTAG ACAGATAAAG CAAGTAGGTA TCAACGGACT GAGGGGCAGC

8641 TGTAGATAAC TACGATACGG GAGGGCTTAC CATCTGGCCC CAGTGCTGCA ATGATACCGC GAGACCCACG CTCACCGGCT
ACATCTATTG ATGCTATGCC CTCCCGAATG GTAGACCGGG GTCACGACGT TACTATGGCG CTCTGGGTGC GAGTGGCCGA

8721 CCAGATTTAT CAGCAATAAA CCAGCCAGCC GGAAGGGCCG AGCGCAGAAG TGGTCCTGCA ACTTTATCCG CCTCCATCCA
GGTCTAAATA GTCGTTATTT GGTCGGTCGG CCTTCCCGGC TCGCGTCTTC ACCAGGACGT TGAAATAGGC GGAGGTAGGT

8801 GTCTATTAAT TGTTGCCGGG AAGCTAGAGT AAGTAGTTCG CCAGTTAATA GTTTGCGCAA CGTTGTTGCC ATTGCTACAG
CAGATAATTA ACAACGGCCC TTCGATCTCA TTCATCAAGC GGTCAATTAT CAAACGCGTT GCAACAACGG TAACGATGTC

8881 GCATCGTGGT GTCACGCTCG TCGTTTGGTA TGGCTTCATT CAGCTCCGGT TCCCAACGAT CAAGGCGAGT TACATGATCC
CGTAGCACCA CAGTGCGAGC AGCAAACCAT ACCGAAGTAA GTCGAGGCCA AGGGTTGCTA GTTCCGCTCA ATGTACTAGG

FIG. 3O pCMV-NS35

```
8961  CCCATGTTGT GCAAAAAAGC GGTTAGCTCC TTCGGTCCTC CGATCGTTGT CAGAAGTAAG TTGGCCGCAG TGTTATCACT
      GGGTACAACA CGTTTTTTCG CCAATCGAGG AAGCCAGGAG GCTAGCAACA GTCTTCATTC AACCGGCGTC ACAATAGTGA

9041  CATGGTTATG GCAGCACTGC ATAATTCTCT TACTGTCATG CCATCCGTAA GATGCTTTTC TGTGACTGGT GAGTACTCAA
      GTACCAATAC CGTCGTGACG TATTAAGAGA ATGACAGTAC GGTAGGCATT CTACGAAAAG ACACTGACCA CTCATGAGTT

9121  CCAAGTCATT CTGAGAATAG TGTATGCGGC GACCGAGTTG CTCTTGCCCG GCGTCAATAC GGGATAATAC CGCGCCACAT
      GGTTCAGTAA GACTCTTATC ACATACGCCG CTGGCTCAAC GAGAACGGGC CGCAGTTATG CCCTATTATG GCGCGGTGTA

9201  AGCAGAACTT TAAAAGTGCT CATCATTGGA AAACGTTCTT CGGGGCGAAA ACTCTCAAGG ATCTTACCGC TGTTGAGATC
      TCGTCTTGAA ATTTTCACGA GTAGTAACCT TTTGCAAGAA GCCCCGCTTT TGAGAGTTCC TAGAATGGCG ACAACTCTAG

9281  CAGTTCGATG TAACCCACTC GTGCACCCAA CTGATCTTCA GCATCTTTTA CTTTCACCAG CGTTTCTGGG TGAGCAAAAA
      GTCAAGCTAC ATTGGGTGAG CACGTGGGTT GACTAGAAGT CGTAGAAAAT GAAAGTGGTC GCAAAGACCC ACTCGTTTTT

9361  CAGGAAGGCA AAATGCCGCA AAAAAGGGAA TAAGGGCGAC ACGGAAATGT TGAATACTCA TACTCTTCCT TTTTCAATAT
      GTCCTTCCGT TTTACGGCGT TTTTTCCCTT ATTCCCGCTG TGCCTTTACA ACTTATGAGT ATGAGAAGGA AAAAGTTATA

9441  TATTGAAGCA TTTATCAGGG TTATTGTCTC ATGAGCGGAT ACATATTTGA ATGTATTTAG AAAAATAAAC AAATAGGGGT
      ATAACTTCGT AAATAGTCCC AATAACAGAG TACTCGCCTA TGTATAAACT TACATAAATC TTTTTATTTG TTTATCCCCA

9521  TCCGCGCACA TTTCCCCGAA AAGTGCCACC TGACGTCTAA GAAACCATTA TTATCATGAC ATTAACCTAT AAAAATAGGC
      AGGCGCGTGT AAAGGGGCTT TTCACGGTGG ACTGCAGATT CTTTGGTAAT AATAGTACTG TAATTGGATA TTTTTATCCG

9601  GTATCACGAG GCCCTTTCGT C
      CATAGTGCTC CGGGAAAGCA G
```

FIG. 3P pCMV-delNS35

```
                                                                           StuI
                                                                          -------
  1  TCGCGCGTTT CGGTGATGAC GGTGAAAACC TCTGACACAT GCAGCTCCCG GAGACGGTCA CAGCTTGTCT GTAAGCGGAT
     AGCGCGCAAA GCCACTACTG CCACTTTTGG AGACTGTGTA CGTCGAGGGC CTCTGCCAGT GTCGAACAGA CATTCGCCTA

 81  GCCGGGAGCA GACAAGCCCG TCAGGGCGCG TCAGCGGGTG TTGGCGGGTG TCGGGGCTGG CTTAACTATG CGGCATCAGA
     CGGCCCTCGT CTGTTCGGGC AGTCCCGCGC AGTCGCCCAC AACCGCCCAC AGCCCCGACC GAATTGATAC GCCGTAGTCT

161  GCAGATTGTA CTGAGAGTGC ACCATATGAA GCTTTTTGCA AAAGCCTAGG CCTCCAAAAA AGCCTCCTCA CTACTTCTGG
     CGTCTAACAT GACTCTCACG TGGTATACTT CGAAAAACGT TTTCGGATCC GGAGGTTTTT TCGGAGGAGT GATGAAGACC

241  AATAGCTCAG AGGCCGAGGC GGCCTCGGCC TCTGCATAAA TAAAAAAAAT TAGTCAGCCA TGGGGCGGAG ATTGGGCGGA
     TTATCGAGTC TCCGGCTCCG CCGGAGCCGG AGACGTATTT ATTTTTTTTA ATCAGTCGGT ACCCCGCCTC TTACCCGCCT

321  ACTGGGCGGG GAGGGAATTA TTGGCTATTG GCCATTGCAT ACGTTGTATC TATATCATAA TATGTACATT TATATTGGCT
     TGACCCGCCC CTCCCTTAAT AACCGATAAC CGGTAACGTA TGCAACATAG ATATAGTATT ATACATGTAA ATATAACCGA

401  CATGTCCAAT ATGACCGCCA TGTTGACATT GATTATTGAC TAGTTATTAA TAGTAATCAA TTACGGGGTC ATTAGTTCAT
     GTACAGGTTA TACTGGCGGT ACAACTGTAA CTAATAACTG ATCAATAATT ATCATTAGTT AATGCCCCAG TAATCAAGTA

481  AGCCCATATA TGGAGTTCCG CGTTACATAA CTTACGGTAA ATGGCCCGCC TGGCTGACCG CCCAACGACC CCCGCCCATT
     TCGGGTATAT ACCTCAAGGC GCAATGTATT GAATGCCATT TACCGGGCGG ACCGACTGGC GGGTTGCTGG GGGCGGGTAA

561  GACGTCAATA ATGACGTATG TTCCCATAGT AACGCCAATA GGGACTTTCC ATTGACGTCA ATGGGTGGAG TATTTACGGT
     CTGCAGTTAT TACTGCATAC AAGGGTATCA TTGCGGTTAT CCCTGAAAGG TAACTGCAGT TACCCACCTC ATAAATGCCA
```

FIG. 5A pCMV-delNS35

```
641   AAACTGCCCA CTTGGCAGTA CATCAAGTGT ATCATATGCC AAGTCCGCCC CCTATTGACG TCAATGACGG TAAATGGCCC
      TTTGACGGGT GAACCGTCAT GTAGTTCACA TAGTATACGG TTCAGGCGGG GGATAACTGC AGTTACTGCC ATTTACCGGG

721   GCCTGGCATT ATGCCCAGTA CATGACCTTA CGGGACTTTC CTACTTGGCA GTACATCTAC GTATTAGTCA TCGCTATTAC
      CGGACCGTAA TACGGGTCAT GTACTGGAAT GCCCTGAAAG GATGAACCGT CATGTAGATG CATAATCAGT AGCGATAATG

801   CATGGTGATG CGGTTTTGGC AGTACACCAA TGGGCGTGGA TAGCGGTTTG ACTCACGGGG ATTTCCAAGT CTCCACCCCA
      GTACCACTAC GCCAAAACCG TCATGTGGTT ACCCGCACCT ATCGCCAAAC TGAGTGCCCC TAAAGGTTCA GAGGTGGGGT

881   TTGACGTCAA TGGGAGTTTG TTTTGGCACC AAAATCAACG GGACTTTCCA AAATGTCGTA ATAACCCCGC CCCGTTGACG
      AACTGCAGTT ACCCTCAAAC AAAACCGTGG TTTTAGTTGC CCTGAAAGGT TTTACAGCAT TATTGGGGCG GGGCAACTGC

961   CAAATGGGCG GTAGGCGTGT ACGGTGGGAG GTCTATATAA GCAGAGCTCG TTTAGTGAAC CGTCAGATCG CCTGGAGACG
      GTTTACCCGC CATCCGCACA TGCCACCCTC CAGATATATT CGTCTCGAGC AAATCACTTG GCAGTCTAGC GGACCTCTGC

1041  CCATCCACGC TGTTTTGACC TCCATAGAAG ACACCGGGAC CGATCCAGCC TCCGCGGCCG GGAACGGTGC ATTGGAACGC
      GGTAGGTGCG ACAAAACTGG AGGTATCTTC TGTGGCCCTG GCTAGGTCGG AGGCGCCGGC CCTTGCCACG TAACCTTGCG

1121  GGATTCCCCG TGCCAAGAGT GACGTAAGTA CCGCCTATAG ACTCTATAGG CACACCCCTT TGGCTCTTAT GCATGCTATA
      CCTAAGGGGC ACGGTTCTCA CTGCATTCAT GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGTGA TGGTATAGCT TAGCCTATAG GTGTGGGTTA
      GACAAAAACC GAACCCCGGA TATGTGGGGG CGAGGAATAC GATATCCACT ACCATATCGA ATCGGATATC CACACCCAAT

1281  TTGACCATTA TTGACCACTC CCCTATTGGT GACGATACTT TCCATTACTA ATCCATAACA TGGCTCTTTG CCACAACTAT
      AACTGGTAAT AACTGGTGAG GGGATAACCA CTGCTATGAA AGGTAATGAT TAGGTATTGT ACCGAGAAAC GGTGTTGATA
```

FIG. 5B pCMV-delNS35

```
1361  CTCTATTGGC TATATGCCAA TACTCTGTCC TTCAGAGACT GACACGGACT CTGTATTTTT ACAGGATGGG GTCCATTTAT
      GAGATAACCG ATATACGGTT ATGAGACAGG AAGTCTCTGA CTGTGCCTGA GACATAAAAA TGTCCTACCC CAGGTAAATA

1441  TATTTACAAA TTCACATATA CAACAACGCC GTCCCCCGTG CCCGCAGTTT TTATTAAACA TAGCGTGGGA TCTCCGACAT
      ATAAATGTTT AAGTGTATAT GTTGTTGCGG CAGGGGGCAC GGGCGTCAAA AATAATTTGT ATCGCACCCT AGAGGCTGTA

1521  CTCGGGTACG TGTTCCGGAC ATGGGCTCTT CTCCGGTAGC GGCGGAGCTT CCACATCCGA GCCCTGGTCC CATCCGTCCA
      GAGCCCATGC ACAAGGCCTG TACCCGAGAA GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA CTTAGGCACA GCACAATGCC CACCACCACC
      CGCCGAGTAC CAGCGAGCCG TCGAGGAACG AGGATTGTCA CCTCCGGTCT GAATCCGTGT CGTGTTACGG GTGGTGGTGG

1681  AGTGTGCCGC ACAAGGCCGT GGCGGTAGGG TATGTGTCTG AAAATGAGCT CGGAGATTGG GCTCGCACCT GGACGCAGAT
      TCACACGGCG TGTTCCGGCA CCGCCATCCC ATACACAGAC TTTTACTCGA GCCTCTAACC CGAGCGTGGA CCTGCGTCTA

1761  GGAAGACTTA AGGCAGCGGC AGAAGAAGAT GCAGGCAGCT GAGTTGTTGT ATTCTGATAA GAGTCAGAGG TAACTCCCGT
      CCTTCTGAAT TCCGTCGCCG TCTTCTTCTA CGTCCGTCGA CTCAACAACA TAAGACTATT CTCAGTCTCC ATTGAGGGCA

1841  TGCGGTGCTG TTAACGGTGG AGGGCAGTGT AGTCTGAGCA GTACTCGTTG CTGCCGCGCG CGCCACCAGA CATAATAGCT
      ACGCCACGAC AATTGCCACC TCCCGTCACA TCAGACTCGT CATGAGCAAC GACGGCGCGC GCGGTGGTCT GTATTATCGA

  +2                                                                               M  A  A
                                                                        EcoRI
                                                                       ------
1921  GACAGACTAA CAGACTGTTC CTTTCCATGG GTCTTTTCTG CAGTCACCGT CGTCGACCTA AGAATTCACC ATGGCTGCAT
      CTGTCTGATT GTCTGACAAG GAAAGGTACC CAGAAAAGAC GTCAGTGGCA GCAGCTGGAT TCTTAAGTGG TACCGACGTA
```

FIG. 5C pCMV-delNS35

```
  +2 Y  A  A  Q   G  Y  K   V  L  V  L   N  P  S   V  A  A   T  L  G  F   G  A  Y   M  S  K
2001 ATGCAGCTCA GGGCTATAAG GTGCTAGTAC TCAACCCCTC TGTTGCTGCA ACACTGGGCT TTGGTGCTTA CATGTCCAAG
     TACGTCGAGT CCCGATATTC CACGATCATG AGTTGGGGAG ACAACGACGT TGTGACCCGA AACCACGAAT GTACAGGTTC

  +2  A  H  G  I   D  P  N   I  R  T   G  V  R  T   I  T  T   G  S  P   I  T  Y  S   T  Y  G
2081 GCTCATGGGA TCGATCCTAA CATCAGGACC GGGGTGAGAA CAATTACCAC TGGCAGCCCC ATCACGTACT CCACCTACGG
     CGAGTACCCT AGCTAGGATT GTAGTCCTGG CCCCACTCTT GTTAATGGTG ACCGTCGGGG TAGTGCATGA GGTGGATGCC

  +2  K  F  L   A  D  G  G   C  S  G   G  A  Y   D  I  I  I   C  D  E   C  H  S   T  D  A
2161 CAAGTTCCTT GCCGACGGCG GGTGCTCGGG GGGCGCTTAT GACATAATAA TTTGTGACGA GTGCCACTCC ACGGATGCCA
     GTTCAAGGAA CGGCTGCCGC CCACGAGCCC CCCGCGAATA CTGTATTATT AAACACTGCT CACGGTGAGG TGCCTACGGT

  +2 T  S  I  L   G  I  G   T  V  L  D   Q  A  E   T  A  G   A  R  L  V   V  L  A   T  A  T
2241 CATCCATCTT GGGCATTGGC ACTGTCCTTG ACCAAGCAGA GACTGCGGGG GCGAGACTGG TTGTGCTCGC CACCGCCACC
     GTAGGTAGAA CCCGTAACCG TGACAGGAAC TGGTTCGTCT CTGACGCCCC CGCTCTGACC AACACGAGCG GTGGCGGTGG

  +2  P  P  G  S   V  T  V   P  H  P   N  I  E  E   V  A  L   S  T  T   G  E  I  P   F  Y  G
2321 CCTCCGGGCT CCGTCACTGT GCCCCATCCC AACATCGAGG AGGTTGCTCT GTCCACCACC GGAGAGATCC CTTTTTACGG
     GGAGGCCCGA GGCAGTGACA CGGGGTAGGG TTGTAGCTCC TCCAACGAGA CAGGTGGTGG CCTCTCTAGG GAAAAATGCC

  +2  K  A  I   P  L  E  V   I  K  G   G  R  H   L  I  F  C   H  S  K   K  K  C   D  E  L
2401 CAAGGCTATC CCCCTCGAAG TAATCAAGGG GGGGAGACAT CTCATCTTCT GTCATTCAAA GAAGAAGTGC GACGAACTCG
     GTTCCGATAG GGGGAGCTTC ATTAGTTCCC CCCCTCTGTA GAGTAGAAGA CAGTAAGTTT CTTCTTCACG CTGCTTGAGC

  +2 A  A  K  L   V  A  L   G  I  N  A   V  A  Y   Y  R  G   L  D  V  S   V  I  P   T  S  G
2481 CCGCAAAGCT GGTCGCATTG GGCATCAATG CCGTGGCCTA CTACCGCGGT CTTGACGTGT CCGTCATCCC GACCAGCGGC
     GGCGTTTCGA CCAGCGTAAC CCGTAGTTAC GGCACCGGAT GATGGCGCCA GAACTGCACA GGCAGTAGGG CTGGTCGCCG
```

FIG. 5D pCMV-delNS35

```
  +2  D  V  V  V   V  A  T   D  A  L   M  T  G  Y   T  G  D   F  D  S   V  I  D  C   N  T  C
2561  GATGTTGTCG TCGTGGCAAC CGATGCCCTC ATGACCGGCT ATACCGGCGA CTTCGACTCG GTGATAGACT GCAATACGTG
      CTACAACAGC AGCACCGTTG GCTACGGGAG TACTGGCCGA TATGGCCGCT GAAGCTGAGC CACTATCTGA CGTTATGCAC

  +2   V  T  Q   T  V  D  F   S  L  D   P  T  F   T  I  E  T   I  T  L   P  Q  D   A  V  S
2641  TGTCACCCAG ACAGTCGATT TCAGCCTTGA CCCTACCTTC ACCATTGAGA CAATCACGCT CCCCCAAGAT GCTGTCTCCC
      ACAGTGGGTC TGTCAGCTAA AGTCGGAACT GGGATGGAAG TGGTAACTCT GTTAGTGCGA GGGGGTTCTA CGACAGAGGG

  +2  R  T  Q  R   R  G  R   T  G  R  G   K  P  G   I  Y  R   F  V  A  P   G  E  R   P  S  G
2721  GCACTCAACG TCGGGGCAGG ACTGGCAGGG GGAAGCCAGG CATCTACAGA TTTGTGGCAC CGGGGGAGCG CCCCTCCGGC
      CGTGAGTTGC AGCCCCGTCC TGACCGTCCC CCTTCGGTCC GTAGATGTCT AAACACCGTG GCCCCCTCGC GGGGAGGCCG

  +2  M  F  D  S   S  V  L   C  E  C   Y  D  A  G   C  A  W   Y  E  L   T  P  A  E   T  T  V
2801  ATGTTCGACT CGTCCGTCCT CTGTGAGTGC TATGACGCAG GCTCTGCTTG GTATGAGCTC ACGCCCGCCG AGACTACAGT
      TACAAGCTGA GCAGGCAGGA GACACTCACG ATACTGCGTC CGACACGAAC CATACTCGAG TGCGGGCGGC TCTGATGTCA

  +2   R  L  R   A  Y  M  N   T  P  G   L  P  V   C  Q  D  H   L  E  F   W  E  G   V  F  T
                                                                                      StuI
                                                                                       --
2881  TAGGCTACGA GCGTACATGA ACACCCCGGG GCTTCCCGTG TGCCAGGACC ATCTTGAATT TTGGGAGGGC GTCTTTACAG
      ATCCGATGCT CGCATGTACT TGTGGGGCCC CGAAGGGCAC ACGGTCCTGG TAGAACTTAA AACCCTCCCG CAGAAATGTC

  +2  G  L  T  H   I  D  A   H  F  L  S   Q  T  K   Q  S  G   E  N  L  P   Y  L  V   A  Y  Q
      StuI
      ----
2961  GCCTCACTCA TATAGATGCC CACTTTCTAT CCCAGACAAA GCAGAGTGGG GAGAACCTTC CTTACCTGGT AGCGTACCAA
      CGGAGTGAGT ATATCTACGG GTGAAAGATA GGGTCTGTTT CGTCTCACCC CTCTTGGAAG GAATGGACCA TCGCATGGTT
```

FIG. 5E pCMV-delNS35

```
+2    A  T  V  C   A  R  A   Q  A  P   P  P  S  W   D  Q  M   W  K  C   L  I  R  L   K  P  T
3041  GCCACCGTGT GCGCTAGGGC TCAAGCCCCT CCCCCATCGT GGGACCAGAT GTGGAAGTGT TTGATTCGCC TCAAGCCCAC
      CGGTGGCACA CGCGATCCCG AGTTCGGGGA GGGGGTAGCA CCCTGGTCTA CACCTTCACA AACTAAGCGG AGTTCGGGTG

+2     L  H  G   P  T  P  L   L  Y  R   L  G  A   V  Q  N  E   I  T  L   T  H  P   V  T  K
3121  CCTCCATGGG CCAACACCCC TGCTATACAG ACTGGGCGCT GTTCAGAATG AAATCACCCT GACGCACCCA GTCACCAAAT
      GGAGGTACCC GGTTGTGGGG ACGATATGTC TGACCCGCGA CAAGTCTTAC TTTAGTGGGA CTGCGTGGGT CAGTGGTTTA

+2    Y  I  M  T   C  M  S   A  D  L  E   V  V  T   S  T  W   V  L  V  G   G  V  L   A  A  L
3201  ACATCATGAC ATGCATGTCG GCCGACCTGG AGGTCGTCAC GAGCACCTGG GTGCTCGTTG GCGGCGTCCT GGCTGCTTTG
      TGTAGTACTG TACGTACAGC CGGCTGGACC TCCAGCAGTG CTCGTGGACC CACGAGCAAC CGCCGCAGGA CCGACGAAAC

+2    A  A  Y  C   L  S  T   G  C  V   V  I  V  G   R  V  V   L  S  G   K  P  A  I   I  P  D
3281  GCCGCGTATT GCCTGTCAAC AGGCTGCGTG GTCATAGTGG GCAGGGTCGT CTTGTCCGGG AAGCCGGCAA TCATACCTGA
      CGGCGCATAA CGGACAGTTG TCCGACGCAC CAGTATCACC CGTCCCAGCA GAACAGGCCC TTCGGCCGTT AGTATGGACT

+2     R  E  V   L  Y  R  E   F  D  E   M  E  E   C  S  Q  H   L  P  Y   I  E  Q   G  M  M
3361  CAGGGAAGTC CTCTACCGAG AGTTCGATGA GATGGAAGAG TGCTCTCAGC ACTTACCGTA CATCGAGCAA GGGATGATGC
      GTCCCTTCAG GAGATGGCTC TCAAGCTACT CTACCTTCTC ACGAGAGTCG TGAATGGCAT GTAGCTCGTT CCCTACTACG

+2    L  A  E  Q   F  K  Q   K  A  L  G   L  L  Q   T  A  S   R  Q  A  E   V  I  A   P  A  V
3441  TCGCCGAGCA GTTCAAGCAG AAGGCCCTCG GCCTCCTGCA GACCGCGTCC CGTCAGGCAG AGGTTATCGC CCCTGCTGTC
      AGCGGCTCGT CAAGTTCGTC TTCCGGGAGC CGGAGGACGT CTGGCGCAGG GCAGTCCGTC TCCAATAGCG GGGACGACAG

+2    Q  T  N  W   Q  K  L   E  T  F   W  A  K  H   M  W  N   F  I  S   G  I  Q  Y   L  A  G
3521  CAGACCAACT GGCAAAAACT CGAGACCTTC TGGGCGAAGC ATATGTGGAA CTTCATCAGT GGGATACAAT ACTTGGCGGG
      GTCTGGTTGA CCGTTTTTGA GCTCTGGAAG ACCCGCTTCG TATACACCTT GAAGTAGTCA CCCTATGTTA TGAACCGCCC
```

FIG. 5F pCMV-delNS35

```
  +2   L  S  T   L  P  G  N   P  A  I   A  S  L   M  A  F  T   A  A  V   T  S  P   L  T  T
3601  CTTGTCAACG CTGCCTGGTA ACCCCGCCAT TGCTTCATTG ATGGCTTTTA CAGCTGCTGT CACCAGCCCA CTAACCACTA
      GAACAGTTGC GACGGACCAT TGGGGCGGTA ACGAAGTAAC TACCGAAAAT GTCGACGACA GTGGTCGGGT GATTGGTGAT

  +2 S  Q  T  L   L  F  N   I  L  G  G   W  V  A   A  Q  L   A  A  P  G   A  A  T   A  F  V
3681  GCCAAACCCT CCTCTTCAAC ATATTGGGGG GGTGGGTGGC TGCCCAGCTC GCCGCCCCCG GTGCCGCTAC TGCCTTTGTG
      CGGTTTGGGA GGAGAAGTTG TATAACCCCC CCACCCACCG ACGGGTCGAG CGGCGGGGGC CACGGCGATG ACGGAAACAC

  +2  G  A  G  L   A  G  A   A  I  G   S  V  G  L   G  K  V   L  I  D   I  L  A  G   Y  G  A
3761  GGCGCTGGCT TAGCTGGCGC CGCCATCGGC AGTGTTGGAC TGGGGAAGGT CCTCATAGAC ATCCTTGCAG GGTATGGCGC
      CCGCGACCGA ATCGACCGCG GCGGTAGCCG TCACAACCTG ACCCCTTCCA GGAGTATCTG TAGGAACGTC CCATACCGCG

  +2   G  V  A   G  A  L  V   A  F  K   I  M  S   G  E  V  P   S  T  E   D  L  V   N  L  L
3841  GGGCGTGGCG GGAGCTCTTG TGGCATTCAA GATCATGAGC GGTGAGGTCC CCTCCACGGA GGACCTGGTC AATCTACTGC
      CCCGCACCGC CCTCGAGAAC ACCGTAAGTT CTAGTACTCG CCACTCCAGG GGAGGTGCCT CCTGGACCAG TTAGATGACG

  +2 P  A  I  L   S  P  G   A  L  V  V   G  V  V   C  A  A   I  L  R  R   H  V  G   P  G  E
3921  CCGCCATCCT CTCGCCCGGA GCCCTCGTAG TCGGCGTGGT CTGTGCAGCA ATACTGCGCC GGCACGTTGG CCCGGGCGAG
      GGCGGTAGGA GAGCGGGCCT CGGGAGCATC AGCCGCACCA GACACGTCGT TATGACGCGG CCGTGCAACC GGGCCCGCTC

  +2  G  A  V  Q   W  M  N   R  L  I   A  F  A  S   R  G  N   H  V  S   P  T  H  Y   V  P  E
4001  GGGGCAGTGC AGTGGATGAA CCGGCTGATA GCCTTCGCCT CCCGGGGGAA CCATGTTTCC CCCACGCACT ACGTGCCGGA
      CCCCGTCACG TCACCTACTT GGCCGACTAT CGGAAGCGGA GGGCCCCCTT GGTACAAAGG GGGTGCGTGA TGCACGGCCT

  +2   S  D  A   A  A  R  V   T  A  I   L  S  S   L  T  V  T   Q  L  L   R  R  L   H  Q  W
4081  GAGCGATGCA GCTGCCCGCG TCACTGCCAT ACTCAGCAGC CTCACTGTAA CCCAGCTCCT GAGGCGACTG CACCAGTGGA
      CTCGCTACGT CGACGGGCGC AGTGACGGTA TGAGTCGTCG GAGTGACATT GGGTCGAGGA CTCCGCTGAC GTGGTCACCT
```

FIG. 5G pCMV-delNS35

```
+2   I  S  S  E    C  T  T    P  C  S  G    S  W  L    R  D  I    W  D  W  I    C  E  V    L  S  D
4161 TAAGCTCGGA GTGTACCACT CCATGCTCCG GTTCCTGGCT AAGGGACATC TGGGACTGGA TATGCGAGGT GTTGAGCGAC
     ATTCGAGCCT CACATGGTGA GGTACGAGGC CAAGGACCGA TTCCCTGTAG ACCCTGACCT ATACGCTCCA CAACTCGCTG

+2    F  K  T  W    L  K  A    K  L  M    P  Q  L  P    G  I  P    F  V  S    C  Q  R  G    Y  K  G
                                                          BamHI
                                                          ------
4241 TTTAAGACCT GGCTAAAAGC TAAGCTCATG CCACAGCTGC CTGGGATCCC CTTTGTGTCC TGCCAGCGCG GGTATAAGGG
     AAATTCTGGA CCGATTTTCG ATTCGAGTAC GGTGTCGACG GACCCTAGGG GAAACACAGG ACGGTCGCGC CCATATTCCC

+2    V  W  R    G  D  G  I    M  H  T    R  C  H    C  G  A  E    I  T  G    H  V  K    N  G  T
4321 GGTCTGGCGA GGGGACGGCA TCATGCACAC TCGCTGCCAC TGTGGAGCTG AGATCACTGG ACATGTCAAA AACGGGACGA
     CCAGACCGCT CCCCTGCCGT AGTACGTGTG AGCGACGGTG ACACCTCGAC TCTAGTGACC TGTACAGTTT TTGCCCTGCT

+2   M  R  I  V    G  P  R    T  C  R  N    M  W  S    G  T  F    P  I  N  A    Y  T  T    G  P  C
4401 TCAGGATCGT CGGTCCTAGG ACCTGCAGGA ACATGTGGAG TGGGACCTTC CCCATTAATG CCTACACCAC GGGCCCCTGT
     ACTCCTAGCA GCCAGGATCC TGGACGTCCT TGTACACCTC ACCCTGGAAG GGGTAATTAC GGATGTGGTG CCCGGGGACA

+2    T  P  L  P    A  P  N    Y  T  F    A  L  W  R    V  S  A    E  E  Y    V  E  I  R    Q  V  G
4481 ACCCCCCTTC CTGCGCCGAA CTACACGTTC GCGCTATGGA GGGTGTCTGC AGAGGAATAC GTGGAGATAA GGCAGGTGGG
     TGGGGGGAAG GACGCGGCTT GATGTGCAAG CGCGATACCT CCCACAGACG TCTCCTTATG CACCTCTATT CCGTCCACCC

+2    D  F  H    Y  V  T  G    M  T  T    D  N  L    K  C  P  C    Q  V  P    S  P  E    F  F  T
4561 GGACTTCCAC TACGTGACGG GTATGACTAC TGACAATCTT AAATGCCCGT GCCAGGTCCC ATCGCCCGAA TTTTTCACAG
     CCTGAAGGTG ATGCACTGCC CATACTGATG ACTGTTAGAA TTTACGGGCA CGGTCCAGGG TAGCGGGCTT AAAAAGTGTC

+2   E  L  D  G    V  R  L    H  R  F  A    P  P  C    K  P  L    L  R  E  E    V  S  F    R  V  G
4641 AATTGGACGG GGTGCGCCTA CATAGGTTTG CGCCCCCCTG CAAGCCCTTG CTGCGGGAGG AGGTATCATT CAGAGTAGGA
     TTAACCTGCC CCACGCGGAT GTATCCAAAC GCGGGGGGAC GTTCGGGAAC GACGCCCTCC TCCATAGTAA GTCTCATCCT
```

FIG. 5H pCMV-delNS35

```
  +2  L  H  E  Y   P  V  G   S  Q  L   P  C  E  P   E  P  D   V  A  V   L  T  S  M   L  T  D
4721  CTCCACGAAT ACCCGGTAGG GTCGCAATTA CCTTGCGAGC CCGAACCGGA CGTGGCCGTG TTGACGTCCA TGCTCACTGA
      GAGGTGCTTA TGGGCCATCC CAGCGTTAAT GGAACGCTCG GGCTTGGCCT GCACCGGCAC AACTGCAGGT ACGAGTGACT

  +2   P  S  H  I  T  A  E   A  A  G   R  R  L   A  R  G  S   P  P  S   V  A  S   S  S  A
4801  TCCCTCCCAT ATAACAGCAG AGGCGGCCGG GCGAAGGTTG GCGAGGGGAT CACCCCCCTC TGTGGCCAGC TCCTCGGCTA
      AGGGAGGGTA TATTGTCGTC TCCGCCGGCC CGCTTCCAAC CGCTCCCCTA GTGGGGGGAG ACACCGGTCG AGGAGCCGAT

  +2 S  Q  L  S   A  P  S   L  K  A  T   C  T  A   N  H  D   S  P  D  A   E  L  I   E  A  N
4881  GCCAGCTATC CGCTCCATCT CTCAAGGCAA CTTGCACCGC TAACCATGAC TCCCCTGATG CTGAGCTCAT AGAGGCCAAC
      CGGTCGATAG GCGAGGTAGA GAGTTCCGTT GAACGTGGCG ATTGGTACTG AGGGGACTAC GACTCGAGTA TCTCCGGTTG

  +2  L  L  W  R   Q  E  M   G  G  N   I  T  R  V   E  S  E   N  K  V   V  I  L  D   S  F  D
4961  CTCCTATGGA GGCAGGAGAT GGGCGGCAAC ATCACCAGGG TTGAGTCAGA AAACAAAGTG GTGATTCTGG ACTCCTTCGA
      GAGGATACCT CCGTCCTCTA CCCGCCGTTG TAGTGGTCCC AACTCAGTCT TTTGTTTCAC CACTAAGACC TGAGGAAGCT

  +2   P  L  V   A  E  E  D   E  R  E   I  S  V   P  A  E  I   L  R  K   S  R  R   F  A  Q
5041  TCCGCTTGTG GCGGAGGAGG ACGAGCGGGA GATCTCCGTA CCCGCAGAAA TCCTGCGGAA GTCTCGGAGA TTCGCCCAGG
      AGGCGAACAC CGCCTCCTCC TGCTCGCCCT CTAGAGGCAT GGGCGTCTTT AGGACGCCTT CAGAGCCTCT AAGCGGGTCC

  +2 A  L  P  V   W  A  R   P  D  Y  N   P  P  L   V  E  T   W  K  K  P   D  Y  E   P  P  V
5121  CCCTGCCCGT TTGGGCGCGG CCGGACTATA ACCCCCCGCT AGTGGAGACG TGGAAAAAGC CCGACTACGA ACCACCTGTG
      GGGACGGGCA AACCCGCGCC GGCCTGATAT TGGGGGGCGA TCACCTCTGC ACCTTTTTCG GGCTGATGCT TGGTGGACAC

  +2  V  H  G  C   P  L  P   P  P  K   S  P  P  V   P  P  P   R  K  K   R  T  V  V   L  T  E
5201  GTCCATGGCT GCCCGCTTCC ACCTCCAAAG TCCCCTCCTG TGCCTCCGCC TCGGAAGAAG CGGACGGTGG TCCTCACTGA
      CAGGTACCGA CGGGCGAAGG TGGAGGTTTC AGGGGAGGAC ACGGAGGCGG AGCCTTCTTC GCCTGCCACC AGGAGTGACT
```

FIG. 5I pCMV-delNS35

```
  +2   S T L    S T A L   A E L    A T R    S F G S    S S T    S G I    T G D
5281   ATCAACCCTA TCTACTGCCT TGGCCGAGCT CGCCACCAGA AGCTTTGGCA GCTCCTCAAC TTCCGGCATT ACGGCGGACA
       TAGTTGGGAT AGATGACGGA ACCGGCTCGA GCGGTGGTCT TCGAAACCGT CGAGGAGTTG AAGGCCGTAA TGCCCGCTGT

  +2 N T T T    S S E    P A P S    G C P    P D S    D A E S    Y S S    M P P
5361   ATACGACAAC ATCCTCTGAG CCCGCCCCTT CTGGCTGCCC CCCCGACTCC GACGCTGAGT CCTATTCCTC CATGCCCCCC
       TATGCTGTTG TAGGAGACTC GGGCGGGGAA GACCGACGGG GGGGCTGAGG CTGCGACTCA GGATAAGGAG GTACGGGGGG

  +2  L E G E    P G D    P D L    S D G S    W S T    V S S    E A N A    E D V
                   BamHI
                  -------
5441   CTGGAGGGGG AGCCTGGGCA TCCGGATCTT AGCGACGGGT CATGGTCAAC GGTCAGTAGT GAGGCCAACG CGGAGGATGT
       GACCTCCCCC TCGGACCCCT AGGCCTAGAA TCGCTGCCCA GTACCAGTTG CCAGTCATCA CTCCGGTTGC GCCTCCTACA

  +2   V C C    S M S Y    S W T    G A L    V T P C    A A E    E Q K    L P I
5521   CGTGTGCTGC TCAATGTCTT ACTCTTGGAC AGGCGCACTC GTCACCCCGT GCGCCGCGGA AGAACAGAAA CTGCCCATCA
       GCACACGACG AGTTACAGAA TGAGAACCTG TCCGCGTGAG CAGTGGGGCA CGCGGCGCCT TCTTGTCTTT GACGGGTAGT

  +2 N A L S    N S L    L R H H    N L V    Y S T    T S R S    A C Q    R Q K
5601   ATGCACTAAG CAACTCGTTG CTACGTCACC ACAATTTGGT GTATTCCACC ACCTCACGCA GTGCTTGCCA AAGGCAGAAG
       TACGTGATTC GTTGAGCAAC GATGCAGTGG TGTTAAACCA CATAAGGTGG TGGAGTGCGT CACGAACGGT TTCCGTCTTC

  +2  K V T F    D R L    Q V L    D S H Y    Q D V    L K E    V K A A    A S K
5681   AAAGTCACAT TTGACAGACT GCAAGTTCTG GACAGCCATT ACCAGGACGT ACTCAAGGAG GTTAAAGCAG CGGCGTCAAA
       TTTCAGTGTA AACTGTCTGA CGTTCAAGAC CTGTCGGTAA TGGTCCTGCA TGAGTTCCTC CAATTTCGTC GCCGCAGTTT

  +2   V K A    N L L S    V E E    A C S    L T P P    H S A    K S K    F G Y
5761   AGTGAAGGCT AACTTGCTAT CCGTAGAGGA AGCTTGCAGC CTGACGCCCC CACACTCAGC CAAATCCAAG TTTGGTTATG
       TCACTTCCGA TTGAACGATA GGCATCTCCT TCGAACGTCG GACTGCGGGG GTGTGAGTCG GTTTAGGTTC AAACCAATAC
```

FIG. 5J pCMV-delNS35

```
  +2 G  A  K  D   V  R  C   H  A  R  K   A  V  T   H  I  N   S  V  W  K   D  L  L   E  D  N
5841  GGGCAAAAGA CGTCCGTTGC CATGCCAGAA AGGCCGTAAC CCACATCAAC TCCGTGTGGA AAGACCTTCT GGAAGACAAT
      CCCGTTTTCT GCAGGCAACG GTACGGTCTT TCCGGCATTG GGTGTAGTTG AGGCACACCT TTCTGGAAGA CCTTCTGTTA

  +2  V  T  P  I   D  T  T   I  M  A   K  N  E  V   F  C  V   Q  P  E   K  G  G  R   K  P  A
5921  GTAACACCAA TAGACACTAC CATCATGGCT AAGAACGAGG TTTTCTGCGT TCAGCCTGAG AAGGGGGGTC GTAAGCCAGC
      CATTGTGGTT ATCTGTGATG GTAGTACCGA TTCTTGCTCC AAAAGACGCA AGTCGGACTC TTCCCCCCAG CATTCGGTCG

  +2   R  L  I   V  F  P  D   L  G  V   R  V  C   E  K  M  A   L  Y  D   V  V  T   K  L  P
6001  TCGTCTCATC GTGTTCCCCG ATCTGGGCGT GCGCGTGTGC GAAAAGATGG CTTTGTACGA CGTGGTTACA AAGCTCCCCT
      AGCAGAGTAG CACAAGGGGC TAGACCCGCA CGCGCACACG CTTTTCTACC GAAACATGCT GCACCAATGT TTCGAGGGGA

  +2 L  A  V  M   G  S  S   Y  G  F  Q   Y  S  P   G  Q  R   V  E  F  L   V  Q  A   W  K  S
                                                                 EcoRI
                                                                -------
6081  TGGCCGTGAT GGGAAGCTCC TACGGATTCC AATACTCACC AGGACAGCGG GTTGAATTCC TCGTGCAAGC GTGGAAGTCC
      ACCGGCACTA CCCTTCGAGG ATGCCTAAGG TTATGAGTGG TCCTGTCGCC CAACTTAAGG AGCACGTTCG CACCTTCAGG

  +2  K  K  T  P   M  G  F   S  Y  D   T  R  C  F   D  S  T   V  T  E   S  D  I  R   T  E  E
6161  AAGAAAACCC CAATGGGGTT CTCGTATGAT ACCCGCTGCT TTGACTCCAC AGTCACTGAG AGCGACATCC GTACGGAGGA
      TTCTTTTGGG GTTACCCCAA GAGCATACTA TGGGCGACGA AACTGAGGTG TCAGTGACTC TCGCTGTAGG CATGCCTCCT

  +2   A  I  Y   Q  C  C  D   L  D  P   Q  A  R   V  A  I  K   S  L  T   E  R  L   Y  V  G
6241  GGCAATCTAC CAATGTTGTG ACCTCGACCC CCAAGCCCGC GTGGCCATCA AGTCCCTCAC CGAGAGGCTT TATGTTGGGG
      CCGTTAGATG GTTACAACAC TGGAGCTGGG GGTTCGGGCG CACCGGTAGT TCAGGGAGTG GCTCTCCGAA ATACAACCCC

  +2 G  P  L  T   N  S  R   G  E  N  C   G  Y  R   R  C  R   A  S  G  V   L  T  T   S  C  G
6321  GCCCTCTTAC CAATTCAAGG GGGGAGAACT GCGGCTATCG CAGGTGCCCC GCGAGCGGCG TACTGACAAC TAGCTGTGGT
      CGGGAGAATG GTTAAGTTCC CCCCTCTTGA CGCCGATAGC GTCCACGGCG CGCTCGCCGC ATGACTGTTG ATCGACACCA
```

FIG. 5K pCMV-delNS35

```
  +2 N  T  L  T   C  Y  I   K  A  R   A  A  C  R   A  A  G   L  Q  D   C  T  M  L   V  C  G
6401 AACACCCTCA CTTGCTACAT CAAGGCCCGG GCAGCCTGTC GAGCCGCAGG GCTCCAGGAC TGCACCATGC TCGTGTGTGG
     TTGTGGGAGT GAACGATGTA GTTCCGGGCC CGTCGGACAG CTCGGCGTCC CGAGGTCCTG ACGTGGTACG AGCACACACC

  +2  D  D  L   V  V  I  C   E  S  A   G  V  Q   E  D  A  A   S  L  R   A  F  T   E  A  M
6481 CGACGACTTA GTCGTTATCT GTGAAAGCGC GGGGGTCCAG GAGGACGCGG CGAGCCTGAG AGCCTTCACG GAGGCTATGA
     GCTGCTGAAT CAGCAATAGA CACTTTCGCG CCCCCAGGTC CTCCTGCGCC GCTCGGACTC TCGGAAGTGC CTCCGATACT

  +2 T  R  Y  S   A  P  P   G  D  P  P   Q  P  E   Y  D  L   E  L  I  T   S  C  S   S  N  V
6561 CCAGGTACTC CGCCCCCCCT GGGGACCCCC CACAACCAGA ATACGACTTG GAGCTCATAA CATCATGCTC CTCCAACGTG
     GGTCCATGAG GCGGGGGGGA CCCCTGGGGG GTGTTGGTCT TATGCTGAAC CTCGAGTATT GTAGTACGAG GAGGTTGCAC

  +2 S  V  A  H   D  G  A   G  K  R   V  Y  Y  L   T  R  D   P  T  T   P  L  A  R   A  A  W
6641 TCAGTCGCCC ACGACGGCGC TGGAAAGAGG GTCTACTACC TCACCCGTGA CCCTACAACC CCCCTCGCGA GAGCTGCGTG
     AGTCAGCGGG TGCTGCCGCG ACCTTTCTCC CAGATGATGG AGTGGGCACT GGGATGTTGG GGGGAGCGCT CTCGACGCAC

  +2  E  T  A   R  H  T  P   V  N  S   W  L  G   N  I  I  M   F  A  P   T  L  W   A  R  M
6721 GGAGACAGCA AGACACACTC CAGTCAATTC CTGGCTAGGC AACATAATCA TGTTTGCCCC CACACTGTGG GCGAGGATGA
     CCTCTGTCGT TCTGTGTGAG GTCAGTTAAG GACCGATCCG TTGTATTAGT ACAAACGGGG GTGTGACACC CGCTCCTACT

  +2 I  L  M  T   H  F  F   S  V  L  I   A  R  D   Q  L  E   Q  A  L  D   C  E  I   Y  G  A
6801 TACTGATGAC CCATTTCTTT AGCGTCCTTA TAGCCAGGGA CCAGCTTGAA CAGGCCCTCG ATTGCGAGAT CTACGGGGCC
     ATGACTACTG GGTAAAGAAA TCGCAGGAAT ATCGGTCCCT GGTCGAACTT GTCCGGGAGC TAACGCTCTA GATGCCCCGG

  +2 C  Y  S  I   E  P  L   D  L  P   P  I  I  Q   R  L  H   G  L  S   A  F  S  L   H  S  Y
6881 TGCTACTCCA TAGAACCACT GGATCTACCT CCAATCATTC AAAGACTCCA TGGCCTCAGC GCATTTTCAC TCCACAGTTA
     ACGATGAGGT ATCTTGGTGA CCTAGATGGA GGTTAGTAAG TTTCTGAGGT ACCGGAGTCG CGTAAAAGTG AGGTGTCAAT
```

FIG. 5L pCMV-delNS35

```
  +2   S  P  G   E  I  N  R   V  A  A   C  L  R   K  L  G  V   P  P  L   R  A  W   R  H  R
6961  CTCTCCAGGT GAAATCAATA GGGTGGCCGC ATGCCTCAGA AAACTTGGGG TACCGCCCTT GCGAGCTTGG AGACACCGGG
      GAGAGGTCCA CTTTAGTTAT CCCACCGGCG TACGGAGTCT TTTGAACCCC ATGGCGGGAA CGCTCGAACC TCTGTGGCCC

  +2 A  R  S  V   R  A  R   L  L  A  R   G  G  R   A  A  I   C  G  K  Y   L  F  N   W  A  V
7041  CCCGGAGCGT CCGCGCTAGG CTTCTGGCCA GAGGAGGCAG GGCTGCCATA TGTGGCAAGT ACCTCTTCAA CTGGGCAGTA
      GGGCCTCGCA GGCGCGATCC GAAGACCGGT CTCCTCCGTC CCGACGGTAT ACACCGTTCA TGGAGAAGTT GACCCGTCAT

  +2  R  T  K  L   K  L  T   P  I  A   A  A  G  Q   L  D  L   S  G  W   F  T  A  G   Y  S  G
7121  AGAACAAAGC TCAAACTCAC TCCAATAGCG GCCGCTGGCC AGCTGGACTT GTCCGGCTGG TTCACGGCTG GCTACAGCGG
      TCTTGTTTCG AGTTTGAGTG AGGTTATCGC CGGCGACCGG TCGACCTGAA CAGGCCGACC AAGTGCCGAC CGATGTCGCC

  +2   G  D  I   Y  H  S  V   S  H  A   R  P  R   W  I  W  F   C  L  L   L  L  A   A  G  V
7201  GGGAGACATT TATCACAGCG TGTCTCATGC CCGGCCCCGC TGGATCTGGT TTTGCCTACT CCTGCTTGCT GCAGGGGTAG
      CCCTCTGTAA ATAGTGTCGC ACAGAGTACG GGCCGGGGCG ACCTAGACCA AAACGGATGA GGACGAACGA CGTCCCCATC

  +2 G  I  Y  L   L  P  N   R
7281  GCATCTACCT CCTCCCCAAC CGATGAAGGT TGGGGTAAAC ACTCCGGCCT AAAAAAAAAA AAAAATCTAG AAAGGCGCGC
      CGTAGATGGA GGAGGGGTTG GCTACTTCCA ACCCCATTTG TGAGGCCGGA TTTTTTTTTT TTTTTAGATC TTTCCGCGCG

                  BamHI      MluI
                 ------     ------
7361  CAAGATATCA AGGATCCACT ACGCGTTAGA GCTCGCTGAT CAGCCTCGAC TGTGCCTTCT AGTTGCCAGC CATCTGTTGT
      GTTCTATAGT TCCTAGGTGA TGCGCAATCT CGAGCGACTA GTCGGAGCTG ACACGGAAGA TCAACGGTCG GTAGACAACA

7441  TTGCCCCTCC CCCGTGCCTT CCTTGACCCT GGAAGGTGCC ACTCCCACTG TCCTTTCCTA ATAAAATGAG GAAATTGCAT
      AACGGGGAGG GGGCACGGAA GGAACTGGGA CCTTCCACGG TGAGGGTGAC AGGAAAGGAT TATTTTACTC CTTTAACGTA
```

FIG. 5M pCMV-delNS35

```
7521  CGCATTGTCT GAGTAGGTGT CATTCTATTC TGGGGGGTGG GGTGGGGCAG GACAGCAAGG GGGAGGATTG GGAAGACAAT
      GCGTAACAGA CTCATCCACA GTAAGATAAG ACCCCCCACC CCACCCCGTC CTGTCGTTCC CCCTCCTAAC CCTTCTGTTA

7601  AGCAGGCATG CTGGGGAGCT CTTCCGCTTC CTCGCTCACT GACTCGCTGC GCTCGGTCGT TCGGCTGCGG CGAGCGGTAT
      TCGTCCGTAC GACCCCTCGA GAAGGCGAAG GAGCGAGTGA CTGAGCGACG CGAGCCAGCA AGCCGACGCC GCTCGCCATA

7681  CAGCTCACTC AAAGGCGGTA ATACGGTTAT CCACAGAATC AGGGGATAAC GCAGGAAAGA ACATGTGAGC AAAAGGCCAG
      GTCGAGTGAG TTTCCGCCAT TATGCCAATA GGTGTCTTAG TCCCCTATTG CGTCCTTTCT TGTACACTCG TTTTCCGGTC

7761  CAAAAGGCCA GGAACCGTAA AAAGGCCGCG TTGCTGGCGT TTTTCCATAG GCTCCGCCCC CCTGACGAGC ATCACAAAAA
      GTTTTCCGGT CCTTGGCATT TTTCCGGCGC AACGACCGCA AAAAGGTATC CGAGGCGGGG GGACTGCTCG TAGTGTTTTT

7841  TCGACGCTCA AGTCAGAGGT GGCGAAACCC GACAGGACTA TAAAGATACC AGGCGTTTCC CCCTGGAAGC TCCCTCGTGC
      AGCTGCGAGT TCAGTCTCCA CCGCTTTGGG CTGTCCTGAT ATTTCTATGG TCCGCAAAGG GGGACCTTCG AGGGAGCACG

7921  GCTCTCCTGT TCCGACCCTG CCGCTTACCG GATACCTGTC CGCCTTTCTC CCTTCGGGAA GCGTGGCGCT TTCTCAATGC
      CGAGAGGACA AGGCTGGGAC GGCGAATGGC CTATGGACAG GCGGAAAGAG GGAAGCCCTT CGCACCGCGA AAGAGTTACG

8001  TCACGCTGTA GGTATCTCAG TTCGGTGTAG GTCGTTCGCT CCAAGCTGGG CTGTGTGCAC GAACCCCCCG TTCAGCCCGA
      AGTGCGACAT CCATAGAGTC AAGCCACATC CAGCAAGCGA GGTTCGACCC GACACACGTG CTTGGGGGGC AAGTCGGGCT

8081  CCGCTGCGCC TTATCCGGTA ACTATCGTCT TGAGTCCAAC CCGGTAAGAC ACGACTTATC GCCACTGGCA GCAGCCACTG
      GGCGACGCGG AATAGGCCAT TGATAGCAGA ACTCAGGTTG GGCCATTCTG TGCTGAATAG CGGTGACCGT CGTCGGTGAC

8161  GTAACAGGAT TAGCAGAGCG AGGTATGTAG GCGGTGCTAC AGAGTTCTTG AAGTGGTGGC CTAACTACGG CTACACTAGA
      CATTGTCCTA ATCGTCTCGC TCCATACATC CGCCACGATG TCTCAAGAAC TTCACCACCG GATTGATGCC GATGTGATCT
```

FIG. 5N pCMV-delNS35

```
8241  AGGACAGTAT TTGGTATCTG CGCTCTGCTG AAGCCAGTTA CCTTCGGAAA AAGAGTTGGT AGCTCTTGAT CCGGCAAACA
      TCCTGTCATA AACCATAGAC GCGAGACGAC TTCGGTCAAT GGAAGCCTTT TTCTCAACCA TCGAGAACTA GGCCGTTTGT

8321  AACCACCGCT GGTAGCGGTG GTTTTTTTGT TTGCAAGCAG CAGATTACGC GCAGAAAAAA AGGATCTCAA GAAGATCCTT
      TTGGTGGCGA CCATCGCCAC CAAAAAAACA AACGTTCGTC GTCTAATGCG CGTCTTTTTT TCCTAGAGTT CTTCTAGGAA

8401  TGATCTTTTC TACGGGGTCT GACGCTCAGT GGAACGAAAA CTCACGTTAA GGGATTTTGG TCATGAGATT ATCAAAAAGG
      ACTAGAAAAG ATGCCCCAGA CTGCGAGTCA CCTTGCTTTT GAGTGCAATT CCCTAAAACC AGTACTCTAA TAGTTTTTCC

8481  ATCTTCACCT AGATCCTTTT AAATTAAAAA TGAAGTTTTA AATCAATCTA AAGTATATAT GAGTAAACTT GGTCTGACAG
      TAGAAGTGGA TCTAGGAAAA TTTAATTTTT ACTTCAAAAT TTAGTTAGAT TTCATATATA CTCATTTGAA CCAGACTGTC

8561  TTACCAATGC TTAATCAGTG AGGCACCTAT CTCAGCGATC TGTCTATTTC GTTCATCCAT AGTTGCCTGA CTCCCCGTCG
      AATGGTTACG AATTAGTCAC TCCGTGGATA GAGTCGCTAG ACAGATAAAG CAAGTAGGTA TCAACGGACT GAGGGGCAGC

8641  TGTAGATAAC TACGATACGG GAGGGCTTAC CATCTGGCCC CAGTGCTGCA ATGATACCGC GAGACCCACG CTCACCGGCT
      ACATCTATTG ATGCTATGCC CTCCCGAATG GTAGACCGGG GTCACGACGT TACTATGGCG CTCTGGGTGC GAGTGGCCGA

8721  CCAGATTTAT CAGCAATAAA CCAGCCAGCC GGAAGGGCCG AGCGCAGAAG TGGTCCTGCA ACTTTATCCG CCTCCATCCA
      GGTCTAAATA GTCGTTATTT GGTCGGTCGG CCTTCCCGGC TCGCGTCTTC ACCAGGACGT TGAAATAGGC GGAGGTAGGT

8801  GTCTATTAAT TGTTGCCGGG AAGCTAGAGT AAGTAGTTCG CCAGTTAATA GTTTGCGCAA CGTTGTTGCC ATTGCTACAG
      CAGATAATTA ACAACGGCCC TTCGATCTCA TTCATCAAGC GGTCAATTAT CAAACGCGTT GCAACAACGG TAACGATGTC

8881  GCATCGTGGT GTCACGCTCG TCGTTTGGTA TGGCTTCATT CAGCTCCGGT TCCCAACGAT CAAGGCGAGT TACATGATCC
      CGTAGCACCA CAGTGCGAGC AGCAAACCAT ACCGAAGTAA GTCGAGGCCA AGGGTTGCTA GTTCCGCTCA ATGTACTAGG
```

FIG. 5O pCMV-delNS35

```
8961  CCCATGTTGT GCAAAAAAGC GGTTAGCTCC TTCGGTCCTC CGATCGTTGT CAGAAGTAAG TTGGCCGCAG TGTTATCACT
      GGGTACAACA CGTTTTTTCG CCAATCGAGG AAGCCAGGAG GCTAGCAACA GTCTTCATTC AACCGGCGTC ACAATAGTGA

9041  CATGGTTATG GCAGCACTGC ATAATTCTCT TACTGTCATG CCATCCGTAA GATGCTTTTC TGTGACTGGT GAGTACTCAA
      GTACCAATAC CGTCGTGACG TATTAAGAGA ATGACAGTAC GGTAGGCATT CTACGAAAAG ACACTGACCA CTCATGAGTT

9121  CCAAGTCATT CTGAGAATAG TGTATGCGGC GACCGAGTTG CTCTTGCCCG GCGTCAATAC GGGATAATAC CGCGCCACAT
      GGTTCAGTAA GACTCTTATC ACATACGCCG CTGGCTCAAC GAGAACGGGC CGCAGTTATG CCCTATTATG GCGCGGTGTA

9201  AGCAGAACTT TAAAAGTGCT CATCATTGGA AAACGTTCTT CGGGGCGAAA ACTCTCAAGG ATCTTACCGC TGTTGAGATC
      TCGTCTTGAA ATTTTCACGA GTAGTAACCT TTTGCAAGAA GCCCCGCTTT TGAGAGTTCC TAGAATGGCG ACAACTCTAG

9281  CAGTTCGATG TAACCCACTC GTGCACCCAA CTGATCTTCA GCATCTTTTA CTTTCACCAG CGTTTCTGGG TGAGCAAAAA
      GTCAAGCTAC ATTGGGTGAG CACGTGGGTT GACTAGAAGT CGTAGAAAAT GAAAGTGGTC GCAAAGACCC ACTCGTTTTT

9361  CAGGAAGGCA AAATGCCGCA AAAAAGGGAA TAAGGGCGAC ACGGAAATGT TGAATACTCA TACTCTTCCT TTTTCAATAT
      GTCCTTCCGT TTTACGGCGT TTTTTCCCTT ATTCCCGCTG TGCCTTTACA ACTTATGAGT ATGAGAAGGA AAAAGTTATA

9441  TATTGAAGCA TTTATCAGGG TTATTGTCTC ATGAGCGGAT ACATATTTGA ATGTATTTAG AAAAATAAAC AAATAGGGGT
      ATAACTTCGT AAATAGTCCC AATAACAGAG TACTCGCCTA TGTATAAACT TACATAAATC TTTTTATTTG TTTATCCCCA

9521  TCCGCGCACA TTTCCCCGAA AAGTGCCACC TGACGTCTAA GAAACCATTA TTATCATGAC ATTAACCTAT AAAAATAGGC
      AGGCGCGTGT AAAGGGGCTT TTCACGGTGG ACTGCAGATT CTTTGGTAAT AATAGTACTG TAATTGGATA TTTTTATCCG

9601  GTATCACGAG GCCCTTTCGT C
      CATAGTGCTC CGGGAAAGCA G
```

FIG. 5P pCMV-II

```
  1 TCGCGCGTTT CGGTGATGAC GGTGAAAACC TCTGACACAT GCAGCTCCCG GAGACGGTCA CAGCTTGTCT GTAAGCGGAT
    AGCGCGCAAA GCCACTACTG CCACTTTTGG AGACTGTGTA CGTCGAGGGC CTCTGCCAGT GTCGAACAGA CATTCGCCTA

 81 GCCGGGAGCA GACAAGCCCG TCAGGGCGCG TCAGCGGGTG TTGGCGGGTG TCGGGGCTGG CTTAACTATG CGGCATCAGA
    CGGCCCTCGT CTGTTCGGGC AGTCCCGCGC AGTCGCCCAC AACCGCCCAC AGCCCCGACC GAATTGATAC GCCGTAGTCT

161 GCAGATTGTA CTGAGAGTGC ACCATATGAA GCTTTTTGCA AAAGCCTAGG CCTCCAAAAA AGCCTCCTCA CTACTTCTGG
    CGTCTAACAT GACTCTCACG TGGTATACTT CGAAAAACGT TTTCGGATCC GGAGGTTTTT TCGGAGGAGT GATGAAGACC

241 AATAGCTCAG AGGCCGAGGC GGCCTCGGCC TCTGCATAAA TAAAAAAAAT TAGTCAGCCA TGGGGCGGAG AATGGGCGGA
    TTATCGAGTC TCCGGCTCCG CCGGAGCCGG AGACGTATTT ATTTTTTTTA ATCAGTCGGT ACCCCGCCTC TTACCCGCCT

321 ACTGGGCGGG GAGGGAATTA TTGGCTATTG GCCATTGCAT ACGTTGTATC TATATCATAA TATGTACATT TATATTGGCT
    TGACCCGCCC CTCCCTTAAT AACCGATAAC CGGTAACGTA TGCAACATAG ATATAGTATT ATACATGTAA ATATAACCGA

401 CATGTCCAAT ATGACCGCCA TGTTGACATT GATTATTGAC TAGTTATTAA TAGTAATCAA TTACGGGGTC ATTAGTTCAT
    GTACAGGTTA TACTGGCGGT ACAACTGTAA CTAATAACTG ATCAATAATT ATCATTAGTT AATGCCCCAG TAATCAAGTA

481 AGCCCATATA TGGAGTTCCG CGTTACATAA CTTACGGTAA ATGGCCCGCC TGGCTGACCG CCCAACGACC CCCGCCCATT
    TCGGGTATAT ACCTCAAGGC GCAATGTATT GAATGCCATT TACCGGGCGG ACCGACTGGC GGGTTGCTGG GGGCGGGTAA

561 GACGTCAATA ATGACGTATG TTCCCATAGT AACGCCAATA GGGACTTTCC ATTGACGTCA ATGGGTGGAG TATTTACGGT
    CTGCAGTTAT TACTGCATAC AAGGGTATCA TTGCGGTTAT CCCTGAAAGG TAACTGCAGT TACCCACCTC ATAAATGCCA

641 AAACTGCCCA CTTGGCAGTA CATCAAGTGT ATCATATGCC AAGTCCGCCC CCTATTGACG TCAATGACGG TAAATGGCCC
    TTTGACGGGT GAACCGTCAT GTAGTTCACA TAGTATACGG TTCAGGCGGG GGATAACTGC AGTTACTGCC ATTTACCGGG
```

FIG. 7A pCMV-II

| | | | | | | | | |
|---|---|---|---|---|---|---|---|---|
| 721 | GCCTGGCATT | ATGCCCAGTA | CATGACCTTA | CGGGACTTTC | CTACTTGGCA | GTACATCTAC | GTATTAGTCA | TCGCTATTAC |
| | CGGACCGTAA | TACGGGTCAT | GTACTGGAAT | GCCCTGAAAG | GATGAACCGT | CATGTAGATG | CATAATCAGT | AGCGATAATG |
| 801 | CATGGTGATG | CGGTTTTGGC | AGTACACCAA | TGGGCGTGGA | TAGCGGTTTG | ACTCACGGGG | ATTTCCAAGT | CTCCACCCCA |
| | GTACCACTAC | GCCAAAACCG | TCATGTGGTT | ACCCGCACCT | ATCGCCAAAC | TGAGTGCCCC | TAAAGGTTCA | GAGGTGGGGT |
| 881 | TTGACGTCAA | TGGGAGTTTG | TTTTGGCACC | AAAATCAACG | GGACTTTCCA | AAATGTCGTA | ATAACCCCGC | CCCGTTGACG |
| | AACTGCAGTT | ACCCTCAAAC | AAAACCGTGG | TTTTAGTTGC | CCTGAAAGGT | TTTACAGCAT | TATTGGGGCG | GGGCAACTGC |
| 961 | CAAATGGGCG | GTAGGCGTGT | ACGGTGGGAG | GTCTATATAA | GCAGAGCTCG | TTTAGTGAAC | CGTCAGATCG | CCTGGAGACG |
| | GTTTACCCGC | CATCCGCACA | TGCCACCCTC | CAGATATATT | CGTCTCGAGC | AAATCACTTG | GCAGTCTAGC | GGACCTCTGC |
| 1041 | CCATCCACGC | TGTTTTGACC | TCCATAGAAG | ACACCGGGAC | CGATCCAGCC | TCCGCGGCCG | GGAACGGTGC | ATTGGAACGC |
| | GGTAGGTGCG | ACAAAACTGG | AGGTATCTTC | TGTGGCCCTG | GCTAGGTCGG | AGGCGCCGGC | CCTTGCCACG | TAACCTTGCG |
| 1121 | GGATTCCCCG | TGCCAAGAGT | GACGTAAGTA | CCGCCTATAG | ACTCTATAGG | CACACCCCTT | TGGCTCTTAT | GCATGCTATA |
| | CCTAAGGGGC | ACGGTTCTCA | CTGCATTCAT | GGCGGATATC | TGAGATATCC | GTGTGGGGAA | ACCGAGAATA | CGTACGATAT |
| 1201 | CTGTTTTTGG | CTTGGGGCCT | ATACACCCCC | GCTCCTTATG | CTATAGGTGA | TGGTATAGCT | TAGCCTATAG | GTGTGGGTTA |
| | GACAAAAACC | GAACCCCGGA | TATGTGGGGG | CGAGGAATAC | GATATCCACT | ACCATATCGA | ATCGGATATC | CACACCCAAT |
| 1281 | TTGACCATTA | TTGACCACTC | CCCTATTGGT | GACGATACTT | TCCATTACTA | ATCCATAACA | TGGCTCTTTG | CCACAACTAT |
| | AACTGGTAAT | AACTGGTGAG | GGGATAACCA | CTGCTATGAA | AGGTAATGAT | TAGGTATTGT | ACCGAGAAAC | GGTGTTGATA |
| 1361 | CTCTATTGGC | TATATGCCAA | TACTCTGTCC | TTCAGAGACT | GACACGGACT | CTGTATTTTT | ACAGGATGGG | GTCCATTTAT |
| | GAGATAACCG | ATATACGGTT | ATGAGACAGG | AAGTCTCTGA | CTGTGCCTGA | GACATAAAAA | TGTCCTACCC | CAGGTAAATA |

FIG. 7B pCMV-II

```
1441  TATTTACAAA TTCACATATA CAACAACGCC GTCCCCCGTG CCCGCAGTTT TTATTAAACA TAGCGTGGGA TCTCCGACAT
      ATAAATGTTT AAGTGTATAT GTTGTTGCGG CAGGGGGCAC GGGCGTCAAA AATAATTTGT ATCGCACCCT AGAGGCTGTA

1521  CTCGGGTACG TGTTCCGGAC ATGGGCTCTT CTCCGGTAGC GGCGGAGCTT CCACATCCGA GCCCTGGTCC CATCCGTCCA
      GAGCCCATGC ACAAGGCCTG TACCCGAGAA GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA CTTAGGCACA GCACAATGCC CACCACCACC
      CGCCGAGTAC CAGCGAGCCG TCGAGGAACG AGGATTGTCA CCTCCGGTCT GAATCCGTGT CGTGTTACGG GTGGTGGTGG

1681  AGTGTGCCGC ACAAGGCCGT GGCGGTAGGG TATGTGTCTG AAAATGAGCT CGGAGATTGG GCTCGCACCT GGACGCAGAT
      TCACACGGCG TGTTCCGGCA CCGCCATCCC ATACACAGAC TTTTACTCGA GCCTCTAACC CGAGCGTGGA CCTGCGTCTA

1761  GGAAGACTTA AGGCAGCGGC AGAAGAAGAT GCAGGCAGCT GAGTTGTTGT ATTCTGATAA GAGTCAAGGG TAACTCCCGT
      CCTTCTGAAT TCCGTCGCCG TCTTCTTCTA CGTCCGTCGA CTCAACAACA TAAGACTATT CTCAGTCTCC ATTGAGGGCA

1841  TGCGGTGCTG TTAACGGTGG AGGGCAGTGT AGTCTGAGCA GTACTCGTTG CTGCCGCGCG CGCCACCAGA CATAATAGCT
      ACGCCACGAC AATTGCCACC TCCCGTCACA TCAGACTCGT CATGAGCAAC GACGGCGCGC GCGGTGGTCT GTATTATCGA

                                                                       EcoRI
                                                                       ------
1921  GACAGACTAA CAGACTGTTC CTTTCCATGG GTCTTTTCTG CAGTCACCGT CGTCGACCTA AGAATTCAGA CTCGAGCAAG
      CTGTCTGATT GTCTGACAAG GAAAGGTACC CAGAAAAGAC GTCAGTGGCA GCAGCTGGAT TCTTAAGTCT GAGCTCGTTC

       XbaI                        BamHI     MluI
      ------                      -------  -------
2001  TCTAGAAAGG CGCGCCAAGA TATCAAGGAT CCACTACGCG TTAGAGCTCG CTGATCAGCC TCGACTGTGC CTTCTAGTTG
      AGATCTTTCC GCGCGGTTCT ATAGTTCCTA GGTGATGCGC AATCTCGAGC GACTAGTCGG AGCTGACACG GAAGATCAAC
```

FIG. 7C pCMV-II

```
2081  CCAGCCATCT GTTGTTTGCC CCTCCCCCGT GCCTTCCTTG ACCCTGGAAG GTGCCACTCC CACTGTCCTT TCCTAATAAA
      GGTCGGTAGA CAACAAACGG GGAGGGGGCA CGGAAGGAAC TGGGACCTTC CACGGTGAGG GTGACAGGAA AGGATTATTT

2161  ATGAGGAAAT TGCATCGCAT TGTCTGAGTA GGTGTCATTC TATTCTGGGG GGTGGGGTGG GGCAGGACAG CAAGGGGGAG
      TACTCCTTTA ACGTAGCGTA ACAGACTCAT CCACAGTAAG ATAAGACCCC CCACCCCACC CCGTCCTGTC GTTCCCCCTC

2241  GATTGGGAAG ACAATAGCAG GCATGCTGGG GAGCTCTTCC GCTTCCTCGC TCACTGACTC GCTGCGCTCG GTCGTTCGGC
      CTAACCCTTC TGTTATCGTC CGTACGACCC CTCGAGAAGG CGAAGGAGCG AGTGACTGAG CGACGCGAGC CAGCAAGCCG

2321  TGCGGCGAGC GGTATCAGCT CACTCAAAGG CGGTAATACG GTTATCCACA GAATCAGGGG ATAACGCAGG AAAGAACATG
      ACGCCGCTCG CCATAGTCGA GTGAGTTTCC GCCATTATGC CAATAGGTGT CTTAGTCCCC TATTGCGTCC TTTCTTGTAC

2401  TGAGCAAAAG GCCAGCAAAA GGCCAGGAAC CGTAAAAAGG CCGCGTTGCT GGCGTTTTTC CATAGGCTCC GCCCCCCTGA
      ACTCGTTTTC CGGTCGTTTT CCGGTCCTTG GCATTTTTCC GGCGCAACGA CCGCAAAAAG GTATCCGAGG CGGGGGGACT

2481  CGAGCATCAC AAAAATCGAC GCTCAAGTCA GAGGTGGCGA AACCCGACAG GACTATAAAG ATACCAGGCG TTTCCCCCTG
      GCTCGTAGTG TTTTTAGCTG CGAGTTCAGT CTCCACCGCT TTGGGCTGTC CTGATATTTC TATGGTCCGC AAAGGGGGAC

2561  GAAGCTCCCT CGTGCGCTCT CCTGTTCCGA CCCTGCCGCT TACCGGATAC CTGTCCGCCT TTCTCCCTTC GGGAAGCGTG
      CTTCGAGGGA GCACGCGAGA GGACAAGGCT GGGACGGCGA ATGGCCTATG GACAGGCGGA AAGAGGGAAG CCCTTCGCAC

2641  GCGCTTTCTC AATGCTCACG CTGTAGGTAT CTCAGTTCGG TGTAGGTCGT TCGCTCCAAG CTGGGCTGTG TGCACGAACC
      CGCGAAAGAG TTACGAGTGC GACATCCATA GAGTCAAGCC ACATCCAGCA AGCGAGGTTC GACCCGACAC ACGTGCTTGG

2721  CCCCGTTCAG CCCGACCGCT GCGCCTTATC CGGTAACTAT CGTCTTGAGT CCAACCCGGT AAGACACGAC TTATCGCCAC
      GGGGCAAGTC GGGCTGGCGA CGCGGAATAG GCCATTGATA GCAGAACTCA GGTTGGGCCA TTCTGTGCTG AATAGCGGTG
```

FIG. 7D pCMV-II

| | | | | | | | | |
|---|---|---|---|---|---|---|---|---|
| 2801 | TGGCAGCAGC | CACTGGTAAC | AGGATTAGCA | GAGCGAGGTA | TGTAGGCGGT | GCTACAGAGT | TCTTGAAGTG | GTGGCCTAAC |
| | ACCGTCGTCG | GTGACCATTG | TCCTAATCGT | CTCGCTCCAT | ACATCCGCCA | CGATGTCTCA | AGAACTTCAC | CACCGGATTG |
| 2881 | TACGGCTACA | CTAGAAGGAC | AGTATTTGGT | ATCTGCGCTC | TGCTGAAGCC | AGTTACCTTC | GGAAAAAGAG | TTGGTAGCTC |
| | ATGCCGATGT | GATCTTCCTG | TCATAAACCA | TAGACGCGAG | ACGACTTCGG | TCAATGGAAG | CCTTTTTCTC | AACCATCGAG |
| 2961 | TTGATCCGGC | AAACAAACCA | CCGCTGGTAG | CGGTGGTTTT | TTTGTTTGCA | AGCAGCAGAT | TACGCGCAGA | AAAAAAGGAT |
| | AACTAGGCCG | TTTGTTTGGT | GGCGACCATC | GCCACCAAAA | AAACAAACGT | TCGTCGTCTA | ATGCGCGTCT | TTTTTTCCTA |
| 3041 | CTCAAGAAGA | TCCTTTGATC | TTTTCTACGG | GGTCTGACGC | TCAGTGGAAC | GAAAACTCAC | GTTAAGGGAT | TTTGGTCATG |
| | GAGTTCTTCT | AGGAAACTAG | AAAAGATGCC | CCAGACTGCG | AGTCACCTTG | CTTTTGAGTG | CAATTCCCTA | AAACCAGTAC |
| 3121 | AGATTATCAA | AAAGGATCTT | CACCTAGATC | CTTTTAAATT | AAAAATGAAG | TTTTAAATCA | ATCTAAAGTA | TATATGAGTA |
| | TCTAATAGTT | TTTCCTAGAA | GTGGATCTAG | GAAAATTTAA | TTTTTACTTC | AAAATTTAGT | TAGATTTCAT | ATATACTCAT |
| 3201 | AACTTGGTCT | GACAGTTACC | AATGCTTAAT | CAGTGAGGCA | CCTATCTCAG | CGATCTGTCT | ATTTCGTTCA | TCCATAGTTG |
| | TTGAACCAGA | CTGTCAATGG | TTACGAATTA | GTCACTCCGT | GGATAGAGTC | GCTAGACAGA | TAAAGCAAGT | AGGTATCAAC |
| 3281 | CCTGACTCCC | CGTCGTGTAG | ATAACTACGA | TACGGGAGGG | CTTACCATCT | GGCCCCAGTG | CTGCAATGAT | ACCGCGAGAC |
| | GGACTGAGGG | GCAGCACATC | TATTGATGCT | ATG CCCTCCC | GAATGGTAGA | CCGGGGTCAC | GACGTTACTA | TGGCGCTCTG |
| 3361 | CCACGCTCAC | CGGCTCCAGA | TTTATCAGCA | ATAAACCAGC | CAGCCGGAAG | GGCCGAGCGC | AGAAGTGGTC | CTGCAACTTT |
| | GGTGCGAGTG | GCCGAGGTCT | AAATAGTCGT | TATTTGGTCG | GTCGGCCTTC | CCGGCTCGCG | TCTTCACCAG | GACGTTGAAA |
| 3441 | ATCCGCCTCC | ATCCAGTCTA | TTAATTGTTG | CCGGGAAGCT | AGAGTAAGTA | GTTCGCCAGT | TAATAGTTTG | CGCAACGTTG |
| | TAGGCGGAGG | TAGGTCAGAT | AATTAACAAC | GGCCCTTCGA | TCTCATTCAT | CAAGCGGTCA | ATTATCAAAC | GCGTTGCAAC |

FIG. 7E pCMV-II

```
3521 TTGCCATTGC TACAGGCATC GTGGTGTCAC GCTCGTCGTT TGGTATGGCT TCATTCAGCT CCGGTTCCCA ACGATCAAGG
     AACGGTAACG ATGTCCGTAG CACCACAGTG CGAGCAGCAA ACCATACCGA AGTAAGTCGA GGCCAAGGGT TGCTAGTTCC

3601 CGAGTTACAT GATCCCCCAT GTTGTGCAAA AAAGCGGTTA GCTCCTTCGG TCCTCCGATC GTTGTCAGAA GTAAGTTGGC
     GCTCAATGTA CTAGGGGGTA CAACACGTTT TTTCGCCAAT CGAGGAAGCC AGGAGGCTAG CAACAGTCTT CATTCAACCG

3681 CGCAGTGTTA TCACTCATGG TTATGGCAGC ACTGCATAAT TCTCTTACTG TCATGCCATC CGTAAGATGC TTTTCTGTGA
     GCGTCACAAT AGTGAGTACC AATACCGTCG TGACGTATTA AGAGAATGAC AGTACGGTAG GCATTCTACG AAAAGACACT

3761 CTGGTGAGTA CTCAACCAAG TCATTCTGAG AATAGTGTAT GCGGCGACCG AGTTGCTCTT GCCCGGCGTC AATACGGGAT
     GACCACTCAT GAGTTGGTTC AGTAAGACTC TTATCACATA CGCCGCTGGC TCAACGAGAA CGGGCCGCAG TTATGCCCTA

3841 AATACCGCGC CACATAGCAG AACTTTAAAA GTGCTCATCA TTGGAAAACG TTCTTCGGGG CGAAAACTCT CAAGGATCTT
     TTATGGCGCG GTGTATCGTC TTGAAATTTT CACGAGTAGT AACCTTTTGC AAGAAGCCCC GCTTTTGAGA GTTCCTAGAA

3921 ACCGCTGTTG AGATCCAGTT CGATGTAACC CACTCGTGCA CCCAACTGAT CTTCAGCATC TTTTACTTTC ACCAGCGTTT
     TGGCGACAAC TCTAGGTCAA GCTACATTGG GTGAGCACGT GGGTTGACTA GAAGTCGTAG AAAATGAAAG TGGTCGCAAA

4001 CTGGGTGAGC AAAAACAGGA AGGCAAAATG CCGCAAAAAA GGGAATAAGG GCGACACGGA AATGTTGAAT ACTCATACTC
     GACCCACTCG TTTTTGTCCT TCCGTTTTAC GGCGTTTTTT CCCTTATTCC CGCTGTGCCT TTACAACTTA TGAGTATGAG

4081 TTCCTTTTTC AATATTATTG AAGCATTTAT CAGGGTTATT GTCTCATGAG CGGATACATA TTTGAATGTA TTTAGAAAAA
     AAGGAAAAAG TTATAATAAC TTCGTAAATA GTCCCAATAA CAGAGTACTC GCCTATGTAT AAACTTACAT AAATCTTTTT

4161 TAAACAAATA GGGGTTCCGC GCACATTTCC CCGAAAAGTG CCACCTGACG TCTAAGAAAC CATTATTATC ATGACATTAA
     ATTTGTTTAT CCCCAAGGCG CGTGTAAAGG GGCTTTTCAC GGTGGACTGC AGATTCTTTG GTAATAATAG TACTGTAATT

4241 CCTATAAAAA TAGGCGTATC ACGAGGCCCT TTCGTC
     GGATATTTTT ATCCGCATAG TGCTCCGGGA AAGCAG
```

FIG. 7F pCMV-NS34A

```
  1  TCGCGCGTTT CGGTGATGAC GGTGAAAACC TCTGACACAT GCAGCTCCCG
     AGCGCGCAAA GCCACTACTG CCACTTTTGG AGACTGTGTA CGTCGAGGGC

 51  GAGACGGTCA CAGCTTGTCT GTAAGCGGAT GCCGGGAGCA GACAAGCCCG
     CTCTGCCAGT GTCGAACAGA CATTCGCCTA CGGCCCTCGT CTGTTCGGGC

101  TCAGGGCGCG TCAGCGGGTG TTGGCGGGTG TCGGGGCTGG CTTAACTATG
     AGTCCCGCGC AGTCGCCCAC AACCGCCCAC AGCCCCGACC GAATTGATAC

151  CGGCATCAGA GCAGATTGTA CTGAGAGTGC ACCATATGAA GCTTTTTGCA
     GCCGTAGTCT CGTCTAACAT GACTCTCACG TGGTATACTT CGAAAAACGT

           StuI
           ~~~~~~~
201  AAAGCCTAGG CCTCCAAAAA AGCCTCCTCA CTACTTCTGG AATAGCTCAG
     TTTCGGATCC GGAGGTTTTT TCGGAGGAGT GATGAAGACC TTATCGAGTC

251  AGGCCGAGGC GGCCTCGGCC TCTGCATAAA TAAAAAAAAT TAGTCAGCCA
     TCCGGCTCCG CCGGAGCCGG AGACGTATTT ATTTTTTTTA ATCAGTCGGT

301  TGGGGCGGAG AATGGGCGGA ACTGGGCGGG GAGGGAATTA TTGGCTATTG
     ACCCCGCCTC TTACCCGCCT TGACCCGCCC CTCCCTTAAT AACCGATAAC

351  GCCATTGCAT ACGTTGTATC TATATCATAA TATGTACATT TATATTGGCT
     CGGTAACGTA TGCAACATAG ATATAGTATT ATACATGTAA ATATAACCGA

401  CATGTCCAAT ATGACCGCCA TGTTGACATT GATTATTGAC TAGTTATTAA
     GTACAGGTTA TACTGGCGGT ACAACTGTAA CTAATAACTG ATCAATAATT

451  TAGTAATCAA TTACGGGGTC ATTAGTTCAT AGCCCATATA TGGAGTTCCG
     ATCATTAGTT AATGCCCCAG TAATCAAGTA TCGGGTATAT ACCTCAAGGC

501  CGTTACATAA CTTACGGTAA ATGGCCCGCC TGGCTGACCG CCCAACGACC
     GCAATGTATT GAATGCCATT TACCGGGCGG ACCGACTGGC GGGTTGCTGG

551  CCCGCCCATT GACGTCAATA ATGACGTATG TTCCCATAGT AACGCCAATA
     GGGCGGGTAA CTGCAGTTAT TACTGCATAC AAGGGTATCA TTGCGGTTAT

601  GGGACTTTCC ATTGACGTCA ATGGGTGGAG TATTTACGGT AAACTGCCCA
     CCCTGAAAGG TAACTGCAGT TACCCACCTC ATAAATGCCA TTTGACGGGT

651  CTTGGCAGTA CATCAAGTGT ATCATATGCC AAGTCCGCCC CCTATTGACG
     GAACCGTCAT GTAGTTCACA TAGTATACGG TTCAGGCGGG GGATAACTGC

701  TCAATGACGG TAAATGGCCC GCCTGGCATT ATGCCCAGTA CATGACCTTA
     AGTTACTGCC ATTTACCGGG CGGACCGTAA TACGGGTCAT GTACTGGAAT

751  CGGGACTTTC CTACTTGGCA GTACATCTAC GTATTAGTCA TCGCTATTAC
     GCCCTGAAAG GATGAACCGT CATGTAGATG CATAATCAGT AGCGATAATG

801  CATGGTGATG CGGTTTTGGC AGTACACCAA TGGGCGTGGA TAGCGGTTTG
     GTACCACTAC GCCAAAACCG TCATGTGGTT ACCCGCACCT ATCGCCAAAC

851  ACTCACGGGG ATTTCCAAGT CTCCACCCCA TTGACGTCAA TGGGAGTTTG
     TGAGTGCCCC TAAAGGTTCA GAGGTGGGGT AACTGCAGTT ACCCTCAAAC
```

FIG. 9A pCMV-NS34A

901 TTTTGGCACC AAAATCAACG GGACTTTCCA AAATGTCGTA ATAACCCCGC
AAAACCGTGG TTTTAGTTGC CCTGAAAGGT TTTACAGCAT TATTGGGGCG

951 CCCGTTGACG CAAATGGGCG GTAGGCGTGT ACGGTGGGAG GTCTATATAA
GGGCAACTGC GTTTACCCGC CATCCGCACA TGCCACCCTC CAGATATATT

1001 GCAGAGCTCG TTTAGTGAAC CGTCAGATCG CCTGGAGACG CCATCCACGC
CGTCTCGAGC AAATCACTTG GCAGTCTAGC GGACCTCTGC GGTAGGTGCG

1051 TGTTTTGACC TCCATAGAAG ACACCGGGAC CGATCCAGCC TCCGCGGCCG
ACAAAACTGG AGGTATCTTC TGTGGCCCTG GCTAGGTCGG AGGCGCCGGC

1101 GGAACGGTGC ATTGGAACGC GGATTCCCCG TGCCAAGAGT GACGTAAGTA
CCTTGCCACG TAACCTTGCG CCTAAGGGGC ACGGTTCTCA CTGCATTCAT

1151 CCGCCTATAG ACTCTATAGG CACACCCCTT TGGCTCTTAT GCATGCTATA
GGCGGATATC TGAGATATCC GTGTGGGGAA ACCGAGAATA CGTACGATAT

1201 CTGTTTTTGG CTTGGGGCCT ATACACCCCC GCTCCTTATG CTATAGGTGA
GACAAAAACC GAACCCCGGA TATGTGGGGG CGAGGAATAC GATATCCACT

1251 TGGTATAGCT TAGCCTATAG GTGTGGGTTA TTGACCATTA TTGACCACTC
ACCATATCGA ATCGGATATC CACACCCAAT AACTGGTAAT AACTGGTGAG

1301 CCCTATTGGT GACGATACTT TCCATTACTA ATCCATAACA TGGCTCTTTG
GGGATAACCA CTGCTATGAA AGGTAATGAT TAGGTATTGT ACCGAGAAAC

1351 CCACAACTAT CTCTATTGGC TATATGCCAA TACTCTGTCC TTCAGAGACT
GGTGTTGATA GAGATAACCG ATATACGGTT ATGAGACAGG AAGTCTCTGA

1401 GACACGGACT CTGTATTTTT ACAGGATGGG GTCCATTTAT TATTTACAAA
CTGTGCCTGA GACATAAAAA TGTCCTACCC CAGGTAAATA ATAAATGTTT

1451 TTCACATATA CAACAACGCC GTCCCCCGTG CCCGCAGTTT TTATTAAACA
AAGTGTATAT GTTGTTGCGG CAGGGGGCAC GGGCGTCAAA AATAATTTGT

1501 TAGCGTGGGA TCTCCGACAT CTCGGGTACG TGTTCCGGAC ATGGGCTCTT
ATCGCACCCT AGAGGCTGTA GAGCCCATGC ACAAGGCCTG TACCCGAGAA

1551 CTCCGGTAGC GGCGGAGCTT CCACATCCGA GCCCTGGTCC CATCCGTCCA
GAGGCCATCG CCGCCTCGAA GGTGTAGGCT CGGGACCAGG GTAGGCAGGT

1601 GCGGCTCATG GTCGCTCGGC AGCTCCTTGC TCCTAACAGT GGAGGCCAGA
CGCCGAGTAC CAGCGAGCCG TCGAGGAACG AGGATTGTCA CCTCCGGTCT

1651 CTTAGGCACA GCACAATGCC CACCACCACC AGTGTGCCGC ACAAGGCCGT
GAATCCGTGT CGTGTTACGG GTGGTGGTGG TCACACGGCG TGTTCCGGCA

1701 GGCGGTAGGG TATGTGTCTG AAAATGAGCT CGGAGATTGG GCTCGCACCT
CCGCCATCCC ATACACAGAC TTTTACTCGA GCCTCTAACC CGAGCGTGGA

1751 GGACGCAGAT GGAAGACTTA AGGCAGCGGC AGAAGAAGAT GCAGGCAGCT
CCTGCGTCTA CCTTCTGAAT TCCGTCGCCG TCTTCTTCTA CGTCCGTCGA

1801 GAGTTGTTGT ATTCTGATAA GAGTCAGAGG TAACTCCCGT TGCGGTGCTG
CTCAACAACA TAAGACTATT CTCAGTCTCC ATTGAGGGCA ACGCCACGAC

FIG. 9B pCMV-NS34A

1851 TTAACGGTGG AGGGCAGTGT AGTCTGAGCA GTACTCGTTG CTGCCGCGCG
AATTGCCACC TCCCGTCACA TCAGACTCGT CATGAGCAAC GACGGCGCGC

1901 CGCCACCAGA CATAATAGCT GACAGACTAA CAGACTGTTC CTTTCCATGG
GCGGTGGTCT GTATTATCGA CTGTCTGATT GTCTGACAAG GAAAGGTACC

+2 M A P
EcoRI
1951 GTCTTTTCTG CAGTCACCGT CGTCGACCTA AGAATTCACC ATGGCGCCCA
CAGAAAAGAC GTCAGTGGCA GCAGCTGGAT TCTTAAGTGG TACCGCGGGT

+2 I T A Y A Q Q T R G L L G C I I T
2001 TCACGGCGTA CGCCCAGCAG ACAAGGGGCC TCCTAGGGTG CATAATCACC
AGTGCCGCAT GCGGGTCGTC TGTTCCCCGG AGGATCCCAC GTATTAGTGG

+2 S L T G R D K N Q V E G E V Q I V
2051 AGCCTAACTG GCCGGGACAA AAACCAAGTG GAGGGTGAGG TCCAGATTGT
TCGGATTGAC CGGCCCTGTT TTTGGTTCAC CTCCCACTCC AGGTCTAACA

+2 S T A A Q T F L A T C I N G V C
2101 GTCAACTGCT GCCCAAACCT TCCTGGCAAC GTGCATCAAT GGGGTGTGCT
CAGTTGACGA CGGGTTTGGA AGGACCGTTG CACGTAGTTA CCCCACACGA

+2 W T V Y H G A G T R T I A S P K G
2151 GGACTGTCTA CCACGGGGCC GGAACGAGGA CCATCGCGTC ACCCAAGGGT
CCTGACAGAT GGTGCCCCGG CCTTGCTCCT GGTAGCGCAG TGGGTTCCCA

-2 P V I Q M Y T N V D Q D L V G W P
2201 CCTGTCATCC AGATGTATAC CAATGTAGAC CAAGACCTTG TGGGCTGGCC
GGACAGTAGG TCTACATATG GTTACATCTG GTTCTGGAAC ACCCGACCGG

+2 A S Q G T R S L T P C T C G S S
2251 CGCTTCGCAA GGTACCCGCT CATTGACACC CTGCACTTGC GGCTCCTCGG
GCGAAGCGTT CCATGGGCGA GTAACTGTGG GACGTGAACG CCGAGGAGCC

+2 D L Y L V T R H A D V I P V R R R
2301 ACCTTTACCT GGTCACGAGG CACGCCGATG TCATTCCCGT GCGCCGGCGG
TGGAAATGGA CCAGTGCTCC GTGCGGCTAC AGTAAGGGCA CGCGGCCGCC

+2 G D S R G S L L S P R P I S Y L K
2351 GGTGATAGCA GGGGCAGCCT GCTGTCGCCC CGGCCCATTT CCTACTTGAA
CCACTATCGT CCCCGTCGGA CGACAGCGGG GCCGGGTAAA GGATGAACTT

+2 G S S G G P L L C P A G H A V G
2401 AGGCTCCTCG GGGGGTCCGC TGTTGTGCCC CGCGGGGCAC GCCGTGGGCA
TCCGAGGAGC CCCCCAGGCG ACAACACGGG GCGCCCCGTG CGGCACCCGT

+2 I F R A A V C T R G V A K A V D F
2451 TATTTAGGGC CGCGGTGTGC ACCCGTGGAG TGGCTAAGGC GGTGGACTTT
ATAAATCCCG GCGCCACACG TGGGCACCTC ACCGATTCCG CCACCTGAAA

+2 I P V E N L E T T M R S P V F T D
2501 ATCCCTGTGG AGAACCTAGA GACAACCATG AGGTCCCCGG TGTTCACGGA
TAGGGACACC TCTTGGATCT CTGTTGGTAC TCCAGGGGCC ACAAGTGCCT

FIG. 9C pCMV-NS34A

```
+2    N  S  S   P  P  V  V   P  Q  S   F  Q  V   A  H  L
2551  TAACTCCTCT CCACCAGTAG TGCCCCAGAG CTTCCAGGTG GCTCACCTCC
      ATTGAGGAGA GGTGGTCATC ACGGGGTCTC GAAGGTCCAC CGAGTGGAGG

+2 H  A  P  T   G  S  G   K  S  T  K   V  P  A   A  Y  A
2601  ATGCTCCCAC AGGCAGCGGC AAAAGCACCA AGGTCCCGGC TGCATATGCA
      TACGAGGGTG TCCGTCGCCG TTTTCGTGGT TCCAGGGCCG ACGTATACGT

+2  A  Q  G  Y   K  V  L   V  L  N   P  S  V  A   A  T  L
2651  GCTCAGGGCT ATAAGGTGCT AGTACTCAAC CCCTCTGTTG CTGCAACACT
      CGAGTCCCGA TATTCCACGA TCATGAGTTG GGGAGACAAC GACGTTGTGA

+2    G  F  G   A  Y  M  S   K  A  H   G  I  D   P  N  I
2701  GGGCTTTGGT GCTTACATGT CCAAGGCTCA TGGGATCGAT CCTAACATCA
      CCCGAAACCA CGAATGTACA GGTTCCGAGT ACCCTAGCTA GGATTGTAGT

+2 R  T  G  V   R  T  I   T  T  G  S   P  I  T   Y  S  T
2751  GGACCGGGGT GAGAACAATT ACCACTGGCA GCCCCATCAC GTACTCCACC
      CCTGGCCCCA CTCTTGTTAA TGGTGACCGT CGGGGTAGTG CATGAGGTGG

+2  Y  G  K  F   L  A  D   G  G  C   S  G  G  A   Y  D  I
2801  TACGGCAAGT TCCTTGCCGA CGGCGGGTGC TCGGGGGGCG CTTATGACAT
      ATGCCGTTCA AGGAACGGCT GCCGCCCACG AGCCCCCCGC GAATACTGTA

+2    I  I  C   D  E  C  H   S  T  D   A  T  S   I  L  G
2851  AATAATTTGT GACGAGTGCC ACTCCACGGA TGCCACATCC ATCTTGGGCA
      TTATTAAACA CTGCTCACGG TGAGGTGCCT ACGGTGTAGG TAGAACCCGT

+2 I  G  T  V   L  D  Q   A  E  T  A   G  A  R   L  V  V
2901  TTGGCACTGT CCTTGACCAA GCAGAGACTG CGGGGGCGAG ACTGGTTGTG
      AACCGTGACA GGAACTGGTT CGTCTCTGAC GCCCCCGCTC TGACCAACAC

+2  L  A  T  A   T  P  P   G  S  V   T  V  P  H   P  N  I
2951  CTCGCCACCG CCACCCCTCC GGGCTCCGTC ACTGTGCCCC ATCCCAACAT
      GAGCGGTGGC GGTGGGGAGG CCCGAGGCAG TGACACGGGG TAGGGTTGTA

+2    E  E  V   A  L  S  T   T  G  E   I  P  F   Y  G  K
3001  CGAGGAGGTT GCTCTGTCCA CCACCGGAGA GATCCCTTTT TACGGCAAGG
      GCTCCTCCAA CGAGACAGGT GGTGGCCTCT CTAGGGAAAA ATGCCGTTCC

+2 A  I  P  L   E  V  I   K  G  G  R   H  L  I   F  C  H
3051  CTATCCCCCT CGAAGTAATC AAGGGGGGGA GACATCTCAT CTTCTGTCAT
      GATAGGGGGA GCTTCATTAG TTCCCCCCCT CTGTAGAGTA GAAGACAGTA

+2  S  K  K  K   C  D  E   L  A  A   K  L  V  A   L  G  I
3101  TCAAAGAAGA AGTGCGACGA ACTCGCCGCA AAGCTGGTCG CATTGGGCAT
      AGTTTCTTCT TCACGCTGCT TGAGCGGCGT TTCGACCAGC GTAACCCGTA

+2    N  A  V   A  Y  Y  R   G  L  D   V  S  V   I  P  T
3151  CAATGCCGTG GCCTACTACC GCGGTCTTGA CGTGTCCGTC ATCCCGACCA
      GTTACGGCAC CGGATGATGG CGCCAGAACT GCACAGGCAG TAGGGCTGGT

+2 S  G  D  V   V  V  V   A  T  D  A   L  M  T   G  Y  T
3201  GCGGCGATGT TGTCGTCGTG GCAACCGATG CCCTCATGAC CGGCTATACC
      CGCCGCTACA ACAGCAGCAC CGTTGGCTAC GGGAGTACTG GCCGATATGG
```

FIG. 9D pCMV-NS34A

```
 +2  G D F D  S V I  D C N  T C V T  Q T V
3251 GGCGACTTCG ACTCGGTGAT AGACTGCAAT ACGTGTGTCA CCCAGACAGT
     CCGCTGAAGC TGAGCCACTA TCTGACGTTA TGCACACAGT GGGTCTGTCA

 +2  D F S  L D P T  F T I  E T I  T L P
3301 CGATTTCAGC CTTGACCCTA CCTTCACCAT TGAGACAATC ACGCTCCCCC
     GCTAAAGTCG GAACTGGGAT GGAAGTGGTA ACTCTGTTAG TGCGAGGGGG

 +2 Q D A V  S R T  Q R R G  R T G  R G K
3351 AAGATGCTGT CTCCCGCACT CAACGTCGGG GCAGGACTGG CAGGGGGAAG
     TTCTACGACA GAGGGCGTGA GTTGCAGCCC CGTCCTGACC GTCCCCCTTC

 +2  P G I Y  R F V  A P G  E R P S  G M F
3401 CCAGGCATCT ACAGATTTGT GGCACCGGGG GAGCGCCCCT CCGGCATGTT
     GGTCCGTAGA TGTCTAAACA CCGTGGCCCC CTCGCGGGGA GGCCGTACAA

 +2  D S S  V L C E  C Y D  A G C  A W Y
3451 CGACTCGTCC GTCCTCTGTG AGTGCTATGA CGCAGGCTGT GCTTGGTATG
     GCTGAGCAGG CAGGAGACAC TCACGATACT GCGTCCGACA CGAACCATAC

 +2 E L T P  A E T  T V R L  R A Y  M N T
3501 AGCTCACGCC CGCCGAGACT ACAGTTAGGC TACGAGCGTA CATGAACACC
     TCGAGTGCGG GCGGCTCTGA TGTCAATCCG ATGCTCGCAT GTACTTGTGG

 +2  P G L P  V C Q  D H L  E F W E  G V F
3551 CCGGGGCTTC CCGTGTGCCA GGACCATCTT GAATTTTGGG AGGGCGTCTT
     GGCCCCGAAG GGCACACGGT CCTGGTAGAA CTTAAAACCC TCCCGCAGAA

 +2  T G L  T H I D  A H F  L S Q  T K Q
       StuI
     ~~~~~~
3601 TACAGGCCTC ACTCATATAG ATGCCCACTT TCTATCCCAG ACAAAGCAGA
     ATGTCCGGAG TGAGTATATC TACGGGTGAA AGATAGGGTC TGTTTCGTCT

 +2 S G E N  L P Y  L V A Y  Q A T  V C A
3651 GTGGGGAGAA CCTTCCTTAC CTGGTAGCGT ACCAAGCCAC CGTGTGCGCT
     CACCCCTCTT GGAAGGAATG GACCATCGCA TGGTTCGGTG GCACACGCGA

 +2  R A Q A  P P P  S W D  Q M W K  C L I
3701 AGGGCTCAAG CCCCTCCCCC ATCGTGGGAC CAGATGTGGA AGTGTTTGAT
     TCCCGAGTTC GGGGAGGGGG TAGCACCCTG GTCTACACCT TCACAAACTA

 +2  R L K  P T L H  G P T  P L L  Y R L
3751 TCGCCTCAAG CCCACCCTCC ATGGGCCAAC ACCCCTGCTA TACAGACTGG
     AGCGGAGTTC GGGTGGGAGG TACCCGGTTG TGGGGACGAT ATGTCTGACC

 +2 G A V Q  N E I  T L T H  P V T  K Y I
3801 GCGCTGTTCA GAATGAAATC ACCCTGACGC ACCCAGTCAC CAAATACATC
     CGCGACAAGT CTTACTTTAG TGGGACTGCG TGGGTCAGTG GTTTATGTAG

 +2  M T C M  S A D  L E V  V T S T  W V L
3851 ATGACATGCA TGTCGGCCGA CCTGGAGGTC GTCACGAGCA CCTGGGTGCT
     TACTGTACGT ACAGCCGGCT GGACCTCCAG CAGTGCTCGT GGACCCACGA

 +2  V G G  V L A A  L A A  Y C L  S T G
3901 CGTTGGCGGC GTCCTGGCTG CTTTGGCCGC GTATTGCCTG TCAACAGGCT
     GCAACCGCCG CAGGACCGAC GAAACCGGCG CATAACGGAC AGTTGTCCGA
```

FIG. 9E pCMV-NS34A

```
 +2  C  V  V  I   V  G  R   V  V  L  S   G  K  P   A  I  I
3951  GCGTGGTCAT AGTGGGCAGG GTCGTCTTGT CCGGGAAGCC GGCAATCATA
      CGCACCAGTA TCACCCGTCC CAGCAGAACA GGCCCTTCGG CCGTTAGTAT

 +2  P  D  R  E   V  L  Y   R  E  F   D  E  M  E   E  C
4001  CCTGACAGGG AAGTCCTCTA CCGAGAGTTC GATGAGATGG AAGAGTGCTA
      GGACTGTCCC TTCAGGAGAT GGCTCTCAAG CTACTCTACC TTCTCACGAT

       BamHI     MluI
       ~~~~~~   ~~~~~~~
4051  GGATCCACTA CGCGTTAGAG CTCGCTGATC AGCCTCGACT GTGCCTTCTA
      CCTAGGTGAT GCGCAATCTC GAGCGACTAG TCGGAGCTGA CACGGAAGAT

4101  GTTGCCAGCC ATCTGTTGTT TGCCCCTCCC CCGTGCCTTC CTTGACCCTG
      CAACGGTCGG TAGACAACAA ACGGGGAGGG GGCACGGAAG GAACTGGGAC

4151  GAAGGTGCCA CTCCCACTGT CCTTTCCTAA TAAAATGAGG AAATTGCATC
      CTTCCACGGT GAGGGTGACA GGAAAGGATT ATTTTACTCC TTTAACGTAG

4201  GCATTGTCTG AGTAGGTGTC ATTCTATTCT GGGGGGTGGG GTGGGGCAGG
      CGTAACAGAC TCATCCACAG TAAGATAAGA CCCCCCACCC CACCCCGTCC

4251  ACAGCAAGGG GGAGGATTGG GAAGACAATA GCAGGCATGC TGGGGAGCTC
      TGTCGTTCCC CCTCCTAACC CTTCTGTTAT CGTCCGTACG ACCCCTCGAG

4301  TTCCGCTTCC TCGCTCACTG ACTCGCTGCG CTCGGTCGTT CGGCTGCGGC
      AAGGCGAAGG AGCGAGTGAC TGAGCGACGC GAGCCAGCAA GCCGACGCCG

4351  GAGCGGTATC AGCTCACTCA AAGGCGGTAA TACGGTTATC CACAGAATCA
      CTCGCCATAG TCGAGTGAGT TTCCGCCATT ATGCCAATAG GTGTCTTAGT

4401  GGGGATAACG CAGGAAAGAA CATGTGAGCA AAAGGCCAGC AAAAGGCCAG
      CCCCTATTGC GTCCTTTCTT GTACACTCGT TTTCCGGTCG TTTTCCGGTC

4451  GAACCGTAAA AAGGCCGCGT TGCTGGCGTT TTTCCATAGG CTCCGCCCCC
      CTTGGCATTT TTCCGGCGCA ACGACCGCAA AAAGGTATCC GAGGCGGGGG

4501  CTGACGAGCA TCACAAAAAT CGACGCTCAA GTCAGAGGTG GCGAAACCCG
      GACTGCTCGT AGTGTTTTTA GCTGCGAGTT CAGTCTCCAC CGCTTTGGGC

4551  ACAGGACTAT AAAGATACCA GGCGTTTCCC CCTGGAAGCT CCCTCGTGCG
      TGTCCTGATA TTTCTATGGT CCGCAAAGGG GGACCTTCGA GGGAGCACGC

4601  CTCTCCTGTT CCGACCCTGC CGCTTACCGG ATACCTGTCC GCCTTTCTCC
      GAGAGGACAA GGCTGGGACG GCGAATGGCC TATGGACAGG CGGAAAGAGG

4651  CTTCGGGAAG CGTGGCGCTT TCTCAATGCT CACGCTGTAG GTATCTCAGT
      GAAGCCCTTC GCACCGCGAA AGAGTTACGA GTGCGACATC CATAGAGTCA

4701  TCGGTGTAGG TCGTTCGCTC CAAGCTGGGC TGTGTGCACG AACCCCCCGT
      AGCCACATCC AGCAAGCGAG GTTCGACCCG ACACACGTGC TTGGGGGGCA

4751  TCAGCCCGAC CGCTGCGCCT TATCCGGTAA CTATCGTCTT GAGTCCAACC
      AGTCGGGCTG GCGACGCGGA ATAGGCCATT GATAGCAGAA CTCAGGTTGG

4801  CGGTAAGACA CGACTTATCG CCACTGGCAG CAGCCACTGG TAACAGGATT
      GCCATTCTGT GCTGAATAGC GGTGACCGTC GTCGGTGACC ATTGTCCTAA
```

FIG. 9F pCMV-NS34A

```
4851  AGCAGAGCGA GGTATGTAGG CGGTGCTACA GAGTTCTTGA AGTGGTGGCC
      TCGTCTCGCT CCATACATCC GCCACGATGT CTCAAGAACT TCACCACCGG

4901  TAACTACGGC TACACTAGAA GGACAGTATT TGGTATCTGC GCTCTGCTGA
      ATTGATGCCG ATGTGATCTT CCTGTCATAA ACCATAGACG CGAGACGACT

4951  AGCCAGTTAC CTTCGGAAAA AGAGTTGGTA GCTCTTGATC CGGCAAACAA
      TCGGTCAATG GAAGCCTTTT TCTCAACCAT CGAGAACTAG GCCGTTTGTT

5001  ACCACCGCTG GTAGCGGTGG TTTTTTTGTT TGCAAGCAGC AGATTACGCG
      TGGTGGCGAC CATCGCCACC AAAAAAACAA ACGTTCGTCG TCTAATGCGC

5051  CAGAAAAAAA GGATCTCAAG AAGATCCTTT GATCTTTTCT ACGGGGTCTG
      GTCTTTTTTT CCTAGAGTTC TTCTAGGAAA CTAGAAAAGA TGCCCCAGAC

5101  ACGCTCAGTG GAACGAAAAC TCACGTTAAG GGATTTTGGT CATGAGATTA
      TGCGAGTCAC CTTGCTTTTG AGTGCAATTC CCTAAAACCA GTACTCTAAT

5151  TCAAAAAGGA TCTTCACCTA GATCCTTTTA AATTAAAAAT GAAGTTTTAA
      AGTTTTTCCT AGAAGTGGAT CTAGGAAAAT TTAATTTTTA CTTCAAAATT

5201  ATCAATCTAA AGTATATATG AGTAAACTTG GTCTGACAGT TACCAATGCT
      TAGTTAGATT TCATATATAC TCATTTGAAC CAGACTGTCA ATGGTTACGA

5251  TAATCAGTGA GGCACCTATC TCAGCGATCT GTCTATTTCG TTCATCCATA
      ATTAGTCACT CCGTGGATAG AGTCGCTAGA CAGATAAAGC AAGTAGGTAT

5301  GTTGCCTGAC TCCCCGTCGT GTAGATAACT ACGATACGGG AGGGCTTACC
      CAACGGACTG AGGGGCAGCA CATCTATTGA TGCTATGCCC TCCCGAATGG

5351  ATCTGGCCCC AGTGCTGCAA TGATACCGCG AGACCCACGC TCACCGGCTC
      TAGACCGGGG TCACGACGTT ACTATGGCGC TCTGGGTGCG AGTGGCCGAG

5401  CAGATTTATC AGCAATAAAC CAGCCAGCCG GAAGGGCCGA GCGCAGAAGT
      GTCTAAATAG TCGTTATTTG GTCGGTCGGC CTTCCCGGCT CGCGTCTTCA

5451  GGTCCTGCAA CTTTATCCGC CTCCATCCAG TCTATTAATT GTTGCCGGGA
      CCAGGACGTT GAAATAGGCG GAGGTAGGTC AGATAATTAA CAACGGCCCT

5501  AGCTAGAGTA AGTAGTTCGC CAGTTAATAG TTTGCGCAAC GTTGTTGCCA
      TCGATCTCAT TCATCAAGCG GTCAATTATC AAACGCGTTG CAACAACGGT

5551  TTGCTACAGG CATCGTGGTG TCACGCTCGT CGTTTGGTAT GGCTTCATTC
      AACGATGTCC GTAGCACCAC AGTGCGAGCA GCAAACCATA CCGAAGTAAG

5601  AGCTCCGGTT CCCAACGATC AAGGCGAGTT ACATGATCCC CCATGTTGTG
      TCGAGGCCAA GGGTTGCTAG TTCCGCTCAA TGTACTAGGG GGTACAACAC

5651  CAAAAAAGCG GTTAGCTCCT TCGGTCCTCC GATCGTTGTC AGAAGTAAGT
      GTTTTTTCGC CAATCGAGGA AGCCAGGAGG CTAGCAACAG TCTTCATTCA

5701  TGGCCGCAGT GTTATCACTC ATGGTTATGG CAGCACTGCA TAATTCTCTT
      ACCGGCGTCA CAATAGTGAG TACCAATACC GTCGTGACGT ATTAAGAGAA

5751  ACTGTCATGC CATCCGTAAG ATGCTTTTCT GTGACTGGTG AGTACTCAAC
      TGACAGTACG GTAGGCATTC TACGAAAAGA CACTGACCAC TCATGAGTTG
```

FIG. 9G pCMV-NS34A

5801 CAAGTCATTC TGAGAATAGT GTATGCGGCG ACCGAGTTGC TCTTGCCCGG
GTTCAGTAAG ACTCTTATCA CATACGCCGC TGGCTCAACG AGAACGGGCC

5851 CGTCAATACG GGATAATACC GCGCCACATA GCAGAACTTT AAAAGTGCTC
GCAGTTATGC CCTATTATGG CGCGGTGTAT CGTCTTGAAA TTTTCACGAG

5901 ATCATTGGAA AACGTTCTTC GGGGCGAAAA CTCTCAAGGA TCTTACCGCT
TAGTAACCTT TTGCAAGAAG CCCCGCTTTT GAGAGTTCCT AGAATGGCGA

5951 GTTGAGATCC AGTTCGATGT AACCCACTCG TGCACCCAAC TGATCTTCAG
CAACTCTAGG TCAAGCTACA TTGGGTGAGC ACGTGGGTTG ACTAGAAGTC

6001 CATCTTTTAC TTTCACCAGC GTTTCTGGGT GAGCAAAAAC AGGAAGGCAA
GTAGAAAATG AAAGTGGTCG CAAAGACCCA CTCGTTTTTG TCCTTCCGTT

6051 AATGCCGCAA AAAAGGGAAT AAGGGCGACA CGGAAATGTT GAATACTCAT
TTACGGCGTT TTTTCCCTTA TTCCCGCTGT GCCTTTACAA CTTATGAGTA

6101 ACTCTTCCTT TTTCAATATT ATTGAAGCAT TTATCAGGGT TATTGTCTCA
TGAGAAGGAA AAAGTTATAA TAACTTCGTA AATAGTCCCA ATAACAGAGT

6151 TGAGCGGATA CATATTTGAA TGTATTTAGA AAAATAAACA AATAGGGGTT
ACTCGCCTAT GTATAAACTT ACATAAATCT TTTTATTTGT TTATCCCCAA

6201 CCGCGCACAT TTCCCCGAAA AGTGCCACCT GACGTCTAAG AAACCATTAT
GGCGCGTGTA AAGGGGCTTT TCACGGTGGA CTGCAGATTC TTTGGTAATA

6251 TATCATGACA TTAACCTATA AAAATAGGCG TATCACGAGG CCCTTTCGTC
ATAGTACTGT AATTGGATAT TTTTATCCGC ATAGTGCTCC GGGAAAGCAG

FIG. 9H

```
                             MetAlaAlaTyrAlaAlaGlnGlyTyrLysValLeuVal
  2   AGCTTACAAAACAAATTCACCATGGCTGCATATGCAGCTCAGGGCTATAAGGTGCTAGTA
      TCGAATGTTTTGTTTAAGTGGTACCGACGTATACGTCGAGTCCCGATATTCCACGATCAT
      ^                  ^         ^                           ^
      1 HIND3, 21 NCOI, 30 NDEI, 58 SCAI,

      LeuAsnProSerValAlaAlaThrLeuGlyPheGlyAlaTyrMetSerLysAlaHisGly
 62   CTCAACCCCTCTGTTGCTGCAACACTGGGCTTTGGTGCTTACATGTCCAAGGCTCATGGG
      GAGTTGGGGAGACAACGACGTTGTGACCCGAAACCACGAATGTACAGGTTCCGAGTACCC

      IleAspProAsnIleArgThrGlyValArgThrIleThrThrGlySerProIleThrTyr
122   ATCGATCCTAACATCAGGACCGGGGTGAGAACAATTACCACTGGCAGCCCCATCACGTAC
      TAGCTAGGATTGTAGTCCTGGCCCCACTCTTGTTAATGGTGACCGTCGGGGTAGTGCATG
      ^
      122 CLAI,

      SerThrTyrGlyLysPheLeuAlaAspGlyGlyCysSerGlyGlyAlaTyrAspIleIle
182   TCCACCTACGGCAAGTTCCTTGCCGACGGCGGGTGCTCGGGGGGCGCTTATGACATAATA
      AGGTGGATGCCGTTCAAGGAACGGCTGCCGCCCACGAGCCCCCCGCGAATACTGTATTAT

      IleCysAspGluCysHisSerThrAspAlaThrSerIleLeuGlyIleGlyThrValLeu
242   ATTTGTGACGAGTGCCACTCCACGGATGCCACATCCATCTTGGGCATTGGCACTGTCCTT
      TAAACACTGCTCACGGTGAGGTGCCTACGGTGTAGGTAGAACCCGTAACCGTGACAGGAA

      AspGlnAlaGluThrAlaGlyAlaArgLeuValValLeuAlaThrAlaThrProProGly
302   GACCAAGCAGAGACTGCGGGGGCGAGACTGGTTGTGCTCGCCACCGCCACCCCTCCGGGC
      CTGGTTCGTCTCTGACGCCCCCGCTCTGACCAACACGAGCGGTGGCGGTGGGGAGGCCCG
             ^
      309 ALWN1,

      SerValThrValProHisProAsnIleGluGluValAlaLeuSerThrThrGlyGluIle
362   TCCGTCACTGTGCCCCATCCCAACATCGAGGAGGTTGCTCTGTCCACCACCGGAGAGATC
      AGGCAGTGACACGGGGTAGGGTTGTAGCTCCTCCAACGAGACAGGTGGTGGCCTCTCTAG

      ProPheTyrGlyLysAlaIleProLeuGluValIleLysGlyGlyArgHisLeuIlePhe
422   CCTTTTTACGGCAAGGCTATCCCCCTCGAAGTAATCAAGGGGGGGAGACATCTCATCTTC
      GGAAAAATGCCGTTCCGATAGGGGGAGCTTCATTAGTTCCCCCCCTCTGTAGAGTAGAAG

      CysHisSerLysLysLysCysAspGluLeuAlaAlaLysLeuValAlaLeuGlyIleAsn
482   TGTCATTCAAAGAAGAAGTGCGACGAACTCGCCGCAAAGCTGGTCGCATTGGGCATCAAT
      ACAGTAAGTTTCTTCTTCACGCTGCTTGAGCGGCGTTTCGACCAGCGTAACCCGTAGTTA

      AlaValAlaTyrTyrArgGlyLeuAspValSerValIleProThrSerGlyAspValVal
542   GCCGTGGCCTACTACCGCGGTCTTGACGTGTCCGTCATCCCGACCAGCGGCGATGTTGTC
      CGGCACCGGATGATGGCGCCAGAACTGCACAGGCAGTAGGGCTGGTCGCCGCTACAACAG
                    ^         ^
      556 SAC2, 566 DRD1,

      ValValAlaThrAspAlaLeuMetThrGlyTyrThrGlyAspPheAspSerValIleAsp
602   GTCGTGGCAACCGATGCCCTCATGACCGGCTATACCGGCGACTTCGACTCGGTGATAGAC
      CAGCACCGTTGGCTACGGGAGTACTGGCCGATATGGCCGCTGAAGCTGAGCCACTATCTG
                         ^
      621 BSPH1,

      CysAsnThrCysValThrGlnThrValAspPheSerLeuAspProThrPheThrIleGlu
```

FIG. 11A

```
662   TGCAATACGTGTGTCACCCAGACAGTCGATTTCAGCCTTGACCCTACCTTCACCATTGAG
      ACGTTATGCACACAGTGGGTCTGTCAGCTAAAGTCGGAACTGGGATGGAAGTGGTAACTC

      ThrIleThrLeuProGlnAspAlaValSerArgThrGlnArgArgGlyArgThrGlyArg
722   ACAATCACGCTCCCCCAAGATGCTGTCTCCCGCACTCAACGTCGGGGCAGGACTGGCAGG
      TGTTAGTGCGAGGGGGTTCTACGACAGAGGGCGTGAGTTGCAGCCCCGTCCTGACCGTCC

      GlyLysProGlyIleTyrArgPheValAlaProGlyGluArgProSerGlyMetPheAsp
782   GGGAAGCCAGGCATCTACAGATTTGTGGCACCGGGGGAGCGCCCCTCCGGCATGTTCGAC
      CCCTTCGGTCCGTAGATGTCTAAACACCGTGGCCCCCTCGCGGGGAGGCCGTACAAGCTG
                                              ^                ^

      822 BGLI, 839 DRD1,

      SerSerValLeuCysGluCysTyrAspAlaGlyCysAlaTrpTyrGluLeuThrProAla
842   TCGTCCGTCCTCTGTGAGTGCTATGACGCAGGCTGTGCTTGGTATGAGCTCACGCCCGCC
      AGCAGGCAGGAGACACTCACGATACTGCGTCCGACACGAACCATACTCGAGTGCGGGCGG
                                                   ^

      887 SACI,

      GluThrThrValArgLeuArgAlaTyrMetAsnThrProGlyLeuProValCysGlnAsp
902   GAGACTACAGTTAGGCTACGAGCGTACATGAACACCCCGGGGCTTCCCGTGTGCCAGGAC
      CTCTGATGTCAATCCGATGCTCGCATGTACTTGTGGGGCCCCGAAGGGCACACGGTCCTG
                                         ^

      937 SMAI XMAI,

      HisLeuGluPheTrpGluGlyValPheThrGlyLeuThrHisIleAspAlaHisPheLeu
962   CATCTTGAATTTTGGGAGGGCGTCTTTACAGGCCTCACTCATATAGATGCCCACTTTCTA
      GTAGAACTTAAAACCCTCCCGCAGAAATGTCCGGAGTGAGTATATCTACGGGTGAAAGAT
                                   ^

      991 STUI,

      SerGlnThrLysGlnSerGlyGluAsnLeuProTyrLeuValAlaTyrGlnAlaThrVal
1022  TCCCAGACAAAGCAGAGTGGGGAGAACCTTCCTTACCTGGTAGCGTACCAAGCCACCGTG
      AGGGTCTGTTTCGTCTCACCCCTCTTGGAAGGAATGGACCATCGCATGGTTCGGTGGCAC
                                                           ^

      1075 DRA3,

      CysAlaArgAlaGlnAlaProProProSerTrpAspGlnMetTrpLysCysLeuIleArg
1082  TGCGCTAGGGCTCAAGCCCCTCCCCCATCGTGGGACCAGATGTGGAAGTGTTTGATTCGC
      ACGCGATCCCGAGTTCGGGGAGGGGGTAGCACCCTGGTCTACACCTTCACAAACTAAGCG

      LeuLysProThrLeuHisGlyProThrProLeuLeuTyrArgLeuGlyAlaValGlnAsn
1142  CTCAAGCCCACCCTCCATGGGCCAACACCCCTGCTATACAGACTGGGCGCTGTTCAGAAT
      GAGTTCGGGTGGGAGGTACCCGGTTGTGGGGACGATATGTCTGACCCGCGACAAGTCTTA
                    ^

      1156 NCOI,

      GluIleThrLeuThrHisProValThrLysTyrIleMetThrCysMetSerAlaAspLeu
1202  GAAATCACCCTGACGCACCCAGTCACCAAATACATCATGACATGCATGTCGGCCGACCTG
      CTTTAGTGGGACTGCGTGGGTCAGTGGTTTATGTAGTACTGTACGTACAGCCGGCTGGAC
                                        ^   ^  ^       ^    ^

      1236 BSPH1, 1240 DRD1, 1243 AVA3, 1251 EAG1 XMA3, 1256 DRD1,

      GluValValThrSerThrTrpValLeuValGlyGlyValLeuAlaAlaLeuAlaAlaTyr
1262  GAGGTCGTCACGAGCACCTGGGTGCTCGTTGGCGGCGTCCTGGCTGCTTTGGCCGCGTAT
      CTCCAGCAGTGCTCGTGGACCCACGAGCAACCGCCGCAGGACCGACGAAACCGGCGCATA
```

FIG. 11B

```
     CysLeuSerThrGlyCysValValIleValGlyArgValValLeuSerGlyLysProAla
1322 TGCCTGTCAACAGGCTGCGTGGTCATAGTGGGCAGGGTCGTCTTGTCCGGGAAGCCGGCA
     ACGGACAGTTGTCCGACGCACCAGTATCACCCGTCCCAGCAGAACAGGCCCTTCGGCCGT
                                                           ^
     1375 NAEI,

     IleIleProAspArgGluValLeuTyrArgGluPheAspGluMetGluGluCysSerGln
1382 ATCATACCTGACAGGGAAGTCCTCTACCGAGAGTTCGATGAGATGGAAGAGTGCTCTCAG
     TAGTATGGACTGTCCCTTCAGGAGATGGCTCTCAAGCTACTCTACCTTCTCACGAGAGTC
              ^
     1391 DRD1,

     HisLeuProTyrIleGluGlnGlyMetMetLeuAlaGluGlnPheLysGlnLysAlaLeu
1442 CACTTACCGTACATCGAGCAAGGGATGATGCTCGCCGAGCAGTTCAAGCAGAAGGCCCTC
     GTGAATGGCATGTAGCTCGTTCCCTACTACGAGCGGCTCGTCAAGTTCGTCTTCCGGGAG

     GlyLeuLeuGlnThrAlaSerArgGlnAlaGluValIleAlaProAlaValGlnThrAsn
1502 GGCCTCCTGCAGACCGCGTCCCGTCAGGCAGAGGTTATCGCCCCTGCTGTCCAGACCAAC
     CCGGAGGACGTCTGGCGCAGGGCAGTCCGTCTCCAATAGCGGGGACGACAGGTCTGGTTG
         ^    ^
     1508 PSTI, 1513 TTH3I,

     TrpGlnLysLeuGluThrPheTrpAlaLysHisMetTrpAsnPheIleSerGlyIleGln
1562 TGGCAAAAACTCGAGACCTTCTGGGCGAAGCATATGTGGAACTTCATCAGTGGGATACAA
     ACCGTTTTTGAGCTCTGGAAGACCCGCTTCGTATACACCTTGAAGTAGTCACCCTATGTT
              ^                    ^
     1571 XHOI, 1592 NDEI,

     TyrLeuAlaGlyLeuSerThrLeuProGlyAsnProAlaIleAlaSerLeuMetAlaPhe
1622 TACTTGGCGGGCTTGTCAACGCTGCCTGGTAACCCCGCCATTGCTTCATTGATGGCTTTT
     ATGAACCGCCCGAACAGTTGCGACGGACCATTGGGGCGGTAACGAAGTAACTACCGAAAA
                                ^
     1649 BSTE2,

     ThrAlaAlaValThrSerProLeuThrThrSerGlnThrLeuLeuPheAsnIleLeuGly
1682 ACAGCTGCTGTCACCAGCCCACTAACCACTAGCCAAACCCTCCTCTTCAACATATTGGGG
     TGTCGACGACAGTGGTCGGGTGATTGGTGATCGGTTTGGGAGGAGAAGTTGTATAACCCC
      ^
     1683 ALWN1 PVU2,

     GlyTrpValAlaAlaGlnLeuAlaAlaProGlyAlaAlaThrAlaPheValGlyAlaGly
1742 GGGTGGGTGGCTGCCCAGCTCGCCGCCCCCGGTGCCGCTACTGCCTTTGTGGGCGCTGGC
     CCCACCCACCGACGGGTCGAGCGGCGGGGGCCACGGCGATGACGGAAACACCCGCGACCG
                                                               ^
     1800 ESP1,

     LeuAlaGlyAlaAlaIleGlySerValGlyLeuGlyLysValLeuIleAspIleLeuAla
1802 TTAGCTGGCGCCGCCATCGGCAGTGTTGGACTGGGGAAGGTCCTCATAGACATCCTTGCA
     AATCGACCGCGGCGGTAGCCGTCACAACCTGACCCCTTCCAGGAGTATCTGTAGGAACGT
         ^
     1808 KAS1 NARI,

     GlyTyrGlyAlaGlyValAlaGlyAlaLeuValAlaPheLysIleMetSerGlyGluVal
1862 GGGTATGGCGCGGGCGTGGCGGGAGCTCTTGTGGCATTCAAGATCATGAGCGGTGAGGTC
     CCCATACCGCGCCCGCACCGCCCTCGAGAACACCGTAAGTTCTAGTACTCGCCACTCCAG
                       ^                ^
```

FIG. 11C

```
     1884 SACI, 1905 BSPH1,

     Pr SerThrGluAspLeuValAsnLeuLeuProAlaIleLeuSerProGlyAlaLeuVal
1922 CCCTCCACGGAGGACCTGGTCAATCTACTGCCCGCCATCCTCTCGCCCGGAGCCCTCGTA
     GGGAGGTGCCTCCTGGACCAGTTAGATGACGGGCGGTAGGAGAGCGGGCCTCGGGAGCAT
                    ^
     1934 TTH3I,

     ValGlyValValCysAlaAlaIleLeuArgArgHisValGlyProGlyGluGlyAlaVal
1982 GTCGGCGTGGTCTGTGCAGCAATACTGCGCCGGCACGTTGGCCCGGGCGAGGGGGCAGTG
     CAGCCGCACCAGACACGTCGTTATGACGCGGCCGTGCAACCGGGCCCGCTCCCCCGTCAC
                                       ^            ^
     2010 NAEI, 2023 SMAI XMAI,

     GlnTrpMetAsnArgLeuIleAlaPheAlaSerArgGlyAsnHisValSerProThrHis
2042 CAGTGGATGAACCGGCTGATAGCCTTCGCCTCCCGGGGAACCATGTTTCCCCCACGCAC
     GTCACCTACTTGGCCGACTATCGGAAGCGGAGGGCCCCCTTGGTACAAAGGGGGTGCGTG
                                          ^                ^
     2073 SMAI XMAI, 2099 DRA3,

     TyrValProGluSerAspAlaAlaAlaArgValThrAlaIleLeuSerSerLeuThrVal
2102 TACGTGCCGGAGAGCGATGCAGCTGCCCGCGTCACTGCCATACTCAGCAGCCTCACTGTA
     ATGCACGGCCTCTCGCTACGTCGACGGGCGCAGTGACGGTATGAGTCGTCGGAGTGACAT
                               ^
     2121 PVU2,

     ThrGlnLeuLeuArgArgLeuHisGlnTrpIleSerSerGluCysThrThrProCysSer
2162 ACCCAGCTCCTGAGGCGACTGCACCAGTGGATAAGCTCGGAGTGTACCACTCCATGCTCC
     TGGGTCGAGGACTCCGCTGACGTGGTCACCTATTCGAGCCTCACATGGTGAGGTACGAGG
        ^    ^
     2165 ALWN1, 2170 MST2,

     GlySerTrpLeuArgAspIleTrpAspTrpIleCysGluValLeuSerAspPheLysThr
2222 GGTTCCTGGCTAAGGGACATCTGGGACTGGATATGCGAGGTGTTGAGCGACTTTAAGACC
     CCAAGGACCGATTCCCTGTAGACCCTGACCTATACGCTCCACAACTCGCTGAAATTCTGG
        ^
     2226 ECON1,

     TrpLeuLysAlaLysLeuMetProGlnLeuProGlyIleProPheValSerCysGlnArg
2282 TGGCTAAAAGCTAAGCTCATGCCACAGCTGCCTGGGATCCCCTTTGTGTCCTGCCAGCGC
     ACCGATTTTCGATTCGAGTACGGTGTCGACGGACCCTAGGGGAAACACAGGACGGTCGCG
              ^              ^         ^
     2291 ESP1, 2306 PVU2, 2316 BAMHI,

     GlyTyrLysGlyValTrpArgGlyAspGlyIleMetHisThrArgCysHisCysGlyAla
2342 GGGTATAAGGGGGTCTGGCGAGGGGACGGCATCATGCACACTCGCTGCCACTGTGGAGCT
     CCCATATTCCCCCAGACCGCTCCCCTGCCGTAGTACGTGTGAGCGACGGTGACACCTCGA

     GluIleThrGlyHisValLysAsnGlyThrMetArgIleValGlyProArgThrCysArg
2402 GAGATCACTGGACATGTCAAAAACGGGACGATGAGGATCGTCGGTCCTAGGACCTGCAGG
     CTCTAGTGACCTGTACAGTTTTTGCCCTGCTACTCCTAGCAGCCAGGATCCTGGACGTCC
                                ^               ^      ^^
     2431 BSAB1, 2447 AVR2, 2454 SSE83871, 2455 PSTI,

     AsnMetTrpSerGlyThrPheProIleAsnAlaTyrThrThrGlyProCysThrProLeu
2462 AACATGTGGAGTGGGACCTTCCCCATTAATGCCTACACCACGGGCCCCTGTACCCCCCTT
     TTGTACACCTCACCCTGGAAGGGGTAATTACGGATGTGGTGCCCGGGGACATGGGGGGAA
```

FIG. 11D

```
     2686 ASE1, 2503 APAI,

     ProAlaProAsnTyrThrPheAlaLeuTrpArgValSerAlaGluGluTyrValGluIle
2522 CCTGCGCCGAACTACACGTTCGCGCTATGGAGGGTGTCTGCAGAGGAATACGTGGAGATA
     GGACGCGGCTTGATGTGCAAGCGCGATACCTCCCACAGACGTCTCCTTATGCACCTCTAT
                                                ^
     2559 PSTI,

     ArgGlnValGlyAspPheHisTyrValThrGlyMetThrThrAspAsnLeuLysCysPro
2582 AGGCAGGTGGGGGACTTCCACTACGTGACGGGTATGACTACTGACAATCTTAAATGCCCG
     TCCGTCCACCCCCTGAAGGTGATGCACTGCCCATACTGATGACTGTTAGAATTTACGGGC
                       ^
     2600 DRA3,

     CysGlnValProSerProGluPhePheThrGluLeuAspGlyValArgLeuHisArgPhe
2642 TGCCAGGTCCCATCGCCCGAATTTTTCACAGAATTGGACGGGGTGCGCCTACATAGGTTT
     ACGGTCCAGGGTAGCGGGCTTAAAAAGTGTCTTAACCTGCCCCACGCGGATGTATCCAAA

     AlaProProCysLysProLeuLeuArgGluGluValSerPheArgValGlyLeuHisGlu
2702 GCGCCCCCCTGCAAGCCCTTGCTGCGGGAGGAGGTATCATTCAGAGTAGGACTCCACGAA
     CGCGGGGGGACGTTCGGGAACGACGCCCTCCTCCATAGTAAGTCTCATCCTGAGGTGCTT

     TyrProValGlySerGlnLeuProCysGluProGluProAspValAlaValLeuThrSer
2762 TACCCGGTAGGGTCGCAATTACCTTGCGAGCCCGAACCGGACGTGGCCGTGTTGACGTCC
     ATGGGCCATCCCAGCGTTAATGGAACGCTCGGGCTTGGCCTGCACCGGCACAACTGCAGG
     ^                                                     ^
     2763 HGIE2, 2815 AAT2,

     MetLeuThrAspProSerHisIleThrAlaGluAlaAlaGlyArgArgLeuAlaArgGly
2822 ATGCTCACTGATCCCTCCCATATAACAGCAGAGGCGGCCGGGCGAAGGTTGGCGAGGGGA
     TACGAGTGACTAGGGAGGGTATATTGTCGTCTCCGCCGGCCCGCTTCCAACCGCTCCCCT
                                              ^
     2856 EAG1 XMA3,

     SerProProSerValAlaSerSerSerAlaSerGlnLeuSerAlaProSerLeuLysAla
2882 TCACCCCCCTCTGTGGCCAGCTCCTCGGCTAGCCAGCTATCCGCTCCATCTCTCAAGGCA
     AGTGGGGGGAGACACCGGTCGAGGAGCCGATCGGTCGATAGGCGAGGTAGAGAGTTCCGT
                 ^              ^
     2895 BALI, 2909 NHEI,

     ThrCysThrAlaAsnHisAspSerProAspAlaGluLeuIleGluAlaAsnLeuLeuTrp
2942 ACTTGCACCGCTAACCATGACTCCCCTGATGCTGAGCTCATAGAGGCCAACCTCCTATGG
     TGAACGTGGCGATTGGTACTGAGGGGACTACGACTCGAGTATCTCCGGTTGGAGGATACC
                                  ^  ^
     2972 ESP1, 2975 SACI,

     ArgGlnGluMetGlyGlyAsnIleThrArgValGluSerGluAsnLysValValIleLeu
3002 AGGCAGGAGATGGGCGGCAACATCACCAGGGTTGAGTCAGAAAACAAAGTGGTGATTCTG
     TCCGTCCTCTACCCGCCGTTGTAGTGGTCCCAACTCAGTCTTTTGTTTCACCACTAAGAC

     AspSerPheAspProLeuValAlaGluGluAspGluArgGluIleSerValProAlaGlu
3062 GACTCCTTCGATCCGCTTGTGGCGGAGGAGGACGAGCGGGAGATCTCCGTACCCGCAGAA
     CTGAGGAAGCTAGGCGAACACCGCCTCCTCCTGCTCGCCCTCTAGAGGCATGGGCGTCTT
                                              ^
     3102 BGL2,
```

FIG. 11E

```
     IleLeuArgLysSerArgArgPheAlaGlnAlaL uProValTrpAlaArgPr AspTyr
3122 ATCCTGCGGAAGTCTCGGAGATTCGCCCAGGCCCTGCCCGTTTGGGCGCGGCCGGACTAT
     TAGGACGCCTTCAGAGCCTCTAAGCGGGTCCGGGACGGGCAAACCCGCGCCGGCCTGATA
                                             ^                    ^

     3149 ALWN1, 3170 EAG1 XMA3,

     AsnProProLeuValGluThrTrpLysLysProAspTyrGluProProValValHisGly
3182 AACCCCCCGCTAGTGGAGACGTGGAAAAAGCCCGACTACGAACCACCTGTGGTCCATGGC
     TTGGGGGGCGATCACCTCTGCACCTTTTTCGGGCTGATGCTTGGTGGACACCAGGTACCG
                                                         ^         ^

     3223 HGIE2, 3235 NCOI,

     CysProLeuProProProLysSerProProValProProProArgLysLysArgThrVal
3242 TGCCCGCTTCCACCTCCAAAGTCCCCTCCTGTGCCTCCGCCTCGGAAGAAGCGGACGGTG
     ACGGGCGAAGGTGGAGGTTTCAGGGGAGGACACGGAGGCGGAGCCTTCTTCGCCTGCCAC

     ValLeuThrGluSerThrLeuSerThrAlaLeuAlaGluLeuAlaThrArgSerPheGly
3302 GTCCTCACTGAATCAACCCTATCTACTGCCTTGGCCGAGCTCGCCACCAGAAGCTTTGGC
     CAGGAGTGACTTAGTTGGGATAGATGACGGAACCGGCTCGAGCGGTGGTCTTCGAAACCG
                                                ^          ^

     3338 SACI, 3352 HIND3,

     SerSerSerThrSerGlyIleThrGlyAspAsnThrThrThrSerSerGluProAlaPro
3362 AGCTCCTCAACTTCCGGCATTACGGGCGACAATACGACAACATCCTCTGAGCCCGCCCCT
     TCGAGGAGTTGAAGGCCGTAATGCCCGCTGTTATGCTGTTGTAGGAGACTCGGGCGGGGA

     SerGlyCysProProAspSerAspAlaGluSerTyrSerSerMetProProLeuGluGly
3422 TCTGGCTGCCCCCCCGACTCCGACGCTGAGTCCTATTCCTCCATGCCCCCCCTGGAGGGG
     AGACCGACGGGGGGGCTGAGGCTGCGACTCAGGATAAGGAGGTACGGGGGGGACCTCCCC
                          ^

     3443 EAM11051,

     GluProGlyAspProAspLeuSerAspGlySerTrpSerThrValSerSerGluAlaAsn
3482 GAGCCTGGGGATCCGGATCTTAGCGACGGGTCATGGTCAACGGTCAGTAGTGAGGCCAAC
     CTCGGACCCCTAGGCCTAGAATCGCTGCCCAGTACCAGTTGCCAGTCATCACTCCGGTTG
             ^^ ^

     3490 BAMHI, 3491 BSAB1, 3493 BSPE1,

     AlaGluAspValValCysCysSerMetSerTyrSerTrpThrGlyAlaLeuValThrPro
3542 GCGGAGGATGTCGTGTGCTGCTCAATGTCTTACTCTTGGACAGGCGCACTCGTCACCCCG
     CGCCTCCTACAGCACACGACGAGTTACAGAATGAGAACCTGTCCGCGTGAGCAGTGGGGC
                                                              ^

     3595 DRA3,

     CysAlaAlaGluGluGlnLysLeuProIleAsnAlaLeuSerAsnSerLeuLeuArgHis
3602 TGCGCCGCGGAAGAACAGAAACTGCCCATCAATGCACTAAGCAACTCGTTGCTACGTCAC
     ACGCGGCGCCTTCTTGTCTTTGACGGGTAGTTACGTGATTCGTTGAGCAACGATGCAGTG
         ^          ^                                            ^

     3606 SAC2, 3617 ALWN1, 3661 PFLM1,

     HisAsnLeuValTyrSerThrThrSerArgSerAlaCysGlnArgGlnLysLysValThr
3662 CACAATTTGGTGTATTCCACCACCTCACGCAGTGCTTGCCAAAGGCAGAAGAAAGTCACA
     GTGTTAAACCACATAAGGTGGTGGAGTGCGTCACGAACGGTTTCCGTCTTCTTTCAGTGT
                              ^

     3687 DRA3,

     PheAspArgLeuGlnValLeuAspSerHisTyrGlnAspValLeuLysGluValLysAla
```

FIG. 11F

```
3722  TTTGACAGACTGCAAGTTCTGGACAGCCATTACCAGGACGTACTCAAGGAGGTTAAAGCA
      AAACTGTCTGACGTTCAAGACCTGTCGGTAATGGTCCTGCATGAGTTCCTCCAATTTCGT

      AlaAlaSerLysValLysAlaAsnLeuLeuSerValGluGluAlaCysSerLeuThrPro
3782  GCGGCGTCAAAAGTGAAGGCTAACTTGCTATCCGTAGAGGAAGCTTGCAGCCTGACGCCC
      CGCCGCAGTTTTCACTTCCGATTGAACGATAGGCATCTCCTTCGAACGTCGGACTGCGGG
                                                ^
      3822 HIND3,

      ProHisSerAlaLysSerLysPheGlyTyrGlyAlaLysAspValArgCysHisAlaArg
3842  CCACACTCAGCCAAATCCAAGTTTGGTTATGGGGCAAAAGACGTCCGTTGCCATGCCAGA
      GGTGTGAGTCGGTTTAGGTTCAAACCAATACCCCGTTTTCTGCAGGCAACGGTACGGTCT
                                               ^           ^
      3881 AAT2, 3896 BGLI,

      LysAlaValThrHisIleAsnSerValTrpLysAspLeuLeuGluAspAsnValThrPro
3902  AAGGCCGTAACCCACATCAACTCCGTGTGGAAAGACCTTCTGGAAGACAATGTAACACCA
      TTCCGGCATTGGGTGTAGTTGAGGCACACCTTTCTGGAAGACCTTCTGTTACATTGTGGT

      IleAspThrThrIleMetAlaLysAsnGluValPheCysValGlnProGluLysGlyGly
3962  ATAGACACTACCATCATGGCTAAGAACGAGGTTTTCTGCGTTCAGCCTGAGAAGGGGGGT
      TATCTGTGATGGTAGTACCGATTCTTGCTCCAAAAGACGCAAGTCGGACTCTTCCCCCCA

      ArgLysProAlaArgLeuIleValPheProAspLeuGlyValArgValCysGluLysMet
4022  CGTAAGCCAGCTCGTCTCATCGTGTTCCCCGATCTGGGCGTGCGCGTGTGCGAAAAGATG
      GCATTCGGTCGAGCAGAGTAGCACAAGGGGCTAGACCCGCACGCGCACACGCTTTTCTAC

      AlaLeuTyrAspValValThrLysLeuProLeuAlaValMetGlySerSerTyrGlyPhe
4082  GCTTTGTACGACGTGGTTACAAAGCTCCCCTTGGCCGTGATGGGAAGCTCCTACGGATTC
      CGAAACATGCTGCACCAATGTTTCGAGGGGAACCGGCACTACCCTTCGAGGATGCCTAAG

      GlnTyrSerProGlyGlnArgValGluPheLeuValGlnAlaTrpLysSerLysLysThr
4142  CAATACTCACCAGGACAGCGGGTTGAATTCCTCGTGCAAGCGTGGAAGTCCAAGAAAACC
      GTTATGAGTGGTCCTGTCGCCCAACTTAAGGAGCACGTTCGCACCTTCAGGTTCTTTTGG
                              ^
      4166 ECORI,

      ProMetGlyPheSerTyrAspThrArgCysPheAspSerThrValThrGluSerAspIle
4202  CCAATGGGGTTCTCGTATGATACCCGCTGCTTTGACTCCACAGTCACTGAGAGCGACATC
      GGTTACCCCAAGAGCATACTATGGGCGACGAAACTGAGGTGTCAGTGACTCTCGCTGTAG
                                         ^        ^
      4235 DRD1, 4242 ALWN1,

      ArgThrGluGluAlaIleTyrGlnCysCysAspLeuAspProGlnAlaArgValAlaIle
4262  CGTACGGAGGAGGCAATCTACCAATGTTGTGACCTCGACCCCCAAGCCCGCGTGGCCATC
      GCATGCCTCCTCCGTTAGATGGTTACAACACTGGAGCTGGGGGTTCGGGCGCACCGGTAG
                                                  ^        ^
      4307 BGLI, 4314 BALI,

      LysSerLeuThrGluArgLeuTyrValGlyGlyProLeuThrAsnSerArgGlyGluAsn
4322  AAGTCCCTCACCGAGAGGCTTTATGTTGGGGGCCCTCTTACCAATTCAAGGGGGGAGAAC
      TTCAGGGAGTGGCTCTCCGAAATACAACCCCCGGGAGAATGGTTAAGTTCCCCCCTCTTG
                                 ^
      4351 APAI,

      CysGlyTyrArgArgCysArgAlaSerGlyValLeuThrThrSerCysGlyAsnThrLeu
4382  TGCGGCTATCGCAGGTGCCGCGCGAGCGGCGTACTGACAACTAGCTGTGGTAACACCCTC
```

FIG. 11G

```
     ACGCCGATAGCGTCCACGGCGCGCTCGCCGCATGACTGTTGATCGACACCATTGTGGGAG

     ThrCysTyrIleLysAlaArgAlaAlaCysArgAlaAlaGlyLeuGlnAspCysThrMet
4442 ACTTGCTACATCAAGGCCCGGGCAGCCTGTCGAGCCGCAGGGCTCCAGGACTGCACCATG
     TGAACGATGTAGTTCCGGGCCCGTCGGACAGCTCGGCGTCCCGAGGTCCTGACGTGGTAC
                       ^
     4458 SMAI XMAI,

     LeuValCysGlyAspAspLeuValValIleCysGluSerAlaGlyValGlnGluAspAla
4502 CTCGTGTGTGGCGACGACTTAGTCGTTATCTGTGAAAGCGCGGGGGTCCAGGAGGACGCG
     GAGCACACACCGCTGCTGAATCAGCAATAGACACTTTCGCGCCCCCAGGTCCTCCTGCGC
                ^  ^
     4514 DRD1, 4517 TTH3I,

     AlaSerLeuArgAlaPheThrGluAlaMetThrArgTyrSerAlaProProGlyAspPro
4562 GCGAGCCTGAGAGCCTTCACGGAGGCTATGACCAGGTACTCCGCCCCCCCTGGGGACCCC
     CGCTCGGACTCTCGGAAGTGCCTCCGATACTGGTCCATGAGGCGGGGGGGACCCCTGGGG

     ProGlnProGluTyrAspLeuGluLeuIleThrSerCysSerSerAsnValSerValAla
4622 CCACAACCAGAATACGACTTGGAGCTCATAACATCATGCTCCTCCAACGTGTCAGTCGCC
     GGTGTTGGTCTTATGCTGAACCTCGAGTATTGTAGTACGAGGAGGTTGCACAGTCAGCGG
                          ^
     4643 SACI,

     HisAspGlyAlaGlyLysArgValTyrTyrLeuThrArgAspProThrThrProLeuAla
4682 CACGACGGCGCTGGAAAGAGGGTCTACTACCTCACCCGTGACCCTACAACCCCCCTCGCG
     GTGCTGCCGCGACCTTTCTCCCAGATGATGGAGTGGGCACTGGGATGTTGGGGGGAGCGC
                                                            ^
     4737 NRUI,

     ArgAlaAlaTrpGluThrAlaArgHisThrProValAsnSerTrpLeuGlyAsnIleIle
4742 AGAGCTGCGTGGGAGACAGCAAGACACACTCCAGTCAATTCCTGGCTAGGCAACATAATC
     TCTCGACGCACCCTCTGTCGTTCTGTGTGAGGTCAGTTAAGGACCGATCCGTTGTATTAG

     MetPheAlaProThrLeuTrpAlaArgMetIleLeuMetThrHisPhePheSerValLeu
4802 ATGTTTGCCCCCACACTGTGGGCGAGGATGATACTGATGACCCATTTCTTTAGCGTCCTT
     TACAAACGGGGGTGTGACACCCGCTCCTACTATGACTACTGGGTAAAGAAATCGCAGGAA
               ^^
     4812 PFLM1, 4813 DRA3,

     IleAlaArgAspGlnLeuGluGlnAlaLeuAspCysGluIleTyrGlyAlaCysTyrSer
4862 ATAGCCAGGGACCAGCTTGAACAGGCCCTCGATTGCGAGATCTACGGGGCCTGCTACTCC
     TATCGGTCCCTGGTCGAACTTGTCCGGGAGCTAACGCTCTAGATGCCCCGGACGATGAGG
                                         ^
     4899 BGL2,

     IleGluProLeuAspLeuProProIleIleGlnArgLeuHisGlyLeuSerAlaPheSer
4922 ATAGAACCACTGGATCTACCTCCAATCATTCAAAGACTCCATGGCCTCAGCGCATTTTCA
     TATCTTGGTGACCTAGATGGAGGTTAGTAAGTTTCTGAGGTACCGGAGTCGCGTAAAAGT
                                          ^
     4960 NCOI,

     LeuHisSerTyrSerProGlyGluIleAsnArgValAlaAlaCysLeuArgLysLeuGly
4982 CTCCACAGTTACTCTCCAGGTGAAATCAATAGGGTGGCCGCATGCCTCAGAAAACTTGGG
     GAGGTGTCAATGAGAGGTCCACTTTAGTTATCCCACCGGCGTACGGAGTCTTTTGAACCC
                                                ^               ^
     5021 SPHI, 5041 KPNI,
```

FIG. 11H

```
     ValProProLeuArgAlaTrpArgHisArgAlaArgSerValArgAlaArgLeuLeuAla
5042 GTACCGCCCTTGCGAGCTTGGAGACACCGGGCCCGGAGCGTCCGCGCTAGGCTTCTGGCC
     CATGGCGGGAACGCTCGAACCTCTGTGGCCCGGGCCTCGCAGGCGCGATCCGAAGACCGG
                                           ^                           ^
     5070 APAI, 5097 BALI,

     ArgGlyGlyArgAlaAlaIleCysGlyLysTyrLeuPheAsnTrpAlaValArgThrLys
5102 AGAGGAGGCAGGGCTGCCATATGTGGCAAGTACCTCTTCAACTGGGCAGTAAGAACAAAG
     TCTCCTCCGTCCCGACGGTATACACCGTTCATGGAGAAGTTGACCCGTCATTCTTGTTTC
                         ^
     5119 NDEI,

     LeuLysLeuThrProIleAlaAlaAlaGlyGlnLeuAspLeuSerGlyTrpPheThrAla
5162 CTCAAACTCACTCCAATAGCGGCCGCTGGCCAGCTGGACTTGTCCGGCTGGTTCACGGCT
     GAGTTTGAGTGAGGTTATCGCCGGCGACCGGTCGACCTGAACAGGCCGACCAAGTGCCGA
                         ^^       ^   ^
     5180 NOTI, 5181 EAG1 XMA3, 5188 BALI, 5192 PVU2,

     GlyTyrSerGlyGlyAspIleTyrHisSerValSerHisAlaArgProArgTrpIleTrp
5222 GGCTACAGCGGGGGAGACATTTATCACAGCGTGTCTCATGCCCGGCCCCGCTGGATCTGG
     CCGATGTCGCCCCCTCTGTAAATAGTGTCGCACAGAGTACGGGCCGGGGCGACCTAGACC
                              ^
     5246 DRA3,

     PheCysLeuLeuLeuLeuAlaAlaGlyValGlyIleTyrLeuLeuProAsnArgOP
5282 TTTTGCCTACTCCTGCTTGCTGCAGGGGTAGGCATCTACCTCCTCCCCAACCGATGAAGG
     AAAACGGATGAGGACGAACGACGTCCCCATCCGTAGATGGAGGAGGGGTTGGCTACTTCC
                          ^                            ^
     5301 PSTI, 5331 HGIE2,

5342 TTGGGGTAAACACTCCGGCCTAAAAAAAAAAAAAAATCTAGAACCCGAGTCGAC
     AACCCCATTTGTGAGGCCGGATTTTTTTTTTTTTTTAGATCTTGGGCTCAGCTG
                                         ^          ^
     5378 XBAI, 5390 SALI,
```

FIG. 11I

```
                       MetAlaAlaTyrAlaAlaGlnGlyTyrLysValLeuValLeuAsn
  2   AGCTTACAAAACAAAATGGCTGCATATGCAGCTCAGGGCTATAAGGTGCTAGTACTCAAC
      TCGAATGTTTTGTTTTACCGACGTATACGTCGAGTCCCGATATTCCACGATCATGAGTTG
      ^                      ^                           ^
      1 HIND3, 24 NDEI, 52 SCAI,

      ProSerValAlaAlaThrLeuGlyPheGlyAlaTyrMetSerLysAlaHisGlyIleAsp
 62   CCCTCTGTTGCTGCAACACTGGGCTTTGGTGCTTACATGTCCAAGGCTCATGGGATCGAT
      GGGAGACAACGACGTTGTGACCCGAAACCACGAATGTACAGGTTCCGAGTACCCTAGCTA
                                                           ^
      116 CLAI,

      ProAsnIleArgThrGlyValArgThrIleThrThrGlySerProIleThrTyrSerThr
122   CCTAACATCAGGACCGGGGTGAGAACAATTACCACTGGCAGCCCCATCACGTACTCCACC
      GGATTGTAGTCCTGGCCCCACTCTTGTTAATGGTGACCGTCGGGGTAGTGCATGAGGTGG

      TyrGlyLysPheLeuAlaAspGlyGlyCysSerGlyGlyAlaTyrAspIleIleIleCys
182   TACGGCAAGTTCCTTGCCGACGGCGGGTGCTCGGGGGGCGCTTATGACATAATAATTTGT
      ATGCCGTTCAAGGAACGGCTGCCGCCCACGAGCCCCCCGCGAATACTGTATTATTAAACA

      AspGluCysHisSerThrAspAlaThrSerIleLeuGlyIleGlyThrValLeuAspGln
242   GACGAGTGCCACTCCACGGATGCCACATCCATCTTGGGCATTGGCACTGTCCTTGACCAA
      CTGCTCACGGTGAGGTGCCTACGGTGTAGGTAGAACCCGTAACCGTGACAGGAACTGGTT

      AlaGluThrAlaGlyAlaArgLeuValValLeuAlaThrAlaThrProProGlySerVal
302   GCAGAGACTGCGGGGGCGAGACTGGTTGTGCTCGCCACCGCCACCCCTCCGGGCTCCGTC
      CGTCTCTGACGCCCCCGCTCTGACCAACACGAGCGGTGGCGGTGGGGAGGCCCGAGGCAG
       ^
      303 ALWN1,

      ThrValProHisProAsnIleGluGluValAlaLeuSerThrThrGlyGluIleProPhe
362   ACTGTGCCCCATCCCAACATCGAGGAGGTTGCTCTGTCCACCACCGGAGAGATCCCTTTT
      TGACACGGGGTAGGGTTGTAGCTCCTCCAACGAGACAGGTGGTGGCCTCTCTAGGGAAAA

      TyrGlyLysAlaIleProLeuGluValIleLysGlyGlyArgHisLeuIlePheCysHis
422   TACGGCAAGGCTATCCCCCTCGAAGTAATCAAGGGGGGGAGACATCTCATCTTCTGTCAT
      ATGCCGTTCCGATAGGGGGAGCTTCATTAGTTCCCCCCCTCTGTAGAGTAGAAGACAGTA

      SerLysLysLysCysAspGluLeuAlaAlaLysLeuValAlaLeuGlyIleAsnAlaVal
482   TCAAAGAAGAAGTGCGACGAACTCGCCGCAAAGCTGGTCGCATTGGGCATCAATGCCGTG
      AGTTTCTTCTTCACGCTGCTTGAGCGGCGTTTCGACCAGCGTAACCCGTAGTTACGGCAC

      AlaTyrTyrArgGlyLeuAspValSerValIleProThrSerGlyAspValValValVal
542   GCCTACTACCGCGGTCTTGACGTGTCCGTCATCCCGACCAGCGGCGATGTTGTCGTCGTG
      CGGATGATGGCGCCAGAACTGCACAGGCAGTAGGGCTGGTCGCCGCTACAACAGCAGCAC
              ^         ^
      550 SAC2, 560 DRD1,

      AlaThrAspAlaLeuMetThrGlyTyrThrGlyAspPheAspSerValIleAspCysAsn
602   GCAACCGATGCCCTCATGACCGGCTATACCGGCGACTTCGACTCGGTGATAGACTGCAAT
      CGTTGGCTACGGGAGTACTGGCCGATATGGCCGCTGAAGCTGAGCCACTATCTGACGTTA
                   ^
      615 BSPH1,

      ThrCysValThrGlnThrValAspPheSerLeuAspProThrPheThrIleGluThrIle
```

FIG. 14A

```
662  ACGTGTGTCACCCAGACAGTCGATTTCAGCCTTGACCCTACCTTCACCATTGAGACAATC
     TGCACACAGTGGGTCTGTCAGCTAAAGTCGGAACTGGGATGGAAGTGGTAACTCTGTTAG

     ThrLeuProGlnAspAlaValSerArgThrGlnArgArgGlyArgThrGlyArgGlyLys
722  ACGCTCCCCCAAGATGCTGTCTCCCGCACTCAACGTCGGGGCAGGACTGGCAGGGGGAAG
     TGCGAGGGGGTTCTACGACAGAGGGCGTGAGTTGCAGCCCCGTCCTGACCGTCCCCCTTC

     ProGlyIleTyrArgPheValAlaProGlyGluArgProSerGlyMetPheAspSerSer
782  CCAGGCATCTACAGATTTGTGGCACCGGGGGAGCGCCCCTCCGGCATGTTCGACTCGTCC
     GGTCCGTAGATGTCTAAACACCGTGGCCCCCTCGCGGGGAGGCCGTACAAGCTGAGCAGG
                                                 ^              ^
     816 BGLI, 833 DRD1,

     ValLeuCysGluCysTyrAspAlaGlyCysAlaTrpTyrGluLeuThrProAlaGluThr
842  GTCCTCTGTGAGTGCTATGACGCAGGCTGTGCTTGGTATGAGCTCACGCCCGCCGAGACT
     CAGGAGACACTCACGATACTGCGTCCGACACGAACCATACTCGAGTGCGGGCGGCTCTGA
                                                    ^
     881 SACI,

     ThrValArgLeuArgAlaTyrMetAsnThrProGlyLeuProValCysGlnAspHisLeu
902  ACAGTTAGGCTACGAGCGTACATGAACACCCCGGGGCTTCCCGTGTGCCAGGACCATCTT
     TGTCAATCCGATGCTCGCATGTACTTGTGGGGCCCCGAAGGGCACACGGTCCTGGTAGAA
                                           ^
     931 SMAI XMAI,

     GluPheTrpGluGlyValPheThrGlyLeuThrHisIleAspAlaHisPheLeuSerGln
962  GAATTTTGGGAGGGCGTCTTTACAGGCCTCACTCATATAGATGCCCACTTTCTATCCCAG
     CTTAAAACCCTCCCGCAGAAATGTCCGGAGTGAGTATATCTACGGGTGAAAGATAGGGTC
                                  ^
     985 STUI,

     ThrLysGlnSerGlyGluAsnLeuProTyrLeuValAlaTyrGlnAlaThrValCysAla
1022 ACAAAGCAGAGTGGGGAGAACCTTCCTTACCTGGTAGCGTACCAAGCCACCGTGTGCGCT
     TGTTTCGTCTCACCCCTCTTGGAAGGAATGGACCATCGCATGGTTCGGTGGCACACGCGA
                                                             ^
     1069 DRA3,

     ArgAlaGlnAlaProProProSerTrpAspGlnMetTrpLysCysLeuIleArgLeuLys
1082 AGGGCTCAAGCCCCTCCCCCATCGTGGGACCAGATGTGGAAGTGTTTGATTCGCCTCAAG
     TCCCGAGTTCGGGGAGGGGGTAGCACCCTGGTCTACACCTTCACAAACTAAGCGGAGTTC

     ProThrLeuHisGlyProThrProLeuLeuTyrArgLeuGlyAlaValGlnAsnGluIle
1142 CCCACCCTCCATGGGCCAACACCCCTGCTATACAGACTGGGCGCTGTTCAGAATGAAATC
     GGGTGGGAGGTACCCGGTTGTGGGGACGATATGTCTGACCCGCGACAAGTCTTACTTTAG
         ^
     1150 NCOI,

     ThrLeuThrHisProValThrLysTyrIleMetThrCysMetSerAlaAspLeuGluVal
1202 ACCCTGACGCACCCAGTCACCAAATACATCATGACATGCATGTCGGCCGACCTGGAGGTC
     TGGGACTGCGTGGGTCAGTGGTTTATGTAGTACTGTACGTACAGCCGGCTGGACCTCCAG
                                   ^  ^  ^      ^    ^
     1230 BSPH1, 1234 DRD1, 1237 AVA3, 1245 EAG1 XMA3, 1250 DRD1,

     ValThrSerThrTrpValLeuValGlyGlyValLeuAlaAlaLeuAlaAlaTyrCysLeu
1262 GTCACGAGCACCTGGGTGCTCGTTGGCGGCGTCCTGGCTGCTTTGGCCGCGTATTGCCTG
     CAGTGCTCGTGGACCCACGAGCAACCGCCGCAGGACCGACGAAACCGGCGCATAACGGAC
```

FIG. 14B

```
     S rThrGlyCysValValIleValGlyArgValValLeuSerGlyLysProAlaIleIle
1322 TCAACAGGCTGCGTGGTCATAGTGGGCAGGGTCGTCTTGTCCGGGAAGCCGGCAATCATA
     AGTTGTCCGACGCACCAGTATCACCCGTCCCAGCAGAACAGGCCCTTCGGCCGTTAGTAT
                                                        ^
     1369 NAEI,

     ProAspArgGluValLeuTyrArgGluPheAspGluMetGluGluCysSerGlnHisLeu
1382 CCTGACAGGGAAGTCCTCTACCGAGAGTTCGATGAGATGGAAGAGTGCTCTCAGCACTTA
     GGACTGTCCCTTCAGGAGATGGCTCTCAAGCTACTCTACCTTCTCACGAGAGTCGTGAAT
        ^
     1385 DRD1,

     ProTyrIleGluGlnGlyMetMetLeuAlaGluGlnPheLysGlnLysAlaLeuGlyLeu
1442 CCGTACATCGAGCAAGGGATGATGCTCGCCGAGCAGTTCAAGCAGAAGGCCCTCGGCCTC
     GGCATGTAGCTCGTTCCCTACTACGAGCGGCTCGTCAAGTTCGTCTTCCGGGAGCCGGAG

     LeuGlnThrAlaSerArgGlnAlaGluValIleAlaProAlaValGlnThrAsnTrpGln
1502 CTGCAGACCGCGTCCCGTCAGGCAGAGGTTATCGCCCCTGCTGTCCAGACCAACTGGCAA
     GACGTCTGGCGCAGGGCAGTCCGTCTCCAATAGCGGGGACGACAGGTCTGGTTGACCGTT
     ^    ^
     1502 PSTI, 1507 TTH3I,

     LysLeuGluThrPheTrpAlaLysHisMetTrpAsnPheIleSerGlyIleGlnTyrLeu
1562 AAACTCGAGACCTTCTGGGCGAAGCATATGTGGAACTTCATCAGTGGGATACAATACTTG
     TTTGAGCTCTGGAAGACCCGCTTCGTATACACCTTGAAGTAGTCACCCTATGTTATGAAC
        ^                    ^
     1565 XHOI, 1586 NDEI,

     AlaGlyLeuSerThrLeuProGlyAsnProAlaIleAlaSerLeuMetAlaPheThrAla
1622 GCGGGCTTGTCAACGCTGCCTGGTAACCCCGCCATTGCTTCATTGATGGCTTTTACAGCT
     CGCCCGAACAGTTGCGACGGACCATTGGGGCGGTAACGAAGTAACTACCGAAAATGTCGA
                          ^                                 ^
     1643 BSTE2, 1677 ALWN1 PVU2,

     AlaValThrSerProLeuThrThrSerGlnThrLeuLeuPheAsnIleLeuGlyGlyTrp
1682 GCTGTCACCAGCCCACTAACCACTAGCCAAACCCTCCTCTTCAACATATTGGGGGGGTGG
     CGACAGTGGTCGGGTGATTGGTGATCGGTTTGGGAGGAGAAGTTGTATAACCCCCCCACC

     ValAlaAlaGlnLeuAlaAlaProGlyAlaAlaThrAlaPheValGlyAlaGlyLeuAla
1742 GTGGCTGCCCAGCTCGCCGCCCCCGGTGCCGCTACTGCCTTTGTGGGCGCTGGCTTAGCT
     CACCGACGGGTCGAGCGGCGGGGGCCACGGCGATGACGGAAACACCCGCGACCGAATCGA
                                                    ^
     1794 ESP1,

     GlyAlaAlaIleGlySerValGlyLeuGlyLysValLeuIleAspIleLeuAlaGlyTyr
1802 GGCGCCGCCATCGGCAGTGTTGGACTGGGGAAGGTCCTCATAGACATCCTTGCAGGGTAT
     CCGCGGCGGTAGCCGTCACAACCTGACCCCTTCCAGGAGTATCTGTAGGAACGTCCCATA
     ^
     1802 KAS1 NARI,

     GlyAlaGlyValAlaGlyAlaLeuValAlaPheLysIleMetSerGlyGluValProSer
1862 GGCGCGGGCGTGGCGGGAGCTCTTGTGGCATTCAAGATCATGAGCGGTGAGGTCCCCTCC
     CCGCGCCCGCACCGCCCTCGAGAACACCGTAAGTTCTAGTACTCGCCACTCCAGGGGAGG
                     ^                    ^
     1878 SACI, 1899 BSPH1,
```

FIG. 14C

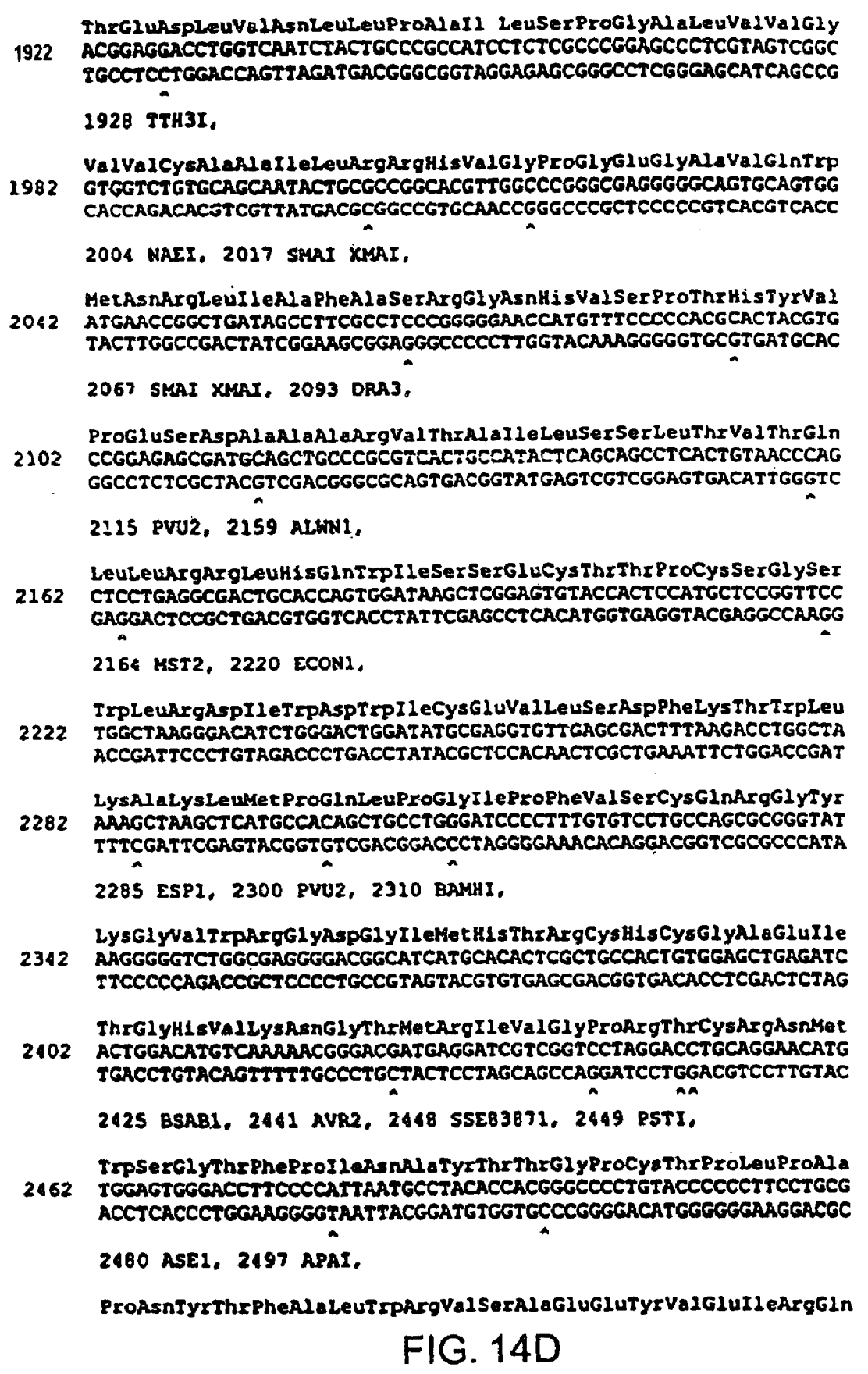

```
     ThrGluAspLeuValAsnLeuLeuProAlaIl LeuSerProGlyAlaLeuValValGly
1922 ACGGAGGACCTGGTCAATCTACTGCCCGCCATCCTCTCGCCCGGAGCCCTCGTAGTCGGC
     TGCCTCCTGGACCAGTTAGATGACGGGCGGTAGGAGAGCGGGCCTCGGGAGCATCAGCCG

     1928 TTH3I,

     ValValCysAlaAlaIleLeuArgArgHisValGlyProGlyGluGlyAlaValGlnTrp
1982 GTGGTCTGTGCAGCAATACTGCGCCGGCACGTTGGCCCGGGCGAGGGGGCAGTGCAGTGG
     CACCAGACACGTCGTTATGACGCGGCCGTGCAACCGGGCCCGCTCCCCCGTCACGTCACC

     2004 NAEI, 2017 SMAI XMAI,

     MetAsnArgLeuIleAlaPheAlaSerArgGlyAsnHisValSerProThrHisTyrVal
2042 ATGAACCGGCTGATAGCCTTCGCCTCCCGGGGGAACCATGTTTCCCCCACGCACTACGTG
     TACTTGGCCGACTATCGGAAGCGGAGGGCCCCCTTGGTACAAAGGGGGTGCGTGATGCAC

     2067 SMAI XMAI, 2093 DRA3,

     ProGluSerAspAlaAlaAlaArgValThrAlaIleLeuSerSerLeuThrValThrGln
2102 CCGGAGAGCGATGCAGCTGCCCGCGTCACTGCCATACTCAGCAGCCTCACTGTAACCCAG
     GGCCTCTCGCTACGTCGACGGGCGCAGTGACGGTATGAGTCGTCGGAGTGACATTGGGTC

     2115 PVU2, 2159 ALWN1,

     LeuLeuArgArgLeuHisGlnTrpIleSerSerGluCysThrThrProCysSerGlySer
2162 CTCCTGAGGCGACTGCACCAGTGGATAAGCTCGGAGTGTACCACTCCATGCTCCGGTTCC
     GAGGACTCCGCTGACGTGGTCACCTATTCGAGCCTCACATGGTGAGGTACGAGGCCAAGG

     2164 MST2, 2220 ECON1,

     TrpLeuArgAspIleTrpAspTrpIleCysGluValLeuSerAspPheLysThrTrpLeu
2222 TGGCTAAGGGACATCTGGGACTGGATATGCGAGGTGTTGAGCGACTTTAAGACCTGGCTA
     ACCGATTCCCTGTAGACCCTGACCTATACGCTCCACAACTCGCTGAAATTCTGGACCGAT

     LysAlaLysLeuMetProGlnLeuProGlyIleProPheValSerCysGlnArgGlyTyr
2282 AAAGCTAAGCTCATGCCACAGCTGCCTGGGATCCCCTTTGTGTCCTGCCAGCGCGGGTAT
     TTTCGATTCGAGTACGGTGTCGACGGACCCTAGGGGAAACACAGGACGGTCGCGCCCATA

     2285 ESP1, 2300 PVU2, 2310 BAMHI,

     LysGlyValTrpArgGlyAspGlyIleMetHisThrArgCysHisCysGlyAlaGluIle
2342 AAGGGGGTCTGGCGAGGGGACGGCATCATGCACACTCGCTGCCACTGTGGAGCTGAGATC
     TTCCCCCAGACCGCTCCCCTGCCGTAGTACGTGTGAGCGACGGTGACACCTCGACTCTAG

     ThrGlyHisValLysAsnGlyThrMetArgIleValGlyProArgThrCysArgAsnMet
2402 ACTGGACATGTCAAAAACGGGACGATGAGGATCGTCGGTCCTAGGACCTGCAGGAACATG
     TGACCTGTACAGTTTTTGCCCTGCTACTCCTAGCAGCCAGGATCCTGGACGTCCTTGTAC

     2425 BSAB1, 2441 AVR2, 2448 SSE83871, 2449 PSTI,

     TrpSerGlyThrPheProIleAsnAlaTyrThrThrGlyProCysThrProLeuProAla
2462 TGGAGTGGGACCTTCCCCATTAATGCCTACACCACGGGCCCCTGTACCCCCCTTCCTGCG
     ACCTCACCCTGGAAGGGGTAATTACGGATGTGGTGCCCGGGGACATGGGGGGAAGGACGC

     2480 ASE1, 2497 APAI,

     ProAsnTyrThrPheAlaLeuTrpArgValSerAlaGluGluTyrValGluIleArgGln
```

FIG. 14D

```
2522  CCGAACTACACGTTCGCGCTATGGAGGGTGTCTGCAGAGGAATACGTGGAGATAAGGCAG
      GGCTTGATGTGCAAGCGCGATACCTCCCACAGACGTCTCCTTATGCACCTCTATTCCGTC
                                     ^
      2553 PSTI,

      ValGlyAspPheHisTyrValThrGlyMetThrThrAspAsnLeuLysCysProCysGln
2582  GTGGGGGACTTCCACTACGTGACGGGTATGACTACTGACAATCTTAAATGCCCGTGCCAG
      CACCCCCTGAAGGTGATGCACTGCCCATACTGATGACTGTTAGAATTTACGGGCACGGTC
                  ^
      2594 DRA3,

      ValProSerProGluPhePheThrGluLeuAspGlyValArgLeuHisArgPheAlaPro
2642  GTCCCATCGCCCGAATTTTTCACAGAATTGGACGGGGTGCGCCTACATAGGTTTGCGCCC
      CAGGGTAGCGGGCTTAAAAAGTGTCTTAACCTGCCCCACGCGGATGTATCCAAACGCGGG

      ProCysLysProLeuLeuArgGluGluValSerPheArgValGlyLeuHisGluTyrPro
2702  CCCTGCAAGCCCTTGCTGCGGGAGGAGGTATCATTCAGAGTAGGACTCCACGAATACCCG
      GGGACGTTCGGGAACGACGCCCTCCTCCATAGTAAGTCTCATCCTGAGGTGCTTATGGGC
                                                             ^
      2757 HGIE2,

      ValGlySerGlnLeuProCysGluProGluProAspValAlaValLeuThrSerMetLeu
2762  GTAGGGTCGCAATTACCTTGCGAGCCCGAACCGGACGTGGCCGTGTTGACGTCCATGCTC
      CATCCCAGCGTTAATGGAACGCTCGGGCTTGGCCTGCACCGGCACAACTGCAGGTACGAG
                                                     ^
      2809 AAT2,

      ThrAspProSerHisIleThrAlaGluAlaAlaGlyArgArgLeuAlaArgGlySerPro
2822  ACTGATCCCTCCCATATAACAGCAGAGGCGGCCGGGCGAAGGTTGGCGAGGGGATCACCC
      TGACTAGGGAGGGTATATTGTCGTCTCCGCCGGCCCGCTTCCAACCGCTCCCCTAGTGGG
                                  ^
      2850 EAG1 XMA3,

      ProSerValAlaSerSerSerAlaSerGlnLeuSerAlaProSerLeuLysAlaThrCys
2882  CCCTCTGTGGCCAGCTCCTCGGCTAGCCAGCTATCCGCTCCATCTCTCAAGGCAACTTGC
      GGGAGACACCGGTCGAGGAGCCGATCGGTCGATAGGCGAGGTAGAGAGTTCCGTTGAACG
             ^             ^
      2889 BALI, 2903 NHEI,

      ThrAlaAsnHisAspSerProAspAlaGluLeuIleGluAlaAsnLeuLeuTrpArgGln
2942  ACCGCTAACCATGACTCCCCTGATGCTGAGCTCATAGAGGCCAACCTCCTATGGAGGCAG
      TGGCGATTGGTACTGAGGGGACTACGACTCGAGTATCTCCGGTTGGAGGATACCTCCGTC
                              ^  ^
      2966 ESP1, 2969 SACI,

      GluMetGlyGlyAsnIleThrArgValGluSerGluAsnLysValValIleLeuAspSer
3002  GAGATGGGCGGCAACATCACCAGGGTTGAGTCAGAAAACAAAGTGGTGATTCTGGACTCC
      CTCTACCCGCCGTTGTAGTGGTCCCAACTCAGTCTTTTGTTTCACCACTAAGACCTGAGG

      PheAspProLeuValAlaGluGluAspGluArgGluIleSerValProAlaGluIleLeu
3062  TTCGATCCGCTTGTGGCGGAGGAGGACGAGCGGGAGATCTCCGTACCCGCAGAAATCCTG
      AAGCTAGGCGAACACCGCCTCCTCCTGCTCGCCCTCTAGAGGCATGGGCGTCTTTAGGAC
                                        ^
      3096 BGL2,

      ArgLysSerArgArgPheAlaGlnAlaLeuProValTrpAlaArgProAspTyrAsnPro
3122  CGGAAGTCTCGGAGATTCGCCCAGGCCCTGCCCGTTTGGGCGCGGCCGGACTATAACCCC
```

FIG. 14E

```
      GCCTTCAGAGCCTCTAAGCGGGTCCGGGACGGGCAAACCCGCGCCGGCCTGATATTGGGG
                           ^                           ^
      3143 ALWN1, 3164 EAG1 XMA3,

      ProLeuValGluThrTrpLysLysProAspTyrGluProProValValHisGlyCysPro
3182  CCGCTAGTGGAGACGTGGAAAAAGCCCGACTACGAACCACCTGTGGTCCATGGCTGCCCG
      GGCGATCACCTCTGCACCTTTTTCGGGCTGATGCTTGGTGGACACCAGGTACCGACGGGC
                                                  ^         ^
      3217 HGIE2, 3229 NCOI,

      LeuProProProLysSer    roValProProProArgLysLysArgThrValValLeu
3242  CTTCCACCTCCAAAGTCCCCTCCTGTGCCTCCGCCTCGGAAGAAGCGGACGGTGGTCCTC
      GAAGGTGGAGGTTTCAGGGGAGGACACGGAGGCGGAGCCTTCTTCGCCTGCCACCAGGAG

      ThrGluSerThrLeuSerThrAlaLeuAlaGluLeuAlaThrArgSerPheGlySerSer
3302  ACTGAATCAACCCTATCTACTGCCTTGGCCGAGCTCGCCACCAGAAGCTTTGGCAGCTCC
      TGACTTAGTTGGGATAGATGACGGAACCGGCTCGAGCGGTGGTCTTCGAAACCGTCGAGG
                                    ^          ^
      3332 SACI, 3346 HIND3,

      SerThrSerGlyIleThrGlyAspAsnThrThrThrSerSerGluProAlaProSerGly
3362  TCAACTTCCGGCATTACGGGCGACAATACGACAACATCCTCTGAGCCCGCCCCTTCTGGC
      AGTTGAAGGCCGTAATGCCCGCTGTTATGCTGTTGTAGGAGACTCGGGCGGGGAAGACCG

      CysProProAspSerAspAlaGluSerTyrSerSerMetProProLeuGluGlyGluPro
3422  TGCCCCCCCGACTCCGACGCTGAGTCCTATTCCTCCATGCCCCCCCTGGAGGGGGAGCCT
      ACGGGGGGGCTGAGGCTGCGACTCAGGATAAGGAGGTACGGGGGGGACCTCCCCCTCGGA
                   ^
      3437 EAM11051,

      GlyAspProAspLeuSerAspGlySerTrpSerThrValSerSerGluAlaAsnAlaGlu
3482  GGGGATCCGGATCTTAGCGACGGGTCATGGTCAACGGTCAGTAGTGAGGCCAACGCGGAG
      CCCCTAGGCCTAGAATCGCTGCCCAGTACCAGTTGCCAGTCATCACTCCGGTTGCGCCTC
        ^^ ^
      3484 BAMHI, 3485 BSAB1, 3487 BSPE1,

      AspValValCysCysSerMetSerTyrSerTrpThrGlyAlaLeuValThrProCysAla
3542  GATGTCGTGTGCTGCTCAATGTCTTACTCTTGGACAGGCGCACTCGTCACCCCGTGCGCC
      CTACAGCACACGACGAGTTACAGAATGAGAACCTGTCCGCGTGAGCAGTGGGGCACGCGG
                                                    ^       ^
      3589 DRA3, 3600 SAC2,

      AlaGluGluGlnLysLeuProIleAsnAlaLeuSerAsnSerLeuLeuArgHisHisAsn
3602  GCGGAAGAACAGAAACTGCCCATCAATGCACTAAGCAACTCGTTGCTACGTCACCACAAT
      CGCCTTCTTGTCTTTGACGGGTAGTTACGTGATTCGTTGAGCAACGATGCAGTGGTGTTA
          ^                                                ^
      3611 ALWN1, 3655 PFLM1,

      LeuValTyrSerThrThrSerArgSerAlaCysGlnArgGlnLysLysValThrPheAsp
3662  TTGGTGTATTCCACCACCTCACGCAGTGCTTGCCAAAGGCAGAAGAAAGTCACATTTGAC
      AACCACATAAGGTGGTGGAGTGCGTCACGAACGGTTTCCGTCTTCTTTCAGTGTAAACTG
                   ^
      3681 DRA3,

      ArgLeuGlnValLeuAspSerHisTyrGlnAspValLeuLysGluValLysAlaAlaAla
3722  AGACTGCAAGTTCTGGACAGCCATTACCAGGACGTACTCAAGGAGGTTAAAGCAGCGGCG
      TCTGACGTTCAAGACCTGTCGGTAATGGTCCTGCATGAGTTCCTCCAATTTCGTCGCCGC
```

FIG. 14F

```
     SerLysValLysAlaAsnLeuLeuSerValGluGluAlaCysS rLeuThrProProHis
3782 TCAAAAGTGAAGGCTAACTTGCTATCCGTAGAGGAAGCTTGCAGCCTGACGCCCCCACAC
     AGTTTTCACTTCCGATTGAACGATAGGCATCTCCTTCGAACGTCGGACTGCGGGGGTGTG
                                                   ^
     3816 HIND3,

     SerAlaLysSerLysPheGlyTyrGlyAlaLysAspValArgCysHisAlaArgLysAla
3842 TCAGCCAAATCCAAGTTTGGTTATGGGGCAAAAGACGTCCGTTGCCATGCCAGAAAGGCC
     AGTCGGTTTAGGTTCAAACCAATACCCCGTTTTCTGCAGGCAACGGTACGGTCTTTCCGG
                                               ^             ^
     3875 AAT2, 3890 BGLI,

     ValThrHisIleAsnSerValTrpLysAspLeuLeuGluAspAsnValThrProIleAsp
3902 GTAACCCACATCAACTCCGTGTGGAAAGACCTTCTGGAAGACAATGTAACACCAATAGAC
     CATTGGGTGTAGTTGAGGCACACCTTTCTGGAAGACCTTCTGTTACATTGTGGTTATCTG

     ThrThrIleMetAlaLysAsnGluValPheCysValGlnProGluLysGlyGlyArgLys
3962 ACTACCATCATGGCTAAGAACGAGGTTTTCTGCGTTCAGCCTGAGAAGGGGGGTCGTAAG
     TGATGGTAGTACCGATTCTTGCTCCAAAAGACGCAAGTCGGACTCTTCCCCCCAGCATTC

     ProAlaArgLeuIleValPheProAspLeuGlyValArgValCysGluLysMetAlaLeu
4022 CCAGCTCGTCTCATCGTGTTCCCCGATCTGGGCGTGCGCGTGTGCGAAAAGATGGCTTTG
     GGTCGAGCAGAGTAGCACAAGGGGCTAGACCCGCACGCGCACACGCTTTTCTACCGAAAC

     TyrAspValValThrLysLeuProLeuAlaValMetGlySerSerTyrGlyPheGlnTyr
4082 TACGACGTGGTTACAAAGCTCCCCTTGGCCGTGATGGGAAGCTCCTACGGATTCCAATAC
     ATGCTGCACCAATGTTTCGAGGGGAACCGGCACTACCCTTCGAGGATGCCTAAGGTTATG

     SerProGlyGlnArgValGluPheLeuValGlnAlaTrpLysSerLysLysThrProMet
4142 TCACCAGGACAGCGGGTTGAATTCCTCGTGCAAGCGTGGAAGTCCAAGAAAACCCCAATG
     AGTGGTCCTGTCGCCCAACTTAAGGAGCACGTTCGCACCTTCAGGTTCTTTTGGGGTTAC
                        ^
     4160 ECORI,

     GlyPheSerTyrAspThrArgCysPheAspSerThrValThrGluSerAspIleArgThr
4202 GGGTTCTCGTATGATACCCGCTGCTTTGACTCCACAGTCACTGAGAGCGACATCCGTACG
     CCCAAGAGCATACTATGGGCGACGAAACTGAGGTGTCAGTGACTCTCGCTGTAGGCATGC
                                    ^       ^
     4229 DRD1, 4236 ALWN1,

     GluGluAlaIleTyrGlnCysCysAspLeuAspProGlnAlaArgValAlaIleLysSer
4262 GAGGAGGCAATCTACCAATGTTGTGACCTCGACCCCCAAGCCCGCGTGGCCATCAAGTCC
     CTCCTCCGTTAGATGGTTACAACACTGGAGCTGGGGGTTCGGGCGCACCGGTAGTTCAGG
                                                    ^       ^
     4301 BGLI, 4308 BALI,

     LeuThrGluArgLeuTyrValGlyGlyProLeuThrAsnSerArgGlyGluAsnCysGly
4322 CTCACCGAGAGGCTTTATGTTGGGGGCCCTCTTACCAATTCAAGGGGGGAGAACTGCGGC
     GAGTGGCTCTCCGAAATACAACCCCCGGGAGAATGGTTAAGTTCCCCCCTCTTGACGCCG
                               ^
     4345 APAI,

     TyrArgArgCysArgAlaSerGlyValLeuThrThrSerCysGlyAsnThrLeuThrCys
4382 TATCGCAGGTGCCGCGCGAGCGGCGTACTGACAACTAGCTGTGGTAACACCCTCACTTGC
     ATAGCGTCCACGGCGCGCTCGCCGCATGACTGTTGATCGACACCATTGTGGGAGTGAACG
```

FIG. 14G

TyrIleLysAlaArgAlaAlaCysArgAlaAlaGlyLeuGlnAspCysThrMetLeuVal
4442 TACATCAAGGCCCGGGCAGCCTGTCGAGCCGCAGGGCTCCAGGACTGCACCATGCTCGTG
ATGTAGTTCCGGGCCCGTCGGACAGCTCGGCGTCCCGAGGTCCTGACGTGGTACGAGCAC
^

4452 SMAI XMAI,

CysGlyAspAspLeuValValIleCysGluSerAlaGlyValGlnGluAspAlaAlaSer
4502 TGTGGCGACGACTTAGTCGTTATCTGTGAAAGCGCGGGGGTCCAGGAGGACGCGGCGAGC
ACACCGCTGCTGAATCAGCAATAGACACTTTCGCGCCCCCAGGTCCTCCTGCGCCGCTCG
^ ^

4508 DRD1, 4511 TTH3I,

LeuArgAlaPheThrGluAlaMetThrArgTyrSerAlaProProGlyAspProProGln
4562 CTGAGAGCCTTCACGGAGGCTATGACCAGGTACTCCGCCCCCCCTGGGGACCCCCCACAA
GACTCTCGGAAGTGCCTCCGATACTGGTCCATGAGGCGGGGGGGACCCCTGGGGGGTGTT

ProGluTyrAspLeuGluLeuIleThrSerCysSerSerAsnValSerValAlaHisAsp
4622 CCAGAATACGACTTGGAGCTCATAACATCATGCTCCTCCAACGTGTCAGTCGCCCACGAC
GGTCTTATGCTGAACCTCGAGTATTGTAGTACGAGGAGGTTGCACAGTCAGCGGGTGCTG
^

4637 SACI,

GlyAlaGlyLysArgValTyrTyrLeuThrArgAspProThrThrProLeuAlaArgAla
4682 GGCGCTGGAAAGAGGGTCTACTACCTCACCCGTGACCCTACAACCCCCCTCGCGAGAGCT
CCGCGACCTTTCTCCCAGATGATGGAGTGGGCACTGGGATGTTGGGGGGAGCGCTCTCGA
^

4731 NRUI,

AlaTrpGluThrAlaArgHisThrProValAsnSerTrpLeuGlyAsnIleIleMetPhe
4742 GCGTGGGAGACAGCAAGACACACTCCAGTCAATTCCTGGCTAGGCAACATAATCATGTTT
CGCACCCTCTGTCGTTCTGTGTGAGGTCAGTTAAGGACCGATCCGTTGTATTAGTACAAA

AlaProThrLeuTrpAlaArgMetIleLeuMetThrHisPhePheSerValLeuIleAla
4802 GCCCCCACACTGTGGGCGAGGATGATACTGATGACCCATTTCTTTAGCGTCCTTATAGCC
CGGGGGTGTGACACCCGCTCCTACTATGACTACTGGGTAAAGAAATCGCAGGAATATCGG
^^

4806 PFLM1, 4807 DRA3,

ArgAspGlnLeuGluGlnAlaLeuAspCysGluIleTyrGlyAlaCysTyrSerIleGlu
4862 AGGGACCAGCTTGAACAGGCCCTCGATTGCGAGATCTACGGGGCCTGCTACTCCATAGAA
TCCCTGGTCGAACTTGTCCGGGAGCTAACGCTCTAGATGCCCCGGACGATGAGGTATCTT
^

4893 BGL2,

ProLeuAspLeuProProIleIleGlnArgLeuHisGlyLeuSerAlaPheSerLeuHis
4922 CCACTGGATCTACCTCCAATCATTCAAAGACTCCATGGCCTCAGCGCATTTTCACTCCAC
GGTGACCTAGATGGAGGTTAGTAAGTTTCTGAGGTACCGGAGTCGCGTAAAAGTGAGGTG
^

4954 NCOI,

SerTyrSerProGlyGluIleAsnArgValAlaAlaCysLeuArgLysLeuGlyValPro
4982 AGTTACTCTCCAGGTGAAATCAATAGGGTGGCCGCATGCCTCAGAAAACTTGGGGTACCG
TCAATGAGAGGTCCACTTTAGTTATCCCACCGGCGTACGGAGTCTTTTGAACCCCATGGC
^ ^

5015 SPHI, 5035 KPNI,

ProLeuArgAlaTrpArgHisArgAlaArgSerValArgAlaArgLeuLeuAlaArgGly

FIG. 14H

```
5042  CCCTTGCGAGCTTGGAGACACCGGGCCCGGAGCGTCCGCGCTAGGCTTCTGGCCAGAGGA
      GGGAACGCTCGAACCTCTGTGGCCCGGGCCTCGCAGGCGCGATCCGAAGACCGGTCTCCT
                                ^                                   ^

      5064 APAI, 5091 BALI,

      GlyArgAlaAlaIleCysGlyLysTyrLeuPheAsnTrpAlaValArgThrLysLeuLys
5102  GGCAGGGCTGCCATATGTGGCAAGTACCTCTTCAACTGGGCAGTAAGAACAAAGCTCAAA
      CCGTCCCGACGGTATACACCGTTCATGGAGAAGTTGACCCGTCATTCTTGTTTCGAGTTT
                ^

      5113 NDEI,

      LeuThrProIleAlaAlaAlaGlyGlnLeuAspLeuSerGlyTrpPheThrAlaGlyTyr
5162  CTCACTCCAATAGCGGCCGCTGGCCAGCTGGACTTGTCCGGCTGGTTCACGGCTGGCTAC
      GAGTGAGGTTATCGCCGGCGACCGGTCGACCTGAACAGGCCGACCAAGTGCCGACCGATG
                    ^^       ^   ^

      5174 NOTI, 5175 EAG1 XMA3, 5182 BALI, 5186 PVU2,

      SerGlyGlyAspIleTyrHisSerValSerHisAlaArgProArgTrpIleTrpPheCys
5222  AGCGGGGGAGACATTTATCACAGCGTGTCTCATGCCCGGCCCCGCTGGATCTGGTTTTGC
      TCGCCCCCTCTGTAAATAGTGTCGCACAGAGTACGGGCCGGGGCGACCTAGACCAAAACG
                          ^

      5240 DRA3,

      LeuLeuLeuLeuAlaAlaGlyValGlyIleTyrLeuLeuProAsnArgOP
5282  CTACTCCTGCTTGCTGCAGGGGTAGGCATCTACCTCCTCCCCAACCGATGAATAGTCGAC
      GATGAGGACGAACGACGTCCCCATCCGTAGATGGAGGAGGGGTTGGCTACTTATCAGCTG
      ^^

      5295 PSTI, 5336 SALI,
```

FIG. 14I

```
                 MetAlaAlaTyrAlaAlaGlnGlyTyrLysValLeuValLeuAsn
  2  AGCTTACAAAACAAAATGGCTGCATATGCAGCTCAGGGCTATAAGGTGCTAGTACTCAAC
     TCGAATGTTTTGTTTTACCGACGTATACGTCGAGTCCCGATATTCCACGATCATGAGTTG
     ^                      ^                           ^
     1 HIND3, 24 NDEI, 52 SCAI,

     ProSerValAlaAlaThrLeuGlyPheGlyAlaTyrMetSerLysAlaHisGlyIleAsp
 62  CCCTCTGTTGCTGCAACACTGGGCTTTGGTGCTTACATGTCCAAGGCTCATGGGATCGAT
     GGGAGACAACGACGTTGTGACCCGAAACCACGAATGTACAGGTTCCGAGTACCCTAGCTA
                                                            ^
     116 CLAI,

     ProAsnIleArgThrGlyValArgThrIleThrThrGlySerProIleThrTyrSerThr
122  CCTAACATCAGGACCGGGGTGAGAACAATTACCACTGGCAGCCCCATCACGTACTCCACC
     GGATTGTAGTCCTGGCCCCACTCTTGTTAATGGTGACCGTCGGGGTAGTGCATGAGGTGG

     TyrGlyLysPheLeuAlaAspGlyGlyCysSerGlyGlyAlaTyrAspIleIleIleCys
182  TACGGCAAGTTCCTTGCCGACGGCGGGTGCTCGGGGGGCGCTTATGACATAATAATTTGT
     ATGCCGTTCAAGGAACGGCTGCCGCCCACGAGCCCCCCGCGAATACTGTATTATTAAACA

     AspGluCysHisSerThrAspAlaThrSerIleLeuGlyIleGlyThrValLeuAspGln
242  GACGAGTGCCACTCCACGGATGCCACATCCATCTTGGGCATTGGCACTGTCCTTGACCAA
     CTGCTCACGGTGAGGTGCCTACGGTGTAGGTAGAACCCGTAACCGTGACAGGAACTGGTT

     AlaGluThrAlaGlyAlaArgLeuValValLeuAlaThrAlaThrProProGlySerVal
302  GCAGAGACTGCGGGGGCGAGACTGGTTGTGCTCGCCACCGCCACCCCTCCGGGCTCCGTC
     CGTCTCTGACGCCCCCGCTCTGACCAACACGAGCGGTGGCGGTGGGGAGGCCCGAGGCAG
      ^
     303 ALWN1,

     ThrValProHisProAsnIleGluGluValAlaLeuSerThrThrGlyGluIleProPhe
362  ACTGTGCCCCATCCCAACATCGAGGAGGTTGCTCTGTCCACCACCGGAGAGATCCCTTTT
     TGACACGGGGTAGGGTTGTAGCTCCTCCAACGAGACAGGTGGTGGCCTCTCTAGGGAAAA

     TyrGlyLysAlaIleProLeuGluValIleLysGlyGlyArgHisLeuIlePheCysHis
422  TACGGCAAGGCTATCCCCCTCGAAGTAATCAAGGGGGGGAGACATCTCATCTTCTGTCAT
     ATGCCGTTCCGATAGGGGGAGCTTCATTAGTTCCCCCCCTCTGTAGAGTAGAAGACAGTA
```

FIG. 17A

```
     SerLysLysLysCysAspGluLeuAlaAlaLysLeuValAlaLeuGlyIleAsnAlaVal
482  TCAAAGAAGAAGTGCGACGAACTCGCCGCAAAGCTGGTCGCATTGGGCATCAATGCCGTG
     AGTTTCTTCTTCACGCTGCTTGAGCGGCGTTTCGACCAGCGTAACCCGTAGTTACGGCAC

     AlaTyrTyrArgGlyLeuAspValSerValIleProThrSerGlyAspValValValVal
542  GCCTACTACCGCGGTCTTGACGTGTCCGTCATCCCGACCAGCGGCGATGTTGTCGTCGTG
     CGGATGATGGCGCCAGAACTGCACAGGCAGTAGGGCTGGTCGCCGCTACAACAGCAGCAC
                ^           ^

     550 SAC2, 560 DRD1,

     AlaThrAspAlaLeuMetThrGlyTyrThrGlyAspPheAspSerValIleAspCysAsn
602  GCAACCGATGCCCTCATGACCGGCTATACCGGCGACTTCGACTCGGTGATAGACTGCAAT
     CGTTGGCTACGGGAGTACTGGCCGATATGGCCGCTGAAGCTGAGCCACTATCTGACGTTA
                  ^

     615 BSPH1,

     ThrCysValThrGlnThrValAspPheSerLeuAspProThrPheThrIleGluThrIle
662  ACGTGTGTCACCCAGACAGTCGATTTCAGCCTTGACCCTACCTTCACCATTGAGACAATC
     TGCACACAGTGGGTCTGTCAGCTAAAGTCGGAACTGGGATGGAAGTGGTAACTCTGTTAG

     ThrLeuProGlnAspAlaValSerArgThrGlnArgArgGlyArgThrGlyArgGlyLys
722  ACGCTCCCCCAAGATGCTGTCTCCCGCACTCAACGTCGGGGCAGGACTGGCAGGGGGAAG
     TGCGAGGGGGTTCTACGACAGAGGGCGTGAGTTGCAGCCCCGTCCTGACCGTCCCCCTTC

     ProGlyIleTyrArgPheValAlaProGlyGluArgProSerGlyMetPheAspSerSer
782  CCAGGCATCTACAGATTTGTGGCACCGGGGGAGCGCCCCTCCGGCATGTTCGACTCGTCC
     GGTCCGTAGATGTCTAAACACCGTGGCCCCCTCGCGGGGAGGCCGTACAAGCTGAGCAGG
                                          ^                 ^

     816 BGLI, 833 DRD1,

     ValLeuCysGluCysTyrAspAlaGlyCysAlaTrpTyrGluLeuThrProAlaGluThr
842  GTCCTCTGTGAGTGCTATGACGCAGGCTGTGCTTGGTATGAGCTCACGCCCGCCGAGACT
     CAGGAGACACTCACGATACTGCGTCCGACACGAACCATACTCGAGTGCGGGCGGCTCTGA
                                              ^

     881 SACI,

     ThrValArgLeuArgAlaTyrMetAsnThrProGlyLeuProValCysGlnAspHisLeu
902  ACAGTTAGGCTACGAGCGTACATGAACACCCCGGGGCTTCCCGTGTGCCAGGACCATCTT
     TGTCAATCCGATGCTCGCATGTACTTGTGGGGCCCCGAAGGGCACACGGTCCTGGTAGAA
                                   ^

     931 SMAI XMAI,

     GluPheTrpGluGlyValPheThrGlyLeuThrHisIleAspAlaHisPheLeuSerGln
962  GAATTTTGGGAGGGCGTCTTTACAGGCCTCACTCATATAGATGCCCACTTTCTATCCCAG
     CTTAAAACCCTCCCGCAGAAATGTCCGGAGTGAGTATATCTACGGGTGAAAGATAGGGTC
                          ^

     985 STUI,

     ThrLysGlnSerGlyGluAsnLeuProTyrLeuValAlaTyrGlnAlaThrValCysAla
1022 ACAAAGCAGAGTGGGGAGAACCTTCCTTACCTGGTAGCGTACCAAGCCACCGTGTGCGCT
     TGTTTCGTCTCACCCCTCTTGGAAGGAATGGACCATCGCATGGTTCGGTGGCACACGCGA
                                                    ^

     1069 DRA3,

     ArgAlaGlnAlaProPr ProS rTrpAspGlnMetTrpLysCysLeuIleArgLeuLys
1082 AGGGCTCAAGCCCCTCCCCCATCGTGGGACCAGATGTGGAAGTGTTTGATTCGCCTCAAG
```

FIG. 17B

TCCCGAGTTCGGGGAGGGGGTAGCACCCTGGTCTACACCTTCACAAACTAAGCGGAGTTC

ProThrLeuHisGlyProThrProLeuLeuTyrArgLeuGlyAlaValGlnAsnGluIle
1142 CCCACCCTCCATGGGCCAACACCCCTGCTATACAGACTGGGCGCTGTTCAGAATGAAATC
GGGTGGGAGGTACCCGGTTGTGGGGACGATATGTCTGACCCGCGACAAGTCTTACTTTAG
^
1150 NCOI,

ThrLeuThrHisProValThrLysTyrIleMetThrCysMetSerAlaAspLeuGluVal
1202 ACCCTGACGCACCCAGTCACCAAATACATCATGACATGCATGTCGGCCGACCTGGAGGTC
TGGGACTGCGTGGGTCAGTGGTTTATGTAGTACTGTACGTACAGCCGGCTGGACCTCCAG
^ ^ ^ ^ ^
1230 BSPH1, 1234 DRD1, 1237 AVA3, 1245 EAG1 XMA3, 1250 DRD1,

ValThrSerThrTrpValLeuValGlyGlyValLeuAlaAlaLeuAlaAlaTyrCysLeu
1262 GTCACGAGCACCTGGGTGCTCGTTGGCGGCGTCCTGGCTGCTTTGGCCGCGTATTGCCTG
CAGTGCTCGTGGACCCACGAGCAACCGCCGCAGGACCGACGAAACCGGCGCATAACGGAC

SerThrGlyCysValValIleValGlyArgValValLeuSerGlyLysProAlaIleIle
1322 TCAACAGGCTGCGTGGTCATAGTGGGCAGGGTCGTCTTGTCCGGGAAGCCGGCAATCATA
AGTTGTCCGACGCACCAGTATCACCCGTCCCAGCAGAACAGGCCCTTCGGCCGTTAGTAT
^
1369 NAEI,

ProAspArgGluValLeuTyrArgGluPheAspGluMetGluGluCysSerGlnHisLeu
1382 CCTGACAGGGAAGTCCTCTACCGAGAGTTCGATGAGATGGAAGAGTGCTCTCAGCACTTA
GGACTGTCCCTTCAGGAGATGGCTCTCAAGCTACTCTACCTTCTCACGAGAGTCGTGAAT
^
1385 DRD1,

ProTyrIleGluGlnGlyMetMetLeuAlaGluGlnPheLysGlnLysAlaLeuGlyLeu
1442 CCGTACATCGAGCAAGGGATGATGCTCGCCGAGCAGTTCAAGCAGAAGGCCCTCGGCCTC
GGCATGTAGCTCGTTCCCTACTACGAGCGGCTCGTCAAGTTCGTCTTCCGGGAGCCGGAG

LeuGlnThrAlaSerArgGlnAlaGluValIleAlaProAlaValGlnThrAsnTrpGln
1502 CTGCAGACCGCGTCCCGTCAGGCAGAGGTTATCGCCCCTGCTGTCCAGACCAACTGGCAA
GACGTCTGGCGCAGGGCAGTCCGTCTCCAATAGCGGGGACGACAGGTCTGGTTGACCGTT
^ ^
1502 PSTI, 1507 TTH3I,

LysLeuGluThrPheTrpAlaLysHisMetTrpAsnPheIleSerGlyIleGlnTyrLeu
1562 AAACTCGAGACCTTCTGGGCGAAGCATATGTGGAACTTCATCAGTGGGATACAATACTTG
TTTGAGCTCTGGAAGACCCGCTTCGTATACACCTTGAAGTAGTCACCCTATGTTATGAAC
^ ^
1565 XHOI, 1586 NDEI,

AlaGlyLeuSerThrLeuProGlyAsnProAlaIleAlaSerLeuMetAlaPheThrAla
1622 GCGGGCTTGTCAACGCTGCCTGGTAACCCCGCCATTGCTTCATTGATGGCTTTTACAGCT
CGCCCGAACAGTTGCGACGGACCATTGGGGCGGTAACGAAGTAACTACCGAAAATGTCGA
^ ^
1643 BSTE2, 1677 ALWN1 PVU2,

AlaValThrSerProLeuThrThrSerGlnThrLeuLeuPheAsnIleLeuGlyGlyTrp
1682 GCTGTCACCAGCCCACTAACCACTAGCCAAACCCTCCTCTTCAACATATTGGGGGGGTGG
CGACAGTGGTCGGGTGATTGGTGATCGGTTTGGGAGGAGAAGTTGTATAACCCCCCCACC

FIG. 17C

```
      ValAlaAlaGlnLeuAlaAlaPr GlyAlaAlaThrAlaPheValGlyAlaGlyLeuAla
1742  GTGGCTGCCCAGCTCGCCGCCCCCGGTGCCGCTACTGCCTTTGTGGGCGCTGGCTTAGCT
      CACCGACGGGTCGAGCGGCGGGGGCCACGGCGATGACGGAAACACCCGCGACCGAATCGA
                                                                ^
      1794 ESP1,

      GlyAlaAlaIleGlySerValGlyLeuGlyLysValLeuIleAspIleLeuAlaGlyTyr
1802  GGCGCCGCCATCGGCAGTGTTGGACTGGGGAAGGTCCTCATAGACATCCTTGCAGGGTAT
      CCGCGGCGGTAGCCGTCACAACCTGACCCCTTCCAGGAGTATCTGTAGGAACGTCCCATA
      ^
      1802 KAS1 NARI,

      GlyAlaGlyValAlaGlyAlaLeuValAlaPheLysIleMetSerGlyGluValProSer
1862  GGCGCGGGCGTGGCGGGAGCTCTTGTGGCATTCAAGATCATGAGCGGTGAGGTCCCCTCC
      CCGCGCCCGCACCGCCCTCGAGAACACCGTAAGTTCTAGTACTCGCCACTCCAGGGGAGG
                     ^                    ^
      1878 SACI, 1899 BSPH1,

      ThrGluAspLeuValAsnLeuLeuProAlaIleLeuSerProGlyAlaLeuValValGly
1922  ACGGAGGACCTGGTCAATCTACTGCCCGCCATCCTCTCGCCCGGAGCCCTCGTAGTCGGC
      TGCCTCCTGGACCAGTTAGATGACGGGCGGTAGGAGAGCGGGCCTCGGGAGCATCAGCCG
        ^
      1928 TTH3I,

      ValValCysAlaAlaIleLeuArgArgHisValGlyProGlyGluGlyAlaValGlnTrp
1982  GTGGTCTGTGCAGCAATACTGCGCCGGCACGTTGGCCCGGGCGAGGGGGCAGTGCAGTGG
      CACCAGACACGTCGTTATGACGCGGCCGTGCAACCGGGCCCGCTCCCCCGTCACGTCACC
                            ^             ^
      2004 NAEI, 2017 SMAI XMAI,

      MetAsnArgLeuIleAlaPheAlaSerArgGlyAsnHisValSerProThrHisTyrVal
2042  ATGAACCGGCTGATAGCCTTCGCCTCCCGGGGGAACCATGTTTCCCCCACGCACTACGTG
      TACTTGGCCGACTATCGGAAGCGGAGGGCCCCCTTGGTACAAAGGGGGTGCGTGATGCAC
                               ^                        ^
      2067 SMAI XMAI, 2093 DRA3,

      ProGluSerAspAlaAlaAlaArgValThrAlaIleLeuSerSerLeuThrValThrGln
2102  CCGGAGAGCGATGCAGCTGCCCGCGTCACTGCCATACTCAGCAGCCTCACTGTAACCCAG
      GGCCTCTCGCTACGTCGACGGGCGCAGTGACGGTATGAGTCGTCGGAGTGACATTGGGTC
                   ^                                          ^
      2115 PVU2, 2159 ALWN1,

      LeuLeuArgArgLeuHisGlnTrpIleSerSerGluCysThrThrProCysSerGlySer
2162  CTCCTGAGGCGACTGCACCAGTGGATAAGCTCGGAGTGTACCACTCCATGCTCCGGTTCC
      GAGGACTCCGCTGACGTGGTCACCTATTCGAGCCTCACATGGTGAGGTACGAGGCCAAGG
        ^                                                      ^
      2164 MST2, 2220 ECON1,

      TrpLeuArgAspIleTrpAspTrpIleCysGluValLeuSerAspPheLysThrTrpLeu
2222  TGGCTAAGGGACATCTGGGACTGGATATGCGAGGTGTTGAGCGACTTTAAGACCTGGCTA
      ACCGATTCCCTGTAGACCCTGACCTATACGCTCCACAACTCGCTGAAATTCTGGACCGAT

      LysAlaLysLeuMetProGlnLeuProGlyIleProPheValSerCysGlnArgGlyTyr
2282  AAAGCTAAGCTCATGCCACAGCTGCCTGGGATCCCCTTTGTGTCCTGCCAGCGCGGGTAT
      TTTCGATTCGAGTACGGTGTCGACGGACCCTAGGGGAAACACAGGACGGTCGCGCCCATA
         ^         ^      ^
      2285 ESP1, 2300 PVU2, 2310 BAMHI,
```

FIG. 17D

```
      LysGlyValTrpArgGlyAspGlyIleMetHisThrArgCysHisCysGlyAlaGluIle
2342  AAGGGGGTCTGGCGAGGGGACGGCATCATGCACACTCGCTGCCACTGTGGAGCTGAGATC
      TTCCCCCAGACCGCTCCCCTGCCGTAGTACGTGTGAGCGACGGTGACACCTCGACTCTAG

      ThrGlyHisValLysAsnGlyThrMetArgIleValGlyProArgThrCysArgAsnMet
2402  ACTGGACATGTCAAAAACGGGACGATGAGGATCGTCGGTCCTAGGACCTGCAGGAACATG
      TGACCTGTACAGTTTTTGCCCTGCTACTCCTAGCAGCCAGGATCCTGGACGTCCTTGTAC
                             ^               ^      ^^
      2425 BSAB1, 2441 AVR2, 2448 SSE83871, 2449 PSTI,

      TrpSerGlyThrPheProIleAsnAlaTyrThrThrGlyProCysThrProLeuProAla
2462  TGGAGTGGGACCTTCCCCATTAATGCCTACACCACGGGCCCCTGTACCCCCCTTCCTGCG
      ACCTCACCCTGGAAGGGGTAATTACGGATGTGGTGCCCGGGGACATGGGGGGAAGGACGC
                        ^                ^
      2480 ASE1, 2497 APAI,

      ProAsnTyrThrPheAlaLeuTrpArgValSerAlaGluGluTyrValGluIleArgGln
2522  CCGAACTACACGTTCGCGCTATGGAGGGTGTCTGCAGAGGAATACGTGGAGATAAGGCAG
      GGCTTGATGTGCAAGCGCGATACCTCCCACAGACGTCTCCTTATGCACCTCTATTCCGTC
                                     ^
      2553 PSTI,

      ValGlyAspPheHisTyrValThrGlyMetThrThrAspAsnLeuLysCysProCysGln
2582  GTGGGGGACTTCCACTACGTGACGGGTATGACTACTGACAATCTTAAATGCCCGTGCCAG
      CACCCCCTGAAGGTGATGCACTGCCCATACTGATGACTGTTAGAATTTACGGGCACGGTC
                  ^
      2594 DRA3,

      ValProSerProGluPhePheThrGluLeuAspGlyValArgLeuHisArgPheAlaPro
2642  GTCCCATCGCCCGAATTTTTCACAGAATTGGACGGGGTGCGCCTACATAGGTTTGCGCCC
      CAGGGTAGCGGGCTTAAAAAGTGTCTTAACCTGCCCCACGCGGATGTATCCAAACGCGGG

      ProCysLysProLeuLeuArgGluGluValSerPheArgValGlyLeuHisGluTyrPro
2702  CCCTGCAAGCCCTTGCTGCGGGAGGAGGTATCATTCAGAGTAGGACTCCACGAATACCCG
      GGGACGTTCGGGAACGACGCCCTCCTCCATAGTAAGTCTCATCCTGAGGTGCTTATGGGC
                                                             ^
      2757 HGIE2,

      ValGlySerGlnLeuProCysGluProGluProAspValAlaValLeuThrSerMetLeu
2762  GTAGGGTCGCAATTACCTTGCGAGCCCGAACCGGACGTGGCCGTGTTGACGTCCATGCTC
      CATCCCAGCGTTAATGGAACGCTCGGGCTTGGCCTGCACCGGCACAACTGCAGGTACGAG
                                                     ^
      2809 AAT2,

      ThrAspProSerHisIleThrAlaGluAlaAlaGlyArgArgLeuAlaArgGlySerPro
2822  ACTGATCCCTCCCATATAACAGCAGAGGCGGCCGGGCGAAGGTTGGCGAGGGGATCACCC
      TGACTAGGGAGGGTATATTGTCGTCTCCGCCGGCCCGCTTCCAACCGCTCCCCTAGTGGG
                                  ^
      2850 EAG1 XMA3,

      ProSerValAlaSerSerSerAlaSerGlnLeuSerAlaProSerLeuLysAlaThrCys
2882  CCCTCTGTGGCCAGCTCCTCGGCTAGCCAGCTATCCGCTCCATCTCTCAAGGCAACTTGC
      GGGAGACACCGGTCGAGGAGCCGATCGGTCGATAGGCGAGGTAGAGAGTTCCGTTGAACG
             ^             ^
      2889 BALI, 2903 NHEI,
```

FIG. 17E

```
     ThrAlaAsnHisAspSerProAspAlaGluLeuIleGluAlaAsnLeuLeuTrpArgGln
2942 ACCGCTAACCATGACTCCCCTGATGCTGAGCTCATAGAGGCCAACCTCCTATGGAGGCAG
     TGGCGATTGGTACTGAGGGGACTACGACTCGAGTATCTCCGGTTGGAGGATACCTCCGTC
                                     ^  ^
     2966 ESP1, 2969 SACI,

     GluMetGlyGlyAsnIleThrArgValGluSerGluAsnLysValValIleLeuAspSer
3002 GAGATGGGCGGCAACATCACCAGGGTTGAGTCAGAAAACAAAGTGGTGATTCTGGACTCC
     CTCTACCCGCCGTTGTAGTGGTCCCAACTCAGTCTTTTGTTTCACCACTAAGACCTGAGG

     PheAspProLeuValAlaGluGluAspGluArgGluIleSerValProAlaGluIleLeu
3062 TTCGATCCGCTTGTGGCGGAGGAGGACGAGCGGGAGATCTCCGTACCCGCAGAAATCCTG
     AAGCTAGGCGAACACCGCCTCCTCCTGCTCGCCCTCTAGAGGCATGGGCGTCTTTAGGAC
                                           ^
     3096 BGL2,

     ArgLysSerArgArgPheAlaGlnAlaLeuProValTrpAlaArgProAspTyrAsnPro
3122 CGGAAGTCTCGGAGATTCGCCCAGGCCCTGCCCGTTTGGGCGCGGCCGGACTATAACCCC
     GCCTTCAGAGCCTCTAAGCGGGTCCGGGACGGGCAAACCCGCGCCGGCCTGATATTGGGG
                    ^                    ^
     3143 ALWN1, 3164 EAG1 XMA3,

     ProLeuValGluThrTrpLysLysProAspTyrGluProProValValHisGlyCysPro
3182 CCGCTAGTGGAGACGTGGAAAAAGCCCGACTACGAACCACCTGTGGTCCATGGCTGCCCG
     GGCGATCACCTCTGCACCTTTTTCGGGCTGATGCTTGGTGGACACCAGGTACCGACGGGC
                                        ^          ^
     3217 HGIE2, 3229 NCOI,

     LeuProProProLysSerProProValProProProArgLysLysArgThrValValLeu
3242 CTTCCACCTCCAAAGTCCCCTCCTGTGCCTCCGCCTCGGAAGAAGCGGACGGTGGTCCTC
     GAAGGTGGAGGTTTCAGGGGAGGACACGGAGGCGGAGCCTTCTTCGCCTGCCACCAGGAG

     ThrGluSerThrLeuSerThrAlaLeuAlaGluLeuAlaThrArgSerPheGlySerSer
3302 ACTGAATCAACCCTATCTACTGCCTTGGCCGAGCTCGCCACCAGAAGCTTTGGCAGCTCC
     TGACTTAGTTGGGATAGATGACGGAACCGGCTCGAGCGGTGGTCTTCGAAACCGTCGAGG
                                  ^           ^
     3332 SACI, 3346 HIND3,

     SerThrSerGlyIleThrGlyAspAsnThrThrThrSerSerGluProAlaProSerGly
3362 TCAACTTCCGGCATTACGGGCGACAATACGACAACATCCTCTGAGCCCGCCCCTTCTGGC
     AGTTGAAGGCCGTAATGCCCGCTGTTATGCTGTTGTAGGAGACTCGGGCGGGGAAGACCG

     CysProProAspSerAspAlaGluSerTyrSerSerMetProProLeuGluGlyGluPro
3422 TGCCCCCCCGACTCCGACGCTGAGTCCTATTCCTCCATGCCCCCCCTGGAGGGGGAGCCT
     ACGGGGGGGCTGAGGCTGCGACTCAGGATAAGGAGGTACGGGGGGGACCTCCCCCTCGGA
                    ^
     3437 EAM11051,

     GlyAspProAspLeuSerAspGlySerTrpSerThrValSerSerGluAlaAsnAlaGlu
3482 GGGGATCCGGATCTTAGCGACGGGTCATGGTCAACGGTCAGTAGTGAGGCCAACGCGGAG
     CCCCTAGGCCTAGAATCGCTGCCCAGTACCAGTTGCCAGTCATCACTCCGGTTGCGCCTC
       ^^ ^
     3484 BAMHI, 3485 BSAB1, 3487 BSPE1,

     AspValValCysCysSerMetSerTyrSerTrpThrGlyAlaLeuValThrProCysAla
3542 GATGTCGTGTGCTGCTCAATGTCTTACTCTTGGACAGGCGCACTCGTCACCCCGTGCGCC
     CTACAGCACACGACGAGTTACAGAATGAGAACCTGTCCGCGTGAGCAGTGGGGCACGCGG
```

FIG. 17F

```
     AlaGluGluGlnLysLeuProIleAsnAlaLeuSerAsnSerLeuLeuArgHisHisAsn
3602 GCGGAAGAACAGAAACTGCCCATCAATGCACTAAGCAACTCGTTGCTACGTCACCACAAT
     CGCCTTCTTGTCTTTGACGGGTAGTTACGTGATTCGTTGAGCAACGATGCAGTGGTGTTA
             ^                                                ^
     3611 ALWN1, 3655 PFLM1,

     LeuValTyrSerThrThrSerArgSerAlaCysGlnArgGlnLysLysValThrPheAsp
3662 TTGGTGTATTCCACCACCTCACGCAGTGCTTGCCAAAGGCAGAAGAAAGTCACATTTGAC
     AACCACATAAGGTGGTGGAGTGCGTCACGAACGGTTTCCGTCTTCTTTCAGTGTAAACTG
                        ^
     3681 DRA3,

     ArgLeuGlnValLeuAspSerHisTyrGlnAspValLeuLysGluValLysAlaAlaAla
3722 AGACTGCAAGTTCTGGACAGCCATTACCAGGACGTACTCAAGGAGGTTAAAGCAGCGGCG
     TCTGACGTTCAAGACCTGTCGGTAATGGTCCTGCATGAGTTCCTCCAATTTCGTCGCCGC

     SerLysValLysAlaAsnLeuLeuSerValGluGluAlaCysSerLeuThrProProHis
3782 TCAAAAGTGAAGGCTAACTTGCTATCCGTAGAGGAAGCTTGCAGCCTGACGCCCCCACAC
     AGTTTTCACTTCCGATTGAACGATAGGCATCTCCTTCGAACGTCGGACTGCGGGGGTGTG
                                       ^
     3816 HIND3,

     SerAlaLysSerLysPheGlyTyrGlyAlaLysAspValArgCysHisAlaArgLysAla
3842 TCAGCCAAATCCAAGTTTGGTTATGGGGCAAAAGACGTCCGTTGCCATGCCAGAAAGGCC
     AGTCGGTTTAGGTTCAAACCAATACCCCGTTTTCTGCAGGCAACGGTACGGTCTTTCCGG
                                    ^              ^
     3875 AAT2, 3890 BGLI,

     ValThrHisIleAsnSerValTrpLysAspLeuLeuGluAspAsnValThrProIleAsp
3902 GTAACCCACATCAACTCCGTGTGGAAAGACCTTCTGGAAGACAATGTAACACCAATAGAC
     CATTGGGTGTAGTTGAGGCACACCTTTCTGGAAGACCTTCTGTTACATTGTGGTTATCTG

     ThrThrIleMetAlaLysAsnGluValPheCysValGlnProGluLysGlyGlyArgLys
3962 ACTACCATCATGGCTAAGAACGAGGTTTTCTGCGTTCAGCCTGAGAAGGGGGGTCGTAAG
     TGATGGTAGTACCGATTCTTGCTCCAAAAGACGCAAGTCGGACTCTTCCCCCCAGCATTC

     ProAlaArgLeuIleValPheProAspLeuGlyValArgValCysGluLysMetAlaLeu
4022 CCAGCTCGTCTCATCGTGTTCCCCGATCTGGGCGTGCGCGTGTGCGAAAAGATGGCTTTG
     GGTCGAGCAGAGTAGCACAAGGGGCTAGACCCGCACGCGCACACGCTTTTCTACCGAAAC

     TyrAspValValThrLysLeuProLeuAlaValMetGlySerSerTyrGlyPheGlnTyr
4082 TACGACGTGGTTACAAAGCTCCCCTTGGCCGTGATGGGAAGCTCCTACGGATTCCAATAC
     ATGCTGCACCAATGTTTCGAGGGGAACCGGCACTACCCTTCGAGGATGCCTAAGGTTATG

     SerProGlyGlnArgValGluPheLeuValGlnAlaTrpLysSerLysLysThrProMet
4142 TCACCAGGACAGCGGGTTGAATTCCTCGTGCAAGCGTGGAAGTCCAAGAAAACCCCAATG
     AGTGGTCCTGTCGCCCAACTTAAGGAGCACGTTCGCACCTTCAGGTTCTTTTGGGGTTAC
                       ^
     4160 ECORI,

     GlyPheSerTyrAspThrArgCysPheAspSerThrValThrGluSerAspIleArgThr
4202 GGGTTCTCGTATGATACCCGCTGCTTTGACTCCACAGTCACTGAGAGCGACATCCGTACG
     CCCAAGAGCATACTATGGGCGACGAAACTGAGGTGTCAGTGACTCTCGCTGTAGGCATGC
                                   ^         ^
```

FIG. 17G

```
     4229 DRD1, 4236 ALWN1,

     GluGluAlaIleTyrGlnCysCysAspLeuAspProGlnAlaArgValAlaIleLysSer
4262 GAGGAGGCAATCTACCAATGTTGTGACCTCGACCCCCAAGCCCGCGTGGCCATCAAGTCC
     CTCCTCCGTTAGATGGTTACAACACTGGAGCTGGGGGTTCGGGCGCACCGGTAGTTCAGG
                                            ^      ^

     4301 BGLI, 4308 BALI,

     LeuThrGluArgLeuTyrValGlyGlyProLeuThrAsnSerArgGlyGluAsnCysGly
4322 CTCACCGAGAGGCTTTATGTTGGGGGCCCTCTTACCAATTCAAGGGGGGAGAACTGCGGC
     GAGTGGCTCTCCGAAATACAACCCCCGGGAGAATGGTTAAGTTCCCCCCTCTTGACGCCG
                            ^

     4345 APAI,

     TyrArgArgCysArgAlaSerGlyValLeuThrThrSerCysGlyAsnThrLeuThrCys
4382 TATCGCAGGTGCCGCGCGAGCGGCGTACTGACAACTAGCTGTGGTAACACCCTCACTTGC
     ATAGCGTCCACGGCGCGCTCGCCGCATGACTGTTGATCGACACCATTGTGGGAGTGAACG

     TyrIleLysAlaArgAlaAlaCysArgAlaAlaGlyLeuGlnAspCysThrMetLeuVal
4442 TACATCAAGGCCCGGGCAGCCTGTCGAGCCGCAGGGCTCCAGGACTGCACCATGCTCGTG
     ATGTAGTTCCGGGCCCGTCGGACAGCTCGGCGTCCCGAGGTCCTGACGTGGTACGAGCAC
               ^

     4452 SMAI XMAI,

     CysGlyAspAspLeuValValIleCysGluSerAlaGlyValGlnGluAspAlaAlaSer
4502 TGTGGCGACGACTTAGTCGTTATCTGTGAAAGCGCGGGGGTCCAGGAGGACGCGGCGAGC
     ACACCGCTGCTGAATCAGCAATAGACACTTTCGCGCCCCCAGGTCCTCCTGCGCCGCTCG
           ^  ^

     4508 DRD1, 4511 TTH3I,

     LeuArgAlaPheThrGluAlaMetThrArgTyrSerAlaProProGlyAspProProGln
4562 CTGAGAGCCTTCACGGAGGCTATGACCAGGTACTCCGCCCCCCCTGGGGACCCCCCACAA
     GACTCTCGGAAGTGCCTCCGATACTGGTCCATGAGGCGGGGGGGACCCCTGGGGGGTGTT

     ProGluTyrAspLeuGluLeuIleThrSerCysSerSerAsnValSerValAlaHisAsp
4622 CCAGAATACGACTTGGAGCTCATAACATCATGCTCCTCCAACGTGTCAGTCGCCCACGAC
     GGTCTTATGCTGAACCTCGAGTATTGTAGTACGAGGAGGTTGCACAGTCAGCGGGTGCTG
                    ^

     4637 SACI,

     GlyAlaGlyLysArgValTyrTyrLeuThrArgAspProThrThrProLeuAlaArgAla
4682 GGCGCTGGAAAGAGGGTCTACTACCTCACCCGTGACCCTACAACCCCCCTCGCGAGAGCT
     CCGCGACCTTTCTCCCAGATGATGGAGTGGGCACTGGGATGTTGGGGGGAGCGCTCTCGA
                                                      ^

     4731 NRUI,

     AlaTrpGluThrAlaArgHisThrProValAsnSerTrpLeuGlyAsnIleIleMetPhe
4742 GCGTGGGAGACAGCAAGACACACTCCAGTCAATTCCTGGCTAGGCAACATAATCATGTTT
     CGCACCCTCTGTCGTTCTGTGTGAGGTCAGTTAAGGACCGATCCGTTGTATTAGTACAAA

     AlaProThrLeuTrpAlaArgMetIleLeuMetThrHisPhePheSerValLeuIleAla
4802 GCCCCCACACTGTGGGCGAGGATGATACTGATGACCCATTTCTTTAGCGTCCTTATAGCC
     CGGGGGTGTGACACCCGCTCCTACTATGACTACTGGGTAAAGAAATCGCAGGAATATCGG
         ^^

     4806 PFLM1, 4807 DRA3,

     ArgAspGlnLeuGluGlnAlaLeuAspCysGluIl TyrGlyAlaCysTyrSerIleGlu
```

FIG. 17H

```
4862 AGGGACCAGCTTGAACAGGCCCTCGATTGCGAGATCTACGGGGCCTGCTACTCCATAGAA
     TCCCTGGTCGAACTTGTCCGGGAGCTAACGCTCTAGATGCCCCGGACGATGAGGTATCTT
                                   ^

     4893 BGL2,

     ProLeuAspLeuProProIleIleGlnArgLeuHisGlyLeuSerAlaPheSerLeuHis
4922 CCACTGGATCTACCTCCAATCATTCAAAGACTCCATGGCCTCAGCGCATTTTCACTCCAC
     GGTGACCTAGATGGAGGTTAGTAAGTTTCTGAGGTACCGGAGTCGCGTAAAAGTGAGGTG
                                    ^

     4954 NCOI,

     SerTyrSerProGlyGluIleAsnArgValAlaAlaCysLeuArgLysLeuGlyValPro
4982 AGTTACTCTCCAGGTGAAATCAATAGGGTGGCCGCATGCCTCAGAAAACTTGGGGTACCG
     TCAATGAGAGGTCCACTTTAGTTATCCCACCGGCGTACGGAGTCTTTTGAACCCCATGGC
                                     ^                        ^

     5015 SPHI, 5035 KPNI,

     ProLeuArgAlaTrpArgHisArgAlaArgSerValArgAlaArgLeuLeuAlaArgGly
5042 CCCTTGCGAGCTTGGAGACACCGGGCCCGGAGCGTCCGCGCTAGGCTTCTGGCCAGAGGA
     GGGAACGCTCGAACCTCTGTGGCCCGGGCCTCGCAGGCGCGATCCGAAGACCGGTCTCCT
                          ^                             ^

     5064 APAI, 5091 BALI,

     GlyArgAlaAlaIleCysGlyLysTyrLeuPheAsnTrpAlaValArgThrLysLeuLys
5102 GGCAGGGCTGCCATATGTGGCAAGTACCTCTTCAACTGGGCAGTAAGAACAAAGCTCAAA
     CCGTCCCGACGGTATACACCGTTCATGGAGAAGTTGACCCGTCATTCTTGTTTCGAGTTT
                ^

     5113 NDEI,

     LeuThrProIleAlaAlaAlaGlyGlnLeuAspLeuSerGlyTrpPheThrAlaGlyTyr
5162 CTCACTCCAATAGCGGCCGCTGGCCAGCTGGACTTGTCCGGCTGGTTCACGGCTGGCTAC
     GAGTGAGGTTATCGCCGGCGACCGGTCGACCTGAACAGGCCGACCAAGTGCCGACCGATG
                 ^^      ^   ^

     5174 NOTI, 5175 EAG1 XMA3, 5182 BALI, 5186 PVU2,

     SerGlyGlyAspIleTyrHisSerValSerHisAlaArgProArgTrpIleTrpPheCys
5222 AGCGGGGGAGACATTTATCACAGCGTGTCTCATGCCCGGCCCCGCTGGATCTGGTTTTGC
     TCGCCCCCTCTGTAAATAGTGTCGCACAGAGTACGGGCCGGGGCGACCTAGACCAAAACG
                        ^

     5240 DRA3,

     LeuLeuLeuLeuAlaAlaGlyValGlyIleTyrLeuLeuProAsnArgMetSerThrAsn
5282 CTACTCCTGCTTGCTGCAGGGGTAGGCATCTACCTCCTCCCCAACCGAATGAGCACGAAT
     GATGAGGACGAACGACGTCCCCATCCGTAGATGGAGGAGGGGTTGGCTTACTCGTGCTTA
                  ^

     5295 PSTI,

     ProLysProGlnArgLysThrLysArgAsnThrAsnArgArgProGlnAspValLysPhe
5342 CCTAAACCTCAAAGAAAGACCAAACGTAACACCAACCGGCGGCCGCAGGACGTCAAGTTC
     GGATTTGGAGTTTCTTTCTGGTTTGCATTGTGGTTGGCCGCCGGCGTCCTGCAGTTCAAG
                                             ^^      ^      ^

     5380 NOTI, 5381 EAG1 XMA3, 5390 AAT2, 5401 SMAI XMAI,

     ProGlyGlyGlyGlnIleValGlyGlyValTyrLeuLeuProArgArgGlyProArgLeu
5402 CCGGGTGGCGGTCAGATCGTTGGTGGAGTTTACTTGTTGCCGCGCAGGGGCCCTAGATTG
     GGCCCACCGCCAGTCTAGCAACCACCTCAAATGAACAACGGCGCGTCCCCGGGATCTAAC
                                                    ^
```

FIG. 17I

```
     5449 APAI,

     GlyValArgAlaThrArgLysThrSerGluArgSerGlnProArgGlyArgArgGlnPro
5462 GGTGTGCGCGCGACGAGAAAGACTTCCGAGCGGTCGCAACCTCGAGGTAGACGTCAGCCT
     CCACACGCGCGCTGCTCTTTCTGAAGGCTCGCCAGCGTTGGAGCTCCATCTGCAGTCGGA
          ^          ^                         ^         ^
     5467 BSSH2, 5478 XMNI, 5502 XHOI, 5511 AAT2,

     IleProLysAlaArgArgProGluGlyArgThrTrpAlaGlnProGlyTyrProTrpPro
5522 ATCCCCAAGGCTCGTCGGCCCGAGGGCAGGACCTGGGCTCAGCCCGGGTACCCTTGGCCC
     TAGGGGTTCCGAGCAGCCGGGCTCCCGTCCTGGACCCGAGTCGGGCCCATGGGAACCGGG
                                   ^         ^      ^   ^
     5548 ALWN1, 5558 ESP1, 5564 SMAI XMAI, 5568 KPNI,

     LeuTyrGlyAsnGluGlyCysGlyTrpAlaGlyTrpLeuLeuSerProArgGlySerArg
5582 CTCTATGGCAATGAGGGCTGCGGGTGGGCGGGATGGCTCCTGTCTCCCCGTGGCTCTCGG
     GAGATACCGTTACTCCCGACGCCCACCCGCCCTACCGAGGACAGAGGGGCACCGAGAGCC

     ProSerTrpGlyProThrAspProArgArgArgSerArgAsnLeuGlyLysOC AM
5642 CCTAGCTGGGGCCCCACAGACCCCCGGCGTAGGTCGCGCAATTTGGGTAAGTAATAGTCG
     GGATCGACCCCGGGGTGTCTGGGGGCCGCATCCAGCGCGTTAAACCCATTCATTATCAGC
          ^                                                 ^
     5650 APAI, 5698 SALI,

5702 AC
     TG
```

```
                      MetAlaAlaTyrAlaAlaGlnGlyTyrLysValLeuValLeuAsn
  2   AGCTTACAAAACAAAATGGCTGCATATGCAGCTCAGGGCTATAAGGTGCTAGTACTCAAC
      TCGAATGTTTTGTTTTACCGACGTATACGTCGAGTCCCGATATTCCACGATCATGAGTTG
      ^                      ^                              ^
      1 HIND3, 24 NDEI, 52 SCAI,

      ProSerValAlaAlaThrLeuGlyPheGlyAlaTyrMetSerLysAlaHisGlyIleAsp
 62   CCCTCTGTTGCTGCAACACTGGGCTTTGGTGCTTACATGTCCAAGGCTCATGGGATCGAT
      GGGAGACAACGACGTTGTGACCCGAAACCACGAATGTACAGGTTCCGAGTACCCTAGCTA
                                                             ^
      116 CLAI,

      ProAsnIleArgThrGlyValArgThrIleThrThrGlySerProIleThrTyrSerThr
122   CCTAACATCAGGACCGGGGTGAGAACAATTACCACTGGCAGCCCCATCACGTACTCCACC
      GGATTGTAGTCCTGGCCCCACTCTTGTTAATGGTGACCGTCGGGGTAGTGCATGAGGTGG

      TyrGlyLysPheLeuAlaAspGlyGlyCysSerGlyGlyAlaTyrAspIleIleIleCys
182   TACGGCAAGTTCCTTGCCGACGGCGGGTGCTCGGGGGGCGCTTATGACATAATAATTTGT
      ATGCCGTTCAAGGAACGGCTGCCGCCCACGAGCCCCCCGCGAATACTGTATTATTAAACA

      AspGluCysHisSerThrAspAlaThrSerIleLeuGlyIleGlyThrValLeuAspGln
242   GACGAGTGCCACTCCACGGATGCCACATCCATCTTGGGCATTGGCACTGTCCTTGACCAA
      CTGCTCACGGTGAGGTGCCTACGGTGTAGGTAGAACCCGTAACCGTGACAGGAACTGGTT

      AlaGluThrAlaGlyAlaArgLeuValValLeuAlaThrAlaThrProProGlySerVal
302   GCAGAGACTGCGGGGGCGAGACTGGTTGTGCTCGCCACCGCCACCCCTCCGGGCTCCGTC
      CGTCTCTGACGCCCCCGCTCTGACCAACACGAGCGGTGGCGGTGGGGAGGCCCGAGGCAG
       ^
      303 ALWN1,

      ThrValProHisProAsnIleGluGluValAlaLeuSerThrThrGlyGluIleProPhe
362   ACTGTGCCCCATCCCAACATCGAGGAGGTTGCTCTGTCCACCACCGGAGAGATCCCTTTT
      TGACACGGGGTAGGGTTGTAGCTCCTCCAACGAGACAGGTGGTGGCCTCTCTAGGGAAAA

      TyrGlyLysAlaIleProLeuGluValIleLysGlyGlyArgHisLeuIlePheCysHis
422   TACGGCAAGGCTATCCCCCTCGAAGTAATCAAGGGGGGGAGACATCTCATCTTCTGTCAT
      ATGCCGTTCCGATAGGGGGAGCTTCATTAGTTCCCCCCCTCTGTAGAGTAGAAGACAGTA

      SerLysLysLysCysAspGluLeuAlaAlaLysLeuValAlaLeuGlyIleAsnAlaVal
482   TCAAAGAAGAAGTGCGACGAACTCGCCGCAAAGCTGGTCGCATTGGGCATCAATGCCGTG
      AGTTTCTTCTTCACGCTGCTTGAGCGGCGTTTCGACCAGCGTAACCCGTAGTTACGGCAC

      AlaTyrTyrArgGlyLeuAspValSerValIleProThrSerGlyAspValValValVal
542   GCCTACTACCGCGGTCTTGACGTGTCCGTCATCCCGACCAGCGGCGATGTTGTCGTCGTG
      CGGATGATGGCGCCAGAACTGCACAGGCAGTAGGGCTGGTCGCCGCTACAACAGCAGCAC
              ^         ^
      550 SAC2, 560 DRD1,

      AlaThrAspAlaLeuMetThrGlyTyrThrGlyAspPheAspSerValIleAspCysAsn
602   GCAACCGATGCCCTCATGACCGGCTATACCGGCGACTTCGACTCGGTGATAGACTGCAAT
      CGTTGGCTACGGGAGTACTGGCCGATATGGCCGCTGAAGCTGAGCCACTATCTGACGTTA
                   ^
      615 BSPH1,
```

FIG. 18A

```
662   ThrCysValThrGlnThrValAspPheSerLeuAspPr ThrPheThrIleGluThrIle
      ACGTGTGTCACCCAGACAGTCGATTTCAGCCTTGACCCTACCTTCACCATTGAGACAATC
      TGCACACAGTGGGTCTGTCAGCTAAAGTCGGAACTGGGATGGAAGTGGTAACTCTGTTAG

      ThrLeuProGlnAspAlaValSerArgThrGlnArgArgGlyArgThrGlyArgGlyLys
722   ACGCTCCCCCAAGATGCTGTCTCCCGCACTCAACGTCGGGGCAGGACTGGCAGGGGGAAG
      TGCGAGGGGGTTCTACGACAGAGGGCGTGAGTTGCAGCCCCGTCCTGACCGTCCCCCTTC

      ProGlyIleTyrArgPheValAlaProGlyGluArgProSerGlyMetPheAspSerSer
782   CCAGGCATCTACAGATTTGTGGCACCGGGGGAGCGCCCCTCCGGCATGTTCGACTCGTCC
      GGTCCGTAGATGTCTAAACACCGTGGCCCCCTCGCGGGGAGGCCGTACAAGCTGAGCAGG
                                        ^                ^
      816 BGLI, 833 DRD1,

      ValLeuCysGluCysTyrAspAlaGlyCysAlaTrpTyrGluLeuThrProAlaGluThr
842   GTCCTCTGTGAGTGCTATGACGCAGGCTGTGCTTGGTATGAGCTCACGCCCGCCGAGACT
      CAGGAGACACTCACGATACTGCGTCCGACACGAACCATACTCGAGTGCGGGCGGCTCTGA
                                             ^
      881 SACI,

      ThrValArgLeuArgAlaTyrMetAsnThrProGlyLeuProValCysGlnAspHisLeu
902   ACAGTTAGGCTACGAGCGTACATGAACACCCCGGGGCTTCCCGTGTGCCAGGACCATCTT
      TGTCAATCCGATGCTCGCATGTACTTGTGGGGCCCCGAAGGGCACACGGTCCTGGTAGAA
                                   ^
      931 SMAI XMAI,

      GluPheTrpGluGlyValPheThrGlyLeuThrHisIleAspAlaHisPheLeuSerGln
962   GAATTTTGGGAGGGCGTCTTTACAGGCCTCACTCATATAGATGCCCACTTTCTATCCCAG
      CTTAAAACCCTCCCGCAGAAATGTCCGGAGTGAGTATATCTACGGGTGAAAGATAGGGTC
                             ^
      985 STOI,

      ThrLysGlnSerGlyGluAsnLeuProTyrLeuValAlaTyrGlnAlaThrValCysAla
1022  ACAAAGCAGAGTGGGGAGAACCTTCCTTACCTGGTAGCGTACCAAGCCACCGTGTGCGCT
      TGTTTCGTCTCACCCCTCTTGGAAGGAATGGACCATCGCATGGTTCGGTGGCACACGCGA
                                                     ^
      1069 DRA3,

      ArgAlaGlnAlaProProProSerTrpAspGlnMetTrpLysCysLeuIleArgLeuLys
1082  AGGGCTCAAGCCCCTCCCCCATCGTGGACCAGATGTGGAAGTGTTTGATTCGCCTCAAG
      TCCCGAGTTCGGGGAGGGGGTAGCACCCTGGTCTACACCTTCACAAACTAAGCGGAGTTC

      ProThrLeuHisGlyProThrProLeuLeuTyrArgLeuGlyAlaValGlnAsnGluIle
1142  CCCACCCTCCATGGGCCAACACCCCTGCTATACAGACTGGGCGCTGTTCAGAATGAAATC
      GGGTGGGAGGTACCCGGTTGTGGGGACGATATGTCTGACCCGCGACAAGTCTTACTTTAG
              ^
      1150 NCOI,

      ThrLeuThrHisProValThrLysTyrIleMetThrCysMetSerAlaAspLeuGluVal
1202  ACCCTGACGCACCCAGTCACCAAATACATCATGACATGCATGTCGGCCGACCTGGAGGTC
      TGGGACTGCGTGGGTCAGTGGTTTATGTAGTACTGTACGTACAGCCGGCTGGACCTCCAG
                                  ^   ^  ^       ^    ^
      1230 BSPH1, 1234 DRD1, 1237 AVA3, 1245 EAG1 XMA3, 1250 DRD1,

      ValThrSerThrTrpValLeuValGlyGlyValLeuAlaAlaLeuAlaAlaTyrCysLeu
1262  GTCACGAGCACCTGGGTGCTCGTTGGCGGCGTCCTGGCTGCTTTGGCCGCGTATTGCCTG
```

FIG. 18B

```
     CAGTGCTCGTGGACCCACGAGCAACCGCCGCAGGACCGACGAAACCGGCGCATAACGGAC

     SerThrGlyCysValValIleValGlyArgValValLeuSerGlyLysProAlaIleIle
1322 TCAACAGGCTGCGTGGTCATAGTGGGCAGGGTCGTCTTGTCCGGGAAGCCGGCAATCATA
     AGTTGTCCGACGCACCAGTATCACCCGTCCCAGCAGAACAGGCCCTTCGGCCGTTAGTAT
                                                    ^
     1369 NAEI,

     ProAspArgGluValLeuTyrArgGluPheAspGluMetGluGluCysSerGlnHisLeu
1382 CCTGACAGGGAAGTCCTCTACCGAGAGTTCGATGAGATGGAAGAGTGCTCTCAGCACTTA
     GGACTGTCCCTTCAGGAGATGGCTCTCAAGCTACTCTACCTTCTCACGAGAGTCGTGAAT
        ^
     1385 DRD1,

     ProTyrIleGluGlnGlyMetMetLeuAlaGluGlnPheLysGlnLysAlaLeuGlyLeu
1442 CCGTACATCGAGCAAGGGATGATGCTCGCCGAGCAGTTCAAGCAGAAGGCCCTCGGCCTC
     GGCATGTAGCTCGTTCCCTACTACGAGCGGCTCGTCAAGTTCGTCTTCCGGGAGCCGGAG

     LeuGlnThrAlaSerArgGlnAlaGluValIleAlaProAlaValGlnThrAsnTrpGln
1502 CTGCAGACCGCGTCCCGTCAGGCAGAGGTTATCGCCCCTGCTGTCCAGACCAACTGGCAA
     GACGTCTGGCGCAGGGCAGTCCGTCTCCAATAGCGGGGACGACAGGTCTGGTTGACCGTT
     ^    ^
     1502 PSTI, 1507 TTH3I,

     LysLeuGluThrPheTrpAlaLysHisMetTrpAsnPheIleSerGlyIleGlnTyrLeu
1562 AAACTCGAGACCTTCTGGGCGAAGCATATGTGGAACTTCATCAGTGGGATACAATACTTG
     TTTGAGCTCTGGAAGACCCGCTTCGTATACACCTTGAAGTAGTCACCCTATGTTATGAAC
        ^                    ^
     1565 XHOI, 1586 NDEI,

     AlaGlyLeuSerThrLeuProGlyAsnProAlaIleAlaSerLeuMetAlaPheThrAla
1622 GCGGGCTTGTCAACGCTGCCTGGTAACCCCGCCATTGCTTCATTGATGGCTTTTACAGCT
     CGCCCGAACAGTTGCGACGGACCATTGGGGCGGTAACGAAGTAACTACCGAAAATGTCGA
                          ^                                  ^
     1643 BSTE2, 1677 ALWN1 PVU2,

     AlaValThrSerProLeuThrThrSerGlnThrLeuLeuPheAsnIleLeuGlyGlyTrp
1682 GCTGTCACCAGCCCACTAACCACTAGCCAAACCCTCCTCTTCAACATATTGGGGGGGTGG
     CGACAGTGGTCGGGTGATTGGTGATCGGTTTGGGAGGAGAAGTTGTATAACCCCCCCACC

     ValAlaAlaGlnLeuAlaAlaProGlyAlaAlaThrAlaPheValGlyAlaGlyLeuAla
1742 GTGGCTGCCCAGCTCGCCGCCCCCGGTGCCGCTACTGCCTTTGTGGGCGCTGGCTTAGCT
     CACCGACGGGTCGAGCGGCGGGGGCCACGGCGATGACGGAAACACCCGCGACCGAATCGA
                                                         ^
     1794 ESP1,

     GlyAlaAlaIleGlySerValGlyLeuGlyLysValLeuIleAspIleLeuAlaGlyTyr
1802 GGCGCCGCCATCGGCAGTGTTGGACTGGGGAAGGTCCTCATAGACATCCTTGCAGGGTAT
     CCGCGGCGGTAGCCGTCACAACCTGACCCCTTCCAGGAGTATCTGTAGGAACGTCCCATA
     ^
     1802 KAS1 NARI,

     GlyAlaGlyValAlaGlyAlaLeuValAlaPheLysIleMetSerGlyGluValProSer
1862 GGCGCGGGCGTGGCGGGAGCTCTTGTGGCATTCAAGATCATGAGCGGTGAGGTCCCCTCC
     CCGCGCCCGCACCGCCCTCGAGAACACCGTAAGTTCTAGTACTCGCCACTCCAGGGGAGG
                     ^                    ^
     1878 SACI, 1899 BSPH1,
```

FIG. 18C

```
     ThrGluAspLeuValAsnLeuLeuPr AlaIleLeuSerPr GlyAlaLeuValValGly
1922 ACGGAGGACCTGGTCAATCTACTGCCCGCCATCCTCTCGCCCGGAGCCCTCGTAGTCGGC
     TGCCTCCTGGACCAGTTAGATGACGGGCGGTAGGAGAGCGGGCCTCGGGAGCATCAGCCG
           ^
     1928 TTH3I,

     ValValCysAlaAlaIleLeuArgArgHisValGlyProGlyGluGlyAlaValGlnTrp
1982 GTGGTCTGTGCAGCAATACTGCGCCGGCACGTTGGCCCGGGCGAGGGGGCAGTGCAGTGG
     CACCAGACACGTCGTTATGACGCGGCCGTGCAACCGGGCCCGCTCCCCCGTCACGTCACC
                               ^             ^
     2004 NAEI, 2017 SMAI XMAI,

     MetAsnArgLeuIleAlaPheAlaSerArgGlyAsnHisValSerProThrHisTyrVal
2042 ATGAACCGGCTGATAGCCTTCGCCTCCCGGGGGAACCATGTTTCCCCCACGCACTACGTG
     TACTTGGCCGACTATCGGAAGCGGAGGGCCCCCTTGGTACAAAGGGGGTGCGTGATGCAC
                           ^                          ^
     2067 SMAI XMAI, 2093 DRA3,

     ProGluSerAspAlaAlaAlaArgValThrAlaIleLeuSerSerLeuThrValThrGln
2102 CCGGAGAGCGATGCAGCTGCCCGCGTCACTGCCATACTCAGCAGCCTCACTGTAACCCAG
     GGCCTCTCGCTACGTCGACGGGCGCAGTGACGGTATGAGTCGTCGGAGTGACATTGGGTC
                  ^                                            ^
     2115 PVU2, 2159 ALWN1,

     LeuLeuArgArgLeuHisGlnTrpIleSerSerGluCysThrThrProCysSerGlySer
2162 CTCCTGAGGCGACTGCACCAGTGGATAAGCTCGGAGTGTACCACTCCATGCTCCGGTTCC
     GAGGACTCCGCTGACGTGGTCACCTATTCGAGCCTCACATGGTGAGGTACGAGGCCAAGG
       ^                                                        ^
     2164 MST2, 2220 ECON1,

     TrpLeuArgAspIleTrpAspTrpIleCysGluValLeuSerAspPheLysThrTrpLeu
2222 TGGCTAAGGGACATCTGGGACTGGATATGCGAGGTGTTGAGCGACTTTAAGACCTGGCTA
     ACCGATTCCCTGTAGACCCTGACCTATACGCTCCACAACTCGCTGAAATTCTGGACCGAT

     LysAlaLysLeuMetProGlnLeuProGlyIleProPheValSerCysGlnArgGlyTyr
2282 AAAGCTAAGCTCATGCCACAGCTGCCTGGGATCCCCTTTGTGTCCTGCCAGCGCGGGTAT
     TTTCGATTCGAGTACGGTGTCGACGGACCCTAGGGGAAACACAGGACGGTCGCGCCCATA
         ^              ^         ^
     2285 ESP1, 2300 PVU2, 2310 BAMHI,

     LysGlyValTrpArgGlyAspGlyIleMetHisThrArgCysHisCysGlyAlaGluIle
2342 AAGGGGGTCTGGCGAGGGGACGGCATCATGCACACTCGCTGCCACTGTGGAGCTGAGATC
     TTCCCCCAGACCGCTCCCCTGCCGTAGTACGTGTGAGCGACGGTGACACCTCGACTCTAG

     ThrGlyHisValLysAsnGlyThrMetArgIleValGlyProArgThrCysArgAsnMet
2402 ACTGGACATGTCAAAAACGGGACGATGAGGATCGTCGGTCCTAGGACCTGCAGGAACATG
     TGACCTGTACAGTTTTTGCCCTGCTACTCCTAGCAGCCAGGATCCTGGACGTCCTTGTAC
                             ^               ^      ^^
     2425 BSAB1, 2441 AVR2, 2448 SSE83871, 2449 PSTI,

     TrpSerGlyThrPheProIleAsnAlaTyrThrThrGlyProCysThrProLeuProAla
2462 TGGAGTGGGACCTTCCCCATTAATGCCTACACCACGGGCCCCTGTACCCCCCTTCCTGCG
     ACCTCACCCTGGAAGGGGTAATTACGGATGTGGTGCCCGGGGACATGGGGGGAAGGACGC
                       ^                ^
     2480 ASE1, 2497 APAI,
```

FIG. 18D

```
     ProAsnTyrThrPheAlaLeuTrpArgValSerAlaGluGluTyrValGluIleArgGln
2522 CCGAACTACACGTTCGCGCTATGGAGGGTGTCTGCAGAGGAATACGTGGAGATAAGGCAG
     GGCTTGATGTGCAAGCGCGATACCTCCCACAGACGTCTCCTTATGCACCTCTATTCCGTC

     2553 PSTI,

     ValGlyAspPheHisTyrValThrGlyMetThrThrAspAsnLeuLysCysProCysGln
2582 GTGGGGGACTTCCACTACGTGACGGGTATGACTACTGACAATCTTAAATGCCCGTGCCAG
     CACCCCCTGAAGGTGATGCACTGCCCATACTGATGACTGTTAGAATTTACGGGCACGGTC

     2594 DRA3,

     ValProSerProGluPhePheThrGluLeuAspGlyValArgLeuHisArgPheAlaPro
2642 GTCCCATCGCCCGAATTTTTCACAGAATTGGACGGGGTGCGCCTACATAGGTTTGCGCCC
     CAGGGTAGCGGGCTTAAAAAGTGTCTTAACCTGCCCCACGCGGATGTATCCAAACGCGGG

     ProCysLysProLeuLeuArgGluGluValSerPheArgValGlyLeuHisGluTyrPro
2702 CCCTGCAAGCCCTTGCTGCGGGAGGAGGTATCATTCAGAGTAGGACTCCACGAATACCCG
     GGGACGTTCGGGAACGACGCCCTCCTCCATAGTAAGTCTCATCCTGAGGTGCTTATGGGC

     2757 HGIE2,

     ValGlySerGlnLeuProCysGluProGluProAspValAlaValLeuThrSerMetLeu
2762 GTAGGGTCGCAATTACCTTGCGAGCCCGAACCGGACGTGGCCGTGTTGACGTCCATGCTC
     CATCCCAGCGTTAATGGAACGCTCGGGCTTGGCCTGCACCGGCACAACTGCAGGTACGAG

     2809 AAT2,

     ThrAspProSerHisIleThrAlaGluAlaAlaGlyArgArgLeuAlaArgGlySerPro
2822 ACTGATCCCTCCCATATAACAGCAGAGGCGGCCGGGCGAAGGTTGGCGAGGGGATCACCC
     TGACTAGGGAGGGTATATTGTCGTCTCCGCCGGCCCGCTTCCAACCGCTCCCCTAGTGGG

     2850 EAG1 XMA3,

     ProSerValAlaSerSerSerAlaSerGlnLeuSerAlaProSerLeuLysAlaThrCys
2882 CCCTCTGTGGCCAGCTCCTCGGCTAGCCAGCTATCCGCTCCATCTCTCAAGGCAACTTGC
     GGGAGACACCGGTCGAGGAGCCGATCGGTCGATAGGCGAGGTAGAGAGTTCCGTTGAACG

     2889 BALI, 2903 NHEI,

     ThrAlaAsnHisAspSerProAspAlaGluLeuIleGluAlaAsnLeuLeuTrpArgGln
2942 ACCGCTAACCATGACTCCCCTGATGCTGAGCTCATAGAGGCCAACCTCCTATGGAGGCAG
     TGGCGATTGGTACTGAGGGGACTACGACTCGAGTATCTCCGGTTGGAGGATACCTCCGTC

     2966 ESP1, 2969 SACI,

     GluMetGlyGlyAsnIleThrArgValGluSerGluAsnLysValValIleLeuAspSer
3002 GAGATGGGCGGCAACATCACCAGGGTTGAGTCAGAAAACAAAGTGGTGATTCTGGACTCC
     CTCTACCCGCCGTTGTAGTGGTCCCAACTCAGTCTTTTGTTTCACCACTAAGACCTGAGG

     PheAspProLeuValAlaGluGluAspGluArgGluIleSerValProAlaGluIleLeu
3062 TTCGATCCGCTTGTGGCGGAGGAGGACGAGCGGGAGATCTCCGTACCCGCAGAAATCCTG
     AAGCTAGGCGAACACCGCCTCCTCCTGCTCGCCCTCTAGAGGCATGGGCGTCTTTAGGAC

     3096 BGL2,

     ArgLysSerArgArgPheAlaGlnAlaLeuProValTrpAlaArgProAspTyrAsnPro
```

FIG. 18E

```
3122  CGGAAGTCTCGGAGATTCGCCCAGGCCCTGCCCGTTTGGGCGCGGCCGGACTATAACCCC
      GCCTTCAGAGCCTCTAAGCGGGTCCGGGACGGGCAAACCCGCGCCGGCCTGATATTGGGG
                           ^                           ^
      3143 ALWN1, 3164 EAG1 XMA3,

      ProLeuValGluThrTrpLysLysProAspTyrGluProProValValHisGlyCysPro
3182  CCGCTAGTGGAGACGTGGAAAAAGCCCGACTACGAACCACCTGTGGTCCATGGCTGCCCG
      GGCGATCACCTCTGCACCTTTTTCGGGCTGATGCTTGGTGGACACCAGGTACCGACGGGC
                                         ^           ^
      3217 HGIE2, 3229 NCOI,

      LeuProProProLysSerProProValProProProArgLysLysArgThrValValLeu
3242  CTTCCACCTCCAAAGTCCCCTCCTGTGCCTCCGCCTCGGAAGAAGCGGACGGTGGTCCTC
      GAAGGTGGAGGTTTCAGGGGAGGACACGGAGGCGGAGCCTTCTTCGCCTGCCACCAGGAG

      ThrGluSerThrLeuSerThrAlaLeuAlaGluLeuAlaThrArgSerPheGlySerSer
3302  ACTGAATCAACCCTATCTACTGCCTTGGCCGAGCTCGCCACCAGAAGCTTTGGCAGCTCC
      TGACTTAGTTGGGATAGATGACGGAACCGGCTCGAGCGGTGGTCTTCGAAACCGTCGAGG
                                    ^             ^
      3332 SACI, 3346 HIND3,

      SerThrSerGlyIleThrGlyAspAsnThrThrThrSerSerGluProAlaProSerGly
3362  TCAACTTCCGGCATTACGGGCGACAATACGACAACATCCTCTGAGCCCGCCCCTTCTGGC
      AGTTGAAGGCCGTAATGCCCGCTGTTATGCTGTTGTAGGAGACTCGGGCGGGGAAGACCG

      CysProProAspSerAspAlaGluSerTyrSerSerMetProProLeuGluGlyGluPro
3422  TGCCCCCCCGACTCCGACGCTGAGTCCTATTCCTCCATGCCCCCCCTGGAGGGGGAGCCT
      ACGGGGGGGCTGAGGCTGCGACTCAGGATAAGGAGGTACGGGGGGGACCTCCCCCTCGGA
                     ^
      3437 EAM11051,

      GlyAspProAspLeuSerAspGlySerTrpSerThrValSerSerGluAlaAsnAlaGlu
3482  GGGGATCCGGATCTTAGCGACGGGTCATGGTCAACGGTCAGTAGTGAGGCCAACGCGGAG
      CCCCTAGGCCTAGAATCGCTGCCCAGTACCAGTTGCCAGTCATCACTCCGGTTGCGCCTC
        ^^ ^
      3484 BAMHI, 3485 BSAB1, 3487 BSPE1,

      AspValValCysCysSerMetSerTyrSerTrpThrGlyAlaLeuValThrProCysAla
3542  GATGTCGTGTGCTGCTCAATGTCTTACTCTTGGACAGGCGCACTCGTCACCCCGTGCGCC
      CTACAGCACACGACGAGTTACAGAATGAGAACCTGTCCGCGTGAGCAGTGGGGCACGCGG
                                                    ^       ^
      3589 DRA3, 3600 SAC2,

      AlaGluGluGlnLysLeuProIleAsnAlaLeuSerAsnSerLeuLeuArgHisHisAsn
3602  GCGGAAGAACAGAAACTGCCCATCAATGCACTAAGCAACTCGTTGCTACGTCACCACAAT
      CGCCTTCTTGTCTTTGACGGGTAGTTACGTGATTCGTTGAGCAACGATGCAGTGGTGTTA
              ^                                          ^
      3611 ALWN1, 3655 PFLM1,

      LeuValTyrSerThrThrSerArgSerAlaCysGlnArgGlnLysLysValThrPheAsp
3662  TTGGTGTATTCCACCACCTCACGCAGTGCTTGCCAAAGGCAGAAGAAAGTCACATTTGAC
      AACCACATAAGGTGGTGGAGTGCGTCACGAACGGTTTCCGTCTTCTTTCAGTGTAAACTG
                        ^
      3681 DRA3,

      ArgLeuGlnValLeuAspSerHisTyrGlnAspValLeuLysGluValLysAlaAlaAla
3722  AGACTGCAAGTTCTGGACAGCCATTACCAGGACGTACTCAAGGAGGTTAAAGCAGCGGCG
```

FIG. 18F

TCTGACGTTCAAGACCTGTCGGTAATGGTCCTGCATGAGTTCCTCCAATTTCGTCGCCGC

SerLysValLysAlaAsnLeuLeuSerValGluGluAlaCysSerLeuThrProProHis
3782 TCAAAAGTGAAGGCTAACTTGCTATCCGTAGAGGAAGCTTGCAGCCTGACGCCCCCACAC
AGTTTTCACTTCCGATTGAACGATAGGCATCTCCTTCGAACGTCGGACTGCGGGGGTGTG
^

3816 HIND3,

SerAlaLysSerLysPheGlyTyrGlyAlaLysAspValArgCysHisAlaArgLysAla
3842 TCAGCCAAATCCAAGTTTGGTTATGGGGCAAAAGACGTCCGTTGCCATGCCAGAAAGGCC
AGTCGGTTTAGGTTCAAACCAATACCCCGTTTTCTGCAGGCAACGGTACGGTCTTTCCGG
^ ^

3875 AAT2, 3890 BGLI,

ValThrHisIleAsnSerValTrpLysAspLeuLeuGluAspAsnValThrProIleAsp
3902 GTAACCCACATCAACTCCGTGTGGAAAGACCTTCTGGAAGACAATGTAACACCAATAGAC
CATTGGGTGTAGTTGAGGCACACCTTTCTGGAAGACCTTCTGTTACATTGTGGTTATCTG

ThrThrIleMetAlaLysAsnGluValPheCysValGlnProGluLysGlyGlyArgLys
3962 ACTACCATCATGGCTAAGAACGAGGTTTTCTGCGTTCAGCCTGAGAAGGGGGGTCGTAAG
TGATGGTAGTACCGATTCTTGCTCCAAAAGACGCAAGTCGGACTCTTCCCCCCAGCATTC

ProAlaArgLeuIleValPheProAspLeuGlyValArgValCysGluLysMetAlaLeu
4022 CCAGCTCGTCTCATCGTGTTCCCCGATCTGGGCGTGCGCGTGTGCGAAAAGATGGCTTTG
GGTCGAGCAGAGTAGCACAAGGGGCTAGACCCGCACGCGCACACGCTTTTCTACCGAAAC

TyrAspValValThrLysLeuProLeuAlaValMetGlySerSerTyrGlyPheGlnTyr
4082 TACGACGTGGTTACAAAGCTCCCCTTGGCCGTGATGGGAAGCTCCTACGGATTCCAATAC
ATGCTGCACCAATGTTTCGAGGGGAACCGGCACTACCCTTCGAGGATGCCTAAGGTTATG

SerProGlyGlnArgValGluPheLeuValGlnAlaTrpLysSerLysLysThrProMet
4142 TCACCAGGACAGCGGGTTGAATTCCTCGTGCAAGCGTGGAAGTCCAAGAAAACCCCAATG
AGTGGTCCTGTCGCCCAACTTAAGGAGCACGTTCGCACCTTCAGGTTCTTTTGGGGTTAC
^

4160 ECORI,

GlyPheSerTyrAspThrArgCysPheAspSerThrValThrGluSerAspIleArgThr
4202 GGGTTCTCGTATGATACCCGCTGCTTTGACTCCACAGTCACTGAGAGCGACATCCGTACG
CCCAAGAGCATACTATGGGCGACGAAACTGAGGTGTCAGTGACTCTCGCTGTAGGCATGC
^ ^

4229 DRD1, 4236 ALWN1,

GluGluAlaIleTyrGlnCysCysAspLeuAspProGlnAlaArgValAlaIleLysSer
4262 GAGGAGGCAATCTACCAATGTTGTGACCTCGACCCCCAAGCCCGCGTGGCCATCAAGTCC
CTCCTCCGTTAGATGGTTACAACACTGGAGCTGGGGGTTCGGGCGCACCGGTAGTTCAGG
^ ^

4301 BGLI, 4308 BALI,

LeuThrGluArgLeuTyrValGlyGlyProLeuThrAsnSerArgGlyGluAsnCysGly
4322 CTCACCGAGAGGCTTTATGTTGGGGGCCCTCTTACCAATTCAAGGGGGGAGAACTGCGGC
GAGTGGCTCTCCGAAATACAACCCCCGGGAGAATGGTTAAGTTCCCCCCTCTTGACGCCG
^

4345 APAI,

TyrArgArgCysArgAlaSerGlyValL uThrThrSerCysGlyAsnThrLeuThrCys
4382 TATCGCAGGTGCCGCGCGAGCGGCGTACTGACAACTAGCTGTGGTAACACCCTCACTTGC
ATAGCGTCCACGGCGCGCTCGCCGCATGACTGTTGATCGACACCATTGTGGGAGTGAACG

FIG. 18G

```
      TyrIleLysAlaArgAlaAlaCysArgAlaAlaGlyLeuGlnAspCysThrMetLeuVal
4442  TACATCAAGGCCCGGGCAGCCTGTCGAGCCGCAGGGCTCCAGGACTGCACCATGCTCGTG
      ATGTAGTTCCGGGCCCGTCGGACAGCTCGGCGTCCCGAGGTCCTGACGTGGTACGAGCAC
                ^
      4452 SMAI XMAI,

      CysGlyAspAspLeuValValIleCysGluSerAlaGlyValGlnGluAspAlaAlaSer
4502  TGTGGCGACGACTTAGTCGTTATCTGTGAAAGCGCGGGGGTCCAGGAGGACGCGGCGAGC
      ACACCGCTGCTGAATCAGCAATAGACACTTTCGCGCCCCCAGGTCCTCCTGCGCCGCTCG
            ^  ^
      4508 DRD1, 4511 TTH3I,

      LeuArgAlaPheThrGluAlaMetThrArgTyrSerAlaProProGlyAspProProGln
4562  CTGAGAGCCTTCACGGAGGCTATGACCAGGTACTCCGCCCCCCCTGGGGACCCCCCACAA
      GACTCTCGGAAGTGCCTCCGATACTGGTCCATGAGGCGGGGGGGACCCCTGGGGGGTGTT

      ProGluTyrAspLeuGluLeuIleThrSerCysSerSerAsnValSerValAlaHisAsp
4622  CCAGAATACGACTTGGAGCTCATAACATCATGCTCCTCCAACGTGTCAGTCGCCCACGAC
      GGTCTTATGCTGAACCTCGAGTATTGTAGTACGAGGAGGTTGCACAGTCAGCGGGTGCTG
                     ^
      4637 SACI,

      GlyAlaGlyLysArgValTyrTyrLeuThrArgAspProThrThrProLeuAlaArgAla
4682  GGCGCTGGAAAGAGGGTCTACTACCTCACCCGTGACCCTACAACCCCCCTCGCGAGAGCT
      CCGCGACCTTTCTCCCAGATGATGGAGTGGGCACTGGGATGTTGGGGGGAGCGCTCTCGA
                                                       ^
      4731 NRUI,

      AlaTrpGluThrAlaArgHisThrProValAsnSerTrpLeuGlyAsnIleIleMetPhe
4742  GCGTGGGAGACAGCAAGACACACTCCAGTCAATTCCTGGCTAGGCAACATAATCATGTTT
      CGCACCCTCTGTCGTTCTGTGTGAGGTCAGTTAAGGACCGATCCGTTGTATTAGTACAAA

      AlaProThrLeuTrpAlaArgMetIleLeuMetThrHisPhePheSerValLeuIleAla
4802  GCCCCCACACTGTGGGCGAGGATGATACTGATGACCCATTTCTTTAGCGTCCTTATAGCC
      CGGGGGTGTGACACCCGCTCCTACTATGACTACTGGGTAAAGAAATCGCAGGAATATCGG
          ^^
      4806 PFLM1, 4807 DRA3,

      ArgAspGlnLeuGluGlnAlaLeuAspCysGluIleTyrGlyAlaCysTyrSerIleGlu
4862  AGGGACCAGCTTGAACAGGCCCTCGATTGCGAGATCTACGGGGCCTGCTACTCCATAGAA
      TCCCTGGTCGAACTTGTCCGGGAGCTAACGCTCTAGATGCCCCGGACGATGAGGTATCTT
                                     ^
      4893 BGL2,

      ProLeuAspLeuProProIleIleGlnArgLeuHisGlyLeuSerAlaPheSerLeuHis
4922  CCACTGGATCTACCTCCAATCATTCAAAGACTCCATGGCCTCAGCGCATTTTCACTCCAC
      GGTGACCTAGATGGAGGTTAGTAAGTTTCTGAGGTACCGGAGTCGCGTAAAAGTGAGGTG
                                      ^
      4954 NCOI,

      SerTyrSerProGlyGluIleAsnArgValAlaAlaCysLeuArgLysLeuGlyValPro
4982  AGTTACTCTCCAGGTGAAATCAATAGGGTGGCCGCATGCCTCAGAAAACTTGGGGTACCG
      TCAATGAGAGGTCCACTTTAGTTATCCCACCGGCGTACGGAGTCTTTTGAACCCCATGGC
                                       ^                   ^
      5015 SPHI, 5035 KPNI,
```

FIG. 18H

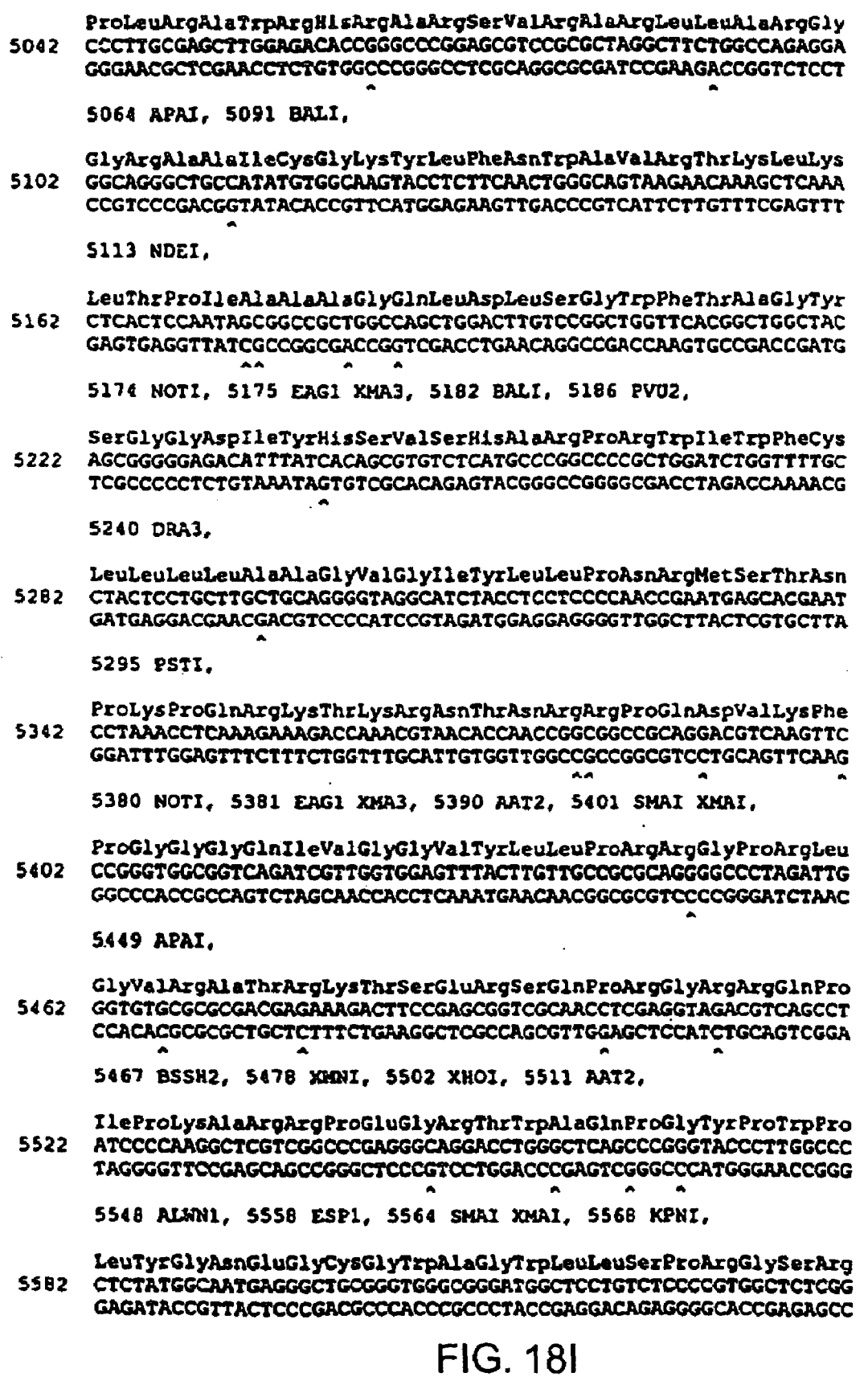

```
     ProLeuArgAlaTrpArgHisArgAlaArgSerValArgAlaArgLeuLeuAlaArgGly
5042 CCCTTGCGAGCTTGGAGACACCGGGCCCGGAGCGTCCGCGCTAGGCTTCTGGCCAGAGGA
     GGGAACGCTCGAACCTCTGTGGCCCGGGCCTCGCAGGCGCGATCCGAAGACCGGTCTCCT

     5064 APAI, 5091 BALI,

     GlyArgAlaAlaIleCysGlyLysTyrLeuPheAsnTrpAlaValArgThrLysLeuLys
5102 GGCAGGGCTGCCATATGTGGCAAGTACCTCTTCAACTGGGCAGTAAGAACAAAGCTCAAA
     CCGTCCCGACGGTATACACCGTTCATGGAGAAGTTGACCCGTCATTCTTGTTTCGAGTTT

     5113 NDEI,

     LeuThrProIleAlaAlaAlaGlyGlnLeuAspLeuSerGlyTrpPheThrAlaGlyTyr
5162 CTCACTCCAATAGCGGCCGCTGGCCAGCTGGACTTGTCCGGCTGGTTCACGGCTGGCTAC
     GAGTGAGGTTATCGCCGGCGACCGGTCGACCTGAACAGGCCGACCAAGTGCCGACCGATG

     5174 NOTI, 5175 EAG1 XMA3, 5182 BALI, 5186 PVU2,

     SerGlyGlyAspIleTyrHisSerValSerHisAlaArgProArgTrpIleTrpPheCys
5222 AGCGGGGGAGACATTTATCACAGCGTGTCTCATGCCCGGCCCCGCTGGATCTGGTTTTGC
     TCGCCCCCTCTGTAAATAGTGTCGCACAGAGTACGGGCCGGGGCGACCTAGACCAAAACG

     5240 DRA3,

     LeuLeuLeuLeuAlaAlaGlyValGlyIleTyrLeuLeuProAsnArgMetSerThrAsn
5282 CTACTCCTGCTTGCTGCAGGGGTAGGCATCTACCTCCTCCCCAACCGAATGAGCACGAAT
     GATGAGGACGAACGACGTCCCCATCCGTAGATGGAGGAGGGGTTGGCTTACTCGTGCTTA

     5295 PSTI,

     ProLysProGlnArgLysThrLysArgAsnThrAsnArgArgProGlnAspValLysPhe
5342 CCTAAACCTCAAAGAAAGACCAAACGTAACACCAACCGGCGGCCGCAGGACGTCAAGTTC
     GGATTTGGAGTTTCTTTCTGGTTTGCATTGTGGTTGGCCGCCGGCGTCCTGCAGTTCAAG

     5380 NOTI, 5381 EAG1 XMA3, 5390 AAT2, 5401 SMAI XMAI,

     ProGlyGlyGlyGlnIleValGlyGlyValTyrLeuLeuProArgArgGlyProArgLeu
5402 CCGGGTGGCGGTCAGATCGTTGGTGGAGTTTACTTGTTGCCGCGCAGGGGCCCTAGATTG
     GGCCCACCGCCAGTCTAGCAACCACCTCAAATGAACAACGGCGCGTCCCCGGGATCTAAC

     5449 APAI,

     GlyValArgAlaThrArgLysThrSerGluArgSerGlnProArgGlyArgArgGlnPro
5462 GGTGTGCGCGCGACGAGAAAGACTTCCGAGCGGTCGCAACCTCGAGGTAGACGTCAGCCT
     CCACACGCGCGCTGCTCTTTCTGAAGGCTCGCCAGCGTTGGAGCTCCATCTGCAGTCGGA

     5467 BSSH2, 5478 XMNI, 5502 XHOI, 5511 AAT2,

     IleProLysAlaArgArgProGluGlyArgThrTrpAlaGlnProGlyTyrProTrpPro
5522 ATCCCCAAGGCTCGTCGGCCCGAGGGCAGGACCTGGGCTCAGCCCGGGTACCCTTGGCCC
     TAGGGGTTCCGAGCAGCCGGGCTCCCGTCCTGGACCCGAGTCGGGCCCATGGGAACCGGG

     5548 ALWN1, 5558 ESP1, 5564 SMAI XMAI, 5568 KPNI,

     LeuTyrGlyAsnGluGlyCysGlyTrpAlaGlyTrpLeuLeuSerProArgGlySerArg
5582 CTCTATGGCAATGAGGGCTGCGGGTGGGCGGGATGGCTCCTGTCTCCCCGTGGCTCTCGG
     GAGATACCGTTACTCCCGACGCCCACCCGCCCTACCGAGGACAGAGGGGCACCGAGAGCC
```

FIG. 18I

```
      ProSerTrpGlyProThrAspProArgArgArgSerArgAsnLeuGlyLysValIleAsp
5642  CCTAGCTGGGGCCCCACAGACCCCCGGCGTAGGTCGCGCAATTTGGGTAAGGTCATCGAT
      GGATCGACCCCGGGGTGTCTGGGGGCCGCATCCAGCGCGTTAAACCCATTCCAGTAGCTA
                   ^                                         ^
      5650 APAI, 5696 CLAI,

      ThrLeuThrCysGlyPheAlaAspLeuMetGlyTyrIleProLeuValGlyAlaProLeu
5702  ACCCTTACGTGCGGCTTCGCCGACCTCATGGGGTACATACCGCTCGTCGGCGCCCCTCTT
      TGGGAATGCACGCCGAAGCGGCTGGAGTACCCCATGTATGGCGAGCAGCCGCGGGGAGAA
                                  ^                    ^       ^
      5724 HGIE2, 5750 KAS1 NARI, 5756 ECON1,

      GlyGlyAlaAlaArgAlaLeuAlaHisGlyValArgValLeuGluAspGlyValAsnTyr
5762  GGAGGCGCTGCCAGGGCCCTGGCGCATGGCGTCCGGGTTCTGGAAGACGGCGTGAACTAT
      CCTCCGCGACGGTCCCGGGACCGCGTACCGCAGGCCCAAGACCTTCTGCCGCACTTGATA
                ^  ^
      5772 BSTXI, 5775 APAI,

      AlaThrGlyAsnLeuProGlyCysSerOC AM
5822  GCAACAGGGAACCTTCCTGGTTGCTCTTAATAGTCGAC
      CGTTGTCCCTTGGAAGGACCAACGAGAATTATCAGCTG
                                    ^
      5854 SALI,
```

FIG. 18J

```
                       MetAlaAlaTyrAlaAlaGlnGlyTyrLysValLeuValLeuAsn
  2  AGCTTACAAAACAAAATGGCTGCATATGCAGCTCAGGGCTATAAGGTGCTAGTACTCAAC
     TCGAATGTTTTGTTTTACCGACGTATACGTCGAGTCCCGATATTCCACGATCATGAGTTG
     ^                       ^                              ^
     1 HIND3, 24 NDEI, 52 SCAI,

     ProSerValAlaAlaThrLeuGlyPheGlyAlaTyrMetSerLysAlaHisGlyIleAsp
 62  CCCTCTGTTGCTGCAACACTGGGCTTTGGTGCTTACATGTCCAAGGCTCATGGGATCGAT
     GGGAGACAACGACGTTGTGACCCGAAACCACGAATGTACAGGTTCCGAGTACCCTAGCTA
                                                             ^
     116 CLAI,

     ProAsnIleArgThrGlyValArgThrIleThrThrGlySerProIleThrTyrSerThr
122  CCTAACATCAGGACCGGGGTGAGAACAATTACCACTGGCAGCCCCATCACGTACTCCACC
     GGATTGTAGTCCTGGCCCCACTCTTGTTAATGGTGACCGTCGGGGTAGTGCATGAGGTGG

     TyrGlyLysPheLeuAlaAspGlyGlyCysSerGlyGlyAlaTyrAspIleIleIleCys
182  TACGGCAAGTTCCTTGCCGACGGCGGGTGCTCGGGGGGCGCTTATGACATAATAATTTGT
     ATGCCGTTCAAGGAACGGCTGCCGCCCACGAGCCCCCCGCGAATACTGTATTATTAAACA

     AspGluCysHisSerThrAspAlaThrSerIleLeuGlyIleGlyThrValLeuAspGln
242  GACGAGTGCCACTCCACGGATGCCACATCCATCTTGGGCATTGGCACTGTCCTTGACCAA
     CTGCTCACGGTGAGGTGCCTACGGTGTAGGTAGAACCCGTAACCGTGACAGGAACTGGTT

     AlaGluThrAlaGlyAlaArgLeuValValLeuAlaThrAlaThrProProGlySerVal
302  GCAGAGACTGCGGGGGCGAGACTGGTTGTGCTCGCCACCGCCACCCCTCCGGGCTCCGTC
     CGTCTCTGACGCCCCCGCTCTGACCAACACGAGCGGTGGCGGTGGGGAGGCCCGAGGCAG
      ^
     303 ALWN1,

     ThrValProHisProAsnIleGluGluValAlaLeuSerThrThrGlyGluIleProPhe
362  ACTGTGCCCCATCCCAACATCGAGGAGGTTGCTCTGTCCACCACCGGAGAGATCCCTTTT
     TGACACGGGGTAGGGTTGTAGCTCCTCCAACGAGACAGGTGGTGGCCTCTCTAGGGAAAA

     TyrGlyLysAlaIleProLeuGluValIleLysGlyGlyArgHisLeuIlePheCysHis
422  TACGGCAAGGCTATCCCCCTCGAAGTAATCAAGGGGGGGAGACATCTCATCTTCTGTCAT
     ATGCCGTTCCGATAGGGGGAGCTTCATTAGTTCCCCCCCTCTGTAGAGTAGAAGACAGTA
```

FIG. 21A

SerLysLysLysCysAspGluLeuAlaAlaLysLeuValAlaLeuGlyIleAsnAlaVal
482 TCAAAGAAGAAGTGCGACGAACTCGCCGCAAAGCTGGTCGCATTGGGCATCAATGCCGTG
AGTTTCTTCTTCACGCTGCTTGAGCGGCGTTTCGACCAGCGTAACCCGTAGTTACGGCAC

AlaTyrTyrArgGlyLeuAspValSerValIleProThrSerGlyAspValValValVal
542 GCCTACTACCGCGGTCTTGACGTGTCCGTCATCCCGACCAGCGGCGATGTTGTCGTCGTG
CGGATGATGGCGCCAGAACTGCACAGGCAGTAGGGCTGGTCGCCGCTACAACAGCAGCAC
^ ^

550 SAC2, 560 DRD1,

AlaThrAspAlaLeuMetThrGlyTyrThrGlyAspPheAspSerValIleAspCysAsn
602 GCAACCGATGCCCTCATGACCGGCTATACCGGCGACTTCGACTCGGTGATAGACTGCAAT
CGTTGGCTACGGGAGTACTGGCCGATATGGCCGCTGAAGCTGAGCCACTATCTGACGTTA
^

615 BSPH1,

ThrCysValThrGlnThrValAspPheSerLeuAspProThrPheThrIleGluThrIle
662 ACGTGTGTCACCCAGACAGTCGATTTCAGCCTTGACCCTACCTTCACCATTGAGACAATC
TGCACACAGTGGGTCTGTCAGCTAAAGTCGGAACTGGGATGGAAGTGGTAACTCTGTTAG

ThrLeuProGlnAspAlaValSerArgThrGlnArgArgGlyArgThrGlyArgGlyLys
722 ACGCTCCCCCAAGATGCTGTCTCCCGCACTCAACGTCGGGGCAGGACTGGCAGGGGGAAG
TGCGAGGGGGTTCTACGACAGAGGGCGTGAGTTGCAGCCCCGTCCTGACCGTCCCCCTTC

ProGlyIleTyrArgPheValAlaProGlyGluArgProSerGlyMetPheAspSerSer
782 CCAGGCATCTACAGATTTGTGGCACCGGGGGAGCGCCCCTCCGGCATGTTCGACTCGTCC
GGTCCGTAGATGTCTAAACACCGTGGCCCCCTCGCGGGGAGGCCGTACAAGCTGAGCAGG
^ ^

816 BGLI, 833 DRD1,

ValLeuCysGluCysTyrAspAlaGlyCysAlaTrpTyrGluLeuThrProAlaGluThr
842 GTCCTCTGTGAGTGCTATGACGCAGGCTGTGCTTGGTATGAGCTCACGCCCGCCGAGACT
CAGGAGACACTCACGATACTGCGTCCGACACGAACCATACTCGAGTGCGGGCGGCTCTGA
^

881 SACI,

ThrValArgLeuArgAlaTyrMetAsnThrProGlyLeuProValCysGlnAspHisLeu
902 ACAGTTAGGCTACGAGCGTACATGAACACCCCGGGGCTTCCCGTGTGCCAGGACCATCTT
TGTCAATCCGATGCTCGCATGTACTTGTGGGGCCCCGAAGGGCACACGGTCCTGGTAGAA
^

931 SMAI XMAI,

GluPheTrpGluGlyValPheThrGlyLeuThrHisIleAspAlaHisPheLeuSerGln
962 GAATTTTGGGAGGGCGTCTTTACAGGCCTCACTCATATAGATGCCCACTTTCTATCCCAG
CTTAAAACCCTCCCGCAGAAATGTCCGGAGTGAGTATATCTACGGGTGAAAGATAGGGTC
^

985 STUI,

ThrLysGlnSerGlyGluAsnLeuProTyrLeuValAlaTyrGlnAlaThrValCysAla
1022 ACAAAGCAGAGTGGGGAGAACCTTCCTTACCTGGTAGCGTACCAAGCCACCGTGTGCGCT
TGTTTCGTCTCACCCCTCTTGGAAGGAATGGACCATCGCATGGTTCGGTGGCACACGCGA
^

1069 DRA3,

ArgAlaGlnAlaProProProSerTrpAspGlnMetTrpLysCysLeuIleArgLeuLys
1082 AGGGCTCAAGCCCCTCCCCCATCGTGGGACCAGATGTGGAAGTGTTTGATTCGCCTCAAG

FIG. 21B

TCCCGAGTTCGGGGAGGGGGTAGCACCCTGGTCTACACCTTCACAAACTAAGCGGAGTTC

ProThrLeuHisGlyProThrProLeuLeuTyrArgLeuGlyAlaValGlnAsnGluIle
1142 CCCACCCTCCATGGGCCAACACCCCTGCTATACAGACTGGGCGCTGTTCAGAATGAAATC
GGGTGGGAGGTACCCGGTTGTGGGGACGATATGTCTGACCCGCGACAAGTCTTACTTTAG
^
1150 NCOI,

ThrLeuThrHisProValThrLysTyrIleMetThrCysMetSerAlaAspLeuGluVal
1202 ACCCTGACGCACCCAGTCACCAAATACATCATGACATGCATGTCGGCCGACCTGGAGGTC
TGGGACTGCGTGGGTCAGTGGTTTATGTAGTACTGTACGTACAGCCGGCTGGACCTCCAG
^ ^ ^ ^ ^
1230 BSPH1, 1234 DRD1, 1237 AVA3, 1245 EAG1 XMA3, 1250 DRD1,

ValThrSerThrTrpValLeuValGlyGlyValLeuAlaAlaLeuAlaAlaTyrCysLeu
1262 GTCACGAGCACCTGGGTGCTCGTTGGCGGCGTCCTGGCTGCTTTGGCCGCGTATTGCCTG
CAGTGCTCGTGGACCCACGAGCAACCGCCGCAGGACCGACGAAACCGGCGCATAACGGAC

SerThrGlyCysValValIleValGlyArgValValLeuSerGlyLysProAlaIleIle
1322 TCAACAGGCTGCGTGGTCATAGTGGGCAGGGTCGTCTTGTCCGGGAAGCCGGCAATCATA
AGTTGTCCGACGCACCAGTATCACCCGTCCCAGCAGAACAGGCCCTTCGGCCGTTAGTAT
^
1369 NAEI,

ProAspArgGluValLeuTyrArgGluPheAspGluMetGluGluCysSerGlnHisLeu
1382 CCTGACAGGGAAGTCCTCTACCGAGAGTTCGATGAGATGGAAGAGTGCTCTCAGCACTTA
GGACTGTCCCTTCAGGAGATGGCTCTCAAGCTACTCTACCTTCTCACGAGAGTCGTGAAT
^
1385 DRD1,

ProTyrIleGluGlnGlyMetMetLeuAlaGluGlnPheLysGlnLysAlaLeuGlyLeu
1442 CCGTACATCGAGCAAGGGATGATGCTCGCCGAGCAGTTCAAGCAGAAGGCCCTCGGCCTC
GGCATGTAGCTCGTTCCCTACTACGAGCGGCTCGTCAAGTTCGTCTTCCGGGAGCCGGAG

LeuGlnThrAlaSerArgGlnAlaGluValIleAlaProAlaValGlnThrAsnTrpGln
1502 CTGCAGACCGCGTCCCGTCAGGCAGAGGTTATCGCCCCTGCTGTCCAGACCAACTGGCAA
GACGTCTGGCGCAGGGCAGTCCGTCTCCAATAGCGGGGACGACAGGTCTGGTTGACCGTT
^ ^
1502 PSTI, 1507 TTH3I,

LysLeuGluThrPheTrpAlaLysHisMetTrpAsnPheIleSerGlyIleGlnTyrLeu
1562 AAACTCGAGACCTTCTGGGCGAAGCATATGTGGAACTTCATCAGTGGGATACAATACTTG
TTTGAGCTCTGGAAGACCCGCTTCGTATACACCTTGAAGTAGTCACCCTATGTTATGAAC
^ ^
1565 XHOI, 1586 NDEI,

AlaGlyLeuSerThrLeuProGlyAsnProAlaIleAlaSerLeuMetAlaPheThrAla
1622 GCGGGCTTGTCAACGCTGCCTGGTAACCCCGCCATTGCTTCATTGATGGCTTTTACAGCT
CGCCCGAACAGTTGCGACGGACCATTGGGGCGGTAACGAAGTAACTACCGAAAATGTCGA
^ ^
1643 BSTE2, 1677 ALWN1 PVU2,

AlaValThrSerProLeuThrThrSerGlnThrLeuLeuPheAsnIleLeuGlyGlyTrp
1682 GCTGTCACCAGCCCACTAACCACTAGCCAAACCCTCCTCTTCAACATATTGGGGGGGTGG
CGACAGTGGTCGGGTGATTGGTGATCGGTTTGGGAGGAGAAGTTGTATAACCCCCCCACC

FIG. 21C

```
     ValAlaAlaGlnLeuAlaAlaProGlyAlaAlaThrAlaPheValGlyAlaGlyLeuAla
1742 GTGGCTGCCCAGCTCGCCGCCCCCGGTGCCGCTACTGCCTTTGTGGGCGCTGGCTTAGCT
     CACCGACGGGTCGAGCGGCGGGGGCCACGGCGATGACGGAAACACCCGCGACCGAATCGA
                                                                ^
     1794 ESP1,

     GlyAlaAlaIleGlySerValGlyLeuGlyLysValLeuIleAspIleLeuAlaGlyTyr
1802 GGCGCCGCCATCGGCAGTGTTGGACTGGGGAAGGTCCTCATAGACATCCTTGCAGGGTAT
     CCGCGGCGGTAGCCGTCACAACCTGACCCCTTCCAGGAGTATCTGTAGGAACGTCCCATA
     ^
     1802 KAS1 NARI,

     GlyAlaGlyValAlaGlyAlaLeuValAlaPheLysIleMetSerGlyGluValProSer
1862 GGCGCGGGCGTGGCGGGAGCTCTTGTGGCATTCAAGATCATGAGCGGTGAGGTCCCCTCC
     CCGCGCCCGCACCGCCCTCGAGAACACCGTAAGTTCTAGTACTCGCCACTCCAGGGGAGG
                     ^                    ^
     1878 SACI, 1899 BSPH1,

     ThrGluAspLeuValAsnLeuLeuProAlaIleLeuSerProGlyAlaLeuValValGly
1922 ACGGAGGACCTGGTCAATCTACTGCCCGCCATCCTCTCGCCCGGAGCCCTCGTAGTCGGC
     TGCCTCCTGGACCAGTTAGATGACGGGCGGTAGGAGAGCGGGCCTCGGGAGCATCAGCCG
           ^
     1928 TTH3I,

     ValValCysAlaAlaIleLeuArgArgHisValGlyProGlyGluGlyAlaValGlnTrp
1982 GTGGTCTGTGCAGCAATACTGCGCCGGCACGTTGGCCCGGGCGAGGGGGCAGTGCAGTGG
     CACCAGACACGTCGTTATGACGCGGCCGTGCAACCGGGCCCGCTCCCCCGTCACGTCACC
                           ^            ^
     2004 NAEI, 2017 SMAI XMAI,

     MetAsnArgLeuIleAlaPheAlaSerArgGlyAsnHisValSerProThrHisTyrVal
2042 ATGAACCGGCTGATAGCCTTCGCCTCCCGGGGGAACCATGTTTCCCCCACGCACTACGTG
     TACTTGGCCGACTATCGGAAGCGGAGGGCCCCCTTGGTACAAAGGGGGTGCGTGATGCAC
                                 ^                         ^
     2067 SMAI XMAI, 2093 DRA3,

     ProGluSerAspAlaAlaAlaArgValThrAlaIleLeuSerSerLeuThrValThrGln
2102 CCGGAGAGCGATGCAGCTGCCCGCGTCACTGCCATACTCAGCAGCCTCACTGTAACCCAG
     GGCCTCTCGCTACGTCGACGGGCGCAGTGACGGTATGAGTCGTCGGAGTGACATTGGGTC
                  ^                                           ^
     2115 PVU2, 2159 ALWN1,

     LeuLeuArgArgLeuHisGlnTrpIleSerSerGluCysThrThrProCysSerGlySer
2162 CTCCTGAGGCGACTGCACCAGTGGATAAGCTCGGAGTGTACCACTCCATGCTCCGGTTCC
     GAGGACTCCGCTGACGTGGTCACCTATTCGAGCCTCACATGGTGAGGTACGAGGCCAAGG
       ^                                                        ^
     2164 MST2, 2220 ECON1,

     TrpLeuArgAspIleTrpAspTrpIleCysGluValLeuSerAspPheLysThrTrpLeu
2222 TGGCTAAGGGACATCTGGGACTGGATATGCGAGGTGTTGAGCGACTTTAAGACCTGGCTA
     ACCGATTCCCTGTAGACCCTGACCTATACGCTCCACAACTCGCTGAAATTCTGGACCGAT

     LysAlaLysLeuMetProGlnLeuProGlyIl ProPheValSerCysGlnArgGlyTyr
2282 AAAGCTAAGCTCATGCCACAGCTGCCTGGGATCCCCTTTGTGTCCTGCCAGCGCGGGTAT
     TTTCGATTCGAGTACGGTGTCGACGGACCCTAGGGGAAACACAGGACGGTCGCGCCCATA
        ^              ^     ^
     2285 ESP1, 2300 PVU2, 2310 BAMHI,
```

FIG. 21D

```
      LysGlyValTrpArgGlyAspGlyIleMetHisThrArgCysHisCysGlyAlaGluIle
2342  AAGGGGGTCTGGCGAGGGGACGGCATCATGCACACTCGCTGCCACTGTGGAGCTGAGATC
      TTCCCCCAGACCGCTCCCCTGCCGTAGTACGTGTGAGCGACGGTGACACCTCGACTCTAG

      ThrGlyHisValLysAsnGlyThrMetArgIleValGlyProArgThrCysArgAsnMet
2402  ACTGGACATGTCAAAAACGGGACGATGAGGATCGTCGGTCCTAGGACCTGCAGGAACATG
      TGACCTGTACAGTTTTTGCCCTGCTACTCCTAGCAGCCAGGATCCTGGACGTCCTTGTAC
                             ^               ^      ^^

      2425 BSAB1, 2441 AVR2, 2448 SSE83871, 2449 PSTI,

      TrpSerGlyThrPheProIleAsnAlaTyrThrThrGlyProCysThrProLeuProAla
2462  TGGAGTGGGACCTTCCCCATTAATGCCTACACCACGGGCCCCTGTACCCCCCTTCCTGCG
      ACCTCACCCTGGAAGGGGTAATTACGGATGTGGTGCCCGGGGACATGGGGGGAAGGACGC
                        ^                ^

      2480 ASE1, 2497 APAI,

      ProAsnTyrThrPheAlaLeuTrpArgValSerAlaGluGluTyrValGluIleArgGln
2522  CCGAACTACACGTTCGCGCTATGGAGGGTGTCTGCAGAGGAATACGTGGAGATAAGGCAG
      GGCTTGATGTGCAAGCGCGATACCTCCCACAGACGTCTCCTTATGCACCTCTATTCCGTC
                                     ^

      2553 PSTI,

      ValGlyAspPheHisTyrValThrGlyMetThrThrAspAsnLeuLysCysProCysGln
2582  GTGGGGGACTTCCACTACGTGACGGGTATGACTACTGACAATCTTAAATGCCCGTGCCAG
      CACCCCCTGAAGGTGATGCACTGCCCATACTGATGACTGTTAGAATTTACGGGCACGGTC
                  ^

      2594 DRA3,

      ValProSerProGluPhePheThrGluLeuAspGlyValArgLeuHisArgPheAlaPro
2642  GTCCCATCGCCCGAATTTTTCACAGAATTGGACGGGGTGCGCCTACATAGGTTTGCGCCC
      CAGGGTAGCGGGCTTAAAAAGTGTCTTAACCTGCCCCACGCGGATGTATCCAAACGCGGG

      ProCysLysProLeuLeuArgGluGluValSerPheArgValGlyLeuHisGluTyrPro
2702  CCCTGCAAGCCCTTGCTGCGGGAGGAGGTATCATTCAGAGTAGGACTCCACGAATACCCG
      GGGACGTTCGGGAACGACGCCCTCCTCCATAGTAAGTCTCATCCTGAGGTGCTTATGGGC
                                                             ^

      2757 HGIE2,

      ValGlySerGlnLeuProCysGluProGluProAspValAlaValLeuThrSerMetLeu
2762  GTAGGGTCGCAATTACCTTGCGAGCCCGAACCGGACGTGGCCGTGTTGACGTCCATGCTC
      CATCCCAGCGTTAATGGAACGCTCGGGCTTGGCCTGCACCGGCACAACTGCAGGTACGAG
                                                     ^

      2809 AAT2,

      ThrAspProSerHisIleThrAlaGluAlaAlaGlyArgArgLeuAlaArgGlySerPro
2822  ACTGATCCCTCCCATATAACAGCAGAGGCGGCCGGGCGAAGGTTGGCGAGGGGATCACCC
      TGACTAGGGAGGGTATATTGTCGTCTCCGCCGGCCCGCTTCCAACCGCTCCCCTAGTGGG
                                  ^

      2850 EAG1 XMA3,

      ProSerValAlaSerSerSerAlaSerGlnLeuSerAlaProSerLeuLysAlaThrCys
2882  CCCTCTGTGGCCAGCTCCTCGGCTAGCCAGCTATCCGCTCCATCTCTCAAGGCAACTTGC
      GGGAGACACCGGTCGAGGAGCCGATCGGTCGATAGGCGAGGTAGAGAGTTCCGTTGAACG
             ^             ^

      2889 BALI, 2903 NHEI,
```

FIG. 21E

```
     ThrAlaAsnHisAspSerProAspAlaGluLeuIleGluAlaAsnLeuLeuTrpArgGln
2942 ACCGCTAACCATGACTCCCCTGATGCTGAGCTCATAGAGGCCAACCTCCTATGGAGGCAG
     TGGCGATTGGTACTGAGGGGACTACGACTCGAGTATCTCCGGTTGGAGGATACCTCCGTC
                                             ^  ^
     2966 ESP1, 2969 SACI,

     GluMetGlyGlyAsnIleThrArgValGluSerGluAsnLysValValIleLeuAspSer
3002 GAGATGGGCGGCAACATCACCAGGGTTGAGTCAGAAAACAAAGTGGTGATTCTGGACTCC
     CTCTACCCGCCGTTGTAGTGGTCCCAACTCAGTCTTTTGTTTCACCACTAAGACCTGAGG

     PheAspProLeuValAlaGluGluAspGluArgGluIleSerValProAlaGluIleLeu
3062 TTCGATCCGCTTGTGGCGGAGGAGGACGAGCGGGAGATCTCCGTACCCGCAGAAATCCTG
     AAGCTAGGCGAACACCGCCTCCTCCTGCTCGCCCTCTAGAGGCATGGGCGTCTTTAGGAC
                                                  ^
     3096 BGL2,

     ArgLysSerArgArgPheAlaGlnAlaLeuProValTrpAlaArgProAspTyrAsnPro
3122 CGGAAGTCTCGGAGATTCGCCCAGGCCCTGCCCGTTTGGGCGCGGCCGGACTATAACCCC
     GCCTTCAGAGCCTCTAAGCGGGTCCGGGACGGGCAAACCCGCGCCGGCCTGATATTGGGG
                          ^                    ^
     3143 ALWN1, 3164 EAG1 XMA3,

     ProLeuValGluThrTrpLysLysProAspTyrGluProProValValHisGlyCysPro
3182 CCGCTAGTGGAGACGTGGAAAAAGCCCGACTACGAACCACCTGTGGTCCATGGCTGCCCG
     GGCGATCACCTCTGCACCTTTTTCGGGCTGATGCTTGGTGGACACCAGGTACCGACGGGC
                                                   ^           ^
     3217 HGIE2, 3229 NCOI,

     LeuProProProLysSerProProValProProProArgLysLysArgThrValValLeu
3242 CTTCCACCTCCAAAGTCCCCTCCTGTGCCTCCGCCTCGGAAGAAGCGGACGGTGGTCCTC
     GAAGGTGGAGGTTTCAGGGGAGGACACGGAGGCGGAGCCTTCTTCGCCTGCCACCAGGAG

     ThrGluSerThrLeuSerThrAlaLeuAlaGluLeuAlaThrArgSerPheGlySerSer
3302 ACTGAATCAACCCTATCTACTGCCTTGGCCGAGCTCGCCACCAGAAGCTTTGGCAGCTCC
     TGACTTAGTTGGGATAGATGACGGAACCGGCTCGAGCGGTGGTCTTCGAAACCGTCGAGG
                                               ^             ^
     3332 SACI, 3346 HIND3,

     SerThrSerGlyIleThrGlyAspAsnThrThrThrSerSerGluProAlaProSerGly
3362 TCAACTTCCGGCATTACGGGCGACAATACGACAACATCCTCTGAGCCCGCCCCTTCTGGC
     AGTTGAAGGCCGTAATGCCCGCTGTTATGCTGTTGTAGGAGACTCGGGCGGGGAAGACCG

     CysProProAspSerAspAlaGluSerTyrSerSerMetProProLeuGluGlyGluPro
3422 TGCCCCCCCGACTCCGACGCTGAGTCCTATTCCTCCATGCCCCCCCTGGAGGGGGAGCCT
     ACGGGGGGGCTGAGGCTGCGACTCAGGATAAGGAGGTACGGGGGGGACCTCCCCCTCGGA
                    ^
     3437 EAM11051,

     GlyAspProAspLeuSerAspGlySerTrpSerThrValSerSerGluAlaAsnAlaGlu
3482 GGGGATCCGGATCTTAGCGACGGGTCATGGTCAACGGTCAGTAGTGAGGCCAACGCGGAG
     CCCCTAGGCCTAGAATCGCTGCCCAGTACCAGTTGCCAGTCATCACTCCGGTTGCGCCTC
       ^^ ^
     3484 BAMHI, 3485 BSAB1, 3487 BSPE1,

     AspValValCysCysS rMetSerTyrS rTrpThrGlyAlaLeuValThrProCysAla
3542 GATGTCGTGTGCTGCTCAATGTCTTACTCTTGGACAGGCGCACTCGTCACCCCGTGCGCC
     CTACAGCACACGACGAGTTACAGAATGAGAACCTGTCCGCGTGAGCAGTGGGGCACGCGG
```

FIG. 21F

```
      3589 DRA3, 3600 SAC2,

      AlaGluGluGlnLysLeuPr IleAsnAlaLeuSerAsnSerLeuLeuArgHisHisAsn
3602  GCGGAAGAACAGAAACTGCCCATCAATGCACTAAGCAACTCGTTGCTACGTCACCACAAT
      CGCCTTCTTGTCTTTGACGGGTAGTTACGTGATTCGTTGAGCAACGATGCAGTGGTGTTA
               ^                                           ^
      3611 ALWN1, 3655 PFLM1,

      LeuValTyrSerThrThrSerArgSerAlaCysGlnArgGlnLysLysValThrPheAsp
3662  TTGGTGTATTCCACCACCTCACGCAGTGCTTGCCAAAGGCAGAAGAAAGTCACATTTGAC
      AACCACATAAGGTGGTGGAGTGCGTCACGAACGGTTTCCGTCTTCTTTCAGTGTAAACTG
                         ^
      3681 DRA3,

      ArgLeuGlnValLeuAspSerHisTyrGlnAspValLeuLysGluValLysAlaAlaAla
3722  AGACTGCAAGTTCTGGACAGCCATTACCAGGACGTACTCAAGGAGGTTAAAGCAGCGGCG
      TCTGACGTTCAAGACCTGTCGGTAATGGTCCTGCATGAGTTCCTCCAATTTCGTCGCCGC

      SerLysValLysAlaAsnLeuLeuSerValGluGluAlaCysSerLeuThrProProHis
3782  TCAAAAGTGAAGGCTAACTTGCTATCCGTAGAGGAAGCTTGCAGCCTGACGCCCCCACAC
      AGTTTTCACTTCCGATTGAACGATAGGCATCTCCTTCGAACGTCGGACTGCGGGGGTGTG
                                        ^
      3816 HIND3,

      SerAlaLysSerLysPheGlyTyrGlyAlaLysAspValArgCysHisAlaArgLysAla
3842  TCAGCCAAATCCAAGTTTGGTTATGGGGCAAAAGACGTCCGTTGCCATGCCAGAAAGGCC
      AGTCGGTTTAGGTTCAAACCAATACCCCGTTTTCTGCAGGCAACGGTACGGTCTTTCCGG
                                       ^              ^
      3875 AAT2, 3890 BGLI,

      ValThrHisIleAsnSerValTrpLysAspLeuLeuGluAspAsnValThrProIleAsp
3902  GTAACCCACATCAACTCCGTGTGGAAAGACCTTCTGGAAGACAATGTAACACCAATAGAC
      CATTGGGTGTAGTTGAGGCACACCTTTCTGGAAGACCTTCTGTTACATTGTGGTTATCTG

      ThrThrIleMetAlaLysAsnGluValPheCysValGlnProGluLysGlyGlyArgLys
3962  ACTACCATCATGGCTAAGAACGAGGTTTTCTGCGTTCAGCCTGAGAAGGGGGGTCGTAAG
      TGATGGTAGTACCGATTCTTGCTCCAAAAGACGCAAGTCGGACTCTTCCCCCCAGCATTC

      ProAlaArgLeuIleValPheProAspLeuGlyValArgValCysGluLysMetAlaLeu
4022  CCAGCTCGTCTCATCGTGTTCCCCGATCTGGGCGTGCGCGTGTGCGAAAAGATGGCTTTG
      GGTCGAGCAGAGTAGCACAAGGGGCTAGACCCGCACGCGCACACGCTTTTCTACCGAAAC

      TyrAspValValThrLysLeuProLeuAlaValMetGlySerSerTyrGlyPheGlnTyr
4082  TACGACGTGGTTACAAAGCTCCCCTTGGCCGTGATGGGAAGCTCCTACGGATTCCAATAC
      ATGCTGCACCAATGTTTCGAGGGGAACCGGCACTACCCTTCGAGGATGCCTAAGGTTATG

      SerProGlyGlnArgValGluPheLeuValGlnAlaTrpLysSerLysLysThrProMet
4142  TCACCAGGACAGCGGGTTGAATTCCTCGTGCAAGCGTGGAAGTCCAAGAAAACCCCAATG
      AGTGGTCCTGTCGCCCAACTTAAGGAGCACGTTCGCACCTTCAGGTTCTTTTGGGGTTAC
                        ^
      4160 ECORI,

      GlyPheSerTyrAspThrArgCysPheAspSerThrValThrGluSerAspIleArgThr
4202  GGGTTCTCGTATGATACCCGCTGCTTTGACTCCACAGTCACTGAGAGCGACATCCGTACG
      CCCAAGAGCATACTATGGGCGACGAAACTGAGGTGTCAGTGACTCTCGCTGTAGGCATGC
                                 ^      ^
```

FIG. 21G

```
     4229 DRD1, 4236 ALWN1,

     GluGluAlaIleTyrGlnCysCysAspLeuAspProGlnAlaArgValAlaIleLysSer
4262 GAGGAGGCAATCTACCAATGTTGTGACCTCGACCCCCAAGCCCGCGTGGCCATCAAGTCC
     CTCCTCCGTTAGATGGTTACAACACTGGAGCTGGGGGTTCGGGCGCACCGGTAGTTCAGG
                                                  ^         ^
     4301 BGLI, 4308 BALI,

     LeuThrGluArgLeuTyrValGlyGlyProLeuThrAsnSerArgGlyGluAsnCysGly
4322 CTCACCGAGAGGCTTTATGTTGGGGGCCCTCTTACCAATTCAAGGGGGGAGAACTGCGGC
     GAGTGGCTCTCCGAAATACAACCCCCGGGAGAATGGTTAAGTTCCCCCCTCTTGACGCCG
                                 ^
     4345 APAI,

     TyrArgArgCysArgAlaSerGlyValLeuThrThrSerCysGlyAsnThrLeuThrCys
4382 TATCGCAGGTGCCGCGCGAGCGGCGTACTGACAACTAGCTGTGGTAACACCCTCACTTGC
     ATAGCGTCCACGGCGCGCTCGCCGCATGACTGTTGATCGACACCATTGTGGGAGTGAACG

     TyrIleLysAlaArgAlaAlaCysArgAlaAlaGlyLeuGlnAspCysThrMetLeuVal
4442 TACATCAAGGCCCGGGCAGCCTGTCGAGCCGCAGGGCTCCAGGACTGCACCATGCTCGTG
     ATGTAGTTCCGGGCCCGTCGGACAGCTCGGCGTCCCGAGGTCCTGACGTGGTACGAGCAC
               ^
     4452 SMAI XMAI,

     CysGlyAspAspLeuValValIleCysGluSerAlaGlyValGlnGluAspAlaAlaSer
4502 TGTGGCGACGACTTAGTCGTTATCTGTGAAAGCGCGGGGGTCCAGGAGGACGCGGCGAGC
     ACACCGCTGCTGAATCAGCAATAGACACTTTCGCGCCCCCAGGTCCTCCTGCGCCGCTCG
          ^  ^
     4508 DRD1, 4511 TTH3I,

     LeuArgAlaPheThrGluAlaMetThrArgTyrSerAlaProProGlyAspProProGln
4562 CTGAGAGCCTTCACGGAGGCTATGACCAGGTACTCCGCCCCCCCTGGGGACCCCCCACAA
     GACTCTCGGAAGTGCCTCCGATACTGGTCCATGAGGCGGGGGGGACCCCTGGGGGGTGTT

     ProGluTyrAspLeuGluLeuIleThrSerCysSerSerAsnValSerValAlaHisAsp
4622 CCAGAATACGACTTGGAGCTCATAACATCATGCTCCTCCAACGTGTCAGTCGCCCACGAC
     GGTCTTATGCTGAACCTCGAGTATTGTAGTACGAGGAGGTTGCACAGTCAGCGGGTGCTG
                    ^
     4637 SACI,

     GlyAlaGlyLysArgValTyrTyrLeuThrArgAspProThrThrProLeuAlaArgAla
4682 GGCGCTGGAAAGAGGGTCTACTACCTCACCCGTGACCCTACAACCCCCCTCGCGAGAGCT
     CCGCGACCTTTCTCCCAGATGATGGAGTGGGCACTGGGATGTTGGGGGGAGCGCTCTCGA
                                                       ^
     4731 NRUI,

     AlaTrpGluThrAlaArgHisThrProValAsnSerTrpLeuGlyAsnIleIleMetPhe
4742 GCGTGGGAGACAGCAAGACACACTCCAGTCAATTCCTGGCTAGGCAACATAATCATGTTT
     CGCACCCTCTGTCGTTCTGTGTGAGGTCAGTTAAGGACCGATCCGTTGTATTAGTACAAA

     AlaProThrLeuTrpAlaArgMetIleLeuMetThrHisPhePheSerValLeuIleAla
4802 GCCCCCACACTGTGGGCGAGGATGATACTGATGACCCATTTCTTTAGCGTCCTTATAGCC
     CGGGGGTGTGACACCCGCTCCTACTATGACTACTGGGTAAAGAAATCGCAGGAATATCGG
        ^^
     4806 PFLM1, 4807 DRA3,

     ArgAspGlnLeuGluGlnAlaLeuAspCysGluIleTyrGlyAlaCysTyrSerIleGlu
```

FIG. 21H

4862 AGGGACCAGCTTGAACAGGCCCTCGATTGCGAGATCTACGGGGCCTGCTACTCCATAGAA
TCCCTGGTCGAACTTGTCCGGGAGCTAACGCTCTAGATGCCCCGGACGATGAGGTATCTT
^

4893 BGL2,

ProLeuAspLeuProProIleIleGlnArgLeuHisGlyLeuSerAlaPheSerLeuHis
4922 CCACTGGATCTACCTCCAATCATTCAAAGACTCCATGGCCTCAGCGCATTTTCACTCCAC
GGTGACCTAGATGGAGGTTAGTAAGTTTCTGAGGTACCGGAGTCGCGTAAAAGTGAGGTG
^

4954 NCOI,

SerTyrSerProGlyGluIleAsnArgValAlaAlaCysLeuArgLysLeuGlyValPro
4982 AGTTACTCTCCAGGTGAAATCAATAGGGTGGCCGCATGCCTCAGAAAACTTGGGGTACCG
TCAATGAGAGGTCCACTTTAGTTATCCCACCGGCGTACGGAGTCTTTTGAACCCCATGGC
^ ^

5015 SPHI, 5035 KPNI,

ProLeuArgAlaTrpArgHisArgAlaArgSerValArgAlaArgLeuLeuAlaArgGly
5042 CCCTTGCGAGCTTGGAGACACCGGGCCCGGAGCGTCCGCGCTAGGCTTCTGGCCAGAGGA
GGGAACGCTCGAACCTCTGTGGCCCGGGCCTCGCAGGCGCGATCCGAAGACCGGTCTCCT
^ ^

5064 APAI, 5091 BALI,

GlyArgAlaAlaIleCysGlyLysTyrLeuPheAsnTrpAlaValArgThrLysLeuLys
5102 GGCAGGGCTGCCATATGTGGCAAGTACCTCTTCAACTGGGCAGTAAGAACAAAGCTCAAA
CCGTCCCGACGGTATACACCGTTCATGGAGAAGTTGACCCGTCATTCTTGTTTCGAGTTT
^

5113 NDEI,

LeuThrProIleAlaAlaAlaGlyGlnLeuAspLeuSerGlyTrpPheThrAlaGlyTyr
5162 CTCACTCCAATAGCGGCCGCTGGCCAGCTGGACTTGTCCGGCTGGTTCACGGCTGGCTAC
GAGTGAGGTTATCGCCGGCGACCGGTCGACCTGAACAGGCCGACCAAGTGCCGACCGATG
^^ ^ ^

5174 NOTI, 5175 EAG1 XMA3, 5182 BALI, 5186 PVU2,

SerGlyGlyAspIleTyrHisSerValSerHisAlaArgProArgTrpIleTrpPheCys
5222 AGCGGGGGAGACATTTATCACAGCGTGTCTCATGCCCGGCCCCGCTGGATCTGGTTTTGC
TCGCCCCCTCTGTAAATAGTGTCGCACAGAGTACGGGCCGGGGCGACCTAGACCAAAACG
^

5240 DRA3,

LeuLeuLeuLeuAlaAlaGlyValGlyIleTyrLeuLeuProAsnArgMetSerThrAsn
5282 CTACTCCTGCTTGCTGCAGGGGTAGGCATCTACCTCCTCCCCAACCGAATGAGCACGAAT
GATGAGGACGAACGACGTCCCCATCCGTAGATGGAGGAGGGGTTGGCTTACTCGTGCTTA
^

5295 PSTI,

ProLysProGlnArgLysThrLysArgAsnThrAsnArgArgProGlnAspValLysPhe
5342 CCTAAACCTCAAAGAAAGACCAAACGTAACACCAACCGGCGGCCGCAGGACGTCAAGTTC
GGATTTGGAGTTTCTTTCTGGTTTGCATTGTGGTTGGCCGCCGGCGTCCTGCAGTTCAAG
^^ ^ ^

5380 NOTI, 5381 EAG1 XMA3, 5390 AAT2, 5401 SMAI XMAI,

ProGlyGlyGlyGlnIleValGlyGlyValTyrLeuLeuProArgArgGlyProArgLeu
5402 CCGGGTGGCGGTCAGATCGTTGGTGGAGTTTACTTGTTGCCGCGCAGGGGCCCTAGATTG
GGCCCACCGCCAGTCTAGCAACCACCTCAAATGAACAACGGCGCGTCCCCGGGATCTAAC
^

FIG. 21I

```
     5449 APAI,

     GlyValArgAlaThrArgLysThrSerGluArgSerGlnProArgGlyArgArgGlnPro
5462 GGTGTGCGCGCGACGAGAAAGACTTCCGAGCGGTCGCAACCTCGAGGTAGACGTCAGCCT
     CCACACGCGCGCTGCTCTTTCTGAAGGCTCGCCAGCGTTGGAGCTCCATCTGCAGTCGGA
         ^            ^                            ^          ^
     5467 BSSH2, 5478 XMNI, 5502 XHOI, 5511 AAT2,

     IleProLysAlaArgArgProGluGlyArgThrTrpAlaGlnProGlyTyrProTrpPro
5522 ATCCCCAAGGCTCGTCGGCCCGAGGGCAGGACCTGGGCTCAGCCCGGGTACCCTTGGCCC
     TAGGGGTTCCGAGCAGCCGGGCTCCCGTCCTGGACCCGAGTCGGGCCCATGGGAACCGGG
                                   ^           ^      ^    ^
     5548 ALWN1, 5558 ESP1, 5564 SMAI XMAI, 5568 KPNI,

     LeuTyrGlyAsnGluGlyCysGlyTrpAlaGlyTrpLeuLeuSerProArgGlySerArg
5582 CTCTATGGCAATGAGGGCTGCGGGTGGGCGGGATGGCTCCTGTCTCCCCGTGGCTCTCGG
     GAGATACCGTTACTCCCGACGCCCACCCGCCCTACCGAGGACAGAGGGGCACCGAGAGCC

     ProSerTrpGlyProThrAspProArgArgArgSerArgAsnLeuGlyLysValIleAsp
5642 CCTAGCTGGGGCCCCACAGACCCCCGGCGTAGGTCGCGCAATTTGGGTAAGGTCATCGAT
     GGATCGACCCCGGGGTGTCTGGGGGCCGCATCCAGCGCGTTAAACCCATTCCAGTAGCTA
             ^                                                ^
     5650 APAI, 5696 CLAI,

     ThrLeuThrCysGlyPheAlaAspLeuMetGlyTyrIleProLeuValOC AM
5702 ACCCTTACGTGCGGCTTCGCCGACCTCATGGGGTACATACCGCTCGTCTAATAGTCGAC
     TGGGAATGCACGCCGAAGCGGCTGGAGTACCCCATGTATGGCGAGCAGATTATCAGCTG
                             ^                               ^
     5724 HGIE2, 5755 SALI,
```

FIG. 21J

```
                         MetAlaAlaTyrAlaAlaGlnGlyTyrLysValLeuValLeuAsn
  2  AGCTTACAAAACAAAATGGCTGCATATGCAGCTCAGGGCTATAAGGTGCTAGTACTCAAC
     TCGAATGTTTTGTTTTACCGACGTATACGTCGAGTCCCGATATTCCACGATCATGAGTTG
     ^                      ^                           ^
     1 HIND3, 24 NDEI, 52 SCAI,

     ProSerValAlaAlaThrLeuGlyPheGlyAlaTyrMetSerLysAlaHisGlyIleAsp
 62  CCCTCTGTTGCTGCAACACTGGGCTTTGGTGCTTACATGTCCAAGGCTCATGGGATCGAT
     GGGAGACAACGACGTTGTGACCCGAAACCACGAATGTACAGGTTCCGAGTACCCTAGCTA
                                                             ^
     116 CLAI,

     ProAsnIleArgThrGlyValArgThrIleThrThrGlySerProIleThrTyrSerThr
122  CCTAACATCAGGACCGGGGTGAGAACAATTACCACTGGCAGCCCCATCACGTACTCCACC
     GGATTGTAGTCCTGGCCCCACTCTTGTTAATGGTGACCGTCGGGGTAGTGCATGAGGTGG

     TyrGlyLysPheLeuAlaAspGlyGlyCysSerGlyGlyAlaTyrAspIleIleIleCys
182  TACGGCAAGTTCCTTGCCGACGGCGGGTGCTCGGGGGGCGCTTATGACATAATAATTTGT
     ATGCCGTTCAAGGAACGGCTGCCGCCCACGAGCCCCCCGCGAATACTGTATTATTAAACA

     AspGluCysHisSerThrAspAlaThrSerIleLeuGlyIleGlyThrValLeuAspGln
242  GACGAGTGCCACTCCACGGATGCCACATCCATCTTGGGCATTGGCACTGTCCTTGACCAA
     CTGCTCACGGTGAGGTGCCTACGGTGTAGGTAGAACCCGTAACCGTGACAGGAACTGGTT

     AlaGluThrAlaGlyAlaArgLeuValValLeuAlaThrAlaThrProProGlySerVal
302  GCAGAGACTGCGGGGGCGAGACTGGTTGTGCTCGCCACCGCCACCCCTCCGGGCTCCGTC
     CGTCTCTGACGCCCCCGCTCTGACCAACACGAGCGGTGGCGGTGGGGAGGCCCGAGGCAG
      ^
     303 ALWN1,

     ThrValProHisProAsnIleGluGluValAlaLeuSerThrThrGlyGluIleProPhe
362  ACTGTGCCCCATCCCAACATCGAGGAGGTTGCTCTGTCCACCACCGGAGAGATCCCTTTT
     TGACACGGGGTAGGGTTGTAGCTCCTCCAACGAGACAGGTGGTGGCCTCTCTAGGGAAAA

     TyrGlyLysAlaIleProLeuGluValIleLysGlyGlyArgHisLeuIlePheCysHis
422  TACGGCAAGGCTATCCCCCTCGAAGTAATCAAGGGGGGGAGACATCTCATCTTCTGTCAT
     ATGCCGTTCCGATAGGGGGAGCTTCATTAGTTCCCCCCCTCTGTAGAGTAGAAGACAGTA
```

FIG. 22A

```
     SerLysLysLysCysAspGluLeuAlaAlaLysLeuValAlaLeuGlyIleAsnAlaVal
 482 TCAAAGAAGAAGTGCGACGAACTCGCCGCAAAGCTGGTCGCATTGGGCATCAATGCCGTG
     AGTTTCTTCTTCACGCTGCTTGAGCGGCGTTTCGACCAGCGTAACCCGTAGTTACGGCAC

     AlaTyrTyrArgGlyLeuAspValSerValIleProThrSerGlyAspValValValVal
 542 GCCTACTACCGCGGTCTTGACGTGTCCGTCATCCCGACCAGCGGCGATGTTGTCGTCGTG
     CGGATGATGGCGCCAGAACTGCACAGGCAGTAGGGCTGGTCGCCGCTACAACAGCAGCAC
               ^         ^
     550 SAC2, 560 DRD1,

     AlaThrAspAlaLeuMetThrGlyTyrThrGlyAspPheAspSerValIleAspCysAsn
 602 GCAACCGATGCCCTCATGACCGGCTATACCGGCGACTTCGACTCGGTGATAGACTGCAAT
     CGTTGGCTACGGGAGTACTGGCCGATATGGCCGCTGAAGCTGAGCCACTATCTGACGTTA
                  ^
     615 BSPH1,

     ThrCysValThrGlnThrValAspPheSerLeuAspProThrPheThrIleGluThrIle
 662 ACGTGTGTCACCCAGACAGTCGATTTCAGCCTTGACCCTACCTTCACCATTGAGACAATC
     TGCACACAGTGGGTCTGTCAGCTAAAGTCGGAACTGGGATGGAAGTGGTAACTCTGTTAG

     ThrLeuProGlnAspAlaValSerArgThrGlnArgArgGlyArgThrGlyArgGlyLys
 722 ACGCTCCCCCAAGATGCTGTCTCCCGCACTCAACGTCGGGGCAGGACTGGCAGGGGGAAG
     TGCGAGGGGGTTCTACGACAGAGGGCGTGAGTTGCAGCCCCGTCCTGACCGTCCCCCTTC

     ProGlyIleTyrArgPheValAlaProGlyGluArgProSerGlyMetPheAspSerSer
 782 CCAGGCATCTACAGATTTGTGGCACCGGGGGAGCGCCCCTCCGGCATGTTCGACTCGTCC
     GGTCCGTAGATGTCTAAACACCGTGGCCCCCTCGCGGGGAGGCCGTACAAGCTGAGCAGG
                                       ^                ^
     816 BGLI, 833 DRD1,

     ValLeuCysGluCysTyrAspAlaGlyCysAlaTrpTyrGluLeuThrProAlaGluThr
 842 GTCCTCTGTGAGTGCTATGACGCAGGCTGTGCTTGGTATGAGCTCACGCCCGCCGAGACT
     CAGGAGACACTCACGATACTGCGTCCGACACGAACCATACTCGAGTGCGGGCGGCTCTGA
                                            ^
     881 SACI,

     ThrValArgLeuArgAlaTyrMetAsnThrProGlyLeuProValCysGlnAspHisLeu
 902 ACAGTTAGGCTACGAGCGTACATGAACACCCCGGGGCTTCCCGTGTGCCAGGACCATCTT
     TGTCAATCCGATGCTCGCATGTACTTGTGGGGCCCCGAAGGGCACACGGTCCTGGTAGAA
                               ^
     931 SMAI XMAI,

     GluPheTrpGluGlyValPheThrGlyLeuThrHisIleAspAlaHisPheLeuSerGln
 962 GAATTTTGGGAGGGCGTCTTTACAGGCCTCACTCATATAGATGCCCACTTTCTATCCCAG
     CTTAAAACCCTCCCGCAGAAATGTCCGGAGTGAGTATATCTACGGGTGAAAGATAGGGTC
                         ^
     985 STUI,

     ThrLysGlnSerGlyGluAsnLeuProTyrLeuValAlaTyrGlnAlaThrValCysAla
1022 ACAAAGCAGAGTGGGGAGAACCTTCCTTACCTGGTAGCGTACCAAGCCACCGTGTGCGCT
     TGTTTCGTCTCACCCCTCTTGGAAGGAATGGACCATCGCATGGTTCGGTGGCACACGCGA
                                                ^
     1069 DRA3,

     ArgAlaGlnAlaProProProS rTrpAspGlnMetTrpLysCysLeuIleArgLeuLys
1082 AGGGCTCAAGCCCCTCCCCCATCGTGGGACCAGATGTGGAAGTGTTTGATTCGCCTCAAG
```

FIG. 22B

```
      TCCCGAGTTCGGGGAGGGGGTAGCACCCTGGTCTACACCTTCACAAACTAAGCGGAGTTC

      Pr ThrLeuHisGlyProThrPr LeuLeuTyrArgLeuGlyAlaValGlnAsnGluIle
1142  CCCACCCTCCATGGGCCAACACCCCTGCTATACAGACTGGGCGCTGTTCAGAATGAAATC
      GGGTGGGAGGTACCCGGTTGTGGGGACGATATGTCTGACCCGCGACAAGTCTTACTTTAG
              ^
      1150 NCOI,

      ThrLeuThrHisProValThrLysTyrIleMetThrCysMetSerAlaAspLeuGluVal
1202  ACCCTGACGCACCCAGTCACCAAATACATCATGACATGCATGTCGGCCGACCTGGAGGTC
      TGGGACTGCGTGGGTCAGTGGTTTATGTAGTACTGTACGTACAGCCGGCTGGACCTCCAG
                                    ^   ^   ^       ^   ^
      1230 BSPH1, 1234 DRD1, 1237 AVA3, 1245 EAG1 XMA3, 1250 DRD1,


      ValThrSerThrTrpValLeuValGlyGlyValLeuAlaAlaLeuAlaAlaTyrCysLeu
1262  GTCACGAGCACCTGGGTGCTCGTTGGCGGCGTCCTGGCTGCTTTGGCCGCGTATTGCCTG
      CAGTGCTCGTGGACCCACGAGCAACCGCCGCAGGACCGACGAAACCGGCGCATAACGGAC

      SerThrGlyCysValValIleValGlyArgValValLeuSerGlyLysProAlaIleIle
1322  TCAACAGGCTGCGTGGTCATAGTGGGCAGGGTCGTCTTGTCCGGGAAGCCGGCAATCATA
      AGTTGTCCGACGCACCAGTATCACCCGTCCCAGCAGAACAGGCCCTTCGGCCGTTAGTAT
                                                     ^
      1369 NAEI,

      ProAspArgGluValLeuTyrArgGluPheAspGluMetGluGluCysSerGlnHisLeu
1382  CCTGACAGGGAAGTCCTCTACCGAGAGTTCGATGAGATGGAAGAGTGCTCTCAGCACTTA
      GGACTGTCCCTTCAGGAGATGGCTCTCAAGCTACTCTACCTTCTCACGAGAGTCGTGAAT
         ^
      1385 DRD1,

      ProTyrIleGluGlnGlyMetMetLeuAlaGluGlnPheLysGlnLysAlaLeuGlyLeu
1442  CCGTACATCGAGCAAGGGATGATGCTCGCCGAGCAGTTCAAGCAGAAGGCCCTCGGCCTC
      GGCATGTAGCTCGTTCCCTACTACGAGCGGCTCGTCAAGTTCGTCTTCCGGGAGCCGGAG

      LeuGlnThrAlaSerArgGlnAlaGluValIleAlaProAlaValGlnThrAsnTrpGln
1502  CTGCAGACCGCGTCCCGTCAGGCAGAGGTTATCGCCCCTGCTGTCCAGACCAACTGGCAA
      GACGTCTGGCGCAGGGCAGTCCGTCTCCAATAGCGGGGACGACAGGTCTGGTTGACCGTT
      ^    ^
      1502 PSTI, 1507 TTH3I,

      LysLeuGluThrPheTrpAlaLysHisMetTrpAsnPheIleSerGlyIleGlnTyrLeu
1562  AAACTCGAGACCTTCTGGGCGAAGCATATGTGGAACTTCATCAGTGGGATACAATACTTG
      TTTGAGCTCTGGAAGACCCGCTTCGTATACACCTTGAAGTAGTCACCCTATGTTATGAAC
         ^                    ^
      1565 XHOI, 1586 NDEI,

      AlaGlyLeuSerThrLeuProGlyAsnProAlaIleAlaSerLeuMetAlaPheThrAla
1622  GCGGGCTTGTCAACGCTGCCTGGTAACCCCGCCATTGCTTCATTGATGGCTTTTACAGCT
      CGCCCGAACAGTTGCGACGGACCATTGGGGCGGTAACGAAGTAACTACCGAAAATGTCGA
                           ^                                  ^
      1643 BSTE2, 1677 ALWN1 PVU2,

      AlaValThrSerPr LeuThrThrSerGlnThrLeuLeuPheAsnIleLeuGlyGlyTrp
1682  GCTGTCACCAGCCCACTAACCACTAGCCAAACCCTCCTCTTCAACATATTGGGGGGGTGG
      CGACAGTGGTCGGGTGATTGGTGATCGGTTTGGGAGGAGAAGTTGTATAACCCCCCCACC
```

FIG. 22C

```
      ValAlaAlaGlnLeuAlaAlaProGlyAlaAlaThrAlaPheValGlyAlaGlyL uAla
1742  GTGGCTGCCCAGCTCGCCGCCCCCGGTGCCGCTACTGCCTTTGTGGGCGCTGGCTTAGCT
      CACCGACGGGTCGAGCGGCGGGGGCCACGGCGATGACGGAAACACCCGCGACCGAATCGA
                                                                 ^
      1794 ESP1,

      GlyAlaAlaIleGlySerValGlyLeuGlyLysValLeuIleAspIleLeuAlaGlyTyr
1802  GGCGCCGCCATCGGCAGTGTTGGACTGGGGAAGGTCCTCATAGACATCCTTGCAGGGTAT
      CCGCGGCGGTAGCCGTCACAACCTGACCCCTTCCAGGAGTATCTGTAGGAACGTCCCATA
      ^
      1802 KAS1 NARI,

      GlyAlaGlyValAlaGlyAlaLeuValAlaPheLysIleMetSerGlyGluValProSer
1862  GGCGCGGGCGTGGCGGGAGCTCTTGTGGCATTCAAGATCATGAGCGGTGAGGTCCCCTCC
      CCGCGCCCGCACCGCCCTCGAGAACACCGTAAGTTCTAGTACTCGCCACTCCAGGGGAGG
                        ^                    ^
      1878 SACI, 1899 BSPH1,

      ThrGluAspLeuValAsnLeuLeuProAlaIleLeuSerProGlyAlaLeuValValGly
1922  ACGGAGGACCTGGTCAATCTACTGCCCGCCATCCTCTCGCCCGGAGCCCTCGTAGTCGGC
      TGCCTCCTGGACCAGTTAGATGACGGGCGGTAGGAGAGCGGGCCTCGGGAGCATCAGCCG
            ^
      1928 TTH3I,

      ValValCysAlaAlaIleLeuArgArgHisValGlyProGlyGluGlyAlaValGlnTrp
1982  GTGGTCTGTGCAGCAATACTGCGCCGGCACGTTGGCCCGGGCGAGGGGGCAGTGCAGTGG
      CACCAGACACGTCGTTATGACGCGGCCGTGCAACCGGGCCCGCTCCCCCGTCACGTCACC
                            ^            ^
      2004 NAEI, 2017 SMAI XMAI,

      MetAsnArgLeuIleAlaPheAlaSerArgGlyAsnHisValSerProThrHisTyrVal
2042  ATGAACCGGCTGATAGCCTTCGCCTCCCGGGGGAACCATGTTTCCCCCACGCACTACGTG
      TACTTGGCCGACTATCGGAAGCGGAGGGCCCCCTTGGTACAAAGGGGGTGCGTGATGCAC
                          ^                          ^
      2067 SMAI XMAI, 2093 DRA3,

      ProGluSerAspAlaAlaAlaArgValThrAlaIleLeuSerSerLeuThrValThrGln
2102  CCGGAGAGCGATGCAGCTGCCCGCGTCACTGCCATACTCAGCAGCCTCACTGTAACCCAG
      GGCCTCTCGCTACGTCGACGGGCGCAGTGACGGTATGAGTCGTCGGAGTGACATTGGGTC
                   ^                                           ^
      2115 PVU2, 2159 ALWN1,

      LeuLeuArgArgLeuHisGlnTrpIleSerSerGluCysThrThrProCysSerGlySer
2162  CTCCTGAGGCGACTGCACCAGTGGATAAGCTCGGAGTGTACCACTCCATGCTCCGGTTCC
      GAGGACTCCGCTGACGTGGTCACCTATTCGAGCCTCACATGGTGAGGTACGAGGCCAAGG
        ^                                                        ^
      2164 MST2, 2220 ECON1,

      TrpLeuArgAspIleTrpAspTrpIleCysGluValLeuSerAspPheLysThrTrpLeu
2222  TGGCTAAGGGACATCTGGGACTGGATATGCGAGGTGTTGAGCGACTTTAAGACCTGGCTA
      ACCGATTCCCTGTAGACCCTGACCTATACGCTCCACAACTCGCTGAAATTCTGGACCGAT

      LysAlaLysLeuMetProGlnLeuProGlyIleProPheValSerCysGlnArgGlyTyr
2282  AAAGCTAAGCTCATGCCACAGCTGCCTGGGATCCCCTTTGTGTCCTGCCAGCGCGGGTAT
      TTTCGATTCGAGTACGGTGTCGACGGACCCTAGGGGAAACACAGGACGGTCGCGCCCATA
         ^          ^       ^
      2285 ESP1, 2300 PVU2, 2310 BAMHI,
```

FIG. 22D

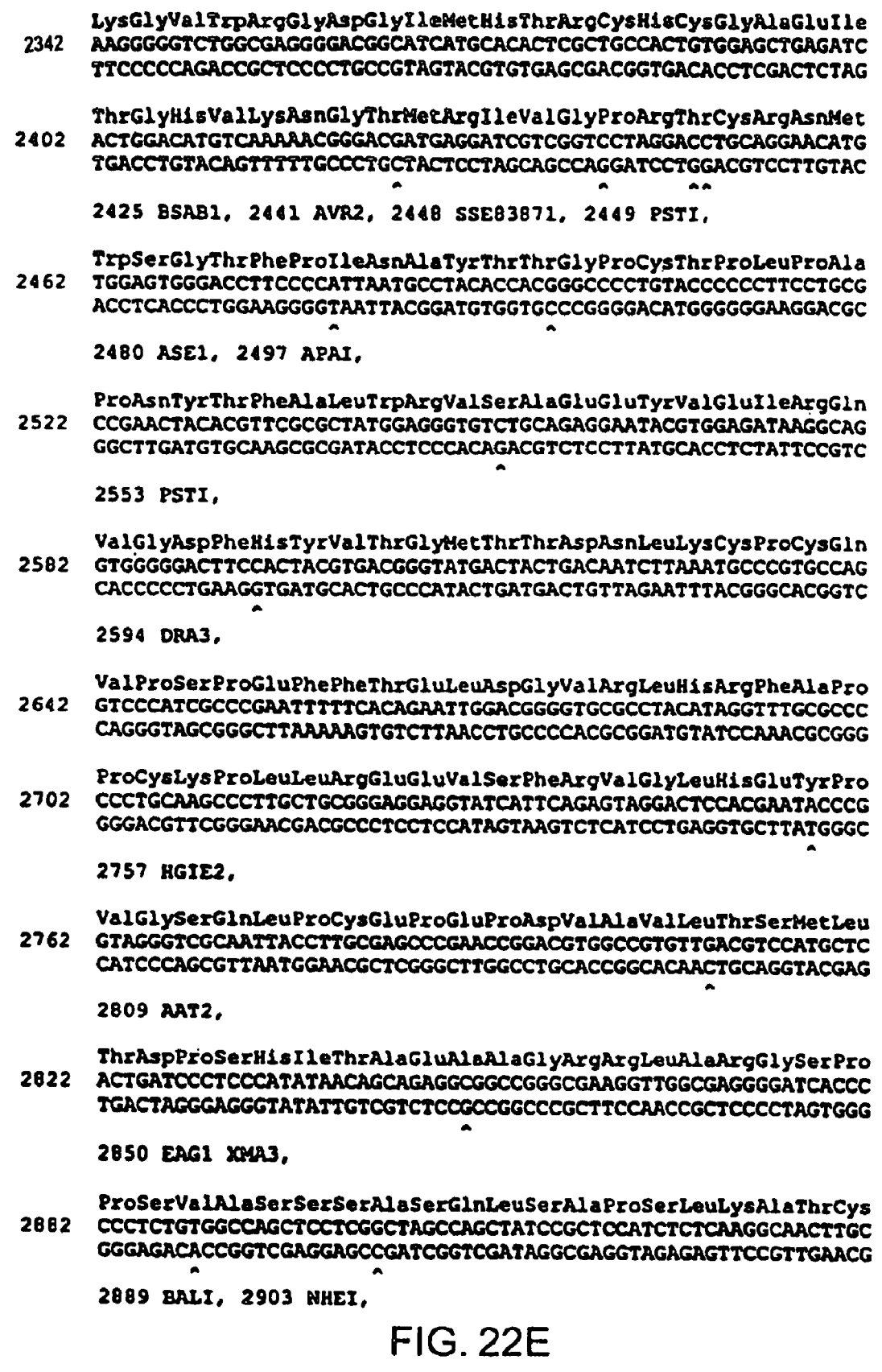

```
     LysGlyValTrpArgGlyAspGlyIleMetHisThrArgCysHisCysGlyAlaGluIle
2342 AAGGGGGTCTGGCGAGGGGACGGCATCATGCACACTCGCTGCCACTGTGGAGCTGAGATC
     TTCCCCCAGACCGCTCCCCTGCCGTAGTACGTGTGAGCGACGGTGACACCTCGACTCTAG

     ThrGlyHisValLysAsnGlyThrMetArgIleValGlyProArgThrCysArgAsnMet
2402 ACTGGACATGTCAAAAACGGGACGATGAGGATCGTCGGTCCTAGGACCTGCAGGAACATG
     TGACCTGTACAGTTTTTGCCCTGCTACTCCTAGCAGCCAGGATCCTGGACGTCCTTGTAC
                           ^               ^      ^^
     2425 BSAB1, 2441 AVR2, 2448 SSE83871, 2449 PSTI,

     TrpSerGlyThrPheProIleAsnAlaTyrThrThrGlyProCysThrProLeuProAla
2462 TGGAGTGGGACCTTCCCCATTAATGCCTACACCACGGGCCCCTGTACCCCCCTTCCTGCG
     ACCTCACCCTGGAAGGGGTAATTACGGATGTGGTGCCCGGGGACATGGGGGGAAGGACGC
                       ^                ^
     2480 ASE1, 2497 APAI,

     ProAsnTyrThrPheAlaLeuTrpArgValSerAlaGluGluTyrValGluIleArgGln
2522 CCGAACTACACGTTCGCGCTATGGAGGGTGTCTGCAGAGGAATACGTGGAGATAAGGCAG
     GGCTTGATGTGCAAGCGCGATACCTCCCACAGACGTCTCCTTATGCACCTCTATTCCGTC
                                    ^
     2553 PSTI,

     ValGlyAspPheHisTyrValThrGlyMetThrThrAspAsnLeuLysCysProCysGln
2582 GTGGGGGACTTCCACTACGTGACGGGTATGACTACTGACAATCTTAAATGCCCGTGCCAG
     CACCCCCTGAAGGTGATGCACTGCCCATACTGATGACTGTTAGAATTTACGGGCACGGTC
                ^
     2594 DRA3,

     ValProSerProGluPhePheThrGluLeuAspGlyValArgLeuHisArgPheAlaPro
2642 GTCCCATCGCCCGAATTTTTCACAGAATTGGACGGGGTGCGCCTACATAGGTTTGCGCCC
     CAGGGTAGCGGGCTTAAAAAGTGTCTTAACCTGCCCCACGCGGATGTATCCAAACGCGGG

     ProCysLysProLeuLeuArgGluGluValSerPheArgValGlyLeuHisGluTyrPro
2702 CCCTGCAAGCCCTTGCTGCGGGAGGAGGTATCATTCAGAGTAGGACTCCACGAATACCCG
     GGGACGTTCGGGAACGACGCCCTCCTCCATAGTAAGTCTCATCCTGAGGTGCTTATGGGC
                                                             ^
     2757 HGIE2,

     ValGlySerGlnLeuProCysGluProGluProAspValAlaValLeuThrSerMetLeu
2762 GTAGGGTCGCAATTACCTTGCGAGCCCGAACCGGACGTGGCCGTGTTGACGTCCATGCTC
     CATCCCAGCGTTAATGGAACGCTCGGGCTTGGCCTGCACCGGCACAACTGCAGGTACGAG
                                                       ^
     2809 AAT2,

     ThrAspProSerHisIleThrAlaGluAlaAlaGlyArgArgLeuAlaArgGlySerPro
2822 ACTGATCCCTCCCATATAACAGCAGAGGCGGCCGGGCGAAGGTTGGCGAGGGGATCACCC
     TGACTAGGGAGGGTATATTGTCGTCTCCGCCGGCCCGCTTCCAACCGCTCCCCTAGTGGG
                                 ^
     2850 EAG1 XMA3,

     ProSerValAlaSerSerSerAlaSerGlnLeuSerAlaProSerLeuLysAlaThrCys
2882 CCCTCTGTGGCCAGCTCCTCGGCTAGCCAGCTATCCGCTCCATCTCTCAAGGCAACTTGC
     GGGAGACACCGGTCGAGGAGCCGATCGGTCGATAGGCGAGGTAGAGAGTTCCGTTGAACG
           ^          ^
     2889 BALI, 2903 NHEI,
```

FIG. 22E

```
     ThrAlaAsnHisAspS rProAspAlaGluLeuIleGluAlaAsnLeuLeuTrpArgGln
2942 ACCGCTAACCATGACTCCCCTGATGCTGAGCTCATAGAGGCCAACCTCCTATGGAGGCAG
     TGGCGATTGGTACTGAGGGGACTACGACTCGAGTATCTCCGGTTGGAGGATACCTCCGTC
                                             ^   ^
     2966 ESP1, 2969 SACI,

     GluMetGlyGlyAsnIleThrArgValGluSerGluAsnLysValValIleLeuAspSer
3002 GAGATGGGCGGCAACATCACCAGGGTTGAGTCAGAAAACAAAGTGGTGATTCTGGACTCC
     CTCTACCCGCCGTTGTAGTGGTCCCAACTCAGTCTTTTGTTTCACCACTAAGACCTGAGG

     PheAspProLeuValAlaGluGluAspGluArgGluIleSerValProAlaGluIleLeu
3062 TTCGATCCGCTTGTGGCGGAGGAGGACGAGCGGGAGATCTCCGTACCCGCAGAAATCCTG
     AAGCTAGGCGAACACCGCCTCCTCCTGCTCGCCCTCTAGAGGCATGGGCGTCTTTAGGAC
                                                    ^
     3096 BGL2,

     ArgLysSerArgArgPheAlaGlnAlaLeuProValTrpAlaArgProAspTyrAsnPro
3122 CGGAAGTCTCGGAGATTCGCCCAGGCCCTGCCCGTTTGGGCGCGGCCGGACTATAACCCC
     GCCTTCAGAGCCTCTAAGCGGGTCCGGGACGGGCAAACCCGCGCCGGCCTGATATTGGGG
                             ^                          ^
     3143 ALWN1, 3164 EAG1 XMA3,

     ProLeuValGluThrTrpLysLysProAspTyrGluProProValValHisGlyCysPro
3182 CCGCTAGTGGAGACGTGGAAAAAGCCCGACTACGAACCACCTGTGGTCCATGGCTGCCCG
     GGCGATCACCTCTGCACCTTTTTCGGGCTGATGCTTGGTGGACACCAGGTACCGACGGGC
                                                   ^          ^
     3217 HGIE2, 3229 NCOI,

     LeuProProProLysSerProProValProProProArgLysLysArgThrValValLeu
3242 CTTCCACCTCCAAAGTCCCCTCCTGTGCCTCCGCCTCGGAAGAAGCGGACGGTGGTCCTC
     GAAGGTGGAGGTTTCAGGGGAGGACACGGAGGCGGAGCCTTCTTCGCCTGCCACCAGGAG

     ThrGluSerThrLeuSerThrAlaLeuAlaGluLeuAlaThrArgSerPheGlySerSer
3302 ACTGAATCAACCCTATCTACTGCCTTGGCCGAGCTCGCCACCAGAAGCTTTGGCAGCTCC
     TGACTTAGTTGGGATAGATGACGGAACCGGCTCGAGCGGTGGTCTTCGAAACCGTCGAGG
                                              ^           ^
     3332 SACI, 3346 HIND3,

     SerThrSerGlyIleThrGlyAspAsnThrThrThrSerSerGluProAlaProSerGly
3362 TCAACTTCCGGCATTACGGGCGACAATACGACAACATCCTCTGAGCCCGCCCCTTCTGGC
     AGTTGAAGGCCGTAATGCCCGCTGTTATGCTGTTGTAGGAGACTCGGGCGGGGAAGACCG

     CysProProAspSerAspAlaGluSerTyrSerSerMetProProLeuGluGlyGluPro
3422 TGCCCCCCCGACTCCGACGCTGAGTCCTATTCCTCCATGCCCCCCCTGGAGGGGGAGCCT
     ACGGGGGGGCTGAGGCTGCGACTCAGGATAAGGAGGTACGGGGGGGACCTCCCCCTCGGA
                    ^
     3437 EAM11051,

     GlyAspProAspLeuSerAspGlySerTrpSerThrValSerSerGluAlaAsnAlaGlu
3482 GGGGATCCGGATCTTAGCGACGGGTCATGGTCAACGGTCAGTAGTGAGGCCAACGCGGAG
     CCCCTAGGCCTAGAATCGCTGCCCAGTACCAGTTGCCAGTCATCACTCCGGTTGCGCCTC
       ^^ ^
     3484 BAMHI, 3485 BSAB1, 3487 BSPE1,

     AspValValCysCysSerMetSerTyrSerTrpThrGlyAlaLeuValThrProCysAla
3542 GATGTCGTGTGCTGCTCAATGTCTTACTCTTGGACAGGCGCACTCGTCACCCCGTGCGCC
     CTACAGCACACGACGAGTTACAGAATGAGAACCTGTCCGCGTGAGCAGTGGGGCACGCGG
```

FIG. 22F

3589 DRA3, 3600 SAC2,

AlaGluGluGlnLysLeuProIleAsnAlaLeuSerAsnSerLeuLeuArgHisHisAsn
3602 GCGGAAGAACAGAAACTGCCCATCAATGCACTAAGCAACTCGTTGCTACGTCACCACAAT
CGCCTTCTTGTCTTTGACGGGTAGTTACGTGATTCGTTGAGCAACGATGCAGTGGTGTTA
^ ^

3611 ALWN1, 3655 PFLM1,

LeuValTyrSerThrThrSerArgSerAlaCysGlnArgGlnLysLysValThrPheAsp
3662 TTGGTGTATTCCACCACCTCACGCAGTGCTTGCCAAAGGCAGAAGAAAGTCACATTTGAC
AACCACATAAGGTGGTGGAGTGCGTCACGAACGGTTTCCGTCTTCTTTCAGTGTAAACTG
^

3681 DRA3,

ArgLeuGlnValLeuAspSerHisTyrGlnAspValLeuLysGluValLysAlaAlaAla
3722 AGACTGCAAGTTCTGGACAGCCATTACCAGGACGTACTCAAGGAGGTTAAAGCAGCGGCG
TCTGACGTTCAAGACCTGTCGGTAATGGTCCTGCATGAGTTCCTCCAATTTCGTCGCCGC

SerLysValLysAlaAsnLeuLeuSerValGluGluAlaCysSerLeuThrProProHis
3782 TCAAAAGTGAAGGCTAACTTGCTATCCGTAGAGGAAGCTTGCAGCCTGACGCCCCCACAC
AGTTTTCACTTCCGATTGAACGATAGGCATCTCCTTCGAACGTCGGACTGCGGGGGTGTG
^

3816 HIND3,

SerAlaLysSerLysPheGlyTyrGlyAlaLysAspValArgCysHisAlaArgLysAla
3842 TCAGCCAAATCCAAGTTTGGTTATGGGGCAAAAGACGTCCGTTGCCATGCCAGAAAGGCC
AGTCGGTTTAGGTTCAAACCAATACCCCGTTTTCTGCAGGCAACGGTACGGTCTTTCCGG
^ ^

3875 AAT2, 3890 BGLI,

ValThrHisIleAsnSerValTrpLysAspLeuLeuGluAspAsnValThrProIleAsp
3902 GTAACCCACATCAACTCCGTGTGGAAAGACCTTCTGGAAGACAATGTAACACCAATAGAC
CATTGGGTGTAGTTGAGGCACACCTTTCTGGAAGACCTTCTGTTACATTGTGGTTATCTG

ThrThrIleMetAlaLysAsnGluValPheCysValGlnProGluLysGlyGlyArgLys
3962 ACTACCATCATGGCTAAGAACGAGGTTTTCTGCGTTCAGCCTGAGAAGGGGGGTCGTAAG
TGATGGTAGTACCGATTCTTGCTCCAAAAGACGCAAGTCGGACTCTTCCCCCCAGCATTC

ProAlaArgLeuIleValPheProAspLeuGlyValArgValCysGluLysMetAlaLeu
4022 CCAGCTCGTCTCATCGTGTTCCCCGATCTGGGCGTGCGCGTGTGCGAAAAGATGGCTTTG
GGTCGAGCAGAGTAGCACAAGGGGCTAGACCCGCACGCGCACACGCTTTTCTACCGAAAC

TyrAspValValThrLysLeuProLeuAlaValMetGlySerSerTyrGlyPheGlnTyr
4082 TACGACGTGGTTACAAAGCTCCCCTTGGCCGTGATGGGAAGCTCCTACGGATTCCAATAC
ATGCTGCACCAATGTTTCGAGGGGAACCGGCACTACCCTTCGAGGATGCCTAAGGTTATG

SerProGlyGlnArgValGluPheLeuValGlnAlaTrpLysSerLysLysThrProMet
4142 TCACCAGGACAGCGGGTTGAATTCCTCGTGCAAGCGTGGAAGTCCAAGAAAACCCCAATG
AGTGGTCCTGTCGCCCAACTTAAGGAGCACGTTCGCACCTTCAGGTTCTTTTGGGGTTAC
^

4160 ECORI,

GlyPheSerTyrAspThrArgCysPheAspSerThrValThrGluSerAspIleArgThr
4202 GGGTTCTCGTATGATACCCGCTGCTTTGACTCCACAGTCACTGAGAGCGACATCCGTACG
CCCAAGAGCATACTATGGGCGACGAAACTGAGGTGTCAGTGACTCTCGCTGTAGGCATGC
^ ^

FIG. 22G

```
     4229 DRD1, 4236 ALWN1,

     GluGluAlaIleTyrGlnCysCysAspLeuAspProGlnAlaArgValAlaIleLysSer
4262 GAGGAGGCAATCTACCAATGTTGTGACCTCGACCCCCAAGCCCGCGTGGCCATCAAGTCC
     CTCCTCCGTTAGATGGTTACAACACTGGAGCTGGGGGTTCGGGCGCACCGGTAGTTCAGG
                                                ^         ^
     4301 BGLI, 4308 BALI,

     LeuThrGluArgLeuTyrValGlyGlyProLeuThrAsnSerArgGlyGluAsnCysGly
4322 CTCACCGAGAGGCTTTATGTTGGGGGCCCTCTTACCAATTCAAGGGGGGAGAACTGCGGC
     GAGTGGCTCTCCGAAATACAACCCCCGGGAGAATGGTTAAGTTCCCCCCTCTTGACGCCG
                                ^
     4345 APAI,

     TyrArgArgCysArgAlaSerGlyValLeuThrThrSerCysGlyAsnThrLeuThrCys
4382 TATCGCAGGTGCCGCGCGAGCGGCGTACTGACAACTAGCTGTGGTAACACCCTCACTTGC
     ATAGCGTCCACGGCGCGCTCGCCGCATGACTGTTGATCGACACCATTGTGGGAGTGAACG

     TyrIleLysAlaArgAlaAlaCysArgAlaAlaGlyLeuGlnAspCysThrMetLeuVal
4442 TACATCAAGGCCCGGGCAGCCTGTCGAGCCGCAGGGCTCCAGGACTGCACCATGCTCGTG
     ATGTAGTTCCGGGCCCGTCGGACAGCTCGGCGTCCCGAGGTCCTGACGTGGTACGAGCAC
              ^
     4452 SMAI XMAI,

     CysGlyAspAspLeuValValIleCysGluSerAlaGlyValGlnGluAspAlaAlaSer
4502 TGTGGCGACGACTTAGTCGTTATCTGTGAAAGCGCGGGGGTCCAGGAGGACGCGGCGAGC
     ACACCGCTGCTGAATCAGCAATAGACACTTTCGCGCCCCCAGGTCCTCCTGCGCCGCTCG
          ^  ^
     4508 DRD1, 4511 TTH3I,

     LeuArgAlaPheThrGluAlaMetThrArgTyrSerAlaProProGlyAspProProGln
4562 CTGAGAGCCTTCACGGAGGCTATGACCAGGTACTCCGCCCCCCCTGGGGACCCCCCACAA
     GACTCTCGGAAGTGCCTCCGATACTGGTCCATGAGGCGGGGGGGACCCCTGGGGGGTGTT

     ProGluTyrAspLeuGluLeuIleThrSerCysSerSerAsnValSerValAlaHisAsp
4622 CCAGAATACGACTTGGAGCTCATAACATCATGCTCCTCCAACGTGTCAGTCGCCCACGAC
     GGTCTTATGCTGAACCTCGAGTATTGTAGTACGAGGAGGTTGCACAGTCAGCGGGTGCTG
                    ^
     4637 SACI,

     GlyAlaGlyLysArgValTyrTyrLeuThrArgAspProThrThrProLeuAlaArgAla
4682 GGCGCTGGAAAGAGGGTCTACTACCTCACCCGTGACCCTACAACCCCCCTCGCGAGAGCT
     CCGCGACCTTTCTCCCAGATGATGGAGTGGGCACTGGGATGTTGGGGGGAGCGCTCTCGA
                                                      ^
     4731 NRUI,

     AlaTrpGluThrAlaArgHisThrProValAsnSerTrpLeuGlyAsnIleIleMetPhe
4742 GCGTGGGAGACAGCAAGACACACTCCAGTCAATTCCTGGCTAGGCAACATAATCATGTTT
     CGCACCCTCTGTCGTTCTGTGTGAGGTCAGTTAAGGACCGATCCGTTGTATTAGTACAAA

     AlaProThrLeuTrpAlaArgMetIleLeuMetThrHisPhePheSerValLeuIleAla
4802 GCCCCCACACTGTGGGCGAGGATGATACTGATGACCCATTTCTTTAGCGTCCTTATAGCC
     CGGGGGTGTGACACCCGCTCCTACTATGACTACTGGGTAAAGAAATCGCAGGAATATCGG
       ^^
     4806 PFLM1, 4807 DRA3,

     ArgAspGlnLeuGluGlnAlaLeuAspCysGluIleTyrGlyAlaCysTyrSerIleGlu
```

FIG. 22H

```
4862 AGGGACCAGCTTGAACAGGCCCTCGATTGCGAGATCTACGGGGCCTGCTACTCCATAGAA
     TCCCTGGTCGAACTTGTCCGGGAGCTAACGCTCTAGATGCCCCGGACGATGAGGTATCTT
                                   ^

     4893 BGL2,

     ProLeuAspLeuProProIleIleGlnArgLeuHisGlyLeuSerAlaPheSerLeuHis
4922 CCACTGGATCTACCTCCAATCATTCAAAGACTCCATGGCCTCAGCGCATTTTCACTCCAC
     GGTGACCTAGATGGAGGTTAGTAAGTTTCTGAGGTACCGGAGTCGCGTAAAAGTGAGGTG
                                   ^

     4954 NCOI,

     SerTyrSerProGlyGluIleAsnArgValAlaAlaCysLeuArgLysLeuGlyValPro
4982 AGTTACTCTCCAGGTGAAATCAATAGGGTGGCCGCATGCCTCAGAAAACTTGGGGTACCG
     TCAATGAGAGGTCCACTTTAGTTATCCCACCGGCGTACGGAGTCTTTTGAACCCCATGGC
                                   ^                   ^

     5015 SPHI, 5035 KPNI,

     ProLeuArgAlaTrpArgHisArgAlaArgSerValArgAlaArgLeuLeuAlaArgGly
5042 CCCTTGCGAGCTTGGAGACACCGGGCCCGGAGCGTCCGCGCTAGGCTTCTGGCCAGAGGA
     GGGAACGCTCGAACCTCTGTGGCCCGGGCCTCGCAGGCGCGATCCGAAGACCGGTCTCCT
                            ^                          ^

     5064 APAI, 5091 BALI,

     GlyArgAlaAlaIleCysGlyLysTyrLeuPheAsnTrpAlaValArgThrLysLeuLys
5102 GGCAGGGCTGCCATATGTGGCAAGTACCTCTTCAACTGGGCAGTAAGAACAAAGCTCAAA
     CCGTCCCGACGGTATACACCGTTCATGGAGAAGTTGACCCGTCATTCTTGTTTCGAGTTT
                ^

     5113 NDEI,

     LeuThrProIleAlaAlaAlaGlyGlnLeuAspLeuSerGlyTrpPheThrAlaGlyTyr
5162 CTCACTCCAATAGCGGCCGCTGGCCAGCTGGACTTGTCCGGCTGGTTCACGGCTGGCTAC
     GAGTGAGGTTATCGCCGGCGACCGGTCGACCTGAACAGGCCGACCAAGTGCCGACCGATG
                  ^^     ^   ^

     5174 NOTI, 5175 EAG1 XMA3, 5182 BALI, 5186 PVU2,

     SerGlyGlyAspIleTyrHisSerValSerHisAlaArgProArgTrpIleTrpPheCys
5222 AGCGGGGGAGACATTTATCACAGCGTGTCTCATGCCCGGCCCCGCTGGATCTGGTTTTGC
     TCGCCCCCTCTGTAAATAGTGTCGCACAGAGTACGGGCCGGGGCGACCTAGACCAAAACG
                      ^

     5240 DRA3,

     LeuLeuLeuLeuAlaAlaGlyValGlyIleTyrLeuLeuProAsnArgMetSerThrAsn
5282 CTACTCCTGCTTGCTGCAGGGGTAGGCATCTACCTCCTCCCCAACCGAATGAGCACGAAT
     GATGAGGACGAACGACGTCCCCATCCGTAGATGGAGGAGGGGTTGGCTTACTCGTGCTTA
                 ^

     5295 PSTI,

     ProLysProGlnArgLysThrLysArgAsnThrAsnArgArgProGlnAspValLysPhe
5342 CCTAAACCTCAAAGAAAGACCAAACGTAACACCAACCGGCGGCCGCAGGACGTCAAGTTC
     GGATTTGGAGTTTCTTTCTGGTTTGCATTGTGGTTGGCCGCCGGCGTCCTGCAGTTCAAG
                                             ^^    ^     ^

     5380 NOTI, 5381 EAG1 XMA3, 5390 AAT2, 5401 SMAI XMAI,

     ProGlyGlyGlyGlnIleValGlyGlyValTyrLeuLeuProArgArgGlyProArgLeu
5402 CCGGGTGGCGGTCAGATCGTTGGTGGAGTTTACTTGTTGCCGCGCAGGGGCCCTAGATTG
     GGCCCACCGCCAGTCTAGCAACCACCTCAAATGAACAACGGCGCGTCCCCGGGATCTAAC
                                                    ^
```

FIG. 22I

```
     5449 APAI,

     GlyValArgAlaThrArgLysThrSerGluArgSerGlnProArgGlyArgArgGlnPro
5462 GGTGTGCGCGCGACGAGAAAGACTTCCGAGCGGTCGCAACCTCGAGGTAGACGTCAGCCT
     CCACACGCGCGCTGCTCTTTCTGAAGGCTCGCCAGCGTTGGAGCTCCATCTGCAGTCGGA
         ^                 ^                       ^             ^

     5467 BSSH2, 5478 XMNI, 5502 XHOI, 5511 AAT2,

     IleProLysAlaArgArgProGluGlyArgThrTrpAlaGlnProGlyTyrProTrpPro
5522 ATCCCCAAGGCTCGTCGGCCCGAGGGCAGGACCTGGGCTCAGCCCGGGTACCCTTGGCCC
     TAGGGGTTCCGAGCAGCCGGGCTCCCGTCCTGGACCCGAGTCGGGCCCATGGGAACCGGG
                                           ^         ^    ^    ^

     5548 ALWN1, 5558 ESP1, 5564 SMAI XMAI, 5568 KPNI,

     LeuTyrGlyAsnGluGlyCysGlyTrpAlaGlyTrpLeuLeuSerProArgGlySerArg
5582 CTCTATGGCAATGAGGGCTGCGGGTGGGCGGGATGGCTCCTGTCTCCCCGTGGCTCTCGG
     GAGATACCGTTACTCCCGACGCCCACCCGCCCTACCGAGGACAGAGGGGCACCGAGAGCC

     ProSerTrpGlyProThrAspProArgArgArgSerArgAsnLeuGlyLysValIleAsp
5642 CCTAGCTGGGGCCCCACAGACCCCCGGCGTAGGTCGCGCAATTTGGGTAAGGTCATCGAT
     GGATCGACCCCGGGGTGTCTGGGGGCCGCATCCAGCGCGTTAAACCCATTCCAGTAGCTA
             ^                                              ^

     5650 APAI, 5696 CLAI,

     ThrLeuThrCysGlyPheAlaAspLeuMetGlyTyrIleProLeuValGlyAlaProLeu
5702 ACCCTTACGTGCGGCTTCGCCGACCTCATGGGGTACATACCGCTCGTCGGCGCCCCTCTT
     TGGGAATGCACGCCGAAGCGGCTGGAGTACCCCATGTATGGCGAGCAGCCGCGGGGAGAA
                           ^                          ^     ^

     5724 HGIE2, 5750 KAS1 NARI, 5756 ECON1,

     GlyGlyAlaAlaArgAlaOC AM
5762 GGAGGCGCTGCCAGGGCCTAATAGTCGAC
     CCTCCGCGACGGTCCCGGATTATCAGCTG
                           ^

     5785 SALI,
```

FIG. 22J

SEQUENCE LISTING

<160> NUMBER OF SEQ ID NOS: 19

<210> SEQ ID NO 1
<211> LENGTH: 9620
<212> TYPE: DNA
<213> ORGANISM: Artificial Sequence
<220> FEATURE:
<221> NAME/KEY: CDS
<222> LOCATION: (1990)..(7302)
<223> OTHER INFORMATION: Description of Artificial Sequence: Hepatitis C
pns345

<400> SEQUENCE: 1
cgcgcgtttc ggtgatgacg gtgaaaacct ctgacacatg cagctcccgg agacggtcac 60
agcttgtctg taagcggatg ccgggagcag acaagcccgt cagggcgcgt cagcgggtgt 120
tggcgggtgt cggggctggc ttaactatgc ggcatcagag cagattgtac tgagagtgca 180
ccatatgaag ctttttgcaa aagcctaggc ctccaaaaaa gcctcctcac tacttctgga 240
atagctcaga ggccgaggcg gcctcggcct ctgcataaat aaaaaaaatt agtcagccat 300
ggggcggaga atgggcggaa ctgggcgggg agggaattat tggctattgg ccattgcata 360
cgttgtatct atatcataat atgtacattt atattggctc atgtccaata tgaccgccat 420
gttgacattg attattgact agttattaat agtaatcaat tacggggtca ttagttcata 480
gcccatatat ggagttccgc gttacataac ttacggtaaa tggcccgcct ggctgaccgc 540
ccaacgaccc ccgcccattg acgtcaataa tgacgtatgt tcccatagta acgccaatag 600
ggactttcca ttgacgtcaa tgggtggagt atttacggta aactgcccac ttggcagtac 660
atcaagtgta tcatatgcca agtccgcccc ctattgacgt caatgacggt aaatggcccg 720
cctggcatta tgcccagtac atgaccttac gggactttcc tacttggcag tacatctacg 780
tattagtcat cgctattacc atggtgatgc ggttttggca gtacaccaat gggcgtggat 840
agcggtttga ctcacgggga tttccaagtc tccaccccat tgacgtcaat gggagtttgt 900
tttggcacca aaatcaacgg gactttccaa aatgtcgtaa taaccccgcc ccgttgacgc 960
aaatgggcgg taggcgtgta cggtgggagg tctatataag cagagctcgt ttagtgaacc 1020
gtcagatcgc ctggagacgc catccacgct gttttgacct ccatagaaga caccgggacc 1080
gatccagcct ccgcggccgg gaacggtgca ttggaacgcg gattccccgt gccaagagtg 1140
acgtaagtac cgcctataga ctctataggc acacccctttt ggctcttatg catgctatac 1200
tgtttttggc ttggggccta tacacccccg ctccttatgc tataggtgat ggtatagctt 1260
agcctatagg tgtgggttat tgaccattat tgaccactcc cctattggtg acgatacttt 1320
ccattactaa tccataacat ggctctttgc cacaactatc tctattggct atatgccaat 1380

-continued

```
actctgtcct tcagagactg acacggactc tgtattttta caggatgggg tccatttatt   1440

atttacaaat tcacatatac aacaacgccg tcccccgtgc ccgcagtttt tattaaacat   1500

agcgtgggat ctccgacatc tcgggtacgt gttccggaca tgggctcttc tccggtagcg   1560

gcggagcttc cacatccgag ccctggtccc atccgtccag cggctcatgg tcgctcggca   1620

gctccttgct cctaacagtg gaggccagac ttaggcacag cacaatgccc accaccacca   1680

gtgtgccgca caaggccgtg gcggtagggt atgtgtctga aaatgagctc ggagattggg   1740

ctcgcacctg gacgcagatg gaagacttaa ggcagcggca gaagaagatg caggcagctg   1800

agttgttgta ttctgataag agtcagaggt aactcccgtt gcggtgctgt taacggtgga   1860

gggcagtgta gtctgagcag tactcgttgc tgccgcgcgc gccaccagac ataatagctg   1920

acagactaac agactgttcc tttccatggg tcttttctgc agtcaccgtc gtcgacctaa   1980

gaattcacc atg gct gca tat gca gct cag ggc tat aag gtg cta gta ctc   2031
          Met Ala Ala Tyr Ala Ala Gln Gly Tyr Lys Val Leu Val Leu
            1               5                  10

aac ccc tct gtt gct gca aca ctg ggc ttt ggt gct tac atg tcc aag     2079
Asn Pro Ser Val Ala Ala Thr Leu Gly Phe Gly Ala Tyr Met Ser Lys
 15                  20                  25                  30

gct cat ggg atc gat cct aac atc agg acc ggg gtg aga aca att acc     2127
Ala His Gly Ile Asp Pro Asn Ile Arg Thr Gly Val Arg Thr Ile Thr
                 35                  40                  45

act ggc agc ccc atc acg tac tcc acc tac ggc aag ttc ctt gcc gac     2175
Thr Gly Ser Pro Ile Thr Tyr Ser Thr Tyr Gly Lys Phe Leu Ala Asp
             50                  55                  60

ggc ggg tgc tcg ggg ggc gct tat gac ata ata att tgt gac gag tgc     2223
Gly Gly Cys Ser Gly Gly Ala Tyr Asp Ile Ile Ile Cys Asp Glu Cys
         65                  70                  75

cac tcc acg gat gcc aca tcc atc ttg ggc att ggc act gtc ctt gac     2271
His Ser Thr Asp Ala Thr Ser Ile Leu Gly Ile Gly Thr Val Leu Asp
     80                  85                  90

caa gca gag act gcg ggg gcg aga ctg gtt gtg ctc gcc acc gcc acc     2319
Gln Ala Glu Thr Ala Gly Ala Arg Leu Val Val Leu Ala Thr Ala Thr
 95                 100                 105                 110

cct ccg ggc tcc gtc act gtg ccc cat ccc aac atc gag gag gtt gct     2367
Pro Pro Gly Ser Val Thr Val Pro His Pro Asn Ile Glu Glu Val Ala
                115                 120                 125

ctg tcc acc acc gga gag atc cct ttt tac ggc aag gct atc ccc ctc     2415
Leu Ser Thr Thr Gly Glu Ile Pro Phe Tyr Gly Lys Ala Ile Pro Leu
            130                 135                 140

gaa gta atc aag ggg ggg aga cat ctc atc ttc tgt cat tca aag aag     2463
Glu Val Ile Lys Gly Gly Arg His Leu Ile Phe Cys His Ser Lys Lys
        145                 150                 155

aag tgc gac gaa ctc gcc gca aag ctg gtc gca ttg ggc atc aat gcc     2511
Lys Cys Asp Glu Leu Ala Ala Lys Leu Val Ala Leu Gly Ile Asn Ala
    160                 165                 170

gtg gcc tac tac cgc ggt ctt gac gtg tcc gtc atc ccg acc agc ggc     2559
Val Ala Tyr Tyr Arg Gly Leu Asp Val Ser Val Ile Pro Thr Ser Gly
175                 180                 185                 190

gat gtt gtc gtc gtg gca acc gat gcc ctc atg acc ggc tat acc ggc     2607
Asp Val Val Val Val Ala Thr Asp Ala Leu Met Thr Gly Tyr Thr Gly
                195                 200                 205

gac ttc gac tcg gtg ata gac tgc aat acg tgt gtc acc cag aca gtc     2655
Asp Phe Asp Ser Val Ile Asp Cys Asn Thr Cys Val Thr Gln Thr Val
            210                 215                 220

gat ttc agc ctt gac cct acc ttc acc att gag aca atc acg ctc ccc     2703
Asp Phe Ser Leu Asp Pro Thr Phe Thr Ile Glu Thr Ile Thr Leu Pro
        225                 230                 235
```

-continued

```
caa gat gct gtc tcc cgc act caa cgt cgg ggc agg act ggc agg ggg      2751
Gln Asp Ala Val Ser Arg Thr Gln Arg Arg Gly Arg Thr Gly Arg Gly
    240                 245                 250

aag cca ggc atc tac aga ttt gtg gca ccg ggg gag cgc ccc tcc ggc      2799
Lys Pro Gly Ile Tyr Arg Phe Val Ala Pro Gly Glu Arg Pro Ser Gly
255                 260                 265                 270

atg ttc gac tcg tcc gtc ctc tgt gag tgc tat gac gca ggc tgt gct      2847
Met Phe Asp Ser Ser Val Leu Cys Glu Cys Tyr Asp Ala Gly Cys Ala
                275                 280                 285

tgg tat gag ctc acg ccc gcc gag act aca gtt agg cta cga gcg tac      2895
Trp Tyr Glu Leu Thr Pro Ala Glu Thr Thr Val Arg Leu Arg Ala Tyr
            290                 295                 300

atg aac acc ccg ggg ctt ccc gtg tgc cag gac cat ctt gaa ttt tgg      2943
Met Asn Thr Pro Gly Leu Pro Val Cys Gln Asp His Leu Glu Phe Trp
        305                 310                 315

gag ggc gtc ttt aca ggc ctc act cat ata gat gcc cac ttt cta tcc      2991
Glu Gly Val Phe Thr Gly Leu Thr His Ile Asp Ala His Phe Leu Ser
    320                 325                 330

cag aca aag cag agt ggg gag aac ctt cct tac ctg gta gcg tac caa      3039
Gln Thr Lys Gln Ser Gly Glu Asn Leu Pro Tyr Leu Val Ala Tyr Gln
335                 340                 345                 350

gcc acc gtg tgc gct agg gct caa gcc cct ccc cca tcg tgg gac cag      3087
Ala Thr Val Cys Ala Arg Ala Gln Ala Pro Pro Pro Ser Trp Asp Gln
                355                 360                 365

atg tgg aag tgt ttg att cgc ctc aag ccc acc ctc cat ggg cca aca      3135
Met Trp Lys Cys Leu Ile Arg Leu Lys Pro Thr Leu His Gly Pro Thr
            370                 375                 380

ccc ctg cta tac aga ctg ggc gct gtt cag aat gaa atc acc ctg acg      3183
Pro Leu Leu Tyr Arg Leu Gly Ala Val Gln Asn Glu Ile Thr Leu Thr
        385                 390                 395

cac cca gtc acc aaa tac atc atg aca tgc atg tcg gcc gac ctg gag      3231
His Pro Val Thr Lys Tyr Ile Met Thr Cys Met Ser Ala Asp Leu Glu
    400                 405                 410

gtc gtc acg agc acc tgg gtg ctc gtt ggc ggc gtc ctg gct gct ttg      3279
Val Val Thr Ser Thr Trp Val Leu Val Gly Gly Val Leu Ala Ala Leu
415                 420                 425                 430

gcc gcg tat tgc ctg tca aca ggc tgc gtg gtc ata gtg ggc agg gtc      3327
Ala Ala Tyr Cys Leu Ser Thr Gly Cys Val Val Ile Val Gly Arg Val
                435                 440                 445

gtc ttg tcc ggg aag ccg gca atc ata cct gac agg gaa gtc ctc tac      3375
Val Leu Ser Gly Lys Pro Ala Ile Ile Pro Asp Arg Glu Val Leu Tyr
            450                 455                 460

cga gag ttc gat gag atg gaa gag tgc tct cag cac tta ccg tac atc      3423
Arg Glu Phe Asp Glu Met Glu Glu Cys Ser Gln His Leu Pro Tyr Ile
        465                 470                 475

gag caa ggg atg atg ctc gcc gag cag ttc aag cag aag gcc ctc ggc      3471
Glu Gln Gly Met Met Leu Ala Glu Gln Phe Lys Gln Lys Ala Leu Gly
    480                 485                 490

ctc ctg cag acc gcg tcc cgt cag gca gag gtt atc gcc cct gct gtc      3519
Leu Leu Gln Thr Ala Ser Arg Gln Ala Glu Val Ile Ala Pro Ala Val
495                 500                 505                 510

cag acc aac tgg caa aaa ctc gag acc ttc tgg gcg aag cat atg tgg      3567
Gln Thr Asn Trp Gln Lys Leu Glu Thr Phe Trp Ala Lys His Met Trp
                515                 520                 525

aac ttc atc agt ggg ata caa tac ttg gcg ggc ttg tca acg ctg cct      3615
Asn Phe Ile Ser Gly Ile Gln Tyr Leu Ala Gly Leu Ser Thr Leu Pro
            530                 535                 540

ggt aac ccc gcc att gct tca ttg atg gct ttt aca gct gct gtc acc      3663
Gly Asn Pro Ala Ile Ala Ser Leu Met Ala Phe Thr Ala Ala Val Thr
```

-continued

```
        545                 550                 555

agc cca cta acc act agc caa acc ctc ctc ttc aac ata ttg ggg ggg      3711
Ser Pro Leu Thr Thr Ser Gln Thr Leu Leu Phe Asn Ile Leu Gly Gly
    560                 565                 570

tgg gtg gct gcc cag ctc gcc gcc ccc ggt gcc gct act gcc ttt gtg      3759
Trp Val Ala Ala Gln Leu Ala Ala Pro Gly Ala Ala Thr Ala Phe Val
575                 580                 585                 590

ggc gct ggc tta gct ggc gcc gcc atc ggc agt gtt gga ctg ggg aag      3807
Gly Ala Gly Leu Ala Gly Ala Ala Ile Gly Ser Val Gly Leu Gly Lys
                595                 600                 605

gtc ctc ata gac atc ctt gca ggg tat ggc gcg ggc gtg gcg gga gct      3855
Val Leu Ile Asp Ile Leu Ala Gly Tyr Gly Ala Gly Val Ala Gly Ala
            610                 615                 620

ctt gtg gca ttc aag atc atg agc ggt gag gtc ccc tcc acg gag gac      3903
Leu Val Ala Phe Lys Ile Met Ser Gly Glu Val Pro Ser Thr Glu Asp
        625                 630                 635

ctg gtc aat cta ctg ccc gcc atc ctc tcg ccc gga gcc ctc gta gtc      3951
Leu Val Asn Leu Leu Pro Ala Ile Leu Ser Pro Gly Ala Leu Val Val
    640                 645                 650

ggc gtg gtc tgt gca gca ata ctg cgc cgg cac gtt ggc ccg ggc gag      3999
Gly Val Val Cys Ala Ala Ile Leu Arg Arg His Val Gly Pro Gly Glu
655                 660                 665                 670

ggg gca gtg cag tgg atg aac cgg ctg ata gcc ttc gcc tcc cgg ggg      4047
Gly Ala Val Gln Trp Met Asn Arg Leu Ile Ala Phe Ala Ser Arg Gly
                675                 680                 685

aac cat gtt tcc ccc acg cac tac gtg ccg gag agc gat gca gct gcc      4095
Asn His Val Ser Pro Thr His Tyr Val Pro Glu Ser Asp Ala Ala Ala
            690                 695                 700

cgc gtc act gcc ata ctc agc agc ctc act gta acc cag ctc ctg agg      4143
Arg Val Thr Ala Ile Leu Ser Ser Leu Thr Val Thr Gln Leu Leu Arg
        705                 710                 715

cga ctg cac cag tgg ata agc tcg gag tgt acc act cca tgc tcc ggt      4191
Arg Leu His Gln Trp Ile Ser Ser Glu Cys Thr Thr Pro Cys Ser Gly
    720                 725                 730

tcc tgg cta agg gac atc tgg gac tgg ata tgc gag gtg ttg agc gac      4239
Ser Trp Leu Arg Asp Ile Trp Asp Trp Ile Cys Glu Val Leu Ser Asp
735                 740                 745                 750

ttt aag acc tgg cta aaa gct aag ctc atg cca cag ctg cct ggg atc      4287
Phe Lys Thr Trp Leu Lys Ala Lys Leu Met Pro Gln Leu Pro Gly Ile
                755                 760                 765

ccc ttt gtg tcc tgc cag cgc ggg tat aag ggg gtc tgg cga ggg gac      4335
Pro Phe Val Ser Cys Gln Arg Gly Tyr Lys Gly Val Trp Arg Gly Asp
            770                 775                 780

ggc atc atg cac act cgc tgc cac tgt gga gct gag atc act gga cat      4383
Gly Ile Met His Thr Arg Cys His Cys Gly Ala Glu Ile Thr Gly His
        785                 790                 795

gtc aaa aac ggg acg atg agg atc gtc ggt cct agg acc tgc agg aac      4431
Val Lys Asn Gly Thr Met Arg Ile Val Gly Pro Arg Thr Cys Arg Asn
    800                 805                 810

atg tgg agt ggg acc ttc ccc att aat gcc tac acc acg ggc ccc tgt      4479
Met Trp Ser Gly Thr Phe Pro Ile Asn Ala Tyr Thr Thr Gly Pro Cys
815                 820                 825                 830

acc ccc ctt cct gcg ccg aac tac acg ttc gcg cta tgg agg gtg tct      4527
Thr Pro Leu Pro Ala Pro Asn Tyr Thr Phe Ala Leu Trp Arg Val Ser
                835                 840                 845

gca gag gaa tac gtg gag ata agg cag gtg ggg gac ttc cac tac gtg      4575
Ala Glu Glu Tyr Val Glu Ile Arg Gln Val Gly Asp Phe His Tyr Val
            850                 855                 860

acg ggt atg act act gac aat ctt aaa tgc ccg tgc cag gtc cca tcg      4623
```

-continued

```
Thr Gly Met Thr Thr Asp Asn Leu Lys Cys Pro Cys Gln Val Pro Ser
        865                 870                 875

ccc gaa ttt ttc aca gaa ttg gac ggg gtg cgc cta cat agg ttt gcg      4671
Pro Glu Phe Phe Thr Glu Leu Asp Gly Val Arg Leu His Arg Phe Ala
    880                 885                 890

ccc ccc tgc aag ccc ttg ctg cgg gag gag gta tca ttc aga gta gga      4719
Pro Pro Cys Lys Pro Leu Leu Arg Glu Glu Val Ser Phe Arg Val Gly
895                 900                 905                 910

ctc cac gaa tac ccg gta ggg tcg caa tta cct tgc gag ccc gaa ccg      4767
Leu His Glu Tyr Pro Val Gly Ser Gln Leu Pro Cys Glu Pro Glu Pro
                915                 920                 925

gac gtg gcc gtg ttg acg tcc atg ctc act gat ccc tcc cat ata aca      4815
Asp Val Ala Val Leu Thr Ser Met Leu Thr Asp Pro Ser His Ile Thr
            930                 935                 940

gca gag gcg gcc ggg cga agg ttg gcg agg gga tca ccc ccc tct gtg      4863
Ala Glu Ala Ala Gly Arg Arg Leu Ala Arg Gly Ser Pro Pro Ser Val
        945                 950                 955

gcc agc tcc tcg gct agc cag cta tcc gct cca tct ctc aag gca act      4911
Ala Ser Ser Ser Ala Ser Gln Leu Ser Ala Pro Ser Leu Lys Ala Thr
    960                 965                 970

tgc acc gct aac cat gac tcc cct gat gct gag ctc ata gag gcc aac      4959
Cys Thr Ala Asn His Asp Ser Pro Asp Ala Glu Leu Ile Glu Ala Asn
975                 980                 985                 990

ctc cta tgg agg cag gag atg ggc ggc aac atc acc agg gtt gag tca      5007
Leu Leu Trp Arg Gln Glu Met Gly Gly Asn Ile Thr Arg Val Glu Ser
                995                1000                1005

gaa aac aaa gtg gtg att ctg gac tcc ttc gat ccg ctt gtg gcg gag      5055
Glu Asn Lys Val Val Ile Leu Asp Ser Phe Asp Pro Leu Val Ala Glu
           1010                1015                1020

gag gac gag cgg gag atc tcc gta ccc gca gaa atc ctg cgg aag tct      5103
Glu Asp Glu Arg Glu Ile Ser Val Pro Ala Glu Ile Leu Arg Lys Ser
       1025                1030                1035

cgg aga ttc gcc cag gcc ctg ccc gtt tgg gcg cgg ccg gac tat aac      5151
Arg Arg Phe Ala Gln Ala Leu Pro Val Trp Ala Arg Pro Asp Tyr Asn
   1040                1045                1050

ccc ccg cta gtg gag acg tgg aaa aag ccc gac tac gaa cca cct gtg      5199
Pro Pro Leu Val Glu Thr Trp Lys Lys Pro Asp Tyr Glu Pro Pro Val
1055               1060                1065                1070

gtc cat ggc tgc ccg ctt cca cct cca aag tcc cct cct gtg cct ccg      5247
Val His Gly Cys Pro Leu Pro Pro Pro Lys Ser Pro Pro Val Pro Pro
               1075                1080                1085

cct cgg aag aag cgg acg gtg gtc ctc act gaa tca acc cta tct act      5295
Pro Arg Lys Lys Arg Thr Val Val Leu Thr Glu Ser Thr Leu Ser Thr
           1090                1095                1100

gcc ttg gcc gag ctc gcc acc aga agc ttt ggc agc tcc tca act tcc      5343
Ala Leu Ala Glu Leu Ala Thr Arg Ser Phe Gly Ser Ser Ser Thr Ser
       1105                1110                1115

ggc att acg ggc gac aat acg aca aca tcc tct gag ccc gcc cct tct      5391
Gly Ile Thr Gly Asp Asn Thr Thr Thr Ser Ser Glu Pro Ala Pro Ser
   1120                1125                1130

ggc tgc ccc ccc gac tcc gac gct gag tcc tat tcc tcc atg ccc ccc      5439
Gly Cys Pro Pro Asp Ser Asp Ala Glu Ser Tyr Ser Ser Met Pro Pro
1135               1140                1145                1150

ctg gag ggg gag cct ggg gat ccg gat ctt agc gac ggg tca tgg tca      5487
Leu Glu Gly Glu Pro Gly Asp Pro Asp Leu Ser Asp Gly Ser Trp Ser
               1155                1160                1165

acg gtc agt agt gag gcc aac gcg gag gat gtc gtg tgc tgc tca atg      5535
Thr Val Ser Ser Glu Ala Asn Ala Glu Asp Val Val Cys Cys Ser Met
           1170                1175                1180
```

-continued

```
tct tac tct tgg aca ggc gca ctc gtc acc ccg tgc gcc gcg gaa gaa      5583
Ser Tyr Ser Trp Thr Gly Ala Leu Val Thr Pro Cys Ala Ala Glu Glu
       1185                1190                1195

cag aaa ctg ccc atc aat gca cta agc aac tcg ttg cta cgt cac cac      5631
Gln Lys Leu Pro Ile Asn Ala Leu Ser Asn Ser Leu Leu Arg His His
   1200                1205                1210

aat ttg gtg tat tcc acc acc tca cgc agt gct tgc caa agg cag aag      5679
Asn Leu Val Tyr Ser Thr Thr Ser Arg Ser Ala Cys Gln Arg Gln Lys
1215                1220                1225                1230

aaa gtc aca ttt gac aga ctg caa gtt ctg gac agc cat tac cag gac      5727
Lys Val Thr Phe Asp Arg Leu Gln Val Leu Asp Ser His Tyr Gln Asp
               1235                1240                1245

gta ctc aag gag gtt aaa gca gcg gcg tca aaa gtg aag gct aac ttg      5775
Val Leu Lys Glu Val Lys Ala Ala Ala Ser Lys Val Lys Ala Asn Leu
           1250                1255                1260

cta tcc gta gag gaa gct tgc agc ctg acg ccc cca cac tca gcc aaa      5823
Leu Ser Val Glu Glu Ala Cys Ser Leu Thr Pro Pro His Ser Ala Lys
       1265                1270                1275

tcc aag ttt ggt tat ggg gca aaa gac gtc cgt tgc cat gcc aga aag      5871
Ser Lys Phe Gly Tyr Gly Ala Lys Asp Val Arg Cys His Ala Arg Lys
   1280                1285                1290

gcc gta acc cac atc aac tcc gtg tgg aaa gac ctt ctg gaa gac aat      5919
Ala Val Thr His Ile Asn Ser Val Trp Lys Asp Leu Leu Glu Asp Asn
1295                1300                1305                1310

gta aca cca ata gac act acc atc atg gct aag aac gag gtt ttc tgc      5967
Val Thr Pro Ile Asp Thr Thr Ile Met Ala Lys Asn Glu Val Phe Cys
               1315                1320                1325

gtt cag cct gag aag ggg ggt cgt aag cca gct cgt ctc atc gtg ttc      6015
Val Gln Pro Glu Lys Gly Gly Arg Lys Pro Ala Arg Leu Ile Val Phe
           1330                1335                1340

ccc gat ctg ggc gtg cgc gtg tgc gaa aag atg gct ttg tac gac gtg      6063
Pro Asp Leu Gly Val Arg Val Cys Glu Lys Met Ala Leu Tyr Asp Val
       1345                1350                1355

gtt aca aag ctc ccc ttg gcc gtg atg gga agc tcc tac gga ttc caa      6111
Val Thr Lys Leu Pro Leu Ala Val Met Gly Ser Ser Tyr Gly Phe Gln
   1360                1365                1370

tac tca cca gga cag cgg gtt gaa ttc ctc gtg caa gcg tgg aag tcc      6159
Tyr Ser Pro Gly Gln Arg Val Glu Phe Leu Val Gln Ala Trp Lys Ser
1375                1380                1385                1390

aag aaa acc cca atg ggg ttc tcg tat gat acc cgc tgc ttt gac tcc      6207
Lys Lys Thr Pro Met Gly Phe Ser Tyr Asp Thr Arg Cys Phe Asp Ser
               1395                1400                1405

aca gtc act gag agc gac atc cgt acg gag gag gca atc tac caa tgt      6255
Thr Val Thr Glu Ser Asp Ile Arg Thr Glu Glu Ala Ile Tyr Gln Cys
           1410                1415                1420

tgt gac ctc gac ccc caa gcc cgc gtg gcc atc aag tcc ctc acc gag      6303
Cys Asp Leu Asp Pro Gln Ala Arg Val Ala Ile Lys Ser Leu Thr Glu
       1425                1430                1435

agg ctt tat gtt ggg ggc cct ctt acc aat tca agg ggg gag aac tgc      6351
Arg Leu Tyr Val Gly Gly Pro Leu Thr Asn Ser Arg Gly Glu Asn Cys
   1440                1445                1450

ggc tat cgc agg tgc cgc gcg agc ggc gta ctg aca act agc tgt ggt      6399
Gly Tyr Arg Arg Cys Arg Ala Ser Gly Val Leu Thr Thr Ser Cys Gly
1455                1460                1465                1470

aac acc ctc act tgc tac atc aag gcc cgg gca gcc tgt cga gcc gca      6447
Asn Thr Leu Thr Cys Tyr Ile Lys Ala Arg Ala Ala Cys Arg Ala Ala
               1475                1480                1485

ggg ctc cag gac tgc acc atg ctc gtg tgt ggc gac gac tta gtc gtt      6495
Gly Leu Gln Asp Cys Thr Met Leu Val Cys Gly Asp Asp Leu Val Val
           1490                1495                1500
```

-continued

```
atc tgt gaa agc gcg ggg gtc cag gag gac gcg gcg agc ctg aga gcc     6543
Ile Cys Glu Ser Ala Gly Val Gln Glu Asp Ala Ala Ser Leu Arg Ala
       1505                1510                1515

ttc acg gag gct atg acc agg tac tcc gcc ccc cct ggg gac ccc cca     6591
Phe Thr Glu Ala Met Thr Arg Tyr Ser Ala Pro Pro Gly Asp Pro Pro
   1520                1525                1530

caa cca gaa tac gac ttg gag ctc ata aca tca tgc tcc tcc aac gtg     6639
Gln Pro Glu Tyr Asp Leu Glu Leu Ile Thr Ser Cys Ser Ser Asn Val
1535                1540                1545                1550

tca gtc gcc cac gac ggc gct gga aag agg gtc tac tac ctc acc cgt     6687
Ser Val Ala His Asp Gly Ala Gly Lys Arg Val Tyr Tyr Leu Thr Arg
               1555                1560                1565

gac cct aca acc ccc ctc gcg aga gct gcg tgg gag aca gca aga cac     6735
Asp Pro Thr Thr Pro Leu Ala Arg Ala Ala Trp Glu Thr Ala Arg His
           1570                1575                1580

act cca gtc aat tcc tgg cta ggc aac ata atc atg ttt gcc ccc aca     6783
Thr Pro Val Asn Ser Trp Leu Gly Asn Ile Ile Met Phe Ala Pro Thr
       1585                1590                1595

ctg tgg gcg agg atg ata ctg atg acc cat ttc ttt agc gtc ctt ata     6831
Leu Trp Ala Arg Met Ile Leu Met Thr His Phe Phe Ser Val Leu Ile
   1600                1605                1610

gcc agg gac cag ctt gaa cag gcc ctc gat tgc gag atc tac ggg gcc     6879
Ala Arg Asp Gln Leu Glu Gln Ala Leu Asp Cys Glu Ile Tyr Gly Ala
1615                1620                1625                1630

tgc tac tcc ata gaa cca ctg gat cta cct cca atc att caa aga ctc     6927
Cys Tyr Ser Ile Glu Pro Leu Asp Leu Pro Pro Ile Ile Gln Arg Leu
               1635                1640                1645

cat ggc ctc agc gca ttt tca ctc cac agt tac tct cca ggt gaa atc     6975
His Gly Leu Ser Ala Phe Ser Leu His Ser Tyr Ser Pro Gly Glu Ile
           1650                1655                1660

aat agg gtg gcc gca tgc ctc aga aaa ctt ggg gta ccg ccc ttg cga     7023
Asn Arg Val Ala Ala Cys Leu Arg Lys Leu Gly Val Pro Pro Leu Arg
       1665                1670                1675

gct tgg aga cac cgg gcc cgg agc gtc cgc gct agg ctt ctg gcc aga     7071
Ala Trp Arg His Arg Ala Arg Ser Val Arg Ala Arg Leu Leu Ala Arg
   1680                1685                1690

gga ggc agg gct gcc ata tgt ggc aag tac ctc ttc aac tgg gca gta     7119
Gly Gly Arg Ala Ala Ile Cys Gly Lys Tyr Leu Phe Asn Trp Ala Val
1695                1700                1705                1710

aga aca aag ctc aaa ctc act cca ata gcg gcc gct ggc cag ctg gac     7167
Arg Thr Lys Leu Lys Leu Thr Pro Ile Ala Ala Ala Gly Gln Leu Asp
               1715                1720                1725

ttg tcc ggc tgg ttc acg gct ggc tac agc ggg gga gac att tat cac     7215
Leu Ser Gly Trp Phe Thr Ala Gly Tyr Ser Gly Gly Asp Ile Tyr His
           1730                1735                1740

agc gtg tct cat gcc cgg ccc cgc tgg atc tgg ttt tgc cta ctc ctg     7263
Ser Val Ser His Ala Arg Pro Arg Trp Ile Trp Phe Cys Leu Leu Leu
       1745                1750                1755

ctt gct gca ggg gta ggc atc tac ctc ctc ccc aac cga tgaaggttgg      7312
Leu Ala Ala Gly Val Gly Ile Tyr Leu Leu Pro Asn Arg
   1760                1765                1770

ggtaaacact ccggcctaaa aaaaaaaaaa aatctagaaa ggcgcgccaa gatatcaagg   7372

atccactacg cgttagagct cgctgatcag cctcgactgt gccttctagt tgccagccat   7432

ctgttgtttg cccctccccc gtgccttcct tgaccctgga aggtgccact cccactgtcc   7492

tttcctaata aaatgaggaa attgcatcgc attgtctgag taggtgtcat tctattctgg   7552

ggggtggggt ggggcaggac agcaaggggg aggattggga agacaatagc aggcatgctg   7612
```

-continued

```
gggagctctt ccgcttcctc gctcactgac tcgctgcgct cggtcgttcg gctgcggcga   7672

gcggtatcag ctcactcaaa ggcggtaata cggttatcca cagaatcagg ggataacgca   7732

ggaaagaaca tgtgagcaaa aggccagcaa aaggccagga accgtaaaaa ggccgcgttg   7792

ctggcgtttt tccataggct ccgcccccct gacgagcatc acaaaaatcg acgctcaagt   7852

cagaggtggc gaaacccgac aggactataa agataccagg cgtttccccc tggaagctcc   7912

ctcgtgcgct ctcctgttcc gaccctgccg cttaccggat acctgtccgc ctttctccct   7972

tcgggaagcg tggcgctttc tcaatgctca cgctgtaggt atctcagttc ggtgtaggtc   8032

gttcgctcca agctgggctg tgtgcacgaa ccccccgttc agcccgaccg ctgcgcctta   8092

tccggtaact atcgtcttga gtccaacccg gtaagacacg acttatcgcc actggcagca   8152

gccactggta acaggattag cagagcgagg tatgtaggcg gtgctacaga gttcttgaag   8212

tggtggccta actacggcta cactagaagg acagtatttg gtatctgcgc tctgctgaag   8272

ccagttacct tcggaaaaag agttggtagc tcttgatccg gcaaacaaac caccgctggt   8332

agcggtggtt tttttgtttg caagcagcag attacgcgca gaaaaaaagg atctcaagaa   8392

gatcctttga tcttttctac ggggtctgac gctcagtgga acgaaaactc acgttaaggg   8452

attttggtca tgagattatc aaaaaggatc ttcacctaga tccttttaaa ttaaaaatga   8512

agttttaaat caatctaaag tatatatgag taaacttggt ctgacagtta ccaatgctta   8572

atcagtgagg cacctatctc agcgatctgt ctatttcgtt catccatagt tgcctgactc   8632

cccgtcgtgt agataactac gatacgggag ggcttaccat ctggccccag tgctgcaatg   8692

ataccgcgag acccacgctc accggctcca gatttatcag caataaacca gccagccgga   8752

agggccgagc gcagaagtgg tcctgcaact ttatccgcct ccatccagtc tattaattgt   8812

tgccgggaag ctagagtaag tagttcgcca gttaatagtt tgcgcaacgt tgttgccatt   8872

gctacaggca tcgtggtgtc acgctcgtcg tttggtatgg cttcattcag ctccggttcc   8932

caacgatcaa ggcgagttac atgatccccc atgttgtgca aaaaagcggt tagctccttc   8992

ggtcctccga tcgttgtcag aagtaagttg gccgcagtgt tatcactcat ggttatggca   9052

gcactgcata attctcttac tgtcatgcca tccgtaagat gcttttctgt gactggtgag   9112

tactcaacca agtcattctg agaatagtgt atgcggcgac cgagttgctc ttgcccggcg   9172

tcaatacggg ataataccgc gccacatagc agaactttaa aagtgctcat cattggaaaa   9232

cgttcttcgg ggcgaaaact ctcaaggatc ttaccgctgt tgagatccag ttcgatgtaa   9292

cccactcgtg cacccaactg atcttcagca tcttttactt tcaccagcgt ttctgggtga   9352

gcaaaaacag gaaggcaaaa tgccgcaaaa aagggaataa gggcgacacg gaaatgttga   9412

atactcatac tcttcctttt tcaatattat tgaagcattt atcagggtta ttgtctcatg   9472

agcggataca tatttgaatg tatttagaaa aataaacaaa taggggttcc gcgcacattt   9532

ccccgaaaag tgccacctga cgtctaagaa accattatta tcatgacatt aacctataaa   9592

aataggcgta tcacgaggcc ctttcgtc                                      9620
```

<210> SEQ ID NO 2
<211> LENGTH: 1771
<212> TYPE: PRT
<213> ORGANISM: Hepatitis C virus
<220> FEATURE:
<223> OTHER INFORMATION: Description of Artificial Sequence: Hepatitis C
      pns345

<400> SEQUENCE: 2

-continued

```
Met Ala Ala Tyr Ala Ala Gln Gly Tyr Lys Val Leu Val Leu Asn Pro
  1               5                  10                  15

Ser Val Ala Ala Thr Leu Gly Phe Gly Ala Tyr Met Ser Lys Ala His
             20                  25                  30

Gly Ile Asp Pro Asn Ile Arg Thr Gly Val Arg Thr Ile Thr Thr Gly
         35                  40                  45

Ser Pro Ile Thr Tyr Ser Thr Tyr Gly Lys Phe Leu Ala Asp Gly Gly
     50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
    370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
```

-continued

```
            420                 425                 430

Tyr Cys Leu Ser Thr Gly Cys Val Val Ile Val Gly Arg Val Val Leu
        435                 440                 445

Ser Gly Lys Pro Ala Ile Ile Pro Asp Arg Glu Val Leu Tyr Arg Glu
    450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
        835                 840                 845
```

-continued

```
Glu Tyr Val Glu Ile Arg Gln Val Gly Asp Phe His Tyr Val Thr Gly
    850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
    930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu Asp
   1010                1015                1020

Glu  Arg Glu Ile Ser Val  Pro Ala Glu Ile Leu  Arg Lys Ser Arg Arg
1025                 1030                 1035                 1040

Phe Ala Gln Ala Leu  Pro Val Trp Ala Arg  Pro Asp Tyr Asn Pro  Pro
                1045                 1050                 1055

Leu Val Glu Thr  Trp Lys Lys Pro Asp  Tyr Glu Pro Pro Val  Val His
            1060                 1065                 1070

Gly Cys Pro  Leu Pro Pro Pro Lys  Ser Pro Pro Val Pro  Pro Pro Arg
        1075                 1080                 1085

Lys Lys  Arg Thr Val Val Leu  Thr Glu Ser Thr Leu  Ser Thr Ala Leu
    1090                 1095                 1100

Ala  Glu Leu Ala Thr Arg  Ser Phe Gly Ser Ser  Ser Thr Ser Gly Ile
1105                 1110                 1115                 1120

Thr Gly Asp Asn Thr  Thr Thr Ser Ser Glu  Pro Ala Pro Ser Gly  Cys
                1125                 1130                 1135

Pro Pro Asp Ser  Asp Ala Glu Ser Tyr  Ser Ser Met Pro Pro  Leu Glu
            1140                 1145                 1150

Gly Glu Pro  Gly Asp Pro Asp Leu  Ser Asp Gly Ser Trp  Ser Thr Val
        1155                 1160                 1165

Ser Ser  Glu Ala Asn Ala Glu  Asp Val Val Cys Cys  Ser Met Ser Tyr
    1170                 1175                 1180

Ser  Trp Thr Gly Ala Leu  Val Thr Pro Cys Ala  Ala Glu Glu Gln Lys
1185                 1190                 1195                 1200

Leu Pro Ile Asn Ala  Leu Ser Asn Ser Leu  Leu Arg His His Asn  Leu
                1205                 1210                 1215

Val Tyr Ser Thr  Thr Ser Arg Ser Ala  Cys Gln Arg Gln Lys  Lys Val
            1220                 1225                 1230

Thr Phe Asp  Arg Leu Gln Val Leu  Asp Ser His Tyr Gln  Asp Val Leu
        1235                 1240                 1245

Lys Glu  Val Lys Ala Ala Ala  Ser Lys Val Lys Ala  Asn Leu Leu Ser
    1250                 1255                 1260
```

-continued

```
Val  Glu Glu Ala Cys Ser  Leu Thr Pro Pro His  Ser Ala Lys Ser Lys
1265                 1270                 1275                 1280

Phe Gly Tyr Gly Ala  Lys Asp Val Arg Cys  His Ala Arg Lys Ala  Val
                1285                 1290                 1295

Thr His Ile Asn  Ser Val Trp Lys Asp  Leu Leu Glu Asp Asn  Val Thr
            1300                 1305                 1310

Pro Ile Asp  Thr Thr Ile Met Ala  Lys Asn Glu Val Phe  Cys Val Gln
        1315                 1320                 1325

Pro Glu  Lys Gly Gly Arg Lys  Pro Ala Arg Leu Ile  Val Phe Pro Asp
    1330                 1335                 1340

Leu  Gly Val Arg Val Cys  Glu Lys Met Ala Leu  Tyr Asp Val Val Thr
1345                 1350                 1355                 1360

Lys Leu Pro Leu Ala  Val Met Gly Ser Ser  Tyr Gly Phe Gln Tyr  Ser
                1365                 1370                 1375

Pro Gly Gln Arg  Val Glu Phe Leu Val  Gln Ala Trp Lys Ser  Lys Lys
            1380                 1385                 1390

Thr Pro Met  Gly Phe Ser Tyr Asp  Thr Arg Cys Phe Asp  Ser Thr Val
        1395                 1400                 1405

Thr Glu  Ser Asp Ile Arg Thr  Glu Glu Ala Ile Tyr  Gln Cys Cys Asp
    1410                 1415                 1420

Leu  Asp Pro Gln Ala Arg  Val Ala Ile Lys Ser  Leu Thr Glu Arg Leu
1425                 1430                 1435                 1440

Tyr Val Gly Gly Pro  Leu Thr Asn Ser Arg  Gly Glu Asn Cys Gly  Tyr
                1445                 1450                 1455

Arg Arg Cys Arg  Ala Ser Gly Val Leu  Thr Thr Ser Cys Gly  Asn Thr
            1460                 1465                 1470

Leu Thr Cys  Tyr Ile Lys Ala Arg  Ala Ala Cys Arg Ala  Ala Gly Leu
        1475                 1480                 1485

Gln Asp  Cys Thr Met Leu Val  Cys Gly Asp Asp Leu  Val Val Ile Cys
    1490                 1495                 1500

Glu  Ser Ala Gly Val Gln  Glu Asp Ala Ala Ser  Leu Arg Ala Phe Thr
1505                 1510                 1515                 1520

Glu Ala Met Thr Arg  Tyr Ser Ala Pro Pro  Gly Asp Pro Pro Gln  Pro
                1525                 1530                 1535

Glu Tyr Asp Leu  Glu Leu Ile Thr Ser  Cys Ser Ser Asn Val  Ser Val
            1540                 1545                 1550

Ala His Asp  Gly Ala Gly Lys Arg  Val Tyr Tyr Leu Thr  Arg Asp Pro
        1555                 1560                 1565

Thr Thr  Pro Leu Ala Arg Ala  Ala Trp Glu Thr Ala  Arg His Thr Pro
    1570                 1575                 1580

Val  Asn Ser Trp Leu Gly  Asn Ile Ile Met Phe  Ala Pro Thr Leu Trp
1585                 1590                 1595                 1600

Ala Arg Met Ile Leu  Met Thr His Phe Phe  Ser Val Leu Ile Ala  Arg
                1605                 1610                 1615

Asp Gln Leu Glu  Gln Ala Leu Asp Cys  Glu Ile Tyr Gly Ala  Cys Tyr
            1620                 1625                 1630

Ser Ile Glu  Pro Leu Asp Leu Pro  Pro Ile Ile Gln Arg  Leu His Gly
        1635                 1640                 1645

Leu Ser  Ala Phe Ser Leu His  Ser Tyr Ser Pro Gly  Glu Ile Asn Arg
    1650                 1655                 1660

Val  Ala Ala Cys Leu Arg  Lys Leu Gly Val Pro  Pro Leu Arg Ala Trp
1665                 1670                 1675                 1680

Arg His Arg Ala Arg  Ser Val Arg Ala Arg  Leu Leu Ala Arg Gly  Gly
```

-continued

```
            1685                1690                1695

Arg Ala Ala Ile  Cys Gly Lys Tyr Leu  Phe Asn Trp Ala Val  Arg Thr
            1700                1705                1710

Lys Leu Lys  Leu Thr Pro Ile Ala  Ala Ala Gly Gln Leu  Asp Leu Ser
        1715                1720                1725

Gly Trp  Phe Thr Ala Gly Tyr  Ser Gly Gly Asp Ile  Tyr His Ser Val
    1730                1735                1740

Ser  His Ala Arg Pro Arg  Trp Ile Trp Phe Cys  Leu Leu Leu Leu Ala
1745                1750                1755                1760

Ala Gly Val Gly Ile  Tyr Leu Leu Pro Asn  Arg
            1765                1770
```

<210> SEQ ID NO 3
<211> LENGTH: 9620
<212> TYPE: DNA
<213> ORGANISM: Artificial Sequence
<220> FEATURE:
<221> NAME/KEY: CDS
<222> LOCATION: (1990)..(7302)
<223> OTHER INFORMATION: Description of Artificial Sequence:
pDeltaNS3NS5

<400> SEQUENCE: 3

```
cgcgcgtttc ggtgatgacg gtgaaaacct ctgacacatg cagctcccgg agacggtcac     60

agcttgtctg taagcggatg ccgggagcag acaagcccgt cagggcgcgt cagcgggtgt    120

tggcgggtgt cggggctggc ttaactatgc ggcatcagag cagattgtac tgagagtgca    180

ccatatgaag ctttttgcaa aagcctaggc ctccaaaaaa gcctcctcac tacttctgga    240

atagctcaga ggccgaggcg gcctcggcct ctgcataaat aaaaaaaatt agtcagccat    300

ggggcggaga atgggcggaa ctgggcgggg agggaattat tggctattgg ccattgcata    360

cgttgtatct atatcataat atgtacattt atattggctc atgtccaata tgaccgccat    420

gttgacattg attattgact agttattaat agtaatcaat tacggggtca ttagttcata    480

gcccatatat ggagttccgc gttacataac ttacggtaaa tggcccgcct ggctgaccgc    540

ccaacgaccc ccgcccattg acgtcaataa tgacgtatgt tcccatagta acgccaatag    600

ggactttcca ttgacgtcaa tgggtggagt atttacggta aactgcccac ttggcagtac    660

atcaagtgta tcatatgcca agtccgcccc ctattgacgt caatgacggt aaatggcccg    720

cctggcatta tgcccagtac atgaccttac gggactttcc tacttggcag tacatctacg    780

tattagtcat cgctattacc atggtgatgc ggttttggca gtacaccaat gggcgtggat    840

agcggtttga ctcacgggga tttccaagtc tccaccccat tgacgtcaat gggagtttgt    900

tttggcacca aaatcaacgg gactttccaa aatgtcgtaa taaccccgcc ccgttgacgc    960

aaatgggcgg taggcgtgta cggtgggagg tctatataag cagagctcgt ttagtgaacc   1020

gtcagatcgc ctggagacgc catccacgct gttttgacct ccatagaaga caccgggacc   1080

gatccagcct ccgcggccgg gaacggtgca ttggaacgcg gattccccgt gccaagagtg   1140

acgtaagtac cgcctataga ctctataggc acaccccttt ggctcttatg catgctatac   1200

tgtttttggc ttggggccta tacacccccg ctccttatgc tataggtgat ggtatagctt   1260

agcctatagg tgtgggttat tgaccattat tgaccactcc cctattggtg acgatacttt   1320

ccattactaa tccataacat ggctctttgc cacaactatc tctattggct atatgccaat   1380

actctgtcct tcagagactg acacggactc tgtattttta caggatgggg tccatttatt   1440

atttacaaat tcacatatac aacaacgccg tcccccgtgc ccgcagtttt tattaaacat   1500
```

-continued

```
agcgtgggat ctccgacatc tcgggtacgt gttccggaca tgggctcttc tccggtagcg   1560

gcggagcttc cacatccgag ccctggtccc atccgtccag cggctcatgg tcgctcggca   1620

gctccttgct cctaacagtg gaggccagac ttaggcacag cacaatgccc accaccacca   1680

gtgtgccgca caaggccgtg gcggtagggt atgtgtctga aaatgagctc ggagattggg   1740

ctcgcacctg gacgcagatg gaagacttaa ggcagcggca gaagaagatg caggcagctg   1800

agttgttgta ttctgataag agtcagaggt aactcccgtt gcggtgctgt taacggtgga   1860

gggcagtgta gtctgagcag tactcgttgc tgccgcgcgc gccaccagac ataatagctg   1920

acagactaac agactgttcc tttccatggg tcttttctgc agtcaccgtc gtcgacctaa   1980

gaattcacc atg gct gca tat gca gct cag ggc tat aag gtg cta gta ctc   2031
          Met Ala Ala Tyr Ala Ala Gln Gly Tyr Lys Val Leu Val Leu
            1               5                  10

aac ccc tct gtt gct gca aca ctg ggc ttt ggt gct tac atg tcc aag     2079
Asn Pro Ser Val Ala Ala Thr Leu Gly Phe Gly Ala Tyr Met Ser Lys
 15                  20                  25                  30

gct cat ggg atc gat cct aac atc agg acc ggg gtg aga aca att acc     2127
Ala His Gly Ile Asp Pro Asn Ile Arg Thr Gly Val Arg Thr Ile Thr
                 35                  40                  45

act ggc agc ccc atc acg tac tcc acc tac ggc aag ttc ctt gcc gac     2175
Thr Gly Ser Pro Ile Thr Tyr Ser Thr Tyr Gly Lys Phe Leu Ala Asp
             50                  55                  60

ggc ggg tgc tcg ggg ggc gct tat gac ata ata att tgt gac gag tgc     2223
Gly Gly Cys Ser Gly Gly Ala Tyr Asp Ile Ile Ile Cys Asp Glu Cys
         65                  70                  75

cac tcc acg gat gcc aca tcc atc ttg ggc att ggc act gtc ctt gac     2271
His Ser Thr Asp Ala Thr Ser Ile Leu Gly Ile Gly Thr Val Leu Asp
     80                  85                  90

caa gca gag act gcg ggg gcg aga ctg gtt gtg ctc gcc acc gcc acc     2319
Gln Ala Glu Thr Ala Gly Ala Arg Leu Val Val Leu Ala Thr Ala Thr
 95                 100                 105                 110

cct ccg ggc tcc gtc act gtg ccc cat ccc aac atc gag gag gtt gct     2367
Pro Pro Gly Ser Val Thr Val Pro His Pro Asn Ile Glu Glu Val Ala
                115                 120                 125

ctg tcc acc acc gga gag atc cct ttt tac ggc aag gct atc ccc ctc     2415
Leu Ser Thr Thr Gly Glu Ile Pro Phe Tyr Gly Lys Ala Ile Pro Leu
            130                 135                 140

gaa gta atc aag ggg ggg aga cat ctc atc ttc tgt cat tca aag aag     2463
Glu Val Ile Lys Gly Gly Arg His Leu Ile Phe Cys His Ser Lys Lys
        145                 150                 155

aag tgc gac gaa ctc gcc gca aag ctg gtc gca ttg ggc atc aat gcc     2511
Lys Cys Asp Glu Leu Ala Ala Lys Leu Val Ala Leu Gly Ile Asn Ala
    160                 165                 170

gtg gcc tac tac cgc ggt ctt gac gtg tcc gtc atc ccg acc agc ggc     2559
Val Ala Tyr Tyr Arg Gly Leu Asp Val Ser Val Ile Pro Thr Ser Gly
175                 180                 185                 190

gat gtt gtc gtc gtg gca acc gat gcc ctc atg acc ggc tat acc ggc     2607
Asp Val Val Val Val Ala Thr Asp Ala Leu Met Thr Gly Tyr Thr Gly
                195                 200                 205

gac ttc gac tcg gtg ata gac tgc aat acg tgt gtc acc cag aca gtc     2655
Asp Phe Asp Ser Val Ile Asp Cys Asn Thr Cys Val Thr Gln Thr Val
            210                 215                 220

gat ttc agc ctt gac cct acc ttc acc att gag aca atc acg ctc ccc     2703
Asp Phe Ser Leu Asp Pro Thr Phe Thr Ile Glu Thr Ile Thr Leu Pro
        225                 230                 235

caa gat gct gtc tcc cgc act caa cgt cgg ggc agg act ggc agg ggg     2751
Gln Asp Ala Val Ser Arg Thr Gln Arg Arg Gly Arg Thr Gly Arg Gly
```

-continued

```
    240                 245                 250

aag cca ggc atc tac aga ttt gtg gca ccg ggg gag cgc ccc tcc ggc     2799
Lys Pro Gly Ile Tyr Arg Phe Val Ala Pro Gly Glu Arg Pro Ser Gly
255                 260                 265                 270

atg ttc gac tcg tcc gtc ctc tgt gag tgc tat gac gca ggc tgt gct     2847
Met Phe Asp Ser Ser Val Leu Cys Glu Cys Tyr Asp Ala Gly Cys Ala
                275                 280                 285

tgg tat gag ctc acg ccc gcc gag act aca gtt agg cta cga gcg tac     2895
Trp Tyr Glu Leu Thr Pro Ala Glu Thr Thr Val Arg Leu Arg Ala Tyr
            290                 295                 300

atg aac acc ccg ggg ctt ccc gtg tgc cag gac cat ctt gaa ttt tgg     2943
Met Asn Thr Pro Gly Leu Pro Val Cys Gln Asp His Leu Glu Phe Trp
        305                 310                 315

gag ggc gtc ttt aca ggc ctc act cat ata gat gcc cac ttt cta tcc     2991
Glu Gly Val Phe Thr Gly Leu Thr His Ile Asp Ala His Phe Leu Ser
    320                 325                 330

cag aca aag cag agt ggg gag aac ctt cct tac ctg gta gcg tac caa     3039
Gln Thr Lys Gln Ser Gly Glu Asn Leu Pro Tyr Leu Val Ala Tyr Gln
335                 340                 345                 350

gcc acc gtg tgc gct agg gct caa gcc cct ccc cca tcg tgg gac cag     3087
Ala Thr Val Cys Ala Arg Ala Gln Ala Pro Pro Pro Ser Trp Asp Gln
                355                 360                 365

atg tgg aag tgt ttg att cgc ctc aag ccc acc ctc cat ggg cca aca     3135
Met Trp Lys Cys Leu Ile Arg Leu Lys Pro Thr Leu His Gly Pro Thr
            370                 375                 380

ccc ctg cta tac aga ctg ggc gct gtt cag aat gaa atc acc ctg acg     3183
Pro Leu Leu Tyr Arg Leu Gly Ala Val Gln Asn Glu Ile Thr Leu Thr
        385                 390                 395

cac cca gtc acc aaa tac atc atg aca tgc atg tcg gcc gac ctg gag     3231
His Pro Val Thr Lys Tyr Ile Met Thr Cys Met Ser Ala Asp Leu Glu
    400                 405                 410

gtc gtc acg agc acc tgg gtg ctc gtt ggc ggc gtc ctg gct gct ttg     3279
Val Val Thr Ser Thr Trp Val Leu Val Gly Gly Val Leu Ala Ala Leu
415                 420                 425                 430

gcc gcg tat tgc ctg tca aca ggc tgc gtg gtc ata gtg ggc agg gtc     3327
Ala Ala Tyr Cys Leu Ser Thr Gly Cys Val Val Ile Val Gly Arg Val
                435                 440                 445

gtc ttg tcc ggg aag ccg gca atc ata cct gac agg gaa gtc ctc tac     3375
Val Leu Ser Gly Lys Pro Ala Ile Ile Pro Asp Arg Glu Val Leu Tyr
            450                 455                 460

cga gag ttc gat gag atg gaa gag tgc tct cag cac tta ccg tac atc     3423
Arg Glu Phe Asp Glu Met Glu Glu Cys Ser Gln His Leu Pro Tyr Ile
        465                 470                 475

gag caa ggg atg atg ctc gcc gag cag ttc aag cag aag gcc ctc ggc     3471
Glu Gln Gly Met Met Leu Ala Glu Gln Phe Lys Gln Lys Ala Leu Gly
    480                 485                 490

ctc ctg cag acc gcg tcc cgt cag gca gag gtt atc gcc cct gct gtc     3519
Leu Leu Gln Thr Ala Ser Arg Gln Ala Glu Val Ile Ala Pro Ala Val
495                 500                 505                 510

cag acc aac tgg caa aaa ctc gag acc ttc tgg gcg aag cat atg tgg     3567
Gln Thr Asn Trp Gln Lys Leu Glu Thr Phe Trp Ala Lys His Met Trp
                515                 520                 525

aac ttc atc agt ggg ata caa tac ttg gcg ggc ttg tca acg ctg cct     3615
Asn Phe Ile Ser Gly Ile Gln Tyr Leu Ala Gly Leu Ser Thr Leu Pro
            530                 535                 540

ggt aac ccc gcc att gct tca ttg atg gct ttt aca gct gct gtc acc     3663
Gly Asn Pro Ala Ile Ala Ser Leu Met Ala Phe Thr Ala Ala Val Thr
        545                 550                 555

agc cca cta acc act agc caa acc ctc ctc ttc aac ata ttg ggg ggg     3711
```

-continued

```
Ser Pro Leu Thr Thr Ser Gln Thr Leu Leu Phe Asn Ile Leu Gly Gly
    560                 565                 570

tgg gtg gct gcc cag ctc gcc gcc ccc ggt gcc gct act gcc ttt gtg     3759
Trp Val Ala Ala Gln Leu Ala Ala Pro Gly Ala Ala Thr Ala Phe Val
575                 580                 585                 590

ggc gct ggc tta gct ggc gcc gcc atc ggc agt gtt gga ctg ggg aag     3807
Gly Ala Gly Leu Ala Gly Ala Ala Ile Gly Ser Val Gly Leu Gly Lys
                595                 600                 605

gtc ctc ata gac atc ctt gca ggg tat ggc gcg ggc gtg gcg gga gct     3855
Val Leu Ile Asp Ile Leu Ala Gly Tyr Gly Ala Gly Val Ala Gly Ala
            610                 615                 620

ctt gtg gca ttc aag atc atg agc ggt gag gtc ccc tcc acg gag gac     3903
Leu Val Ala Phe Lys Ile Met Ser Gly Glu Val Pro Ser Thr Glu Asp
        625                 630                 635

ctg gtc aat cta ctg ccc gcc atc ctc tcg ccc gga gcc ctc gta gtc     3951
Leu Val Asn Leu Leu Pro Ala Ile Leu Ser Pro Gly Ala Leu Val Val
    640                 645                 650

ggc gtg gtc tgt gca gca ata ctg cgc cgg cac gtt ggc ccg ggc gag     3999
Gly Val Val Cys Ala Ala Ile Leu Arg Arg His Val Gly Pro Gly Glu
655                 660                 665                 670

ggg gca gtg cag tgg atg aac cgg ctg ata gcc ttc gcc tcc cgg ggg     4047
Gly Ala Val Gln Trp Met Asn Arg Leu Ile Ala Phe Ala Ser Arg Gly
                675                 680                 685

aac cat gtt tcc ccc acg cac tac gtg ccg gag agc gat gca gct gcc     4095
Asn His Val Ser Pro Thr His Tyr Val Pro Glu Ser Asp Ala Ala Ala
            690                 695                 700

cgc gtc act gcc ata ctc agc agc ctc act gta acc cag ctc ctg agg     4143
Arg Val Thr Ala Ile Leu Ser Ser Leu Thr Val Thr Gln Leu Leu Arg
        705                 710                 715

cga ctg cac cag tgg ata agc tcg gag tgt acc act cca tgc tcc ggt     4191
Arg Leu His Gln Trp Ile Ser Ser Glu Cys Thr Thr Pro Cys Ser Gly
    720                 725                 730

tcc tgg cta agg gac atc tgg gac tgg ata tgc gag gtg ttg agc gac     4239
Ser Trp Leu Arg Asp Ile Trp Asp Trp Ile Cys Glu Val Leu Ser Asp
735                 740                 745                 750

ttt aag acc tgg cta aaa gct aag ctc atg cca cag ctg cct ggg atc     4287
Phe Lys Thr Trp Leu Lys Ala Lys Leu Met Pro Gln Leu Pro Gly Ile
                755                 760                 765

ccc ttt gtg tcc tgc cag cgc ggg tat aag ggg gtc tgg cga ggg gac     4335
Pro Phe Val Ser Cys Gln Arg Gly Tyr Lys Gly Val Trp Arg Gly Asp
            770                 775                 780

ggc atc atg cac act cgc tgc cac tgt gga gct gag atc act gga cat     4383
Gly Ile Met His Thr Arg Cys His Cys Gly Ala Glu Ile Thr Gly His
        785                 790                 795

gtc aaa aac ggg acg atg agg atc gtc ggt cct agg acc tgc agg aac     4431
Val Lys Asn Gly Thr Met Arg Ile Val Gly Pro Arg Thr Cys Arg Asn
    800                 805                 810

atg tgg agt ggg acc ttc ccc att aat gcc tac acc acg ggc ccc tgt     4479
Met Trp Ser Gly Thr Phe Pro Ile Asn Ala Tyr Thr Thr Gly Pro Cys
815                 820                 825                 830

acc ccc ctt cct gcg ccg aac tac acg ttc gcg cta tgg agg gtg tct     4527
Thr Pro Leu Pro Ala Pro Asn Tyr Thr Phe Ala Leu Trp Arg Val Ser
                835                 840                 845

gca gag gaa tac gtg gag ata agg cag gtg ggg gac ttc cac tac gtg     4575
Ala Glu Glu Tyr Val Glu Ile Arg Gln Val Gly Asp Phe His Tyr Val
            850                 855                 860

acg ggt atg act act gac aat ctt aaa tgc ccg tgc cag gtc cca tcg     4623
Thr Gly Met Thr Thr Asp Asn Leu Lys Cys Pro Cys Gln Val Pro Ser
        865                 870                 875
```

-continued ccc gaa ttt ttc aca gaa ttg gac ggg gtg cgc cta cat agg ttt gcg 4671
Pro Glu Phe Phe Thr Glu Leu Asp Gly Val Arg Leu His Arg Phe Ala
880 885 890 ccc ccc tgc aag ccc ttg ctg cgg gag gag gta tca ttc aga gta gga 4719
Pro Pro Cys Lys Pro Leu Leu Arg Glu Glu Val Ser Phe Arg Val Gly
895 900 905 910 ctc cac gaa tac ccg gta ggg tcg caa tta cct tgc gag ccc gaa ccg 4767
Leu His Glu Tyr Pro Val Gly Ser Gln Leu Pro Cys Glu Pro Glu Pro
915 920 925 gac gtg gcc gtg ttg acg tcc atg ctc act gat ccc tcc cat ata aca 4815
Asp Val Ala Val Leu Thr Ser Met Leu Thr Asp Pro Ser His Ile Thr
930 935 940 gca gag gcg gcc ggg cga agg ttg gcg agg gga tca ccc ccc tct gtg 4863
Ala Glu Ala Ala Gly Arg Arg Leu Ala Arg Gly Ser Pro Pro Ser Val
945 950 955 gcc agc tcc tcg gct agc cag cta tcc gct cca tct ctc aag gca act 4911
Ala Ser Ser Ser Ala Ser Gln Leu Ser Ala Pro Ser Leu Lys Ala Thr
960 965 970 tgc acc gct aac cat gac tcc cct gat gct gag ctc ata gag gcc aac 4959
Cys Thr Ala Asn His Asp Ser Pro Asp Ala Glu Leu Ile Glu Ala Asn
975 980 985 990 ctc cta tgg agg cag gag atg ggc ggc aac atc acc agg gtt gag tca 5007
Leu Leu Trp Arg Gln Glu Met Gly Gly Asn Ile Thr Arg Val Glu Ser
995 1000 1005 gaa aac aaa gtg gtg att ctg gac tcc ttc gat ccg ctt gtg gcg gag 5055
Glu Asn Lys Val Val Ile Leu Asp Ser Phe Asp Pro Leu Val Ala Glu
1010 1015 1020 gag gac gag cgg gag atc tcc gta ccc gca gaa atc ctg cgg aag tct 5103
Glu Asp Glu Arg Glu Ile Ser Val Pro Ala Glu Ile Leu Arg Lys Ser
1025 1030 1035 cgg aga ttc gcc cag gcc ctg ccc gtt tgg gcg cgg ccg gac tat aac 5151
Arg Arg Phe Ala Gln Ala Leu Pro Val Trp Ala Arg Pro Asp Tyr Asn
1040 1045 1050 ccc ccg cta gtg gag acg tgg aaa aag ccc gac tac gaa cca cct gtg 5199
Pro Pro Leu Val Glu Thr Trp Lys Lys Pro Asp Tyr Glu Pro Pro Val
1055 1060 1065 1070 gtc cat ggc tgc ccg ctt cca cct cca aag tcc cct cct gtg cct ccg 5247
Val His Gly Cys Pro Leu Pro Pro Pro Lys Ser Pro Pro Val Pro Pro
1075 1080 1085 cct cgg aag aag cgg acg gtg gtc ctc act gaa tca acc cta tct act 5295
Pro Arg Lys Lys Arg Thr Val Val Leu Thr Glu Ser Thr Leu Ser Thr
1090 1095 1100 gcc ttg gcc gag ctc gcc acc aga agc ttt ggc agc tcc tca act tcc 5343
Ala Leu Ala Glu Leu Ala Thr Arg Ser Phe Gly Ser Ser Ser Thr Ser
1105 1110 1115 ggc att acg ggc gac aat acg aca aca tcc tct gag ccc gcc cct tct 5391
Gly Ile Thr Gly Asp Asn Thr Thr Thr Ser Ser Glu Pro Ala Pro Ser
1120 1125 1130 ggc tgc ccc ccc gac tcc gac gct gag tcc tat tcc tcc atg ccc ccc 5439
Gly Cys Pro Pro Asp Ser Asp Ala Glu Ser Tyr Ser Ser Met Pro Pro
1135 1140 1145 1150 ctg gag ggg gag cct ggg gat ccg gat ctt agc gac ggg tca tgg tca 5487
Leu Glu Gly Glu Pro Gly Asp Pro Asp Leu Ser Asp Gly Ser Trp Ser
1155 1160 1165 acg gtc agt agt gag gcc aac gcg gag gat gtc gtg tgc tgc tca atg 5535
Thr Val Ser Ser Glu Ala Asn Ala Glu Asp Val Val Cys Cys Ser Met
1170 1175 1180 tct tac tct tgg aca ggc gca ctc gtc acc ccg tgc gcc gcg gaa gaa 5583
Ser Tyr Ser Trp Thr Gly Ala Leu Val Thr Pro Cys Ala Ala Glu Glu
1185 1190 1195

-continued cag aaa ctg ccc atc aat gca cta agc aac tcg ttg cta cgt cac cac 5631
Gln Lys Leu Pro Ile Asn Ala Leu Ser Asn Ser Leu Leu Arg His His
1200 1205 1210 aat ttg gtg tat tcc acc acc tca cgc agt gct tgc caa agg cag aag 5679
Asn Leu Val Tyr Ser Thr Thr Ser Arg Ser Ala Cys Gln Arg Gln Lys
1215 1220 1225 1230 aaa gtc aca ttt gac aga ctg caa gtt ctg gac agc cat tac cag gac 5727
Lys Val Thr Phe Asp Arg Leu Gln Val Leu Asp Ser His Tyr Gln Asp
1235 1240 1245 gta ctc aag gag gtt aaa gca gcg gcg tca aaa gtg aag gct aac ttg 5775
Val Leu Lys Glu Val Lys Ala Ala Ala Ser Lys Val Lys Ala Asn Leu
1250 1255 1260 cta tcc gta gag gaa gct tgc agc ctg acg ccc cca cac tca gcc aaa 5823
Leu Ser Val Glu Glu Ala Cys Ser Leu Thr Pro Pro His Ser Ala Lys
1265 1270 1275 tcc aag ttt ggt tat ggg gca aaa gac gtc cgt tgc cat gcc aga aag 5871
Ser Lys Phe Gly Tyr Gly Ala Lys Asp Val Arg Cys His Ala Arg Lys
1280 1285 1290 gcc gta acc cac atc aac tcc gtg tgg aaa gac ctt ctg gaa gac aat 5919
Ala Val Thr His Ile Asn Ser Val Trp Lys Asp Leu Leu Glu Asp Asn
1295 1300 1305 1310 gta aca cca ata gac act acc atc atg gct aag aac gag gtt ttc tgc 5967
Val Thr Pro Ile Asp Thr Thr Ile Met Ala Lys Asn Glu Val Phe Cys
1315 1320 1325 gtt cag cct gag aag ggg ggt cgt aag cca gct cgt ctc atc gtg ttc 6015
Val Gln Pro Glu Lys Gly Gly Arg Lys Pro Ala Arg Leu Ile Val Phe
1330 1335 1340 ccc gat ctg ggc gtg cgc gtg tgc gaa aag atg gct ttg tac gac gtg 6063
Pro Asp Leu Gly Val Arg Val Cys Glu Lys Met Ala Leu Tyr Asp Val
1345 1350 1355 gtt aca aag ctc ccc ttg gcc gtg atg gga agc tcc tac gga ttc caa 6111
Val Thr Lys Leu Pro Leu Ala Val Met Gly Ser Ser Tyr Gly Phe Gln
1360 1365 1370 tac tca cca gga cag cgg gtt gaa ttc ctc gtg caa gcg tgg aag tcc 6159
Tyr Ser Pro Gly Gln Arg Val Glu Phe Leu Val Gln Ala Trp Lys Ser
1375 1380 1385 1390 aag aaa acc cca atg ggg ttc tcg tat gat acc cgc tgc ttt gac tcc 6207
Lys Lys Thr Pro Met Gly Phe Ser Tyr Asp Thr Arg Cys Phe Asp Ser
1395 1400 1405 aca gtc act gag agc gac atc cgt acg gag gag gca atc tac caa tgt 6255
Thr Val Thr Glu Ser Asp Ile Arg Thr Glu Glu Ala Ile Tyr Gln Cys
1410 1415 1420 tgt gac ctc gac ccc caa gcc cgc gtg gcc atc aag tcc ctc acc gag 6303
Cys Asp Leu Asp Pro Gln Ala Arg Val Ala Ile Lys Ser Leu Thr Glu
1425 1430 1435 agg ctt tat gtt ggg ggc cct ctt acc aat tca agg ggg gag aac tgc 6351
Arg Leu Tyr Val Gly Gly Pro Leu Thr Asn Ser Arg Gly Glu Asn Cys
1440 1445 1450 ggc tat cgc agg tgc cgc gcg agc ggc gta ctg aca act agc tgt ggt 6399
Gly Tyr Arg Arg Cys Arg Ala Ser Gly Val Leu Thr Thr Ser Cys Gly
1455 1460 1465 1470 aac acc ctc act tgc tac atc aag gcc cgg gca gcc tgt cga gcc gca 6447
Asn Thr Leu Thr Cys Tyr Ile Lys Ala Arg Ala Ala Cys Arg Ala Ala
1475 1480 1485 ggg ctc cag gac tgc acc atg ctc gtg tgt ggc gac gac tta gtc gtt 6495
Gly Leu Gln Asp Cys Thr Met Leu Val Cys Gly Asp Asp Leu Val Val
1490 1495 1500 atc tgt gaa agc gcg ggg gtc cag gag gac gcg gcg agc ctg aga gcc 6543
Ile Cys Glu Ser Ala Gly Val Gln Glu Asp Ala Ala Ser Leu Arg Ala -continued

```
      1505                1510                1515

ttc acg gag gct atg acc agg tac tcc gcc ccc cct ggg gac ccc cca      6591
Phe Thr Glu Ala Met Thr Arg Tyr Ser Ala Pro Pro Gly Asp Pro Pro
   1520                1525                1530

caa cca gaa tac gac ttg gag ctc ata aca tca tgc tcc tcc aac gtg      6639
Gln Pro Glu Tyr Asp Leu Glu Leu Ile Thr Ser Cys Ser Ser Asn Val
1535                1540                1545                1550

tca gtc gcc cac gac ggc gct gga aag agg gtc tac tac ctc acc cgt      6687
Ser Val Ala His Asp Gly Ala Gly Lys Arg Val Tyr Tyr Leu Thr Arg
               1555                1560                1565

gac cct aca acc ccc ctc gcg aga gct gcg tgg gag aca gca aga cac      6735
Asp Pro Thr Thr Pro Leu Ala Arg Ala Ala Trp Glu Thr Ala Arg His
           1570                1575                1580

act cca gtc aat tcc tgg cta ggc aac ata atc atg ttt gcc ccc aca      6783
Thr Pro Val Asn Ser Trp Leu Gly Asn Ile Ile Met Phe Ala Pro Thr
       1585                1590                1595

ctg tgg gcg agg atg ata ctg atg acc cat ttc ttt agc gtc ctt ata      6831
Leu Trp Ala Arg Met Ile Leu Met Thr His Phe Phe Ser Val Leu Ile
   1600                1605                1610

gcc agg gac cag ctt gaa cag gcc ctc gat tgc gag atc tac ggg gcc      6879
Ala Arg Asp Gln Leu Glu Gln Ala Leu Asp Cys Glu Ile Tyr Gly Ala
1615                1620                1625                1630

tgc tac tcc ata gaa cca ctg gat cta cct cca atc att caa aga ctc      6927
Cys Tyr Ser Ile Glu Pro Leu Asp Leu Pro Pro Ile Ile Gln Arg Leu
               1635                1640                1645

cat ggc ctc agc gca ttt tca ctc cac agt tac tct cca ggt gaa atc      6975
His Gly Leu Ser Ala Phe Ser Leu His Ser Tyr Ser Pro Gly Glu Ile
           1650                1655                1660

aat agg gtg gcc gca tgc ctc aga aaa ctt ggg gta ccg ccc ttg cga      7023
Asn Arg Val Ala Ala Cys Leu Arg Lys Leu Gly Val Pro Pro Leu Arg
       1665                1670                1675

gct tgg aga cac cgg gcc cgg agc gtc cgc gct agg ctt ctg gcc aga      7071
Ala Trp Arg His Arg Ala Arg Ser Val Arg Ala Arg Leu Leu Ala Arg
   1680                1685                1690

gga ggc agg gct gcc ata tgt ggc aag tac ctc ttc aac tgg gca gta      7119
Gly Gly Arg Ala Ala Ile Cys Gly Lys Tyr Leu Phe Asn Trp Ala Val
1695                1700                1705                1710

aga aca aag ctc aaa ctc act cca ata gcg gcc gct ggc cag ctg gac      7167
Arg Thr Lys Leu Lys Leu Thr Pro Ile Ala Ala Ala Gly Gln Leu Asp
               1715                1720                1725

ttg tcc ggc tgg ttc acg gct ggc tac agc ggg gga gac att tat cac      7215
Leu Ser Gly Trp Phe Thr Ala Gly Tyr Ser Gly Gly Asp Ile Tyr His
           1730                1735                1740

agc gtg tct cat gcc cgg ccc cgc tgg atc tgg ttt tgc cta ctc ctg      7263
Ser Val Ser His Ala Arg Pro Arg Trp Ile Trp Phe Cys Leu Leu Leu
       1745                1750                1755

ctt gct gca ggg gta ggc atc tac ctc ctc ccc aac cga tgaaggttgg      7312
Leu Ala Ala Gly Val Gly Ile Tyr Leu Leu Pro Asn Arg
   1760                1765                1770

ggtaaacact ccggcctaaa aaaaaaaaaa aatctagaaa ggcgcgccaa gatatcaagg   7372

atccactacg cgttagagct cgctgatcag cctcgactgt gccttctagt tgccagccat   7432

ctgttgtttg cccctccccc gtgccttcct tgaccctgga aggtgccact cccactgtcc   7492

tttcctaata aaatgaggaa attgcatcgc attgtctgag taggtgtcat tctattctgg   7552

ggggtggggt ggggcaggac agcaaggggg aggattggga agacaatagc aggcatgctg   7612

gggagctctt ccgcttcctc gctcactgac tcgctgcgct cggtcgttcg gctgcggcga   7672

gcggtatcag ctcactcaaa ggcggtaata cggttatcca cagaatcagg ggataacgca   7732
```

-continued

```
ggaaagaaca tgtgagcaaa aggccagcaa aaggccagga accgtaaaaa ggccgcgttg   7792

ctggcgtttt tccataggct ccgcccccct gacgagcatc acaaaaatcg acgctcaagt   7852

cagaggtggc gaaacccgac aggactataa agataccagg cgtttccccc tggaagctcc   7912

ctcgtgcgct ctcctgttcc gaccctgccg cttaccggat acctgtccgc ctttctccct   7972

tcgggaagcg tggcgctttc tcaatgctca cgctgtaggt atctcagttc ggtgtaggtc   8032

gttcgctcca agctgggctg tgtgcacgaa ccccccgttc agcccgaccg ctgcgcctta   8092

tccggtaact atcgtcttga gtccaacccg gtaagacacg acttatcgcc actggcagca   8152

gccactggta acaggattag cagagcgagg tatgtaggcg gtgctacaga gttcttgaag   8212

tggtggccta actacggcta cactagaagg acagtatttg gtatctgcgc tctgctgaag   8272

ccagttacct tcggaaaaag agttggtagc tcttgatccg gcaaacaaac caccgctggt   8332

agcggtggtt tttttgtttg caagcagcag attacgcgca gaaaaaaagg atctcaagaa   8392

gatcctttga tcttttctac ggggtctgac gctcagtgga acgaaaactc acgttaaggg   8452

attttggtca tgagattatc aaaaaggatc ttcacctaga tccttttaaa ttaaaaatga   8512

agttttaaat caatctaaag tatatatgag taaacttggt ctgacagtta ccaatgctta   8572

atcagtgagg cacctatctc agcgatctgt ctatttcgtt catccatagt tgcctgactc   8632

cccgtcgtgt agataactac gatacgggag ggcttaccat ctggccccag tgctgcaatg   8692

ataccgcgag acccacgctc accggctcca gatttatcag caataaacca gccagccgga   8752

agggccgagc gcagaagtgg tcctgcaact ttatccgcct ccatccagtc tattaattgt   8812

tgccgggaag ctagagtaag tagttcgcca gttaatagtt tgcgcaacgt tgttgccatt   8872

gctacaggca tcgtggtgtc acgctcgtcg tttggtatgg cttcattcag ctccggttcc   8932

caacgatcaa ggcgagttac atgatccccc atgttgtgca aaaaagcggt tagctccttc   8992

ggtcctccga tcgttgtcag aagtaagttg gccgcagtgt tatcactcat ggttatggca   9052

gcactgcata attctcttac tgtcatgcca tccgtaagat gcttttctgt gactggtgag   9112

tactcaacca agtcattctg agaatagtgt atgcggcgac cgagttgctc ttgcccggcg   9172

tcaatacggg ataataccgc gccacatagc agaactttaa aagtgctcat cattggaaaa   9232

cgttcttcgg ggcgaaaact ctcaaggatc ttaccgctgt tgagatccag ttcgatgtaa   9292

cccactcgtg cacccaactg atcttcagca tcttttactt tcaccagcgt ttctgggtga   9352

gcaaaaacag gaaggcaaaa tgccgcaaaa aagggaataa gggcgacacg gaaatgttga   9412

atactcatac tcttcctttt tcaatattat tgaagcattt atcagggtta ttgtctcatg   9472

agcggataca tatttgaatg tatttagaaa aataaacaaa taggggttcc gcgcacattt   9532

ccccgaaaag tgccacctga cgtctaagaa accattatta tcatgacatt aacctataaa   9592

aataggcgta tcacgaggcc ctttcgtc                                      9620
```

<210> SEQ ID NO 4
<211> LENGTH: 1771
<212> TYPE: PRT
<213> ORGANISM: Artificial Sequence
<220> FEATURE:
<223> OTHER INFORMATION: Description of Artificial Sequence:
pDeltaNS3NS5

<400> SEQUENCE: 4

```
Met Ala Ala Tyr Ala Ala Gln Gly Tyr Lys Val Leu Val Leu Asn Pro
  1               5                  10                  15
```

-continued

```
Ser Val Ala Ala Thr Leu Gly Phe Gly Ala Tyr Met Ser Lys Ala His
            20                  25                  30

Gly Ile Asp Pro Asn Ile Arg Thr Gly Val Arg Thr Ile Thr Thr Gly
        35                  40                  45

Ser Pro Ile Thr Tyr Ser Thr Tyr Gly Lys Phe Leu Ala Asp Gly Gly
    50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
    370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
```

-continued

```
        435                 440                 445

Ser Gly Lys Pro Ala Ile Ile Pro Asp Arg Glu Val Leu Tyr Arg Glu
    450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
        835                 840                 845

Glu Tyr Val Glu Ile Arg Gln Val Gly Asp Phe His Tyr Val Thr Gly
    850                 855                 860
```

-continued

```
Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
    930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu Asp
   1010                1015                1020

Glu  Arg Glu Ile Ser Val  Pro Ala Glu Ile Leu  Arg Lys Ser Arg Arg
1025                 1030                 1035                 1040

Phe Ala Gln Ala Leu  Pro Val Trp Ala Arg  Pro Asp Tyr Asn Pro  Pro
                1045                 1050                 1055

Leu Val Glu Thr  Trp Lys Lys Pro Asp  Tyr Glu Pro Pro Val  Val His
            1060                 1065                 1070

Gly Cys Pro  Leu Pro Pro Pro Lys  Ser Pro Pro Val Pro  Pro Pro Arg
        1075                 1080                 1085

Lys Lys  Arg Thr Val Val Leu  Thr Glu Ser Thr Leu  Ser Thr Ala Leu
    1090                 1095                 1100

Ala  Glu Leu Ala Thr Arg  Ser Phe Gly Ser Ser  Ser Thr Ser Gly Ile
1105                 1110                 1115                 1120

Thr Gly Asp Asn Thr  Thr Thr Ser Ser Glu  Pro Ala Pro Ser Gly  Cys
                1125                 1130                 1135

Pro Pro Asp Ser  Asp Ala Glu Ser Tyr  Ser Ser Met Pro Pro  Leu Glu
            1140                 1145                 1150

Gly Glu Pro  Gly Asp Pro Asp Leu  Ser Asp Gly Ser Trp  Ser Thr Val
        1155                 1160                 1165

Ser Ser  Glu Ala Asn Ala Glu  Asp Val Val Cys Cys  Ser Met Ser Tyr
    1170                 1175                 1180

Ser  Trp Thr Gly Ala Leu  Val Thr Pro Cys Ala  Ala Glu Glu Gln Lys
1185                 1190                 1195                 1200

Leu Pro Ile Asn Ala  Leu Ser Asn Ser Leu  Leu Arg His His Asn  Leu
                1205                 1210                 1215

Val Tyr Ser Thr  Thr Ser Arg Ser Ala  Cys Gln Arg Gln Lys  Lys Val
            1220                 1225                 1230

Thr Phe Asp  Arg Leu Gln Val Leu  Asp Ser His Tyr Gln  Asp Val Leu
        1235                 1240                 1245

Lys Glu  Val Lys Ala Ala Ala  Ser Lys Val Lys Ala  Asn Leu Leu Ser
    1250                 1255                 1260

Val  Glu Glu Ala Cys Ser  Leu Thr Pro Pro His  Ser Ala Lys Ser Lys
1265                 1270                 1275                 1280
```

-continued

```
Phe Gly Tyr Gly Ala  Lys Asp Val Arg Cys  His Ala Arg Lys Ala  Val
                1285                 1290                 1295

Thr His Ile Asn  Ser Val Trp Lys Asp  Leu Leu Glu Asp Asn  Val Thr
            1300                 1305                 1310

Pro Ile Asp  Thr Thr Ile Met Ala  Lys Asn Glu Val Phe  Cys Val Gln
        1315                 1320                 1325

Pro Glu  Lys Gly Gly Arg Lys  Pro Ala Arg Leu Ile  Val Phe Pro Asp
    1330                 1335                 1340

Leu  Gly Val Arg Val Cys  Glu Lys Met Ala Leu  Tyr Asp Val Val Thr
1345                 1350                 1355                 1360

Lys Leu Pro Leu Ala  Val Met Gly Ser Ser  Tyr Gly Phe Gln Tyr  Ser
                1365                 1370                 1375

Pro Gly Gln Arg  Val Glu Phe Leu Val  Gln Ala Trp Lys Ser  Lys Lys
            1380                 1385                 1390

Thr Pro Met  Gly Phe Ser Tyr Asp  Thr Arg Cys Phe Asp  Ser Thr Val
        1395                 1400                 1405

Thr Glu  Ser Asp Ile Arg Thr  Glu Glu Ala Ile Tyr  Gln Cys Cys Asp
    1410                 1415                 1420

Leu  Asp Pro Gln Ala Arg  Val Ala Ile Lys Ser  Leu Thr Glu Arg Leu
1425                 1430                 1435                 1440

Tyr Val Gly Gly Pro  Leu Thr Asn Ser Arg  Gly Glu Asn Cys Gly  Tyr
                1445                 1450                 1455

Arg Arg Cys Arg  Ala Ser Gly Val Leu  Thr Thr Ser Cys Gly  Asn Thr
            1460                 1465                 1470

Leu Thr Cys  Tyr Ile Lys Ala Arg  Ala Ala Cys Arg Ala  Ala Gly Leu
        1475                 1480                 1485

Gln Asp  Cys Thr Met Leu Val  Cys Gly Asp Asp Leu  Val Val Ile Cys
    1490                 1495                 1500

Glu  Ser Ala Gly Val Gln  Glu Asp Ala Ala Ser  Leu Arg Ala Phe Thr
1505                 1510                 1515                 1520

Glu Ala Met Thr Arg  Tyr Ser Ala Pro Pro  Gly Asp Pro Pro Gln  Pro
                1525                 1530                 1535

Glu Tyr Asp Leu  Glu Leu Ile Thr Ser  Cys Ser Ser Asn Val  Ser Val
            1540                 1545                 1550

Ala His Asp  Gly Ala Gly Lys Arg  Val Tyr Tyr Leu Thr  Arg Asp Pro
        1555                 1560                 1565

Thr Thr  Pro Leu Ala Arg Ala  Ala Trp Glu Thr Ala  Arg His Thr Pro
    1570                 1575                 1580

Val  Asn Ser Trp Leu Gly  Asn Ile Ile Met Phe  Ala Pro Thr Leu Trp
1585                 1590                 1595                 1600

Ala Arg Met Ile Leu  Met Thr His Phe Phe  Ser Val Leu Ile Ala  Arg
                1605                 1610                 1615

Asp Gln Leu Glu  Gln Ala Leu Asp Cys  Glu Ile Tyr Gly Ala  Cys Tyr
            1620                 1625                 1630

Ser Ile Glu  Pro Leu Asp Leu Pro  Pro Ile Ile Gln Arg  Leu His Gly
        1635                 1640                 1645

Leu Ser  Ala Phe Ser Leu His  Ser Tyr Ser Pro Gly  Glu Ile Asn Arg
    1650                 1655                 1660

Val  Ala Ala Cys Leu Arg  Lys Leu Gly Val Pro  Pro Leu Arg Ala Trp
1665                 1670                 1675                 1680

Arg His Arg Ala Arg  Ser Val Arg Ala Arg  Leu Leu Ala Arg Gly  Gly
                1685                 1690                 1695

Arg Ala Ala Ile  Cys Gly Lys Tyr Leu  Phe Asn Trp Ala Val  Arg Thr
```

-continued

```
            1700                1705                1710

Lys Leu Lys  Leu Thr Pro Ile Ala  Ala Ala Gly Gln Leu  Asp Leu Ser
        1715                1720                1725

Gly Trp  Phe Thr Ala Gly Tyr  Ser Gly Gly Asp Ile  Tyr His Ser Val
    1730                1735                1740

Ser  His Ala Arg Pro Arg  Trp Ile Trp Phe Cys  Leu Leu Leu Leu Ala
1745                1750                1755                1760

Ala Gly Val Gly Ile  Tyr Leu Leu Pro Asn  Arg
                1765                1770


<210> SEQ ID NO 5
<211> LENGTH: 4282
<212> TYPE: DNA
<213> ORGANISM: Artificial Sequence
<220> FEATURE:
<223> OTHER INFORMATION: Description of Artificial Sequence: pCMVII

<400> SEQUENCE: 5

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgaa gctttttgca aaagcctagg cctccaaaaa agcctcctca ctacttctgg    240

aatagctcag aggccgaggc ggcctcggcc tctgcataaa taaaaaaaat tagtcagcca    300

tggggcggag aatgggcgga actgggcggg gagggaatta ttggctattg gccattgcat    360

acgttgtatc tatatcataa tatgtacatt tatattggct catgtccaat atgaccgcca    420

tgttgacatt gattattgac tagttattaa tagtaatcaa ttacggggtc attagttcat    480

agcccatata tggagttccg cgttacataa cttacggtaa atggcccgcc tggctgaccg    540

cccaacgacc cccgcccatt gacgtcaata atgacgtatg ttcccatagt aacgccaata    600

gggactttcc attgacgtca atgggtggag tatttacggt aaactgccca cttggcagta    660

catcaagtgt atcatatgcc aagtccgccc cctattgacg tcaatgacgg taaatggccc    720

gcctggcatt atgcccagta catgacctta cgggactttc ctacttggca gtacatctac    780

gtattagtca tcgctattac catggtgatg cggttttggc agtacaccaa tgggcgtgga    840

tagcggtttg actcacgggg atttccaagt ctccacccca ttgacgtcaa tgggagtttg    900

ttttggcacc aaaatcaacg ggactttcca aaatgtcgta ataaccccgc cccgttgacg    960

caaatgggcg gtaggcgtgt acggtgggag gtctatataa gcagagctcg tttagtgaac   1020

cgtcagatcg cctggagacg ccatccacgc tgttttgacc tccatagaag acaccgggac   1080

cgatccagcc tccgcggccg ggaacggtgc attggaacgc ggattccccg tgccaagagt   1140

gacgtaagta ccgcctatag actctatagg cacacccctt tggctcttat gcatgctata   1200

ctgtttttgg cttggggcct atacaccccc gcttccttat gctataggtg atggtatagc   1260

ttagcctata ggtgtgggtt attgaccatt attgaccact cccctattgg tgacgatact   1320

ttccattact aatccataac atggctcttt gccacaacta tctctattgg ctatatgcca   1380

atactctgtc cttcagagac tgacacggac tctgtatttt tacaggatgg ggtcccattt   1440

attatttaca aattcacata tacaacaacg ccgtcccccg tgcccgcagt ttttattaaa   1500

catagcgtgg gatctccacg cgaatctcgg gtacgtgttc cggacatggg ctcttctccg   1560

gtagcggcgg agcttccaca tccgagccct ggtcccatgc ctccagcggc tcatggtcgc   1620

tcggcagctc cttgctccta acagtggagg ccagacttag gcacagcaca atgcccacca   1680
```

-continued

```
ccaccagtgt gccgcacaag gccgtggcgg tagggtatgt gtctgaaaat gagctcggag   1740
attgggctcg caccgctgac gcagatggaa gacttaaggc agcggcagaa gaagatgcag   1800
gcagctgagt tgttgtattc tgataagagt cagaggtaac tcccgttgcg gtgctgttaa   1860
cggtggaggg cagtgtagtc tgagcagtac tcgttgctgc cgcgcgcgcc accagacata   1920
atagctgaca gactaacaga ctgttccttt ccatgggtct tttctgcagt caccgtcgtc   1980
gacctaagaa ttcagactcg agcaagtcta gaaaggcgcg ccaagatatc aaggatccac   2040
tacgcgttag agctcgctga tcagcctcga ctgtgccttc tagttgccag ccatctgttg   2100
tttgcccctc ccccgtgcct tccttgaccc tggaaggtgc cactcccact gtcctttcct   2160
aataaaatga ggaaattgca tcgcattgtc tgagtaggtg tcattctatt ctggggggtg   2220
gggtggggca ggacagcaag ggggaggatt gggaagacaa tagcaggcat gctggggagc   2280
tcttccgctt cctcgctcac tgactcgctg cgctcggtcg ttcggctgcg gcgagcggta   2340
tcagctcact caaaggcggt aatacggtta tccacagaat caggggataa cgcaggaaag   2400
aacatgtgag caaaaggcca gcaaaaggcc aggaaccgta aaaaggccgc gttgctggcg   2460
tttttccata ggctccgccc ccctgacgag catcacaaaa atcgacgctc aagtcagagg   2520
tggcgaaacc cgacaggact ataaagatac caggcgtttc cccctggaag ctccctcgtg   2580
cgctctcctg ttccgaccct gccgcttacc ggatacctgt ccgcctttct cccttcggga   2640
agcgtggcgc tttctcaatg ctcacgctgt aggtatctca gttcggtgta ggtcgttcgc   2700
tccaagctgg gctgtgtgca cgaacccccc gttcagcccg accgctgcgc cttatccggt   2760
aactatcgtc ttgagtccaa cccggtaaga cacgacttat cgccactggc agcagccact   2820
ggtaacagga ttagcagagc gaggtatgta ggcggtgcta cagagttctt gaagtggtgg   2880
cctaactacg gctacactag aaggacagta tttggtatct gcgctctgct gaagccagtt   2940
accttcggaa aaagagttgg tagctcttga tccggcaaac aaaccaccgc tggtagcggt   3000
ggtttttttg tttgcaagca gcagattacg cgcagaaaaa aaggatctca agaagatcct   3060
ttgatctttt ctacggggtc tgacgctcag tggaacgaaa actcacgtta agggattttg   3120
gtcatgagat tatcaaaaag gatcttcacc tagatccttt taaattaaaa atgaagtttt   3180
aaatcaatct aaagtatata tgagtaaact tggtctgaca gttaccaatg cttaatcagt   3240
gaggcaccta tctcagcgat ctgtctattt cgttcatcca tagttgcctg actccccgtc   3300
gtgtagataa ctacgatacg ggagggctta ccatctggcc ccagtgctgc aatgataccg   3360
cgagacccac gctcaccggc tccagattta tcagcaataa accagccagc cggaagggcc   3420
gagcgcagaa gtggtcctgc aactttatcc gcctccatcc agtctattaa ttgttgccgg   3480
gaagctagag taagtagttc gccagttaat agtttgcgca acgttgttgc cattgctaca   3540
ggcatcgtgg tgtcacgctc gtcgtttggt atggcttcat tcagctccgg ttcccaacga   3600
tcaaggcgag ttacatgatc ccccatgttg tgcaaaaaag cggttagctc cttcggtcct   3660
ccgatcgttg tcagaagtaa gttggccgca gtgttatcac tcatggttat ggcagcactg   3720
cataattctc ttactgtcat gccatccgta agatgctttt ctgtgactgg tgagtactca   3780
accaagtcat tctgagaata gtgtatgcgg cgaccgagtt gctcttgccc ggcgtcaata   3840
cgggataata ccgcgccaca tagcagaact ttaaaagtgc tcatcattgg aaaacgttct   3900
tcggggcgaa aactctcaag gatcttaccg ctgttgagat ccagttcgat gtaacccact   3960
cgtgcaccca actgatcttc agcatctttt actttcacca gcgtttctgg gtgagcaaaa   4020
```

-continued

```
acaggaaggc aaaatgccgc aaaaaaggga ataagggcga cacggaaatg ttgaatactc   4080

atactcttcc tttttcaata ttattgaagc atttatcagg gttattgtct catgagcgga   4140

tacatatttg aatgtattta gaaaaataaa caaatagggg ttccgcgcac atttccccga   4200

aaagtgccac ctgacgtcta agaaaccatt attatcatga cattaaccta taaaaatagg   4260

cgtatcacga ggccctttcg tc                                            4282
```

<210> SEQ ID NO 6
<211> LENGTH: 6299
<212> TYPE: DNA
<213> ORGANISM: Artificial Sequence
<220> FEATURE:
<223> OTHER INFORMATION: Description of Artificial Sequence: pNS34a
<221> NAME/KEY: CDS
<222> LOCATION: (1990)..(4047)

<400> SEQUENCE: 6

```
cgcgcgtttc ggtgatgacg gtgaaaacct ctgacacatg cagctcccgg agacggtcac     60

agcttgtctg taagcggatg ccgggagcag acaagcccgt cagggcgcgt cagcgggtgt    120

tggcgggtgt cggggctggc ttaactatgc ggcatcagag cagattgtac tgagagtgca    180

ccatatgaag ctttttgcaa aagcctaggc ctccaaaaaa gcctcctcac tacttctgga    240

atagctcaga ggccgaggcg gcctcggcct ctgcataaat aaaaaaaatt agtcagccat    300

ggggcggaga atgggcggaa ctgggcgggg agggaattat tggctattgg ccattgcata    360

cgttgtatct atatcataat atgtacattt atattggctc atgtccaata tgaccgccat    420

gttgacattg attattgact agttattaat agtaatcaat tacggggtca ttagttcata    480

gcccatatat ggagttccgc gttacataac ttacggtaaa tggcccgcct ggctgaccgc    540

ccaacgaccc ccgcccattg acgtcaataa tgacgtatgt tcccatagta acgccaatag    600

ggactttcca ttgacgtcaa tgggtggagt atttacggta aactgcccac ttggcagtac    660

atcaagtgta tcatatgcca agtccgcccc ctattgacgt caatgacggt aaatggcccg    720

cctggcatta tgcccagtac atgaccttac gggactttcc tacttggcag tacatctacg    780

tattagtcat cgctattacc atggtgatgc ggttttggca gtacaccaat gggcgtggat    840

agcggtttga ctcacgggga tttccaagtc tccaccccat tgacgtcaat gggagtttgt    900

tttggcacca aaatcaacgg gactttccaa aatgtcgtaa taaccccgcc ccgttgacgc    960

aaatgggcgg taggcgtgta cggtgggagg tctatataag cagagctcgt ttagtgaacc   1020

gtcagatcgc ctggagacgc catccacgct gttttgacct ccatagaaga caccgggacc   1080

gatccagcct ccgcggccgg gaacggtgca ttggaacgcg gattccccgt gccaagagtg   1140

acgtaagtac cgcctataga ctctataggc acaccccttt ggctcttatg catgctatac   1200

tgtttttggc ttggggccta tacacccccg ctccttatgc tataggtgat ggtatagctt   1260

agcctatagg tgtgggttat tgaccattat tgaccactcc cctattggtg acgatacttt   1320

ccattactaa tccataacat ggctctttgc cacaactatc tctattggct atatgccaat   1380

actctgtcct tcagagactg acacggactc tgtattttta caggatgggg tccatttatt   1440

atttacaaat tcacatatac aacaacgccg tcccccgtgc ccgcagtttt tattaaacat   1500

agcgtgggat ctccgacatc tcgggtacgt gttccggaca tgggctcttc tccggtagcg   1560

gcggagcttc cacatccgag ccctggtccc atccgtccag cggctcatgg tcgctcggca   1620

gctccttgct cctaacagtg gaggccagac ttaggcacag cacaatgccc accaccacca   1680

gtgtgccgca caaggccgtg gcggtagggt atgtgtctga aaatgagctc ggagattggg   1740
```

-continued

```
ctcgcacctg gacgcagatg gaagacttaa ggcagcggca gaagaagatg caggcagctg   1800

agttgttgta ttctgataag agtcagaggt aactcccgtt gcggtgctgt taacggtgga   1860

gggcagtgta gtctgagcag tactcgttgc tgccgcgcgc gccaccagac ataatagctg   1920

acagactaac agactgttcc tttccatggg tcttttctgc agtcaccgtc gtcgacctaa   1980

gaattcacc atg gcg ccc atc acg gcg tac gcc cag cag aca agg ggc ctc   2031
          Met Ala Pro Ile Thr Ala Tyr Ala Gln Gln Thr Arg Gly Leu
            1               5                  10

cta ggg tgc ata atc acc agc cta act ggc cgg gac aaa aac caa gtg     2079
Leu Gly Cys Ile Ile Thr Ser Leu Thr Gly Arg Asp Lys Asn Gln Val
 15                  20                  25                  30

gag ggt gag gtc cag att gtg tca act gct gcc caa acc ttc ctg gca     2127
Glu Gly Glu Val Gln Ile Val Ser Thr Ala Ala Gln Thr Phe Leu Ala
                 35                  40                  45

acg tgc atc aat ggg gtg tgc tgg act gtc tac cac ggg gcc gga acg     2175
Thr Cys Ile Asn Gly Val Cys Trp Thr Val Tyr His Gly Ala Gly Thr
             50                  55                  60

agg acc atc gcg tca ccc aag ggt cct gtc atc cag atg tat acc aat     2223
Arg Thr Ile Ala Ser Pro Lys Gly Pro Val Ile Gln Met Tyr Thr Asn
         65                  70                  75

gta gac caa gac ctt gtg ggc tgg ccc gct tcg caa ggt acc cgc tca     2271
Val Asp Gln Asp Leu Val Gly Trp Pro Ala Ser Gln Gly Thr Arg Ser
     80                  85                  90

ttg aca ccc tgc act tgc ggc tcc tcg gac ctt tac ctg gtc acg agg     2319
Leu Thr Pro Cys Thr Cys Gly Ser Ser Asp Leu Tyr Leu Val Thr Arg
 95                 100                 105                 110

cac gcc gat gtc att ccc gtg cgc cgg cgg ggt gat agc agg ggc agc     2367
His Ala Asp Val Ile Pro Val Arg Arg Arg Gly Asp Ser Arg Gly Ser
                115                 120                 125

ctg ctg tcg ccc cgg ccc att tcc tac ttg aaa ggc tcc tcg ggg ggt     2415
Leu Leu Ser Pro Arg Pro Ile Ser Tyr Leu Lys Gly Ser Ser Gly Gly
            130                 135                 140

ccg ctg ttg tgc ccc gcg ggg cac gcc gtg ggc ata ttt agg gcc gcg     2463
Pro Leu Leu Cys Pro Ala Gly His Ala Val Gly Ile Phe Arg Ala Ala
        145                 150                 155

gtg tgc acc cgt gga gtg gct aag gcg gtg gac ttt atc cct gtg gag     2511
Val Cys Thr Arg Gly Val Ala Lys Ala Val Asp Phe Ile Pro Val Glu
    160                 165                 170

aac cta gag aca acc atg agg tcc ccg gtg ttc acg gat aac tcc tct     2559
Asn Leu Glu Thr Thr Met Arg Ser Pro Val Phe Thr Asp Asn Ser Ser
175                 180                 185                 190

cca cca gta gtg ccc cag agc ttc cag gtg gct cac ctc cat gct ccc     2607
Pro Pro Val Val Pro Gln Ser Phe Gln Val Ala His Leu His Ala Pro
                195                 200                 205

aca ggc agc ggc aaa agc acc aag gtc ccg gct gca tat gca gct cag     2655
Thr Gly Ser Gly Lys Ser Thr Lys Val Pro Ala Ala Tyr Ala Ala Gln
            210                 215                 220

ggc tat aag gtg cta gta ctc aac ccc tct gtt gct gca aca ctg ggc     2703
Gly Tyr Lys Val Leu Val Leu Asn Pro Ser Val Ala Ala Thr Leu Gly
        225                 230                 235

ttt ggt gct tac atg tcc aag gct cat ggg atc gat cct aac atc agg     2751
Phe Gly Ala Tyr Met Ser Lys Ala His Gly Ile Asp Pro Asn Ile Arg
    240                 245                 250

acc ggg gtg aga aca att acc act ggc agc ccc atc acg tac tcc acc     2799
Thr Gly Val Arg Thr Ile Thr Thr Gly Ser Pro Ile Thr Tyr Ser Thr
255                 260                 265                 270

tac ggc aag ttc ctt gcc gac ggc ggg tgc tcg ggg ggc gct tat gac     2847
Tyr Gly Lys Phe Leu Ala Asp Gly Gly Cys Ser Gly Gly Ala Tyr Asp
```

-continued

```
              275                 280                 285

ata ata att tgt gac gag tgc cac tcc acg gat gcc aca tcc atc ttg     2895
Ile Ile Ile Cys Asp Glu Cys His Ser Thr Asp Ala Thr Ser Ile Leu
            290                 295                 300

ggc att ggc act gtc ctt gac caa gca gag act gcg ggg gcg aga ctg     2943
Gly Ile Gly Thr Val Leu Asp Gln Ala Glu Thr Ala Gly Ala Arg Leu
        305                 310                 315

gtt gtg ctc gcc acc gcc acc cct ccg ggc tcc gtc act gtg ccc cat     2991
Val Val Leu Ala Thr Ala Thr Pro Pro Gly Ser Val Thr Val Pro His
    320                 325                 330

ccc aac atc gag gag gtt gct ctg tcc acc acc gga gag atc cct ttt     3039
Pro Asn Ile Glu Glu Val Ala Leu Ser Thr Thr Gly Glu Ile Pro Phe
335                 340                 345                 350

tac ggc aag gct atc ccc ctc gaa gta atc aag ggg ggg aga cat ctc     3087
Tyr Gly Lys Ala Ile Pro Leu Glu Val Ile Lys Gly Gly Arg His Leu
                355                 360                 365

atc ttc tgt cat tca aag aag aag tgc gac gaa ctc gcc gca aag ctg     3135
Ile Phe Cys His Ser Lys Lys Lys Cys Asp Glu Leu Ala Ala Lys Leu
            370                 375                 380

gtc gca ttg ggc atc aat gcc gtg gcc tac tac cgc ggt ctt gac gtg     3183
Val Ala Leu Gly Ile Asn Ala Val Ala Tyr Tyr Arg Gly Leu Asp Val
        385                 390                 395

tcc gtc atc ccg acc agc ggc gat gtt gtc gtc gtg gca acc gat gcc     3231
Ser Val Ile Pro Thr Ser Gly Asp Val Val Val Val Ala Thr Asp Ala
    400                 405                 410

ctc atg acc ggc tat acc ggc gac ttc gac tcg gtg ata gac tgc aat     3279
Leu Met Thr Gly Tyr Thr Gly Asp Phe Asp Ser Val Ile Asp Cys Asn
415                 420                 425                 430

acg tgt gtc acc cag aca gtc gat ttc agc ctt gac cct acc ttc acc     3327
Thr Cys Val Thr Gln Thr Val Asp Phe Ser Leu Asp Pro Thr Phe Thr
                435                 440                 445

att gag aca atc acg ctc ccc caa gat gct gtc tcc cgc act caa cgt     3375
Ile Glu Thr Ile Thr Leu Pro Gln Asp Ala Val Ser Arg Thr Gln Arg
            450                 455                 460

cgg ggc agg act ggc agg ggg aag cca ggc atc tac aga ttt gtg gca     3423
Arg Gly Arg Thr Gly Arg Gly Lys Pro Gly Ile Tyr Arg Phe Val Ala
        465                 470                 475

ccg ggg gag cgc ccc tcc ggc atg ttc gac tcg tcc gtc ctc tgt gag     3471
Pro Gly Glu Arg Pro Ser Gly Met Phe Asp Ser Ser Val Leu Cys Glu
    480                 485                 490

tgc tat gac gca ggc tgt gct tgg tat gag ctc acg ccc gcc gag act     3519
Cys Tyr Asp Ala Gly Cys Ala Trp Tyr Glu Leu Thr Pro Ala Glu Thr
495                 500                 505                 510

aca gtt agg cta cga gcg tac atg aac acc ccg ggg ctt ccc gtg tgc     3567
Thr Val Arg Leu Arg Ala Tyr Met Asn Thr Pro Gly Leu Pro Val Cys
                515                 520                 525

cag gac cat ctt gaa ttt tgg gag ggc gtc ttt aca ggc ctc act cat     3615
Gln Asp His Leu Glu Phe Trp Glu Gly Val Phe Thr Gly Leu Thr His
            530                 535                 540

ata gat gcc cac ttt cta tcc cag aca aag cag agt ggg gag aac ctt     3663
Ile Asp Ala His Phe Leu Ser Gln Thr Lys Gln Ser Gly Glu Asn Leu
        545                 550                 555

cct tac ctg gta gcg tac caa gcc acc gtg tgc gct agg gct caa gcc     3711
Pro Tyr Leu Val Ala Tyr Gln Ala Thr Val Cys Ala Arg Ala Gln Ala
    560                 565                 570

cct ccc cca tcg tgg gac cag atg tgg aag tgt ttg att cgc ctc aag     3759
Pro Pro Pro Ser Trp Asp Gln Met Trp Lys Cys Leu Ile Arg Leu Lys
575                 580                 585                 590

ccc acc ctc cat ggg cca aca ccc ctg cta tac aga ctg ggc gct gtt     3807
```

-continued

```
Pro Thr Leu His Gly Pro Thr Pro Leu Leu Tyr Arg Leu Gly Ala Val
                595                 600                 605

cag aat gaa atc acc ctg acg cac cca gtc acc aaa tac atc atg aca     3855
Gln Asn Glu Ile Thr Leu Thr His Pro Val Thr Lys Tyr Ile Met Thr
            610                 615                 620

tgc atg tcg gcc gac ctg gag gtc gtc acg agc acc tgg gtg ctc gtt     3903
Cys Met Ser Ala Asp Leu Glu Val Val Thr Ser Thr Trp Val Leu Val
        625                 630                 635

ggc ggc gtc ctg gct gct ttg gcc gcg tat tgc ctg tca aca ggc tgc     3951
Gly Gly Val Leu Ala Ala Leu Ala Ala Tyr Cys Leu Ser Thr Gly Cys
    640                 645                 650

gtg gtc ata gtg ggc agg gtc gtc ttg tcc ggg aag ccg gca atc ata     3999
Val Val Ile Val Gly Arg Val Val Leu Ser Gly Lys Pro Ala Ile Ile
655                 660                 665                 670

cct gac agg gaa gtc ctc tac cga gag ttc gat gag atg gaa gag tgc     4047
Pro Asp Arg Glu Val Leu Tyr Arg Glu Phe Asp Glu Met Glu Glu Cys
                675                 680                 685

taggatccac tacgcgttag agctcgctga tcagcctcga ctgtgccttc tagttgccag    4107

ccatctgttg tttgcccctc ccccgtgcct tccttgaccc tggaaggtgc cactcccact    4167

gtcctttcct aataaaatga ggaaattgca tcgcattgtc tgagtaggtg tcattctatt    4227

ctggggggtg gggtggggca ggacagcaag ggggaggatt gggaagacaa tagcaggcat    4287

gctggggagc tcttccgctt cctcgctcac tgactcgctg cgctcggtcg ttcggctgcg    4347

gcgagcggta tcagctcact caaaggcggt aatacggtta tccacagaat caggggataa    4407

cgcaggaaag aacatgtgag caaaaggcca gcaaaaggcc aggaaccgta aaaaggccgc    4467

gttgctggcg tttttccata ggctccgccc ccctgacgag catcacaaaa atcgacgctc    4527

aagtcagagg tggcgaaacc cgacaggact ataaagatac caggcgtttc cccctggaag    4587

ctccctcgtg cgctctcctg ttccgaccct gccgcttacc ggatacctgt ccgcctttct    4647

cccttcggga agcgtggcgc tttctcaatg ctcacgctgt aggtatctca gttcggtgta    4707

ggtcgttcgc tccaagctgg gctgtgtgca cgaacccccc gttcagcccg accgctgcgc    4767

cttatccggt aactatcgtc ttgagtccaa cccggtaaga cacgacttat cgccactggc    4827

agcagccact ggtaacagga ttagcagagc gaggtatgta ggcggtgcta cagagttctt    4887

gaagtggtgg cctaactacg gctacactag aaggacagta tttggtatct gcgctctgct    4947

gaagccagtt accttcggaa aaagagttgg tagctcttga tccggcaaac aaaccaccgc    5007

tggtagcggt ggtttttttg tttgcaagca gcagattacg cgcagaaaaa aaggatctca    5067

agaagatcct ttgatctttt ctacggggtc tgacgctcag tggaacgaaa actcacgtta    5127

agggattttg gtcatgagat tatcaaaaag gatcttcacc tagatccttt taaattaaaa    5187

atgaagtttt aaatcaatct aaagtatata tgagtaaact tggtctgaca gttaccaatg    5247

cttaatcagt gaggcaccta tctcagcgat ctgtctattt cgttcatcca tagttgcctg    5307

actccccgtc gtgtagataa ctacgatacg ggagggctta ccatctggcc ccagtgctgc    5367

aatgataccg cgagacccac gctcaccggc tccagattta tcagcaataa accagccagc    5427

cggaagggcc gagcgcagaa gtggtcctgc aactttatcc gcctccatcc agtctattaa    5487

ttgttgccgg gaagctagag taagtagttc gccagttaat agtttgcgca acgttgttgc    5547

cattgctaca ggcatcgtgg tgtcacgctc gtcgtttggt atggcttcat tcagctccgg    5607

ttcccaacga tcaaggcgag ttacatgatc ccccatgttg tgcaaaaaag cggttagctc    5667

cttcggtcct ccgatcgttg tcagaagtaa gttggccgca gtgttatcac tcatggttat    5727
```

-continued

```
ggcagcactg cataattctc ttactgtcat gccatccgta agatgctttt ctgtgactgg   5787

tgagtactca accaagtcat tctgagaata gtgtatgcgg cgaccgagtt gctcttgccc   5847

ggcgtcaata cgggataata ccgcgccaca tagcagaact ttaaaagtgc tcatcattgg   5907

aaaacgttct tcggggcgaa aactctcaag gatcttaccg ctgttgagat ccagttcgat   5967

gtaacccact cgtgcaccca actgatcttc agcatctttt actttcacca gcgtttctgg   6027

gtgagcaaaa acaggaaggc aaaatgccgc aaaaaaggga ataagggcga cacggaaatg   6087

ttgaatactc atactcttcc tttttcaata ttattgaagc atttatcagg gttattgtct   6147

catgagcgga tacatatttg aatgtattta gaaaaataaa caaatagggg ttccgcgcac   6207

atttccccga aaagtgccac ctgacgtcta agaaaccatt attatcatga cattaaccta   6267

taaaaatagg cgtatcacga ggccctttcg tc                                 6299
```

```
<210> SEQ ID NO 7
<211> LENGTH: 686
<212> TYPE: PRT
<213> ORGANISM: Artificial Sequence
<220> FEATURE:
<223> OTHER INFORMATION: Description of Artificial Sequence: pNS34a

<400> SEQUENCE: 7

Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
         35                  40                  45

Ile Asn Gly Val Cys Trp Thr Val Tyr His Gly Ala Gly Thr Arg Thr
     50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Ser Gln Gly Thr Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser Pro Val Phe Thr Asp Asn Ser Ser Pro Pro
            180                 185                 190

Val Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
```

-continued

```
        260                 265                 270

Lys Phe Leu Ala Asp Gly Gly Cys Ser Gly Gly Ala Tyr Asp Ile Ile
    275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Val Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Ile Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Tyr Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Ile Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Val Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685
```

-continued

<210> SEQ ID NO 8
<211> LENGTH: 19912
<212> TYPE: DNA
<213> ORGANISM: Artificial Sequence
<220> FEATURE:
<223> OTHER INFORMATION: Description of Artificial Sequence:
pd.deltaNS3NS5
<221> NAME/KEY: CDS
<222> LOCATION: (12745)..(18057)

<400> SEQUENCE: 8
atcgatccta ccccttgcgc taaagaagta tatgtgccta ctaacgcttg tctttgtctc 60
tgtcactaaa cactggatta ttactcccag atacttattt tggactaatt taaatgattt 120
cggatcaacg ttcttaatat cgctgaatct tccacaattg atgaaagtag ctaggaagag 180
gaattggtat aaagtttttg tttttgtaaa tctcgaagta tactcaaacg aatttagtat 240
tttctcagtg atctcccaga tgctttcacc ctcacttaga agtgctttaa gcattttttt 300
actgtggcta tttcccttat ctgcttcttc cgatgattcg aactgtaatt gcaaactact 360
tacaatatca gtgatatcag attgatgttt ttgtccatag taaggaataa ttgtaaattc 420
ccaagcagga atcaatttct ttaatgaggc ttccagaatt gttgcttttt gcgtcttgta 480
tttaaactgg agtgatttat tgacaatatc gaaactcagc gaattgctta tgatagtatt 540
atagctcatg aatgtggctc tcttgattgc tgttccgtta tgtgtaatca tccaacataa 600
ataggttagt tcagcagcac ataatgctat tttctcacct gaaggtcttt caaacctttc 660
cacaaactga cgaacaagca ccttaggtgg tgttttacat aatatatcaa attgtggcat 720
gcttagcgcc gatcttgtgt gcaattgata tctagtttca actactctat ttatcttgta 780
tcttgcagta ttcaaacacg ctaactcgaa aaactaactt taattgtcct gtttgtctcg 840
cgttctttcg aaaaatgcac cggccgcgca ttatttgtac tgcgaaaata attggtactg 900
cggtatcttc atttcatatt ttaaaaatgc acctttgctg cttttcctta atttttagac 960
ggcccgcagg ttcgttttgc ggtactatct tgtgataaaa agttgttttg acatgtgatc 1020
tgcacagatt ttataatgta ataagcaaga atacattatc aaacgaacaa tactggtaaa 1080
agaaaaccaa aatggacgac attgaaacag ccaagaatct gacggtaaaa gcacgtacag 1140
cttatagcgt ctgggatgta tgtcggctgt ttattgaaat gattgctcct gatgtagata 1200
ttgatataga gagtaaacgt aagtctgatg agctactctt tccaggatat gtcataaggc 1260
ccatggaatc tctcacaacc ggtaggccgt atggtcttga ttctagcgca gaagattcca 1320
gcgtatcttc tgactccagt gctgaggtaa ttttgcctgc tgcgaagatg gttaaggaaa 1380
ggtttgattc gattggaaat ggtatgctct cttcacaaga agcaagtcag gctgccatag 1440
atttgatgct acagaataac aagctgttag acaatagaaa gcaactatac aaatctattg 1500
ctataataat aggaagattg cccgagaaag acaagaagag agctaccgaa atgctcatga 1560
gaaaaatgga ttgtacacag ttattagtcc caccagctcc aacggaagaa gatgttatga 1620
agctcgtaag cgtcgttacc caattgctta ctttagttcc accagatcgt caagctgctt 1680
taataggtga tttattcatc ccggaatctc taaaggatat attcaatagt ttcaatgaac 1740
tggcggcaga gaatcgttta cagcaaaaaa agagtgagtt ggaaggaagg actgaagtga 1800
accatgctaa tacaaatgaa gaagttccct ccaggcgaac aagaagtaga gacacaaatg 1860
caagaggagc atataaatta caaaacacca tcactgaggg ccctaaagcg gttcccacga 1920
aaaaaaggag agtagcaacg agggtaaggg gcagaaaatc acgtaatact tctagggtat 1980

-continued gatccaatat caaaggaaat gatagcattg aaggatgaga ctaatccaat tgaggagtgg 2040
cagcatatag aacagctaaa gggtagtgct gaaggaagca tacgataccc cgcatggaat 2100
gggataatat cacaggaggt actagactac ctttcatcct acataaatag acgcatataa 2160
gtacgcattt aagcataaac acgcactatg ccgttcttct catgtatata tatatacagg 2220
caacacgcag atataggtgc gacgtgaaca gtgagctgta tgtgcgcagc tcgcgttgca 2280
ttttcggaag cgctcgtttt cggaaacgct ttgaagttcc tattccgaag ttcctattct 2340
ctagaaagta taggaacttc agagcgcttt tgaaaaccaa aagcgctctg aagacgcact 2400
ttcaaaaaac caaaaacgca ccggactgta acgagctact aaaatattgc gaataccgct 2460
tccacaaaca ttgctcaaaa gtatctcttt gctatatatc tctgtgctat atccctatat 2520
aacctaccca tccacctttc gctccttgaa cttgcatcta aactcgacct ctacatcaac 2580
aggcttccaa tgctcttcaa attttactgt caagtagacc catacggctg taatatgctg 2640
ctcttcataa tgtaagctta tctttatcga atcgtgtgaa aaactactac cgcgataaac 2700
ctttacggtt ccctgagatt gaattagttc ctttagtata tgatacaaga cacttttgaa 2760
ctttgtacga cgaattttga ggttcgccat cctctggcta tttccaatta tcctgtcggc 2820
gaaacatgct gcttaaaact ccaagcggta ggagaccgat aaaggttaat aggacagccg 2880
tattatctcc gcctcagttt gatcttccgc ttcagactgc catttttcac ataatgaatc 2940
tatttcaccc cacaatcctt catccgcctc cgcatcttgt tccgttaaac tattgacttc 3000
atgttgtaca ttgtttagtt cacgagaagg gtcctcttca ggcggtagct cctgatctcc 3060
tatatgacct ttatcctgtt ctctttccac aaacttagaa atgtattcat gaattatgga 3120
gcacctaata acattcttca aggcggagaa gtttgggcca gatgcccaat atgcttgaca 3180
tgaaaacgtg agaatgaatt tagtattatt gtgatattct gaggcaattt tattataatc 3240
tcgaagataa gagaagaatg cagtgacctt tgtattgaca aatggagatt ccatgtatct 3300
aaaaaatacg cctttaggcc ttctgatacc ctttcccctg cggtttagcg tgccttttac 3360
attaatatct aaaccctctc cgatggtggc ctttaactga ctaataaatg caaccgatat 3420
aaactgtgat aattctgggt gatttatgat tcgatcgaca attgtattgt acactagtgc 3480
aggatcaggc caatccagtt ctttttcaat taccggtgtg tcgtctgtat tcagtacatg 3540
tccaacaaat gcaaatgcta acgttttgta tttcttataa ttgtcaggaa ctggaaaagt 3600
ccccttgtc gtctcgatta cacacctact ttcatcgtac accataggtt ggaagtgctg 3660
cataatacat tgcttaatac aagcaagcag tctctcgcca ttcatatttc agttattttc 3720
cattacagct gatgtcattg tatatcagcg ctgtaaaaat ctatctgtta cagaaggttt 3780
tcgcggtttt tataaacaaa actttcgtta cgaaatcgag caatcacccc agctgcgtat 3840
ttggaaattc gggaaaaagt agagcaacgc gagttgcatt ttttacacca taatgcatga 3900
ttaacttcga gaagggatta aggctaattt cactagtatg tttcaaaaac ctcaatctgt 3960
ccattgaatg ccttataaaa cagctataga ttgcatagaa gagttagcta ctcaatgctt 4020
tttgtcaaag cttactgatg atgatgtgtc tactttcagg cgggtctgta gtaaggagaa 4080
tgacattata aagctggcac ttagaattcc acggactata gactatacta gtatactccg 4140
tctactgtac gatacacttc cgctcaggtc cttgtccttt aacgaggcct taccactctt 4200
ttgttactct attgatccag ctcagcaaag gcagtgtgat ctaagattct atcttcgcga 4260
tgtagtaaaa ctagctagac cgagaaagag actagaaatg caaaaggcac ttctacaatg 4320

-continued

```
gctgccatca ttattatccg atgtgacgct gcattttttt tttttttttt tttttttttt   4380
tttttttttt tttttttttt ttttttggta caaatatcat aaaaaaagag aatcttttta   4440
agcaaggatt ttcttaactt cttcggcgac agcatcaccg acttcggtgg tactgttgga   4500
accacctaaa tcaccagttc tgatacctgc atccaaaacc tttttaactg catcttcaat   4560
ggctttacct tcttcaggca agttcaatga caatttcaac atcattgcag cagacaagat   4620
agtggcgata gggttgacct tattctttgg caaatctgga gcggaaccat ggcatggttc   4680
gtacaaacca aatgcggtgt tcttgtctgg caaagaggcc aaggacgcag atggcaacaa   4740
acccaaggag cctgggataa cggaggcttc atcggagatg atatcaccaa acatgttgct   4800
ggtgattata ataccattta ggtgggttgg gttcttaact aggatcatgg cggcagaatc   4860
aatcaattga tgttgaactt tcaatgtagg gaattcgttc ttgatggttt cctccacagt   4920
ttttctccat aatcttgaag aggccaaaac attagcttta tccaaggacc aaataggcaa   4980
tggtggctca tgttgtaggg ccatgaaagc ggccattctt gtgattcttt gcacttctgg   5040
aacggtgtat tgttcactat cccaagcgac accatcacca tcgtcttcct ttctcttacc   5100
aaagtaaata cctcccacta attctctaac aacaacgaag tcagtacctt tagcaaattg   5160
tggcttgatt ggagataagt ctaaaagaga gtcggatgca aagttacatg gtcttaagtt   5220
ggcgtacaat tgaagttctt tacggatttt tagtaaacct tgttcaggtc taacactacc   5280
ggtaccccat ttaggaccac ccacagcacc taacaaaacg gcatcagcct tcttggaggc   5340
ttccagcgcc tcatctggaa gtggaacacc tgtagcatcg atagcagcac caccaattaa   5400
atgattttcg aaatcgaact tgacattgga acgaacatca gaaatagctt taagaacctt   5460
aatggcttcg gctgtgattt cttgaccaac gtggtcacct ggcaaaacga cgatcttctt   5520
aggggcagac attacaatgg tatatccttg aaatatatat aaaaaaaaaa aaaaaaaaaa   5580
aaaaaaaaaa atgcagcttc tcaatgatat tcgaatacgc tttgaggaga tacagcctaa   5640
tatccgacaa actgttttac agatttacga tcgtacttgt tacccatcat tgaattttga   5700
acatccgaac ctgggagttt tccctgaaac agatagtata tttgaacctg tataataata   5760
tatagtctag cgctttacgg aagacaatgt atgtatttcg gttcctggag aaactattgc   5820
atctattgca taggtaatct tgcacgtcgc atccccggtt cattttctgc gtttccatct   5880
tgcacttcaa tagcatatct ttgttaacga agcatctgtg cttcattttg tagaacaaaa   5940
atgcaacgcg agagcgctaa tttttcaaac aaagaatctg agctgcattt ttacagaaca   6000
gaaatgcaac gcgaaagcgc tattttacca acgaagaatc tgtgcttcat ttttgtaaaa   6060
caaaaatgca acgcgagagc gctaattttt caaacaaaga atctgagctg catttttaca   6120
gaacagaaat gcaacgcgag agcgctattt taccaacaaa gaatctatac ttcttttttg   6180
ttctacaaaa atgcatcccg agagcgctat ttttctaaca aagcatctta gattactttt   6240
tttctccttt gtgcgctcta taatgcagtc tcttgataac tttttgcact gtaggtccgt   6300
taaggttaga agaaggctac tttggtgtct attttctctt ccataaaaaa agcctgactc   6360
cacttcccgc gtttactgat tactagcgaa gctgcgggtg cattttttca agataaaggc   6420
atccccgatt atattctata ccgatgtgga ttgcgcatac tttgtgaaca gaaagtgata   6480
gcgttgatga ttcttcattg gtcagaaaat tatgaacggt ttcttctatt ttgtctctat   6540
atactacgta taggaaatgt ttacattttc gtattgtttt cgattcactc tatgaatagt   6600
tcttactaca atttttttgt ctaaagagta atactagaga taaacataaa aaatgtagag   6660
gtcgagttta gatgcaagtt caaggagcga aaggtggatg ggtaggttat atagggatat   6720
```

-continued

```
agcacagaga tatatagcaa agagatactt ttgagcaatg tttgtggaag cggtattcgc   6780
aatattttag tagctcgtta cagtccggtg cgtttttggt tttttgaaag tgcgtcttca   6840
gagcgctttt ggttttcaaa agcgctctga agttcctata ctttctagag aataggaact   6900
tcggaatagg aacttcaaag cgtttccgaa aacgagcgct tccgaaaatg caacgcgagc   6960
tgcgcacata cagctcactg ttcacgtcgc acctatatct gcgtgttgcc tgtatatata   7020
tatacatgag aagaacggca tagtgcgtgt ttatgcttaa atgcgtactt atatgcgtct   7080
atttatgtag gatgaaaggt agtctagtac ctcctgtgat attatcccat tccatgcggg   7140
gtatcgtatg cttccttcag cactaccctt tagctgttct atatgctgcc actcctcaat   7200
tggattagtc tcatccttca atgctatcat ttcctttgat attggatcat atgcatagta   7260
ccgagaaact agtgcgaagt agtgatcagg tattgctgtt atctgatgag tatacgttgt   7320
cctggccacg gcagaagcac gcttatcgct ccaatttccc acaacattag tcaactccgt   7380
taggcccttc attgaaagaa atgaggtcat caaatgtctt ccaatgtgag attttgggcc   7440
atttttata gcaaagattg aataaggcgc atttttcttc aaagctttat tgtacgatct   7500
gactaagtta tcttttaata attggtattc ctgtttattg cttgaagaat tgccggtcct   7560
atttactcgt tttaggactg gttcagaatt cctcaaaaat tcatccaaat atacaagtgg   7620
atcgatgata agctgtcaaa catgagaatt cttgaagacg aaagggcctc gtgatacgcc   7680
tatttttata ggttaatgtc atgataataa tggtttctta gacgtcaggt ggcacttttc   7740
ggggaaatgt gcgcggaacc cctatttgtt tatttttcta aatacattca aatatgtatc   7800
cgctcatgag acaataaccc tgataaatgc ttcaataata ttgaaaaagg aagagtatga   7860
gtattcaaca tttccgtgtc gcccttattc cctttttttgc ggcattttgc cttcctgttt   7920
ttgctcaccc agaaacgctg gtgaaagtaa aagatgctga agatcagttg ggtgcacgag   7980
tgggttacat cgaactggat ctcaacagcg gtaagatcct tgagagtttt cgccccgaag   8040
aacgttttcc aatgatgagc acttttaaag ttctgctatg tggcgcggta ttatcccgtg   8100
ttgacgccgg gcaagagcaa ctcggtcgcc gcatacacta ttctcagaat gacttggttg   8160
agtactcacc agtcacagaa aagcatctta cggatggcat gacagtaaga gaattatgca   8220
gtgctgccat aaccatgagt gataacactg cggccaactt acttctgaca acgatcggag   8280
gaccgaagga gctaaccgct tttttgcaca acatggggga tcatgtaact cgccttgatc   8340
gttgggaacc ggagctgaat gaagccatac caaacgacga gcgtgacacc acgatgcctg   8400
cagcaatggc aacaacgttg cgcaaactat taactggcga actacttact ctagcttccc   8460
ggcaacaatt aatagactgg atggaggcgg ataaagttgc aggaccactt ctgcgctcgg   8520
cccttccggc tggctggttt attgctgata aatctggagc cggtgagcgt gggtctcgcg   8580
gtatcattgc agcactgggg ccagatggta agccctcccg tatcgtagtt atctacacga   8640
cggggagtca ggcaactatg gatgaacgaa atagacagat cgctgagata ggtgcctcac   8700
tgattaagca ttggtaactg tcagaccaag tttactcata tatactttag attgatttaa   8760
aacttcattt ttaatttaaa aggatctagg tgaagatcct ttttgataat ctcatgacca   8820
aaatccctta acgtgagttt tcgttccact gagcgtcaga ccccgtagaa aagatcaaag   8880
gatcttcttg agatcctttt tttctgcgcg taatctgctg cttgcaaaca aaaaaaccac   8940
cgctaccagc ggtggtttgt ttgccggatc aagagctacc aactcttttt ccgaaggtaa   9000
ctggcttcag cagagcgcag ataccaaata ctgtccttct agtgtagccg tagttaggcc   9060
```

-continued

```
accacttcaa gaactctgta gcaccgccta catacctcgc tctgctaatc ctgttaccag   9120
tggctgctgc cagtggcgat aagtcgtgtc ttaccgggtt ggactcaaga cgatagttac   9180
cggataaggc gcagcggtcg ggctgaacgg ggggttcgtg cacacagccc agcttggagc   9240
gaacgaccta caccgaactg agatacctac agcgtgagct atgagaaagc gccacgcttc   9300
ccgaagggag aaaggcggac aggtatccgg taagcggcag ggtcggaaca ggagagcgca   9360
cgagggagct tccaggggga aacgcctggt atctttatag tcctgtcggg tttcgccacc   9420
tctgacttga gcgtcgattt ttgtgatgct cgtcaggggg gcggagccta tggaaaaacg   9480
ccagcaacgc ggccttttta cggttcctgg ccttttgctg gccttttgct cacatgttct   9540
ttcctgcgtt atcccctgat tctgtggata accgtattac cgcctttgag tgagctgata   9600
ccgctcgccg cagccgaacg accgagcgca gcgagtcagt gagcgaggaa gcggaagagc   9660
gcctgatgcg gtattttctc cttacgcatc tgtgcggtat ttcacaccgc atatggtgca   9720
ctctcagtac aatctgctct gatgccgcat agttaagcca gtatacactc cgctatcgct   9780
acgtgactgg gtcatggctg cgccccgaca cccgccaaca cccgctgacg cgccctgacg   9840
ggcttgtctg ctcccggcat ccgcttacag acaagctgtg accgtctccg ggagctgcat   9900
gtgtcagagg ttttcaccgt catcaccgaa acgcgcgagg cagctgcggt aaagctcatc   9960
agcgtggtcg tgaagcgatt cacagatgtc tgcctgttca tccgcgtcca gctcgttgag  10020
tttctccaga agcgttaatg tctggcttct gataaagcgg gccatgttaa gggcggtttt  10080
ttcctgtttg gtcactgatg cctccgtgta agggggattt ctgttcatgg gggtaatgat  10140
accgatgaaa cgagagagga tgctcacgat acgggttact gatgatgaac atgcccggtt  10200
actggaacgt tgtgagggta aacaactggc ggtatggatg cggcgggacc agagaaaaat  10260
cactcagggt caatgccagc gcttcgttaa tacagatgta ggtgttccac agggtagcca  10320
gcagcatcct gcgatgcaga tccggaacat aatggtgcag ggcgctgact tccgcgtttc  10380
cagactttac gaaacacgga aaccgaagac cattcatgtt gttgctcagg tcgcagacgt  10440
tttgcagcag cagtcgcttc acgttcgctc gcgtatcggt gattcattct gctaaccagt  10500
aaggcaaccc cgccagccta gccgggtcct caacgacagg agcacgatca tgcgcacccg  10560
tggccaggac ccaacgctgc ccgagatgcg ccgcgtgcgg ctgctggaga tggcggacgc  10620
gatggatatg ttctgccaag ggttggtttg cgcattcaca gttctccgca agaattgatt  10680
ggctccaatt cttggagtgg tgaatccgtt agcgaggtgc cgccggcttc cattcaggtc  10740
gaggtggccc ggctccatgc accgcgacgc aacgcgggga ggcagacaag gtatagggcg  10800
gcgcctacaa tccatgccaa cccgttccat gtgctcgccg aggcggcata aatcgccgtg  10860
acgatcagcg gtccaatgat cgaagttagg ctggtaagag ccgcgagcga tccttgaagc  10920
tgtccctgat ggtcgtcatc tacctgcctg gacagcatgg cctgcaacgc gggcatcccg  10980
atgccgccgg aagcgagaag aatcataatg gggaaggcca tccagcctcg cgtcgcgaac  11040
gccagcaaga cgtagcccag cgcgtcggcc gccatgccgg cgataatggc ctgcttctcg  11100
ccgaaacgtt tggtggcggg accagtgacg aaggcttgag cgagggcgtg caagattccg  11160
aataccgcaa gcgacaggcc gatcatcgtc gcgctccagc gaaagcggtc ctcgccgaaa  11220
atgacccaga gcgctgccgg cacctgtcct acgagttgca tgataaagaa gacagtcata  11280
agtgcggcga cgatagtcat gccccgcgcc caccggaagg agctgactgg gttgaaggct  11340
ctcaagggca tcggtcgagg atccttcaat atgcgcacat acgctgttat gttcaaggtc  11400
ccttcgttta agaacgaaag cggtcttcct tttgagggat gtttcaagtt gttcaaatct  11460
```

-continued

```
atcaaatttg caaatcccca gtctgtatct agagcgttga atcggtgatg cgatttgtta  11520

attaaattga tggtgtcacc attaccaggt ctagatatac caatggcaaa ctgagcacaa  11580

caataccagt ccggatcaac tggcaccatc tctcccgtag tctcatctaa tttttcttcc  11640

ggatgaggtt ccagatatac cgcaacacct ttattatggt ttccctgagg gaataataga  11700

atgtcccatt cgaaatcacc aattctaaac ctgggcgaat tgtatttcgg gtttgttaac  11760

tcgttccagt caggaatgtt ccacgtgaag ctatcttcca gcaaagtctc cacttcttca  11820

tcaaattgtg gagaatactc ccaatgctct tatctatggg acttccggga aacacagtac  11880

cgatacttcc caattcgtct tcagagctca ttgtttgttt gaagagacta atcaaagaat  11940

cgttttctca aaaaaattaa tatcttaact gatagtttga tcaaaggggc aaaacgtagg  12000

ggcaaacaaa cggaaaaatc gtttctcaaa ttttctgatg ccaagaactc taaccagtct  12060

tatctaaaaa ttgccttatg atccgtctct ccggttacag cctgtgtaac tgattaatcc  12120

tgcctttcta atcaccattc taatgtttta attaagggat tttgtcttca ttaacggctt  12180

tcgctcataa aaatgttatg acgttttgcc cgcaggcggg aaaccatcca cttcacgaga  12240

ctgatctcct ctgccggaac accgggcatc tccaacttat aagttggaga aataagagaa  12300

tttcagattg agagaatgaa aaaaaaaaac ccttagttca taggtccatt ctcttagcgc  12360

aactacagag aacaggggca caaacaggca aaaaacgggc acaacctcaa tggagtgatg  12420

caacctgcct ggagtaaatg atgacacaag gcaattgacc cacgcatgta tctatctcat  12480

tttcttacac cttctattac cttctgctct ctctgatttg gaaaaagctg aaaaaaaagg  12540

ttgaaaccag ttccctgaaa ttattcccct acttgactaa taagtatata aagacggtag  12600

gtattgattg taattctgta aatctatttc ttaaacttct taaattctac ttttatagtt  12660

agtctttttt ttagttttaa aacaccaaga acttagtttc gaataaacac acataaacaa  12720

acaagcttac aaaacaaatt cacc atg gct gca tat gca gct cag ggc tat     12771
                           Met Ala Ala Tyr Ala Ala Gln Gly Tyr
                            1               5

aag gtg cta gta ctc aac ccc tct gtt gct gca aca ctg ggc ttt ggt    12819
Lys Val Leu Val Leu Asn Pro Ser Val Ala Ala Thr Leu Gly Phe Gly
 10                  15                  20                  25

gct tac atg tcc aag gct cat ggg atc gat cct aac atc agg acc ggg    12867
Ala Tyr Met Ser Lys Ala His Gly Ile Asp Pro Asn Ile Arg Thr Gly
                 30                  35                  40

gtg aga aca att acc act ggc agc ccc atc acg tac tcc acc tac ggc    12915
Val Arg Thr Ile Thr Thr Gly Ser Pro Ile Thr Tyr Ser Thr Tyr Gly
             45                  50                  55

aag ttc ctt gcc gac ggc ggg tgc tcg ggg ggc gct tat gac ata ata    12963
Lys Phe Leu Ala Asp Gly Gly Cys Ser Gly Gly Ala Tyr Asp Ile Ile
         60                  65                  70

att tgt gac gag tgc cac tcc acg gat gcc aca tcc atc ttg ggc att    13011
Ile Cys Asp Glu Cys His Ser Thr Asp Ala Thr Ser Ile Leu Gly Ile
     75                  80                  85

ggc act gtc ctt gac caa gca gag act gcg ggg gcg aga ctg gtt gtg    13059
Gly Thr Val Leu Asp Gln Ala Glu Thr Ala Gly Ala Arg Leu Val Val
 90                  95                 100                 105

ctc gcc acc gcc acc cct ccg ggc tcc gtc act gtg ccc cat ccc aac    13107
Leu Ala Thr Ala Thr Pro Pro Gly Ser Val Thr Val Pro His Pro Asn
                110                 115                 120

atc gag gag gtt gct ctg tcc acc acc gga gag atc cct ttt tac ggc    13155
Ile Glu Glu Val Ala Leu Ser Thr Thr Gly Glu Ile Pro Phe Tyr Gly
            125                 130                 135
```

-continued

```
aag gct atc ccc ctc gaa gta atc aag ggg ggg aga cat ctc atc ttc     13203
Lys Ala Ile Pro Leu Glu Val Ile Lys Gly Gly Arg His Leu Ile Phe
        140                 145                 150

tgt cat tca aag aag aag tgc gac gaa ctc gcc gca aag ctg gtc gca     13251
Cys His Ser Lys Lys Lys Cys Asp Glu Leu Ala Ala Lys Leu Val Ala
    155                 160                 165

ttg ggc atc aat gcc gtg gcc tac tac cgc ggt ctt gac gtg tcc gtc     13299
Leu Gly Ile Asn Ala Val Ala Tyr Tyr Arg Gly Leu Asp Val Ser Val
170                 175                 180                 185

atc ccg acc agc ggc gat gtt gtc gtc gtg gca acc gat gcc ctc atg     13347
Ile Pro Thr Ser Gly Asp Val Val Val Val Ala Thr Asp Ala Leu Met
                190                 195                 200

acc ggc tat acc ggc gac ttc gac tcg gtg ata gac tgc aat acg tgt     13395
Thr Gly Tyr Thr Gly Asp Phe Asp Ser Val Ile Asp Cys Asn Thr Cys
            205                 210                 215

gtc acc cag aca gtc gat ttc agc ctt gac cct acc ttc acc att gag     13443
Val Thr Gln Thr Val Asp Phe Ser Leu Asp Pro Thr Phe Thr Ile Glu
        220                 225                 230

aca atc acg ctc ccc caa gat gct gtc tcc cgc act caa cgt cgg ggc     13491
Thr Ile Thr Leu Pro Gln Asp Ala Val Ser Arg Thr Gln Arg Arg Gly
    235                 240                 245

agg act ggc agg ggg aag cca ggc atc tac aga ttt gtg gca ccg ggg     13539
Arg Thr Gly Arg Gly Lys Pro Gly Ile Tyr Arg Phe Val Ala Pro Gly
250                 255                 260                 265

gag cgc ccc tcc ggc atg ttc gac tcg tcc gtc ctc tgt gag tgc tat     13587
Glu Arg Pro Ser Gly Met Phe Asp Ser Ser Val Leu Cys Glu Cys Tyr
                270                 275                 280

gac gca ggc tgt gct tgg tat gag ctc acg ccc gcc gag act aca gtt     13635
Asp Ala Gly Cys Ala Trp Tyr Glu Leu Thr Pro Ala Glu Thr Thr Val
            285                 290                 295

agg cta cga gcg tac atg aac acc ccg ggg ctt ccc gtg tgc cag gac     13683
Arg Leu Arg Ala Tyr Met Asn Thr Pro Gly Leu Pro Val Cys Gln Asp
        300                 305                 310

cat ctt gaa ttt tgg gag ggc gtc ttt aca ggc ctc act cat ata gat     13731
His Leu Glu Phe Trp Glu Gly Val Phe Thr Gly Leu Thr His Ile Asp
    315                 320                 325

gcc cac ttt cta tcc cag aca aag cag agt ggg gag aac ctt cct tac     13779
Ala His Phe Leu Ser Gln Thr Lys Gln Ser Gly Glu Asn Leu Pro Tyr
330                 335                 340                 345

ctg gta gcg tac caa gcc acc gtg tgc gct agg gct caa gcc cct ccc     13827
Leu Val Ala Tyr Gln Ala Thr Val Cys Ala Arg Ala Gln Ala Pro Pro
                350                 355                 360

cca tcg tgg gac cag atg tgg aag tgt ttg att cgc ctc aag ccc acc     13875
Pro Ser Trp Asp Gln Met Trp Lys Cys Leu Ile Arg Leu Lys Pro Thr
            365                 370                 375

ctc cat ggg cca aca ccc ctg cta tac aga ctg ggc gct gtt cag aat     13923
Leu His Gly Pro Thr Pro Leu Leu Tyr Arg Leu Gly Ala Val Gln Asn
        380                 385                 390

gaa atc acc ctg acg cac cca gtc acc aaa tac atc atg aca tgc atg     13971
Glu Ile Thr Leu Thr His Pro Val Thr Lys Tyr Ile Met Thr Cys Met
    395                 400                 405

tcg gcc gac ctg gag gtc gtc acg agc acc tgg gtg ctc gtt ggc ggc     14019
Ser Ala Asp Leu Glu Val Val Thr Ser Thr Trp Val Leu Val Gly Gly
410                 415                 420                 425

gtc ctg gct gct ttg gcc gcg tat tgc ctg tca aca ggc tgc gtg gtc     14067
Val Leu Ala Ala Leu Ala Ala Tyr Cys Leu Ser Thr Gly Cys Val Val
                430                 435                 440

ata gtg ggc agg gtc gtc ttg tcc ggg aag ccg gca atc ata cct gac     14115
Ile Val Gly Arg Val Val Leu Ser Gly Lys Pro Ala Ile Ile Pro Asp
            445                 450                 455
```

-continued

```
agg gaa gtc ctc tac cga gag ttc gat gag atg gaa gag tgc tct cag     14163
Arg Glu Val Leu Tyr Arg Glu Phe Asp Glu Met Glu Glu Cys Ser Gln
        460                 465                 470

cac tta ccg tac atc gag caa ggg atg atg ctc gcc gag cag ttc aag     14211
His Leu Pro Tyr Ile Glu Gln Gly Met Met Leu Ala Glu Gln Phe Lys
    475                 480                 485

cag aag gcc ctc ggc ctc ctg cag acc gcg tcc cgt cag gca gag gtt     14259
Gln Lys Ala Leu Gly Leu Leu Gln Thr Ala Ser Arg Gln Ala Glu Val
490                 495                 500                 505

atc gcc cct gct gtc cag acc aac tgg caa aaa ctc gag acc ttc tgg     14307
Ile Ala Pro Ala Val Gln Thr Asn Trp Gln Lys Leu Glu Thr Phe Trp
                510                 515                 520

gcg aag cat atg tgg aac ttc atc agt ggg ata caa tac ttg gcg ggc     14355
Ala Lys His Met Trp Asn Phe Ile Ser Gly Ile Gln Tyr Leu Ala Gly
            525                 530                 535

ttg tca acg ctg cct ggt aac ccc gcc att gct tca ttg atg gct ttt     14403
Leu Ser Thr Leu Pro Gly Asn Pro Ala Ile Ala Ser Leu Met Ala Phe
        540                 545                 550

aca gct gct gtc acc agc cca cta acc act agc caa acc ctc ctc ttc     14451
Thr Ala Ala Val Thr Ser Pro Leu Thr Thr Ser Gln Thr Leu Leu Phe
    555                 560                 565

aac ata ttg ggg ggg tgg gtg gct gcc cag ctc gcc gcc ccc ggt gcc     14499
Asn Ile Leu Gly Gly Trp Val Ala Ala Gln Leu Ala Ala Pro Gly Ala
570                 575                 580                 585

gct act gcc ttt gtg ggc gct ggc tta gct ggc gcc gcc atc ggc agt     14547
Ala Thr Ala Phe Val Gly Ala Gly Leu Ala Gly Ala Ala Ile Gly Ser
                590                 595                 600

gtt gga ctg ggg aag gtc ctc ata gac atc ctt gca ggg tat ggc gcg     14595
Val Gly Leu Gly Lys Val Leu Ile Asp Ile Leu Ala Gly Tyr Gly Ala
            605                 610                 615

ggc gtg gcg gga gct ctt gtg gca ttc aag atc atg agc ggt gag gtc     14643
Gly Val Ala Gly Ala Leu Val Ala Phe Lys Ile Met Ser Gly Glu Val
        620                 625                 630

ccc tcc acg gag gac ctg gtc aat cta ctg ccc gcc atc ctc tcg ccc     14691
Pro Ser Thr Glu Asp Leu Val Asn Leu Leu Pro Ala Ile Leu Ser Pro
    635                 640                 645

gga gcc ctc gta gtc ggc gtg gtc tgt gca gca ata ctg cgc cgg cac     14739
Gly Ala Leu Val Val Gly Val Val Cys Ala Ala Ile Leu Arg Arg His
650                 655                 660                 665

gtt ggc ccg ggc gag ggg gca gtg cag tgg atg aac cgg ctg ata gcc     14787
Val Gly Pro Gly Glu Gly Ala Val Gln Trp Met Asn Arg Leu Ile Ala
                670                 675                 680

ttc gcc tcc cgg ggg aac cat gtt tcc ccc acg cac tac gtg ccg gag     14835
Phe Ala Ser Arg Gly Asn His Val Ser Pro Thr His Tyr Val Pro Glu
            685                 690                 695

agc gat gca gct gcc cgc gtc act gcc ata ctc agc agc ctc act gta     14883
Ser Asp Ala Ala Ala Arg Val Thr Ala Ile Leu Ser Ser Leu Thr Val
        700                 705                 710

acc cag ctc ctg agg cga ctg cac cag tgg ata agc tcg gag tgt acc     14931
Thr Gln Leu Leu Arg Arg Leu His Gln Trp Ile Ser Ser Glu Cys Thr
    715                 720                 725

act cca tgc tcc ggt tcc tgg cta agg gac atc tgg gac tgg ata tgc     14979
Thr Pro Cys Ser Gly Ser Trp Leu Arg Asp Ile Trp Asp Trp Ile Cys
730                 735                 740                 745

gag gtg ttg agc gac ttt aag acc tgg cta aaa gct aag ctc atg cca     15027
Glu Val Leu Ser Asp Phe Lys Thr Trp Leu Lys Ala Lys Leu Met Pro
                750                 755                 760

cag ctg cct ggg atc ccc ttt gtg tcc tgc cag cgc ggg tat aag ggg     15075
Gln Leu Pro Gly Ile Pro Phe Val Ser Cys Gln Arg Gly Tyr Lys Gly
```

-continued

```
            765                 770                 775

gtc tgg cga ggg gac ggc atc atg cac act cgc tgc cac tgt gga gct    15123
Val Trp Arg Gly Asp Gly Ile Met His Thr Arg Cys His Cys Gly Ala
        780                 785                 790

gag atc act gga cat gtc aaa aac ggg acg atg agg atc gtc ggt cct    15171
Glu Ile Thr Gly His Val Lys Asn Gly Thr Met Arg Ile Val Gly Pro
    795                 800                 805

agg acc tgc agg aac atg tgg agt ggg acc ttc ccc att aat gcc tac    15219
Arg Thr Cys Arg Asn Met Trp Ser Gly Thr Phe Pro Ile Asn Ala Tyr
810                 815                 820                 825

acc acg ggc ccc tgt acc ccc ctt cct gcg ccg aac tac acg ttc gcg    15267
Thr Thr Gly Pro Cys Thr Pro Leu Pro Ala Pro Asn Tyr Thr Phe Ala
                830                 835                 840

cta tgg agg gtg tct gca gag gaa tac gtg gag ata agg cag gtg ggg    15315
Leu Trp Arg Val Ser Ala Glu Glu Tyr Val Glu Ile Arg Gln Val Gly
            845                 850                 855

gac ttc cac tac gtg acg ggt atg act act gac aat ctt aaa tgc ccg    15363
Asp Phe His Tyr Val Thr Gly Met Thr Thr Asp Asn Leu Lys Cys Pro
        860                 865                 870

tgc cag gtc cca tcg ccc gaa ttt ttc aca gaa ttg gac ggg gtg cgc    15411
Cys Gln Val Pro Ser Pro Glu Phe Phe Thr Glu Leu Asp Gly Val Arg
    875                 880                 885

cta cat agg ttt gcg ccc ccc tgc aag ccc ttg ctg cgg gag gag gta    15459
Leu His Arg Phe Ala Pro Pro Cys Lys Pro Leu Leu Arg Glu Glu Val
890                 895                 900                 905

tca ttc aga gta gga ctc cac gaa tac ccg gta ggg tcg caa tta cct    15507
Ser Phe Arg Val Gly Leu His Glu Tyr Pro Val Gly Ser Gln Leu Pro
                910                 915                 920

tgc gag ccc gaa ccg gac gtg gcc gtg ttg acg tcc atg ctc act gat    15555
Cys Glu Pro Glu Pro Asp Val Ala Val Leu Thr Ser Met Leu Thr Asp
            925                 930                 935

ccc tcc cat ata aca gca gag gcg gcc ggg cga agg ttg gcg agg gga    15603
Pro Ser His Ile Thr Ala Glu Ala Ala Gly Arg Arg Leu Ala Arg Gly
        940                 945                 950

tca ccc ccc tct gtg gcc agc tcc tcg gct agc cag cta tcc gct cca    15651
Ser Pro Pro Ser Val Ala Ser Ser Ser Ala Ser Gln Leu Ser Ala Pro
    955                 960                 965

tct ctc aag gca act tgc acc gct aac cat gac tcc cct gat gct gag    15699
Ser Leu Lys Ala Thr Cys Thr Ala Asn His Asp Ser Pro Asp Ala Glu
970                 975                 980                 985

ctc ata gag gcc aac ctc cta tgg agg cag gag atg ggc ggc aac atc    15747
Leu Ile Glu Ala Asn Leu Leu Trp Arg Gln Glu Met Gly Gly Asn Ile
                990                 995                1000

acc agg gtt gag tca gaa aac aaa gtg gtg att ctg gac tcc ttc gat    15795
Thr Arg Val Glu Ser Glu Asn Lys Val Val Ile Leu Asp Ser Phe Asp
           1005                1010                1015

ccg ctt gtg gcg gag gag gac gag cgg gag atc tcc gta ccc gca gaa    15843
Pro Leu Val Ala Glu Glu Asp Glu Arg Glu Ile Ser Val Pro Ala Glu
       1020                1025                1030

atc ctg cgg aag tct cgg aga ttc gcc cag gcc ctg ccc gtt tgg gcg    15891
Ile Leu Arg Lys Ser Arg Arg Phe Ala Gln Ala Leu Pro Val Trp Ala
   1035                1040                1045

cgg ccg gac tat aac ccc ccg cta gtg gag acg tgg aaa aag ccc gac    15939
Arg Pro Asp Tyr Asn Pro Pro Leu Val Glu Thr Trp Lys Lys Pro Asp
1050               1055                1060                1065

tac gaa cca cct gtg gtc cat ggc tgc ccg ctt cca cct cca aag tcc    15987
Tyr Glu Pro Pro Val Val His Gly Cys Pro Leu Pro Pro Pro Lys Ser
               1070                1075                1080

cct cct gtg cct ccg cct cgg aag aag cgg acg gtg gtc ctc act gaa    16035
```

-continued

```
Pro Pro Val Pro Pro Pro Arg Lys Lys Arg Thr Val Val Leu Thr Glu
            1085                1090                1095

tca acc cta tct act gcc ttg gcc gag ctc gcc acc aga agc ttt ggc    16083
Ser Thr Leu Ser Thr Ala Leu Ala Glu Leu Ala Thr Arg Ser Phe Gly
        1100                1105                1110

agc tcc tca act tcc ggc att acg ggc gac aat acg aca aca tcc tct    16131
Ser Ser Ser Thr Ser Gly Ile Thr Gly Asp Asn Thr Thr Thr Ser Ser
    1115                1120                1125

gag ccc gcc cct tct ggc tgc ccc ccc gac tcc gac gct gag tcc tat    16179
Glu Pro Ala Pro Ser Gly Cys Pro Pro Asp Ser Asp Ala Glu Ser Tyr
1130                1135                1140                1145

tcc tcc atg ccc ccc ctg gag ggg gag cct ggg gat ccg gat ctt agc    16227
Ser Ser Met Pro Pro Leu Glu Gly Glu Pro Gly Asp Pro Asp Leu Ser
                1150                1155                1160

gac ggg tca tgg tca acg gtc agt agt gag gcc aac gcg gag gat gtc    16275
Asp Gly Ser Trp Ser Thr Val Ser Ser Glu Ala Asn Ala Glu Asp Val
            1165                1170                1175

gtg tgc tgc tca atg tct tac tct tgg aca ggc gca ctc gtc acc ccg    16323
Val Cys Cys Ser Met Ser Tyr Ser Trp Thr Gly Ala Leu Val Thr Pro
        1180                1185                1190

tgc gcc gcg gaa gaa cag aaa ctg ccc atc aat gca cta agc aac tcg    16371
Cys Ala Ala Glu Glu Gln Lys Leu Pro Ile Asn Ala Leu Ser Asn Ser
    1195                1200                1205

ttg cta cgt cac cac aat ttg gtg tat tcc acc acc tca cgc agt gct    16419
Leu Leu Arg His His Asn Leu Val Tyr Ser Thr Thr Ser Arg Ser Ala
1210                1215                1220                1225

tgc caa agg cag aag aaa gtc aca ttt gac aga ctg caa gtt ctg gac    16467
Cys Gln Arg Gln Lys Lys Val Thr Phe Asp Arg Leu Gln Val Leu Asp
                1230                1235                1240

agc cat tac cag gac gta ctc aag gag gtt aaa gca gcg gcg tca aaa    16515
Ser His Tyr Gln Asp Val Leu Lys Glu Val Lys Ala Ala Ala Ser Lys
            1245                1250                1255

gtg aag gct aac ttg cta tcc gta gag gaa gct tgc agc ctg acg ccc    16563
Val Lys Ala Asn Leu Leu Ser Val Glu Glu Ala Cys Ser Leu Thr Pro
        1260                1265                1270

cca cac tca gcc aaa tcc aag ttt ggt tat ggg gca aaa gac gtc cgt    16611
Pro His Ser Ala Lys Ser Lys Phe Gly Tyr Gly Ala Lys Asp Val Arg
    1275                1280                1285

tgc cat gcc aga aag gcc gta acc cac atc aac tcc gtg tgg aaa gac    16659
Cys His Ala Arg Lys Ala Val Thr His Ile Asn Ser Val Trp Lys Asp
1290                1295                1300                1305

ctt ctg gaa gac aat gta aca cca ata gac act acc atc atg gct aag    16707
Leu Leu Glu Asp Asn Val Thr Pro Ile Asp Thr Thr Ile Met Ala Lys
                1310                1315                1320

aac gag gtt ttc tgc gtt cag cct gag aag ggg ggt cgt aag cca gct    16755
Asn Glu Val Phe Cys Val Gln Pro Glu Lys Gly Gly Arg Lys Pro Ala
            1325                1330                1335

cgt ctc atc gtg ttc ccc gat ctg ggc gtg cgc gtg tgc gaa aag atg    16803
Arg Leu Ile Val Phe Pro Asp Leu Gly Val Arg Val Cys Glu Lys Met
        1340                1345                1350

gct ttg tac gac gtg gtt aca aag ctc ccc ttg gcc gtg atg gga agc    16851
Ala Leu Tyr Asp Val Val Thr Lys Leu Pro Leu Ala Val Met Gly Ser
    1355                1360                1365

tcc tac gga ttc caa tac tca cca gga cag cgg gtt gaa ttc ctc gtg    16899
Ser Tyr Gly Phe Gln Tyr Ser Pro Gly Gln Arg Val Glu Phe Leu Val
1370                1375                1380                1385

caa gcg tgg aag tcc aag aaa acc cca atg ggg ttc tcg tat gat acc    16947
Gln Ala Trp Lys Ser Lys Lys Thr Pro Met Gly Phe Ser Tyr Asp Thr
                1390                1395                1400
```

-continued

```
cgc tgc ttt gac tcc aca gtc act gag agc gac atc cgt acg gag gag    16995
Arg Cys Phe Asp Ser Thr Val Thr Glu Ser Asp Ile Arg Thr Glu Glu
            1405                1410                1415

gca atc tac caa tgt tgt gac ctc gac ccc caa gcc cgc gtg gcc atc    17043
Ala Ile Tyr Gln Cys Cys Asp Leu Asp Pro Gln Ala Arg Val Ala Ile
        1420                1425                1430

aag tcc ctc acc gag agg ctt tat gtt ggg ggc cct ctt acc aat tca    17091
Lys Ser Leu Thr Glu Arg Leu Tyr Val Gly Gly Pro Leu Thr Asn Ser
    1435                1440                1445

agg ggg gag aac tgc ggc tat cgc agg tgc cgc gcg agc ggc gta ctg    17139
Arg Gly Glu Asn Cys Gly Tyr Arg Arg Cys Arg Ala Ser Gly Val Leu
1450                1455                1460                1465

aca act agc tgt ggt aac acc ctc act tgc tac atc aag gcc cgg gca    17187
Thr Thr Ser Cys Gly Asn Thr Leu Thr Cys Tyr Ile Lys Ala Arg Ala
                1470                1475                1480

gcc tgt cga gcc gca ggg ctc cag gac tgc acc atg ctc gtg tgt ggc    17235
Ala Cys Arg Ala Ala Gly Leu Gln Asp Cys Thr Met Leu Val Cys Gly
            1485                1490                1495

gac gac tta gtc gtt atc tgt gaa agc gcg ggg gtc cag gag gac gcg    17283
Asp Asp Leu Val Val Ile Cys Glu Ser Ala Gly Val Gln Glu Asp Ala
        1500                1505                1510

gcg agc ctg aga gcc ttc acg gag gct atg acc agg tac tcc gcc ccc    17331
Ala Ser Leu Arg Ala Phe Thr Glu Ala Met Thr Arg Tyr Ser Ala Pro
    1515                1520                1525

cct ggg gac ccc cca caa cca gaa tac gac ttg gag ctc ata aca tca    17379
Pro Gly Asp Pro Pro Gln Pro Glu Tyr Asp Leu Glu Leu Ile Thr Ser
1530                1535                1540                1545

tgc tcc tcc aac gtg tca gtc gcc cac gac ggc gct gga aag agg gtc    17427
Cys Ser Ser Asn Val Ser Val Ala His Asp Gly Ala Gly Lys Arg Val
                1550                1555                1560

tac tac ctc acc cgt gac cct aca acc ccc ctc gcg aga gct gcg tgg    17475
Tyr Tyr Leu Thr Arg Asp Pro Thr Thr Pro Leu Ala Arg Ala Ala Trp
            1565                1570                1575

gag aca gca aga cac act cca gtc aat tcc tgg cta ggc aac ata atc    17523
Glu Thr Ala Arg His Thr Pro Val Asn Ser Trp Leu Gly Asn Ile Ile
        1580                1585                1590

atg ttt gcc ccc aca ctg tgg gcg agg atg ata ctg atg acc cat ttc    17571
Met Phe Ala Pro Thr Leu Trp Ala Arg Met Ile Leu Met Thr His Phe
    1595                1600                1605

ttt agc gtc ctt ata gcc agg gac cag ctt gaa cag gcc ctc gat tgc    17619
Phe Ser Val Leu Ile Ala Arg Asp Gln Leu Glu Gln Ala Leu Asp Cys
1610                1615                1620                1625

gag atc tac ggg gcc tgc tac tcc ata gaa cca ctg gat cta cct cca    17667
Glu Ile Tyr Gly Ala Cys Tyr Ser Ile Glu Pro Leu Asp Leu Pro Pro
                1630                1635                1640

atc att caa aga ctc cat ggc ctc agc gca ttt tca ctc cac agt tac    17715
Ile Ile Gln Arg Leu His Gly Leu Ser Ala Phe Ser Leu His Ser Tyr
            1645                1650                1655

tct cca ggt gaa atc aat agg gtg gcc gca tgc ctc aga aaa ctt ggg    17763
Ser Pro Gly Glu Ile Asn Arg Val Ala Ala Cys Leu Arg Lys Leu Gly
        1660                1665                1670

gta ccg ccc ttg cga gct tgg aga cac cgg gcc cgg agc gtc cgc gct    17811
Val Pro Pro Leu Arg Ala Trp Arg His Arg Ala Arg Ser Val Arg Ala
    1675                1680                1685

agg ctt ctg gcc aga gga ggc agg gct gcc ata tgt ggc aag tac ctc    17859
Arg Leu Leu Ala Arg Gly Gly Arg Ala Ala Ile Cys Gly Lys Tyr Leu
1690                1695                1700                1705

ttc aac tgg gca gta aga aca aag ctc aaa ctc act cca ata gcg gcc    17907
Phe Asn Trp Ala Val Arg Thr Lys Leu Lys Leu Thr Pro Ile Ala Ala
                1710                1715                1720
```

-continued

```
gct ggc cag ctg gac ttg tcc ggc tgg ttc acg gct ggc tac agc ggg    17955
Ala Gly Gln Leu Asp Leu Ser Gly Trp Phe Thr Ala Gly Tyr Ser Gly
          1725                1730                1735

gga gac att tat cac agc gtg tct cat gcc cgg ccc cgc tgg atc tgg    18003
Gly Asp Ile Tyr His Ser Val Ser His Ala Arg Pro Arg Trp Ile Trp
      1740                1745                1750

ttt tgc cta ctc ctg ctt gct gca ggg gta ggc atc tac ctc ctc ccc    18051
Phe Cys Leu Leu Leu Leu Ala Ala Gly Val Gly Ile Tyr Leu Leu Pro
   1755                1760                1765

aac cga tgaaggttgg ggtaaacact ccggcctaaa aaaaaaaaaa aatctagaac     18107
Asn Arg
1770

ccgagtcgac tttgttccca ctgtactttt agctcgtaca aaatacaata tacttttcat  18167

ttctccgtaa acaacatgtt ttcccatgta atatcctttt ctatttttcg ttccgttacc  18227

aactttacac atactttata tagctattca cttctataca ctaaaaaact aagacaattt  18287

taattttgct gcctgccata tttcaatttg ttataaattc ctataattta tcctattagt  18347

agctaaaaaa agatgaatgt gaatcgaatc ctaagagaat tggatctgat ccacaggacg  18407

ggtgtggtcg ccatgatcgc gtagtcgata gtggctccaa gtagcgaagc gagcaggact  18467

gggcggcggc caaagcggtc ggacagtgct ccgagaacgg gtgcgcatag aaattgcatc  18527

aacgcatata gcgctagcag cacgccatag tgactggcga tgctgtcgga atggacgata  18587

tcccgcaaga ggcccggcag taccggcata accaagccta tgcctacagc atccagggtg  18647

acggtgccga ggatgacgat gagcgcattg ttagatttca tacacggtgc ctgactgcgt  18707

tagcaattta actgtgataa actaccgcat taaagctttt tctttccaat tttttttttt  18767

tcgtcattat aaaaatcatt acgaccgaga ttcccgggta ataactgata taattaaatt  18827

gaagctctaa tttgtgagtt tagtatacat gcatttactt ataatacagt tttttagttt  18887

tgctggccgc atcttctcaa atatgcttcc cagcctgctt ttctgtaacg ttcaccctct  18947

accttagcat cccttccctt tgcaaatagt cctcttccaa caataataat gtcagatcct  19007

gtagagacca catcatccac ggttctatac tgttgaccca atgcgtctcc cttgtcatct  19067

aaacccacac cgggtgtcat aatcaaccaa tcgtaacctt catctcttcc acccatgtct  19127

ctttgagcaa taaagccgat aacaaaatct ttgtcgctct tcgcaatgtc aacagtaccc  19187

ttagtatatt ctccagtaga tagggagccc ttgcatgaca attctgctaa catcaaaagg  19247

cctctaggtt cctttgttac ttcttctgcc gcctgcttca aaccgctaac aatacctggg  19307

cccaccacac cgtgtgcatt cgtaatgtct gcccattctg ctattctgta tacacccgca  19367

gagtactgca atttgactgt attaccaatg tcagcaaatt ttctgtcttc gaagagtaaa  19427

aaattgtact tggcggataa tgcctttagc ggcttaactg tgccctccat ggaaaaatca  19487

gtcaagatat ccacatgtgt ttttagtaaa caaattttgg gacctaatgc ttcaactaac  19547

tccagtaatt ccttggtggt acgaacatcc aatgaagcac acaagtttgt ttgcttttcg  19607

tgcatgatat taaatagctt ggcagcaaca ggactaggat gagtagcagc acgttcctta  19667

tatgtagctt tcgacatgat ttatcttcgt ttcctgcagg tttttgttct gtgcagttgg  19727

gttaagaata ctgggcaatt tcatgtttct tcaacactac atatgcgtat atataccaat  19787

ctaagtctgt gctccttcct tcgttcttcc ttctgttcgg agattaccga atcaaaaaaa  19847

tttcaaggaa accgaaatca aaaaaaagaa taaaaaaaaa atgatgaatt gaaaagctta  19907

tcgat                                                              19912
```

-continued

<210> SEQ ID NO 9
<211> LENGTH: 1771
<212> TYPE: PRT
<213> ORGANISM: Artificial Sequence
<220> FEATURE:
<223> OTHER INFORMATION: Description of Artificial Sequence:
pd.deltaNS3NS5

<400> SEQUENCE: 9

```
Met Ala Ala Tyr Ala Ala Gln Gly Tyr Lys Val Leu Val Leu Asn Pro
  1               5                  10                  15

Ser Val Ala Ala Thr Leu Gly Phe Gly Ala Tyr Met Ser Lys Ala His
             20                  25                  30

Gly Ile Asp Pro Asn Ile Arg Thr Gly Val Arg Thr Ile Thr Thr Gly
         35                  40                  45

Ser Pro Ile Thr Tyr Ser Thr Tyr Gly Lys Phe Leu Ala Asp Gly Gly
     50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365
```

-continued

```
Lys Cys Leu Ile Arg Leu Lys Pro Thr Leu His Gly Pro Thr Pro Leu
    370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
        435                 440                 445

Ser Gly Lys Pro Ala Ile Ile Pro Asp Arg Glu Val Leu Tyr Arg Glu
    450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780
```

-continued

```
Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
        835                 840                 845

Glu Tyr Val Glu Ile Arg Gln Val Gly Asp Phe His Tyr Val Thr Gly
    850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
    930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu Asp
   1010                 1015                1020

Glu  Arg Glu Ile Ser Val  Pro Ala Glu Ile Leu  Arg Lys Ser Arg Arg
1025                 1030                 1035                 1040

Phe Ala Gln Ala Leu  Pro Val Trp Ala Arg  Pro Asp Tyr Asn Pro  Pro
                1045                 1050                 1055

Leu Val Glu Thr  Trp Lys Lys Pro Asp  Tyr Glu Pro Pro Val  Val His
            1060                 1065                 1070

Gly Cys Pro  Leu Pro Pro Pro Lys  Ser Pro Pro Val Pro  Pro Pro Arg
        1075                 1080                 1085

Lys Lys  Arg Thr Val Val Leu  Thr Glu Ser Thr Leu  Ser Thr Ala Leu
    1090                 1095                 1100

Ala  Glu Leu Ala Thr Arg  Ser Phe Gly Ser Ser  Ser Thr Ser Gly Ile
1105                 1110                 1115                 1120

Thr Gly Asp Asn Thr  Thr Thr Ser Ser Glu  Pro Ala Pro Ser Gly  Cys
                1125                 1130                 1135

Pro Pro Asp Ser  Asp Ala Glu Ser Tyr  Ser Ser Met Pro Pro  Leu Glu
            1140                 1145                 1150

Gly Glu Pro  Gly Asp Pro Asp Leu  Ser Asp Gly Ser Trp  Ser Thr Val
        1155                 1160                 1165

Ser Ser  Glu Ala Asn Ala Glu  Asp Val Val Cys Cys  Ser Met Ser Tyr
    1170                 1175                 1180

Ser  Trp Thr Gly Ala Leu  Val Thr Pro Cys Ala  Ala Glu Glu Gln Lys
1185                 1190                 1195                 1200

Leu Pro Ile Asn Ala  Leu Ser Asn Ser Leu  Leu Arg His His Asn  Leu
```

-continued

```
            1205                1210                1215

Val Tyr Ser Thr Thr Ser Arg Ser Ala Cys Gln Arg Gln Lys Lys Val
        1220                1225                1230

Thr Phe Asp Arg Leu Gln Val Leu Asp Ser His Tyr Gln Asp Val Leu
    1235                1240                1245

Lys Glu Val Lys Ala Ala Ala Ser Lys Val Lys Ala Asn Leu Leu Ser
    1250                1255                1260

Val Glu Glu Ala Cys Ser Leu Thr Pro Pro His Ser Ala Lys Ser Lys
1265                1270                1275                1280

Phe Gly Tyr Gly Ala Lys Asp Val Arg Cys His Ala Arg Lys Ala Val
            1285                1290                1295

Thr His Ile Asn Ser Val Trp Lys Asp Leu Leu Glu Asp Asn Val Thr
        1300                1305                1310

Pro Ile Asp Thr Thr Ile Met Ala Lys Asn Glu Val Phe Cys Val Gln
    1315                1320                1325

Pro Glu Lys Gly Gly Arg Lys Pro Ala Arg Leu Ile Val Phe Pro Asp
    1330                1335                1340

Leu Gly Val Arg Val Cys Glu Lys Met Ala Leu Tyr Asp Val Val Thr
1345                1350                1355                1360

Lys Leu Pro Leu Ala Val Met Gly Ser Ser Tyr Gly Phe Gln Tyr Ser
            1365                1370                1375

Pro Gly Gln Arg Val Glu Phe Leu Val Gln Ala Trp Lys Ser Lys Lys
        1380                1385                1390

Thr Pro Met Gly Phe Ser Tyr Asp Thr Arg Cys Phe Asp Ser Thr Val
    1395                1400                1405

Thr Glu Ser Asp Ile Arg Thr Glu Glu Ala Ile Tyr Gln Cys Cys Asp
    1410                1415                1420

Leu Asp Pro Gln Ala Arg Val Ala Ile Lys Ser Leu Thr Glu Arg Leu
1425                1430                1435                1440

Tyr Val Gly Gly Pro Leu Thr Asn Ser Arg Gly Glu Asn Cys Gly Tyr
            1445                1450                1455

Arg Arg Cys Arg Ala Ser Gly Val Leu Thr Thr Ser Cys Gly Asn Thr
        1460                1465                1470

Leu Thr Cys Tyr Ile Lys Ala Arg Ala Ala Cys Arg Ala Ala Gly Leu
    1475                1480                1485

Gln Asp Cys Thr Met Leu Val Cys Gly Asp Asp Leu Val Val Ile Cys
    1490                1495                1500

Glu Ser Ala Gly Val Gln Glu Asp Ala Ala Ser Leu Arg Ala Phe Thr
1505                1510                1515                1520

Glu Ala Met Thr Arg Tyr Ser Ala Pro Pro Gly Asp Pro Pro Gln Pro
            1525                1530                1535

Glu Tyr Asp Leu Glu Leu Ile Thr Ser Cys Ser Ser Asn Val Ser Val
        1540                1545                1550

Ala His Asp Gly Ala Gly Lys Arg Val Tyr Tyr Leu Thr Arg Asp Pro
    1555                1560                1565

Thr Thr Pro Leu Ala Arg Ala Ala Trp Glu Thr Ala Arg His Thr Pro
    1570                1575                1580

Val Asn Ser Trp Leu Gly Asn Ile Ile Met Phe Ala Pro Thr Leu Trp
1585                1590                1595                1600

Ala Arg Met Ile Leu Met Thr His Phe Phe Ser Val Leu Ile Ala Arg
            1605                1610                1615

Asp Gln Leu Glu Gln Ala Leu Asp Cys Glu Ile Tyr Gly Ala Cys Tyr
        1620                1625                1630
```

-continued

Ser Ile Glu Pro Leu Asp Leu Pro Pro Ile Ile Gln Arg Leu His Gly
        1635                1640                1645

Leu Ser Ala Phe Ser Leu His Ser Tyr Ser Pro Gly Glu Ile Asn Arg
    1650                1655                1660

Val Ala Ala Cys Leu Arg Lys Leu Gly Val Pro Pro Leu Arg Ala Trp
1665                1670                1675                1680

Arg His Arg Ala Arg Ser Val Arg Ala Arg Leu Leu Ala Arg Gly Gly
                1685                1690                1695

Arg Ala Ala Ile Cys Gly Lys Tyr Leu Phe Asn Trp Ala Val Arg Thr
            1700                1705                1710

Lys Leu Lys Leu Thr Pro Ile Ala Ala Ala Gly Gln Leu Asp Leu Ser
        1715                1720                1725

Gly Trp Phe Thr Ala Gly Tyr Ser Gly Gly Asp Ile Tyr His Ser Val
    1730                1735                1740

Ser His Ala Arg Pro Arg Trp Ile Trp Phe Cys Leu Leu Leu Leu Ala
1745                1750                1755                1760

Ala Gly Val Gly Ile Tyr Leu Leu Pro Asn Arg
                1765                1770

<210> SEQ ID NO 10
<211> LENGTH: 19798
<212> TYPE: DNA
<213> ORGANISM: Artificial Sequence
<220> FEATURE:
<223> OTHER INFORMATION: Description of Artificial Sequence:
pd.deltaNS3NS5.pj
<221> NAME/KEY: CDS
<222> LOCATION: (12679)..(17991)

<400> SEQUENCE: 10
atcgatccta ccccttgcgc taaagaagta tatgtgccta ctaacgcttg tctttgtctc 60
tgtcactaaa cactggatta ttactcccag atacttattt tggactaatt taaatgattt 120
cggatcaacg ttcttaatat cgctgaatct tccacaattg atgaaagtag ctaggaagag 180
gaattggtat aaagtttttg tttttgtaaa tctcgaagta tactcaaacg aatttagtat 240
tttctcagtg atctcccaga tgctttcacc ctcacttaga agtgctttaa gcattttttt 300
actgtggcta tttcccttat ctgcttcttc cgatgattcg aactgtaatt gcaaactact 360
tacaatatca gtgatatcag attgatgttt ttgtccatag taaggaataa ttgtaaattc 420
ccaagcagga atcaatttct ttaatgaggc ttccagaatt gttgcttttt gcgtcttgta 480
tttaaactgg agtgatttat tgacaatatc gaaactcagc gaattgctta tgatagtatt 540
atagctcatg aatgtggctc tcttgattgc tgttccgtta tgtgtaatca tccaacataa 600
ataggttagt tcagcagcac ataatgctat tttctcacct gaaggtcttt caaacctttc 660
cacaaactga cgaacaagca ccttaggtgg tgttttacat aatatatcaa attgtggcat 720
gcttagcgcc gatcttgtgt gcaattgata tctagtttca actactctat ttatcttgta 780
tcttgcagta ttcaaacacg ctaactcgaa aaactaactt taattgtcct gtttgtctcg 840
cgttctttcg aaaaatgcac cggccgcgca ttatttgtac tgcgaaaata attggtactg 900
cggtatcttc atttcatatt ttaaaaatgc acctttgctg cttttcctta atttttagac 960
ggcccgcagg ttcgttttgc ggtactatct tgtgataaaa agttgttttg acatgtgatc 1020
tgcacagatt ttataatgta ataagcaaga atacattatc aaacgaacaa tactggtaaa 1080
agaaaaccaa aatggacgac attgaaacag ccaagaatct gacggtaaaa gcacgtacag 1140

-continued

```
cttatagcgt ctgggatgta tgtcggctgt ttattgaaat gattgctcct gatgtagata   1200
ttgatataga gagtaaacgt aagtctgatg agctactctt tccaggatat gtcataaggc   1260
ccatggaatc tctcacaacc ggtaggccgt atggtcttga ttctagcgca gaagattcca   1320
gcgtatcttc tgactccagt gctgaggtaa ttttgcctgc tgcgaagatg gttaaggaaa   1380
ggtttgattc gattggaaat ggtatgctct cttcacaaga agcaagtcag gctgccatag   1440
atttgatgct acagaataac aagctgttag acaatagaaa gcaactatac aaatctattg   1500
ctataataat aggaagattg cccgagaaag acaagaagag agctaccgaa atgctcatga   1560
gaaaaatgga ttgtacacag ttattagtcc caccagctcc aacggaagaa gatgttatga   1620
agctcgtaag cgtcgttacc caattgctta ctttagttcc accagatcgt caagctgctt   1680
taataggtga tttattcatc ccggaatctc taaaggatat attcaatagt ttcaatgaac   1740
tggcggcaga gaatcgttta cagcaaaaaa agagtgagtt ggaaggaagg actgaagtga   1800
accatgctaa tacaaatgaa gaagttccct ccaggcgaac aagaagtaga gacacaaatg   1860
caagaggagc atataaatta caaaacacca tcactgaggg ccctaaagcg gttcccacga   1920
aaaaaaggag agtagcaacg agggtaaggg gcagaaaatc acgtaatact tctagggtat   1980
gatccaatat caaaggaaat gatagcattg aaggatgaga ctaatccaat tgaggagtgg   2040
cagcatatag aacagctaaa gggtagtgct gaaggaagca tacgataccc cgcatggaat   2100
gggataatat cacaggaggt actagactac ctttcatcct acataaatag acgcatataa   2160
gtacgcattt aagcataaac acgcactatg ccgttcttct catgtatata tatatacagg   2220
caacacgcag atataggtgc gacgtgaaca gtgagctgta tgtgcgcagc tcgcgttgca   2280
ttttcggaag cgctcgtttt cggaaacgct ttgaagttcc tattccgaag ttcctattct   2340
ctagaaagta taggaacttc agagcgcttt tgaaaaccaa aagcgctctg aagacgcact   2400
ttcaaaaaac caaaaacgca ccggactgta acgagctact aaaatattgc gaataccgct   2460
tccacaaaca ttgctcaaaa gtatctcttt gctatatatc tctgtgctat atccctatat   2520
aacctaccca tccacctttc gctccttgaa cttgcatcta aactcgacct ctacatcaac   2580
aggcttccaa tgctcttcaa attttactgt caagtagacc catacggctg taatatgctg   2640
ctcttcataa tgtaagctta tctttatcga atcgtgtgaa aaactactac cgcgataaac   2700
ctttacggtt ccctgagatt gaattagttc ctttagtata tgatacaaga cacttttgaa   2760
ctttgtacga cgaattttga ggttcgccat cctctggcta tttccaatta tcctgtcggc   2820
tattatctcc gcctcagttt gatcttccgc ttcagactgc catttttcac ataatgaatc   2880
tatttcaccc cacaatcctt catccgcctc cgcatcttgt tccgttaaac tattgacttc   2940
atgttgtaca ttgtttagtt cacgagaagg gtcctcttca ggcggtagct cctgatctcc   3000
tatatgacct ttatcctgtt ctctttccac aaacttagaa atgtattcat gaattatgga   3060
gcacctaata acattcttca aggcggagaa gtttgggcca gatgcccaat atgcttgaca   3120
tgaaaacgtg agaatgaatt tagtattatt gtgatattct gaggcaattt tattataatc   3180
tcgaagataa gagaagaatg cagtgacctt tgtattgaca aatggagatt ccatgtatct   3240
aaaaaatacg cctttaggcc ttctgatacc ctttcccctg cggtttagcg tgccttttac   3300
attaatatct aaaccctctc cgatggtggc ctttaactga ctaataaatg caaccgatat   3360
aaactgtgat aattctgggt gatttatgat tcgatcgaca attgtattgt acactagtgc   3420
aggatcaggc caatccagtt ctttttcaat taccggtgtg tcgtctgtat tcagtacatg   3480
tccaacaaat gcaaatgcta acgttttgta tttcttataa ttgtcaggaa ctggaaaagt   3540
```

-continued

```
ccccttgtc gtctcgatta cacacctact ttcatcgtac accataggtt ggaagtgctg   3600
cataatacat tgcttaatac aagcaagcag tctctcgcca ttcatatttc agttattttc   3660
cattacagct gatgtcattg tatatcagcg ctgtaaaaat ctatctgtta cagaaggttt   3720
tcgcggtttt tataaacaaa actttcgtta cgaaatcgag caatcacccc agctgcgtat   3780
ttggaaattc gggaaaaagt agagcaacgc gagttgcatt ttttacacca taatgcatga   3840
ttaacttcga gaagggatta aggctaattt cactagtatg tttcaaaaac ctcaatctgt   3900
ccattgaatg ccttataaaa cagctataga ttgcatagaa gagttagcta ctcaatgctt   3960
tttgtcaaag cttactgatg atgatgtgtc tactttcagg cgggtctgta gtaaggagaa   4020
tgacattata aagctggcac ttagaattcc acggactata gactatacta gtatactccg   4080
tctactgtac gatacacttc cgctcaggtc cttgtccttt aacgaggcct taccactctt   4140
ttgttactct attgatccag ctcagcaaag gcagtgtgat ctaagattct atcttcgcga   4200
tgtagtaaaa ctagctagac cgagaaagag actagaaatg caaaaggcac ttctacaatg   4260
gctgccatca ttattatccg atgtgacgct gcattttttt tttttttttt tttttttttt   4320
tttttttttt tttttttttt ttttttggta caaatatcat aaaaaaagag aatcttttta   4380
agcaaggatt ttcttaactt cttcggcgac agcatcaccg acttcggtgg tactgttgga   4440
accacctaaa tcaccagttc tgatacctgc atccaaaacc tttttaactg catcttcaat   4500
ggctttacct tcttcaggca agttcaatga caatttcaac atcattgcag cagacaagat   4560
agtggcgata gggttgacct tattctttgg caaatctgga gcggaaccat ggcatggttc   4620
gtacaaacca aatgcggtgt tcttgtctgg caaagaggcc aaggacgcag atggcaacaa   4680
acccaaggag cctgggataa cggaggcttc atcggagatg atatcaccaa acatgttgct   4740
ggtgattata ataccattta ggtgggttgg gttcttaact aggatcatgg cggcagaatc   4800
aatcaattga tgttgaactt tcaatgtagg gaattcgttc ttgatggttt cctccacagt   4860
ttttctccat aatcttgaag aggccaaaac attagcttta tccaaggacc aaataggcaa   4920
tggtggctca tgttgtaggg ccatgaaagc ggccattctt gtgattcttt gcacttctgg   4980
aacggtgtat tgttcactat cccaagcgac accatcacca tcgtcttcct ttctcttacc   5040
aaagtaaata cctcccacta attctctaac aacaacgaag tcagtacctt tagcaaattg   5100
tggcttgatt ggagataagt ctaaaagaga gtcggatgca aagttacatg gtcttaagtt   5160
ggcgtacaat tgaagttctt tacggatttt tagtaaacct tgttcaggtc taacactacc   5220
ggtaccccat ttaggaccac ccacagcacc taacaaaacg gcatcagcct tcttggaggc   5280
ttccagcgcc tcatctggaa gtggaacacc tgtagcatcg atagcagcac caccaattaa   5340
atgattttcg aaatcgaact tgacattgga acgaacatca gaaatagctt taagaacctt   5400
aatggcttcg gctgtgattt cttgaccaac gtggtcacct ggcaaaacga cgatcttctt   5460
aggggcagac attacaatgg tatatccttg aaatatatat aaaaaaaaaa aaaaaaaaaa   5520
aaaaaaaaaa atgcagcttc tcaatgatat tcgaatacgc tttgaggaga tacagcctaa   5580
tatccgacaa actgttttac agatttacga tcgtacttgt tacccatcat tgaattttga   5640
acatccgaac ctgggagttt tccctgaaac agatagtata tttgaacctg tataataata   5700
tatagtctag cgctttacgg aagacaatgt atgtatttcg gttcctggag aaactattgc   5760
atctattgca taggtaatct tgcacgtcgc atccccggtt cattttctgc gtttccatct   5820
tgcacttcaa tagcatatct ttgttaacga agcatctgtg cttcattttg tagaacaaaa   5880
```

-continued

```
atgcaacgcg agagcgctaa tttttcaaac aaagaatctg agctgcattt ttacagaaca   5940
gaaatgcaac gcgaaagcgc tattttacca acgaagaatc tgtgcttcat ttttgtaaaa   6000
caaaaatgca acgcgagagc gctaattttt caaacaaaga atctgagctg catttttaca   6060
gaacagaaat gcaacgcgag agcgctattt taccaacaaa gaatctatac ttcttttttg   6120
ttctacaaaa atgcatcccg agagcgctat ttttctaaca aagcatctta gattactttt   6180
tttctccttt gtgcgctcta taatgcagtc tcttgataac tttttgcact gtaggtccgt   6240
taaggttaga agaaggctac tttggtgtct attttctctt ccataaaaaa agcctgactc   6300
cacttcccgc gtttactgat tactagcgaa gctgcgggtg catttttca agataaaggc    6360
atccccgatt atattctata ccgatgtgga ttgcgcatac tttgtgaaca gaaagtgata   6420
gcgttgatga ttcttcattg gtcagaaaat tatgaacggt ttcttctatt ttgtctctat   6480
atactacgta taggaaatgt ttacattttc gtattgtttt cgattcactc tatgaatagt   6540
tcttactaca atttttttgt ctaaagagta atactagaga taaacataaa aaatgtagag   6600
gtcgagttta gatgcaagtt caaggagcga aaggtggatg ggtaggttat atagggatat   6660
agcacagaga tatatagcaa agagatactt ttgagcaatg tttgtggaag cggtattcgc   6720
aatattttag tagctcgtta cagtccggtg cgtttttggt tttttgaaag tgcgtcttca   6780
gagcgctttt ggttttcaaa agcgctctga agttcctata ctttctagag aataggaact   6840
tcggaatagg aacttcaaag cgtttccgaa aacgagcgct tccgaaaatg caacgcgagc   6900
tgcgcacata cagctcactg ttcacgtcgc acctatatct gcgtgttgcc tgtatatata   6960
tatacatgag aagaacggca tagtgcgtgt ttatgcttaa atgcgtactt atatgcgtct   7020
atttatgtag gatgaaaggt agtctagtac ctcctgtgat attatcccat tccatgcggg   7080
gtatcgtatg cttccttcag cactaccctt tagctgttct atatgctgcc actcctcaat   7140
tggattagtc tcatccttca atgctatcat ttcctttgat attggatcat atgcatagta   7200
ccgagaaact agtgcgaagt agtgatcagg tattgctgtt atctgatgag tatacgttgt   7260
cctggccacg gcagaagcac gcttatcgct ccaatttccc acaacattag tcaactccgt   7320
taggcccttc attgaaagaa atgaggtcat caaatgtctt ccaatgtgag attttgggcc   7380
atttttttata gcaaagattg aataaggcgc atttttcttc aaagctttat tgtacgatct  7440
gactaagtta tcttttaata attggtattc ctgtttattg cttgaagaat tgccggtcct   7500
atttactcgt tttaggactg gttcagaatt cctcaaaaat tcatccaaat atacaagtgg   7560
atcgatgata agctgtcaaa catgagaatt cttgaagacg aaagggcctc gtgatacgcc   7620
tatttttata ggttaatgtc atgataataa tggtttctta gacgtcaggt ggcacttttc   7680
ggggaaatgt gcgcggaacc cctatttgtt tatttttcta aatacattca aatatgtatc   7740
cgctcatgag acaataaccc tgataaatgc ttcaataata ttgaaaaagg aagagtatga   7800
gtattcaaca tttccgtgtc gcccttattc cctttttttgc ggcattttgc cttcctgttt  7860
ttgctcaccc agaaacgctg gtgaaagtaa aagatgctga agatcagttg ggtgcacgag   7920
tgggttacat cgaactggat ctcaacagcg gtaagatcct tgagagtttt cgccccgaag   7980
aacgttttcc aatgatgagc acttttaaag ttctgctatg tggcgcggta ttatcccgtg   8040
ttgacgccgg gcaagagcaa ctcggtcgcc gcatacacta ttctcagaat gacttggttg   8100
agtactcacc agtcacagaa aagcatctta cggatggcat gacagtaaga gaattatgca   8160
gtgctgccat aaccatgagt gataacactg cggccaactt acttctgaca acgatcggag   8220
gaccgaagga gctaaccgct tttttgcaca acatggggga tcatgtaact cgccttgatc   8280
```

-continued

```
gttgggaacc ggagctgaat gaagccatac caaacgacga gcgtgacacc acgatgcctg   8340
cagcaatggc aacaacgttg cgcaaactat taactggcga actacttact ctagcttccc   8400
ggcaacaatt aatagactgg atggaggcgg ataaagttgc aggaccactt ctgcgctcgg   8460
cccttccggc tggctggttt attgctgata aatctggagc cggtgagcgt gggtctcgcg   8520
gtatcattgc agcactgggg ccagatggta agccctcccg tatcgtagtt atctacacga   8580
cggggagtca ggcaactatg gatgaacgaa atagacagat cgctgagata ggtgcctcac   8640
tgattaagca ttggtaactg tcagaccaag tttactcata tatactttag attgatttaa   8700
aacttcattt ttaatttaaa aggatctagg tgaagatcct ttttgataat ctcatgacca   8760
aaatccctta acgtgagttt tcgttccact gagcgtcaga ccccgtagaa aagatcaaag   8820
gatcttcttg agatcctttt tttctgcgcg taatctgctg cttgcaaaca aaaaaaccac   8880
cgctaccagc ggtggtttgt ttgccggatc aagagctacc aactcttttt ccgaaggtaa   8940
ctggcttcag cagagcgcag ataccaaata ctgtccttct agtgtagccg tagttaggcc   9000
accacttcaa gaactctgta gcaccgccta catacctcgc tctgctaatc ctgttaccag   9060
tggctgctgc cagtggcgat aagtcgtgtc ttaccgggtt ggactcaaga cgatagttac   9120
cggataaggc gcagcggtcg ggctgaacgg ggggttcgtg cacacagccc agcttggagc   9180
gaacgaccta caccgaactg agatacctac agcgtgagct atgagaaagc gccacgcttc   9240
ccgaagggag aaaggcggac aggtatccgg taagcggcag ggtcggaaca ggagagcgca   9300
cgagggagct tccaggggga aacgcctggt atctttatag tcctgtcggg tttcgccacc   9360
tctgacttga gcgtcgattt ttgtgatgct cgtcaggggg gcggagccta tggaaaaacg   9420
ccagcaacgc ggccttttta cggttcctgg ccttttgctg gccttttgct cacatgttct   9480
ttcctgcgtt atcccctgat tctgtggata accgtattac cgcctttgag tgagctgata   9540
ccgctcgccg cagccgaacg accgagcgca gcgagtcagt gagcgaggaa gcggaagagc   9600
gcctgatgcg gtattttctc cttacgcatc tgtgcggtat ttcacaccgc atatggtgca   9660
ctctcagtac aatctgctct gatgccgcat agttaagcca gtatacactc cgctatcgct   9720
acgtgactgg gtcatggctg cgccccgaca cccgccaaca cccgctgacg cgccctgacg   9780
ggcttgtctg ctcccggcat ccgcttacag acaagctgtg accgtctccg ggagctgcat   9840
gtgtcagagg ttttcaccgt catcaccgaa acgcgcgagg cagctgcggt aaagctcatc   9900
agcgtggtcg tgaagcgatt cacagatgtc tgcctgttca tccgcgtcca gctcgttgag   9960
tttctccaga agcgttaatg tctggcttct gataaagcgg gccatgttaa gggcggtttt  10020
ttcctgtttg gtcactgatg cctccgtgta agggggattt ctgttcatgg gggtaatgat  10080
accgatgaaa cgagagagga tgctcacgat acgggttact gatgatgaac atgcccggtt  10140
actggaacgt tgtgagggta aacaactggc ggtatggatg cggcgggacc agagaaaaat  10200
cactcagggt caatgccagc gcttcgttaa tacagatgta ggtgttccac agggtagcca  10260
gcagcatcct gcgatgcaga tccggaacat aatggtgcag ggcgctgact tccgcgtttc  10320
cagactttac gaaacacgga aaccgaagac cattcatgtt gttgctcagg tcgcagacgt  10380
tttgcagcag cagtcgcttc acgttcgctc gcgtatcggt gattcattct gctaaccagt  10440
aaggcaaccc cgccagccta gccgggtcct caacgacagg agcacgatca tgcgcacccg  10500
tggccaggac ccaacgctgc ccgagatgcg ccgcgtgcgg ctgctggaga tggcggacgc  10560
gatggatatg ttctgccaag ggttggtttg cgcattcaca gttctccgca agaattgatt  10620
```

-continued

```
ggctccaatt cttggagtgg tgaatccgtt agcgaggtgc cgccggcttc cattcaggtc  10680

gaggtggccc ggctccatgc accgcgacgc aacgcgggga ggcagacaag gtatagggcg  10740

gcgcctacaa tccatgccaa cccgttccat gtgctcgccg aggcggcata aatcgccgtg  10800

acgatcagcg gtccaatgat cgaagttagg ctggtaagag ccgcgagcga tccttgaagc  10860

tgtccctgat ggtcgtcatc tacctgcctg gacagcatgg cctgcaacgc gggcatcccg  10920

atgccgccgg aagcgagaag aatcataatg gggaaggcca tccagcctcg cgtcgcgaac  10980

gccagcaaga cgtagcccag cgcgtcggcc gccatgccgg cgataatggc ctgcttctcg  11040

ccgaaacgtt tggtggcggg accagtgacg aaggcttgag cgagggcgtg caagattccg  11100

aataccgcaa gcgacaggcc gatcatcgtc gcgctccagc gaaagcggtc ctcgccgaaa  11160

atgacccaga gcgctgccgg cacctgtcct acgagttgca tgataaagaa gacagtcata  11220

agtgcggcga cgatagtcat gccccgcgcc caccggaagg agctgactgg gttgaaggct  11280

ctcaagggca tcggtcgagg atccttcaat atgcgcacat acgctgttat gttcaaggtc  11340

ccttcgttta agaacgaaag cggtcttcct tttgagggat gtttcaagtt gttcaaatct  11400

atcaaatttg caaatcccca gtctgtatct agagcgttga atcggtgatg cgatttgtta  11460

attaaattga tggtgtcacc attaccaggt ctagatatac caatggcaaa ctgagcacaa  11520

caataccagt ccggatcaac tggcaccatc tctcccgtag tctcatctaa tttttcttcc  11580

ggatgaggtt ccagatatac cgcaacacct ttattatggt ttccctgagg gaataataga  11640

atgtcccatt cgaaatcacc aattctaaac ctgggcgaat tgtatttcgg gtttgttaac  11700

tcgttccagt caggaatgtt ccacgtgaag ctatcttcca gcaaagtctc cacttcttca  11760

tcaaattgtg gagaatactc ccaatgctct tatctatggg acttccggga aacacagtac  11820

cgatacttcc caattcgtct tcagagctca ttgtttgttt gaagagacta atcaaagaat  11880

cgttttctca aaaaaattaa tatcttaact gatagtttga tcaaaggggc aaaacgtagg  11940

ggcaaacaaa cggaaaaatc gtttctcaaa ttttctgatg ccaagaactc taaccagtct  12000

tatctaaaaa ttgccttatg atccgtctct ccggttacag cctgtgtaac tgattaatcc  12060

tgcctttcta atcaccattc taatgtttta attaagggat tttgtcttca ttaacggctt  12120

tcgctcataa aaatgttatg acgttttgcc cgcaggcggg aaaccatcca cttcacgaga  12180

ctgatctcct ctgccggaac accgggcatc tccaacttat aagttggaga aataagagaa  12240

tttcagattg agagaatgaa aaaaaaaaac ccttagttca taggtccatt ctcttagcgc  12300

aactacagag aacaggggca caaacaggca aaaaacgggc acaacctcaa tggagtgatg  12360

caacctgcct ggagtaaatg atgacacaag gcaattgacc cacgcatgta tctatctcat  12420

tttcttacac cttctattac cttctgctct ctctgatttg gaaaaagctg aaaaaaaagg  12480

ttgaaaccag ttccctgaaa ttattcccct acttgactaa taagtatata aagacggtag  12540

gtattgattg taattctgta aatctatttc ttaaacttct taaattctac ttttatagtt  12600

agtctttttt ttagttttaa aacaccaaga acttagtttc gaataaacac acataaacaa  12660

acaagcttac aaaacaaa atg gct gca tat gca gct cag ggc tat aag gtg    12711
                    Met Ala Ala Tyr Ala Ala Gln Gly Tyr Lys Val
                     1               5                  10

cta gta ctc aac ccc tct gtt gct gca aca ctg ggc ttt ggt gct tac    12759
Leu Val Leu Asn Pro Ser Val Ala Ala Thr Leu Gly Phe Gly Ala Tyr
            15                  20                  25

atg tcc aag gct cat ggg atc gat cct aac atc agg acc ggg gtg aga    12807
Met Ser Lys Ala His Gly Ile Asp Pro Asn Ile Arg Thr Gly Val Arg
        30                  35                  40
```

-continued

```
aca att acc act ggc agc ccc atc acg tac tcc acc tac ggc aag ttc     12855
Thr Ile Thr Thr Gly Ser Pro Ile Thr Tyr Ser Thr Tyr Gly Lys Phe
     45                  50                  55

ctt gcc gac ggc ggg tgc tcg ggg ggc gct tat gac ata ata att tgt     12903
Leu Ala Asp Gly Gly Cys Ser Gly Gly Ala Tyr Asp Ile Ile Ile Cys
 60                  65                  70                  75

gac gag tgc cac tcc acg gat gcc aca tcc atc ttg ggc att ggc act     12951
Asp Glu Cys His Ser Thr Asp Ala Thr Ser Ile Leu Gly Ile Gly Thr
                 80                  85                  90

gtc ctt gac caa gca gag act gcg ggg gcg aga ctg gtt gtg ctc gcc     12999
Val Leu Asp Gln Ala Glu Thr Ala Gly Ala Arg Leu Val Val Leu Ala
             95                 100                 105

acc gcc acc cct ccg ggc tcc gtc act gtg ccc cat ccc aac atc gag     13047
Thr Ala Thr Pro Pro Gly Ser Val Thr Val Pro His Pro Asn Ile Glu
        110                 115                 120

gag gtt gct ctg tcc acc acc gga gag atc cct ttt tac ggc aag gct     13095
Glu Val Ala Leu Ser Thr Thr Gly Glu Ile Pro Phe Tyr Gly Lys Ala
    125                 130                 135

atc ccc ctc gaa gta atc aag ggg ggg aga cat ctc atc ttc tgt cat     13143
Ile Pro Leu Glu Val Ile Lys Gly Gly Arg His Leu Ile Phe Cys His
140                 145                 150                 155

tca aag aag aag tgc gac gaa ctc gcc gca aag ctg gtc gca ttg ggc     13191
Ser Lys Lys Lys Cys Asp Glu Leu Ala Ala Lys Leu Val Ala Leu Gly
                160                 165                 170

atc aat gcc gtg gcc tac tac cgc ggt ctt gac gtg tcc gtc atc ccg     13239
Ile Asn Ala Val Ala Tyr Tyr Arg Gly Leu Asp Val Ser Val Ile Pro
            175                 180                 185

acc agc ggc gat gtt gtc gtc gtg gca acc gat gcc ctc atg acc ggc     13287
Thr Ser Gly Asp Val Val Val Val Ala Thr Asp Ala Leu Met Thr Gly
        190                 195                 200

tat acc ggc gac ttc gac tcg gtg ata gac tgc aat acg tgt gtc acc     13335
Tyr Thr Gly Asp Phe Asp Ser Val Ile Asp Cys Asn Thr Cys Val Thr
    205                 210                 215

cag aca gtc gat ttc agc ctt gac cct acc ttc acc att gag aca atc     13383
Gln Thr Val Asp Phe Ser Leu Asp Pro Thr Phe Thr Ile Glu Thr Ile
220                 225                 230                 235

acg ctc ccc caa gat gct gtc tcc cgc act caa cgt cgg ggc agg act     13431
Thr Leu Pro Gln Asp Ala Val Ser Arg Thr Gln Arg Arg Gly Arg Thr
                240                 245                 250

ggc agg ggg aag cca ggc atc tac aga ttt gtg gca ccg ggg gag cgc     13479
Gly Arg Gly Lys Pro Gly Ile Tyr Arg Phe Val Ala Pro Gly Glu Arg
            255                 260                 265

ccc tcc ggc atg ttc gac tcg tcc gtc ctc tgt gag tgc tat gac gca     13527
Pro Ser Gly Met Phe Asp Ser Ser Val Leu Cys Glu Cys Tyr Asp Ala
        270                 275                 280

ggc tgt gct tgg tat gag ctc acg ccc gcc gag act aca gtt agg cta     13575
Gly Cys Ala Trp Tyr Glu Leu Thr Pro Ala Glu Thr Thr Val Arg Leu
    285                 290                 295

cga gcg tac atg aac acc ccg ggg ctt ccc gtg tgc cag gac cat ctt     13623
Arg Ala Tyr Met Asn Thr Pro Gly Leu Pro Val Cys Gln Asp His Leu
300                 305                 310                 315

gaa ttt tgg gag ggc gtc ttt aca ggc ctc act cat ata gat gcc cac     13671
Glu Phe Trp Glu Gly Val Phe Thr Gly Leu Thr His Ile Asp Ala His
                320                 325                 330

ttt cta tcc cag aca aag cag agt ggg gag aac ctt cct tac ctg gta     13719
Phe Leu Ser Gln Thr Lys Gln Ser Gly Glu Asn Leu Pro Tyr Leu Val
            335                 340                 345

gcg tac caa gcc acc gtg tgc gct agg gct caa gcc cct ccc cca tcg     13767
Ala Tyr Gln Ala Thr Val Cys Ala Arg Ala Gln Ala Pro Pro Pro Ser
```

-continued

```
        350                 355                 360

tgg gac cag atg tgg aag tgt ttg att cgc ctc aag ccc acc ctc cat    13815
Trp Asp Gln Met Trp Lys Cys Leu Ile Arg Leu Lys Pro Thr Leu His
    365                 370                 375

ggg cca aca ccc ctg cta tac aga ctg ggc gct gtt cag aat gaa atc    13863
Gly Pro Thr Pro Leu Leu Tyr Arg Leu Gly Ala Val Gln Asn Glu Ile
380                 385                 390                 395

acc ctg acg cac cca gtc acc aaa tac atc atg aca tgc atg tcg gcc    13911
Thr Leu Thr His Pro Val Thr Lys Tyr Ile Met Thr Cys Met Ser Ala
                400                 405                 410

gac ctg gag gtc gtc acg agc acc tgg gtg ctc gtt ggc ggc gtc ctg    13959
Asp Leu Glu Val Val Thr Ser Thr Trp Val Leu Val Gly Gly Val Leu
            415                 420                 425

gct gct ttg gcc gcg tat tgc ctg tca aca ggc tgc gtg gtc ata gtg    14007
Ala Ala Leu Ala Ala Tyr Cys Leu Ser Thr Gly Cys Val Val Ile Val
        430                 435                 440

ggc agg gtc gtc ttg tcc ggg aag ccg gca atc ata cct gac agg gaa    14055
Gly Arg Val Val Leu Ser Gly Lys Pro Ala Ile Ile Pro Asp Arg Glu
    445                 450                 455

gtc ctc tac cga gag ttc gat gag atg gaa gag tgc tct cag cac tta    14103
Val Leu Tyr Arg Glu Phe Asp Glu Met Glu Glu Cys Ser Gln His Leu
460                 465                 470                 475

ccg tac atc gag caa ggg atg atg ctc gcc gag cag ttc aag cag aag    14151
Pro Tyr Ile Glu Gln Gly Met Met Leu Ala Glu Gln Phe Lys Gln Lys
                480                 485                 490

gcc ctc ggc ctc ctg cag acc gcg tcc cgt cag gca gag gtt atc gcc    14199
Ala Leu Gly Leu Leu Gln Thr Ala Ser Arg Gln Ala Glu Val Ile Ala
            495                 500                 505

cct gct gtc cag acc aac tgg caa aaa ctc gag acc ttc tgg gcg aag    14247
Pro Ala Val Gln Thr Asn Trp Gln Lys Leu Glu Thr Phe Trp Ala Lys
        510                 515                 520

cat atg tgg aac ttc atc agt ggg ata caa tac ttg gcg ggc ttg tca    14295
His Met Trp Asn Phe Ile Ser Gly Ile Gln Tyr Leu Ala Gly Leu Ser
    525                 530                 535

acg ctg cct ggt aac ccc gcc att gct tca ttg atg gct ttt aca gct    14343
Thr Leu Pro Gly Asn Pro Ala Ile Ala Ser Leu Met Ala Phe Thr Ala
540                 545                 550                 555

gct gtc acc agc cca cta acc act agc caa acc ctc ctc ttc aac ata    14391
Ala Val Thr Ser Pro Leu Thr Thr Ser Gln Thr Leu Leu Phe Asn Ile
                560                 565                 570

ttg ggg ggg tgg gtg gct gcc cag ctc gcc gcc ccc ggt gcc gct act    14439
Leu Gly Gly Trp Val Ala Ala Gln Leu Ala Ala Pro Gly Ala Ala Thr
            575                 580                 585

gcc ttt gtg ggc gct ggc tta gct ggc gcc gcc atc ggc agt gtt gga    14487
Ala Phe Val Gly Ala Gly Leu Ala Gly Ala Ala Ile Gly Ser Val Gly
        590                 595                 600

ctg ggg aag gtc ctc ata gac atc ctt gca ggg tat ggc gcg ggc gtg    14535
Leu Gly Lys Val Leu Ile Asp Ile Leu Ala Gly Tyr Gly Ala Gly Val
    605                 610                 615

gcg gga gct ctt gtg gca ttc aag atc atg agc ggt gag gtc ccc tcc    14583
Ala Gly Ala Leu Val Ala Phe Lys Ile Met Ser Gly Glu Val Pro Ser
620                 625                 630                 635

acg gag gac ctg gtc aat cta ctg ccc gcc atc ctc tcg ccc gga gcc    14631
Thr Glu Asp Leu Val Asn Leu Leu Pro Ala Ile Leu Ser Pro Gly Ala
                640                 645                 650

ctc gta gtc ggc gtg gtc tgt gca gca ata ctg cgc cgg cac gtt ggc    14679
Leu Val Val Gly Val Val Cys Ala Ala Ile Leu Arg Arg His Val Gly
            655                 660                 665

ccg ggc gag ggg gca gtg cag tgg atg aac cgg ctg ata gcc ttc gcc    14727
```

-continued

```
Pro Gly Glu Gly Ala Val Gln Trp Met Asn Arg Leu Ile Ala Phe Ala
        670                 675                 680

tcc cgg ggg aac cat gtt tcc ccc acg cac tac gtg ccg gag agc gat    14775
Ser Arg Gly Asn His Val Ser Pro Thr His Tyr Val Pro Glu Ser Asp
    685                 690                 695

gca gct gcc cgc gtc act gcc ata ctc agc agc ctc act gta acc cag    14823
Ala Ala Ala Arg Val Thr Ala Ile Leu Ser Ser Leu Thr Val Thr Gln
700                 705                 710                 715

ctc ctg agg cga ctg cac cag tgg ata agc tcg gag tgt acc act cca    14871
Leu Leu Arg Arg Leu His Gln Trp Ile Ser Ser Glu Cys Thr Thr Pro
                720                 725                 730

tgc tcc ggt tcc tgg cta agg gac atc tgg gac tgg ata tgc gag gtg    14919
Cys Ser Gly Ser Trp Leu Arg Asp Ile Trp Asp Trp Ile Cys Glu Val
            735                 740                 745

ttg agc gac ttt aag acc tgg cta aaa gct aag ctc atg cca cag ctg    14967
Leu Ser Asp Phe Lys Thr Trp Leu Lys Ala Lys Leu Met Pro Gln Leu
        750                 755                 760

cct ggg atc ccc ttt gtg tcc tgc cag cgc ggg tat aag ggg gtc tgg    15015
Pro Gly Ile Pro Phe Val Ser Cys Gln Arg Gly Tyr Lys Gly Val Trp
    765                 770                 775

cga ggg gac ggc atc atg cac act cgc tgc cac tgt gga gct gag atc    15063
Arg Gly Asp Gly Ile Met His Thr Arg Cys His Cys Gly Ala Glu Ile
780                 785                 790                 795

act gga cat gtc aaa aac ggg acg atg agg atc gtc ggt cct agg acc    15111
Thr Gly His Val Lys Asn Gly Thr Met Arg Ile Val Gly Pro Arg Thr
                800                 805                 810

tgc agg aac atg tgg agt ggg acc ttc ccc att aat gcc tac acc acg    15159
Cys Arg Asn Met Trp Ser Gly Thr Phe Pro Ile Asn Ala Tyr Thr Thr
            815                 820                 825

ggc ccc tgt acc ccc ctt cct gcg ccg aac tac acg ttc gcg cta tgg    15207
Gly Pro Cys Thr Pro Leu Pro Ala Pro Asn Tyr Thr Phe Ala Leu Trp
        830                 835                 840

agg gtg tct gca gag gaa tac gtg gag ata agg cag gtg ggg gac ttc    15255
Arg Val Ser Ala Glu Glu Tyr Val Glu Ile Arg Gln Val Gly Asp Phe
    845                 850                 855

cac tac gtg acg ggt atg act act gac aat ctt aaa tgc ccg tgc cag    15303
His Tyr Val Thr Gly Met Thr Thr Asp Asn Leu Lys Cys Pro Cys Gln
860                 865                 870                 875

gtc cca tcg ccc gaa ttt ttc aca gaa ttg gac ggg gtg cgc cta cat    15351
Val Pro Ser Pro Glu Phe Phe Thr Glu Leu Asp Gly Val Arg Leu His
                880                 885                 890

agg ttt gcg ccc ccc tgc aag ccc ttg ctg cgg gag gag gta tca ttc    15399
Arg Phe Ala Pro Pro Cys Lys Pro Leu Leu Arg Glu Glu Val Ser Phe
            895                 900                 905

aga gta gga ctc cac gaa tac ccg gta ggg tcg caa tta cct tgc gag    15447
Arg Val Gly Leu His Glu Tyr Pro Val Gly Ser Gln Leu Pro Cys Glu
        910                 915                 920

ccc gaa ccg gac gtg gcc gtg ttg acg tcc atg ctc act gat ccc tcc    15495
Pro Glu Pro Asp Val Ala Val Leu Thr Ser Met Leu Thr Asp Pro Ser
    925                 930                 935

cat ata aca gca gag gcg gcc ggg cga agg ttg gcg agg gga tca ccc    15543
His Ile Thr Ala Glu Ala Ala Gly Arg Arg Leu Ala Arg Gly Ser Pro
940                 945                 950                 955

ccc tct gtg gcc agc tcc tcg gct agc cag cta tcc gct cca tct ctc    15591
Pro Ser Val Ala Ser Ser Ser Ala Ser Gln Leu Ser Ala Pro Ser Leu
                960                 965                 970

aag gca act tgc acc gct aac cat gac tcc cct gat gct gag ctc ata    15639
Lys Ala Thr Cys Thr Ala Asn His Asp Ser Pro Asp Ala Glu Leu Ile
            975                 980                 985
```

-continued gag gcc aac ctc cta tgg agg cag gag atg ggc ggc aac atc acc agg 15687
Glu Ala Asn Leu Leu Trp Arg Gln Glu Met Gly Gly Asn Ile Thr Arg
990 995 1000 gtt gag tca gaa aac aaa gtg gtg att ctg gac tcc ttc gat ccg ctt 15735
Val Glu Ser Glu Asn Lys Val Val Ile Leu Asp Ser Phe Asp Pro Leu
1005 1010 1015 gtg gcg gag gag gac gag cgg gag atc tcc gta ccc gca gaa atc ctg 15783
Val Ala Glu Glu Asp Glu Arg Glu Ile Ser Val Pro Ala Glu Ile Leu
1020 1025 1030 1035 cgg aag tct cgg aga ttc gcc cag gcc ctg ccc gtt tgg gcg cgg ccg 15831
Arg Lys Ser Arg Arg Phe Ala Gln Ala Leu Pro Val Trp Ala Arg Pro
1040 1045 1050 gac tat aac ccc ccg cta gtg gag acg tgg aaa aag ccc gac tac gaa 15879
Asp Tyr Asn Pro Pro Leu Val Glu Thr Trp Lys Lys Pro Asp Tyr Glu
1055 1060 1065 cca cct gtg gtc cat ggc tgc ccg ctt cca cct cca aag tcc cct cct 15927
Pro Pro Val Val His Gly Cys Pro Leu Pro Pro Pro Lys Ser Pro Pro
1070 1075 1080 gtg cct ccg cct cgg aag aag cgg acg gtg gtc ctc act gaa tca acc 15975
Val Pro Pro Pro Arg Lys Lys Arg Thr Val Val Leu Thr Glu Ser Thr
1085 1090 1095 cta tct act gcc ttg gcc gag ctc gcc acc aga agc ttt ggc agc tcc 16023
Leu Ser Thr Ala Leu Ala Glu Leu Ala Thr Arg Ser Phe Gly Ser Ser
1100 1105 1110 1115 tca act tcc ggc att acg ggc gac aat acg aca aca tcc tct gag ccc 16071
Ser Thr Ser Gly Ile Thr Gly Asp Asn Thr Thr Thr Ser Ser Glu Pro
1120 1125 1130 gcc cct tct ggc tgc ccc ccc gac tcc gac gct gag tcc tat tcc tcc 16119
Ala Pro Ser Gly Cys Pro Pro Asp Ser Asp Ala Glu Ser Tyr Ser Ser
1135 1140 1145 atg ccc ccc ctg gag ggg gag cct ggg gat ccg gat ctt agc gac ggg 16167
Met Pro Pro Leu Glu Gly Glu Pro Gly Asp Pro Asp Leu Ser Asp Gly
1150 1155 1160 tca tgg tca acg gtc agt agt gag gcc aac gcg gag gat gtc gtg tgc 16215
Ser Trp Ser Thr Val Ser Ser Glu Ala Asn Ala Glu Asp Val Val Cys
1165 1170 1175 tgc tca atg tct tac tct tgg aca ggc gca ctc gtc acc ccg tgc gcc 16263
Cys Ser Met Ser Tyr Ser Trp Thr Gly Ala Leu Val Thr Pro Cys Ala
1180 1185 1190 1195 gcg gaa gaa cag aaa ctg ccc atc aat gca cta agc aac tcg ttg cta 16311
Ala Glu Glu Gln Lys Leu Pro Ile Asn Ala Leu Ser Asn Ser Leu Leu
1200 1205 1210 cgt cac cac aat ttg gtg tat tcc acc acc tca cgc agt gct tgc caa 16359
Arg His His Asn Leu Val Tyr Ser Thr Thr Ser Arg Ser Ala Cys Gln
1215 1220 1225 agg cag aag aaa gtc aca ttt gac aga ctg caa gtt ctg gac agc cat 16407
Arg Gln Lys Lys Val Thr Phe Asp Arg Leu Gln Val Leu Asp Ser His
1230 1235 1240 tac cag gac gta ctc aag gag gtt aaa gca gcg gcg tca aaa gtg aag 16455
Tyr Gln Asp Val Leu Lys Glu Val Lys Ala Ala Ala Ser Lys Val Lys
1245 1250 1255 gct aac ttg cta tcc gta gag gaa gct tgc agc ctg acg ccc cca cac 16503
Ala Asn Leu Leu Ser Val Glu Glu Ala Cys Ser Leu Thr Pro Pro His
1260 1265 1270 1275 tca gcc aaa tcc aag ttt ggt tat ggg gca aaa gac gtc cgt tgc cat 16551
Ser Ala Lys Ser Lys Phe Gly Tyr Gly Ala Lys Asp Val Arg Cys His
1280 1285 1290 gcc aga aag gcc gta acc cac atc aac tcc gtg tgg aaa gac ctt ctg 16599
Ala Arg Lys Ala Val Thr His Ile Asn Ser Val Trp Lys Asp Leu Leu
1295 1300 1305

-continued

```
gaa gac aat gta aca cca ata gac act acc atc atg gct aag aac gag    16647
Glu Asp Asn Val Thr Pro Ile Asp Thr Thr Ile Met Ala Lys Asn Glu
       1310                1315                1320

gtt ttc tgc gtt cag cct gag aag ggg ggt cgt aag cca gct cgt ctc    16695
Val Phe Cys Val Gln Pro Glu Lys Gly Gly Arg Lys Pro Ala Arg Leu
   1325                1330                1335

atc gtg ttc ccc gat ctg ggc gtg cgc gtg tgc gaa aag atg gct ttg    16743
Ile Val Phe Pro Asp Leu Gly Val Arg Val Cys Glu Lys Met Ala Leu
1340                1345                1350                1355

tac gac gtg gtt aca aag ctc ccc ttg gcc gtg atg gga agc tcc tac    16791
Tyr Asp Val Val Thr Lys Leu Pro Leu Ala Val Met Gly Ser Ser Tyr
               1360                1365                1370

gga ttc caa tac tca cca gga cag cgg gtt gaa ttc ctc gtg caa gcg    16839
Gly Phe Gln Tyr Ser Pro Gly Gln Arg Val Glu Phe Leu Val Gln Ala
           1375                1380                1385

tgg aag tcc aag aaa acc cca atg ggg ttc tcg tat gat acc cgc tgc    16887
Trp Lys Ser Lys Lys Thr Pro Met Gly Phe Ser Tyr Asp Thr Arg Cys
       1390                1395                1400

ttt gac tcc aca gtc act gag agc gac atc cgt acg gag gag gca atc    16935
Phe Asp Ser Thr Val Thr Glu Ser Asp Ile Arg Thr Glu Glu Ala Ile
   1405                1410                1415

tac caa tgt tgt gac ctc gac ccc caa gcc cgc gtg gcc atc aag tcc    16983
Tyr Gln Cys Cys Asp Leu Asp Pro Gln Ala Arg Val Ala Ile Lys Ser
1420                1425                1430                1435

ctc acc gag agg ctt tat gtt ggg ggc cct ctt acc aat tca agg ggg    17031
Leu Thr Glu Arg Leu Tyr Val Gly Gly Pro Leu Thr Asn Ser Arg Gly
               1440                1445                1450

gag aac tgc ggc tat cgc agg tgc cgc gcg agc ggc gta ctg aca act    17079
Glu Asn Cys Gly Tyr Arg Arg Cys Arg Ala Ser Gly Val Leu Thr Thr
           1455                1460                1465

agc tgt ggt aac acc ctc act tgc tac atc aag gcc cgg gca gcc tgt    17127
Ser Cys Gly Asn Thr Leu Thr Cys Tyr Ile Lys Ala Arg Ala Ala Cys
       1470                1475                1480

cga gcc gca ggg ctc cag gac tgc acc atg ctc gtg tgt ggc gac gac    17175
Arg Ala Ala Gly Leu Gln Asp Cys Thr Met Leu Val Cys Gly Asp Asp
   1485                1490                1495

tta gtc gtt atc tgt gaa agc gcg ggg gtc cag gag gac gcg gcg agc    17223
Leu Val Val Ile Cys Glu Ser Ala Gly Val Gln Glu Asp Ala Ala Ser
1500                1505                1510                1515

ctg aga gcc ttc acg gag gct atg acc agg tac tcc gcc ccc cct ggg    17271
Leu Arg Ala Phe Thr Glu Ala Met Thr Arg Tyr Ser Ala Pro Pro Gly
               1520                1525                1530

gac ccc cca caa cca gaa tac gac ttg gag ctc ata aca tca tgc tcc    17319
Asp Pro Pro Gln Pro Glu Tyr Asp Leu Glu Leu Ile Thr Ser Cys Ser
           1535                1540                1545

tcc aac gtg tca gtc gcc cac gac ggc gct gga aag agg gtc tac tac    17367
Ser Asn Val Ser Val Ala His Asp Gly Ala Gly Lys Arg Val Tyr Tyr
       1550                1555                1560

ctc acc cgt gac cct aca acc ccc ctc gcg aga gct gcg tgg gag aca    17415
Leu Thr Arg Asp Pro Thr Thr Pro Leu Ala Arg Ala Ala Trp Glu Thr
   1565                1570                1575

gca aga cac act cca gtc aat tcc tgg cta ggc aac ata atc atg ttt    17463
Ala Arg His Thr Pro Val Asn Ser Trp Leu Gly Asn Ile Ile Met Phe
1580                1585                1590                1595

gcc ccc aca ctg tgg gcg agg atg ata ctg atg acc cat ttc ttt agc    17511
Ala Pro Thr Leu Trp Ala Arg Met Ile Leu Met Thr His Phe Phe Ser
               1600                1605                1610

gtc ctt ata gcc agg gac cag ctt gaa cag gcc ctc gat tgc gag atc    17559
Val Leu Ile Ala Arg Asp Gln Leu Glu Gln Ala Leu Asp Cys Glu Ile
```

-continued

```
          1615                1620                1625

tac ggg gcc tgc tac tcc ata gaa cca ctg gat cta cct cca atc att    17607
Tyr Gly Ala Cys Tyr Ser Ile Glu Pro Leu Asp Leu Pro Pro Ile Ile
      1630                1635                1640

caa aga ctc cat ggc ctc agc gca ttt tca ctc cac agt tac tct cca    17655
Gln Arg Leu His Gly Leu Ser Ala Phe Ser Leu His Ser Tyr Ser Pro
   1645                1650                1655

ggt gaa atc aat agg gtg gcc gca tgc ctc aga aaa ctt ggg gta ccg    17703
Gly Glu Ile Asn Arg Val Ala Ala Cys Leu Arg Lys Leu Gly Val Pro
1660                1665                1670                1675

ccc ttg cga gct tgg aga cac cgg gcc cgg agc gtc cgc gct agg ctt    17751
Pro Leu Arg Ala Trp Arg His Arg Ala Arg Ser Val Arg Ala Arg Leu
               1680                1685                1690

ctg gcc aga gga ggc agg gct gcc ata tgt ggc aag tac ctc ttc aac    17799
Leu Ala Arg Gly Gly Arg Ala Ala Ile Cys Gly Lys Tyr Leu Phe Asn
          1695                1700                1705

tgg gca gta aga aca aag ctc aaa ctc act cca ata gcg gcc gct ggc    17847
Trp Ala Val Arg Thr Lys Leu Lys Leu Thr Pro Ile Ala Ala Ala Gly
      1710                1715                1720

cag ctg gac ttg tcc ggc tgg ttc acg gct ggc tac agc ggg gga gac    17895
Gln Leu Asp Leu Ser Gly Trp Phe Thr Ala Gly Tyr Ser Gly Gly Asp
   1725                1730                1735

att tat cac agc gtg tct cat gcc cgg ccc cgc tgg atc tgg ttt tgc    17943
Ile Tyr His Ser Val Ser His Ala Arg Pro Arg Trp Ile Trp Phe Cys
1740                1745                1750                1755

cta ctc ctg ctt gct gca ggg gta ggc atc tac ctc ctc ccc aac cga    17991
Leu Leu Leu Leu Ala Ala Gly Val Gly Ile Tyr Leu Leu Pro Asn Arg
               1760                1765                1770

tgaatagtcg actttgttcc cactgtactt ttagctcgta caaaatacaa tatacttttc  18051

atttctccgt aaacaacatg ttttcccatg taatatcctt ttctattttt cgttccgtta  18111

ccaactttac acatacttta tatagctatt cacttctata cactaaaaaa ctaagacaat  18171

tttaattttg ctgcctgcca tatttcaatt tgttataaat tcctataatt tatcctatta  18231

gtagctaaaa aaagatgaat gtgaatcgaa tcctaagaga attggatctg atccacagga  18291

cgggtgtggt cgccatgatc gcgtagtcga tagtggctcc aagtagcgaa gcgagcagga  18351

ctgggcggcg gccaaagcgg tcggacagtg ctccgagaac gggtgcgcat agaaattgca  18411

tcaacgcata tagcgctagc agcacgccat agtgactggc gatgctgtcg gaatggacga  18471

tatcccgcaa gaggcccggc agtaccggca taaccaagcc tatgcctaca gcatccaggg  18531

tgacggtgcc gaggatgacg atgagcgcat tgttagattt catacacggt gcctgactgc  18591

gttagcaatt taactgtgat aaactaccgc attaaagctt tttctttcca attttttttt  18651

tttcgtcatt ataaaaatca ttacgaccga gattcccggg taataactga tataattaaa  18711

ttgaagctct aatttgtgag tttagtatac atgcatttac ttataataca gttttttagt  18771

tttgctggcc gcatcttctc aaatatgctt cccagcctgc ttttctgtaa cgttcaccct  18831

ctaccttagc atcccttccc tttgcaaata gtcctcttcc aacaataata atgtcagatc  18891

ctgtagagac cacatcatcc acggttctat actgttgacc caatgcgtct cccttgtcat  18951

ctaaacccac accgggtgtc ataatcaacc aatcgtaacc ttcatctctt ccacccatgt  19011

ctctttgagc aataaagccg ataacaaaat ctttgtcgct cttcgcaatg tcaacagtac  19071

ccttagtata ttctccagta gatagggagc ccttgcatga caattctgct aacatcaaaa  19131

ggcctctagg ttcctttgtt acttcttctg ccgcctgctt caaaccgcta acaataccctg  19191

ggcccaccac accgtgtgca ttcgtaatgt ctgcccattc tgctattctg tatacacccg  19251
```

-continued

```
cagagtactg caatttgact gtattaccaa tgtcagcaaa ttttctgtct tcgaagagta  19311

aaaaattgta cttggcggat aatgccttta gcggcttaac tgtgccctcc atggaaaaat  19371

cagtcaagat atccacatgt gtttttagta aacaaatttt gggacctaat gcttcaacta  19431

actccagtaa ttccttggtg gtacgaacat ccaatgaagc acacaagttt gtttgctttt  19491

cgtgcatgat attaaatagc ttggcagcaa caggactagg atgagtagca gcacgttcct  19551

tatatgtagc tttcgacatg atttatcttc gtttcctgca ggtttttgtt ctgtgcagtt  19611

gggttaagaa tactgggcaa tttcatgttt cttcaacact acatatgcgt atatatacca  19671

atctaagtct gtgctccttc cttcgttctt ccttctgttc ggagattacc gaatcaaaaa  19731

aatttcaagg aaaccgaaat caaaaaaaag aataaaaaaa aaatgatgaa ttgaaaagct  19791

tatcgat                                                            19798
```

<210> SEQ ID NO 11
<211> LENGTH: 1771
<212> TYPE: PRT
<213> ORGANISM: Artificial Sequence
<220> FEATURE:
<223> OTHER INFORMATION: Description of Artificial Sequence:
      pd.deltaNS3NS5.pj

<400> SEQUENCE: 11

```
Met Ala Ala Tyr Ala Ala Gln Gly Tyr Lys Val Leu Val Leu Asn Pro
  1               5                  10                  15

Ser Val Ala Ala Thr Leu Gly Phe Gly Ala Tyr Met Ser Lys Ala His
             20                  25                  30

Gly Ile Asp Pro Asn Ile Arg Thr Gly Val Arg Thr Ile Thr Thr Gly
         35                  40                  45

Ser Pro Ile Thr Tyr Ser Thr Tyr Gly Lys Phe Leu Ala Asp Gly Gly
     50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255
```

-continued

```
Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
    370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
        435                 440                 445

Ser Gly Lys Pro Ala Ile Ile Pro Asp Arg Glu Val Leu Tyr Arg Glu
    450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670
```

-continued

```
Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
        835                 840                 845

Glu Tyr Val Glu Ile Arg Gln Val Gly Asp Phe His Tyr Val Thr Gly
    850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
    930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                1000                1005

Lys Val Val Ile Leu Asp Ser Phe Asp Pro Leu Val Ala Glu Glu Asp
   1010                1015                1020

Glu  Arg Glu Ile Ser Val  Pro Ala Glu Ile Leu  Arg Lys Ser Arg Arg
1025                 1030                 1035                 1040

Phe Ala Gln Ala Leu  Pro Val Trp Ala Arg  Pro Asp Tyr Asn Pro  Pro
                1045                 1050                 1055

Leu Val Glu Thr  Trp Lys Lys Pro Asp  Tyr Glu Pro Pro Val  Val His
            1060                 1065                 1070

Gly Cys Pro  Leu Pro Pro Pro Lys  Ser Pro Pro Val Pro  Pro Pro Arg
        1075                 1080                 1085

Lys Lys  Arg Thr Val Val Leu  Thr Glu Ser Thr Leu  Ser Thr Ala Leu
```

-continued

```
    1090                1095                1100

Ala  Glu Leu Ala Thr Arg  Ser Phe Gly Ser Ser  Ser Thr Ser Gly Ile
1105                1110                1115                1120

Thr Gly Asp Asn Thr  Thr Thr Ser Ser Glu  Pro Ala Pro Ser Gly  Cys
                1125                1130                1135

Pro Pro Asp Ser  Asp Ala Glu Ser Tyr  Ser Ser Met Pro Pro  Leu Glu
            1140                1145                1150

Gly Glu Pro  Gly Asp Pro Asp Leu  Ser Asp Gly Ser Trp  Ser Thr Val
        1155                1160                1165

Ser Ser  Glu Ala Asn Ala Glu  Asp Val Val Cys Cys  Ser Met Ser Tyr
    1170                1175                1180

Ser  Trp Thr Gly Ala Leu  Val Thr Pro Cys Ala  Ala Glu Glu Gln Lys
1185                1190                1195                1200

Leu Pro Ile Asn Ala  Leu Ser Asn Ser Leu  Leu Arg His His Asn  Leu
                1205                1210                1215

Val Tyr Ser Thr  Thr Ser Arg Ser Ala  Cys Gln Arg Gln Lys  Lys Val
            1220                1225                1230

Thr Phe Asp  Arg Leu Gln Val Leu  Asp Ser His Tyr Gln  Asp Val Leu
        1235                1240                1245

Lys Glu  Val Lys Ala Ala Ala  Ser Lys Val Lys Ala  Asn Leu Leu Ser
    1250                1255                1260

Val  Glu Glu Ala Cys Ser  Leu Thr Pro Pro His  Ser Ala Lys Ser Lys
1265                1270                1275                1280

Phe Gly Tyr Gly Ala  Lys Asp Val Arg Cys  His Ala Arg Lys Ala  Val
                1285                1290                1295

Thr His Ile Asn  Ser Val Trp Lys Asp  Leu Leu Glu Asp Asn  Val Thr
            1300                1305                1310

Pro Ile Asp  Thr Thr Ile Met Ala  Lys Asn Glu Val Phe  Cys Val Gln
        1315                1320                1325

Pro Glu  Lys Gly Gly Arg Lys  Pro Ala Arg Leu Ile  Val Phe Pro Asp
    1330                1335                1340

Leu  Gly Val Arg Val Cys  Glu Lys Met Ala Leu  Tyr Asp Val Val Thr
1345                1350                1355                1360

Lys Leu Pro Leu Ala  Val Met Gly Ser Ser  Tyr Gly Phe Gln Tyr  Ser
                1365                1370                1375

Pro Gly Gln Arg  Val Glu Phe Leu Val  Gln Ala Trp Lys Ser  Lys Lys
            1380                1385                1390

Thr Pro Met  Gly Phe Ser Tyr Asp  Thr Arg Cys Phe Asp  Ser Thr Val
        1395                1400                1405

Thr Glu  Ser Asp Ile Arg Thr  Glu Glu Ala Ile Tyr  Gln Cys Cys Asp
    1410                1415                1420

Leu  Asp Pro Gln Ala Arg  Val Ala Ile Lys Ser  Leu Thr Glu Arg Leu
1425                1430                1435                1440

Tyr Val Gly Gly Pro  Leu Thr Asn Ser Arg  Gly Glu Asn Cys Gly  Tyr
                1445                1450                1455

Arg Arg Cys Arg  Ala Ser Gly Val Leu  Thr Thr Ser Cys Gly  Asn Thr
            1460                1465                1470

Leu Thr Cys  Tyr Ile Lys Ala Arg  Ala Ala Cys Arg Ala  Ala Gly Leu
        1475                1480                1485

Gln Asp  Cys Thr Met Leu Val  Cys Gly Asp Asp Leu  Val Val Ile Cys
    1490                1495                1500

Glu  Ser Ala Gly Val Gln  Glu Asp Ala Ala Ser  Leu Arg Ala Phe Thr
1505                1510                1515                1520
```

-continued

```
Glu Ala Met Thr Arg  Tyr Ser Ala Pro Pro  Gly Asp Pro Pro Gln  Pro
                1525                 1530                 1535

Glu Tyr Asp Leu  Glu Leu Ile Thr Ser  Cys Ser Ser Asn Val  Ser Val
            1540                 1545                 1550

Ala His Asp  Gly Ala Gly Lys Arg  Val Tyr Tyr Leu Thr  Arg Asp Pro
        1555                 1560                 1565

Thr Thr  Pro Leu Ala Arg Ala  Ala Trp Glu Thr Ala  Arg His Thr Pro
    1570                 1575                 1580

Val  Asn Ser Trp Leu Gly  Asn Ile Ile Met Phe  Ala Pro Thr Leu Trp
1585                 1590                 1595                 1600

Ala Arg Met Ile Leu  Met Thr His Phe Phe  Ser Val Leu Ile Ala  Arg
                1605                 1610                 1615

Asp Gln Leu Glu  Gln Ala Leu Asp Cys  Glu Ile Tyr Gly Ala  Cys Tyr
            1620                 1625                 1630

Ser Ile Glu  Pro Leu Asp Leu Pro  Pro Ile Ile Gln Arg  Leu His Gly
        1635                 1640                 1645

Leu Ser  Ala Phe Ser Leu His  Ser Tyr Ser Pro Gly  Glu Ile Asn Arg
    1650                 1655                 1660

Val  Ala Ala Cys Leu Arg  Lys Leu Gly Val Pro  Pro Leu Arg Ala Trp
1665                 1670                 1675                 1680

Arg His Arg Ala Arg  Ser Val Arg Ala Arg  Leu Leu Ala Arg Gly  Gly
                1685                 1690                 1695

Arg Ala Ala Ile  Cys Gly Lys Tyr Leu  Phe Asn Trp Ala Val  Arg Thr
            1700                 1705                 1710

Lys Leu Lys  Leu Thr Pro Ile Ala  Ala Ala Gly Gln Leu  Asp Leu Ser
        1715                 1720                 1725

Gly Trp  Phe Thr Ala Gly Tyr  Ser Gly Gly Asp Ile  Tyr His Ser Val
    1730                 1735                 1740

Ser  His Ala Arg Pro Arg  Trp Ile Trp Phe Cys  Leu Leu Leu Leu Ala
1745                 1750                 1755                 1760

Ala Gly Val Gly Ile  Tyr Leu Leu Pro Asn  Arg
                1765                 1770
```

<210> SEQ ID NO 12
<211> LENGTH: 20160
<212> TYPE: DNA
<213> ORGANISM: Artificial Sequence
<220> FEATURE:
<223> OTHER INFORMATION: Description of Artificial Sequence:
pd.delta.NS3NS5.pj.core121
<221> NAME/KEY: CDS
<222> LOCATION: (12679)..(18354)

<400> SEQUENCE: 12

```
atcgatccta ccccttgcgc taaagaagta tatgtgccta ctaacgcttg tctttgtctc     60

tgtcactaaa cactggatta ttactcccag atacttattt tggactaatt taaatgattt    120

cggatcaacg ttcttaatat cgctgaatct tccacaattg atgaaagtag ctaggaagag    180

gaattggtat aaagtttttg tttttgtaaa tctcgaagta tactcaaacg aatttagtat    240

tttctcagtg atctcccaga tgctttcacc ctcacttaga agtgctttaa gcattttttt    300

actgtggcta tttcccttat ctgcttcttc cgatgattcg aactgtaatt gcaaactact    360

tacaatatca gtgatatcag attgatgttt ttgtccatag taaggaataa ttgtaaattc    420

ccaagcagga atcaatttct ttaatgaggc ttccagaatt gttgcttttt gcgtcttgta    480

tttaaactgg agtgatttat tgacaatatc gaaactcagc gaattgctta tgatagtatt    540
```

-continued

```
atagctcatg aatgtggctc tcttgattgc tgttccgtta tgtgtaatca tccaacataa    600
ataggttagt tcagcagcac ataatgctat tttctcacct gaaggtcttt caaacctttc    660
cacaaactga cgaacaagca ccttaggtgg tgttttacat aatatatcaa attgtggcat    720
gcttagcgcc gatcttgtgt gcaattgata tctagtttca actactctat ttatcttgta    780
tcttgcagta ttcaaacacg ctaactcgaa aaactaactt taattgtcct gtttgtctcg    840
cgttctttcg aaaaatgcac cggccgcgca ttatttgtac tgcgaaaata attggtactg    900
cggtatcttc atttcatatt ttaaaaatgc acctttgctg cttttcctta atttttagac    960
ggcccgcagg ttcgttttgc ggtactatct tgtgataaaa agttgttttg acatgtgatc   1020
tgcacagatt ttataatgta ataagcaaga atacattatc aaacgaacaa tactggtaaa   1080
agaaaaccaa aatggacgac attgaaacag ccaagaatct gacggtaaaa gcacgtacag   1140
cttatagcgt ctgggatgta tgtcggctgt ttattgaaat gattgctcct gatgtagata   1200
ttgatataga gagtaaacgt aagtctgatg agctactctt tccaggatat gtcataaggc   1260
ccatggaatc tctcacaacc ggtaggccgt atggtcttga ttctagcgca gaagattcca   1320
gcgtatcttc tgactccagt gctgaggtaa ttttgcctgc tgcgaagatg gttaaggaaa   1380
ggtttgattc gattggaaat ggtatgctct cttcacaaga agcaagtcag gctgccatag   1440
atttgatgct acagaataac aagctgttag acaatagaaa gcaactatac aaatctattg   1500
ctataataat aggaagattg cccgagaaag acaagaagag agctaccgaa atgctcatga   1560
gaaaaatgga ttgtacacag ttattagtcc caccagctcc aacggaagaa gatgttatga   1620
agctcgtaag cgtcgttacc caattgctta ctttagttcc accagatcgt caagctgctt   1680
taataggtga tttattcatc ccggaatctc taaaggatat attcaatagt ttcaatgaac   1740
tggcggcaga gaatcgttta cagcaaaaaa agagtgagtt ggaaggaagg actgaagtga   1800
accatgctaa tacaaatgaa gaagttccct ccaggcgaac aagaagtaga gacacaaatg   1860
caagaggagc atataaatta caaaacacca tcactgaggg ccctaaagcg gttcccacga   1920
aaaaaaggag agtagcaacg agggtaaggg gcagaaaatc acgtaatact tctagggtat   1980
gatccaatat caaaggaaat gatagcattg aaggatgaga ctaatccaat tgaggagtgg   2040
cagcatatag aacagctaaa gggtagtgct gaaggaagca tacgataccc cgcatggaat   2100
gggataatat cacaggaggt actagactac ctttcatcct acataaatag acgcatataa   2160
gtacgcattt aagcataaac acgcactatg ccgttcttct catgtatata tatatacagg   2220
caacacgcag atataggtgc gacgtgaaca gtgagctgta tgtgcgcagc tcgcgttgca   2280
ttttcggaag cgctcgtttt cggaaacgct ttgaagttcc tattccgaag ttcctattct   2340
ctagaaagta taggaacttc agagcgcttt tgaaaaccaa aagcgctctg aagacgcact   2400
ttcaaaaaac caaaaacgca ccggactgta acgagctact aaaatattgc gaataccgct   2460
tccacaaaca ttgctcaaaa gtatctcttt gctatatatc tctgtgctat atccctatat   2520
aacctaccca tccacctttc gctccttgaa cttgcatcta aactcgacct ctacatcaac   2580
aggcttccaa tgctcttcaa attttactgt caagtagacc catacggctg taatatgctg   2640
ctcttcataa tgtaagctta tctttatcga atcgtgtgaa aaactactac cgcgataaac   2700
ctttacggtt ccctgagatt gaattagttc ctttagtata tgatacaaga cacttttgaa   2760
ctttgtacga cgaattttga ggttcgccat cctctggcta tttccaatta tcctgtcggc   2820
tattatctcc gcctcagttt gatcttccgc ttcagactgc catttttcac ataatgaatc   2880
```

-continued

```
tatttcaccc cacaatcctt catccgcctc cgcatcttgt tccgttaaac tattgacttc   2940
atgttgtaca ttgtttagtt cacgagaagg gtcctcttca ggcggtagct cctgatctcc   3000
tatatgacct ttatcctgtt ctctttccac aaacttagaa atgtattcat gaattatgga   3060
gcacctaata acattcttca aggcggagaa gtttgggcca gatgcccaat atgcttgaca   3120
tgaaaacgtg agaatgaatt tagtattatt gtgatattct gaggcaattt tattataatc   3180
tcgaagataa gagaagaatg cagtgacctt tgtattgaca aatggagatt ccatgtatct   3240
aaaaaatacg cctttaggcc ttctgatacc ctttcccctg cggtttagcg tgccttttac   3300
attaatatct aaaccctctc cgatggtggc ctttaactga ctaataaatg caaccgatat   3360
aaactgtgat aattctgggt gatttatgat tcgatcgaca attgtattgt acactagtgc   3420
aggatcaggc caatccagtt ctttttcaat taccggtgtg tcgtctgtat tcagtacatg   3480
tccaacaaat gcaaatgcta acgttttgta tttcttataa ttgtcaggaa ctggaaaagt   3540
ccccccttgtc gtctcgatta cacacctact ttcatcgtac accataggtt ggaagtgctg   3600
cataatacat tgcttaatac aagcaagcag tctctcgcca ttcatatttc agttattttc   3660
cattacagct gatgtcattg tatatcagcg ctgtaaaaat ctatctgtta cagaaggttt   3720
tcgcggtttt tataaacaaa actttcgtta cgaaatcgag caatcacccc agctgcgtat   3780
ttggaaattc gggaaaaagt agagcaacgc gagttgcatt ttttacacca taatgcatga   3840
ttaacttcga gaagggatta aggctaattt cactagtatg tttcaaaaac ctcaatctgt   3900
ccattgaatg ccttataaaa cagctataga ttgcatagaa gagttagcta ctcaatgctt   3960
tttgtcaaag cttactgatg atgatgtgtc tactttcagg cgggtctgta gtaaggagaa   4020
tgacattata aagctggcac ttagaattcc acggactata gactatacta gtatactccg   4080
tctactgtac gatacacttc cgctcaggtc cttgtccttt aacgaggcct taccactctt   4140
ttgttactct attgatccag ctcagcaaag gcagtgtgat ctaagattct atcttcgcga   4200
tgtagtaaaa ctagctagac cgagaaagag actagaaatg caaaaggcac ttctacaatg   4260
gctgccatca ttattatccg atgtgacgct gcattttttt tttttttttt tttttttttt   4320
tttttttttt tttttttttt ttttttggta caaatatcat aaaaaaagag aatcttttta   4380
agcaaggatt ttcttaactt cttcggcgac agcatcaccg acttcggtgg tactgttgga   4440
accacctaaa tcaccagttc tgatacctgc atccaaaacc tttttaactg catcttcaat   4500
ggctttacct tcttcaggca agttcaatga caatttcaac atcattgcag cagacaagat   4560
agtggcgata gggttgacct tattctttgg caaatctgga gcggaaccat ggcatggttc   4620
gtacaaacca aatgcggtgt tcttgtctgg caaagaggcc aaggacgcag atggcaacaa   4680
acccaaggag cctgggataa cggaggcttc atcggagatg atatcaccaa acatgttgct   4740
ggtgattata ataccattta ggtgggttgg gttcttaact aggatcatgg cggcagaatc   4800
aatcaattga tgttgaactt tcaatgtagg gaattcgttc ttgatggttt cctccacagt   4860
ttttctccat aatcttgaag aggccaaaac attagcttta tccaaggacc aaataggcaa   4920
tggtggctca tgttgtaggg ccatgaaagc ggccattctt gtgattcttt gcacttctgg   4980
aacggtgtat tgttcactat cccaagcgac accatcacca tcgtcttcct ttctcttacc   5040
aaagtaaata cctcccacta attctctaac aacaacgaag tcagtacctt tagcaaattg   5100
tggcttgatt ggagataagt ctaaaagaga gtcggatgca aagttacatg gtcttaagtt   5160
ggcgtacaat tgaagttctt tacggatttt tagtaaacct tgttcaggtc taacactacc   5220
ggtaccccat ttaggaccac ccacagcacc taacaaaacg gcatcagcct tcttggaggc   5280
```

-continued

```
ttccagcgcc tcatctggaa gtggaacacc tgtagcatcg atagcagcac caccaattaa   5340
atgattttcg aaatcgaact tgacattgga acgaacatca gaaatagctt taagaacctt   5400
aatggcttcg gctgtgattt cttgaccaac gtggtcacct ggcaaaacga cgatcttctt   5460
aggggcagac attacaatgg tatatccttg aaatatatat aaaaaaaaaa aaaaaaaaaa   5520
aaaaaaaaaa atgcagcttc tcaatgatat tcgaatacgc tttgaggaga tacagcctaa   5580
tatccgacaa actgttttac agatttacga tcgtacttgt tacccatcat tgaattttga   5640
acatccgaac ctgggagttt tccctgaaac agatagtata tttgaacctg tataataata   5700
tatagtctag cgctttacgg aagacaatgt atgtatttcg gttcctggag aaactattgc   5760
atctattgca taggtaatct tgcacgtcgc atccccggtt cattttctgc gtttccatct   5820
tgcacttcaa tagcatatct ttgttaacga agcatctgtg cttcattttg tagaacaaaa   5880
atgcaacgcg agagcgctaa tttttcaaac aaagaatctg agctgcattt ttacagaaca   5940
gaaatgcaac gcgaaagcgc tattttacca acgaagaatc tgtgcttcat ttttgtaaaa   6000
caaaaatgca acgcgagagc gctaattttt caaacaaaga atctgagctg catttttaca   6060
gaacagaaat gcaacgcgag agcgctattt taccaacaaa gaatctatac ttcttttttg   6120
ttctacaaaa atgcatcccg agagcgctat ttttctaaca aagcatctta gattactttt   6180
tttctccttt gtgcgctcta taatgcagtc tcttgataac tttttgcact gtaggtccgt   6240
taaggttaga agaaggctac tttggtgtct attttctctt ccataaaaaa agcctgactc   6300
cacttcccgc gtttactgat tactagcgaa gctgcgggtg catttttttca agataaaggc   6360
atccccgatt atattctata ccgatgtgga ttgcgcatac tttgtgaaca gaaagtgata   6420
gcgttgatga ttcttcattg gtcagaaaat tatgaacggt ttcttctatt ttgtctctat   6480
atactacgta taggaaatgt ttacattttc gtattgtttt cgattcactc tatgaatagt   6540
tcttactaca attttttttgt ctaaagagta atactagaga taaacataaa aaatgtagag   6600
gtcgagttta gatgcaagtt caaggagcga aaggtggatg ggtaggttat atagggatat   6660
agcacagaga tatatagcaa agagatactt ttgagcaatg tttgtggaag cggtattcgc   6720
aatattttag tagctcgtta cagtccggtg cgtttttggt tttttgaaag tgcgtcttca   6780
gagcgctttt ggttttcaaa agcgctctga agttcctata ctttctagag aataggaact   6840
tcggaatagg aacttcaaag cgtttccgaa aacgagcgct tccgaaaatg caacgcgagc   6900
tgcgcacata cagctcactg ttcacgtcgc acctatatct gcgtgttgcc tgtatatata   6960
tatacatgag aagaacggca tagtgcgtgt ttatgcttaa atgcgtactt atatgcgtct   7020
atttatgtag gatgaaaggt agtctagtac ctcctgtgat attatcccat tccatgcggg   7080
gtatcgtatg cttccttcag cactaccctt tagctgttct atatgctgcc actcctcaat   7140
tggattagtc tcatccttca atgctatcat ttcctttgat attggatcat atgcatagta   7200
ccgagaaact agtgcgaagt agtgatcagg tattgctgtt atctgatgag tatacgttgt   7260
cctggccacg gcagaagcac gcttatcgct ccaatttccc acaacattag tcaactccgt   7320
taggcccttc attgaaagaa atgaggtcat caaatgtctt ccaatgtgag attttgggcc   7380
atttttttata gcaaagattg aataaggcgc atttttcttc aaagctttat tgtacgatct   7440
gactaagtta tcttttaata attggtattc ctgtttattg cttgaagaat tgccggtcct   7500
atttactcgt tttaggactg gttcagaatt cctcaaaaat tcatccaaat atacaagtgg   7560
atcgatgata agctgtcaaa catgagaatt cttgaagacg aaagggcctc gtgatacgcc   7620
```

-continued

```
tatttttata ggttaatgtc atgataataa tggtttctta gacgtcaggt ggcacttttc   7680
ggggaaatgt gcgcggaacc cctatttgtt tatttttcta aatacattca aatatgtatc   7740
cgctcatgag acaataaccc tgataaatgc ttcaataata ttgaaaaagg aagagtatga   7800
gtattcaaca tttccgtgtc gcccttattc ccttttttgc ggcattttgc cttcctgttt   7860
ttgctcaccc agaaacgctg gtgaaagtaa aagatgctga agatcagttg ggtgcacgag   7920
tgggttacat cgaactggat ctcaacagcg gtaagatcct tgagagtttt cgccccgaag   7980
aacgttttcc aatgatgagc acttttaaag ttctgctatg tggcgcggta ttatcccgtg   8040
ttgacgccgg gcaagagcaa ctcggtcgcc gcatacacta ttctcagaat gacttggttg   8100
agtactcacc agtcacagaa aagcatctta cggatggcat gacagtaaga gaattatgca   8160
gtgctgccat aaccatgagt gataacactg cggccaactt acttctgaca acgatcggag   8220
gaccgaagga gctaaccgct tttttgcaca acatggggga tcatgtaact cgccttgatc   8280
gttgggaacc ggagctgaat gaagccatac caaacgacga gcgtgacacc acgatgcctg   8340
cagcaatggc aacaacgttg cgcaaactat taactggcga actacttact ctagcttccc   8400
ggcaacaatt aatagactgg atggaggcgg ataaagttgc aggaccactt ctgcgctcgg   8460
cccttccggc tggctggttt attgctgata aatctggagc cggtgagcgt gggtctcgcg   8520
gtatcattgc agcactgggg ccagatggta agccctcccg tatcgtagtt atctacacga   8580
cggggagtca ggcaactatg gatgaacgaa atagacagat cgctgagata ggtgcctcac   8640
tgattaagca ttggtaactg tcagaccaag tttactcata tatactttag attgatttaa   8700
aacttcattt ttaatttaaa aggatctagg tgaagatcct ttttgataat ctcatgacca   8760
aaatccctta acgtgagttt tcgttccact gagcgtcaga ccccgtagaa aagatcaaag   8820
gatcttcttg agatcctttt tttctgcgcg taatctgctg cttgcaaaca aaaaaaccac   8880
cgctaccagc ggtggtttgt ttgccggatc aagagctacc aactcttttt ccgaaggtaa   8940
ctggcttcag cagagcgcag ataccaaata ctgtccttct agtgtagccg tagttaggcc   9000
accacttcaa gaactctgta gcaccgccta catacctcgc tctgctaatc ctgttaccag   9060
tggctgctgc cagtggcgat aagtcgtgtc ttaccgggtt ggactcaaga cgatagttac   9120
cggataaggc gcagcggtcg ggctgaacgg ggggttcgtg cacacagccc agcttggagc   9180
gaacgaccta caccgaactg agatacctac agcgtgagct atgagaaagc gccacgcttc   9240
ccgaagggag aaaggcggac aggtatccgg taagcggcag ggtcggaaca ggagagcgca   9300
cgagggagct tccaggggga aacgcctggt atctttatag tcctgtcggg tttcgccacc   9360
tctgacttga gcgtcgattt ttgtgatgct cgtcaggggg gcggagccta tggaaaaacg   9420
ccagcaacgc ggccttttta cggttcctgg ccttttgctg gccttttgct cacatgttct   9480
ttcctgcgtt atcccctgat tctgtggata accgtattac cgcctttgag tgagctgata   9540
ccgctcgccg cagccgaacg accgagcgca gcgagtcagt gagcgaggaa gcggaagagc   9600
gcctgatgcg gtattttctc cttacgcatc tgtgcggtat ttcacaccgc atatggtgca   9660
ctctcagtac aatctgctct gatgccgcat agttaagcca gtatacactc cgctatcgct   9720
acgtgactgg gtcatggctg cgccccgaca cccgccaaca cccgctgacg cgccctgacg   9780
ggcttgtctg ctcccggcat ccgcttacag acaagctgtg accgtctccg ggagctgcat   9840
gtgtcagagg ttttcaccgt catcaccgaa acgcgcgagg cagctgcggt aaagctcatc   9900
agcgtggtcg tgaagcgatt cacagatgtc tgcctgttca tccgcgtcca gctcgttgag   9960
tttctccaga agcgttaatg tctggcttct gataaagcgg gccatgttaa gggcggtttt  10020
```

-continued ttcctgtttg gtcactgatg cctccgtgta agggggattt ctgttcatgg gggtaatgat 10080
accgatgaaa cgagagagga tgctcacgat acgggttact gatgatgaac atgcccggtt 10140
actggaacgt tgtgagggta aacaactggc ggtatggatg cggcgggacc agagaaaaat 10200
cactcagggt caatgccagc gcttcgttaa tacagatgta ggtgttccac agggtagcca 10260
gcagcatcct gcgatgcaga tccggaacat aatggtgcag ggcgctgact tccgcgtttc 10320
cagactttac gaaacacgga aaccgaagac cattcatgtt gttgctcagg tcgcagacgt 10380
tttgcagcag cagtcgcttc acgttcgctc gcgtatcggt gattcattct gctaaccagt 10440
aaggcaaccc cgccagccta gccgggtcct caacgacagg agcacgatca tgcgcacccg 10500
tggccaggac ccaacgctgc ccgagatgcg ccgcgtgcgg ctgctggaga tggcggacgc 10560
gatggatatg ttctgccaag ggttggtttg cgcattcaca gttctccgca agaattgatt 10620
ggctccaatt cttggagtgg tgaatccgtt agcgaggtgc cgccggcttc cattcaggtc 10680
gaggtggccc ggctccatgc accgcgacgc aacgcgggga ggcagacaag gtatagggcg 10740
gcgcctacaa tccatgccaa cccgttccat gtgctcgccg aggcggcata aatcgccgtg 10800
acgatcagcg gtccaatgat cgaagttagg ctggtaagag ccgcgagcga tccttgaagc 10860
tgtccctgat ggtcgtcatc tacctgcctg gacagcatgg cctgcaacgc gggcatcccg 10920
atgccgccgg aagcgagaag aatcataatg gggaaggcca tccagcctcg cgtcgcgaac 10980
gccagcaaga cgtagcccag cgcgtcggcc gccatgccgg cgataatggc ctgcttctcg 11040
ccgaaacgtt tggtggcggg accagtgacg aaggcttgag cgagggcgtg caagattccg 11100
aataccgcaa gcgacaggcc gatcatcgtc gcgctccagc gaaagcggtc ctcgccgaaa 11160
atgacccaga gcgctgccgg cacctgtcct acgagttgca tgataaagaa gacagtcata 11220
agtgcggcga cgatagtcat gccccgcgcc caccggaagg agctgactgg gttgaaggct 11280
ctcaagggca tcggtcgagg atccttcaat atgcgcacat acgctgttat gttcaaggtc 11340
ccttcgttta agaacgaaag cggtcttcct tttgagggat gtttcaagtt gttcaaatct 11400
atcaaatttg caaatcccca gtctgtatct agagcgttga atcggtgatg cgatttgtta 11460
attaaattga tggtgtcacc attaccaggt ctagatatac caatggcaaa ctgagcacaa 11520
caataccagt ccggatcaac tggcaccatc tctcccgtag tctcatctaa tttttcttcc 11580
ggatgaggtt ccagatatac cgcaacacct ttattatggt ttccctgagg gaataataga 11640
atgtcccatt cgaaatcacc aattctaaac ctgggcgaat tgtatttcgg gtttgttaac 11700
tcgttccagt caggaatgtt ccacgtgaag ctatcttcca gcaaagtctc cacttcttca 11760
tcaaattgtg gagaatactc ccaatgctct tatctatggg acttccggga aacacagtac 11820
cgatacttcc caattcgtct tcagagctca ttgtttgttt gaagagacta atcaaagaat 11880
cgttttctca aaaaaattaa tatcttaact gatagtttga tcaaaggggc aaaacgtagg 11940
ggcaaacaaa cggaaaaatc gtttctcaaa ttttctgatg ccaagaactc taaccagtct 12000
tatctaaaaa ttgccttatg atccgtctct ccggttacag cctgtgtaac tgattaatcc 12060
tgcctttcta atcaccattc taatgtttta attaagggat tttgtcttca ttaacggctt 12120
tcgctcataa aaatgttatg acgttttgcc cgcaggcggg aaaccatcca cttcacgaga 12180
ctgatctcct ctgccggaac accgggcatc tccaacttat aagttggaga aataagagaa 12240
tttcagattg agagaatgaa aaaaaaaaac ccttagttca taggtccatt ctcttagcgc 12300
aactacagag aacaggggca caaacaggca aaaaacgggc acaacctcaa tggagtgatg 12360

-continued

```
caacctgcct ggagtaaatg atgacacaag gcaattgacc cacgcatgta tctatctcat  12420

tttcttacac cttctattac cttctgctct ctctgatttg gaaaaagctg aaaaaaaagg  12480

ttgaaaccag ttccctgaaa ttattcccct acttgactaa taagtatata aagacggtag  12540

gtattgattg taattctgta aatctatttc ttaaacttct taaattctac ttttatagtt  12600

agtctttttt ttagttttaa aacaccaaga acttagtttc gaataaacac acataaacaa  12660

acaagcttac aaaacaaa atg gct gca tat gca gct cag ggc tat aag gtg    12711
                    Met Ala Ala Tyr Ala Ala Gln Gly Tyr Lys Val
                     1               5                  10

cta gta ctc aac ccc tct gtt gct gca aca ctg ggc ttt ggt gct tac    12759
Leu Val Leu Asn Pro Ser Val Ala Ala Thr Leu Gly Phe Gly Ala Tyr
            15                  20                  25

atg tcc aag gct cat ggg atc gat cct aac atc agg acc ggg gtg aga    12807
Met Ser Lys Ala His Gly Ile Asp Pro Asn Ile Arg Thr Gly Val Arg
        30                  35                  40

aca att acc act ggc agc ccc atc acg tac tcc acc tac ggc aag ttc    12855
Thr Ile Thr Thr Gly Ser Pro Ile Thr Tyr Ser Thr Tyr Gly Lys Phe
    45                  50                  55

ctt gcc gac ggc ggg tgc tcg ggg ggc gct tat gac ata ata att tgt    12903
Leu Ala Asp Gly Gly Cys Ser Gly Gly Ala Tyr Asp Ile Ile Ile Cys
60                  65                  70                  75

gac gag tgc cac tcc acg gat gcc aca tcc atc ttg ggc att ggc act    12951
Asp Glu Cys His Ser Thr Asp Ala Thr Ser Ile Leu Gly Ile Gly Thr
                80                  85                  90

gtc ctt gac caa gca gag act gcg ggg gcg aga ctg gtt gtg ctc gcc    12999
Val Leu Asp Gln Ala Glu Thr Ala Gly Ala Arg Leu Val Val Leu Ala
            95                  100                 105

acc gcc acc cct ccg ggc tcc gtc act gtg ccc cat ccc aac atc gag    13047
Thr Ala Thr Pro Pro Gly Ser Val Thr Val Pro His Pro Asn Ile Glu
        110                 115                 120

gag gtt gct ctg tcc acc acc gga gag atc cct ttt tac ggc aag gct    13095
Glu Val Ala Leu Ser Thr Thr Gly Glu Ile Pro Phe Tyr Gly Lys Ala
    125                 130                 135

atc ccc ctc gaa gta atc aag ggg ggg aga cat ctc atc ttc tgt cat    13143
Ile Pro Leu Glu Val Ile Lys Gly Gly Arg His Leu Ile Phe Cys His
140                 145                 150                 155

tca aag aag aag tgc gac gaa ctc gcc gca aag ctg gtc gca ttg ggc    13191
Ser Lys Lys Lys Cys Asp Glu Leu Ala Ala Lys Leu Val Ala Leu Gly
                160                 165                 170

atc aat gcc gtg gcc tac tac cgc ggt ctt gac gtg tcc gtc atc ccg    13239
Ile Asn Ala Val Ala Tyr Tyr Arg Gly Leu Asp Val Ser Val Ile Pro
            175                 180                 185

acc agc ggc gat gtt gtc gtc gtg gca acc gat gcc ctc atg acc ggc    13287
Thr Ser Gly Asp Val Val Val Val Ala Thr Asp Ala Leu Met Thr Gly
        190                 195                 200

tat acc ggc gac ttc gac tcg gtg ata gac tgc aat acg tgt gtc acc    13335
Tyr Thr Gly Asp Phe Asp Ser Val Ile Asp Cys Asn Thr Cys Val Thr
    205                 210                 215

cag aca gtc gat ttc agc ctt gac cct acc ttc acc att gag aca atc    13383
Gln Thr Val Asp Phe Ser Leu Asp Pro Thr Phe Thr Ile Glu Thr Ile
220                 225                 230                 235

acg ctc ccc caa gat gct gtc tcc cgc act caa cgt cgg ggc agg act    13431
Thr Leu Pro Gln Asp Ala Val Ser Arg Thr Gln Arg Arg Gly Arg Thr
                240                 245                 250

ggc agg ggg aag cca ggc atc tac aga ttt gtg gca ccg ggg gag cgc    13479
Gly Arg Gly Lys Pro Gly Ile Tyr Arg Phe Val Ala Pro Gly Glu Arg
            255                 260                 265

ccc tcc ggc atg ttc gac tcg tcc gtc ctc tgt gag tgc tat gac gca    13527
```

-continued

```
Pro Ser Gly Met Phe Asp Ser Ser Val Leu Cys Glu Cys Tyr Asp Ala
        270                 275                 280

ggc tgt gct tgg tat gag ctc acg ccc gcc gag act aca gtt agg cta    13575
Gly Cys Ala Trp Tyr Glu Leu Thr Pro Ala Glu Thr Thr Val Arg Leu
    285                 290                 295

cga gcg tac atg aac acc ccg ggg ctt ccc gtg tgc cag gac cat ctt    13623
Arg Ala Tyr Met Asn Thr Pro Gly Leu Pro Val Cys Gln Asp His Leu
300                 305                 310                 315

gaa ttt tgg gag ggc gtc ttt aca ggc ctc act cat ata gat gcc cac    13671
Glu Phe Trp Glu Gly Val Phe Thr Gly Leu Thr His Ile Asp Ala His
                320                 325                 330

ttt cta tcc cag aca aag cag agt ggg gag aac ctt cct tac ctg gta    13719
Phe Leu Ser Gln Thr Lys Gln Ser Gly Glu Asn Leu Pro Tyr Leu Val
            335                 340                 345

gcg tac caa gcc acc gtg tgc gct agg gct caa gcc cct ccc cca tcg    13767
Ala Tyr Gln Ala Thr Val Cys Ala Arg Ala Gln Ala Pro Pro Pro Ser
        350                 355                 360

tgg gac cag atg tgg aag tgt ttg att cgc ctc aag ccc acc ctc cat    13815
Trp Asp Gln Met Trp Lys Cys Leu Ile Arg Leu Lys Pro Thr Leu His
    365                 370                 375

ggg cca aca ccc ctg cta tac aga ctg ggc gct gtt cag aat gaa atc    13863
Gly Pro Thr Pro Leu Leu Tyr Arg Leu Gly Ala Val Gln Asn Glu Ile
380                 385                 390                 395

acc ctg acg cac cca gtc acc aaa tac atc atg aca tgc atg tcg gcc    13911
Thr Leu Thr His Pro Val Thr Lys Tyr Ile Met Thr Cys Met Ser Ala
                400                 405                 410

gac ctg gag gtc gtc acg agc acc tgg gtg ctc gtt ggc ggc gtc ctg    13959
Asp Leu Glu Val Val Thr Ser Thr Trp Val Leu Val Gly Gly Val Leu
            415                 420                 425

gct gct ttg gcc gcg tat tgc ctg tca aca ggc tgc gtg gtc ata gtg    14007
Ala Ala Leu Ala Ala Tyr Cys Leu Ser Thr Gly Cys Val Val Ile Val
        430                 435                 440

ggc agg gtc gtc ttg tcc ggg aag ccg gca atc ata cct gac agg gaa    14055
Gly Arg Val Val Leu Ser Gly Lys Pro Ala Ile Ile Pro Asp Arg Glu
    445                 450                 455

gtc ctc tac cga gag ttc gat gag atg gaa gag tgc tct cag cac tta    14103
Val Leu Tyr Arg Glu Phe Asp Glu Met Glu Glu Cys Ser Gln His Leu
460                 465                 470                 475

ccg tac atc gag caa ggg atg atg ctc gcc gag cag ttc aag cag aag    14151
Pro Tyr Ile Glu Gln Gly Met Met Leu Ala Glu Gln Phe Lys Gln Lys
                480                 485                 490

gcc ctc ggc ctc ctg cag acc gcg tcc cgt cag gca gag gtt atc gcc    14199
Ala Leu Gly Leu Leu Gln Thr Ala Ser Arg Gln Ala Glu Val Ile Ala
            495                 500                 505

cct gct gtc cag acc aac tgg caa aaa ctc gag acc ttc tgg gcg aag    14247
Pro Ala Val Gln Thr Asn Trp Gln Lys Leu Glu Thr Phe Trp Ala Lys
        510                 515                 520

cat atg tgg aac ttc atc agt ggg ata caa tac ttg gcg ggc ttg tca    14295
His Met Trp Asn Phe Ile Ser Gly Ile Gln Tyr Leu Ala Gly Leu Ser
    525                 530                 535

acg ctg cct ggt aac ccc gcc att gct tca ttg atg gct ttt aca gct    14343
Thr Leu Pro Gly Asn Pro Ala Ile Ala Ser Leu Met Ala Phe Thr Ala
540                 545                 550                 555

gct gtc acc agc cca cta acc act agc caa acc ctc ctc ttc aac ata    14391
Ala Val Thr Ser Pro Leu Thr Thr Ser Gln Thr Leu Leu Phe Asn Ile
                560                 565                 570

ttg ggg ggg tgg gtg gct gcc cag ctc gcc gcc ccc ggt gcc gct act    14439
Leu Gly Gly Trp Val Ala Ala Gln Leu Ala Ala Pro Gly Ala Ala Thr
            575                 580                 585
```

-continued

```
gcc ttt gtg ggc gct ggc tta gct ggc gcc gcc atc ggc agt gtt gga     14487
Ala Phe Val Gly Ala Gly Leu Ala Gly Ala Ala Ile Gly Ser Val Gly
        590                 595                 600

ctg ggg aag gtc ctc ata gac atc ctt gca ggg tat ggc gcg ggc gtg     14535
Leu Gly Lys Val Leu Ile Asp Ile Leu Ala Gly Tyr Gly Ala Gly Val
    605                 610                 615

gcg gga gct ctt gtg gca ttc aag atc atg agc ggt gag gtc ccc tcc     14583
Ala Gly Ala Leu Val Ala Phe Lys Ile Met Ser Gly Glu Val Pro Ser
620                 625                 630                 635

acg gag gac ctg gtc aat cta ctg ccc gcc atc ctc tcg ccc gga gcc     14631
Thr Glu Asp Leu Val Asn Leu Leu Pro Ala Ile Leu Ser Pro Gly Ala
                640                 645                 650

ctc gta gtc ggc gtg gtc tgt gca gca ata ctg cgc cgg cac gtt ggc     14679
Leu Val Val Gly Val Val Cys Ala Ala Ile Leu Arg Arg His Val Gly
            655                 660                 665

ccg ggc gag ggg gca gtg cag tgg atg aac cgg ctg ata gcc ttc gcc     14727
Pro Gly Glu Gly Ala Val Gln Trp Met Asn Arg Leu Ile Ala Phe Ala
        670                 675                 680

tcc cgg ggg aac cat gtt tcc ccc acg cac tac gtg ccg gag agc gat     14775
Ser Arg Gly Asn His Val Ser Pro Thr His Tyr Val Pro Glu Ser Asp
    685                 690                 695

gca gct gcc cgc gtc act gcc ata ctc agc agc ctc act gta acc cag     14823
Ala Ala Ala Arg Val Thr Ala Ile Leu Ser Ser Leu Thr Val Thr Gln
700                 705                 710                 715

ctc ctg agg cga ctg cac cag tgg ata agc tcg gag tgt acc act cca     14871
Leu Leu Arg Arg Leu His Gln Trp Ile Ser Ser Glu Cys Thr Thr Pro
                720                 725                 730

tgc tcc ggt tcc tgg cta agg gac atc tgg gac tgg ata tgc gag gtg     14919
Cys Ser Gly Ser Trp Leu Arg Asp Ile Trp Asp Trp Ile Cys Glu Val
            735                 740                 745

ttg agc gac ttt aag acc tgg cta aaa gct aag ctc atg cca cag ctg     14967
Leu Ser Asp Phe Lys Thr Trp Leu Lys Ala Lys Leu Met Pro Gln Leu
        750                 755                 760

cct ggg atc ccc ttt gtg tcc tgc cag cgc ggg tat aag ggg gtc tgg     15015
Pro Gly Ile Pro Phe Val Ser Cys Gln Arg Gly Tyr Lys Gly Val Trp
    765                 770                 775

cga ggg gac ggc atc atg cac act cgc tgc cac tgt gga gct gag atc     15063
Arg Gly Asp Gly Ile Met His Thr Arg Cys His Cys Gly Ala Glu Ile
780                 785                 790                 795

act gga cat gtc aaa aac ggg acg atg agg atc gtc ggt cct agg acc     15111
Thr Gly His Val Lys Asn Gly Thr Met Arg Ile Val Gly Pro Arg Thr
                800                 805                 810

tgc agg aac atg tgg agt ggg acc ttc ccc att aat gcc tac acc acg     15159
Cys Arg Asn Met Trp Ser Gly Thr Phe Pro Ile Asn Ala Tyr Thr Thr
            815                 820                 825

ggc ccc tgt acc ccc ctt cct gcg ccg aac tac acg ttc gcg cta tgg     15207
Gly Pro Cys Thr Pro Leu Pro Ala Pro Asn Tyr Thr Phe Ala Leu Trp
        830                 835                 840

agg gtg tct gca gag gaa tac gtg gag ata agg cag gtg ggg gac ttc     15255
Arg Val Ser Ala Glu Glu Tyr Val Glu Ile Arg Gln Val Gly Asp Phe
    845                 850                 855

cac tac gtg acg ggt atg act act gac aat ctt aaa tgc ccg tgc cag     15303
His Tyr Val Thr Gly Met Thr Thr Asp Asn Leu Lys Cys Pro Cys Gln
860                 865                 870                 875

gtc cca tcg ccc gaa ttt ttc aca gaa ttg gac ggg gtg cgc cta cat     15351
Val Pro Ser Pro Glu Phe Phe Thr Glu Leu Asp Gly Val Arg Leu His
                880                 885                 890

agg ttt gcg ccc ccc tgc aag ccc ttg ctg cgg gag gag gta tca ttc     15399
Arg Phe Ala Pro Pro Cys Lys Pro Leu Leu Arg Glu Glu Val Ser Phe
            895                 900                 905
```

-continued

```
aga gta gga ctc cac gaa tac ccg gta ggg tcg caa tta cct tgc gag    15447
Arg Val Gly Leu His Glu Tyr Pro Val Gly Ser Gln Leu Pro Cys Glu
        910                 915                 920

ccc gaa ccg gac gtg gcc gtg ttg acg tcc atg ctc act gat ccc tcc    15495
Pro Glu Pro Asp Val Ala Val Leu Thr Ser Met Leu Thr Asp Pro Ser
    925                 930                 935

cat ata aca gca gag gcg gcc ggg cga agg ttg gcg agg gga tca ccc    15543
His Ile Thr Ala Glu Ala Ala Gly Arg Arg Leu Ala Arg Gly Ser Pro
940                 945                 950                 955

ccc tct gtg gcc agc tcc tcg gct agc cag cta tcc gct cca tct ctc    15591
Pro Ser Val Ala Ser Ser Ser Ala Ser Gln Leu Ser Ala Pro Ser Leu
                960                 965                 970

aag gca act tgc acc gct aac cat gac tcc cct gat gct gag ctc ata    15639
Lys Ala Thr Cys Thr Ala Asn His Asp Ser Pro Asp Ala Glu Leu Ile
            975                 980                 985

gag gcc aac ctc cta tgg agg cag gag atg ggc ggc aac atc acc agg    15687
Glu Ala Asn Leu Leu Trp Arg Gln Glu Met Gly Gly Asn Ile Thr Arg
        990                 995                 1000

gtt gag tca gaa aac aaa gtg gtg att ctg gac tcc ttc gat ccg ctt    15735
Val Glu Ser Glu Asn Lys Val Val Ile Leu Asp Ser Phe Asp Pro Leu
   1005                1010                1015

gtg gcg gag gag gac gag cgg gag atc tcc gta ccc gca gaa atc ctg    15783
Val Ala Glu Glu Asp Glu Arg Glu Ile Ser Val Pro Ala Glu Ile Leu
1020                1025                1030                1035

cgg aag tct cgg aga ttc gcc cag gcc ctg ccc gtt tgg gcg cgg ccg    15831
Arg Lys Ser Arg Arg Phe Ala Gln Ala Leu Pro Val Trp Ala Arg Pro
               1040                1045                1050

gac tat aac ccc ccg cta gtg gag acg tgg aaa aag ccc gac tac gaa    15879
Asp Tyr Asn Pro Pro Leu Val Glu Thr Trp Lys Lys Pro Asp Tyr Glu
           1055                1060                1065

cca cct gtg gtc cat ggc tgc ccg ctt cca cct cca aag tcc cct cct    15927
Pro Pro Val Val His Gly Cys Pro Leu Pro Pro Pro Lys Ser Pro Pro
       1070                1075                1080

gtg cct ccg cct cgg aag aag cgg acg gtg gtc ctc act gaa tca acc    15975
Val Pro Pro Pro Arg Lys Lys Arg Thr Val Val Leu Thr Glu Ser Thr
   1085                1090                1095

cta tct act gcc ttg gcc gag ctc gcc acc aga agc ttt ggc agc tcc    16023
Leu Ser Thr Ala Leu Ala Glu Leu Ala Thr Arg Ser Phe Gly Ser Ser
1100                1105                1110                1115

tca act tcc ggc att acg ggc gac aat acg aca aca tcc tct gag ccc    16071
Ser Thr Ser Gly Ile Thr Gly Asp Asn Thr Thr Thr Ser Ser Glu Pro
               1120                1125                1130

gcc cct tct ggc tgc ccc ccc gac tcc gac gct gag tcc tat tcc tcc    16119
Ala Pro Ser Gly Cys Pro Pro Asp Ser Asp Ala Glu Ser Tyr Ser Ser
           1135                1140                1145

atg ccc ccc ctg gag ggg gag cct ggg gat ccg gat ctt agc gac ggg    16167
Met Pro Pro Leu Glu Gly Glu Pro Gly Asp Pro Asp Leu Ser Asp Gly
       1150                1155                1160

tca tgg tca acg gtc agt agt gag gcc aac gcg gag gat gtc gtg tgc    16215
Ser Trp Ser Thr Val Ser Ser Glu Ala Asn Ala Glu Asp Val Val Cys
   1165                1170                1175

tgc tca atg tct tac tct tgg aca ggc gca ctc gtc acc ccg tgc gcc    16263
Cys Ser Met Ser Tyr Ser Trp Thr Gly Ala Leu Val Thr Pro Cys Ala
1180                1185                1190                1195

gcg gaa gaa cag aaa ctg ccc atc aat gca cta agc aac tcg ttg cta    16311
Ala Glu Glu Gln Lys Leu Pro Ile Asn Ala Leu Ser Asn Ser Leu Leu
               1200                1205                1210

cgt cac cac aat ttg gtg tat tcc acc acc tca cgc agt gct tgc caa    16359
Arg His His Asn Leu Val Tyr Ser Thr Thr Ser Arg Ser Ala Cys Gln
```

-continued

```
        1215                1220                1225

agg cag aag aaa gtc aca ttt gac aga ctg caa gtt ctg gac agc cat    16407
Arg Gln Lys Lys Val Thr Phe Asp Arg Leu Gln Val Leu Asp Ser His
     1230                1235                1240

tac cag gac gta ctc aag gag gtt aaa gca gcg gcg tca aaa gtg aag    16455
Tyr Gln Asp Val Leu Lys Glu Val Lys Ala Ala Ala Ser Lys Val Lys
  1245                1250                1255

gct aac ttg cta tcc gta gag gaa gct tgc agc ctg acg ccc cca cac    16503
Ala Asn Leu Leu Ser Val Glu Glu Ala Cys Ser Leu Thr Pro Pro His
1260                1265                1270                1275

tca gcc aaa tcc aag ttt ggt tat ggg gca aaa gac gtc cgt tgc cat    16551
Ser Ala Lys Ser Lys Phe Gly Tyr Gly Ala Lys Asp Val Arg Cys His
            1280                1285                1290

gcc aga aag gcc gta acc cac atc aac tcc gtg tgg aaa gac ctt ctg    16599
Ala Arg Lys Ala Val Thr His Ile Asn Ser Val Trp Lys Asp Leu Leu
        1295                1300                1305

gaa gac aat gta aca cca ata gac act acc atc atg gct aag aac gag    16647
Glu Asp Asn Val Thr Pro Ile Asp Thr Thr Ile Met Ala Lys Asn Glu
     1310                1315                1320

gtt ttc tgc gtt cag cct gag aag ggg ggt cgt aag cca gct cgt ctc    16695
Val Phe Cys Val Gln Pro Glu Lys Gly Gly Arg Lys Pro Ala Arg Leu
  1325                1330                1335

atc gtg ttc ccc gat ctg ggc gtg cgc gtg tgc gaa aag atg gct ttg    16743
Ile Val Phe Pro Asp Leu Gly Val Arg Val Cys Glu Lys Met Ala Leu
1340                1345                1350                1355

tac gac gtg gtt aca aag ctc ccc ttg gcc gtg atg gga agc tcc tac    16791
Tyr Asp Val Val Thr Lys Leu Pro Leu Ala Val Met Gly Ser Ser Tyr
            1360                1365                1370

gga ttc caa tac tca cca gga cag cgg gtt gaa ttc ctc gtg caa gcg    16839
Gly Phe Gln Tyr Ser Pro Gly Gln Arg Val Glu Phe Leu Val Gln Ala
        1375                1380                1385

tgg aag tcc aag aaa acc cca atg ggg ttc tcg tat gat acc cgc tgc    16887
Trp Lys Ser Lys Lys Thr Pro Met Gly Phe Ser Tyr Asp Thr Arg Cys
     1390                1395                1400

ttt gac tcc aca gtc act gag agc gac atc cgt acg gag gag gca atc    16935
Phe Asp Ser Thr Val Thr Glu Ser Asp Ile Arg Thr Glu Glu Ala Ile
  1405                1410                1415

tac caa tgt tgt gac ctc gac ccc caa gcc cgc gtg gcc atc aag tcc    16983
Tyr Gln Cys Cys Asp Leu Asp Pro Gln Ala Arg Val Ala Ile Lys Ser
1420                1425                1430                1435

ctc acc gag agg ctt tat gtt ggg ggc cct ctt acc aat tca agg ggg    17031
Leu Thr Glu Arg Leu Tyr Val Gly Gly Pro Leu Thr Asn Ser Arg Gly
            1440                1445                1450

gag aac tgc ggc tat cgc agg tgc cgc gcg agc ggc gta ctg aca act    17079
Glu Asn Cys Gly Tyr Arg Arg Cys Arg Ala Ser Gly Val Leu Thr Thr
        1455                1460                1465

agc tgt ggt aac acc ctc act tgc tac atc aag gcc cgg gca gcc tgt    17127
Ser Cys Gly Asn Thr Leu Thr Cys Tyr Ile Lys Ala Arg Ala Ala Cys
     1470                1475                1480

cga gcc gca ggg ctc cag gac tgc acc atg ctc gtg tgt ggc gac gac    17175
Arg Ala Ala Gly Leu Gln Asp Cys Thr Met Leu Val Cys Gly Asp Asp
  1485                1490                1495

tta gtc gtt atc tgt gaa agc gcg ggg gtc cag gag gac gcg gcg agc    17223
Leu Val Val Ile Cys Glu Ser Ala Gly Val Gln Glu Asp Ala Ala Ser
1500                1505                1510                1515

ctg aga gcc ttc acg gag gct atg acc agg tac tcc gcc ccc cct ggg    17271
Leu Arg Ala Phe Thr Glu Ala Met Thr Arg Tyr Ser Ala Pro Pro Gly
            1520                1525                1530

gac ccc cca caa cca gaa tac gac ttg gag ctc ata aca tca tgc tcc    17319
```

-continued

```
Asp Pro Pro Gln Pro Glu Tyr Asp Leu Glu Leu Ile Thr Ser Cys Ser
           1535                1540                1545

tcc aac gtg tca gtc gcc cac gac ggc gct gga aag agg gtc tac tac    17367
Ser Asn Val Ser Val Ala His Asp Gly Ala Gly Lys Arg Val Tyr Tyr
       1550                1555                1560

ctc acc cgt gac cct aca acc ccc ctc gcg aga gct gcg tgg gag aca    17415
Leu Thr Arg Asp Pro Thr Thr Pro Leu Ala Arg Ala Ala Trp Glu Thr
   1565                1570                1575

gca aga cac act cca gtc aat tcc tgg cta ggc aac ata atc atg ttt    17463
Ala Arg His Thr Pro Val Asn Ser Trp Leu Gly Asn Ile Ile Met Phe
1580                1585                1590                1595

gcc ccc aca ctg tgg gcg agg atg ata ctg atg acc cat ttc ttt agc    17511
Ala Pro Thr Leu Trp Ala Arg Met Ile Leu Met Thr His Phe Phe Ser
               1600                1605                1610

gtc ctt ata gcc agg gac cag ctt gaa cag gcc ctc gat tgc gag atc    17559
Val Leu Ile Ala Arg Asp Gln Leu Glu Gln Ala Leu Asp Cys Glu Ile
           1615                1620                1625

tac ggg gcc tgc tac tcc ata gaa cca ctg gat cta cct cca atc att    17607
Tyr Gly Ala Cys Tyr Ser Ile Glu Pro Leu Asp Leu Pro Pro Ile Ile
       1630                1635                1640

caa aga ctc cat ggc ctc agc gca ttt tca ctc cac agt tac tct cca    17655
Gln Arg Leu His Gly Leu Ser Ala Phe Ser Leu His Ser Tyr Ser Pro
   1645                1650                1655

ggt gaa atc aat agg gtg gcc gca tgc ctc aga aaa ctt ggg gta ccg    17703
Gly Glu Ile Asn Arg Val Ala Ala Cys Leu Arg Lys Leu Gly Val Pro
1660                1665                1670                1675

ccc ttg cga gct tgg aga cac cgg gcc cgg agc gtc cgc gct agg ctt    17751
Pro Leu Arg Ala Trp Arg His Arg Ala Arg Ser Val Arg Ala Arg Leu
               1680                1685                1690

ctg gcc aga gga ggc agg gct gcc ata tgt ggc aag tac ctc ttc aac    17799
Leu Ala Arg Gly Gly Arg Ala Ala Ile Cys Gly Lys Tyr Leu Phe Asn
           1695                1700                1705

tgg gca gta aga aca aag ctc aaa ctc act cca ata gcg gcc gct ggc    17847
Trp Ala Val Arg Thr Lys Leu Lys Leu Thr Pro Ile Ala Ala Ala Gly
       1710                1715                1720

cag ctg gac ttg tcc ggc tgg ttc acg gct ggc tac agc ggg gga gac    17895
Gln Leu Asp Leu Ser Gly Trp Phe Thr Ala Gly Tyr Ser Gly Gly Asp
   1725                1730                1735

att tat cac agc gtg tct cat gcc cgg ccc cgc tgg atc tgg ttt tgc    17943
Ile Tyr His Ser Val Ser His Ala Arg Pro Arg Trp Ile Trp Phe Cys
1740                1745                1750                1755

cta ctc ctg ctt gct gca ggg gta ggc atc tac ctc ctc ccc aac cga    17991
Leu Leu Leu Leu Ala Ala Gly Val Gly Ile Tyr Leu Leu Pro Asn Arg
               1760                1765                1770

atg agc acg aat cct aaa cct caa aga aag acc aaa cgt aac acc aac    18039
Met Ser Thr Asn Pro Lys Pro Gln Arg Lys Thr Lys Arg Asn Thr Asn
           1775                1780                1785

cgg cgg ccg cag gac gtc aag ttc ccg ggt ggc ggt cag atc gtt ggt    18087
Arg Arg Pro Gln Asp Val Lys Phe Pro Gly Gly Gly Gln Ile Val Gly
       1790                1795                1800

gga gtt tac ttg ttg ccg cgc agg ggc cct aga ttg ggt gtg cgc gcg    18135
Gly Val Tyr Leu Leu Pro Arg Arg Gly Pro Arg Leu Gly Val Arg Ala
   1805                1810                1815

acg aga aag act tcc gag cgg tcg caa cct cga ggt aga cgt cag cct    18183
Thr Arg Lys Thr Ser Glu Arg Ser Gln Pro Arg Gly Arg Arg Gln Pro
1820                1825                1830                1835

atc ccc aag gct cgt cgg ccc gag ggc agg acc tgg gct cag ccc ggg    18231
Ile Pro Lys Ala Arg Arg Pro Glu Gly Arg Thr Trp Ala Gln Pro Gly
               1840                1845                1850
```

-continued

```
tac cct tgg ccc ctc tat ggc aat gag ggc tgc ggg tgg gcg gga tgg    18279
Tyr Pro Trp Pro Leu Tyr Gly Asn Glu Gly Cys Gly Trp Ala Gly Trp
            1855                1860                1865

ctc ctg tct ccc cgt ggc tct cgg cct agc tgg ggc ccc aca gac ccc    18327
Leu Leu Ser Pro Arg Gly Ser Arg Pro Ser Trp Gly Pro Thr Asp Pro
        1870                1875                1880

cgg cgt agg tcg cgc aat ttg ggt aag taatagtcga ctttgttccc          18374
Arg Arg Arg Ser Arg Asn Leu Gly Lys
    1885                1890

actgtacttt tagctcgtac aaaatacaat atacttttca tttctccgta aacaacatgt  18434

tttcccatgt aatatccttt tctatttttc gttccgttac caactttaca catactttat  18494

atagctattc acttctatac actaaaaaac taagacaatt ttaattttgc tgcctgccat  18554

atttcaattt gttataaatt cctataattt atcctattag tagctaaaaa aagatgaatg  18614

tgaatcgaat cctaagagaa ttggatctga tccacaggac gggtgtggtc gccatgatcg  18674

cgtagtcgat agtggctcca agtagcgaag cgagcaggac tgggcggcgg ccaaagcggt  18734

cggacagtgc tccgagaacg ggtgcgcata gaaattgcat caacgcatat agcgctagca  18794

gcacgccata gtgactggcg atgctgtcgg aatggacgat atcccgcaag aggcccggca  18854

gtaccggcat aaccaagcct atgcctacag catccagggt gacggtgccg aggatgacga  18914

tgagcgcatt gttagatttc atacacggtg cctgactgcg ttagcaattt aactgtgata  18974

aactaccgca ttaaagcttt ttctttccaa tttttttttt ttcgtcatta taaaaatcat  19034

tacgaccgag attcccgggt aataactgat ataattaaat tgaagctcta atttgtgagt  19094

ttagtataca tgcatttact tataatacag ttttttagtt ttgctggccg catcttctca  19154

aatatgcttc ccagcctgct tttctgtaac gttcaccctc taccttagca tcccttccct  19214

ttgcaaatag tcctcttcca acaataataa tgtcagatcc tgtagagacc acatcatcca  19274

cggttctata ctgttgaccc aatgcgtctc ccttgtcatc taaacccaca ccgggtgtca  19334

taatcaacca atcgtaacct tcatctcttc cacccatgtc tctttgagca ataaagccga  19394

taacaaaatc tttgtcgctc ttcgcaatgt caacagtacc cttagtatat tctccagtag  19454

atagggagcc cttgcatgac aattctgcta acatcaaaag gcctctaggt tcctttgtta  19514

cttcttctgc cgcctgcttc aaaccgctaa caatacctgg gcccaccaca ccgtgtgcat  19574

tcgtaatgtc tgcccattct gctattctgt atacacccgc agagtactgc aatttgactg  19634

tattaccaat gtcagcaaat tttctgtctt cgaagagtaa aaaattgtac ttggcggata  19694

atgcctttag cggcttaact gtgccctcca tggaaaaatc agtcaagata tccacatgtg  19754

tttttagtaa acaaattttg ggacctaatg cttcaactaa ctccagtaat tccttggtgg  19814

tacgaacatc caatgaagca cacaagtttg tttgcttttc gtgcatgata ttaaatagct  19874

tggcagcaac aggactagga tgagtagcag cacgttcctt atatgtagct ttcgacatga  19934

tttatcttcg tttcctgcag gtttttgttc tgtgcagttg ggttaagaat actgggcaat  19994

ttcatgtttc ttcaacacta catatgcgta tatataccaa tctaagtctg tgctccttcc  20054

ttcgttcttc cttctgttcg gagattaccg aatcaaaaaa atttcaagga aaccgaaatc  20114

aaaaaaaaga ataaaaaaaa aatgatgaat tgaaaagctt atcgat                 20160
```

<210> SEQ ID NO 13
<211> LENGTH: 1892
<212> TYPE: PRT
<213> ORGANISM: Artificial Sequence
<220> FEATURE:
<223> OTHER INFORMATION: Description of Artificial Sequence:

-continued pd.delta.NS3NS5.pj.core121

<400> SEQUENCE: 13

```
Met Ala Ala Tyr Ala Ala Gln Gly Tyr Lys Val Leu Val Leu Asn Pro
  1               5                  10                  15

Ser Val Ala Ala Thr Leu Gly Phe Gly Ala Tyr Met Ser Lys Ala His
             20                  25                  30

Gly Ile Asp Pro Asn Ile Arg Thr Gly Val Arg Thr Ile Thr Thr Gly
         35                  40                  45

Ser Pro Ile Thr Tyr Ser Thr Tyr Gly Lys Phe Leu Ala Asp Gly Gly
     50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
    370                 375                 380

Leu Tyr Arg Leu Gly Ala Val Gln Asn Glu Ile Thr Leu Thr His Pro
385                 390                 395                 400
```

-continued

```
Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
        435                 440                 445

Ser Gly Lys Pro Ala Ile Ile Pro Asp Arg Glu Val Leu Tyr Arg Glu
    450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
```

-continued

```
            820                 825                 830

Leu Pro Ala Pro Asn Tyr Thr Phe Ala Leu Trp Arg Val Ser Ala Glu
        835                 840                 845

Glu Tyr Val Glu Ile Arg Gln Val Gly Asp Phe His Tyr Val Thr Gly
    850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
    930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu Asp
   1010                 1015                1020

Glu  Arg Glu Ile Ser Val  Pro Ala Glu Ile Leu  Arg Lys Ser Arg Arg
1025                 1030                 1035                 1040

Phe Ala Gln Ala Leu  Pro Val Trp Ala Arg  Pro Asp Tyr Asn Pro  Pro
                1045                 1050                 1055

Leu Val Glu Thr  Trp Lys Lys Pro Asp  Tyr Glu Pro Pro Val  Val His
            1060                 1065                 1070

Gly Cys Pro  Leu Pro Pro Pro Lys  Ser Pro Pro Val Pro  Pro Pro Arg
        1075                 1080                 1085

Lys Lys  Arg Thr Val Val Leu  Thr Glu Ser Thr Leu  Ser Thr Ala Leu
    1090                 1095                 1100

Ala  Glu Leu Ala Thr Arg  Ser Phe Gly Ser Ser  Ser Thr Ser Gly Ile
1105                 1110                 1115                 1120

Thr Gly Asp Asn Thr  Thr Thr Ser Ser Glu  Pro Ala Pro Ser Gly  Cys
                1125                 1130                 1135

Pro Pro Asp Ser  Asp Ala Glu Ser Tyr  Ser Ser Met Pro Pro  Leu Glu
            1140                 1145                 1150

Gly Glu Pro  Gly Asp Pro Asp Leu  Ser Asp Gly Ser Trp  Ser Thr Val
        1155                 1160                 1165

Ser Ser  Glu Ala Asn Ala Glu  Asp Val Val Cys Cys  Ser Met Ser Tyr
    1170                 1175                 1180

Ser  Trp Thr Gly Ala Leu  Val Thr Pro Cys Ala  Ala Glu Glu Gln Lys
1185                 1190                 1195                 1200

Leu Pro Ile Asn Ala  Leu Ser Asn Ser Leu  Leu Arg His His Asn  Leu
                1205                 1210                 1215

Val Tyr Ser Thr  Thr Ser Arg Ser Ala  Cys Gln Arg Gln Lys  Lys Val
            1220                 1225                 1230

Thr Phe Asp  Arg Leu Gln Val Leu  Asp Ser His Tyr Gln  Asp Val Leu
        1235                 1240                 1245
```

-continued

```
Lys Glu  Val Lys Ala Ala Ala  Ser Lys Val Lys Ala  Asn Leu Leu Ser
    1250                 1255                 1260

Val  Glu Glu Ala Cys Ser  Leu Thr Pro Pro His  Ser Ala Lys Ser Lys
1265                 1270                 1275                 1280

Phe Gly Tyr Gly Ala  Lys Asp Val Arg Cys  His Ala Arg Lys Ala  Val
                1285                 1290                 1295

Thr His Ile Asn  Ser Val Trp Lys Asp  Leu Leu Glu Asp Asn  Val Thr
            1300                 1305                 1310

Pro Ile Asp  Thr Thr Ile Met Ala  Lys Asn Glu Val Phe  Cys Val Gln
        1315                 1320                 1325

Pro Glu  Lys Gly Gly Arg Lys  Pro Ala Arg Leu Ile  Val Phe Pro Asp
    1330                 1335                 1340

Leu  Gly Val Arg Val Cys  Glu Lys Met Ala Leu  Tyr Asp Val Val Thr
1345                 1350                 1355                 1360

Lys Leu Pro Leu Ala  Val Met Gly Ser Ser  Tyr Gly Phe Gln Tyr  Ser
                1365                 1370                 1375

Pro Gly Gln Arg  Val Glu Phe Leu Val  Gln Ala Trp Lys Ser  Lys Lys
            1380                 1385                 1390

Thr Pro Met  Gly Phe Ser Tyr Asp  Thr Arg Cys Phe Asp  Ser Thr Val
        1395                 1400                 1405

Thr Glu  Ser Asp Ile Arg Thr  Glu Glu Ala Ile Tyr  Gln Cys Cys Asp
    1410                 1415                 1420

Leu  Asp Pro Gln Ala Arg  Val Ala Ile Lys Ser  Leu Thr Glu Arg Leu
1425                 1430                 1435                 1440

Tyr Val Gly Gly Pro  Leu Thr Asn Ser Arg  Gly Glu Asn Cys Gly  Tyr
                1445                 1450                 1455

Arg Arg Cys Arg  Ala Ser Gly Val Leu  Thr Thr Ser Cys Gly  Asn Thr
            1460                 1465                 1470

Leu Thr Cys  Tyr Ile Lys Ala Arg  Ala Ala Cys Arg Ala  Ala Gly Leu
        1475                 1480                 1485

Gln Asp  Cys Thr Met Leu Val  Cys Gly Asp Asp Leu  Val Val Ile Cys
    1490                 1495                 1500

Glu  Ser Ala Gly Val Gln  Glu Asp Ala Ala Ser  Leu Arg Ala Phe Thr
1505                 1510                 1515                 1520

Glu Ala Met Thr Arg  Tyr Ser Ala Pro Pro  Gly Asp Pro Pro Gln  Pro
                1525                 1530                 1535

Glu Tyr Asp Leu  Glu Leu Ile Thr Ser  Cys Ser Ser Asn Val  Ser Val
            1540                 1545                 1550

Ala His Asp  Gly Ala Gly Lys Arg  Val Tyr Tyr Leu Thr  Arg Asp Pro
        1555                 1560                 1565

Thr Thr  Pro Leu Ala Arg Ala  Ala Trp Glu Thr Ala  Arg His Thr Pro
    1570                 1575                 1580

Val  Asn Ser Trp Leu Gly  Asn Ile Ile Met Phe  Ala Pro Thr Leu Trp
1585                 1590                 1595                 1600

Ala Arg Met Ile Leu  Met Thr His Phe Phe  Ser Val Leu Ile Ala Arg
                1605                 1610                 1615

Asp Gln Leu Glu  Gln Ala Leu Asp Cys  Glu Ile Tyr Gly Ala  Cys Tyr
            1620                 1625                 1630

Ser Ile Glu  Pro Leu Asp Leu Pro  Pro Ile Ile Gln Arg  Leu His Gly
        1635                 1640                 1645

Leu Ser  Ala Phe Ser Leu His  Ser Tyr Ser Pro Gly  Glu Ile Asn Arg
    1650                 1655                 1660
```

-continued

```
Val  Ala Ala Cys Leu Arg  Lys Leu Gly Val Pro  Pro Leu Arg Ala Trp
1665                1670                1675                1680

Arg His Arg Ala Arg  Ser Val Arg Ala Arg  Leu Leu Ala Arg Gly  Gly
                1685                1690                1695

Arg Ala Ala Ile  Cys Gly Lys Tyr Leu  Phe Asn Trp Ala Val  Arg Thr
            1700                1705                1710

Lys Leu Lys  Leu Thr Pro Ile Ala  Ala Ala Gly Gln Leu  Asp Leu Ser
        1715                1720                1725

Gly Trp  Phe Thr Ala Gly Tyr  Ser Gly Gly Asp Ile  Tyr His Ser Val
    1730                1735                1740

Ser  His Ala Arg Pro Arg  Trp Ile Trp Phe Cys  Leu Leu Leu Leu Ala
1745                1750                1755                1760

Ala Gly Val Gly Ile  Tyr Leu Leu Pro Asn  Arg Met Ser Thr Asn  Pro
                1765                1770                1775

Lys Pro Gln Arg  Lys Thr Lys Arg Asn  Thr Asn Arg Arg Pro  Gln Asp
            1780                1785                1790

Val Lys Phe  Pro Gly Gly Gly Gln  Ile Val Gly Gly Val  Tyr Leu Leu
        1795                1800                1805

Pro Arg  Arg Gly Pro Arg Leu  Gly Val Arg Ala Thr  Arg Lys Thr Ser
    1810                1815                1820

Glu  Arg Ser Gln Pro Arg  Gly Arg Arg Gln Pro  Ile Pro Lys Ala Arg
1825                1830                1835                1840

Arg Pro Glu Gly Arg  Thr Trp Ala Gln Pro  Gly Tyr Pro Trp Pro  Leu
                1845                1850                1855

Tyr Gly Asn Glu  Gly Cys Gly Trp Ala  Gly Trp Leu Leu Ser  Pro Arg
            1860                1865                1870

Gly Ser Arg  Pro Ser Trp Gly Pro  Thr Asp Pro Arg Arg  Arg Ser Arg
        1875                1880                1885

Asn Leu  Gly Lys
    1890
```

<210> SEQ ID NO 14
<211> LENGTH: 20316
<212> TYPE: DNA
<213> ORGANISM: Artificial Sequence
<220> FEATURE:
<223> OTHER INFORMATION: Description of Artificial Sequence:
pd.delta.NS3NS5.pj.core173
<221> NAME/KEY: CDS
<222> LOCATION: (12679)..(18510)

<400> SEQUENCE: 14

```
atcgatccta ccccttgcgc taaagaagta tatgtgccta ctaacgcttg tctttgtctc     60

tgtcactaaa cactggatta ttactcccag atacttattt tggactaatt taaatgattt    120

cggatcaacg ttcttaatat cgctgaatct tccacaattg atgaaagtag ctaggaagag    180

gaattggtat aaagtttttg tttttgtaaa tctcgaagta tactcaaacg aatttagtat    240

tttctcagtg atctcccaga tgctttcacc ctcacttaga agtgctttaa gcattttttt    300

actgtggcta tttcccttat ctgcttcttc cgatgattcg aactgtaatt gcaaactact    360

tacaatatca gtgatatcag attgatgttt ttgtccatag taaggaataa ttgtaaattc    420

ccaagcagga atcaatttct ttaatgaggc ttccagaatt gttgcttttt gcgtcttgta    480

tttaaactgg agtgatttat tgacaatatc gaaactcagc gaattgctta tgatagtatt    540

atagctcatg aatgtggctc tcttgattgc tgttccgtta tgtgtaatca tccaacataa    600

ataggttagt tcagcagcac ataatgctat tttctcacct gaaggtcttt caaacctttc    660
```

-continued

```
cacaaactga cgaacaagca ccttaggtgg tgttttacat aatatatcaa attgtggcat    720
gcttagcgcc gatcttgtgt gcaattgata tctagtttca actactctat ttatcttgta    780
tcttgcagta ttcaaacacg ctaactcgaa aaactaactt taattgtcct gtttgtctcg    840
cgttctttcg aaaaatgcac cggccgcgca ttatttgtac tgcgaaaata attggtactg    900
cggtatcttc atttcatatt ttaaaaatgc acctttgctg cttttcctta atttttagac    960
ggcccgcagg ttcgttttgc ggtactatct tgtgataaaa agttgttttg acatgtgatc   1020
tgcacagatt ttataatgta ataagcaaga atacattatc aaacgaacaa tactggtaaa   1080
agaaaaccaa aatggacgac attgaaacag ccaagaatct gacggtaaaa gcacgtacag   1140
cttatagcgt ctgggatgta tgtcggctgt ttattgaaat gattgctcct gatgtagata   1200
ttgatataga gagtaaacgt aagtctgatg agctactctt tccaggatat gtcataaggc   1260
ccatggaatc tctcacaacc ggtaggccgt atggtcttga ttctagcgca gaagattcca   1320
gcgtatcttc tgactccagt gctgaggtaa ttttgcctgc tgcgaagatg gttaaggaaa   1380
ggtttgattc gattggaaat ggtatgctct cttcacaaga agcaagtcag gctgccatag   1440
atttgatgct acagaataac aagctgttag acaatagaaa gcaactatac aaatctattg   1500
ctataataat aggaagattg cccgagaaag acaagaagag agctaccgaa atgctcatga   1560
gaaaaatgga ttgtacacag ttattagtcc caccagctcc aacggaagaa gatgttatga   1620
agctcgtaag cgtcgttacc caattgctta ctttagttcc accagatcgt caagctgctt   1680
taataggtga tttattcatc ccggaatctc taaaggatat attcaatagt ttcaatgaac   1740
tggcggcaga gaatcgttta cagcaaaaaa agagtgagtt ggaaggaagg actgaagtga   1800
accatgctaa tacaaatgaa gaagttccct ccaggcgaac aagaagtaga gacacaaatg   1860
caagaggagc atataaatta caaaacacca tcactgaggg ccctaaagcg gttcccacga   1920
aaaaaaggag agtagcaacg agggtaaggg gcagaaaatc acgtaatact tctagggtat   1980
gatccaatat caaaggaaat gatagcattg aaggatgaga ctaatccaat tgaggagtgg   2040
cagcatatag aacagctaaa gggtagtgct gaaggaagca tacgataccc cgcatggaat   2100
gggataatat cacaggaggt actagactac ctttcatcct acataaatag acgcatataa   2160
gtacgcattt aagcataaac acgcactatg ccgttcttct catgtatata tatatacagg   2220
caacacgcag atataggtgc gacgtgaaca gtgagctgta tgtgcgcagc tcgcgttgca   2280
ttttcggaag cgctcgtttt cggaaacgct ttgaagttcc tattccgaag ttcctattct   2340
ctagaaagta taggaacttc agagcgcttt tgaaaaccaa aagcgctctg aagacgcact   2400
ttcaaaaaac caaaaacgca ccggactgta acgagctact aaaatattgc gaataccgct   2460
tccacaaaca ttgctcaaaa gtatctcttt gctatatatc tctgtgctat atccctatat   2520
aacctaccca tccacctttc gctccttgaa cttgcatcta aactcgacct ctacatcaac   2580
aggcttccaa tgctcttcaa attttactgt caagtagacc catacggctg taatatgctg   2640
ctcttcataa tgtaagctta tctttatcga atcgtgtgaa aaactactac cgcgataaac   2700
ctttacggtt ccctgagatt gaattagttc ctttagtata tgatacaaga cacttttgaa   2760
ctttgtacga cgaattttga ggttcgccat cctctggcta tttccaatta tcctgtcggc   2820
tattatctcc gcctcagttt gatcttccgc ttcagactgc catttttcac ataatgaatc   2880
tatttcaccc cacaatcctt catccgcctc cgcatcttgt tccgttaaac tattgacttc   2940
atgttgtaca ttgtttagtt cacgagaagg gtcctcttca ggcggtagct cctgatctcc   3000
```

-continued

```
tatatgacct ttatcctgtt ctctttccac aaacttagaa atgtattcat gaattatgga   3060
gcacctaata acattcttca aggcggagaa gtttgggcca gatgcccaat atgcttgaca   3120
tgaaaacgtg agaatgaatt tagtattatt gtgatattct gaggcaattt tattataatc   3180
tcgaagataa gagaagaatg cagtgacctt tgtattgaca aatggagatt ccatgtatct   3240
aaaaaatacg cctttaggcc ttctgatacc ctttcccctg cggtttagcg tgccttttac   3300
attaatatct aaaccctctc cgatggtggc ctttaactga ctaataaatg caaccgatat   3360
aaactgtgat aattctgggt gatttatgat tcgatcgaca attgtattgt acactagtgc   3420
aggatcaggc caatccagtt ctttttcaat taccggtgtg tcgtctgtat tcagtacatg   3480
tccaacaaat gcaaatgcta acgttttgta tttcttataa ttgtcaggaa ctggaaaagt   3540
ccccttgtc gtctcgatta cacacctact ttcatcgtac accataggtt ggaagtgctg   3600
cataatacat tgcttaatac aagcaagcag tctctcgcca ttcatatttc agttattttc   3660
cattacagct gatgtcattg tatatcagcg ctgtaaaaat ctatctgtta cagaaggttt   3720
tcgcggtttt tataaacaaa actttcgtta cgaaatcgag caatcacccc agctgcgtat   3780
ttggaaattc gggaaaaagt agagcaacgc gagttgcatt ttttacacca taatgcatga   3840
ttaacttcga gaagggatta aggctaattt cactagtatg tttcaaaaac ctcaatctgt   3900
ccattgaatg ccttataaaa cagctataga ttgcatagaa gagttagcta ctcaatgctt   3960
tttgtcaaag cttactgatg atgatgtgtc tactttcagg cgggtctgta gtaaggagaa   4020
tgacattata aagctggcac ttagaattcc acggactata gactatacta gtatactccg   4080
tctactgtac gatacacttc cgctcaggtc cttgtccttt aacgaggcct taccactctt   4140
ttgttactct attgatccag ctcagcaaag gcagtgtgat ctaagattct atcttcgcga   4200
tgtagtaaaa ctagctagac cgagaaagag actagaaatg caaaaggcac ttctacaatg   4260
gctgccatca ttattatccg atgtgacgct gcattttttt tttttttttt tttttttttt   4320
tttttttttt tttttttttt ttttttggta caaatatcat aaaaaaagag aatcttttta   4380
agcaaggatt ttcttaactt cttcggcgac agcatcaccg acttcggtgg tactgttgga   4440
accacctaaa tcaccagttc tgatacctgc atccaaaacc tttttaactg catcttcaat   4500
ggctttacct tcttcaggca agttcaatga caatttcaac atcattgcag cagacaagat   4560
agtggcgata gggttgacct tattctttgg caaatctgga gcggaaccat ggcatggttc   4620
gtacaaacca aatgcggtgt tcttgtctgg caaagaggcc aaggacgcag atggcaacaa   4680
acccaaggag cctgggataa cggaggcttc atcggagatg atatcaccaa acatgttgct   4740
ggtgattata ataccattta ggtgggttgg gttcttaact aggatcatgg cggcagaatc   4800
aatcaattga tgttgaactt tcaatgtagg gaattcgttc ttgatggttt cctccacagt   4860
ttttctccat aatcttgaag aggccaaaac attagcttta tccaaggacc aaataggcaa   4920
tggtggctca tgttgtaggg ccatgaaagc ggccattctt gtgattcttt gcacttctgg   4980
aacggtgtat tgttcactat cccaagcgac accatcacca tcgtcttcct ttctcttacc   5040
aaagtaaata cctcccacta attctctaac aacaacgaag tcagtacctt tagcaaattg   5100
tggcttgatt ggagataagt ctaaaagaga gtcggatgca aagttacatg gtcttaagtt   5160
ggcgtacaat tgaagttctt tacggatttt tagtaaacct tgttcaggtc taacactacc   5220
ggtaccccat ttaggaccac ccacagcacc taacaaaacg gcatcagcct tcttggaggc   5280
ttccagcgcc tcatctggaa gtggaacacc tgtagcatcg atagcagcac caccaattaa   5340
atgattttcg aaatcgaact tgacattgga acgaacatca gaaatagctt taagaacctt   5400
```

-continued

```
aatggcttcg gctgtgattt cttgaccaac gtggtcacct ggcaaaacga cgatcttctt   5460
aggggcagac attacaatgg tatatccttg aaatatatat aaaaaaaaaa aaaaaaaaaa   5520
aaaaaaaaaa atgcagcttc tcaatgatat tcgaatacgc tttgaggaga tacagcctaa   5580
tatccgacaa actgttttac agatttacga tcgtacttgt tacccatcat tgaattttga   5640
acatccgaac ctgggagttt tccctgaaac agatagtata tttgaacctg tataataata   5700
tatagtctag cgctttacgg aagacaatgt atgtatttcg gttcctggag aaactattgc   5760
atctattgca taggtaatct tgcacgtcgc atccccggtt cattttctgc gtttccatct   5820
tgcacttcaa tagcatatct ttgttaacga agcatctgtg cttcattttg tagaacaaaa   5880
atgcaacgcg agagcgctaa tttttcaaac aaagaatctg agctgcattt ttacagaaca   5940
gaaatgcaac gcgaaagcgc tattttacca acgaagaatc tgtgcttcat ttttgtaaaa   6000
caaaaatgca acgcgagagc gctaattttt caaacaaaga atctgagctg catttttaca   6060
gaacagaaat gcaacgcgag agcgctattt taccaacaaa gaatctatac ttcttttttg   6120
ttctacaaaa atgcatcccg agagcgctat ttttctaaca aagcatctta gattactttt   6180
tttctccttt gtgcgctcta taatgcagtc tcttgataac tttttgcact gtaggtccgt   6240
taaggttaga agaaggctac tttggtgtct attttctctt ccataaaaaa agcctgactc   6300
cacttcccgc gtttactgat tactagcgaa gctgcgggtg cattttttca agataaaggc   6360
atccccgatt atattctata ccgatgtgga ttgcgcatac tttgtgaaca gaaagtgata   6420
gcgttgatga ttcttcattg gtcagaaaat tatgaacggt ttcttctatt ttgtctctat   6480
atactacgta taggaaatgt ttacattttc gtattgtttt cgattcactc tatgaatagt   6540
tcttactaca atttttttgt ctaaagagta atactagaga taaacataaa aaatgtagag   6600
gtcgagttta gatgcaagtt caaggagcga aaggtggatg ggtaggttat atagggatat   6660
agcacagaga tatatagcaa agagatactt ttgagcaatg tttgtggaag cggtattcgc   6720
aatattttag tagctcgtta cagtccggtg cgtttttggt tttttgaaag tgcgtcttca   6780
gagcgctttt ggttttcaaa agcgctctga agttcctata ctttctagag aataggaact   6840
tcggaatagg aacttcaaag cgtttccgaa aacgagcgct tccgaaaatg caacgcgagc   6900
tgcgcacata cagctcactg ttcacgtcgc acctatatct gcgtgttgcc tgtatatata   6960
tatacatgag aagaacggca tagtgcgtgt ttatgcttaa atgcgtactt atatgcgtct   7020
atttatgtag gatgaaaggt agtctagtac ctcctgtgat attatcccat tccatgcggg   7080
gtatcgtatg cttccttcag cactaccctt tagctgttct atatgctgcc actcctcaat   7140
tggattagtc tcatccttca atgctatcat ttcctttgat attggatcat atgcatagta   7200
ccgagaaact agtgcgaagt agtgatcagg tattgctgtt atctgatgag tatacgttgt   7260
cctggccacg gcagaagcac gcttatcgct ccaatttccc acaacattag tcaactccgt   7320
taggcccttc attgaaagaa atgaggtcat caaatgtctt ccaatgtgag attttgggcc   7380
attttttata gcaaagattg aataaggcgc atttttcttc aaagctttat tgtacgatct   7440
gactaagtta tcttttaata attggtattc ctgtttattg cttgaagaat tgccggtcct   7500
atttactcgt tttaggactg gttcagaatt cctcaaaaat tcatccaaat atacaagtgg   7560
atcgatgata agctgtcaaa catgagaatt cttgaagacg aaagggcctc gtgatacgcc   7620
tatttttata ggttaatgtc atgataataa tggtttctta gacgtcaggt ggcacttttc   7680
ggggaaatgt gcgcggaacc cctatttgtt tatttttcta aatacattca aatatgtatc   7740
```

-continued

```
cgctcatgag acaataaccc tgataaatgc ttcaataata ttgaaaaagg aagagtatga   7800
gtattcaaca tttccgtgtc gcccttattc ccttttttgc ggcattttgc cttcctgttt   7860
ttgctcaccc agaaacgctg gtgaaagtaa aagatgctga agatcagttg ggtgcacgag   7920
tgggttacat cgaactggat ctcaacagcg gtaagatcct tgagagtttt cgccccgaag   7980
aacgttttcc aatgatgagc acttttaaag ttctgctatg tggcgcggta ttatcccgtg   8040
ttgacgccgg gcaagagcaa ctcggtcgcc gcatacacta ttctcagaat gacttggttg   8100
agtactcacc agtcacagaa aagcatctta cggatggcat gacagtaaga gaattatgca   8160
gtgctgccat aaccatgagt gataacactg cggccaactt acttctgaca acgatcggag   8220
gaccgaagga gctaaccgct tttttgcaca acatggggga tcatgtaact cgccttgatc   8280
gttgggaacc ggagctgaat gaagccatac caaacgacga gcgtgacacc acgatgcctg   8340
cagcaatggc aacaacgttg cgcaaactat taactggcga actacttact ctagcttccc   8400
ggcaacaatt aatagactgg atggaggcgg ataaagttgc aggaccactt ctgcgctcgg   8460
cccttccggc tggctggttt attgctgata aatctggagc cggtgagcgt gggtctcgcg   8520
gtatcattgc agcactgggg ccagatggta agccctcccg tatcgtagtt atctacacga   8580
cggggagtca ggcaactatg gatgaacgaa atagacagat cgctgagata ggtgcctcac   8640
tgattaagca ttggtaactg tcagaccaag tttactcata tatactttag attgatttaa   8700
aacttcattt ttaatttaaa aggatctagg tgaagatcct ttttgataat ctcatgacca   8760
aaatccctta acgtgagttt tcgttccact gagcgtcaga ccccgtagaa aagatcaaag   8820
gatcttcttg agatcctttt tttctgcgcg taatctgctg cttgcaaaca aaaaaaccac   8880
cgctaccagc ggtggtttgt ttgccggatc aagagctacc aactcttttt ccgaaggtaa   8940
ctggcttcag cagagcgcag ataccaaata ctgtccttct agtgtagccg tagttaggcc   9000
accacttcaa gaactctgta gcaccgccta catacctcgc tctgctaatc ctgttaccag   9060
tggctgctgc cagtggcgat aagtcgtgtc ttaccgggtt ggactcaaga cgatagttac   9120
cggataaggc gcagcggtcg ggctgaacgg ggggttcgtg cacacagccc agcttggagc   9180
gaacgaccta caccgaactg agatacctac agcgtgagct atgagaaagc gccacgcttc   9240
ccgaagggag aaaggcggac aggtatccgg taagcggcag ggtcggaaca ggagagcgca   9300
cgagggagct tccaggggga aacgcctggt atctttatag tcctgtcggg tttcgccacc   9360
tctgacttga gcgtcgattt ttgtgatgct cgtcaggggg gcggagccta tggaaaaacg   9420
ccagcaacgc ggccttttta cggttcctgg ccttttgctg gccttttgct cacatgttct   9480
ttcctgcgtt atcccctgat tctgtggata accgtattac cgcctttgag tgagctgata   9540
ccgctcgccg cagccgaacg accgagcgca gcgagtcagt gagcgaggaa gcggaagagc   9600
gcctgatgcg gtattttctc cttacgcatc tgtgcggtat ttcacaccgc atatggtgca   9660
ctctcagtac aatctgctct gatgccgcat agttaagcca gtatacactc cgctatcgct   9720
acgtgactgg gtcatggctg cgccccgaca cccgccaaca cccgctgacg cgccctgacg   9780
ggcttgtctg ctcccggcat ccgcttacag acaagctgtg accgtctccg ggagctgcat   9840
gtgtcagagg ttttcaccgt catcaccgaa acgcgcgagg cagctgcggt aaagctcatc   9900
agcgtggtcg tgaagcgatt cacagatgtc tgcctgttca tccgcgtcca gctcgttgag   9960
tttctccaga agcgttaatg tctggcttct gataaagcgg gccatgttaa gggcggtttt  10020
ttcctgtttg gtcactgatg cctccgtgta agggggattt ctgttcatgg gggtaatgat  10080
accgatgaaa cgagagagga tgctcacgat acgggttact gatgatgaac atgcccggtt  10140
```

-continued

```
actggaacgt tgtgagggta aacaactggc ggtatggatg cggcgggacc agagaaaaat  10200
cactcagggt caatgccagc gcttcgttaa tacagatgta ggtgttccac agggtagcca  10260
gcagcatcct gcgatgcaga tccggaacat aatggtgcag ggcgctgact tccgcgtttc  10320
cagactttac gaaacacgga aaccgaagac cattcatgtt gttgctcagg tcgcagacgt  10380
tttgcagcag cagtcgcttc acgttcgctc gcgtatcggt gattcattct gctaaccagt  10440
aaggcaaccc cgccagccta gccgggtcct caacgacagg agcacgatca tgcgcacccg  10500
tggccaggac ccaacgctgc ccgagatgcg ccgcgtgcgg ctgctggaga tggcggacgc  10560
gatggatatg ttctgccaag ggttggtttg cgcattcaca gttctccgca agaattgatt  10620
ggctccaatt cttggagtgg tgaatccgtt agcgaggtgc cgccggcttc cattcaggtc  10680
gaggtggccc ggctccatgc accgcgacgc aacgcgggga ggcagacaag gtatagggcg  10740
gcgcctacaa tccatgccaa cccgttccat gtgctcgccg aggcggcata aatcgccgtg  10800
acgatcagcg gtccaatgat cgaagttagg ctggtaagag ccgcgagcga tccttgaagc  10860
tgtccctgat ggtcgtcatc tacctgcctg gacagcatgg cctgcaacgc gggcatcccg  10920
atgccgccgg aagcgagaag aatcataatg gggaaggcca tccagcctcg cgtcgcgaac  10980
gccagcaaga cgtagcccag cgcgtcggcc gccatgccgg cgataatggc ctgcttctcg  11040
ccgaaacgtt tggtggcggg accagtgacg aaggcttgag cgagggcgtg caagattccg  11100
aataccgcaa gcgacaggcc gatcatcgtc gcgctccagc gaaagcggtc ctcgccgaaa  11160
atgacccaga gcgctgccgg cacctgtcct acgagttgca tgataaagaa gacagtcata  11220
agtgcggcga cgatagtcat gccccgcgcc caccggaagg agctgactgg gttgaaggct  11280
ctcaagggca tcggtcgagg atccttcaat atgcgcacat acgctgttat gttcaaggtc  11340
ccttcgttta agaacgaaag cggtcttcct tttgagggat gtttcaagtt gttcaaatct  11400
atcaaatttg caaatcccca gtctgtatct agagcgttga atcggtgatg cgatttgtta  11460
attaaattga tggtgtcacc attaccaggt ctagatatac caatggcaaa ctgagcacaa  11520
caataccagt ccggatcaac tggcaccatc tctcccgtag tctcatctaa tttttcttcc  11580
ggatgaggtt ccagatatac cgcaacacct ttattatggt ttccctgagg gaataataga  11640
atgtcccatt cgaaatcacc aattctaaac ctgggcgaat tgtatttcgg gtttgttaac  11700
tcgttccagt caggaatgtt ccacgtgaag ctatcttcca gcaaagtctc cacttcttca  11760
tcaaattgtg gagaatactc ccaatgctct tatctatggg acttccggga aacacagtac  11820
cgatacttcc caattcgtct tcagagctca ttgtttgttt gaagagacta atcaaagaat  11880
cgttttctca aaaaaattaa tatcttaact gatagtttga tcaaaggggc aaaacgtagg  11940
ggcaaacaaa cggaaaaatc gtttctcaaa ttttctgatg ccaagaactc taaccagtct  12000
tatctaaaaa ttgccttatg atccgtctct ccggttacag cctgtgtaac tgattaatcc  12060
tgcctttcta atcaccattc taatgtttta attaagggat tttgtcttca ttaacggctt  12120
tcgctcataa aaatgttatg acgttttgcc cgcaggcggg aaaccatcca cttcacgaga  12180
ctgatctcct ctgccggaac accgggcatc tccaacttat aagttggaga aataagagaa  12240
tttcagattg agagaatgaa aaaaaaaaac ccttagttca taggtccatt ctcttagcgc  12300
aactacagag aacaggggca caaacaggca aaaaacgggc acaacctcaa tggagtgatg  12360
caacctgcct ggagtaaatg atgacacaag gcaattgacc cacgcatgta tctatctcat  12420
tttcttacac cttctattac cttctgctct ctctgatttg gaaaaagctg aaaaaaaagg  12480
```

-continued

```
ttgaaaccag ttccctgaaa ttattcccct acttgactaa taagtatata aagacggtag  12540

gtattgattg taattctgta aatctatttc ttaaacttct taaattctac ttttatagtt  12600

agtctttttt ttagttttaa aacaccaaga acttagtttc gaataaacac acataaacaa  12660

acaagcttac aaaacaaa atg gct gca tat gca gct cag ggc tat aag gtg    12711
                    Met Ala Ala Tyr Ala Ala Gln Gly Tyr Lys Val
                     1               5                  10

cta gta ctc aac ccc tct gtt gct gca aca ctg ggc ttt ggt gct tac    12759
Leu Val Leu Asn Pro Ser Val Ala Ala Thr Leu Gly Phe Gly Ala Tyr
            15                  20                  25

atg tcc aag gct cat ggg atc gat cct aac atc agg acc ggg gtg aga    12807
Met Ser Lys Ala His Gly Ile Asp Pro Asn Ile Arg Thr Gly Val Arg
        30                  35                  40

aca att acc act ggc agc ccc atc acg tac tcc acc tac ggc aag ttc    12855
Thr Ile Thr Thr Gly Ser Pro Ile Thr Tyr Ser Thr Tyr Gly Lys Phe
    45                  50                  55

ctt gcc gac ggc ggg tgc tcg ggg ggc gct tat gac ata ata att tgt    12903
Leu Ala Asp Gly Gly Cys Ser Gly Gly Ala Tyr Asp Ile Ile Ile Cys
 60                  65                  70                  75

gac gag tgc cac tcc acg gat gcc aca tcc atc ttg ggc att ggc act    12951
Asp Glu Cys His Ser Thr Asp Ala Thr Ser Ile Leu Gly Ile Gly Thr
                80                  85                  90

gtc ctt gac caa gca gag act gcg ggg gcg aga ctg gtt gtg ctc gcc    12999
Val Leu Asp Gln Ala Glu Thr Ala Gly Ala Arg Leu Val Val Leu Ala
            95                 100                 105

acc gcc acc cct ccg ggc tcc gtc act gtg ccc cat ccc aac atc gag    13047
Thr Ala Thr Pro Pro Gly Ser Val Thr Val Pro His Pro Asn Ile Glu
        110                 115                 120

gag gtt gct ctg tcc acc acc gga gag atc cct ttt tac ggc aag gct    13095
Glu Val Ala Leu Ser Thr Thr Gly Glu Ile Pro Phe Tyr Gly Lys Ala
    125                 130                 135

atc ccc ctc gaa gta atc aag ggg ggg aga cat ctc atc ttc tgt cat    13143
Ile Pro Leu Glu Val Ile Lys Gly Gly Arg His Leu Ile Phe Cys His
140                 145                 150                 155

tca aag aag aag tgc gac gaa ctc gcc gca aag ctg gtc gca ttg ggc    13191
Ser Lys Lys Lys Cys Asp Glu Leu Ala Ala Lys Leu Val Ala Leu Gly
                160                 165                 170

atc aat gcc gtg gcc tac tac cgc ggt ctt gac gtg tcc gtc atc ccg    13239
Ile Asn Ala Val Ala Tyr Tyr Arg Gly Leu Asp Val Ser Val Ile Pro
            175                 180                 185

acc agc ggc gat gtt gtc gtc gtg gca acc gat gcc ctc atg acc ggc    13287
Thr Ser Gly Asp Val Val Val Val Ala Thr Asp Ala Leu Met Thr Gly
        190                 195                 200

tat acc ggc gac ttc gac tcg gtg ata gac tgc aat acg tgt gtc acc    13335
Tyr Thr Gly Asp Phe Asp Ser Val Ile Asp Cys Asn Thr Cys Val Thr
    205                 210                 215

cag aca gtc gat ttc agc ctt gac cct acc ttc acc att gag aca atc    13383
Gln Thr Val Asp Phe Ser Leu Asp Pro Thr Phe Thr Ile Glu Thr Ile
220                 225                 230                 235

acg ctc ccc caa gat gct gtc tcc cgc act caa cgt cgg ggc agg act    13431
Thr Leu Pro Gln Asp Ala Val Ser Arg Thr Gln Arg Arg Gly Arg Thr
                240                 245                 250

ggc agg ggg aag cca ggc atc tac aga ttt gtg gca ccg ggg gag cgc    13479
Gly Arg Gly Lys Pro Gly Ile Tyr Arg Phe Val Ala Pro Gly Glu Arg
            255                 260                 265

ccc tcc ggc atg ttc gac tcg tcc gtc ctc tgt gag tgc tat gac gca    13527
Pro Ser Gly Met Phe Asp Ser Ser Val Leu Cys Glu Cys Tyr Asp Ala
        270                 275                 280

ggc tgt gct tgg tat gag ctc acg ccc gcc gag act aca gtt agg cta    13575
```

-continued

```
Gly Cys Ala Trp Tyr Glu Leu Thr Pro Ala Glu Thr Thr Val Arg Leu
    285                 290                 295

cga gcg tac atg aac acc ccg ggg ctt ccc gtg tgc cag gac cat ctt    13623
Arg Ala Tyr Met Asn Thr Pro Gly Leu Pro Val Cys Gln Asp His Leu
300                 305                 310                 315

gaa ttt tgg gag ggc gtc ttt aca ggc ctc act cat ata gat gcc cac    13671
Glu Phe Trp Glu Gly Val Phe Thr Gly Leu Thr His Ile Asp Ala His
                320                 325                 330

ttt cta tcc cag aca aag cag agt ggg gag aac ctt cct tac ctg gta    13719
Phe Leu Ser Gln Thr Lys Gln Ser Gly Glu Asn Leu Pro Tyr Leu Val
            335                 340                 345

gcg tac caa gcc acc gtg tgc gct agg gct caa gcc cct ccc cca tcg    13767
Ala Tyr Gln Ala Thr Val Cys Ala Arg Ala Gln Ala Pro Pro Pro Ser
        350                 355                 360

tgg gac cag atg tgg aag tgt ttg att cgc ctc aag ccc acc ctc cat    13815
Trp Asp Gln Met Trp Lys Cys Leu Ile Arg Leu Lys Pro Thr Leu His
    365                 370                 375

ggg cca aca ccc ctg cta tac aga ctg ggc gct gtt cag aat gaa atc    13863
Gly Pro Thr Pro Leu Leu Tyr Arg Leu Gly Ala Val Gln Asn Glu Ile
380                 385                 390                 395

acc ctg acg cac cca gtc acc aaa tac atc atg aca tgc atg tcg gcc    13911
Thr Leu Thr His Pro Val Thr Lys Tyr Ile Met Thr Cys Met Ser Ala
                400                 405                 410

gac ctg gag gtc gtc acg agc acc tgg gtg ctc gtt ggc ggc gtc ctg    13959
Asp Leu Glu Val Val Thr Ser Thr Trp Val Leu Val Gly Gly Val Leu
            415                 420                 425

gct gct ttg gcc gcg tat tgc ctg tca aca ggc tgc gtg gtc ata gtg    14007
Ala Ala Leu Ala Ala Tyr Cys Leu Ser Thr Gly Cys Val Val Ile Val
        430                 435                 440

ggc agg gtc gtc ttg tcc ggg aag ccg gca atc ata cct gac agg gaa    14055
Gly Arg Val Val Leu Ser Gly Lys Pro Ala Ile Ile Pro Asp Arg Glu
    445                 450                 455

gtc ctc tac cga gag ttc gat gag atg gaa gag tgc tct cag cac tta    14103
Val Leu Tyr Arg Glu Phe Asp Glu Met Glu Glu Cys Ser Gln His Leu
460                 465                 470                 475

ccg tac atc gag caa ggg atg atg ctc gcc gag cag ttc aag cag aag    14151
Pro Tyr Ile Glu Gln Gly Met Met Leu Ala Glu Gln Phe Lys Gln Lys
                480                 485                 490

gcc ctc ggc ctc ctg cag acc gcg tcc cgt cag gca gag gtt atc gcc    14199
Ala Leu Gly Leu Leu Gln Thr Ala Ser Arg Gln Ala Glu Val Ile Ala
            495                 500                 505

cct gct gtc cag acc aac tgg caa aaa ctc gag acc ttc tgg gcg aag    14247
Pro Ala Val Gln Thr Asn Trp Gln Lys Leu Glu Thr Phe Trp Ala Lys
        510                 515                 520

cat atg tgg aac ttc atc agt ggg ata caa tac ttg gcg ggc ttg tca    14295
His Met Trp Asn Phe Ile Ser Gly Ile Gln Tyr Leu Ala Gly Leu Ser
    525                 530                 535

acg ctg cct ggt aac ccc gcc att gct tca ttg atg gct ttt aca gct    14343
Thr Leu Pro Gly Asn Pro Ala Ile Ala Ser Leu Met Ala Phe Thr Ala
540                 545                 550                 555

gct gtc acc agc cca cta acc act agc caa acc ctc ctc ttc aac ata    14391
Ala Val Thr Ser Pro Leu Thr Thr Ser Gln Thr Leu Leu Phe Asn Ile
                560                 565                 570

ttg ggg ggg tgg gtg gct gcc cag ctc gcc gcc ccc ggt gcc gct act    14439
Leu Gly Gly Trp Val Ala Ala Gln Leu Ala Ala Pro Gly Ala Ala Thr
            575                 580                 585

gcc ttt gtg ggc gct ggc tta gct ggc gcc gcc atc ggc agt gtt gga    14487
Ala Phe Val Gly Ala Gly Leu Ala Gly Ala Ala Ile Gly Ser Val Gly
        590                 595                 600
```

-continued

```
ctg ggg aag gtc ctc ata gac atc ctt gca ggg tat ggc gcg ggc gtg     14535
Leu Gly Lys Val Leu Ile Asp Ile Leu Ala Gly Tyr Gly Ala Gly Val
    605                 610                 615

gcg gga gct ctt gtg gca ttc aag atc atg agc ggt gag gtc ccc tcc     14583
Ala Gly Ala Leu Val Ala Phe Lys Ile Met Ser Gly Glu Val Pro Ser
620                 625                 630                 635

acg gag gac ctg gtc aat cta ctg ccc gcc atc ctc tcg ccc gga gcc     14631
Thr Glu Asp Leu Val Asn Leu Leu Pro Ala Ile Leu Ser Pro Gly Ala
                640                 645                 650

ctc gta gtc ggc gtg gtc tgt gca gca ata ctg cgc cgg cac gtt ggc     14679
Leu Val Val Gly Val Val Cys Ala Ala Ile Leu Arg Arg His Val Gly
            655                 660                 665

ccg ggc gag ggg gca gtg cag tgg atg aac cgg ctg ata gcc ttc gcc     14727
Pro Gly Glu Gly Ala Val Gln Trp Met Asn Arg Leu Ile Ala Phe Ala
        670                 675                 680

tcc cgg ggg aac cat gtt tcc ccc acg cac tac gtg ccg gag agc gat     14775
Ser Arg Gly Asn His Val Ser Pro Thr His Tyr Val Pro Glu Ser Asp
    685                 690                 695

gca gct gcc cgc gtc act gcc ata ctc agc agc ctc act gta acc cag     14823
Ala Ala Ala Arg Val Thr Ala Ile Leu Ser Ser Leu Thr Val Thr Gln
700                 705                 710                 715

ctc ctg agg cga ctg cac cag tgg ata agc tcg gag tgt acc act cca     14871
Leu Leu Arg Arg Leu His Gln Trp Ile Ser Ser Glu Cys Thr Thr Pro
                720                 725                 730

tgc tcc ggt tcc tgg cta agg gac atc tgg gac tgg ata tgc gag gtg     14919
Cys Ser Gly Ser Trp Leu Arg Asp Ile Trp Asp Trp Ile Cys Glu Val
            735                 740                 745

ttg agc gac ttt aag acc tgg cta aaa gct aag ctc atg cca cag ctg     14967
Leu Ser Asp Phe Lys Thr Trp Leu Lys Ala Lys Leu Met Pro Gln Leu
        750                 755                 760

cct ggg atc ccc ttt gtg tcc tgc cag cgc ggg tat aag ggg gtc tgg     15015
Pro Gly Ile Pro Phe Val Ser Cys Gln Arg Gly Tyr Lys Gly Val Trp
    765                 770                 775

cga ggg gac ggc atc atg cac act cgc tgc cac tgt gga gct gag atc     15063
Arg Gly Asp Gly Ile Met His Thr Arg Cys His Cys Gly Ala Glu Ile
780                 785                 790                 795

act gga cat gtc aaa aac ggg acg atg agg atc gtc ggt cct agg acc     15111
Thr Gly His Val Lys Asn Gly Thr Met Arg Ile Val Gly Pro Arg Thr
                800                 805                 810

tgc agg aac atg tgg agt ggg acc ttc ccc att aat gcc tac acc acg     15159
Cys Arg Asn Met Trp Ser Gly Thr Phe Pro Ile Asn Ala Tyr Thr Thr
            815                 820                 825

ggc ccc tgt acc ccc ctt cct gcg ccg aac tac acg ttc gcg cta tgg     15207
Gly Pro Cys Thr Pro Leu Pro Ala Pro Asn Tyr Thr Phe Ala Leu Trp
        830                 835                 840

agg gtg tct gca gag gaa tac gtg gag ata agg cag gtg ggg gac ttc     15255
Arg Val Ser Ala Glu Glu Tyr Val Glu Ile Arg Gln Val Gly Asp Phe
    845                 850                 855

cac tac gtg acg ggt atg act act gac aat ctt aaa tgc ccg tgc cag     15303
His Tyr Val Thr Gly Met Thr Thr Asp Asn Leu Lys Cys Pro Cys Gln
860                 865                 870                 875

gtc cca tcg ccc gaa ttt ttc aca gaa ttg gac ggg gtg cgc cta cat     15351
Val Pro Ser Pro Glu Phe Phe Thr Glu Leu Asp Gly Val Arg Leu His
                880                 885                 890

agg ttt gcg ccc ccc tgc aag ccc ttg ctg cgg gag gag gta tca ttc     15399
Arg Phe Ala Pro Pro Cys Lys Pro Leu Leu Arg Glu Glu Val Ser Phe
            895                 900                 905

aga gta gga ctc cac gaa tac ccg gta ggg tcg caa tta cct tgc gag     15447
Arg Val Gly Leu His Glu Tyr Pro Val Gly Ser Gln Leu Pro Cys Glu
        910                 915                 920
```

-continued

```
ccc gaa ccg gac gtg gcc gtg ttg acg tcc atg ctc act gat ccc tcc     15495
Pro Glu Pro Asp Val Ala Val Leu Thr Ser Met Leu Thr Asp Pro Ser
    925                 930                 935

cat ata aca gca gag gcg gcc ggg cga agg ttg gcg agg gga tca ccc     15543
His Ile Thr Ala Glu Ala Ala Gly Arg Arg Leu Ala Arg Gly Ser Pro
940                 945                 950                 955

ccc tct gtg gcc agc tcc tcg gct agc cag cta tcc gct cca tct ctc     15591
Pro Ser Val Ala Ser Ser Ser Ala Ser Gln Leu Ser Ala Pro Ser Leu
                960                 965                 970

aag gca act tgc acc gct aac cat gac tcc cct gat gct gag ctc ata     15639
Lys Ala Thr Cys Thr Ala Asn His Asp Ser Pro Asp Ala Glu Leu Ile
            975                 980                 985

gag gcc aac ctc cta tgg agg cag gag atg ggc ggc aac atc acc agg     15687
Glu Ala Asn Leu Leu Trp Arg Gln Glu Met Gly Gly Asn Ile Thr Arg
        990                 995                1000

gtt gag tca gaa aac aaa gtg gtg att ctg gac tcc ttc gat ccg ctt     15735
Val Glu Ser Glu Asn Lys Val Val Ile Leu Asp Ser Phe Asp Pro Leu
   1005                1010                1015

gtg gcg gag gag gac gag cgg gag atc tcc gta ccc gca gaa atc ctg     15783
Val Ala Glu Glu Asp Glu Arg Glu Ile Ser Val Pro Ala Glu Ile Leu
1020                1025                1030                1035

cgg aag tct cgg aga ttc gcc cag gcc ctg ccc gtt tgg gcg cgg ccg     15831
Arg Lys Ser Arg Arg Phe Ala Gln Ala Leu Pro Val Trp Ala Arg Pro
               1040                1045                1050

gac tat aac ccc ccg cta gtg gag acg tgg aaa aag ccc gac tac gaa     15879
Asp Tyr Asn Pro Pro Leu Val Glu Thr Trp Lys Lys Pro Asp Tyr Glu
           1055                1060                1065

cca cct gtg gtc cat ggc tgc ccg ctt cca cct cca aag tcc cct cct     15927
Pro Pro Val Val His Gly Cys Pro Leu Pro Pro Pro Lys Ser Pro Pro
       1070                1075                1080

gtg cct ccg cct cgg aag aag cgg acg gtg gtc ctc act gaa tca acc     15975
Val Pro Pro Pro Arg Lys Lys Arg Thr Val Val Leu Thr Glu Ser Thr
   1085                1090                1095

cta tct act gcc ttg gcc gag ctc gcc acc aga agc ttt ggc agc tcc     16023
Leu Ser Thr Ala Leu Ala Glu Leu Ala Thr Arg Ser Phe Gly Ser Ser
1100                1105                1110                1115

tca act tcc ggc att acg ggc gac aat acg aca aca tcc tct gag ccc     16071
Ser Thr Ser Gly Ile Thr Gly Asp Asn Thr Thr Thr Ser Ser Glu Pro
               1120                1125                1130

gcc cct tct ggc tgc ccc ccc gac tcc gac gct gag tcc tat tcc tcc     16119
Ala Pro Ser Gly Cys Pro Pro Asp Ser Asp Ala Glu Ser Tyr Ser Ser
           1135                1140                1145

atg ccc ccc ctg gag ggg gag cct ggg gat ccg gat ctt agc gac ggg     16167
Met Pro Pro Leu Glu Gly Glu Pro Gly Asp Pro Asp Leu Ser Asp Gly
       1150                1155                1160

tca tgg tca acg gtc agt agt gag gcc aac gcg gag gat gtc gtg tgc     16215
Ser Trp Ser Thr Val Ser Ser Glu Ala Asn Ala Glu Asp Val Val Cys
   1165                1170                1175

tgc tca atg tct tac tct tgg aca ggc gca ctc gtc acc ccg tgc gcc     16263
Cys Ser Met Ser Tyr Ser Trp Thr Gly Ala Leu Val Thr Pro Cys Ala
1180                1185                1190                1195

gcg gaa gaa cag aaa ctg ccc atc aat gca cta agc aac tcg ttg cta     16311
Ala Glu Glu Gln Lys Leu Pro Ile Asn Ala Leu Ser Asn Ser Leu Leu
               1200                1205                1210

cgt cac cac aat ttg gtg tat tcc acc acc tca cgc agt gct tgc caa     16359
Arg His His Asn Leu Val Tyr Ser Thr Thr Ser Arg Ser Ala Cys Gln
           1215                1220                1225

agg cag aag aaa gtc aca ttt gac aga ctg caa gtt ctg gac agc cat     16407
Arg Gln Lys Lys Val Thr Phe Asp Arg Leu Gln Val Leu Asp Ser His
```

-continued

```
      1230                1235                1240

tac cag gac gta ctc aag gag gtt aaa gca gcg gcg tca aaa gtg aag    16455
Tyr Gln Asp Val Leu Lys Glu Val Lys Ala Ala Ala Ser Lys Val Lys
   1245                1250                1255

gct aac ttg cta tcc gta gag gaa gct tgc agc ctg acg ccc cca cac    16503
Ala Asn Leu Leu Ser Val Glu Glu Ala Cys Ser Leu Thr Pro Pro His
1260                1265                1270                1275

tca gcc aaa tcc aag ttt ggt tat ggg gca aaa gac gtc cgt tgc cat    16551
Ser Ala Lys Ser Lys Phe Gly Tyr Gly Ala Lys Asp Val Arg Cys His
               1280                1285                1290

gcc aga aag gcc gta acc cac atc aac tcc gtg tgg aaa gac ctt ctg    16599
Ala Arg Lys Ala Val Thr His Ile Asn Ser Val Trp Lys Asp Leu Leu
           1295                1300                1305

gaa gac aat gta aca cca ata gac act acc atc atg gct aag aac gag    16647
Glu Asp Asn Val Thr Pro Ile Asp Thr Thr Ile Met Ala Lys Asn Glu
       1310                1315                1320

gtt ttc tgc gtt cag cct gag aag ggg ggt cgt aag cca gct cgt ctc    16695
Val Phe Cys Val Gln Pro Glu Lys Gly Gly Arg Lys Pro Ala Arg Leu
   1325                1330                1335

atc gtg ttc ccc gat ctg ggc gtg cgc gtg tgc gaa aag atg gct ttg    16743
Ile Val Phe Pro Asp Leu Gly Val Arg Val Cys Glu Lys Met Ala Leu
1340                1345                1350                1355

tac gac gtg gtt aca aag ctc ccc ttg gcc gtg atg gga agc tcc tac    16791
Tyr Asp Val Val Thr Lys Leu Pro Leu Ala Val Met Gly Ser Ser Tyr
               1360                1365                1370

gga ttc caa tac tca cca gga cag cgg gtt gaa ttc ctc gtg caa gcg    16839
Gly Phe Gln Tyr Ser Pro Gly Gln Arg Val Glu Phe Leu Val Gln Ala
           1375                1380                1385

tgg aag tcc aag aaa acc cca atg ggg ttc tcg tat gat acc cgc tgc    16887
Trp Lys Ser Lys Lys Thr Pro Met Gly Phe Ser Tyr Asp Thr Arg Cys
       1390                1395                1400

ttt gac tcc aca gtc act gag agc gac atc cgt acg gag gag gca atc    16935
Phe Asp Ser Thr Val Thr Glu Ser Asp Ile Arg Thr Glu Glu Ala Ile
   1405                1410                1415

tac caa tgt tgt gac ctc gac ccc caa gcc cgc gtg gcc atc aag tcc    16983
Tyr Gln Cys Cys Asp Leu Asp Pro Gln Ala Arg Val Ala Ile Lys Ser
1420                1425                1430                1435

ctc acc gag agg ctt tat gtt ggg ggc cct ctt acc aat tca agg ggg    17031
Leu Thr Glu Arg Leu Tyr Val Gly Gly Pro Leu Thr Asn Ser Arg Gly
               1440                1445                1450

gag aac tgc ggc tat cgc agg tgc cgc gcg agc ggc gta ctg aca act    17079
Glu Asn Cys Gly Tyr Arg Arg Cys Arg Ala Ser Gly Val Leu Thr Thr
           1455                1460                1465

agc tgt ggt aac acc ctc act tgc tac atc aag gcc cgg gca gcc tgt    17127
Ser Cys Gly Asn Thr Leu Thr Cys Tyr Ile Lys Ala Arg Ala Ala Cys
       1470                1475                1480

cga gcc gca ggg ctc cag gac tgc acc atg ctc gtg tgt ggc gac gac    17175
Arg Ala Ala Gly Leu Gln Asp Cys Thr Met Leu Val Cys Gly Asp Asp
   1485                1490                1495

tta gtc gtt atc tgt gaa agc gcg ggg gtc cag gag gac gcg gcg agc    17223
Leu Val Val Ile Cys Glu Ser Ala Gly Val Gln Glu Asp Ala Ala Ser
1500                1505                1510                1515

ctg aga gcc ttc acg gag gct atg acc agg tac tcc gcc ccc cct ggg    17271
Leu Arg Ala Phe Thr Glu Ala Met Thr Arg Tyr Ser Ala Pro Pro Gly
               1520                1525                1530

gac ccc cca caa cca gaa tac gac ttg gag ctc ata aca tca tgc tcc    17319
Asp Pro Pro Gln Pro Glu Tyr Asp Leu Glu Leu Ile Thr Ser Cys Ser
           1535                1540                1545

tcc aac gtg tca gtc gcc cac gac ggc gct gga aag agg gtc tac tac    17367
```

-continued

```
Ser Asn Val Ser Val Ala His Asp Gly Ala Gly Lys Arg Val Tyr Tyr
       1550                1555                1560

ctc acc cgt gac cct aca acc ccc ctc gcg aga gct gcg tgg gag aca    17415
Leu Thr Arg Asp Pro Thr Thr Pro Leu Ala Arg Ala Ala Trp Glu Thr
   1565                1570                1575

gca aga cac act cca gtc aat tcc tgg cta ggc aac ata atc atg ttt    17463
Ala Arg His Thr Pro Val Asn Ser Trp Leu Gly Asn Ile Ile Met Phe
1580                1585                1590                1595

gcc ccc aca ctg tgg gcg agg atg ata ctg atg acc cat ttc ttt agc    17511
Ala Pro Thr Leu Trp Ala Arg Met Ile Leu Met Thr His Phe Phe Ser
                1600                1605                1610

gtc ctt ata gcc agg gac cag ctt gaa cag gcc ctc gat tgc gag atc    17559
Val Leu Ile Ala Arg Asp Gln Leu Glu Gln Ala Leu Asp Cys Glu Ile
            1615                1620                1625

tac ggg gcc tgc tac tcc ata gaa cca ctg gat cta cct cca atc att    17607
Tyr Gly Ala Cys Tyr Ser Ile Glu Pro Leu Asp Leu Pro Pro Ile Ile
       1630                1635                1640

caa aga ctc cat ggc ctc agc gca ttt tca ctc cac agt tac tct cca    17655
Gln Arg Leu His Gly Leu Ser Ala Phe Ser Leu His Ser Tyr Ser Pro
   1645                1650                1655

ggt gaa atc aat agg gtg gcc gca tgc ctc aga aaa ctt ggg gta ccg    17703
Gly Glu Ile Asn Arg Val Ala Ala Cys Leu Arg Lys Leu Gly Val Pro
1660                1665                1670                1675

ccc ttg cga gct tgg aga cac cgg gcc cgg agc gtc cgc gct agg ctt    17751
Pro Leu Arg Ala Trp Arg His Arg Ala Arg Ser Val Arg Ala Arg Leu
                1680                1685                1690

ctg gcc aga gga ggc agg gct gcc ata tgt ggc aag tac ctc ttc aac    17799
Leu Ala Arg Gly Gly Arg Ala Ala Ile Cys Gly Lys Tyr Leu Phe Asn
            1695                1700                1705

tgg gca gta aga aca aag ctc aaa ctc act cca ata gcg gcc gct ggc    17847
Trp Ala Val Arg Thr Lys Leu Lys Leu Thr Pro Ile Ala Ala Ala Gly
       1710                1715                1720

cag ctg gac ttg tcc ggc tgg ttc acg gct ggc tac agc ggg gga gac    17895
Gln Leu Asp Leu Ser Gly Trp Phe Thr Ala Gly Tyr Ser Gly Gly Asp
   1725                1730                1735

att tat cac agc gtg tct cat gcc cgg ccc cgc tgg atc tgg ttt tgc    17943
Ile Tyr His Ser Val Ser His Ala Arg Pro Arg Trp Ile Trp Phe Cys
1740                1745                1750                1755

cta ctc ctg ctt gct gca ggg gta ggc atc tac ctc ctc ccc aac cga    17991
Leu Leu Leu Leu Ala Ala Gly Val Gly Ile Tyr Leu Leu Pro Asn Arg
                1760                1765                1770

atg agc acg aat cct aaa cct caa aga aag acc aaa cgt aac acc aac    18039
Met Ser Thr Asn Pro Lys Pro Gln Arg Lys Thr Lys Arg Asn Thr Asn
            1775                1780                1785

cgg cgg ccg cag gac gtc aag ttc ccg ggt ggc ggt cag atc gtt ggt    18087
Arg Arg Pro Gln Asp Val Lys Phe Pro Gly Gly Gly Gln Ile Val Gly
       1790                1795                1800

gga gtt tac ttg ttg ccg cgc agg ggc cct aga ttg ggt gtg cgc gcg    18135
Gly Val Tyr Leu Leu Pro Arg Arg Gly Pro Arg Leu Gly Val Arg Ala
   1805                1810                1815

acg aga aag act tcc gag cgg tcg caa cct cga ggt aga cgt cag cct    18183
Thr Arg Lys Thr Ser Glu Arg Ser Gln Pro Arg Gly Arg Arg Gln Pro
1820                1825                1830                1835

atc ccc aag gct cgt cgg ccc gag ggc agg acc tgg gct cag ccc ggg    18231
Ile Pro Lys Ala Arg Arg Pro Glu Gly Arg Thr Trp Ala Gln Pro Gly
                1840                1845                1850

tac cct tgg ccc ctc tat ggc aat gag ggc tgc ggg tgg gcg gga tgg    18279
Tyr Pro Trp Pro Leu Tyr Gly Asn Glu Gly Cys Gly Trp Ala Gly Trp
            1855                1860                1865
```

-continued

```
ctc ctg tct ccc cgt ggc tct cgg cct agc tgg ggc ccc aca gac ccc    18327
Leu Leu Ser Pro Arg Gly Ser Arg Pro Ser Trp Gly Pro Thr Asp Pro
       1870                1875                1880

cgg cgt agg tcg cgc aat ttg ggt aag gtc atc gat acc ctt acg tgc    18375
Arg Arg Arg Ser Arg Asn Leu Gly Lys Val Ile Asp Thr Leu Thr Cys
   1885                1890                1895

ggc ttc gcc gac ctc atg ggg tac ata ccg ctc gtc ggc gcc cct ctt    18423
Gly Phe Ala Asp Leu Met Gly Tyr Ile Pro Leu Val Gly Ala Pro Leu
1900                1905                1910                1915

gga ggc gct gcc agg gcc ctg gcg cat ggc gtc cgg gtt ctg gaa gac    18471
Gly Gly Ala Ala Arg Ala Leu Ala His Gly Val Arg Val Leu Glu Asp
               1920                1925                1930

ggc gtg aac tat gca aca ggg aac ctt cct ggt tgc tct taatagtcga     18520
Gly Val Asn Tyr Ala Thr Gly Asn Leu Pro Gly Cys Ser
           1935                1940

ctttgttccc actgtacttt tagctcgtac aaaatacaat atacttttca tttctccgta  18580

aacaacatgt tttcccatgt aatatccttt tctatttttc gttccgttac caactttaca  18640

catactttat atagctattc acttctatac actaaaaaac taagacaatt ttaattttgc  18700

tgcctgccat atttcaattt gttataaatt cctataattt atcctattag tagctaaaaa  18760

aagatgaatg tgaatcgaat cctaagagaa ttggatctga tccacaggac gggtgtggtc  18820

gccatgatcg cgtagtcgat agtggctcca agtagcgaag cgagcaggac tgggcggcgg  18880

ccaaagcggt cggacagtgc tccgagaacg ggtgcgcata gaaattgcat caacgcatat  18940

agcgctagca gcacgccata gtgactggcg atgctgtcgg aatggacgat atcccgcaag  19000

aggcccggca gtaccggcat aaccaagcct atgcctacag catccagggt gacggtgccg  19060

aggatgacga tgagcgcatt gttagatttc atacacggtg cctgactgcg ttagcaattt  19120

aactgtgata aactaccgca ttaaagcttt ttctttccaa tttttttttt ttcgtcatta  19180

taaaaatcat tacgaccgag attcccgggt aataactgat ataattaaat tgaagctcta  19240

atttgtgagt ttagtataca tgcatttact tataatacag ttttttagtt ttgctggccg  19300

catcttctca aatatgcttc ccagcctgct tttctgtaac gttcaccctc taccttagca  19360

tcccttccct ttgcaaatag tcctcttcca acaataataa tgtcagatcc tgtagagacc  19420

acatcatcca cggttctata ctgttgaccc aatgcgtctc ccttgtcatc taaacccaca  19480

ccgggtgtca taatcaacca atcgtaacct tcatctcttc cacccatgtc tctttgagca  19540

ataaagccga taacaaaatc tttgtcgctc ttcgcaatgt caacagtacc cttagtatat  19600

tctccagtag atagggagcc cttgcatgac aattctgcta acatcaaaag gcctctaggt  19660

tcctttgtta cttcttctgc cgcctgcttc aaaccgctaa caatacctgg gcccaccaca  19720

ccgtgtgcat tcgtaatgtc tgcccattct gctattctgt atacacccgc agagtactgc  19780

aatttgactg tattaccaat gtcagcaaat tttctgtctt cgaagagtaa aaaattgtac  19840

ttggcggata atgcctttag cggcttaact gtgccctcca tggaaaaatc agtcaagata  19900

tccacatgtg tttttagtaa acaaattttg ggacctaatg cttcaactaa ctccagtaat  19960

tccttggtgg tacgaacatc caatgaagca cacaagtttg tttgcttttc gtgcatgata  20020

ttaaatagct tggcagcaac aggactagga tgagtagcag cacgttcctt atatgtagct  20080

ttcgacatga tttatcttcg tttcctgcag gtttttgttc tgtgcagttg ggttaagaat  20140

actgggcaat ttcatgtttc ttcaacacta catatgcgta tatataccaa tctaagtctg  20200

tgctccttcc ttcgttcttc cttctgttcg gagattaccg aatcaaaaaa atttcaagga  20260

aaccgaaatc aaaaaaaaga ataaaaaaaa aatgatgaat tgaaaagctt atcgat      20316
```

-continued

<210> SEQ ID NO 15
<211> LENGTH: 1944
<212> TYPE: PRT
<213> ORGANISM: Artificial Sequence
<220> FEATURE:
<223> OTHER INFORMATION: Description of Artificial Sequence:
pd.delta.NS3NS5.pj.core173

<400> SEQUENCE: 15

```
Met Ala Ala Tyr Ala Ala Gln Gly Tyr Lys Val Leu Val Leu Asn Pro
  1               5                  10                  15

Ser Val Ala Ala Thr Leu Gly Phe Gly Ala Tyr Met Ser Lys Ala His
             20                  25                  30

Gly Ile Asp Pro Asn Ile Arg Thr Gly Val Arg Thr Ile Thr Thr Gly
         35                  40                  45

Ser Pro Ile Thr Tyr Ser Thr Tyr Gly Lys Phe Leu Ala Asp Gly Gly
     50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
```

-continued

```
        355                 360                 365

Lys Cys Leu Ile Arg Leu Lys Pro Thr Leu His Gly Pro Thr Pro Leu
    370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
        435                 440                 445

Ser Gly Lys Pro Ala Ile Ile Pro Asp Arg Glu Val Leu Tyr Arg Glu
    450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780
```

-continued

```
Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
        835                 840                 845

Glu Tyr Val Glu Ile Arg Gln Val Gly Asp Phe His Tyr Val Thr Gly
    850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
    930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu Asp
   1010                 1015                1020

Glu  Arg Glu Ile Ser Val  Pro Ala Glu Ile Leu  Arg Lys Ser Arg Arg
1025                 1030                 1035                 1040

Phe Ala Gln Ala Leu  Pro Val Trp Ala Arg  Pro Asp Tyr Asn Pro  Pro
                1045                 1050                 1055

Leu Val Glu Thr  Trp Lys Lys Pro Asp  Tyr Glu Pro Pro Val  Val His
            1060                 1065                 1070

Gly Cys Pro  Leu Pro Pro Pro Lys  Ser Pro Pro Val Pro  Pro Pro Arg
        1075                 1080                 1085

Lys Lys  Arg Thr Val Val Leu  Thr Glu Ser Thr Leu  Ser Thr Ala Leu
    1090                 1095                 1100

Ala  Glu Leu Ala Thr Arg  Ser Phe Gly Ser Ser  Ser Thr Ser Gly Ile
1105                 1110                 1115                 1120

Thr Gly Asp Asn Thr  Thr Thr Ser Ser Glu  Pro Ala Pro Ser Gly  Cys
                1125                 1130                 1135

Pro Pro Asp Ser  Asp Ala Glu Ser Tyr  Ser Ser Met Pro Pro  Leu Glu
            1140                 1145                 1150

Gly Glu Pro  Gly Asp Pro Asp Leu  Ser Asp Gly Ser Trp  Ser Thr Val
        1155                 1160                 1165

Ser Ser  Glu Ala Asn Ala Glu  Asp Val Val Cys Cys  Ser Met Ser Tyr
    1170                 1175                 1180

Ser  Trp Thr Gly Ala Leu  Val Thr Pro Cys Ala  Ala Glu Glu Gln Lys
1185                 1190                 1195                 1200
```

-continued

```
Leu Pro Ile Asn Ala  Leu Ser Asn Ser Leu  Leu Arg His His Asn  Leu
                1205                 1210                 1215

Val Tyr Ser Thr  Thr Ser Arg Ser Ala  Cys Gln Arg Gln Lys  Lys Val
            1220                 1225                 1230

Thr Phe Asp  Arg Leu Gln Val Leu  Asp Ser His Tyr Gln  Asp Val Leu
        1235                 1240                 1245

Lys Glu  Val Lys Ala Ala Ala  Ser Lys Val Lys Ala  Asn Leu Leu Ser
    1250                 1255                 1260

Val  Glu Glu Ala Cys Ser  Leu Thr Pro Pro His  Ser Ala Lys Ser Lys
1265                 1270                 1275                 1280

Phe Gly Tyr Gly Ala  Lys Asp Val Arg Cys  His Ala Arg Lys Ala  Val
                1285                 1290                 1295

Thr His Ile Asn  Ser Val Trp Lys Asp  Leu Leu Glu Asp Asn  Val Thr
            1300                 1305                 1310

Pro Ile Asp  Thr Thr Ile Met Ala  Lys Asn Glu Val Phe  Cys Val Gln
        1315                 1320                 1325

Pro Glu  Lys Gly Gly Arg Lys  Pro Ala Arg Leu Ile  Val Phe Pro Asp
    1330                 1335                 1340

Leu  Gly Val Arg Val Cys  Glu Lys Met Ala Leu  Tyr Asp Val Val Thr
1345                 1350                 1355                 1360

Lys Leu Pro Leu Ala  Val Met Gly Ser Ser  Tyr Gly Phe Gln Tyr  Ser
                1365                 1370                 1375

Pro Gly Gln Arg  Val Glu Phe Leu Val  Gln Ala Trp Lys Ser  Lys Lys
            1380                 1385                 1390

Thr Pro Met  Gly Phe Ser Tyr Asp  Thr Arg Cys Phe Asp  Ser Thr Val
        1395                 1400                 1405

Thr Glu  Ser Asp Ile Arg Thr  Glu Glu Ala Ile Tyr  Gln Cys Cys Asp
    1410                 1415                 1420

Leu  Asp Pro Gln Ala Arg  Val Ala Ile Lys Ser  Leu Thr Glu Arg Leu
1425                 1430                 1435                 1440

Tyr Val Gly Gly Pro  Leu Thr Asn Ser Arg  Gly Glu Asn Cys Gly  Tyr
                1445                 1450                 1455

Arg Arg Cys Arg  Ala Ser Gly Val Leu  Thr Thr Ser Cys Gly  Asn Thr
            1460                 1465                 1470

Leu Thr Cys  Tyr Ile Lys Ala Arg  Ala Ala Cys Arg Ala  Ala Gly Leu
        1475                 1480                 1485

Gln Asp  Cys Thr Met Leu Val  Cys Gly Asp Asp Leu  Val Val Ile Cys
    1490                 1495                 1500

Glu  Ser Ala Gly Val Gln  Glu Asp Ala Ala Ser  Leu Arg Ala Phe Thr
1505                 1510                 1515                 1520

Glu Ala Met Thr Arg  Tyr Ser Ala Pro Pro  Gly Asp Pro Pro Gln  Pro
                1525                 1530                 1535

Glu Tyr Asp Leu  Glu Leu Ile Thr Ser  Cys Ser Ser Asn Val  Ser Val
            1540                 1545                 1550

Ala His Asp  Gly Ala Gly Lys Arg  Val Tyr Tyr Leu Thr  Arg Asp Pro
        1555                 1560                 1565

Thr Thr  Pro Leu Ala Arg Ala  Ala Trp Glu Thr Ala  Arg His Thr Pro
    1570                 1575                 1580

Val  Asn Ser Trp Leu Gly  Asn Ile Ile Met Phe  Ala Pro Thr Leu Trp
1585                 1590                 1595                 1600

Ala Arg Met Ile Leu  Met Thr His Phe Phe  Ser Val Leu Ile Ala  Arg
                1605                 1610                 1615

Asp Gln Leu Glu  Gln Ala Leu Asp Cys  Glu Ile Tyr Gly Ala  Cys Tyr
```

-continued

```
            1620                1625                1630

Ser Ile Glu  Pro Leu Asp Leu Pro  Pro Ile Ile Gln Arg  Leu His Gly
        1635                1640                1645

Leu Ser  Ala Phe Ser Leu His  Ser Tyr Ser Pro Gly  Glu Ile Asn Arg
    1650                1655                1660

Val  Ala Ala Cys Leu Arg  Lys Leu Gly Val Pro  Pro Leu Arg Ala Trp
1665                1670                1675                1680

Arg His Arg Ala Arg  Ser Val Arg Ala Arg  Leu Leu Ala Arg Gly  Gly
                1685                1690                1695

Arg Ala Ala Ile  Cys Gly Lys Tyr Leu  Phe Asn Trp Ala Val  Arg Thr
            1700                1705                1710

Lys Leu Lys  Leu Thr Pro Ile Ala  Ala Ala Gly Gln Leu  Asp Leu Ser
        1715                1720                1725

Gly Trp  Phe Thr Ala Gly Tyr  Ser Gly Gly Asp Ile  Tyr His Ser Val
    1730                1735                1740

Ser  His Ala Arg Pro Arg  Trp Ile Trp Phe Cys  Leu Leu Leu Leu Ala
1745                1750                1755                1760

Ala Gly Val Gly Ile  Tyr Leu Leu Pro Asn  Arg Met Ser Thr Asn  Pro
                1765                1770                1775

Lys Pro Gln Arg  Lys Thr Lys Arg Asn  Thr Asn Arg Arg Pro  Gln Asp
            1780                1785                1790

Val Lys Phe  Pro Gly Gly Gly Gln  Ile Val Gly Gly Val  Tyr Leu Leu
        1795                1800                1805

Pro Arg  Arg Gly Pro Arg Leu  Gly Val Arg Ala Thr  Arg Lys Thr Ser
    1810                1815                1820

Glu  Arg Ser Gln Pro Arg  Gly Arg Arg Gln Pro  Ile Pro Lys Ala Arg
1825                1830                1835                1840

Arg Pro Glu Gly Arg  Thr Trp Ala Gln Pro  Gly Tyr Pro Trp Pro  Leu
                1845                1850                1855

Tyr Gly Asn Glu  Gly Cys Gly Trp Ala  Gly Trp Leu Leu Ser  Pro Arg
            1860                1865                1870

Gly Ser Arg  Pro Ser Trp Gly Pro  Thr Asp Pro Arg Arg  Arg Ser Arg
        1875                1880                1885

Asn Leu  Gly Lys Val Ile Asp  Thr Leu Thr Cys Gly  Phe Ala Asp Leu
    1890                1895                1900

Met  Gly Tyr Ile Pro Leu  Val Gly Ala Pro Leu  Gly Gly Ala Ala Arg
1905                1910                1915                1920

Ala Leu Ala His Gly  Val Arg Val Leu Glu  Asp Gly Val Asn Tyr  Ala
                1925                1930                1935

Thr Gly Asn Leu  Pro Gly Cys Ser
            1940
```

```
<210> SEQ ID NO 16
<211> LENGTH: 20217
<212> TYPE: DNA
<213> ORGANISM: Artificial Sequence
<220> FEATURE:
<223> OTHER INFORMATION: Description of Artificial Sequence:
      pd.delta.NS3NS5.pj.core140
<221> NAME/KEY: CDS
<222> LOCATION: (12679)..(18411)

<400> SEQUENCE: 16

atcgatccta ccccttgcgc taaagaagta tatgtgccta ctaacgcttg tctttgtctc     60

tgtcactaaa cactggatta ttactcccag atacttattt tggactaatt taaatgattt    120
```

-continued

```
cggatcaacg ttcttaatat cgctgaatct tccacaattg atgaaagtag ctaggaagag    180
gaattggtat aaagtttttg tttttgtaaa tctcgaagta tactcaaacg aatttagtat    240
tttctcagtg atctcccaga tgctttcacc ctcacttaga agtgctttaa gcattttttt    300
actgtggcta tttcccttat ctgcttcttc cgatgattcg aactgtaatt gcaaactact    360
tacaatatca gtgatatcag attgatgttt ttgtccatag taaggaataa ttgtaaattc    420
ccaagcagga atcaatttct ttaatgaggc ttccagaatt gttgcttttt gcgtcttgta    480
tttaaactgg agtgatttat tgacaatatc gaaactcagc gaattgctta tgatagtatt    540
atagctcatg aatgtggctc tcttgattgc tgttccgtta tgtgtaatca tccaacataa    600
ataggttagt tcagcagcac ataatgctat tttctcacct gaaggtcttt caaacctttc    660
cacaaactga cgaacaagca ccttaggtgg tgttttacat aatatatcaa attgtggcat    720
gcttagcgcc gatcttgtgt gcaattgata tctagtttca actactctat ttatcttgta    780
tcttgcagta ttcaaacacg ctaactcgaa aaactaactt taattgtcct gtttgtctcg    840
cgttctttcg aaaaatgcac cggccgcgca ttatttgtac tgcgaaaata attggtactg    900
cggtatcttc atttcatatt ttaaaaatgc acctttgctg cttttcctta atttttagac    960
ggcccgcagg ttcgttttgc ggtactatct tgtgataaaa agttgttttg acatgtgatc   1020
tgcacagatt ttataatgta ataagcaaga atacattatc aaacgaacaa tactggtaaa   1080
agaaaaccaa aatggacgac attgaaacag ccaagaatct gacggtaaaa gcacgtacag   1140
cttatagcgt ctgggatgta tgtcggctgt ttattgaaat gattgctcct gatgtagata   1200
ttgatataga gagtaaacgt aagtctgatg agctactctt tccaggatat gtcataaggc   1260
ccatggaatc tctcacaacc ggtaggccgt atggtcttga ttctagcgca gaagattcca   1320
gcgtatcttc tgactccagt gctgaggtaa ttttgcctgc tgcgaagatg gttaaggaaa   1380
ggtttgattc gattggaaat ggtatgctct cttcacaaga agcaagtcag gctgccatag   1440
atttgatgct acagaataac aagctgttag acaatagaaa gcaactatac aaatctattg   1500
ctataataat aggaagattg cccgagaaag acaagaagag agctaccgaa atgctcatga   1560
gaaaaatgga ttgtacacag ttattagtcc caccagctcc aacggaagaa gatgttatga   1620
agctcgtaag cgtcgttacc caattgctta ctttagttcc accagatcgt caagctgctt   1680
taataggtga tttattcatc ccggaatctc taaaggatat attcaatagt ttcaatgaac   1740
tggcggcaga gaatcgttta cagcaaaaaa agagtgagtt ggaaggaagg actgaagtga   1800
accatgctaa tacaaatgaa gaagttccct ccaggcgaac aagaagtaga gacacaaatg   1860
caagaggagc atataaatta caaaacacca tcactgaggg ccctaaagcg gttcccacga   1920
aaaaaaggag agtagcaacg agggtaaggg gcagaaaatc acgtaatact tctagggtat   1980
gatccaatat caaaggaaat gatagcattg aaggatgaga ctaatccaat tgaggagtgg   2040
cagcatatag aacagctaaa gggtagtgct gaaggaagca tacgataccc cgcatggaat   2100
gggataatat cacaggaggt actagactac ctttcatcct acataaatag acgcatataa   2160
gtacgcattt aagcataaac acgcactatg ccgttcttct catgtatata tatatacagg   2220
caacacgcag atataggtgc gacgtgaaca gtgagctgta tgtgcgcagc tcgcgttgca   2280
ttttcggaag cgctcgtttt cggaaacgct ttgaagttcc tattccgaag ttcctattct   2340
ctagaaagta taggaacttc agagcgcttt tgaaaaccaa aagcgctctg aagacgcact   2400
ttcaaaaaac caaaaacgca ccggactgta acgagctact aaaatattgc gaataccgct   2460
tccacaaaca ttgctcaaaa gtatctcttt gctatatatc tctgtgctat atccctatat   2520
```

-continued

```
aacctaccca tccacctttc gctccttgaa cttgcatcta aactcgacct ctacatcaac   2580
aggcttccaa tgctcttcaa attttactgt caagtagacc catacggctg taatatgctg   2640
ctcttcataa tgtaagctta tctttatcga atcgtgtgaa aaactactac cgcgataaac   2700
ctttacggtt ccctgagatt gaattagttc ctttagtata tgatacaaga cacttttgaa   2760
ctttgtacga cgaattttga ggttcgccat cctctggcta tttccaatta tcctgtcggc   2820
tattatctcc gcctcagttt gatcttccgc ttcagactgc catttttcac ataatgaatc   2880
tatttcaccc cacaatcctt catccgcctc cgcatcttgt tccgttaaac tattgacttc   2940
atgttgtaca ttgtttagtt cacgagaagg gtcctcttca ggcggtagct cctgatctcc   3000
tatatgacct ttatcctgtt ctctttccac aaacttagaa atgtattcat gaattatgga   3060
gcacctaata acattcttca aggcggagaa gtttgggcca gatgcccaat atgcttgaca   3120
tgaaaacgtg agaatgaatt tagtattatt gtgatattct gaggcaattt tattataatc   3180
tcgaagataa gagaagaatg cagtgacctt tgtattgaca aatggagatt ccatgtatct   3240
aaaaaatacg cctttaggcc ttctgatacc ctttcccctg cggtttagcg tgccttttac   3300
attaatatct aaaccctctc cgatggtggc ctttaactga ctaataaatg caaccgatat   3360
aaactgtgat aattctgggt gatttatgat tcgatcgaca attgtattgt acactagtgc   3420
aggatcaggc caatccagtt ctttttcaat taccggtgtg tcgtctgtat tcagtacatg   3480
tccaacaaat gcaaatgcta acgttttgta tttcttataa ttgtcaggaa ctggaaaagt   3540
ccccccttgtc gtctcgatta cacacctact ttcatcgtac accataggtt ggaagtgctg   3600
cataatacat tgcttaatac aagcaagcag tctctcgcca ttcatatttc agttattttc   3660
cattacagct gatgtcattg tatatcagcg ctgtaaaaat ctatctgtta cagaaggttt   3720
tcgcggtttt tataaacaaa actttcgtta cgaaatcgag caatcacccc agctgcgtat   3780
ttggaaattc gggaaaaagt agagcaacgc gagttgcatt ttttacacca taatgcatga   3840
ttaacttcga gaagggatta aggctaattt cactagtatg tttcaaaaac ctcaatctgt   3900
ccattgaatg ccttataaaa cagctataga ttgcatagaa gagttagcta ctcaatgctt   3960
tttgtcaaag cttactgatg atgatgtgtc tactttcagg cgggtctgta gtaaggagaa   4020
tgacattata aagctggcac ttagaattcc acggactata gactatacta gtatactccg   4080
tctactgtac gatacacttc cgctcaggtc cttgtccttt aacgaggcct taccactctt   4140
ttgttactct attgatccag ctcagcaaag gcagtgtgat ctaagattct atcttcgcga   4200
tgtagtaaaa ctagctagac cgagaaagag actagaaatg caaaaggcac ttctacaatg   4260
gctgccatca ttattatccg atgtgacgct gcattttttt tttttttttt tttttttttt   4320
tttttttttt tttttttttt ttttttggta caaatatcat aaaaaaagag aatcttttta   4380
agcaaggatt ttcttaactt cttcggcgac agcatcaccg acttcggtgg tactgttgga   4440
accacctaaa tcaccagttc tgatacctgc atccaaaacc tttttaactg catcttcaat   4500
ggctttacct tcttcaggca agttcaatga caatttcaac atcattgcag cagacaagat   4560
agtggcgata gggttgacct tattctttgg caaatctgga gcggaaccat ggcatggttc   4620
gtacaaacca aatgcggtgt tcttgtctgg caaagaggcc aaggacgcag atggcaacaa   4680
acccaaggag cctgggataa cggaggcttc atcggagatg atatcaccaa acatgttgct   4740
ggtgattata ataccattta ggtgggttgg gttcttaact aggatcatgg cggcagaatc   4800
aatcaattga tgttgaactt tcaatgtagg gaattcgttc ttgatggttt cctccacagt   4860
```

-continued

```
ttttctccat aatcttgaag aggccaaaac attagcttta tccaaggacc aaataggcaa   4920
tggtggctca tgttgtaggg ccatgaaagc ggccattctt gtgattcttt gcacttctgg   4980
aacggtgtat tgttcactat cccaagcgac accatcacca tcgtcttcct ttctcttacc   5040
aaagtaaata cctcccacta attctctaac aacaacgaag tcagtacctt tagcaaattg   5100
tggcttgatt ggagataagt ctaaaagaga gtcggatgca aagttacatg gtcttaagtt   5160
ggcgtacaat tgaagttctt tacggatttt tagtaaacct tgttcaggtc taacactacc   5220
ggtaccccat ttaggaccac ccacagcacc taacaaaacg gcatcagcct tcttggaggc   5280
ttccagcgcc tcatctggaa gtggaacacc tgtagcatcg atagcagcac caccaattaa   5340
atgattttcg aaatcgaact tgacattgga acgaacatca gaaatagctt taagaacctt   5400
aatggcttcg gctgtgattt cttgaccaac gtggtcacct ggcaaaacga cgatcttctt   5460
aggggcagac attacaatgg tatatccttg aaatatatat aaaaaaaaaa aaaaaaaaaa   5520
aaaaaaaaaa atgcagcttc tcaatgatat tcgaatacgc tttgaggaga tacagcctaa   5580
tatccgacaa actgttttac agatttacga tcgtacttgt tacccatcat tgaattttga   5640
acatccgaac ctgggagttt tccctgaaac agatagtata tttgaacctg tataataata   5700
tatagtctag cgctttacgg aagacaatgt atgtatttcg gttcctggag aaactattgc   5760
atctattgca taggtaatct tgcacgtcgc atccccggtt cattttctgc gtttccatct   5820
tgcacttcaa tagcatatct ttgttaacga agcatctgtg cttcattttg tagaacaaaa   5880
atgcaacgcg agagcgctaa tttttcaaac aaagaatctg agctgcattt ttacagaaca   5940
gaaatgcaac gcgaaagcgc tattttacca acgaagaatc tgtgcttcat ttttgtaaaa   6000
caaaaatgca acgcgagagc gctaattttt caaacaaaga atctgagctg catttttaca   6060
gaacagaaat gcaacgcgag agcgctattt taccaacaaa gaatctatac ttcttttttg   6120
ttctacaaaa atgcatcccg agagcgctat ttttctaaca aagcatctta gattactttt   6180
tttctccttt gtgcgctcta taatgcagtc tcttgataac tttttgcact gtaggtccgt   6240
taaggttaga agaaggctac tttggtgtct attttctctt ccataaaaaa agcctgactc   6300
cacttcccgc gtttactgat tactagcgaa gctgcgggtg catttttttca agataaaggc   6360
atccccgatt atattctata ccgatgtgga ttgcgcatac tttgtgaaca gaaagtgata   6420
gcgttgatga ttcttcattg gtcagaaaat tatgaacggt ttcttctatt ttgtctctat   6480
atactacgta taggaaatgt ttacattttc gtattgtttt cgattcactc tatgaatagt   6540
tcttactaca attttttgt ctaaagagta atactagaga taaacataaa aaatgtagag   6600
gtcgagttta gatgcaagtt caaggagcga aaggtggatg ggtaggttat atagggatat   6660
agcacagaga tatatagcaa agagatactt ttgagcaatg tttgtggaag cggtattcgc   6720
aatattttag tagctcgtta cagtccggtg cgtttttggt tttttgaaag tgcgtcttca   6780
gagcgctttt ggttttcaaa agcgctctga agttcctata ctttctagag aataggaact   6840
tcggaatagg aacttcaaag cgtttccgaa aacgagcgct tccgaaaatg caacgcgagc   6900
tgcgcacata cagctcactg ttcacgtcgc acctatatct gcgtgttgcc tgtatatata   6960
tatacatgag aagaacggca tagtgcgtgt ttatgcttaa atgcgtactt atatgcgtct   7020
atttatgtag gatgaaaggt agtctagtac ctcctgtgat attatcccat tccatgcggg   7080
gtatcgtatg cttccttcag cactaccctt tagctgttct atatgctgcc actcctcaat   7140
tggattagtc tcatccttca atgctatcat ttcctttgat attggatcat atgcatagta   7200
ccgagaaact agtgcgaagt agtgatcagg tattgctgtt atctgatgag tatacgttgt   7260
```

-continued cctggccacg gcagaagcac gcttatcgct ccaatttccc acaacattag tcaactccgt 7320
taggcccttc attgaaagaa atgaggtcat caaatgtctt ccaatgtgag attttgggcc 7380
attttttata gcaaagattg aataaggcgc atttttcttc aaagctttat tgtacgatct 7440
gactaagtta tcttttaata attggtattc ctgtttattg cttgaagaat tgccggtcct 7500
atttactcgt tttaggactg gttcagaatt cctcaaaaat tcatccaaat atacaagtgg 7560
atcgatgata agctgtcaaa catgagaatt cttgaagacg aaagggcctc gtgatacgcc 7620
tatttttata ggttaatgtc atgataataa tggtttctta gacgtcaggt ggcacttttc 7680
ggggaaatgt gcgcggaacc cctatttgtt tatttttcta aatacattca aatatgtatc 7740
cgctcatgag acaataaccc tgataaatgc ttcaataata ttgaaaaagg aagagtatga 7800
gtattcaaca tttccgtgtc gcccttattc ccttttttgc ggcattttgc cttcctgttt 7860
ttgctcaccc agaaacgctg gtgaaagtaa aagatgctga agatcagttg ggtgcacgag 7920
tgggttacat cgaactggat ctcaacagcg gtaagatcct tgagagtttt cgccccgaag 7980
aacgttttcc aatgatgagc acttttaaag ttctgctatg tggcgcggta ttatcccgtg 8040
ttgacgccgg gcaagagcaa ctcggtcgcc gcatacacta ttctcagaat gacttggttg 8100
agtactcacc agtcacagaa aagcatctta cggatggcat gacagtaaga gaattatgca 8160
gtgctgccat aaccatgagt gataacactg cggccaactt acttctgaca acgatcggag 8220
gaccgaagga gctaaccgct tttttgcaca acatggggga tcatgtaact cgccttgatc 8280
gttgggaacc ggagctgaat gaagccatac caaacgacga gcgtgacacc acgatgcctg 8340
cagcaatggc aacaacgttg cgcaaactat taactggcga actacttact ctagcttccc 8400
ggcaacaatt aatagactgg atggaggcgg ataaagttgc aggaccactt ctgcgctcgg 8460
cccttccggc tggctggttt attgctgata aatctggagc cggtgagcgt gggtctcgcg 8520
gtatcattgc agcactgggg ccagatggta agccctcccg tatcgtagtt atctacacga 8580
cggggagtca ggcaactatg gatgaacgaa atagacagat cgctgagata ggtgcctcac 8640
tgattaagca ttggtaactg tcagaccaag tttactcata tatactttag attgatttaa 8700
aacttcattt ttaatttaaa aggatctagg tgaagatcct ttttgataat ctcatgacca 8760
aaatccctta acgtgagttt tcgttccact gagcgtcaga ccccgtagaa aagatcaaag 8820
gatcttcttg agatcctttt tttctgcgcg taatctgctg cttgcaaaca aaaaaaccac 8880
cgctaccagc ggtggtttgt ttgccggatc aagagctacc aactcttttt ccgaaggtaa 8940
ctggcttcag cagagcgcag ataccaaata ctgtccttct agtgtagccg tagttaggcc 9000
accacttcaa gaactctgta gcaccgccta catacctcgc tctgctaatc ctgttaccag 9060
tggctgctgc cagtggcgat aagtcgtgtc ttaccgggtt ggactcaaga cgatagttac 9120
cggataaggc gcagcggtcg ggctgaacgg ggggttcgtg cacacagccc agcttggagc 9180
gaacgaccta caccgaactg agatacctac agcgtgagct atgagaaagc gccacgcttc 9240
ccgaagggag aaaggcggac aggtatccgg taagcggcag ggtcggaaca ggagagcgca 9300
cgagggagct tccaggggga aacgcctggt atctttatag tcctgtcggg tttcgccacc 9360
tctgacttga gcgtcgattt ttgtgatgct cgtcaggggg gcggagccta tggaaaaacg 9420
ccagcaacgc ggccttttta cggttcctgg ccttttgctg gccttttgct cacatgttct 9480
ttcctgcgtt atcccctgat tctgtggata accgtattac cgcctttgag tgagctgata 9540
ccgctcgccg cagccgaacg accgagcgca gcgagtcagt gagcgaggaa gcggaagagc 9600

-continued gcctgatgcg gtattttctc cttacgcatc tgtgcggtat ttcacaccgc atatggtgca 9660
ctctcagtac aatctgctct gatgccgcat agttaagcca gtatacactc cgctatcgct 9720
acgtgactgg gtcatggctg cgccccgaca cccgccaaca cccgctgacg cgccctgacg 9780
ggcttgtctg ctcccggcat ccgcttacag acaagctgtg accgtctccg ggagctgcat 9840
gtgtcagagg ttttcaccgt catcaccgaa acgcgcgagg cagctgcggt aaagctcatc 9900
agcgtggtcg tgaagcgatt cacagatgtc tgcctgttca tccgcgtcca gctcgttgag 9960
tttctccaga agcgttaatg tctggcttct gataaagcgg gccatgttaa gggcggtttt 10020
ttcctgtttg gtcactgatg cctccgtgta agggggattt ctgttcatgg gggtaatgat 10080
accgatgaaa cgagagagga tgctcacgat acgggttact gatgatgaac atgcccggtt 10140
actggaacgt tgtgagggta aacaactggc ggtatggatg cggcgggacc agagaaaaat 10200
cactcagggt caatgccagc gcttcgttaa tacagatgta ggtgttccac agggtagcca 10260
gcagcatcct gcgatgcaga tccggaacat aatggtgcag ggcgctgact tccgcgtttc 10320
cagactttac gaaacacgga aaccgaagac cattcatgtt gttgctcagg tcgcagacgt 10380
tttgcagcag cagtcgcttc acgttcgctc gcgtatcggt gattcattct gctaaccagt 10440
aaggcaaccc cgccagccta gccgggtcct caacgacagg agcacgatca tgcgcacccg 10500
tggccaggac ccaacgctgc ccgagatgcg ccgcgtgcgg ctgctggaga tggcggacgc 10560
gatggatatg ttctgccaag ggttggtttg cgcattcaca gttctccgca agaattgatt 10620
ggctccaatt cttggagtgg tgaatccgtt agcgaggtgc cgccggcttc cattcaggtc 10680
gaggtggccc ggctccatgc accgcgacgc aacgcgggga ggcagacaag gtatagggcg 10740
gcgcctacaa tccatgccaa cccgttccat gtgctcgccg aggcggcata aatcgccgtg 10800
acgatcagcg gtccaatgat cgaagttagg ctggtaagag ccgcgagcga tccttgaagc 10860
tgtccctgat ggtcgtcatc tacctgcctg gacagcatgg cctgcaacgc gggcatcccg 10920
atgccgccgg aagcgagaag aatcataatg gggaaggcca tccagcctcg cgtcgcgaac 10980
gccagcaaga cgtagcccag cgcgtcggcc gccatgccgg cgataatggc ctgcttctcg 11040
ccgaaacgtt tggtggcggg accagtgacg aaggcttgag cgagggcgtg caagattccg 11100
aataccgcaa gcgacaggcc gatcatcgtc gcgctccagc gaaagcggtc ctcgccgaaa 11160
atgacccaga gcgctgccgg cacctgtcct acgagttgca tgataaagaa gacagtcata 11220
agtgcggcga cgatagtcat gccccgcgcc caccggaagg agctgactgg gttgaaggct 11280
ctcaagggca tcggtcgagg atccttcaat atgcgcacat acgctgttat gttcaaggtc 11340
ccttcgttta agaacgaaag cggtcttcct tttgagggat gtttcaagtt gttcaaatct 11400
atcaaatttg caaatcccca gtctgtatct agagcgttga atcggtgatg cgatttgtta 11460
attaaattga tggtgtcacc attaccaggt ctagatatac caatggcaaa ctgagcacaa 11520
caataccagt ccggatcaac tggcaccatc tctcccgtag tctcatctaa tttttcttcc 11580
ggatgaggtt ccagatatac cgcaacacct ttattatggt ttccctgagg gaataataga 11640
atgtcccatt cgaaatcacc aattctaaac ctgggcgaat tgtatttcgg gtttgttaac 11700
tcgttccagt caggaatgtt ccacgtgaag ctatcttcca gcaaagtctc cacttcttca 11760
tcaaattgtg gagaatactc ccaatgctct tatctatggg acttccggga aacacagtac 11820
cgatacttcc caattcgtct tcagagctca ttgtttgttt gaagagacta atcaaagaat 11880
cgttttctca aaaaaattaa tatcttaact gatagtttga tcaaaggggc aaaacgtagg 11940
ggcaaacaaa cggaaaaatc gtttctcaaa ttttctgatg ccaagaactc taaccagtct 12000

-continued

```
tatctaaaaa ttgccttatg atccgtctct ccggttacag cctgtgtaac tgattaatcc  12060

tgcctttcta atcaccattc taatgtttta attaagggat tttgtcttca ttaacggctt  12120

tcgctcataa aaatgttatg acgttttgcc cgcaggcggg aaaccatcca cttcacgaga  12180

ctgatctcct ctgccggaac accgggcatc tccaacttat aagttggaga aataagagaa  12240

tttcagattg agagaatgaa aaaaaaaaac ccttagttca taggtccatt ctcttagcgc  12300

aactacagag aacaggggca caaacaggca aaaaacgggc acaacctcaa tggagtgatg  12360

caacctgcct ggagtaaatg atgacacaag gcaattgacc cacgcatgta tctatctcat  12420

tttcttacac cttctattac cttctgctct ctctgatttg gaaaaagctg aaaaaaaagg  12480

ttgaaaccag ttccctgaaa ttattcccct acttgactaa taagtatata aagacggtag  12540

gtattgattg taattctgta aatctatttc ttaaacttct taaattctac ttttatagtt  12600

agtctttttt ttagttttaa aacaccaaga acttagtttc gaataaacac acataaacaa  12660

acaagcttac aaaacaaa atg gct gca tat gca gct cag ggc tat aag gtg    12711
                    Met Ala Ala Tyr Ala Ala Gln Gly Tyr Lys Val
                    1               5                   10

cta gta ctc aac ccc tct gtt gct gca aca ctg ggc ttt ggt gct tac    12759
Leu Val Leu Asn Pro Ser Val Ala Ala Thr Leu Gly Phe Gly Ala Tyr
            15                  20                  25

atg tcc aag gct cat ggg atc gat cct aac atc agg acc ggg gtg aga    12807
Met Ser Lys Ala His Gly Ile Asp Pro Asn Ile Arg Thr Gly Val Arg
        30                  35                  40

aca att acc act ggc agc ccc atc acg tac tcc acc tac ggc aag ttc    12855
Thr Ile Thr Thr Gly Ser Pro Ile Thr Tyr Ser Thr Tyr Gly Lys Phe
    45                  50                  55

ctt gcc gac ggc ggg tgc tcg ggg ggc gct tat gac ata ata att tgt    12903
Leu Ala Asp Gly Gly Cys Ser Gly Gly Ala Tyr Asp Ile Ile Ile Cys
60                  65                  70                  75

gac gag tgc cac tcc acg gat gcc aca tcc atc ttg ggc att ggc act    12951
Asp Glu Cys His Ser Thr Asp Ala Thr Ser Ile Leu Gly Ile Gly Thr
                80                  85                  90

gtc ctt gac caa gca gag act gcg ggg gcg aga ctg gtt gtg ctc gcc    12999
Val Leu Asp Gln Ala Glu Thr Ala Gly Ala Arg Leu Val Val Leu Ala
            95                  100                 105

acc gcc acc cct ccg ggc tcc gtc act gtg ccc cat ccc aac atc gag    13047
Thr Ala Thr Pro Pro Gly Ser Val Thr Val Pro His Pro Asn Ile Glu
        110                 115                 120

gag gtt gct ctg tcc acc acc gga gag atc cct ttt tac ggc aag gct    13095
Glu Val Ala Leu Ser Thr Thr Gly Glu Ile Pro Phe Tyr Gly Lys Ala
    125                 130                 135

atc ccc ctc gaa gta atc aag ggg ggg aga cat ctc atc ttc tgt cat    13143
Ile Pro Leu Glu Val Ile Lys Gly Gly Arg His Leu Ile Phe Cys His
140                 145                 150                 155

tca aag aag aag tgc gac gaa ctc gcc gca aag ctg gtc gca ttg ggc    13191
Ser Lys Lys Lys Cys Asp Glu Leu Ala Ala Lys Leu Val Ala Leu Gly
                160                 165                 170

atc aat gcc gtg gcc tac tac cgc ggt ctt gac gtg tcc gtc atc ccg    13239
Ile Asn Ala Val Ala Tyr Tyr Arg Gly Leu Asp Val Ser Val Ile Pro
            175                 180                 185

acc agc ggc gat gtt gtc gtc gtg gca acc gat gcc ctc atg acc ggc    13287
Thr Ser Gly Asp Val Val Val Val Ala Thr Asp Ala Leu Met Thr Gly
        190                 195                 200

tat acc ggc gac ttc gac tcg gtg ata gac tgc aat acg tgt gtc acc    13335
Tyr Thr Gly Asp Phe Asp Ser Val Ile Asp Cys Asn Thr Cys Val Thr
    205                 210                 215
```

-continued

```
cag aca gtc gat ttc agc ctt gac cct acc ttc acc att gag aca atc    13383
Gln Thr Val Asp Phe Ser Leu Asp Pro Thr Phe Thr Ile Glu Thr Ile
220                 225                 230                 235

acg ctc ccc caa gat gct gtc tcc cgc act caa cgt cgg ggc agg act    13431
Thr Leu Pro Gln Asp Ala Val Ser Arg Thr Gln Arg Arg Gly Arg Thr
                240                 245                 250

ggc agg ggg aag cca ggc atc tac aga ttt gtg gca ccg ggg gag cgc    13479
Gly Arg Gly Lys Pro Gly Ile Tyr Arg Phe Val Ala Pro Gly Glu Arg
            255                 260                 265

ccc tcc ggc atg ttc gac tcg tcc gtc ctc tgt gag tgc tat gac gca    13527
Pro Ser Gly Met Phe Asp Ser Ser Val Leu Cys Glu Cys Tyr Asp Ala
        270                 275                 280

ggc tgt gct tgg tat gag ctc acg ccc gcc gag act aca gtt agg cta    13575
Gly Cys Ala Trp Tyr Glu Leu Thr Pro Ala Glu Thr Thr Val Arg Leu
    285                 290                 295

cga gcg tac atg aac acc ccg ggg ctt ccc gtg tgc cag gac cat ctt    13623
Arg Ala Tyr Met Asn Thr Pro Gly Leu Pro Val Cys Gln Asp His Leu
300                 305                 310                 315

gaa ttt tgg gag ggc gtc ttt aca ggc ctc act cat ata gat gcc cac    13671
Glu Phe Trp Glu Gly Val Phe Thr Gly Leu Thr His Ile Asp Ala His
                320                 325                 330

ttt cta tcc cag aca aag cag agt ggg gag aac ctt cct tac ctg gta    13719
Phe Leu Ser Gln Thr Lys Gln Ser Gly Glu Asn Leu Pro Tyr Leu Val
            335                 340                 345

gcg tac caa gcc acc gtg tgc gct agg gct caa gcc cct ccc cca tcg    13767
Ala Tyr Gln Ala Thr Val Cys Ala Arg Ala Gln Ala Pro Pro Pro Ser
        350                 355                 360

tgg gac cag atg tgg aag tgt ttg att cgc ctc aag ccc acc ctc cat    13815
Trp Asp Gln Met Trp Lys Cys Leu Ile Arg Leu Lys Pro Thr Leu His
    365                 370                 375

ggg cca aca ccc ctg cta tac aga ctg ggc gct gtt cag aat gaa atc    13863
Gly Pro Thr Pro Leu Leu Tyr Arg Leu Gly Ala Val Gln Asn Glu Ile
380                 385                 390                 395

acc ctg acg cac cca gtc acc aaa tac atc atg aca tgc atg tcg gcc    13911
Thr Leu Thr His Pro Val Thr Lys Tyr Ile Met Thr Cys Met Ser Ala
                400                 405                 410

gac ctg gag gtc gtc acg agc acc tgg gtg ctc gtt ggc ggc gtc ctg    13959
Asp Leu Glu Val Val Thr Ser Thr Trp Val Leu Val Gly Gly Val Leu
            415                 420                 425

gct gct ttg gcc gcg tat tgc ctg tca aca ggc tgc gtg gtc ata gtg    14007
Ala Ala Leu Ala Ala Tyr Cys Leu Ser Thr Gly Cys Val Val Ile Val
        430                 435                 440

ggc agg gtc gtc ttg tcc ggg aag ccg gca atc ata cct gac agg gaa    14055
Gly Arg Val Val Leu Ser Gly Lys Pro Ala Ile Ile Pro Asp Arg Glu
    445                 450                 455

gtc ctc tac cga gag ttc gat gag atg gaa gag tgc tct cag cac tta    14103
Val Leu Tyr Arg Glu Phe Asp Glu Met Glu Glu Cys Ser Gln His Leu
460                 465                 470                 475

ccg tac atc gag caa ggg atg atg ctc gcc gag cag ttc aag cag aag    14151
Pro Tyr Ile Glu Gln Gly Met Met Leu Ala Glu Gln Phe Lys Gln Lys
                480                 485                 490

gcc ctc ggc ctc ctg cag acc gcg tcc cgt cag gca gag gtt atc gcc    14199
Ala Leu Gly Leu Leu Gln Thr Ala Ser Arg Gln Ala Glu Val Ile Ala
            495                 500                 505

cct gct gtc cag acc aac tgg caa aaa ctc gag acc ttc tgg gcg aag    14247
Pro Ala Val Gln Thr Asn Trp Gln Lys Leu Glu Thr Phe Trp Ala Lys
        510                 515                 520

cat atg tgg aac ttc atc agt ggg ata caa tac ttg gcg ggc ttg tca    14295
His Met Trp Asn Phe Ile Ser Gly Ile Gln Tyr Leu Ala Gly Leu Ser
    525                 530                 535
```

-continued

```
acg ctg cct ggt aac ccc gcc att gct tca ttg atg gct ttt aca gct     14343
Thr Leu Pro Gly Asn Pro Ala Ile Ala Ser Leu Met Ala Phe Thr Ala
540                 545                 550                 555

gct gtc acc agc cca cta acc act agc caa acc ctc ctc ttc aac ata     14391
Ala Val Thr Ser Pro Leu Thr Thr Ser Gln Thr Leu Leu Phe Asn Ile
                560                 565                 570

ttg ggg ggg tgg gtg gct gcc cag ctc gcc gcc ccc ggt gcc gct act     14439
Leu Gly Gly Trp Val Ala Ala Gln Leu Ala Ala Pro Gly Ala Ala Thr
            575                 580                 585

gcc ttt gtg ggc gct ggc tta gct ggc gcc gcc atc ggc agt gtt gga     14487
Ala Phe Val Gly Ala Gly Leu Ala Gly Ala Ala Ile Gly Ser Val Gly
        590                 595                 600

ctg ggg aag gtc ctc ata gac atc ctt gca ggg tat ggc gcg ggc gtg     14535
Leu Gly Lys Val Leu Ile Asp Ile Leu Ala Gly Tyr Gly Ala Gly Val
    605                 610                 615

gcg gga gct ctt gtg gca ttc aag atc atg agc ggt gag gtc ccc tcc     14583
Ala Gly Ala Leu Val Ala Phe Lys Ile Met Ser Gly Glu Val Pro Ser
620                 625                 630                 635

acg gag gac ctg gtc aat cta ctg ccc gcc atc ctc tcg ccc gga gcc     14631
Thr Glu Asp Leu Val Asn Leu Leu Pro Ala Ile Leu Ser Pro Gly Ala
                640                 645                 650

ctc gta gtc ggc gtg gtc tgt gca gca ata ctg cgc cgg cac gtt ggc     14679
Leu Val Val Gly Val Val Cys Ala Ala Ile Leu Arg Arg His Val Gly
            655                 660                 665

ccg ggc gag ggg gca gtg cag tgg atg aac cgg ctg ata gcc ttc gcc     14727
Pro Gly Glu Gly Ala Val Gln Trp Met Asn Arg Leu Ile Ala Phe Ala
        670                 675                 680

tcc cgg ggg aac cat gtt tcc ccc acg cac tac gtg ccg gag agc gat     14775
Ser Arg Gly Asn His Val Ser Pro Thr His Tyr Val Pro Glu Ser Asp
    685                 690                 695

gca gct gcc cgc gtc act gcc ata ctc agc agc ctc act gta acc cag     14823
Ala Ala Ala Arg Val Thr Ala Ile Leu Ser Ser Leu Thr Val Thr Gln
700                 705                 710                 715

ctc ctg agg cga ctg cac cag tgg ata agc tcg gag tgt acc act cca     14871
Leu Leu Arg Arg Leu His Gln Trp Ile Ser Ser Glu Cys Thr Thr Pro
                720                 725                 730

tgc tcc ggt tcc tgg cta agg gac atc tgg gac tgg ata tgc gag gtg     14919
Cys Ser Gly Ser Trp Leu Arg Asp Ile Trp Asp Trp Ile Cys Glu Val
            735                 740                 745

ttg agc gac ttt aag acc tgg cta aaa gct aag ctc atg cca cag ctg     14967
Leu Ser Asp Phe Lys Thr Trp Leu Lys Ala Lys Leu Met Pro Gln Leu
        750                 755                 760

cct ggg atc ccc ttt gtg tcc tgc cag cgc ggg tat aag ggg gtc tgg     15015
Pro Gly Ile Pro Phe Val Ser Cys Gln Arg Gly Tyr Lys Gly Val Trp
    765                 770                 775

cga ggg gac ggc atc atg cac act cgc tgc cac tgt gga gct gag atc     15063
Arg Gly Asp Gly Ile Met His Thr Arg Cys His Cys Gly Ala Glu Ile
780                 785                 790                 795

act gga cat gtc aaa aac ggg acg atg agg atc gtc ggt cct agg acc     15111
Thr Gly His Val Lys Asn Gly Thr Met Arg Ile Val Gly Pro Arg Thr
                800                 805                 810

tgc agg aac atg tgg agt ggg acc ttc ccc att aat gcc tac acc acg     15159
Cys Arg Asn Met Trp Ser Gly Thr Phe Pro Ile Asn Ala Tyr Thr Thr
            815                 820                 825

ggc ccc tgt acc ccc ctt cct gcg ccg aac tac acg ttc gcg cta tgg     15207
Gly Pro Cys Thr Pro Leu Pro Ala Pro Asn Tyr Thr Phe Ala Leu Trp
        830                 835                 840

agg gtg tct gca gag gaa tac gtg gag ata agg cag gtg ggg gac ttc     15255
Arg Val Ser Ala Glu Glu Tyr Val Glu Ile Arg Gln Val Gly Asp Phe
```

-continued

```
    845                 850                 855

cac tac gtg acg ggt atg act act gac aat ctt aaa tgc ccg tgc cag    15303
His Tyr Val Thr Gly Met Thr Thr Asp Asn Leu Lys Cys Pro Cys Gln
860                 865                 870                 875

gtc cca tcg ccc gaa ttt ttc aca gaa ttg gac ggg gtg cgc cta cat    15351
Val Pro Ser Pro Glu Phe Phe Thr Glu Leu Asp Gly Val Arg Leu His
                880                 885                 890

agg ttt gcg ccc ccc tgc aag ccc ttg ctg cgg gag gag gta tca ttc    15399
Arg Phe Ala Pro Pro Cys Lys Pro Leu Leu Arg Glu Glu Val Ser Phe
            895                 900                 905

aga gta gga ctc cac gaa tac ccg gta ggg tcg caa tta cct tgc gag    15447
Arg Val Gly Leu His Glu Tyr Pro Val Gly Ser Gln Leu Pro Cys Glu
        910                 915                 920

ccc gaa ccg gac gtg gcc gtg ttg acg tcc atg ctc act gat ccc tcc    15495
Pro Glu Pro Asp Val Ala Val Leu Thr Ser Met Leu Thr Asp Pro Ser
    925                 930                 935

cat ata aca gca gag gcg gcc ggg cga agg ttg gcg agg gga tca ccc    15543
His Ile Thr Ala Glu Ala Ala Gly Arg Arg Leu Ala Arg Gly Ser Pro
940                 945                 950                 955

ccc tct gtg gcc agc tcc tcg gct agc cag cta tcc gct cca tct ctc    15591
Pro Ser Val Ala Ser Ser Ser Ala Ser Gln Leu Ser Ala Pro Ser Leu
                960                 965                 970

aag gca act tgc acc gct aac cat gac tcc cct gat gct gag ctc ata    15639
Lys Ala Thr Cys Thr Ala Asn His Asp Ser Pro Asp Ala Glu Leu Ile
            975                 980                 985

gag gcc aac ctc cta tgg agg cag gag atg ggc ggc aac atc acc agg    15687
Glu Ala Asn Leu Leu Trp Arg Gln Glu Met Gly Gly Asn Ile Thr Arg
        990                 995                1000

gtt gag tca gaa aac aaa gtg gtg att ctg gac tcc ttc gat ccg ctt    15735
Val Glu Ser Glu Asn Lys Val Val Ile Leu Asp Ser Phe Asp Pro Leu
   1005                1010                1015

gtg gcg gag gag gac gag cgg gag atc tcc gta ccc gca gaa atc ctg    15783
Val Ala Glu Glu Asp Glu Arg Glu Ile Ser Val Pro Ala Glu Ile Leu
1020                1025                1030                1035

cgg aag tct cgg aga ttc gcc cag gcc ctg ccc gtt tgg gcg cgg ccg    15831
Arg Lys Ser Arg Arg Phe Ala Gln Ala Leu Pro Val Trp Ala Arg Pro
               1040                1045                1050

gac tat aac ccc ccg cta gtg gag acg tgg aaa aag ccc gac tac gaa    15879
Asp Tyr Asn Pro Pro Leu Val Glu Thr Trp Lys Lys Pro Asp Tyr Glu
           1055                1060                1065

cca cct gtg gtc cat ggc tgc ccg ctt cca cct cca aag tcc cct cct    15927
Pro Pro Val Val His Gly Cys Pro Leu Pro Pro Pro Lys Ser Pro Pro
       1070                1075                1080

gtg cct ccg cct cgg aag aag cgg acg gtg gtc ctc act gaa tca acc    15975
Val Pro Pro Pro Arg Lys Lys Arg Thr Val Val Leu Thr Glu Ser Thr
   1085                1090                1095

cta tct act gcc ttg gcc gag ctc gcc acc aga agc ttt ggc agc tcc    16023
Leu Ser Thr Ala Leu Ala Glu Leu Ala Thr Arg Ser Phe Gly Ser Ser
1100                1105                1110                1115

tca act tcc ggc att acg ggc gac aat acg aca aca tcc tct gag ccc    16071
Ser Thr Ser Gly Ile Thr Gly Asp Asn Thr Thr Thr Ser Ser Glu Pro
               1120                1125                1130

gcc cct tct ggc tgc ccc ccc gac tcc gac gct gag tcc tat tcc tcc    16119
Ala Pro Ser Gly Cys Pro Pro Asp Ser Asp Ala Glu Ser Tyr Ser Ser
           1135                1140                1145

atg ccc ccc ctg gag ggg gag cct ggg gat ccg gat ctt agc gac ggg    16167
Met Pro Pro Leu Glu Gly Glu Pro Gly Asp Pro Asp Leu Ser Asp Gly
       1150                1155                1160

tca tgg tca acg gtc agt agt gag gcc aac gcg gag gat gtc gtg tgc    16215
```

-continued

```
Ser Trp Ser Thr Val Ser Ser Glu Ala Asn Ala Glu Asp Val Val Cys
   1165                1170                1175

tgc tca atg tct tac tct tgg aca ggc gca ctc gtc acc ccg tgc gcc    16263
Cys Ser Met Ser Tyr Ser Trp Thr Gly Ala Leu Val Thr Pro Cys Ala
1180                1185                1190                1195

gcg gaa gaa cag aaa ctg ccc atc aat gca cta agc aac tcg ttg cta    16311
Ala Glu Glu Gln Lys Leu Pro Ile Asn Ala Leu Ser Asn Ser Leu Leu
                1200                1205                1210

cgt cac cac aat ttg gtg tat tcc acc acc tca cgc agt gct tgc caa    16359
Arg His His Asn Leu Val Tyr Ser Thr Thr Ser Arg Ser Ala Cys Gln
            1215                1220                1225

agg cag aag aaa gtc aca ttt gac aga ctg caa gtt ctg gac agc cat    16407
Arg Gln Lys Lys Val Thr Phe Asp Arg Leu Gln Val Leu Asp Ser His
        1230                1235                1240

tac cag gac gta ctc aag gag gtt aaa gca gcg gcg tca aaa gtg aag    16455
Tyr Gln Asp Val Leu Lys Glu Val Lys Ala Ala Ala Ser Lys Val Lys
   1245                1250                1255

gct aac ttg cta tcc gta gag gaa gct tgc agc ctg acg ccc cca cac    16503
Ala Asn Leu Leu Ser Val Glu Glu Ala Cys Ser Leu Thr Pro Pro His
1260                1265                1270                1275

tca gcc aaa tcc aag ttt ggt tat ggg gca aaa gac gtc cgt tgc cat    16551
Ser Ala Lys Ser Lys Phe Gly Tyr Gly Ala Lys Asp Val Arg Cys His
                1280                1285                1290

gcc aga aag gcc gta acc cac atc aac tcc gtg tgg aaa gac ctt ctg    16599
Ala Arg Lys Ala Val Thr His Ile Asn Ser Val Trp Lys Asp Leu Leu
            1295                1300                1305

gaa gac aat gta aca cca ata gac act acc atc atg gct aag aac gag    16647
Glu Asp Asn Val Thr Pro Ile Asp Thr Thr Ile Met Ala Lys Asn Glu
        1310                1315                1320

gtt ttc tgc gtt cag cct gag aag ggg ggt cgt aag cca gct cgt ctc    16695
Val Phe Cys Val Gln Pro Glu Lys Gly Gly Arg Lys Pro Ala Arg Leu
   1325                1330                1335

atc gtg ttc ccc gat ctg ggc gtg cgc gtg tgc gaa aag atg gct ttg    16743
Ile Val Phe Pro Asp Leu Gly Val Arg Val Cys Glu Lys Met Ala Leu
1340                1345                1350                1355

tac gac gtg gtt aca aag ctc ccc ttg gcc gtg atg gga agc tcc tac    16791
Tyr Asp Val Val Thr Lys Leu Pro Leu Ala Val Met Gly Ser Ser Tyr
                1360                1365                1370

gga ttc caa tac tca cca gga cag cgg gtt gaa ttc ctc gtg caa gcg    16839
Gly Phe Gln Tyr Ser Pro Gly Gln Arg Val Glu Phe Leu Val Gln Ala
            1375                1380                1385

tgg aag tcc aag aaa acc cca atg ggg ttc tcg tat gat acc cgc tgc    16887
Trp Lys Ser Lys Lys Thr Pro Met Gly Phe Ser Tyr Asp Thr Arg Cys
        1390                1395                1400

ttt gac tcc aca gtc act gag agc gac atc cgt acg gag gag gca atc    16935
Phe Asp Ser Thr Val Thr Glu Ser Asp Ile Arg Thr Glu Glu Ala Ile
   1405                1410                1415

tac caa tgt tgt gac ctc gac ccc caa gcc cgc gtg gcc atc aag tcc    16983
Tyr Gln Cys Cys Asp Leu Asp Pro Gln Ala Arg Val Ala Ile Lys Ser
1420                1425                1430                1435

ctc acc gag agg ctt tat gtt ggg ggc cct ctt acc aat tca agg ggg    17031
Leu Thr Glu Arg Leu Tyr Val Gly Gly Pro Leu Thr Asn Ser Arg Gly
                1440                1445                1450

gag aac tgc ggc tat cgc agg tgc cgc gcg agc ggc gta ctg aca act    17079
Glu Asn Cys Gly Tyr Arg Arg Cys Arg Ala Ser Gly Val Leu Thr Thr
            1455                1460                1465

agc tgt ggt aac acc ctc act tgc tac atc aag gcc cgg gca gcc tgt    17127
Ser Cys Gly Asn Thr Leu Thr Cys Tyr Ile Lys Ala Arg Ala Ala Cys
        1470                1475                1480
```

-continued

```
cga gcc gca ggg ctc cag gac tgc acc atg ctc gtg tgt ggc gac gac    17175
Arg Ala Ala Gly Leu Gln Asp Cys Thr Met Leu Val Cys Gly Asp Asp
   1485                1490                1495

tta gtc gtt atc tgt gaa agc gcg ggg gtc cag gag gac gcg gcg agc    17223
Leu Val Val Ile Cys Glu Ser Ala Gly Val Gln Glu Asp Ala Ala Ser
1500                1505                1510                1515

ctg aga gcc ttc acg gag gct atg acc agg tac tcc gcc ccc cct ggg    17271
Leu Arg Ala Phe Thr Glu Ala Met Thr Arg Tyr Ser Ala Pro Pro Gly
               1520                1525                1530

gac ccc cca caa cca gaa tac gac ttg gag ctc ata aca tca tgc tcc    17319
Asp Pro Pro Gln Pro Glu Tyr Asp Leu Glu Leu Ile Thr Ser Cys Ser
           1535                1540                1545

tcc aac gtg tca gtc gcc cac gac ggc gct gga aag agg gtc tac tac    17367
Ser Asn Val Ser Val Ala His Asp Gly Ala Gly Lys Arg Val Tyr Tyr
       1550                1555                1560

ctc acc cgt gac cct aca acc ccc ctc gcg aga gct gcg tgg gag aca    17415
Leu Thr Arg Asp Pro Thr Thr Pro Leu Ala Arg Ala Ala Trp Glu Thr
   1565                1570                1575

gca aga cac act cca gtc aat tcc tgg cta ggc aac ata atc atg ttt    17463
Ala Arg His Thr Pro Val Asn Ser Trp Leu Gly Asn Ile Ile Met Phe
1580                1585                1590                1595

gcc ccc aca ctg tgg gcg agg atg ata ctg atg acc cat ttc ttt agc    17511
Ala Pro Thr Leu Trp Ala Arg Met Ile Leu Met Thr His Phe Phe Ser
               1600                1605                1610

gtc ctt ata gcc agg gac cag ctt gaa cag gcc ctc gat tgc gag atc    17559
Val Leu Ile Ala Arg Asp Gln Leu Glu Gln Ala Leu Asp Cys Glu Ile
           1615                1620                1625

tac ggg gcc tgc tac tcc ata gaa cca ctg gat cta cct cca atc att    17607
Tyr Gly Ala Cys Tyr Ser Ile Glu Pro Leu Asp Leu Pro Pro Ile Ile
       1630                1635                1640

caa aga ctc cat ggc ctc agc gca ttt tca ctc cac agt tac tct cca    17655
Gln Arg Leu His Gly Leu Ser Ala Phe Ser Leu His Ser Tyr Ser Pro
   1645                1650                1655

ggt gaa atc aat agg gtg gcc gca tgc ctc aga aaa ctt ggg gta ccg    17703
Gly Glu Ile Asn Arg Val Ala Ala Cys Leu Arg Lys Leu Gly Val Pro
1660                1665                1670                1675

ccc ttg cga gct tgg aga cac cgg gcc cgg agc gtc cgc gct agg ctt    17751
Pro Leu Arg Ala Trp Arg His Arg Ala Arg Ser Val Arg Ala Arg Leu
               1680                1685                1690

ctg gcc aga gga ggc agg gct gcc ata tgt ggc aag tac ctc ttc aac    17799
Leu Ala Arg Gly Gly Arg Ala Ala Ile Cys Gly Lys Tyr Leu Phe Asn
           1695                1700                1705

tgg gca gta aga aca aag ctc aaa ctc act cca ata gcg gcc gct ggc    17847
Trp Ala Val Arg Thr Lys Leu Lys Leu Thr Pro Ile Ala Ala Ala Gly
       1710                1715                1720

cag ctg gac ttg tcc ggc tgg ttc acg gct ggc tac agc ggg gga gac    17895
Gln Leu Asp Leu Ser Gly Trp Phe Thr Ala Gly Tyr Ser Gly Gly Asp
   1725                1730                1735

att tat cac agc gtg tct cat gcc cgg ccc cgc tgg atc tgg ttt tgc    17943
Ile Tyr His Ser Val Ser His Ala Arg Pro Arg Trp Ile Trp Phe Cys
1740                1745                1750                1755

cta ctc ctg ctt gct gca ggg gta ggc atc tac ctc ctc ccc aac cga    17991
Leu Leu Leu Leu Ala Ala Gly Val Gly Ile Tyr Leu Leu Pro Asn Arg
               1760                1765                1770

atg agc acg aat cct aaa cct caa aga aag acc aaa cgt aac acc aac    18039
Met Ser Thr Asn Pro Lys Pro Gln Arg Lys Thr Lys Arg Asn Thr Asn
           1775                1780                1785

cgg cgg ccg cag gac gtc aag ttc ccg ggt ggc ggt cag atc gtt ggt    18087
Arg Arg Pro Gln Asp Val Lys Phe Pro Gly Gly Gly Gln Ile Val Gly
       1790                1795                1800
```

-continued

```
gga gtt tac ttg ttg ccg cgc agg ggc cct aga ttg ggt gtg cgc gcg    18135
Gly Val Tyr Leu Leu Pro Arg Arg Gly Pro Arg Leu Gly Val Arg Ala
   1805               1810               1815

acg aga aag act tcc gag cgg tcg caa cct cga ggt aga cgt cag cct    18183
Thr Arg Lys Thr Ser Glu Arg Ser Gln Pro Arg Gly Arg Arg Gln Pro
1820               1825               1830               1835

atc ccc aag gct cgt cgg ccc gag ggc agg acc tgg gct cag ccc ggg    18231
Ile Pro Lys Ala Arg Arg Pro Glu Gly Arg Thr Trp Ala Gln Pro Gly
               1840               1845               1850

tac cct tgg ccc ctc tat ggc aat gag ggc tgc ggg tgg gcg gga tgg    18279
Tyr Pro Trp Pro Leu Tyr Gly Asn Glu Gly Cys Gly Trp Ala Gly Trp
           1855               1860               1865

ctc ctg tct ccc cgt ggc tct cgg cct agc tgg ggc ccc aca gac ccc    18327
Leu Leu Ser Pro Arg Gly Ser Arg Pro Ser Trp Gly Pro Thr Asp Pro
       1870               1875               1880

cgg cgt agg tcg cgc aat ttg ggt aag gtc atc gat acc ctt acg tgc    18375
Arg Arg Arg Ser Arg Asn Leu Gly Lys Val Ile Asp Thr Leu Thr Cys
   1885               1890               1895

ggc ttc gcc gac ctc atg ggg tac ata ccg ctc gtc taatagtcga         18421
Gly Phe Ala Asp Leu Met Gly Tyr Ile Pro Leu Val
1900               1905               1910

ctttgttccc actgtacttt tagctcgtac aaaatacaat atacttttca tttctccgta  18481

aacaacatgt tttcccatgt aatatccttt tctatttttc gttccgttac caactttaca  18541

catactttat atagctattc acttctatac actaaaaaac taagacaatt ttaattttgc  18601

tgcctgccat atttcaattt gttataaatt cctataattt atcctattag tagctaaaaa  18661

aagatgaatg tgaatcgaat cctaagagaa ttggatctga tccacaggac gggtgtggtc  18721

gccatgatcg cgtagtcgat agtggctcca agtagcgaag cgagcaggac tgggcggcgg  18781

ccaaagcggt cggacagtgc tccgagaacg ggtgcgcata gaaattgcat caacgcatat  18841

agcgctagca gcacgccata gtgactggcg atgctgtcgg aatggacgat atcccgcaag  18901

aggcccggca gtaccggcat aaccaagcct atgcctacag catccagggt gacggtgccg  18961

aggatgacga tgagcgcatt gttagatttc atacacggtg cctgactgcg ttagcaattt  19021

aactgtgata aactaccgca ttaaagcttt ttctttccaa tttttttttt ttcgtcatta  19081

taaaaatcat tacgaccgag attcccgggt aataactgat ataattaaat tgaagctcta  19141

atttgtgagt ttagtataca tgcatttact tataatacag ttttttagtt ttgctggccg  19201

catcttctca aatatgcttc ccagcctgct tttctgtaac gttcaccctc taccttagca  19261

tcccttccct ttgcaaatag tcctcttcca acaataataa tgtcagatcc tgtagagacc  19321

acatcatcca cggttctata ctgttgaccc aatgcgtctc ccttgtcatc taaacccaca  19381

ccgggtgtca taatcaacca atcgtaacct tcatctcttc cacccatgtc tctttgagca  19441

ataaagccga taacaaaatc tttgtcgctc ttcgcaatgt caacagtacc cttagtatat  19501

tctccagtag atagggagcc cttgcatgac aattctgcta acatcaaaag gcctctaggt  19561

tcctttgtta cttcttctgc cgcctgcttc aaaccgctaa caatacctgg gcccaccaca  19621

ccgtgtgcat tcgtaatgtc tgcccattct gctattctgt atacacccgc agagtactgc  19681

aatttgactg tattaccaat gtcagcaaat tttctgtctt cgaagagtaa aaaattgtac  19741

ttggcggata atgcctttag cggcttaact gtgccctcca tggaaaaatc agtcaagata  19801

tccacatgtg tttttagtaa acaaattttg ggacctaatg cttcaactaa ctccagtaat  19861

tccttggtgg tacgaacatc caatgaagca cacaagtttg tttgcttttc gtgcatgata  19921
```

-continued

```
ttaaatagct tggcagcaac aggactagga tgagtagcag cacgttcctt atatgtagct  19981

ttcgacatga tttatcttcg tttcctgcag gtttttgttc tgtgcagttg ggttaagaat  20041

actgggcaat ttcatgtttc ttcaacacta catatgcgta tatataccaa tctaagtctg  20101

tgctccttcc ttcgttcttc cttctgttcg gagattaccg aatcaaaaaa atttcaagga  20161

aaccgaaatc aaaaaaaaga ataaaaaaaa aatgatgaat tgaaaagctt atcgat      20217
```

<210> SEQ ID NO 17
<211> LENGTH: 1911
<212> TYPE: PRT
<213> ORGANISM: Artificial Sequence
<220> FEATURE:
<223> OTHER INFORMATION: Description of Artificial Sequence:
      pd.delta.NS3NS5.pj.core140

<400> SEQUENCE: 17

```
Met Ala Ala Tyr Ala Ala Gln Gly Tyr Lys Val Leu Val Leu Asn Pro
  1               5                  10                  15

Ser Val Ala Ala Thr Leu Gly Phe Gly Ala Tyr Met Ser Lys Ala His
             20                  25                  30

Gly Ile Asp Pro Asn Ile Arg Thr Gly Val Arg Thr Ile Thr Thr Gly
         35                  40                  45

Ser Pro Ile Thr Tyr Ser Thr Tyr Gly Lys Phe Leu Ala Asp Gly Gly
     50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
```

-continued

```
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
    370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
        435                 440                 445

Ser Gly Lys Pro Ala Ile Ile Pro Asp Arg Glu Val Leu Tyr Arg Glu
    450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735
```

-continued

```
Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
        835                 840                 845

Glu Tyr Val Glu Ile Arg Gln Val Gly Asp Phe His Tyr Val Thr Gly
    850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
    930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu Asp
   1010                 1015                1020

Glu  Arg Glu Ile Ser Val  Pro Ala Glu Ile Leu  Arg Lys Ser Arg Arg
1025                 1030                 1035                 1040

Phe Ala Gln Ala Leu  Pro Val Trp Ala Arg  Pro Asp Tyr Asn Pro  Pro
                1045                 1050                 1055

Leu Val Glu Thr  Trp Lys Lys Pro Asp  Tyr Glu Pro Pro Val  Val His
            1060                 1065                 1070

Gly Cys Pro  Leu Pro Pro Pro Lys  Ser Pro Pro Val Pro  Pro Pro Arg
        1075                 1080                 1085

Lys Lys  Arg Thr Val Val Leu  Thr Glu Ser Thr Leu  Ser Thr Ala Leu
    1090                 1095                 1100

Ala  Glu Leu Ala Thr Arg  Ser Phe Gly Ser Ser  Ser Thr Ser Gly Ile
1105                 1110                 1115                 1120

Thr Gly Asp Asn Thr  Thr Thr Ser Ser Glu  Pro Ala Pro Ser Gly  Cys
                1125                 1130                 1135

Pro Pro Asp Ser  Asp Ala Glu Ser Tyr  Ser Ser Met Pro Pro  Leu Glu
            1140                 1145                 1150
```

-continued

Gly Glu Pro Gly Asp Pro Asp Leu Ser Asp Gly Ser Trp Ser Thr Val
1155 1160 1165

Ser Ser Glu Ala Asn Ala Glu Asp Val Val Cys Cys Ser Met Ser Tyr
1170 1175 1180

Ser Trp Thr Gly Ala Leu Val Thr Pro Cys Ala Ala Glu Glu Gln Lys
1185 1190 1195 1200

Leu Pro Ile Asn Ala Leu Ser Asn Ser Leu Leu Arg His His Asn Leu
1205 1210 1215

Val Tyr Ser Thr Thr Ser Arg Ser Ala Cys Gln Arg Gln Lys Lys Val
1220 1225 1230

Thr Phe Asp Arg Leu Gln Val Leu Asp Ser His Tyr Gln Asp Val Leu
1235 1240 1245

Lys Glu Val Lys Ala Ala Ala Ser Lys Val Lys Ala Asn Leu Leu Ser
1250 1255 1260

Val Glu Glu Ala Cys Ser Leu Thr Pro Pro His Ser Ala Lys Ser Lys
1265 1270 1275 1280

Phe Gly Tyr Gly Ala Lys Asp Val Arg Cys His Ala Arg Lys Ala Val
1285 1290 1295

Thr His Ile Asn Ser Val Trp Lys Asp Leu Leu Glu Asp Asn Val Thr
1300 1305 1310

Pro Ile Asp Thr Thr Ile Met Ala Lys Asn Glu Val Phe Cys Val Gln
1315 1320 1325

Pro Glu Lys Gly Gly Arg Lys Pro Ala Arg Leu Ile Val Phe Pro Asp
1330 1335 1340

Leu Gly Val Arg Val Cys Glu Lys Met Ala Leu Tyr Asp Val Val Thr
1345 1350 1355 1360

Lys Leu Pro Leu Ala Val Met Gly Ser Ser Tyr Gly Phe Gln Tyr Ser
1365 1370 1375

Pro Gly Gln Arg Val Glu Phe Leu Val Gln Ala Trp Lys Ser Lys Lys
1380 1385 1390

Thr Pro Met Gly Phe Ser Tyr Asp Thr Arg Cys Phe Asp Ser Thr Val
1395 1400 1405

Thr Glu Ser Asp Ile Arg Thr Glu Glu Ala Ile Tyr Gln Cys Cys Asp
1410 1415 1420

Leu Asp Pro Gln Ala Arg Val Ala Ile Lys Ser Leu Thr Glu Arg Leu
1425 1430 1435 1440

Tyr Val Gly Gly Pro Leu Thr Asn Ser Arg Gly Glu Asn Cys Gly Tyr
1445 1450 1455

Arg Arg Cys Arg Ala Ser Gly Val Leu Thr Thr Ser Cys Gly Asn Thr
1460 1465 1470

Leu Thr Cys Tyr Ile Lys Ala Arg Ala Ala Cys Arg Ala Ala Gly Leu
1475 1480 1485

Gln Asp Cys Thr Met Leu Val Cys Gly Asp Asp Leu Val Val Ile Cys
1490 1495 1500

Glu Ser Ala Gly Val Gln Glu Asp Ala Ala Ser Leu Arg Ala Phe Thr
1505 1510 1515 1520

Glu Ala Met Thr Arg Tyr Ser Ala Pro Pro Gly Asp Pro Pro Gln Pro
1525 1530 1535

Glu Tyr Asp Leu Glu Leu Ile Thr Ser Cys Ser Ser Asn Val Ser Val
1540 1545 1550

Ala His Asp Gly Ala Gly Lys Arg Val Tyr Tyr Leu Thr Arg Asp Pro
1555 1560 1565

Thr Thr Pro Leu Ala Arg Ala Ala Trp Glu Thr Ala Arg His Thr Pro

-continued

```
    1570                1575                1580

Val  Asn Ser Trp Leu Gly  Asn Ile Ile Met Phe  Ala Pro Thr Leu Trp
1585                1590                1595                1600

Ala Arg Met Ile Leu  Met Thr His Phe Phe  Ser Val Leu Ile Ala  Arg
                1605                1610                1615

Asp Gln Leu Glu  Gln Ala Leu Asp Cys  Glu Ile Tyr Gly Ala  Cys Tyr
            1620                1625                1630

Ser Ile Glu  Pro Leu Asp Leu Pro  Pro Ile Ile Gln Arg  Leu His Gly
        1635                1640                1645

Leu Ser  Ala Phe Ser Leu His  Ser Tyr Ser Pro Gly  Glu Ile Asn Arg
    1650                1655                1660

Val  Ala Ala Cys Leu Arg  Lys Leu Gly Val Pro  Pro Leu Arg Ala Trp
1665                1670                1675                1680

Arg His Arg Ala Arg  Ser Val Arg Ala Arg  Leu Leu Ala Arg Gly  Gly
                1685                1690                1695

Arg Ala Ala Ile  Cys Gly Lys Tyr Leu  Phe Asn Trp Ala Val  Arg Thr
            1700                1705                1710

Lys Leu Lys  Leu Thr Pro Ile Ala  Ala Ala Gly Gln Leu  Asp Leu Ser
        1715                1720                1725

Gly Trp  Phe Thr Ala Gly Tyr  Ser Gly Gly Asp Ile  Tyr His Ser Val
    1730                1735                1740

Ser  His Ala Arg Pro Arg  Trp Ile Trp Phe Cys  Leu Leu Leu Leu Ala
1745                1750                1755                1760

Ala Gly Val Gly Ile  Tyr Leu Leu Pro Asn  Arg Met Ser Thr Asn  Pro
                1765                1770                1775

Lys Pro Gln Arg  Lys Thr Lys Arg Asn  Thr Asn Arg Arg Pro  Gln Asp
            1780                1785                1790

Val Lys Phe  Pro Gly Gly Gly Gln  Ile Val Gly Gly Val  Tyr Leu Leu
        1795                1800                1805

Pro Arg  Arg Gly Pro Arg Leu  Gly Val Arg Ala Thr  Arg Lys Thr Ser
    1810                1815                1820

Glu  Arg Ser Gln Pro Arg  Gly Arg Arg Gln Pro  Ile Pro Lys Ala Arg
1825                1830                1835                1840

Arg Pro Glu Gly Arg  Thr Trp Ala Gln Pro  Gly Tyr Pro Trp Pro  Leu
                1845                1850                1855

Tyr Gly Asn Glu  Gly Cys Gly Trp Ala  Gly Trp Leu Leu Ser  Pro Arg
            1860                1865                1870

Gly Ser Arg  Pro Ser Trp Gly Pro  Thr Asp Pro Arg Arg  Arg Ser Arg
        1875                1880                1885

Asn Leu  Gly Lys Val Ile Asp  Thr Leu Thr Cys Gly  Phe Ala Asp Leu
    1890                1895                1900

Met  Gly Tyr Ile Pro Leu Val
1905                1910
```

```
<210> SEQ ID NO 18
<211> LENGTH: 20247
<212> TYPE: DNA
<213> ORGANISM: Artificial Sequence
<220> FEATURE:
<223> OTHER INFORMATION: Description of Artificial Sequence:
      pd.delta.NS3NS5.pj.core150
<221> NAME/KEY: CDS
<222> LOCATION: (12679)..(18441)

<400> SEQUENCE: 18

atcgatccta ccccttgcgc taaagaagta tatgtgccta ctaacgcttg tctttgtctc     60
```

-continued

```
tgtcactaaa cactggatta ttactcccag atacttattt tggactaatt taaatgattt    120
cggatcaacg ttcttaatat cgctgaatct tccacaattg atgaaagtag ctaggaagag    180
gaattggtat aaagtttttg tttttgtaaa tctcgaagta tactcaaacg aatttagtat    240
tttctcagtg atctcccaga tgctttcacc ctcacttaga agtgctttaa gcattttttt    300
actgtggcta tttcccttat ctgcttcttc cgatgattcg aactgtaatt gcaaactact    360
tacaatatca gtgatatcag attgatgttt ttgtccatag taaggaataa ttgtaaattc    420
ccaagcagga atcaatttct ttaatgaggc ttccagaatt gttgcttttt gcgtcttgta    480
tttaaactgg agtgatttat tgacaatatc gaaactcagc gaattgctta tgatagtatt    540
atagctcatg aatgtggctc tcttgattgc tgttccgtta tgtgtaatca tccaacataa    600
ataggttagt tcagcagcac ataatgctat tttctcacct gaaggtcttt caaacctttc    660
cacaaactga cgaacaagca ccttaggtgg tgttttacat aatatatcaa attgtggcat    720
gcttagcgcc gatcttgtgt gcaattgata tctagtttca actactctat ttatcttgta    780
tcttgcagta ttcaaacacg ctaactcgaa aaactaactt taattgtcct gtttgtctcg    840
cgttctttcg aaaaatgcac cggccgcgca ttatttgtac tgcgaaaata attggtactg    900
cggtatcttc atttcatatt ttaaaaatgc acctttgctg cttttcctta atttttagac    960
ggcccgcagg ttcgttttgc ggtactatct tgtgataaaa agttgttttg acatgtgatc   1020
tgcacagatt ttataatgta ataagcaaga atacattatc aaacgaacaa tactggtaaa   1080
agaaaaccaa aatggacgac attgaaacag ccaagaatct gacggtaaaa gcacgtacag   1140
cttatagcgt ctgggatgta tgtcggctgt ttattgaaat gattgctcct gatgtagata   1200
ttgatataga gagtaaacgt aagtctgatg agctactctt tccaggatat gtcataaggc   1260
ccatggaatc tctcacaacc ggtaggccgt atggtcttga ttctagcgca gaagattcca   1320
gcgtatcttc tgactccagt gctgaggtaa ttttgcctgc tgcgaagatg gttaaggaaa   1380
ggtttgattc gattggaaat ggtatgctct cttcacaaga agcaagtcag gctgccatag   1440
atttgatgct acagaataac aagctgttag acaatagaaa gcaactatac aaatctattg   1500
ctataataat aggaagattg cccgagaaag acaagaagag agctaccgaa atgctcatga   1560
gaaaaatgga ttgtacacag ttattagtcc caccagctcc aacggaagaa gatgttatga   1620
agctcgtaag cgtcgttacc caattgctta ctttagttcc accagatcgt caagctgctt   1680
taataggtga tttattcatc ccggaatctc taaaggatat attcaatagt ttcaatgaac   1740
tggcggcaga gaatcgttta cagcaaaaaa agagtgagtt ggaaggaagg actgaagtga   1800
accatgctaa tacaaatgaa gaagttccct ccaggcgaac aagaagtaga gacacaaatg   1860
caagaggagc atataaatta caaaacacca tcactgaggg ccctaaagcg gttcccacga   1920
aaaaaaggag agtagcaacg agggtaaggg gcagaaaatc acgtaatact tctagggtat   1980
gatccaatat caaaggaaat gatagcattg aaggatgaga ctaatccaat tgaggagtgg   2040
cagcatatag aacagctaaa gggtagtgct gaaggaagca tacgataccc cgcatggaat   2100
gggataatat cacaggaggt actagactac ctttcatcct acataaatag acgcatataa   2160
gtacgcattt aagcataaac acgcactatg ccgttcttct catgtatata tatatacagg   2220
caacacgcag atataggtgc gacgtgaaca gtgagctgta tgtgcgcagc tcgcgttgca   2280
ttttcggaag cgctcgtttt cggaaacgct ttgaagttcc tattccgaag ttcctattct   2340
ctagaaagta taggaacttc agagcgcttt tgaaaaccaa aagcgctctg aagacgcact   2400
```

-continued

```
ttcaaaaaac caaaaacgca ccggactgta acgagctact aaaatattgc gaataccgct   2460
tccacaaaca ttgctcaaaa gtatctcttt gctatatatc tctgtgctat atccctatat   2520
aacctaccca tccacctttc gctccttgaa cttgcatcta aactcgacct ctacatcaac   2580
aggcttccaa tgctcttcaa attttactgt caagtagacc catacggctg taatatgctg   2640
ctcttcataa tgtaagctta tctttatcga atcgtgtgaa aaactactac cgcgataaac   2700
ctttacggtt ccctgagatt gaattagttc ctttagtata tgatacaaga cacttttgaa   2760
ctttgtacga cgaattttga ggttcgccat cctctggcta tttccaatta tcctgtcggc   2820
tattatctcc gcctcagttt gatcttccgc ttcagactgc catttttcac ataatgaatc   2880
tatttcaccc cacaatcctt catccgcctc cgcatcttgt tccgttaaac tattgacttc   2940
atgttgtaca ttgtttagtt cacgagaagg gtcctcttca ggcggtagct cctgatctcc   3000
tatatgacct ttatcctgtt ctctttccac aaacttagaa atgtattcat gaattatgga   3060
gcacctaata acattcttca aggcggagaa gtttgggcca gatgcccaat atgcttgaca   3120
tgaaaacgtg agaatgaatt tagtattatt gtgatattct gaggcaattt tattataatc   3180
tcgaagataa gagaagaatg cagtgacctt tgtattgaca aatggagatt ccatgtatct   3240
aaaaaatacg cctttaggcc ttctgatacc ctttcccctg cggtttagcg tgccttttac   3300
attaatatct aaaccctctc cgatggtggc ctttaactga ctaataaatg caaccgatat   3360
aaactgtgat aattctgggt gatttatgat tcgatcgaca attgtattgt acactagtgc   3420
aggatcaggc caatccagtt ctttttcaat taccggtgtg tcgtctgtat tcagtacatg   3480
tccaacaaat gcaaatgcta acgttttgta tttcttataa ttgtcaggaa ctggaaaagt   3540
ccccccttgtc gtctcgatta cacacctact ttcatcgtac accataggtt ggaagtgctg   3600
cataatacat tgcttaatac aagcaagcag tctctcgcca ttcatatttc agttattttc   3660
cattacagct gatgtcattg tatatcagcg ctgtaaaaat ctatctgtta cagaaggttt   3720
tcgcggtttt tataaacaaa actttcgtta cgaaatcgag caatcacccc agctgcgtat   3780
ttggaaattc gggaaaaagt agagcaacgc gagttgcatt ttttacacca taatgcatga   3840
ttaacttcga gaagggatta aggctaattt cactagtatg tttcaaaaac ctcaatctgt   3900
ccattgaatg ccttataaaa cagctataga ttgcatagaa gagttagcta ctcaatgctt   3960
tttgtcaaag cttactgatg atgatgtgtc tactttcagg cgggtctgta gtaaggagaa   4020
tgacattata aagctggcac ttagaattcc acggactata gactatacta gtatactccg   4080
tctactgtac gatacacttc cgctcaggtc cttgtccttt aacgaggcct taccactctt   4140
ttgttactct attgatccag ctcagcaaag gcagtgtgat ctaagattct atcttcgcga   4200
tgtagtaaaa ctagctagac cgagaaagag actagaaatg caaaaggcac ttctacaatg   4260
gctgccatca ttattatccg atgtgacgct gcattttttt tttttttttt tttttttttt   4320
tttttttttt tttttttttt ttttttggta caaatatcat aaaaaaagag aatcttttta   4380
agcaaggatt ttcttaactt cttcggcgac agcatcaccg acttcggtgg tactgttgga   4440
accacctaaa tcaccagttc tgatacctgc atccaaaacc tttttaactg catcttcaat   4500
ggctttacct tcttcaggca agttcaatga caatttcaac atcattgcag cagacaagat   4560
agtggcgata gggttgacct tattctttgg caaatctgga gcggaaccat ggcatggttc   4620
gtacaaacca aatgcggtgt tcttgtctgg caaagaggcc aaggacgcag atggcaacaa   4680
acccaaggag cctgggataa cggaggcttc atcggagatg atatcaccaa acatgttgct   4740
ggtgattata ataccattta ggtgggttgg gttcttaact aggatcatgg cggcagaatc   4800
```

-continued

```
aatcaattga tgttgaactt tcaatgtagg gaattcgttc ttgatggttt cctccacagt   4860
ttttctccat aatcttgaag aggccaaaac attagcttta tccaaggacc aaataggcaa   4920
tggtggctca tgttgtaggg ccatgaaagc ggccattctt gtgattcttt gcacttctgg   4980
aacggtgtat tgttcactat cccaagcgac accatcacca tcgtcttcct ttctcttacc   5040
aaagtaaata cctcccacta attctctaac aacaacgaag tcagtacctt tagcaaattg   5100
tggcttgatt ggagataagt ctaaaagaga gtcggatgca aagttacatg gtcttaagtt   5160
ggcgtacaat tgaagttctt tacggatttt tagtaaacct tgttcaggtc taacactacc   5220
ggtaccccat ttaggaccac ccacagcacc taacaaaacg gcatcagcct tcttggaggc   5280
ttccagcgcc tcatctggaa gtggaacacc tgtagcatcg atagcagcac caccaattaa   5340
atgattttcg aaatcgaact tgacattgga acgaacatca gaaatagctt taagaacctt   5400
aatggcttcg gctgtgattt cttgaccaac gtggtcacct ggcaaaacga cgatcttctt   5460
aggggcagac attacaatgg tatatccttg aaatatatat aaaaaaaaaa aaaaaaaaaa   5520
aaaaaaaaaa atgcagcttc tcaatgatat tcgaatacgc tttgaggaga tacagcctaa   5580
tatccgacaa actgttttac agatttacga tcgtacttgt tacccatcat tgaattttga   5640
acatccgaac ctgggagttt tccctgaaac agatagtata tttgaacctg tataataata   5700
tatagtctag cgctttacgg aagacaatgt atgtatttcg gttcctggag aaactattgc   5760
atctattgca taggtaatct tgcacgtcgc atccccggtt cattttctgc gtttccatct   5820
tgcacttcaa tagcatatct ttgttaacga agcatctgtg cttcattttg tagaacaaaa   5880
atgcaacgcg agagcgctaa tttttcaaac aaagaatctg agctgcattt ttacagaaca   5940
gaaatgcaac gcgaaagcgc tattttacca acgaagaatc tgtgcttcat ttttgtaaaa   6000
caaaaatgca acgcgagagc gctaattttt caaacaaaga atctgagctg catttttaca   6060
gaacagaaat gcaacgcgag agcgctattt taccaacaaa gaatctatac ttcttttttg   6120
ttctacaaaa atgcatcccg agagcgctat ttttctaaca aagcatctta gattactttt   6180
tttctccttt gtgcgctcta taatgcagtc tcttgataac tttttgcact gtaggtccgt   6240
taaggttaga agaaggctac tttggtgtct attttctctt ccataaaaaa agcctgactc   6300
cacttcccgc gtttactgat tactagcgaa gctgcgggtg catttttttca agataaaggc   6360
atccccgatt atattctata ccgatgtgga ttgcgcatac tttgtgaaca gaaagtgata   6420
gcgttgatga ttcttcattg gtcagaaaat tatgaacggt ttcttctatt ttgtctctat   6480
atactacgta taggaaatgt ttacattttc gtattgtttt cgattcactc tatgaatagt   6540
tcttactaca attttttttgt ctaaagagta atactagaga taaacataaa aaatgtagag   6600
gtcgagttta gatgcaagtt caaggagcga aaggtggatg ggtaggttat atagggatat   6660
agcacagaga tatatagcaa agagatactt ttgagcaatg tttgtggaag cggtattcgc   6720
aatattttag tagctcgtta cagtccggtg cgtttttggt tttttgaaag tgcgtcttca   6780
gagcgctttt ggttttcaaa agcgctctga agttcctata ctttctagag aataggaact   6840
tcggaatagg aacttcaaag cgtttccgaa aacgagcgct tccgaaaatg caacgcgagc   6900
tgcgcacata cagctcactg ttcacgtcgc acctatatct gcgtgttgcc tgtatatata   6960
tatacatgag aagaacggca tagtgcgtgt ttatgcttaa atgcgtactt atatgcgtct   7020
atttatgtag gatgaaaggt agtctagtac ctcctgtgat attatcccat tccatgcggg   7080
gtatcgtatg cttccttcag cactaccctt tagctgttct atatgctgcc actcctcaat   7140
```

-continued

```
tggattagtc tcatccttca atgctatcat ttcctttgat attggatcat atgcatagta   7200
ccgagaaact agtgcgaagt agtgatcagg tattgctgtt atctgatgag tatacgttgt   7260
cctggccacg gcagaagcac gcttatcgct ccaatttccc acaacattag tcaactccgt   7320
taggcccttc attgaaagaa atgaggtcat caaatgtctt ccaatgtgag attttgggcc   7380
attttttata gcaaagattg aataaggcgc atttttcttc aaagctttat tgtacgatct   7440
gactaagtta tcttttaata attggtattc ctgtttattg cttgaagaat tgccggtcct   7500
atttactcgt tttaggactg gttcagaatt cctcaaaaat tcatccaaat atacaagtgg   7560
atcgatgata agctgtcaaa catgagaatt cttgaagacg aaagggcctc gtgatacgcc   7620
tatttttata ggttaatgtc atgataataa tggtttctta gacgtcaggt ggcacttttc   7680
ggggaaatgt gcgcggaacc cctatttgtt tatttttcta aatacattca aatatgtatc   7740
cgctcatgag acaataaccc tgataaatgc ttcaataata ttgaaaaagg aagagtatga   7800
gtattcaaca tttccgtgtc gcccttattc ccttttttgc ggcattttgc cttcctgttt   7860
ttgctcaccc agaaacgctg gtgaaagtaa aagatgctga agatcagttg ggtgcacgag   7920
tgggttacat cgaactggat ctcaacagcg gtaagatcct tgagagtttt cgccccgaag   7980
aacgttttcc aatgatgagc acttttaaag ttctgctatg tggcgcggta ttatcccgtg   8040
ttgacgccgg gcaagagcaa ctcggtcgcc gcatacacta ttctcagaat gacttggttg   8100
agtactcacc agtcacagaa aagcatctta cggatggcat gacagtaaga gaattatgca   8160
gtgctgccat aaccatgagt gataacactg cggccaactt acttctgaca acgatcggag   8220
gaccgaagga gctaaccgct tttttgcaca acatggggga tcatgtaact cgccttgatc   8280
gttgggaacc ggagctgaat gaagccatac caaacgacga gcgtgacacc acgatgcctg   8340
cagcaatggc aacaacgttg cgcaaactat taactggcga actacttact ctagcttccc   8400
ggcaacaatt aatagactgg atggaggcgg ataaagttgc aggaccactt ctgcgctcgg   8460
cccttccggc tggctggttt attgctgata aatctggagc cggtgagcgt gggtctcgcg   8520
gtatcattgc agcactgggg ccagatggta agccctcccg tatcgtagtt atctacacga   8580
cggggagtca ggcaactatg gatgaacgaa atagacagat cgctgagata ggtgcctcac   8640
tgattaagca ttggtaactg tcagaccaag tttactcata tatactttag attgatttaa   8700
aacttcattt ttaatttaaa aggatctagg tgaagatcct ttttgataat ctcatgacca   8760
aaatccctta acgtgagttt tcgttccact gagcgtcaga ccccgtagaa aagatcaaag   8820
gatcttcttg agatcctttt tttctgcgcg taatctgctg cttgcaaaca aaaaaaccac   8880
cgctaccagc ggtggtttgt ttgccggatc aagagctacc aactcttttt ccgaaggtaa   8940
ctggcttcag cagagcgcag ataccaaata ctgtccttct agtgtagccg tagttaggcc   9000
accacttcaa gaactctgta gcaccgccta catacctcgc tctgctaatc ctgttaccag   9060
tggctgctgc cagtggcgat aagtcgtgtc ttaccgggtt ggactcaaga cgatagttac   9120
cggataaggc gcagcggtcg ggctgaacgg ggggttcgtg cacacagccc agcttggagc   9180
gaacgaccta caccgaactg agatacctac agcgtgagct atgagaaagc gccacgcttc   9240
ccgaagggag aaaggcggac aggtatccgg taagcggcag ggtcggaaca ggagagcgca   9300
cgagggagct tccaggggga aacgcctggt atctttatag tcctgtcggg tttcgccacc   9360
tctgacttga gcgtcgattt ttgtgatgct cgtcaggggg gcggagccta tggaaaaacg   9420
ccagcaacgc ggccttttta cggttcctgg ccttttgctg gccttttgct cacatgttct   9480
ttcctgcgtt atcccctgat tctgtggata accgtattac cgcctttgag tgagctgata   9540
```

-continued

```
ccgctcgccg cagccgaacg accgagcgca gcgagtcagt gagcgaggaa gcggaagagc   9600
gcctgatgcg gtattttctc cttacgcatc tgtgcggtat ttcacaccgc atatggtgca   9660
ctctcagtac aatctgctct gatgccgcat agttaagcca gtatacactc cgctatcgct   9720
acgtgactgg gtcatggctg cgccccgaca cccgccaaca cccgctgacg cgccctgacg   9780
ggcttgtctg ctcccggcat ccgcttacag acaagctgtg accgtctccg ggagctgcat   9840
gtgtcagagg ttttcaccgt catcaccgaa acgcgcgagg cagctgcggt aaagctcatc   9900
agcgtggtcg tgaagcgatt cacagatgtc tgcctgttca tccgcgtcca gctcgttgag   9960
tttctccaga agcgttaatg tctggcttct gataaagcgg gccatgttaa gggcggtttt  10020
ttcctgtttg gtcactgatg cctccgtgta agggggattt ctgttcatgg gggtaatgat  10080
accgatgaaa cgagagagga tgctcacgat acgggttact gatgatgaac atgcccggtt  10140
actggaacgt tgtgagggta aacaactggc ggtatggatg cggcgggacc agagaaaaat  10200
cactcagggt caatgccagc gcttcgttaa tacagatgta ggtgttccac agggtagcca  10260
gcagcatcct gcgatgcaga tccggaacat aatggtgcag ggcgctgact tccgcgtttc  10320
cagactttac gaaacacgga aaccgaagac cattcatgtt gttgctcagg tcgcagacgt  10380
tttgcagcag cagtcgcttc acgttcgctc gcgtatcggt gattcattct gctaaccagt  10440
aaggcaaccc cgccagccta gccgggtcct caacgacagg agcacgatca tgcgcacccg  10500
tggccaggac ccaacgctgc ccgagatgcg ccgcgtgcgg ctgctggaga tggcggacgc  10560
gatggatatg ttctgccaag ggttggtttg cgcattcaca gttctccgca agaattgatt  10620
ggctccaatt cttggagtgg tgaatccgtt agcgaggtgc cgccggcttc cattcaggtc  10680
gaggtggccc ggctccatgc accgcgacgc aacgcgggga ggcagacaag gtatagggcg  10740
gcgcctacaa tccatgccaa cccgttccat gtgctcgccg aggcggcata aatcgccgtg  10800
acgatcagcg gtccaatgat cgaagttagg ctggtaagag ccgcgagcga tccttgaagc  10860
tgtccctgat ggtcgtcatc tacctgcctg gacagcatgg cctgcaacgc gggcatcccg  10920
atgccgccgg aagcgagaag aatcataatg gggaaggcca tccagcctcg cgtcgcgaac  10980
gccagcaaga cgtagcccag cgcgtcggcc gccatgccgg cgataatggc ctgcttctcg  11040
ccgaaacgtt tggtggcggg accagtgacg aaggcttgag cgagggcgtg caagattccg  11100
aataccgcaa gcgacaggcc gatcatcgtc gcgctccagc gaaagcggtc ctcgccgaaa  11160
atgacccaga gcgctgccgg cacctgtcct acgagttgca tgataaagaa gacagtcata  11220
agtgcggcga cgatagtcat gccccgcgcc caccggaagg agctgactgg gttgaaggct  11280
ctcaagggca tcggtcgagg atccttcaat atgcgcacat acgctgttat gttcaaggtc  11340
ccttcgttta agaacgaaag cggtcttcct tttgagggat gtttcaagtt gttcaaatct  11400
atcaaatttg caaatcccca gtctgtatct agagcgttga atcggtgatg cgatttgtta  11460
attaaattga tggtgtcacc attaccaggt ctagatatac caatggcaaa ctgagcacaa  11520
caataccagt ccggatcaac tggcaccatc tctcccgtag tctcatctaa tttttcttcc  11580
ggatgaggtt ccagatatac cgcaacacct ttattatggt ttccctgagg gaataataga  11640
atgtcccatt cgaaatcacc aattctaaac ctgggcgaat tgtatttcgg gtttgttaac  11700
tcgttccagt caggaatgtt ccacgtgaag ctatcttcca gcaaagtctc cacttcttca  11760
tcaaattgtg gagaatactc ccaatgctct tatctatggg acttccggga aacacagtac  11820
cgatacttcc caattcgtct tcagagctca ttgtttgttt gaagagacta atcaaagaat  11880
```

-continued

```
cgttttctca aaaaaattaa tatcttaact gatagtttga tcaaaggggc aaaacgtagg  11940

ggcaaacaaa cggaaaaatc gtttctcaaa ttttctgatg ccaagaactc taaccagtct  12000

tatctaaaaa ttgccttatg atccgtctct ccggttacag cctgtgtaac tgattaatcc  12060

tgcctttcta atcaccattc taatgtttta attaagggat tttgtcttca ttaacggctt  12120

tcgctcataa aaatgttatg acgttttgcc cgcaggcggg aaaccatcca cttcacgaga  12180

ctgatctcct ctgccggaac accgggcatc tccaacttat aagttggaga aataagagaa  12240

tttcagattg agagaatgaa aaaaaaaaac ccttagttca taggtccatt ctcttagcgc  12300

aactacagag aacaggggca caaacaggca aaaaacgggc acaacctcaa tggagtgatg  12360

caacctgcct ggagtaaatg atgacacaag gcaattgacc cacgcatgta tctatctcat  12420

tttcttacac cttctattac cttctgctct ctctgatttg gaaaaagctg aaaaaaaagg  12480

ttgaaaccag ttccctgaaa ttattcccct acttgactaa taagtatata aagacggtag  12540

gtattgattg taattctgta aatctatttc ttaaacttct taaattctac ttttatagtt  12600

agtctttttt ttagttttaa aacaccaaga acttagtttc gaataaacac acataaacaa  12660

acaagcttac aaaacaaa atg gct gca tat gca gct cag ggc tat aag gtg    12711
                    Met Ala Ala Tyr Ala Ala Gln Gly Tyr Lys Val
                     1               5                  10

cta gta ctc aac ccc tct gtt gct gca aca ctg ggc ttt ggt gct tac    12759
Leu Val Leu Asn Pro Ser Val Ala Ala Thr Leu Gly Phe Gly Ala Tyr
            15                  20                  25

atg tcc aag gct cat ggg atc gat cct aac atc agg acc ggg gtg aga    12807
Met Ser Lys Ala His Gly Ile Asp Pro Asn Ile Arg Thr Gly Val Arg
        30                  35                  40

aca att acc act ggc agc ccc atc acg tac tcc acc tac ggc aag ttc    12855
Thr Ile Thr Thr Gly Ser Pro Ile Thr Tyr Ser Thr Tyr Gly Lys Phe
    45                  50                  55

ctt gcc gac ggc ggg tgc tcg ggg ggc gct tat gac ata ata att tgt    12903
Leu Ala Asp Gly Gly Cys Ser Gly Gly Ala Tyr Asp Ile Ile Ile Cys
60                  65                  70                  75

gac gag tgc cac tcc acg gat gcc aca tcc atc ttg ggc att ggc act    12951
Asp Glu Cys His Ser Thr Asp Ala Thr Ser Ile Leu Gly Ile Gly Thr
                80                  85                  90

gtc ctt gac caa gca gag act gcg ggg gcg aga ctg gtt gtg ctc gcc    12999
Val Leu Asp Gln Ala Glu Thr Ala Gly Ala Arg Leu Val Val Leu Ala
            95                  100                 105

acc gcc acc cct ccg ggc tcc gtc act gtg ccc cat ccc aac atc gag    13047
Thr Ala Thr Pro Pro Gly Ser Val Thr Val Pro His Pro Asn Ile Glu
        110                 115                 120

gag gtt gct ctg tcc acc acc gga gag atc cct ttt tac ggc aag gct    13095
Glu Val Ala Leu Ser Thr Thr Gly Glu Ile Pro Phe Tyr Gly Lys Ala
    125                 130                 135

atc ccc ctc gaa gta atc aag ggg ggg aga cat ctc atc ttc tgt cat    13143
Ile Pro Leu Glu Val Ile Lys Gly Gly Arg His Leu Ile Phe Cys His
140                 145                 150                 155

tca aag aag aag tgc gac gaa ctc gcc gca aag ctg gtc gca ttg ggc    13191
Ser Lys Lys Lys Cys Asp Glu Leu Ala Ala Lys Leu Val Ala Leu Gly
                160                 165                 170

atc aat gcc gtg gcc tac tac cgc ggt ctt gac gtg tcc gtc atc ccg    13239
Ile Asn Ala Val Ala Tyr Tyr Arg Gly Leu Asp Val Ser Val Ile Pro
            175                 180                 185

acc agc ggc gat gtt gtc gtc gtg gca acc gat gcc ctc atg acc ggc    13287
Thr Ser Gly Asp Val Val Val Val Ala Thr Asp Ala Leu Met Thr Gly
        190                 195                 200

tat acc ggc gac ttc gac tcg gtg ata gac tgc aat acg tgt gtc acc    13335
```

-continued

```
Tyr Thr Gly Asp Phe Asp Ser Val Ile Asp Cys Asn Thr Cys Val Thr
    205                 210                 215

cag aca gtc gat ttc agc ctt gac cct acc ttc acc att gag aca atc    13383
Gln Thr Val Asp Phe Ser Leu Asp Pro Thr Phe Thr Ile Glu Thr Ile
220                 225                 230                 235

acg ctc ccc caa gat gct gtc tcc cgc act caa cgt cgg ggc agg act    13431
Thr Leu Pro Gln Asp Ala Val Ser Arg Thr Gln Arg Arg Gly Arg Thr
                240                 245                 250

ggc agg ggg aag cca ggc atc tac aga ttt gtg gca ccg ggg gag cgc    13479
Gly Arg Gly Lys Pro Gly Ile Tyr Arg Phe Val Ala Pro Gly Glu Arg
            255                 260                 265

ccc tcc ggc atg ttc gac tcg tcc gtc ctc tgt gag tgc tat gac gca    13527
Pro Ser Gly Met Phe Asp Ser Ser Val Leu Cys Glu Cys Tyr Asp Ala
        270                 275                 280

ggc tgt gct tgg tat gag ctc acg ccc gcc gag act aca gtt agg cta    13575
Gly Cys Ala Trp Tyr Glu Leu Thr Pro Ala Glu Thr Thr Val Arg Leu
    285                 290                 295

cga gcg tac atg aac acc ccg ggg ctt ccc gtg tgc cag gac cat ctt    13623
Arg Ala Tyr Met Asn Thr Pro Gly Leu Pro Val Cys Gln Asp His Leu
300                 305                 310                 315

gaa ttt tgg gag ggc gtc ttt aca ggc ctc act cat ata gat gcc cac    13671
Glu Phe Trp Glu Gly Val Phe Thr Gly Leu Thr His Ile Asp Ala His
                320                 325                 330

ttt cta tcc cag aca aag cag agt ggg gag aac ctt cct tac ctg gta    13719
Phe Leu Ser Gln Thr Lys Gln Ser Gly Glu Asn Leu Pro Tyr Leu Val
            335                 340                 345

gcg tac caa gcc acc gtg tgc gct agg gct caa gcc cct ccc cca tcg    13767
Ala Tyr Gln Ala Thr Val Cys Ala Arg Ala Gln Ala Pro Pro Pro Ser
        350                 355                 360

tgg gac cag atg tgg aag tgt ttg att cgc ctc aag ccc acc ctc cat    13815
Trp Asp Gln Met Trp Lys Cys Leu Ile Arg Leu Lys Pro Thr Leu His
    365                 370                 375

ggg cca aca ccc ctg cta tac aga ctg ggc gct gtt cag aat gaa atc    13863
Gly Pro Thr Pro Leu Leu Tyr Arg Leu Gly Ala Val Gln Asn Glu Ile
380                 385                 390                 395

acc ctg acg cac cca gtc acc aaa tac atc atg aca tgc atg tcg gcc    13911
Thr Leu Thr His Pro Val Thr Lys Tyr Ile Met Thr Cys Met Ser Ala
                400                 405                 410

gac ctg gag gtc gtc acg agc acc tgg gtg ctc gtt ggc ggc gtc ctg    13959
Asp Leu Glu Val Val Thr Ser Thr Trp Val Leu Val Gly Gly Val Leu
            415                 420                 425

gct gct ttg gcc gcg tat tgc ctg tca aca ggc tgc gtg gtc ata gtg    14007
Ala Ala Leu Ala Ala Tyr Cys Leu Ser Thr Gly Cys Val Val Ile Val
        430                 435                 440

ggc agg gtc gtc ttg tcc ggg aag ccg gca atc ata cct gac agg gaa    14055
Gly Arg Val Val Leu Ser Gly Lys Pro Ala Ile Ile Pro Asp Arg Glu
    445                 450                 455

gtc ctc tac cga gag ttc gat gag atg gaa gag tgc tct cag cac tta    14103
Val Leu Tyr Arg Glu Phe Asp Glu Met Glu Glu Cys Ser Gln His Leu
460                 465                 470                 475

ccg tac atc gag caa ggg atg atg ctc gcc gag cag ttc aag cag aag    14151
Pro Tyr Ile Glu Gln Gly Met Met Leu Ala Glu Gln Phe Lys Gln Lys
                480                 485                 490

gcc ctc ggc ctc ctg cag acc gcg tcc cgt cag gca gag gtt atc gcc    14199
Ala Leu Gly Leu Leu Gln Thr Ala Ser Arg Gln Ala Glu Val Ile Ala
            495                 500                 505

cct gct gtc cag acc aac tgg caa aaa ctc gag acc ttc tgg gcg aag    14247
Pro Ala Val Gln Thr Asn Trp Gln Lys Leu Glu Thr Phe Trp Ala Lys
        510                 515                 520
```

-continued

```
cat atg tgg aac ttc atc agt ggg ata caa tac ttg gcg ggc ttg tca    14295
His Met Trp Asn Phe Ile Ser Gly Ile Gln Tyr Leu Ala Gly Leu Ser
    525                 530                 535

acg ctg cct ggt aac ccc gcc att gct tca ttg atg gct ttt aca gct    14343
Thr Leu Pro Gly Asn Pro Ala Ile Ala Ser Leu Met Ala Phe Thr Ala
540                 545                 550                 555

gct gtc acc agc cca cta acc act agc caa acc ctc ctc ttc aac ata    14391
Ala Val Thr Ser Pro Leu Thr Thr Ser Gln Thr Leu Leu Phe Asn Ile
                560                 565                 570

ttg ggg ggg tgg gtg gct gcc cag ctc gcc gcc ccc ggt gcc gct act    14439
Leu Gly Gly Trp Val Ala Ala Gln Leu Ala Ala Pro Gly Ala Ala Thr
            575                 580                 585

gcc ttt gtg ggc gct ggc tta gct ggc gcc gcc atc ggc agt gtt gga    14487
Ala Phe Val Gly Ala Gly Leu Ala Gly Ala Ala Ile Gly Ser Val Gly
        590                 595                 600

ctg ggg aag gtc ctc ata gac atc ctt gca ggg tat ggc gcg ggc gtg    14535
Leu Gly Lys Val Leu Ile Asp Ile Leu Ala Gly Tyr Gly Ala Gly Val
    605                 610                 615

gcg gga gct ctt gtg gca ttc aag atc atg agc ggt gag gtc ccc tcc    14583
Ala Gly Ala Leu Val Ala Phe Lys Ile Met Ser Gly Glu Val Pro Ser
620                 625                 630                 635

acg gag gac ctg gtc aat cta ctg ccc gcc atc ctc tcg ccc gga gcc    14631
Thr Glu Asp Leu Val Asn Leu Leu Pro Ala Ile Leu Ser Pro Gly Ala
                640                 645                 650

ctc gta gtc ggc gtg gtc tgt gca gca ata ctg cgc cgg cac gtt ggc    14679
Leu Val Val Gly Val Val Cys Ala Ala Ile Leu Arg Arg His Val Gly
            655                 660                 665

ccg ggc gag ggg gca gtg cag tgg atg aac cgg ctg ata gcc ttc gcc    14727
Pro Gly Glu Gly Ala Val Gln Trp Met Asn Arg Leu Ile Ala Phe Ala
        670                 675                 680

tcc cgg ggg aac cat gtt tcc ccc acg cac tac gtg ccg gag agc gat    14775
Ser Arg Gly Asn His Val Ser Pro Thr His Tyr Val Pro Glu Ser Asp
    685                 690                 695

gca gct gcc cgc gtc act gcc ata ctc agc agc ctc act gta acc cag    14823
Ala Ala Ala Arg Val Thr Ala Ile Leu Ser Ser Leu Thr Val Thr Gln
700                 705                 710                 715

ctc ctg agg cga ctg cac cag tgg ata agc tcg gag tgt acc act cca    14871
Leu Leu Arg Arg Leu His Gln Trp Ile Ser Ser Glu Cys Thr Thr Pro
                720                 725                 730

tgc tcc ggt tcc tgg cta agg gac atc tgg gac tgg ata tgc gag gtg    14919
Cys Ser Gly Ser Trp Leu Arg Asp Ile Trp Asp Trp Ile Cys Glu Val
            735                 740                 745

ttg agc gac ttt aag acc tgg cta aaa gct aag ctc atg cca cag ctg    14967
Leu Ser Asp Phe Lys Thr Trp Leu Lys Ala Lys Leu Met Pro Gln Leu
        750                 755                 760

cct ggg atc ccc ttt gtg tcc tgc cag cgc ggg tat aag ggg gtc tgg    15015
Pro Gly Ile Pro Phe Val Ser Cys Gln Arg Gly Tyr Lys Gly Val Trp
    765                 770                 775

cga ggg gac ggc atc atg cac act cgc tgc cac tgt gga gct gag atc    15063
Arg Gly Asp Gly Ile Met His Thr Arg Cys His Cys Gly Ala Glu Ile
780                 785                 790                 795

act gga cat gtc aaa aac ggg acg atg agg atc gtc ggt cct agg acc    15111
Thr Gly His Val Lys Asn Gly Thr Met Arg Ile Val Gly Pro Arg Thr
                800                 805                 810

tgc agg aac atg tgg agt ggg acc ttc ccc att aat gcc tac acc acg    15159
Cys Arg Asn Met Trp Ser Gly Thr Phe Pro Ile Asn Ala Tyr Thr Thr
            815                 820                 825

ggc ccc tgt acc ccc ctt cct gcg ccg aac tac acg ttc gcg cta tgg    15207
Gly Pro Cys Thr Pro Leu Pro Ala Pro Asn Tyr Thr Phe Ala Leu Trp
        830                 835                 840
```

-continued

```
agg gtg tct gca gag gaa tac gtg gag ata agg cag gtg ggg gac ttc     15255
Arg Val Ser Ala Glu Glu Tyr Val Glu Ile Arg Gln Val Gly Asp Phe
    845                 850                 855

cac tac gtg acg ggt atg act act gac aat ctt aaa tgc ccg tgc cag     15303
His Tyr Val Thr Gly Met Thr Thr Asp Asn Leu Lys Cys Pro Cys Gln
860                 865                 870                 875

gtc cca tcg ccc gaa ttt ttc aca gaa ttg gac ggg gtg cgc cta cat     15351
Val Pro Ser Pro Glu Phe Phe Thr Glu Leu Asp Gly Val Arg Leu His
                880                 885                 890

agg ttt gcg ccc ccc tgc aag ccc ttg ctg cgg gag gag gta tca ttc     15399
Arg Phe Ala Pro Pro Cys Lys Pro Leu Leu Arg Glu Glu Val Ser Phe
            895                 900                 905

aga gta gga ctc cac gaa tac ccg gta ggg tcg caa tta cct tgc gag     15447
Arg Val Gly Leu His Glu Tyr Pro Val Gly Ser Gln Leu Pro Cys Glu
        910                 915                 920

ccc gaa ccg gac gtg gcc gtg ttg acg tcc atg ctc act gat ccc tcc     15495
Pro Glu Pro Asp Val Ala Val Leu Thr Ser Met Leu Thr Asp Pro Ser
    925                 930                 935

cat ata aca gca gag gcg gcc ggg cga agg ttg gcg agg gga tca ccc     15543
His Ile Thr Ala Glu Ala Ala Gly Arg Arg Leu Ala Arg Gly Ser Pro
940                 945                 950                 955

ccc tct gtg gcc agc tcc tcg gct agc cag cta tcc gct cca tct ctc     15591
Pro Ser Val Ala Ser Ser Ser Ala Ser Gln Leu Ser Ala Pro Ser Leu
                960                 965                 970

aag gca act tgc acc gct aac cat gac tcc cct gat gct gag ctc ata     15639
Lys Ala Thr Cys Thr Ala Asn His Asp Ser Pro Asp Ala Glu Leu Ile
            975                 980                 985

gag gcc aac ctc cta tgg agg cag gag atg ggc ggc aac atc acc agg     15687
Glu Ala Asn Leu Leu Trp Arg Gln Glu Met Gly Gly Asn Ile Thr Arg
        990                 995                 1000

gtt gag tca gaa aac aaa gtg gtg att ctg gac tcc ttc gat ccg ctt     15735
Val Glu Ser Glu Asn Lys Val Val Ile Leu Asp Ser Phe Asp Pro Leu
   1005                1010                1015

gtg gcg gag gag gac gag cgg gag atc tcc gta ccc gca gaa atc ctg     15783
Val Ala Glu Glu Asp Glu Arg Glu Ile Ser Val Pro Ala Glu Ile Leu
1020                1025                1030                1035

cgg aag tct cgg aga ttc gcc cag gcc ctg ccc gtt tgg gcg cgg ccg     15831
Arg Lys Ser Arg Arg Phe Ala Gln Ala Leu Pro Val Trp Ala Arg Pro
               1040                1045                1050

gac tat aac ccc ccg cta gtg gag acg tgg aaa aag ccc gac tac gaa     15879
Asp Tyr Asn Pro Pro Leu Val Glu Thr Trp Lys Lys Pro Asp Tyr Glu
           1055                1060                1065

cca cct gtg gtc cat ggc tgc ccg ctt cca cct cca aag tcc cct cct     15927
Pro Pro Val Val His Gly Cys Pro Leu Pro Pro Pro Lys Ser Pro Pro
       1070                1075                1080

gtg cct ccg cct cgg aag aag cgg acg gtg gtc ctc act gaa tca acc     15975
Val Pro Pro Pro Arg Lys Lys Arg Thr Val Val Leu Thr Glu Ser Thr
   1085                1090                1095

cta tct act gcc ttg gcc gag ctc gcc acc aga agc ttt ggc agc tcc     16023
Leu Ser Thr Ala Leu Ala Glu Leu Ala Thr Arg Ser Phe Gly Ser Ser
1100                1105                1110                1115

tca act tcc ggc att acg ggc gac aat acg aca aca tcc tct gag ccc     16071
Ser Thr Ser Gly Ile Thr Gly Asp Asn Thr Thr Thr Ser Ser Glu Pro
               1120                1125                1130

gcc cct tct ggc tgc ccc ccc gac tcc gac gct gag tcc tat tcc tcc     16119
Ala Pro Ser Gly Cys Pro Pro Asp Ser Asp Ala Glu Ser Tyr Ser Ser
           1135                1140                1145

atg ccc ccc ctg gag ggg gag cct ggg gat ccg gat ctt agc gac ggg     16167
Met Pro Pro Leu Glu Gly Glu Pro Gly Asp Pro Asp Leu Ser Asp Gly
```

-continued

```
      1150                1155                1160

tca tgg tca acg gtc agt agt gag gcc aac gcg gag gat gtc gtg tgc    16215
Ser Trp Ser Thr Val Ser Ser Glu Ala Asn Ala Glu Asp Val Val Cys
   1165                1170                1175

tgc tca atg tct tac tct tgg aca ggc gca ctc gtc acc ccg tgc gcc    16263
Cys Ser Met Ser Tyr Ser Trp Thr Gly Ala Leu Val Thr Pro Cys Ala
1180                1185                1190                1195

gcg gaa gaa cag aaa ctg ccc atc aat gca cta agc aac tcg ttg cta    16311
Ala Glu Glu Gln Lys Leu Pro Ile Asn Ala Leu Ser Asn Ser Leu Leu
               1200                1205                1210

cgt cac cac aat ttg gtg tat tcc acc acc tca cgc agt gct tgc caa    16359
Arg His His Asn Leu Val Tyr Ser Thr Thr Ser Arg Ser Ala Cys Gln
           1215                1220                1225

agg cag aag aaa gtc aca ttt gac aga ctg caa gtt ctg gac agc cat    16407
Arg Gln Lys Lys Val Thr Phe Asp Arg Leu Gln Val Leu Asp Ser His
       1230                1235                1240

tac cag gac gta ctc aag gag gtt aaa gca gcg gcg tca aaa gtg aag    16455
Tyr Gln Asp Val Leu Lys Glu Val Lys Ala Ala Ala Ser Lys Val Lys
   1245                1250                1255

gct aac ttg cta tcc gta gag gaa gct tgc agc ctg acg ccc cca cac    16503
Ala Asn Leu Leu Ser Val Glu Glu Ala Cys Ser Leu Thr Pro Pro His
1260                1265                1270                1275

tca gcc aaa tcc aag ttt ggt tat ggg gca aaa gac gtc cgt tgc cat    16551
Ser Ala Lys Ser Lys Phe Gly Tyr Gly Ala Lys Asp Val Arg Cys His
               1280                1285                1290

gcc aga aag gcc gta acc cac atc aac tcc gtg tgg aaa gac ctt ctg    16599
Ala Arg Lys Ala Val Thr His Ile Asn Ser Val Trp Lys Asp Leu Leu
           1295                1300                1305

gaa gac aat gta aca cca ata gac act acc atc atg gct aag aac gag    16647
Glu Asp Asn Val Thr Pro Ile Asp Thr Thr Ile Met Ala Lys Asn Glu
       1310                1315                1320

gtt ttc tgc gtt cag cct gag aag ggg ggt cgt aag cca gct cgt ctc    16695
Val Phe Cys Val Gln Pro Glu Lys Gly Gly Arg Lys Pro Ala Arg Leu
   1325                1330                1335

atc gtg ttc ccc gat ctg ggc gtg cgc gtg tgc gaa aag atg gct ttg    16743
Ile Val Phe Pro Asp Leu Gly Val Arg Val Cys Glu Lys Met Ala Leu
1340                1345                1350                1355

tac gac gtg gtt aca aag ctc ccc ttg gcc gtg atg gga agc tcc tac    16791
Tyr Asp Val Val Thr Lys Leu Pro Leu Ala Val Met Gly Ser Ser Tyr
               1360                1365                1370

gga ttc caa tac tca cca gga cag cgg gtt gaa ttc ctc gtg caa gcg    16839
Gly Phe Gln Tyr Ser Pro Gly Gln Arg Val Glu Phe Leu Val Gln Ala
           1375                1380                1385

tgg aag tcc aag aaa acc cca atg ggg ttc tcg tat gat acc cgc tgc    16887
Trp Lys Ser Lys Lys Thr Pro Met Gly Phe Ser Tyr Asp Thr Arg Cys
       1390                1395                1400

ttt gac tcc aca gtc act gag agc gac atc cgt acg gag gag gca atc    16935
Phe Asp Ser Thr Val Thr Glu Ser Asp Ile Arg Thr Glu Glu Ala Ile
   1405                1410                1415

tac caa tgt tgt gac ctc gac ccc caa gcc cgc gtg gcc atc aag tcc    16983
Tyr Gln Cys Cys Asp Leu Asp Pro Gln Ala Arg Val Ala Ile Lys Ser
1420                1425                1430                1435

ctc acc gag agg ctt tat gtt ggg ggc cct ctt acc aat tca agg ggg    17031
Leu Thr Glu Arg Leu Tyr Val Gly Gly Pro Leu Thr Asn Ser Arg Gly
               1440                1445                1450

gag aac tgc ggc tat cgc agg tgc cgc gcg agc ggc gta ctg aca act    17079
Glu Asn Cys Gly Tyr Arg Arg Cys Arg Ala Ser Gly Val Leu Thr Thr
           1455                1460                1465

agc tgt ggt aac acc ctc act tgc tac atc aag gcc cgg gca gcc tgt    17127
```

-continued

```
Ser Cys Gly Asn Thr Leu Thr Cys Tyr Ile Lys Ala Arg Ala Ala Cys
       1470                1475                1480

cga gcc gca ggg ctc cag gac tgc acc atg ctc gtg tgt ggc gac gac    17175
Arg Ala Ala Gly Leu Gln Asp Cys Thr Met Leu Val Cys Gly Asp Asp
   1485                1490                1495

tta gtc gtt atc tgt gaa agc gcg ggg gtc cag gag gac gcg gcg agc    17223
Leu Val Val Ile Cys Glu Ser Ala Gly Val Gln Glu Asp Ala Ala Ser
1500                1505                1510                1515

ctg aga gcc ttc acg gag gct atg acc agg tac tcc gcc ccc cct ggg    17271
Leu Arg Ala Phe Thr Glu Ala Met Thr Arg Tyr Ser Ala Pro Pro Gly
               1520                1525                1530

gac ccc cca caa cca gaa tac gac ttg gag ctc ata aca tca tgc tcc    17319
Asp Pro Pro Gln Pro Glu Tyr Asp Leu Glu Leu Ile Thr Ser Cys Ser
           1535                1540                1545

tcc aac gtg tca gtc gcc cac gac ggc gct gga aag agg gtc tac tac    17367
Ser Asn Val Ser Val Ala His Asp Gly Ala Gly Lys Arg Val Tyr Tyr
       1550                1555                1560

ctc acc cgt gac cct aca acc ccc ctc gcg aga gct gcg tgg gag aca    17415
Leu Thr Arg Asp Pro Thr Thr Pro Leu Ala Arg Ala Ala Trp Glu Thr
   1565                1570                1575

gca aga cac act cca gtc aat tcc tgg cta ggc aac ata atc atg ttt    17463
Ala Arg His Thr Pro Val Asn Ser Trp Leu Gly Asn Ile Ile Met Phe
1580                1585                1590                1595

gcc ccc aca ctg tgg gcg agg atg ata ctg atg acc cat ttc ttt agc    17511
Ala Pro Thr Leu Trp Ala Arg Met Ile Leu Met Thr His Phe Phe Ser
               1600                1605                1610

gtc ctt ata gcc agg gac cag ctt gaa cag gcc ctc gat tgc gag atc    17559
Val Leu Ile Ala Arg Asp Gln Leu Glu Gln Ala Leu Asp Cys Glu Ile
           1615                1620                1625

tac ggg gcc tgc tac tcc ata gaa cca ctg gat cta cct cca atc att    17607
Tyr Gly Ala Cys Tyr Ser Ile Glu Pro Leu Asp Leu Pro Pro Ile Ile
       1630                1635                1640

caa aga ctc cat ggc ctc agc gca ttt tca ctc cac agt tac tct cca    17655
Gln Arg Leu His Gly Leu Ser Ala Phe Ser Leu His Ser Tyr Ser Pro
   1645                1650                1655

ggt gaa atc aat agg gtg gcc gca tgc ctc aga aaa ctt ggg gta ccg    17703
Gly Glu Ile Asn Arg Val Ala Ala Cys Leu Arg Lys Leu Gly Val Pro
1660                1665                1670                1675

ccc ttg cga gct tgg aga cac cgg gcc cgg agc gtc cgc gct agg ctt    17751
Pro Leu Arg Ala Trp Arg His Arg Ala Arg Ser Val Arg Ala Arg Leu
               1680                1685                1690

ctg gcc aga gga ggc agg gct gcc ata tgt ggc aag tac ctc ttc aac    17799
Leu Ala Arg Gly Gly Arg Ala Ala Ile Cys Gly Lys Tyr Leu Phe Asn
           1695                1700                1705

tgg gca gta aga aca aag ctc aaa ctc act cca ata gcg gcc gct ggc    17847
Trp Ala Val Arg Thr Lys Leu Lys Leu Thr Pro Ile Ala Ala Ala Gly
       1710                1715                1720

cag ctg gac ttg tcc ggc tgg ttc acg gct ggc tac agc ggg gga gac    17895
Gln Leu Asp Leu Ser Gly Trp Phe Thr Ala Gly Tyr Ser Gly Gly Asp
   1725                1730                1735

att tat cac agc gtg tct cat gcc cgg ccc cgc tgg atc tgg ttt tgc    17943
Ile Tyr His Ser Val Ser His Ala Arg Pro Arg Trp Ile Trp Phe Cys
1740                1745                1750                1755

cta ctc ctg ctt gct gca ggg gta ggc atc tac ctc ctc ccc aac cga    17991
Leu Leu Leu Leu Ala Ala Gly Val Gly Ile Tyr Leu Leu Pro Asn Arg
               1760                1765                1770

atg agc acg aat cct aaa cct caa aga aag acc aaa cgt aac acc aac    18039
Met Ser Thr Asn Pro Lys Pro Gln Arg Lys Thr Lys Arg Asn Thr Asn
           1775                1780                1785
```

-continued

```
cgg cgg ccg cag gac gtc aag ttc ccg ggt ggc ggt cag atc gtt ggt    18087
Arg Arg Pro Gln Asp Val Lys Phe Pro Gly Gly Gly Gln Ile Val Gly
       1790                1795                1800

gga gtt tac ttg ttg ccg cgc agg ggc cct aga ttg ggt gtg cgc gcg    18135
Gly Val Tyr Leu Leu Pro Arg Arg Gly Pro Arg Leu Gly Val Arg Ala
   1805                1810                1815

acg aga aag act tcc gag cgg tcg caa cct cga ggt aga cgt cag cct    18183
Thr Arg Lys Thr Ser Glu Arg Ser Gln Pro Arg Gly Arg Arg Gln Pro
1820                1825                1830                1835

atc ccc aag gct cgt cgg ccc gag ggc agg acc tgg gct cag ccc ggg    18231
Ile Pro Lys Ala Arg Arg Pro Glu Gly Arg Thr Trp Ala Gln Pro Gly
                1840                1845                1850

tac cct tgg ccc ctc tat ggc aat gag ggc tgc ggg tgg gcg gga tgg    18279
Tyr Pro Trp Pro Leu Tyr Gly Asn Glu Gly Cys Gly Trp Ala Gly Trp
           1855                1860                1865

ctc ctg tct ccc cgt ggc tct cgg cct agc tgg ggc ccc aca gac ccc    18327
Leu Leu Ser Pro Arg Gly Ser Arg Pro Ser Trp Gly Pro Thr Asp Pro
       1870                1875                1880

cgg cgt agg tcg cgc aat ttg ggt aag gtc atc gat acc ctt acg tgc    18375
Arg Arg Arg Ser Arg Asn Leu Gly Lys Val Ile Asp Thr Leu Thr Cys
   1885                1890                1895

ggc ttc gcc gac ctc atg ggg tac ata ccg ctc gtc ggc gcc cct ctt    18423
Gly Phe Ala Asp Leu Met Gly Tyr Ile Pro Leu Val Gly Ala Pro Leu
1900                1905                1910                1915

gga ggc gct gcc agg gcc taatagtcga ctttgttccc actgtacttt           18471
Gly Gly Ala Ala Arg Ala
                1920

tagctcgtac aaaatacaat atacttttca tttctccgta aacaacatgt tttcccatgt  18531

aatatccttt tctatttttc gttccgttac caactttaca catactttat atagctattc  18591

acttctatac actaaaaaac taagacaatt ttaattttgc tgcctgccat atttcaattt  18651

gttataaatt cctataattt atcctattag tagctaaaaa aagatgaatg tgaatcgaat  18711

cctaagagaa ttggatctga tccacaggac gggtgtggtc gccatgatcg cgtagtcgat  18771

agtggctcca agtagcgaag cgagcaggac tgggcggcgg ccaaagcggt cggacagtgc  18831

tccgagaacg ggtgcgcata gaaattgcat caacgcatat agcgctagca gcacgccata  18891

gtgactggcg atgctgtcgg aatggacgat atcccgcaag aggcccggca gtaccggcat  18951

aaccaagcct atgcctacag catccagggt gacggtgccg aggatgacga tgagcgcatt  19011

gttagatttc atacacggtg cctgactgcg ttagcaattt aactgtgata aactaccgca  19071

ttaaagcttt ttctttccaa tttttttttt ttcgtcatta taaaaatcat tacgaccgag  19131

attcccgggt aataactgat ataattaaat tgaagctcta atttgtgagt ttagtataca  19191

tgcatttact tataatacag ttttttagtt ttgctggccg catcttctca aatatgcttc  19251

ccagcctgct tttctgtaac gttcaccctc taccttagca tcccttccct ttgcaaatag  19311

tcctcttcca acaataataa tgtcagatcc tgtagagacc acatcatcca cggttctata  19371

ctgttgaccc aatgcgtctc ccttgtcatc taaacccaca ccgggtgtca taatcaacca  19431

atcgtaacct tcatctcttc cacccatgtc tctttgagca ataaagccga taacaaaatc  19491

tttgtcgctc ttcgcaatgt caacagtacc cttagtatat tctccagtag atagggagcc  19551

cttgcatgac aattctgcta acatcaaaag gcctctaggt tcctttgtta cttcttctgc  19611

cgcctgcttc aaaccgctaa caatacctgg gcccaccaca ccgtgtgcat tcgtaatgtc  19671

tgcccattct gctattctgt atacacccgc agagtactgc aatttgactg tattaccaat  19731

gtcagcaaat tttctgtctt cgaagagtaa aaaattgtac ttggcggata atgcctttag  19791
```

-continued

```
cggcttaact gtgccctcca tggaaaaatc agtcaagata tccacatgtg tttttagtaa  19851

acaaattttg ggacctaatg cttcaactaa ctccagtaat tccttggtgg tacgaacatc  19911

caatgaagca cacaagtttg tttgcttttc gtgcatgata ttaaatagct tggcagcaac  19971

aggactagga tgagtagcag cacgttcctt atatgtagct ttcgacatga tttatcttcg  20031

tttcctgcag gtttttgttc tgtgcagttg ggttaagaat actgggcaat ttcatgtttc  20091

ttcaacacta catatgcgta tatataccaa tctaagtctg tgctccttcc ttcgttcttc  20151

cttctgttcg gagattaccg aatcaaaaaa atttcaagga aaccgaaatc aaaaaaaaga  20211

ataaaaaaaa aatgatgaat tgaaaagctt atcgat                            20247
```

<210> SEQ ID NO 19
<211> LENGTH: 1921
<212> TYPE: PRT
<213> ORGANISM: Artificial Sequence
<220> FEATURE:
<223> OTHER INFORMATION: Description of Artificial Sequence:
pd.delta.NS3NS5.pj.core150

<400> SEQUENCE: 19

```
Met Ala Ala Tyr Ala Ala Gln Gly Tyr Lys Val Leu Val Leu Asn Pro
  1               5                  10                  15

Ser Val Ala Ala Thr Leu Gly Phe Gly Ala Tyr Met Ser Lys Ala His
             20                  25                  30

Gly Ile Asp Pro Asn Ile Arg Thr Gly Val Arg Thr Ile Thr Thr Gly
         35                  40                  45

Ser Pro Ile Thr Tyr Ser Thr Tyr Gly Lys Phe Leu Ala Asp Gly Gly
     50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270
```

-continued

```
Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
    370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
        435                 440                 445

Ser Gly Lys Pro Ala Ile Ile Pro Asp Arg Glu Val Leu Tyr Arg Glu
    450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
```

-continued

```
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
        835                 840                 845

Glu Tyr Val Glu Ile Arg Gln Val Gly Asp Phe His Tyr Val Thr Gly
    850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
    930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                1000                1005

Lys Val Val Ile Leu Asp Ser Phe Asp Pro Leu Val Ala Glu Glu Asp
   1010                1015                1020

Glu  Arg Glu Ile Ser Val  Pro Ala Glu Ile Leu  Arg Lys Ser Arg Arg
1025                 1030                 1035                 1040

Phe Ala Gln Ala Leu  Pro Val Trp Ala Arg  Pro Asp Tyr Asn Pro  Pro
                1045                 1050                 1055

Leu Val Glu Thr  Trp Lys Lys Pro Asp  Tyr Glu Pro Pro Val  Val His
            1060                 1065                 1070

Gly Cys Pro  Leu Pro Pro Pro Lys  Ser Pro Pro Val Pro  Pro Pro Arg
        1075                 1080                 1085

Lys Lys  Arg Thr Val Val Leu  Thr Glu Ser Thr Leu  Ser Thr Ala Leu
    1090                 1095                 1100

Ala  Glu Leu Ala Thr Arg  Ser Phe Gly Ser Ser  Ser Thr Ser Gly Ile
1105                 1110                 1115                 1120
```

-continued

```
Thr Gly Asp Asn Thr  Thr Thr Ser Ser Glu  Pro Ala Pro Ser Gly  Cys
                1125                 1130                 1135

Pro Pro Asp Ser  Asp Ala Glu Ser Tyr  Ser Ser Met Pro Pro  Leu Glu
            1140                 1145                 1150

Gly Glu Pro  Gly Asp Pro Asp Leu  Ser Asp Gly Ser Trp  Ser Thr Val
        1155                 1160                 1165

Ser Ser  Glu Ala Asn Ala Glu  Asp Val Val Cys Cys  Ser Met Ser Tyr
    1170                 1175                 1180

Ser  Trp Thr Gly Ala Leu  Val Thr Pro Cys Ala  Ala Glu Glu Gln Lys
1185                 1190                 1195                 1200

Leu Pro Ile Asn Ala  Leu Ser Asn Ser Leu  Leu Arg His His Asn  Leu
                1205                 1210                 1215

Val Tyr Ser Thr  Thr Ser Arg Ser Ala  Cys Gln Arg Gln Lys  Lys Val
            1220                 1225                 1230

Thr Phe Asp  Arg Leu Gln Val Leu  Asp Ser His Tyr Gln  Asp Val Leu
        1235                 1240                 1245

Lys Glu  Val Lys Ala Ala Ala  Ser Lys Val Lys Ala  Asn Leu Leu Ser
    1250                 1255                 1260

Val  Glu Glu Ala Cys Ser  Leu Thr Pro Pro His  Ser Ala Lys Ser Lys
1265                 1270                 1275                 1280

Phe Gly Tyr Gly Ala  Lys Asp Val Arg Cys  His Ala Arg Lys Ala  Val
                1285                 1290                 1295

Thr His Ile Asn  Ser Val Trp Lys Asp  Leu Leu Glu Asp Asn  Val Thr
            1300                 1305                 1310

Pro Ile Asp  Thr Thr Ile Met Ala  Lys Asn Glu Val Phe  Cys Val Gln
        1315                 1320                 1325

Pro Glu  Lys Gly Gly Arg Lys  Pro Ala Arg Leu Ile  Val Phe Pro Asp
    1330                 1335                 1340

Leu  Gly Val Arg Val Cys  Glu Lys Met Ala Leu  Tyr Asp Val Val Thr
1345                 1350                 1355                 1360

Lys Leu Pro Leu Ala  Val Met Gly Ser Ser  Tyr Gly Phe Gln Tyr  Ser
                1365                 1370                 1375

Pro Gly Gln Arg  Val Glu Phe Leu Val  Gln Ala Trp Lys Ser  Lys Lys
            1380                 1385                 1390

Thr Pro Met  Gly Phe Ser Tyr Asp  Thr Arg Cys Phe Asp  Ser Thr Val
        1395                 1400                 1405

Thr Glu  Ser Asp Ile Arg Thr  Glu Glu Ala Ile Tyr  Gln Cys Cys Asp
    1410                 1415                 1420

Leu  Asp Pro Gln Ala Arg  Val Ala Ile Lys Ser  Leu Thr Glu Arg Leu
1425                 1430                 1435                 1440

Tyr Val Gly Gly Pro  Leu Thr Asn Ser Arg  Gly Glu Asn Cys Gly  Tyr
                1445                 1450                 1455

Arg Arg Cys Arg  Ala Ser Gly Val Leu  Thr Thr Ser Cys Gly  Asn Thr
            1460                 1465                 1470

Leu Thr Cys  Tyr Ile Lys Ala Arg  Ala Ala Cys Arg Ala  Ala Gly Leu
        1475                 1480                 1485

Gln Asp  Cys Thr Met Leu Val  Cys Gly Asp Asp Leu  Val Val Ile Cys
    1490                 1495                 1500

Glu  Ser Ala Gly Val Gln  Glu Asp Ala Ala Ser  Leu Arg Ala Phe Thr
1505                 1510                 1515                 1520

Glu Ala Met Thr Arg  Tyr Ser Ala Pro Pro  Gly Asp Pro Pro Gln  Pro
                1525                 1530                 1535
```

-continued

```
Glu Tyr Asp Leu  Glu Leu Ile Thr Ser  Cys Ser Ser Asn Val  Ser Val
            1540                 1545                 1550

Ala His Asp  Gly Ala Gly Lys Arg  Val Tyr Tyr Leu Thr  Arg Asp Pro
        1555                 1560                 1565

Thr Thr  Pro Leu Ala Arg Ala  Ala Trp Glu Thr Ala  Arg His Thr Pro
    1570                 1575                 1580

Val  Asn Ser Trp Leu Gly  Asn Ile Ile Met Phe  Ala Pro Thr Leu Trp
1585                 1590                 1595                 1600

Ala Arg Met Ile Leu  Met Thr His Phe Phe  Ser Val Leu Ile Ala  Arg
                1605                 1610                 1615

Asp Gln Leu Glu  Gln Ala Leu Asp Cys  Glu Ile Tyr Gly Ala  Cys Tyr
            1620                 1625                 1630

Ser Ile Glu  Pro Leu Asp Leu Pro  Pro Ile Ile Gln Arg  Leu His Gly
        1635                 1640                 1645

Leu Ser  Ala Phe Ser Leu His  Ser Tyr Ser Pro Gly  Glu Ile Asn Arg
    1650                 1655                 1660

Val  Ala Ala Cys Leu Arg  Lys Leu Gly Val Pro  Pro Leu Arg Ala Trp
1665                 1670                 1675                 1680

Arg His Arg Ala Arg  Ser Val Arg Ala Arg  Leu Leu Ala Arg Gly  Gly
                1685                 1690                 1695

Arg Ala Ala Ile  Cys Gly Lys Tyr Leu  Phe Asn Trp Ala Val  Arg Thr
            1700                 1705                 1710

Lys Leu Lys  Leu Thr Pro Ile Ala  Ala Ala Gly Gln Leu  Asp Leu Ser
        1715                 1720                 1725

Gly Trp  Phe Thr Ala Gly Tyr  Ser Gly Gly Asp Ile  Tyr His Ser Val
    1730                 1735                 1740

Ser  His Ala Arg Pro Arg  Trp Ile Trp Phe Cys  Leu Leu Leu Leu Ala
1745                 1750                 1755                 1760

Ala Gly Val Gly Ile  Tyr Leu Leu Pro Asn  Arg Met Ser Thr Asn  Pro
                1765                 1770                 1775

Lys Pro Gln Arg  Lys Thr Lys Arg Asn  Thr Asn Arg Arg Pro  Gln Asp
            1780                 1785                 1790

Val Lys Phe  Pro Gly Gly Gly Gln  Ile Val Gly Gly Val  Tyr Leu Leu
        1795                 1800                 1805

Pro Arg  Arg Gly Pro Arg Leu  Gly Val Arg Ala Thr  Arg Lys Thr Ser
    1810                 1815                 1820

Glu  Arg Ser Gln Pro Arg  Gly Arg Arg Gln Pro  Ile Pro Lys Ala Arg
1825                 1830                 1835                 1840

Arg Pro Glu Gly Arg  Thr Trp Ala Gln Pro  Gly Tyr Pro Trp Pro  Leu
                1845                 1850                 1855

Tyr Gly Asn Glu  Gly Cys Gly Trp Ala  Gly Trp Leu Leu Ser  Pro Arg
            1860                 1865                 1870

Gly Ser Arg  Pro Ser Trp Gly Pro  Thr Asp Pro Arg Arg  Arg Ser Arg
        1875                 1880                 1885

Asn Leu  Gly Lys Val Ile Asp  Thr Leu Thr Cys Gly  Phe Ala Asp Leu
    1890                 1895                 1900

Met  Gly Tyr Ile Pro Leu  Val Gly Ala Pro Leu  Gly Gly Ala Ala Arg
1905                 1910                 1915                 1920

Ala
```

IMMUNOGENIC HEPATITIS C VIRUS NON-STRUCTURAL POLYPEPTIDES

CROSS-REFERENCE TO RELATED APPLICATION

This application is related to provisional patent application Ser. No. 60/167,502, filed Nov. 24, 1999 from which priority is claimed under 35 USC §119(e)(1) and which is incorporated herein by reference in its entirety.

FIELD OF THE INVENTION

The present invention relates to polypeptides comprising a mutant non-structural Hepatitis C virus ("HCV") polypeptide useful for immunogenic compounds for use against HCV, methods of preparing and using the same, and immunogenic compositions comprising the same. The present invention also relates to compositions comprising (a) a mutant non-structural HCV polypeptide and (b) a viral polypeptide that is not a non-structural HCV polypeptide and methods of using these compositions.

BACKGROUND OF THE INVENTION

HCV is now recognized as the major agent of chronic hepatitis and liver disease worldwide. It is estimated that HCV infects about 400 million people worldwide, corresponding to more than 3% of the world population.

Hepatitis C virus ("HCV") is a small enveloped RNA flavivirus, which contains a positive-stranded RNA genome of about 10 kilobases. The genome has a single uninterrupted ORF that encodes a protein of 3010–3011 amino acids. The structural proteins of HCV include a core protein (C), which is highly immunogenic, as well as two envelope proteins (E1 and E2), which likely form a heterodimer in vivo, and non-structural proteins NS2–NS5. It is known that the NS3 region of the virus is important for post-translational processing of the polyprotein into individual proteins, and the NS5 region encodes an RNA-dependant RNA polymerase.

Virus-specific T lymphocytes, along with neutralizing antibodies, are the mainstay of the antiviral immune defense in established viral infections. Whereas $CD8^+$ cytotoxic T cells eliminate virus-infected-cells, $CD4^+$ T helper cells are essential for the efficient regulation of the antiviral immune response. $CD4^+$ T helper cells recognize specific antigens as peptides bound to autologous HLA class II molecules (viral antigens or particles are taken up by professional antigen-presenting cells, processed to peptides, bound to HLA class II molecules in the lysosomal compartment, and transported back to the cell surface). Several observations support an important role of $CD4^+$ T cells in the elimination of HCV infection. Tsai et al., 1997 Hepatology 25:449–458; Diepolder et al 1995 Lancet 346:1006–1007; Missale et al 1996 JCI 98: 706–714; Botarelli et al 1993; Gastro 104: 580–587; Diepolder et al 1997 J. Virol 71: 6011. Immunogenic peptides usually have a minimal length of 8–11 amino acids. However, since the peptide binding groove of HLA class II molecules seems to be open at both ends, longer peptides are tolerated. Thus peptides eluted from HLA class II molecules are typically in the range of 15–25 amino acids. HLA class II molecules are extremely polymorphic and each allele seems to have its individual requirements for peptide binding. Thus the HLA class II repertoire of a given individual determines which viral peptides can be presented to T cells. Recognition of the specific HLA-peptide complex by the T cell receptor accompanied by appropriate costimulatory signals lead to T cell activation, secretion of cytokines, and T cell proliferation.

Numerous studies demonstrate that HLA Class II restricted $CD4^+$ responses are determined by stimulating peripheral blood mononuclear cells with recombinant viral antigens or peptides. Botarelli et al., (1993) Gastroenterology 104:580–587; Farrari et al., (1994) Hepatology 19:286–295; Minutello et al., (1993) C. J. Exp. Med. 178: 17–25; Hoffmann et al., (1995) Hepatology 21:632–638; Iwata et al., (1995) Hepatology 22:1057–1064; and Tsai.et al., (1995) Hepatology 21:908–912.

Polyclonal multispecific $CD8^+$ T cell responses have been detected in patients with chronic hepatitis C. Additionally, $CD8^+$ CTL's were shown to be important in resolving acute HCV infection in chimpanzees (Cooper et al., Immunity 1999). About 50% of patients with chronic hepatitis C demonstrate a detectable virus-specific $CD4^+$ T cell response, which is most frequently directed against HCV core and/or NS4 and tends to be more common in patients who achieve sustained viral clearance during interferon-$\alpha$ therapy.

Depending on the pattern of lymphokines, $CD4^+$ T helper cells have been classified as TH1, TH0, or TH2. Cytokines of the TH1 type are typically IFN-$\gamma$, lymphotoxin, and interleukin-2 (IL-2), which are believed to support activation of virus-specific $CD8^+$ T cells and natural killer cells. The TH2 cytokines IL-4, IL-5, IL-10, and IL-13 are important for B cell activation and differentiation, thus inducing a humoral immune response.

During acute hepatitis C infection a strong and sustained TH1/TH0 response to NS3 and possibly to other nonstructural proteins is associated with a self-limited course of the disease. Diapolder et al., (1995) Lancet 346:1006–1007, showed all $CD4^+$ T cell clones to have a TH1 or TH0 cytokine profile, suggesting that the clones support cytotoxic immune mechanisms in vivo. The majority of $CD4^+$ T cell clones responded to a relatively short segment of NS3, namely amino acids 1207–1278, suggesting that this region of NS3 is immunodominant for $CD4^+$ T cells. More than 70% of those who contract HCV develop chronic infection and hepatitis, and a significant portion of them progress to cirrhosis and eventually hepatocellular carcinoma. The only approved therapy at present is a 6- to 12-month course of interferon $\alpha$, which leads to sustained improvement in only 20% of patients. So far, no commercial vaccine is available.

Thus, there remains a need for compositions and methods capable of promoting anti-HCV responses.

SUMMARY OF THE INVENTION

In one aspect, the present invention relates to isolated polypeptides comprising mutant hepatitis C ("HCV") polypeptides comprising at least portions of NS3, NS4, and NS5. In a preferred aspect, NS3 is encoded by a nucleic acid sequence having an N-terminal deletion to remove the catalytic domain. The NS mutant polypeptides can include NS3, NS4s, NS4b, NS5a, NS5b or portions thereof. For example, in various embodiments, the mutant NS polypeptide comprises NS3, NS4 (NS4a and NS4b) and NS5 (NS5a and NS5b). In other embodiments, the NS polypeptide consists of NS3 and NS4 (for example, NS4a and/or NS4b) or NS3 and NS5 (for example, NS5a and/or NS5b). Other combinations of full-length or fragments of non-structural components are also contemplated.

In another preferred aspect, the polypeptides further comprise a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Such polypeptides need not be encoded by a natural HCV genome, and include, for example, truncated or otherwise mutant HCV polypeptides or polypeptides derived from other genomes, such as, for example, polypeptides of HBV. Thus, the invention includes an isolated mutant non-structural ("NS") HCV polypeptide comprising a polypeptide having a mutation in the catalytic domain of NS3 that functionally disrupts the catalytic domain. The mutation can be, for example, a deletion or a substitution mutation. In certain embodiments, the mutant NS polypeptide comprises NS3, NS4 and NS5. In other embodiments, the mutant NS polypeptides described herein further comprise a second viral polypeptide that is not NS3, NS4, or NS5 of HCV, for example an HCV Core polypeptide ("C"), or fragment thereof, or an HCV envelope protein ("E"), for example E1 and/or E2. In certain embodiments, C is truncated (e.g., at amino acid 121).

In another aspect, the present invention relates to compositions comprising any of the mutant hepatitis C ("HCV") polypeptides described herein, for example polypeptides comprising at least portions of NS3, NS4, and NS5. In a preferred aspect, NS3 is encoded by a nucleic acid sequence having an N-terminal deletion to disrupt the function of the catalytic domain, for example by removing this domain. In another preferred aspect, the polypeptides further comprise a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV Such polypeptides need not be encoded by a natural HCV genome, and include, for example, truncated or otherwise mutant HCV polypeptides or polypeptides derived from other genomes, such as, for example, polypeptides of HBV. In another aspect, the invention includes a composition comprising (a) any of the polypeptides described herein; and (b) a pharmaceutically acceptable excipient (e.g., carrier and/or adjuvant).

In another aspect, the invention includes an isolated and purified polynucleotide which encodes any of the mutant HCV polypeptides described herein. In certain embodiments, the invention includes a composition comprising (a) the isolated purified polynucleotide encoding any of the mutant HCV polypeptides; and (b) a pharmaceutically acceptable excipient. The polynucleotide, can be for example, DNA in a plasmid, or is in a plasmid. Additionally, the polynucleotides described herein may be included in an expression vector as shown in the attached Figures and Sequence Listings.

In another aspect, the present invention relates to host cells transformed with expression vectors comprising a nucleic acid sequence encoding a mutant HCV polypeptide comprising at least portions of NS3, NS4, and NS5. In a preferred aspect, the expression vectors of the host cells further comprises at least one nucleic acid sequence encoding a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Such polypeptides need not be encoded by a natural HCV genome, and include, for example, truncated or otherwise mutant HCV polypeptides or polypeptides derived from other genomes, such as, for example, polypeptides of HBV. In another preferred aspect the nucleic acid sequences of the expression vectors are coexpressed. In yet another preferred aspect, the host cells are yeast cells or mammalian cells.

In another aspect, the present invention relates to expression vectors comprising a nucleic acid sequence encoding a mutant HCV polypeptide comprising NS3, NS4, and NS5. In a preferred aspect, the expression vectors of the host cells further comprises at least one nucleic acid sequence encoding a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Importantly, such polypeptides need not be encoded by a natural HCV genome, such as, for example, truncated or otherwise mutant HCV polypeptides or polypeptides derived from other genomes, such as, for example, polypeptides of HBV. In another aspect, the present invention relates to methods of preparing a mutant HCV polypeptides. In a preferred aspect, the method comprises the steps of transforming a host cell with an expression vector, said vector comprising a nucleic acid sequence encoding a mutant HCV polypeptide comprising at least portions of NS3, NS4, and NS5, and isolating said polypeptide. In another preferred aspect the HCV polypeptide further comprises a viral polypeptide that is not a non- structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Such polypeptides need not be encoded by a natural HCV genome, and include, for example, truncated or otherwise mutant HCV polypeptides or polypeptides derived from other genomes, such as, for example, polypeptides of HBV. In another preferred aspect the host cells are yeast cells or mammalian cells.

In another aspect, the present invention relates to antibodies which specifically bind to mutant HCV polypeptide comprising NS3, NS4, and NS5, and to methods of making and using the same. In a preferred aspect, the HCV polypeptide further comprises a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Such polypeptides need not be encoded by a natural HCV genome, such as, for example, truncated or otherwise mutant HCV polypeptides or polypeptides derived from other genomes, and include, for example, polypeptides of HBV. In another preferred aspect, the antibody is either monoclonal or polyclonal.

In yet another aspect, a method of preparing a mutant NS HCV polypeptide, wherein the method comprises the steps of (a) transforming a host cell with any of the expression vectors described herein, under conditions wherein the polypeptide is expressed; and (b) isolating the polypeptide. The host cell can be, for example, a yeast cell, a mammalian cell a plant cell or an insect cell. The polypeptide can be expressed and isolated intracellularly or can be secreted and isolated from the surrounding environment.

In a still further aspect, a method of eliciting an immune response in a subject is provided. The immune response can be elicited by administering any of the polynucleotides and/or polypeptides described herein in one or multiple doses.

These and other embodiments of the subject invention will readily occur to those of skill in the art in light of the disclosure herein.

BRIEF DESCRIPTION OF THE FIGURES

FIG. 3 shows the nucleic acid sequence of pCMV-NS35 (SEQ ID NO:1), including the nucleic acid sequence of the NS35 ORF, and also the translation of NS35 (SEQ ID NO:2).

FIG. 5 shows the nucleic acid sequence of pCMV-delNS35 (SEQ ID NO:3), including the nucleic acid sequence of the delNS35 ORF, and also the translation of the delNS35 polypeptide (SEQ ID NO:4).

FIG. 7 shows the nucleic acid sequence of pCMV-II (SEQ ID NO:5).

FIG. 9 shows the nucleic acid sequence of pCMV-NS34A (SEQ ID NO:6), including the nucleic acid sequence of the NS34A ORF, and also the translation of NS34A (SEQ ID NO:7).

FIG. 11 shows the nucleic and amino acid sequences of pd.ΔNS3NS5 (SEQ ID NO:8 and 9).

FIG. 14 shows the nucleic and amino acid sequences of pd.ΔNS3NS5.pj (SEQ ID NO:10 and 11).

FIG. 17 shows the nucleic and amino acid sequences of pd.ΔNS3NS5.pj.core121 (SEQ ID NO:12 and 13).

FIG. 18 shows the nucleic and amino acid sequences of pd.ΔNS3NS5.pj.core173 (SEQ ID NO:14 and 15).

FIG. 21 shows the nucleic and amino acid sequences of pd.ΔNS3NS5.pj.core140 (SEQ ID NO:16 and 17).

FIG. 22 shows the nucleic and amino acid sequences of pd.ΔNS3NS5.pj.core150 (SEQ ID NO:18 and 19).

DETAILED DESCRIPTION OF THE INVENTION

Figure 1:
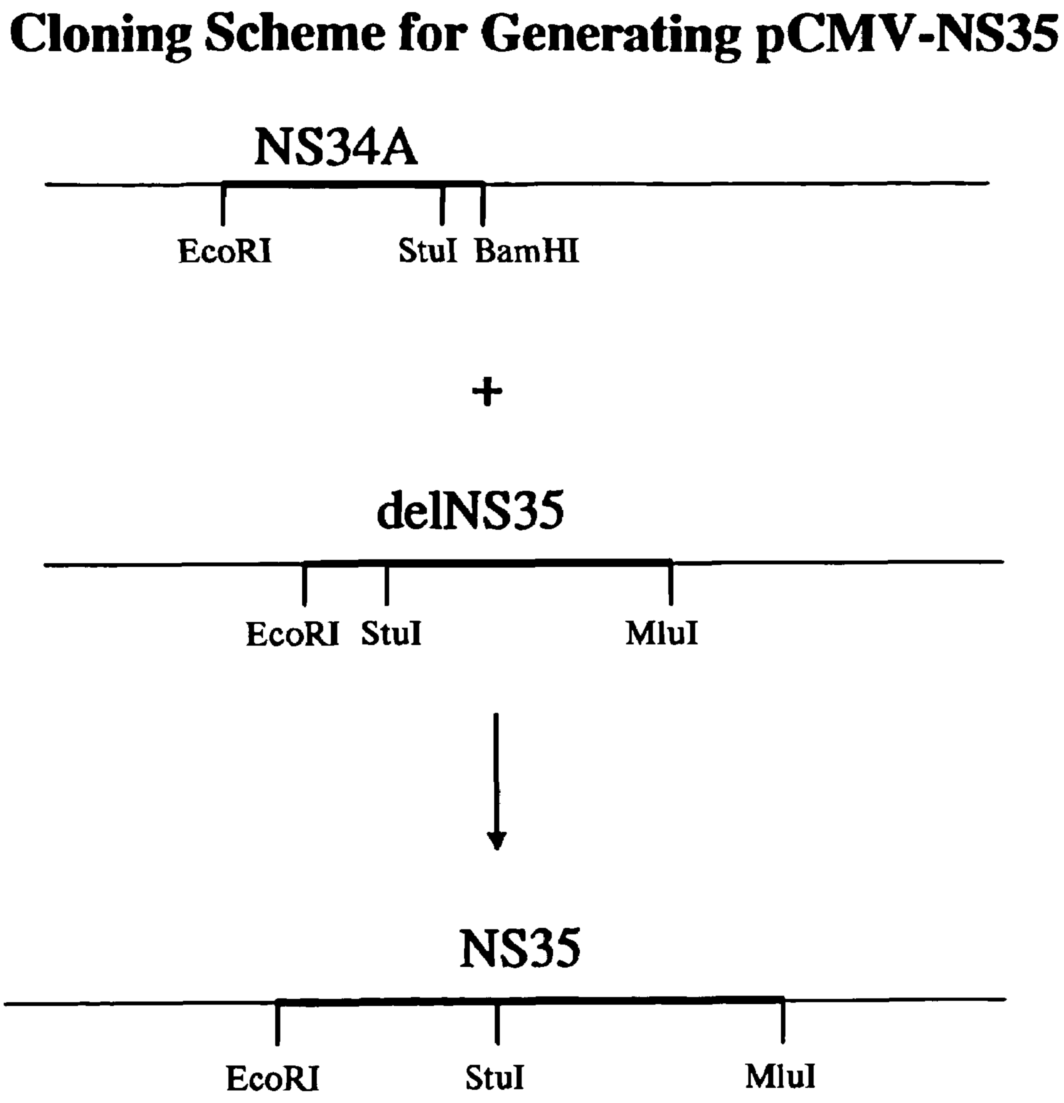
FIG. 1 shows the cloning scheme for generating pCMV-NS35.
Figure 2:
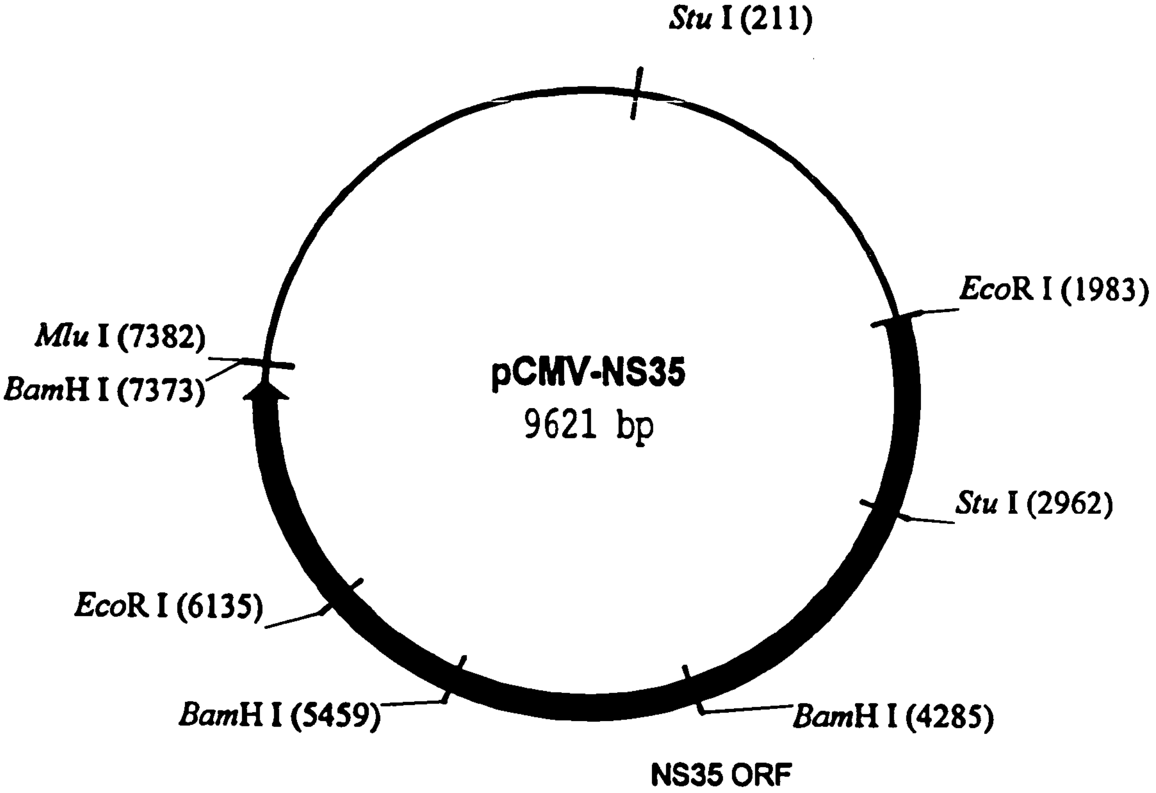
FIG. 2 shows the 9621 bp vector pCMV-NS35.
Figure 4:
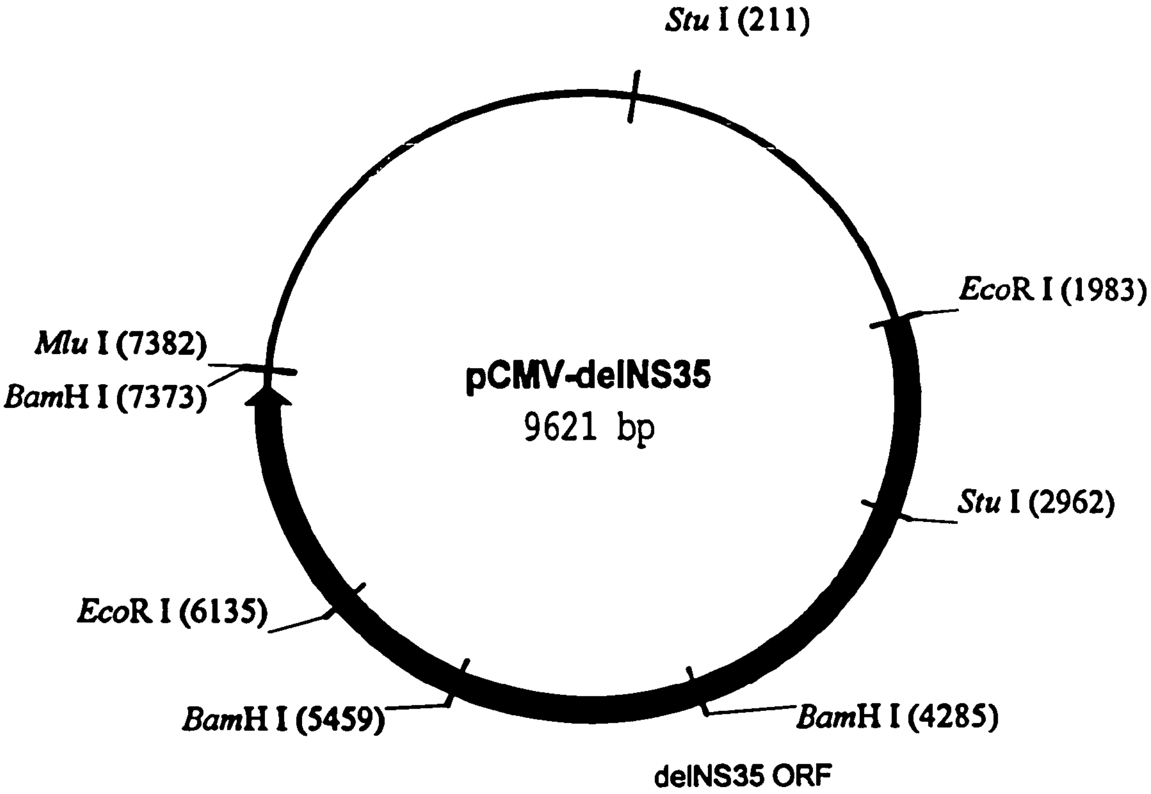
FIG. 4 shows the 9621 bp pCMV-delNS35.
Figure 6:
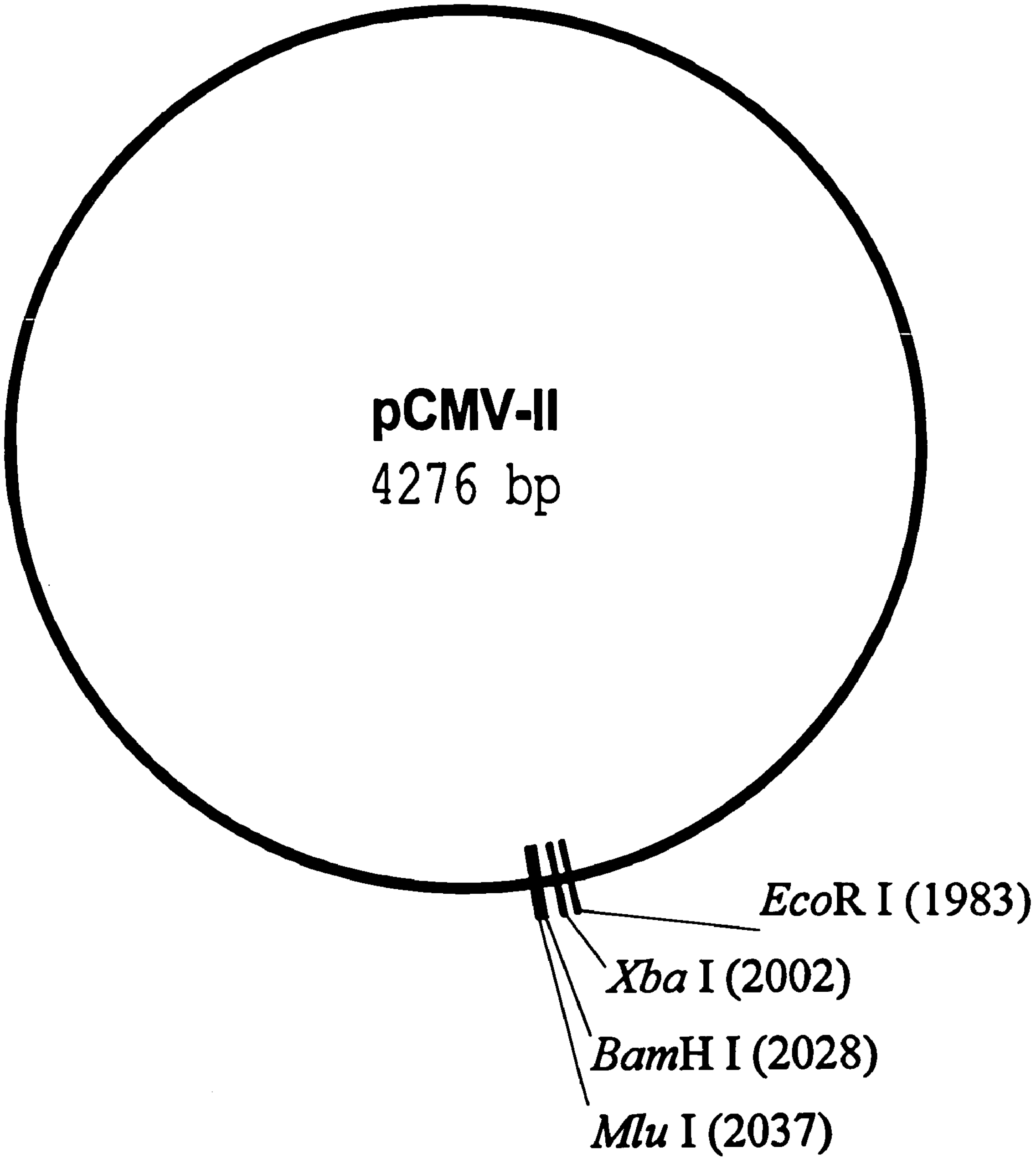
FIG. 6 shows the 4276 bp pCMV-II.
Figure 8:
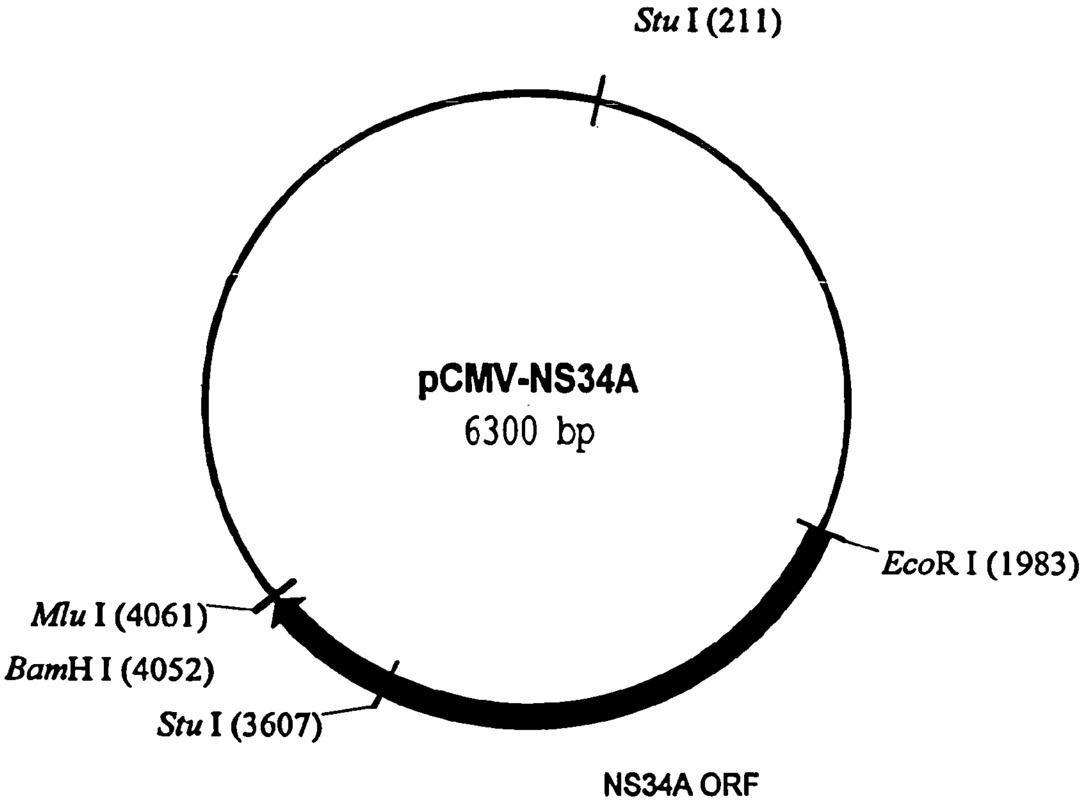
FIG. 8 shows the 6300 bp pCMV-NS34A.

The practice of the present invention will employ, unless otherwise indicated, conventional techniques of molecular biology, microbiology, recombinant DNA techniques, and immunology, which are within the skill of the art. Such techniques are explained fully in the literature. See e.g., Sambrook, et al., MOLECULAR CLONING; A LABORATORY MANUAL (1989); DNA CLONING, VOLUMES I AND II (D. N. Glover ed. 1985); OLIGONUCLEOTIDE SYNTHESIS (M. J. Gait ed., 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS OF ENZYMOLOGY (Academic Press, Inc.); GENE TRANSFER VECTORS FOR MAMMALIAN CELLS (J. H. Miller and M. P. Calos eds. 1987, Cold Springs Harbor Laboratory), Methods in Enzymology Vol. 154 and Vol. 155 (Wu and Grossman, and Wu, eds., respectively); Mayer and Walker eds. (1987), IMMUNOHISTOCHEMICAL METHODS IN CELL AND MOLECULAR BIOLOGY (Academic Press, London); Scopes, (1987), PROTEIN PURIFICATION: PRINCIPALS AND PRACTICE, Second Edition (Springer-Verlag, New York); and HANDBOOK OF EXPERIMENTAL IMMUNOLOGY, VOLUMES I–IV (D. M. Weir and C. C. Blackwell eds. 1986).

All publications, patents and patent applications cited herein, whether supra or infra, are hereby incorporated by reference in their entirety.

It must be noted that, as used in this specification and the appended claims, the singular forms “a”, “an” and “the” include plural referents unless the content clearly dictates otherwise. Thus, for example, reference to “an antigen” includes a mixture of two or more antigens, and the like.

I. Definitions

In describing the present invention, the following terms will be employed, and are intended to be defined as indicated below.

The term “hepatitis C virus” (HCV) refers to an agent causative of Non-A, Non-B Hepatitis (NANBH). The nucleic acid sequence and putative amino acid sequence of HCV is described in U.S. Pat. Nos. 5,856,437 and 5,350,671. The disease caused by HCV is called hepatitis C, formerly called NANBH. The term HCV, as used herein, denotes a viral species of which pathenogenic strains cause NANBH, as well as attenuated strains or defective interfering particles derived therefrom.

HCV is a member of the viral family flaviviridae. The morphology and composition of Flavivirus particles are known, and are discussed in Reed et al., *Curr. Stud. Hematol. Blood Transfus*. (1998), 62:1–37; HEPATITIS C VIRUSES IN FIELDS VIROLOGY (B. N. Fields, D. M. Knipe, P. M. Howley, eds.) (3d ed. 1996). It has recently been found that portions of the HCV genome are also homologous to pestiviruses. Generally, with respect to morphology, Flaviviruses contain a central nucleocapsid surrounded by a lipid bilayer. Virions are spherical and have a diameter of about 40–50 nm. Their cores are about 25–30 nm in diameter. Along the outer surface of the virion envelope are projections that are about 5–10 nm long with terminal knobs about 2 nm in diameter.

The HCV genome is comprised of RNA. It is known that RNA containing viruses have relatively high rates of spontaneous mutation. Therefore, there can be multiple strains, which can be virulent or avirulent, within the HCV class or species. The ORF of HCV, including the translation spans of the core, non-structural, and envelope proteins, is shown in U.S. Pat. Nos. 5,856,437 and 5,350,671.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains, such as from strains 1, 2, 3 or 4 of HCV. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned and homology determined by any of the programs or algorithms described herein. Thus, for example, the term "NS4" polypeptide refers to native NS4 from any of the various HCV strains, as well as NS4 analogs, muteins and immunogenic fragments, as defined further below.

Further, the terms "ΔNS35," "delNS35," "ΔNS3NS5," and "ΔNS3-5" as used herein refer to a mutant polypeptide, comprising at least portions of NS3, NS4, or NS5, comprising a deletion in, or mutation of, the NS3 protease active site region to render the protease non-functional. In one embodiment, ΔNS3–5 comprises amino acids 1242–3011, as shown in FIG. 5, or polypeptides substantially homologous thereto. It will be readily apparent to one of ordinary skill in the art how to determine that NS3 protease has been rendered non-functional. If the protease is functional, one will obtain protein of the expected molecular weight upon expression. As set forth in Example 2 and FIG. 15, using SDS-page, 4–20%, a protein having a molecular weight of approximately 194 kD was obtained when strain AD3 was transformed with pd.ΔNS3NS5.PJ clone #5. One skilled in the art could readily determine whether a protein of the desired molecular weight was expressed for any given deletion or mutation.

The terms "analog" and "mutein" refer to biologically active derivatives of the reference molecule, or fragments of such derivatives, that retain desired activity, such as the ability to stimulate a cell-mediated immune response, as defined below. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5–10 contiguous amino acid residues of the full-length molecule, preferably at least about 15–25 contiguous amino acid residues of the full-length molecule, and most preferably at least about 20–50 or more contiguous amino acid residues of the full-length molecule, that define an epitope, or any integer between 5 amino acids and the full-length sequence, provided that the fragment in question retains immunogenic activity, as measured by the assays described herein. For a description of various HCV epitopes, see, e.g., Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; commonly owned, allowed U.S. patent application Ser. Nos. 08/403,590 and 08/444,818.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are herein incorporated by reference in their entirety.

An "immunological response" to an HCV antigen (including both polypeptide and polynucleotides encoding polypeptides that are expressed in vivo) or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189–4199; Doe et al., *Eur. J. Immunol.* (1994) 24:2369–2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection or alleviation of symptoms to an immunized host. Such responses can be determined using standard immunoassays and neutralization assays, well known in the art.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

A "nucleic acid" molecule or "polynucleotide" can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and especially synthetic DNA sequences. The term also captures sequences that include any of the known base analogs of DNA and RNA.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

By "isolated" is meant, when referring to a polypeptide, that the indicated molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "purified" as used herein preferably means at least 75% by weight, more preferably at least 85% by weight, more preferably still at least 95% by weight, and most preferably at least 98% by weight, of biological macromolecules of the same type are present.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%–85%, preferably at least about 90%, and most preferably at least about 95%–98%, or more, sequence identity over a defined length of the molecules. As used herein, substantially homologous also refers to sequences showing complete identity to the specified DNA or polypeptide sequence. The term "substantially homologous" as used herein in reference to ΔNS35 generally refers to an HCV nucleic or amino acid sequence that is at least 60% identical to the entire sequence of the polypeptide encoded by ΔNS35 (see FIG. 5), where the sequence identity is preferably at least 75%, more preferably at least 80%, still more preferably at least about 85%, especially more than about 90%, most preferably 95% or greater, particularly 98% or greater. These homologous polypeptides include fragments, including mutants and allelic variants of the fragments. Identity between the two sequences is preferably determined by the Smith-Waterman homology search algorithm as implemented in the MPSRCH program (Oxford Molecular), using an affine gap search with parameters gap open penalty=12 and gap extension penalty=1. Thus, for example, the present invention includes an isolate which is 80% identical to a polypeptide encoded by ΔNS35. In some aspects of the invention, the polypeptide of the present invention is substantially homologous to the ΔNS35.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above.

For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the world wide.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 μg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 μg of yeast DNA, blotting for two hours, and hybridizing for 4–8 hours with a probe of $10^8$ cpm/μg. For a single-copy mammalian gene a conservative approach would start with 10 μg of DNA, blot overnight, and hybridize overnight in the presence of 10% dextran sulfate using a probe of greater than $10^8$ cpm/μg, resulting in an exposure time of ~24 hours.

Several factors can affect the melting temperature (Tm) of a DNA—DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10}Ci)+0.4[\%(G+C)]-0.6(\%\ \text{formamide})-600/n-1.5(\%\ \text{mismatch}).$$

where Ci is the salt concentration (monovalent ions) and n is the length of the hybrid in base pairs (slightly modified from Meinkoth & Wahl (1984) *Anal. Biochem.* 138: 267–284). In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

By "nucleic acid immunization" is meant the introduction of a nucleic acid molecule encoding one or more selected antigens into a host cell, for the in vivo expression of the antigen or antigens. The nucleic acid molecule can be introduced directly into the recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

An "open reading frame" or ORF is a region of a polynucleotide sequence which encodes a polypeptide; this region can represent a portion of a coding sequence or a total coding sequence.

As used herein, the term "antibody" refers to a polypeptide or group of polypeptides which comprise at least one antigen binding site. An "antigen binding site" is formed from the folding of the variable domains of an antibody molecule(s) to form three-dimensional binding sites with an internal surface shape and charge distribution complementary to the features of an epitope of an antigen, which allows specific binding to form an antibody-antigen complex. An antigen binding site may be formed from a heavy- and/or light-chain domain (VH and VL, respectively), which form hypervariable loops which contribute to antigen binding. The term "antibody" includes, without limitation, polyclonal antibodies, monoclonal antibodies, chimeric antibodies, altered antibodies, univalent antibodies, Fab proteins, and single-domain antibodies. In many cases, the binding phenomena of antibodies to antigens is equivalent to other ligand/anti-ligand binding.

If polyclonal antibodies are desired, a selected mammal (e.g., mouse, rabbit, goat, horse, etc.) is immunized with an immunogenic polypeptide bearing an HCV epitope(s). Serum from the immunized animal is collected and treated according to known procedures. If serum containing polyclonal antibodies to an HCV epitope contains antibodies to other antigens, the polyclonal antibodies can be purified by immunoaffinity chromatography. Techniques for producing and processing polyclonal antisera are known in the art, see for example, Mayer and Walker, eds. (1987) IMMUNOCHEMICAL METHODS IN CELL AND MOLECULAR BIOLOGY (Academic Press, London).

Monoclonal antibodies directed against HCV epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980) HYBRIDOMA TECHNIQUES; Hammerling et al. (1981), MONOCLONAL ANTIBODIES AND T-CELL HYBRIDOMAS; Kennett et al. (1980) MONOCLONAL ANTIBODIES; see also, U.S. Pat. Nos. 4,341,761; 4,399,121; 4,427,783; 4,444,887; 4,466,917; 4,472,500; 4,491,632; and 4,493,890. Panels of monoclonal antibodies produced against HCV epitopes can be screened for various properties; i.e., for isotype, epitope affinity, etc. As used herein, a "single domain antibody" (dAb) is an antibody which is comprised of an HL domain, which binds specifically with a designated antigen. A dAb does not contain a VL domain, but may contain other antigen binding domains known to exist to antibodies, for example, the kappa and lambda domains. Methods for preparing dabs are known in the art. See, for example, Ward et al, Nature 341: 544 (1989).

Antibodies can also be comprised of VH and VL domains, as well as other known antigen binding domains. Examples of these types of antibodies and methods for their preparation and known in the art (see, e.g., U.S. Pat. No. 4,816,467, which is incorporated herein by reference), and include the following. For example, "vertebrate antibodies" refers to antibodies which are tetramers or aggregates thereof, comprising light and heavy chains which are usually aggregated in a "Y" configuration and which may or may not have covalent linkages between the chains. In vertebrate antibodies, the amino acid sequences of the chains are homologous with those sequences found in antibodies produced in vertebrates, whether in situ or in vitro (for example, in hybridomas). Vertebrate antibodies include, for example, purified polyclonal antibodies and monoclonal antibodies, methods for the preparation of which are described infra.

"Hybrid antibodies" are antibodies where chains are separately homologous with reference to mammalian antibody chains and represent novel assemblies of them, so that two different antigens are precipitable by the tetramer or aggregate. In hybrid antibodies, one pair of heavy and light chains are homologous to those found in an antibody raised against a first antigen, while a second pair of chains are homologous to those found in an antibody raised against a second antibody. This results in the property of "divalence", i.e., the ability to bind two antigens simultaneously. Such hybrids can also be formed using chimeric chains, as set forth below.

"Chimeric antibodies" refers to antibodies in which the heavy and/or light chains are fusion proteins. Typically, one portion of the amino acid sequences of the chain is homologous to corresponding sequences in an antibody derived from a particular species or a particular class, while the remaining segment of the chain is homologous to the sequences derived from another species and/or class. Usually, the variable region of both light and heavy chains mimics the variable regions or antibodies derived from one species of vertebrates, while the constant portions are homologous to the sequences in the antibodies derived from another species of vertebrates. However, the definition is not limited to this particular example. Also included is any antibody in which either or both of the heavy or light chains are composed of combinations of sequences mimicking the sequences in antibodies of different sources, whether these sources be from differing classes or different species of origin, and whether or not the fusion point is at the variable/constant boundary. Thus, it is possible to produce antibodies in which neither the constant nor the variable region mimic know antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varies. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region can be made to alter antigen binding characteristics. The antibody can also be engineered to aid the specific delivery of a molecule or substance to a specific cell or tissue site. The desired alterations can be made by known techniques in molecular biology, e.g., recombinant techniques, site-directed mutagenesis, etc.

Yet another example are "univalent antibodies", which are aggregates comprised of a heavy-chain/light-chain dimer bound to the Fc (i.e., stem) region of a second heavy chain. This type of antibody escapes antigenic modulation. See, e.g., Glennie et al. Nature 295: 712 (1982). Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)2), which are capable of selectively reacting with a designated antigen or antigen family. Fab antibodies can be divided into subsets analogous to those described above, i.e., "vertebrate Fab", "hybrid Fab", "chimeric Fab", and "altered Fab". Methods of producing Fab fragments of antibodies are known within the art and include, for example, proteolysis, and synthesis by recombinant techniques.

"Antigen-antibody complex" refers to the complex formed by an antibody that is specifically bound to an epitope on an antigen.

"Immunogenic polypeptide" refers to a polypeptide that elicits a cellular and/or humoral immune response in a mammal, whether alone or linked to a carrier, in the presence or absence of an adjuvant.

"Antigenic determinant" refers to the site on an antigen or hapten to which a specific antibody molecule or specific cell surface receptor binds.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

General Overview

An aim of an HCV vaccine is to generate broad immunity to a wide breadth of antigens because HCV is so divergent and because humoral as well as cellular immune responses are desirable to combat this human pathogen. While antibodies generated against the envelope glycoprotein(s) might aid in virus neutralization, there is additional benefit to be derived from a vaccine that includes other regions. The likelihood of T-helper responses generated against a polypeptide would be helpful in a vaccine setting as would generation of cytotoxic T cells. The non-structural region represents such a candidate antigen, but processing by the protease generates several polypeptides, making purification complicated. It would be advantageous, therefore, to derive a non-structural cassette that is unprocessed by the NS3 protease.

The present invention solves this and other problems using compositions and methods involving an N-terminal deletion in NS3, which removes the catalytic domain. As such, some or all of the remainder of the non-structural region (through NS5B) is expressed as an intact polypeptide. Expression of this species has been documented in mammalian cells as well as in yeast. Further, in certain aspects, polynucleotides encoding HCV core polypeptides (or fragments thereof) are added (e.g., operably linked) to the carboxy-terminus of the non-structural cassette. As the core coding region is relatively highly conserved among HCV isolates, the presence of this region may enhance the immune response. Because core has at its C-terminus a very hydrophobic domain (amino acids 174–191), shorter versions of core were also engineered onto the polypeptide. As described in detail herein, the truncation of core to amino acid 121 yielded higher expression than the amino acid 173 truncation when engineered onto the C-terminus of the mutant NS polypeptide. The combination of most of the non-structural region fused to a C-terminally truncated core into a polypeptide is novel and has advantages for vaccine immunization. Moreover, because the aim is not necessarily to generate antibody responses to this polypeptide, there is no need to maintain a native conformation, enabling a more facile purification protocol.

Mutant HCV Non-Structural Polypeptides

Genomes of HCV strains contain a single open reading frame of approximately 9,000 to 12,000 nucleotides, which is transcribed into a polyprotein. An HCV polyprotein is cleaved to produce at least ten distinct products, in the order of $NH_2$—Core-E1-E2-p7-NS2—NS3-NS4a-NS4b-NS5a-NS5b-COOH. Mutant HCV polypeptides of the invention contain an N-terminal deletion in NS3, which removes or disables the catalytic domain. Preferably, the polypeptides also include the remainder of the non-structural region, although in certain embodiments, the polypeptides may include less than all of the remaining NS polypeptides, for example mutant NS polypeptides including any combinations of NS2-NS3-NS4a-NS4b-NS5a-NS5b (e.g., NS3NS3-NS5a-NS5b; NS3-NS4a-NS4b; NS3-NS4a-NS4b-NS5a; NS3-NS4b-NS5a-NS5b; NS3-NS4a-NS5a; NS3-NS4b-NS5a; NS3-NS4b-NS5b; etc.).

The HCV NS3 protein functions as a protease and a helicase and occurs at approximately amino acid 1027 to amino acid 1657 of the polyprotein (numbered relative to HCV-1). See Choo et al. (1991) Proc. Natl. Acad. Sci. USA 88:2451–2455. HCV NS4 occurs at approximately amino acid 1658 to amino acid 1972, NS5a occurs at approximately amino acid 1973 to amino acid 2420, and HCV NS5b occurs at approximately amino acid 2421 to amino acid 3011 of the polyprotein (numbered relative to HCV-1) (Choo et al., 1991).

The mutant polypeptides described herein can either be full-length polypeptides or portions of NS3, NS4 (NS4a and NS4b), NS5a, and NS5b polypeptides. Epitopes of NS3, NS4 (NS4a and NS4b), NS5a, NS5b, NS3NS4NS5a, and NS3NS4NS5aNS5b can be identified by several methods. For example, NS3, NS4, NS5a, NS5b polypeptides or fusion proteins comprising any combination of the above, can be isolated, for example, by immunoaffinity purification using a monoclonal antibody for the polypeptide or protein. The isolated protein sequence can then be screened by preparing a series of short peptides by proteolytic cleavage of the purified protein, which together span the entire protein sequence. By starting with, for example, 100-mer polypeptides, each polypeptide can be tested for the presence of epitopes recognized by a T cell receptor on an HCV-activated T cell, progressively smaller and overlapping fragments can then be tested from an identified 100-mer to map the epitope of interest.

Epitopes recognized by a T cell receptor on an HCV-activated T cell can be identified by, for example, $^{51}$Cr release assay (see Example 2) or by lymphoproliferation assay (see Example 4). In a $^{51}$Cr release assay, target cells can be constructed that display the epitope of interest by cloning a polynucleotide encoding the epitope into an expression vector and transforming the expression vector into the target cells. Non-structural polypeptides can occur in any order in the fusion protein. If desired, at least 2, 3, 4, 5, 6, 7, 8, 9, or 10 or more of one or more of the polypeptides may occur in the fusion protein. Multiple viral strains of HCV occur, and NS3, NS4, NS5a, and NS5b polypeptides of any of these strains can be used in a fusion protein.

Nucleic acid and amino acid sequences of a number of HCV strains and isolates, including nucleic acid and amino acid sequences of NS3, NS4, NS5a, NS5b genes and polypeptides have been determined. For example, isolate HCV J1.1 is described in Kubo et al. (1989) Japan. Nucl. Acids Res. 17:10367–10372; Takeuchi et al.(1990) Gene 91:287–291; Takeuchi et al. (1990) J. Gen. Virol. 71:3027–3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524–9528 and Takamizawa et al., (1991) J. Virol. 65:1105–1113 respectively.

Publications that describe HCV-1 isolates include Choo et al. (1990) Brit. Med. Bull. 46:423–441; Choo et al. (1991) Proc. Natl. Acad. Sci. USA 88:2451–2455 and Han et al. (1991) Proc. Natl. Acad. Sci. USA 88:1711–1715. HCV isolates HC-J1 and HC-J4 are described in Okamoto et al. (1991) Japan J. Exp. Med. 60:167–177. HCV isolates HCT 18~, HCT 23, Th, HCT 27, EC1 and EC10 are described in Weiner et al. (1991) Virol. 180:842–848. HCV isolates Pt-1, HCV-K1 and HCV-K2 are described in Enomoto et al. (1990) Biochem. Biophys. Res. Commun. 170:1021–1025. HCV isolates A, C, D & E are described in Tsukiyama-Kohara et al. (1991) Virus Genes 5:243–254.

Each of the mutant HCV polypeptides containing at least portions of NS3, NS4 and NS5 can be obtained from the same HCV strain or isolate or from different HCV strains or isolates. Thus, each non-structural region of the polypeptide can be from the same HCV strain or isolate or from each different HCV strains or isolates. In addition to the mutant HCV non-structural polypeptides described herein, the proteins can contain other polypeptides derived from the HCV polyprotein. For example, it may be desirable to include polypeptides derived from the core region of the HCV polyprotein. This region occurs at amino acid positions 1–191 of the HCV polyprotein, numbered relative to HCV-1. Either the full-length protein or epitopes of the full-length protein may be used in the subject fusions, such as those epitopes found between amino acids 10–53, amino acids 10–45, amino acids 67–88, amino acids 120–130, or any of the core epitopes identified in, e.g., Houghton et al., U.S. Pat. No. 5,350,671; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; and commonly owned, U.S. Pat. No. 6,150,087, the disclosures of which are incorporated herein by reference in their entireties. When present, additional non-structural HCV polypeptides such as core can be obtained from the same HCV strain or isolate or from different HCV strains or isolates.

Preferably, the above-described mutant proteins, as well as the individual components of these proteins, are produced recombinantly. A polynucleotide encoding these proteins can be introduced into an expression vector which can be expressed in a suitable expression system. A variety of bacterial, yeast, mammalian, insect and plant expression systems are available in the art and any such expression system can be used. Optionally, a polynucleotide encoding these proteins can be translated in a cell-free translation system. Such methods are well known in the art. The proteins also can be constructed by solid phase protein synthesis.

If desired, the mutant polypeptides, or the individual components of these polypeptides, also can contain other amino acid sequences, such as amino acid linkers or signal sequences, as well as ligands useful in protein purification, such as glutathione-S-transferase and staphylococcal protein A.

Polynucleotides

The polynucleotides of the present invention are not necessarily physically derived from the nucleotide sequences shown, but can be generated in any manner, including, for example, chemical synthesis or DNA replication or reverse transcription or transcription. In addition, combinations of regions corresponding to that of the designated sequences can be modified in ways known to the art to be consistent with an intended use.

The DNA encoding the desired polypeptide, whether in fused or mature form, and whether or not containing a signal sequence to permit secretion, can be ligated into expression vectors suitable for any convenient host. Both eukaryotic and prokaryotic host systems are presently used in forming recombinant polypeptides, and a summary of some of the more common control systems and host cell is given below. The polypeptide produced in such host cells is then isolated from lysed cells or from the culture medium and purified to the extent needed for its intended use.

Purification can be by techniques known in the art, for example, differential extraction, salt fractionation, chromatography on ion exchange resins, affinity chromatography, centrifugation, alkali resolubilization of insoluble protein, and the like. See, for example, Methods in Enzymology for a variety of methods for purifying proteins.

Polynucleotides contain less than an entire HCV genome and can be RNA or single- or double-stranded DNA. Preferably, the polynucleotides are isolated free of other components, such as proteins and lipids. Polynucleotides of the invention can also comprise other nucleotide sequences, such as sequences coding for linkers, signal sequences, or ligands useful in protein purification such as glutathione-S-transferase and staphylococcal protein A.

Polynucleotides encoding mutant HCV non-structural polypeptides can be isolated from a genomic library derived from nucleic acid sequences present in, for example, the plasma, serum, or liver homogenate of an HCV infected individual or can be synthesized in the laboratory, for example, using an automatic synthesizer. An amplification method such as PCR can be used to amplify polynucleotides from either HCV genomic DNA or cDNA.

Further, while the polypeptides that are not NS3, NS4, or NS5 of HCV of the present invention can comprise a substantially complete viral domain, in many applications all that is required is that the polypeptide comprise an antigenic or immunogenic region of the virus. An antigenic region of a polypeptide is generally relatively small-typically 8 to 10 amino acids or less in length. Fragments of as few as 5 amino acids can characterize an antigenic region. These segments can correspond to regions of, for example, C, E1, or E2 epitopes. Accordingly, using the cDNAs of C, E1, or E2 as a basis, DNAs encoding short segments of C, E1, or E2 polypeptides can be expressed recombinantly either as fusion proteins, or as isolated polypeptides. In addition, short amino acid sequences can be conveniently obtained by chemical synthesis.

Polynucleotides encoding the polypeptides described herein can comprise coding sequences for these polypeptides which occur naturally or can be artificial sequences which do not occur in nature. These polynucleotides can be ligated to form a coding sequence for the fusion proteins using standard molecular biology techniques. If desired, polynucleotides can be cloned into an expression vector and transformed into, for example, bacterial, yeast, insect, plant or mammalian cells so that the fusion proteins of the invention can be expressed in and isolated from a cell culture.

The expression of polypeptides containing these domains in a variety of recombinant host cells, including, for example, bacteria, yeast, insect, plant and vertebrate cells, give rise to important immunological reagents which can be used for diagnosis, detection, and vaccines.

The general techniques used in extracting the genome from a virus, preparing and probing a cDNA library, sequencing clones, constructing expression vectors, transforming cells, performing immunological assays such as radioimmunoassays and. ELISA assays, for growing cells in culture, and the like are known in the art and laboratory manuals are available describing these techniques. However, as a general guide, the following sets forth some sources currently available for such procedures, and for materials useful in carrying them out.

Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems (Chang et al. (1977), Nature 198:1056), the tryptophan (trp) promoter system (Goeddel et al. (1980) Nucleic Acid Res. 8:4057), the lambda-derived P[L]promoter and N gene ribosome binding site (Shimatake et al. (1981) Nature 292:128) and the hybrid tac promoter (De Boer et al. (1983) Proc. Natl. Acad. Sci. U.S.A. 292:128) derived from sequences of the trp and lac UV5 promoters. The foregoing systems are particularly compatible with *E. coli*; if desired, other prokaryotic hosts such as strains of *Bacillus* or *Pseudomonas* may be used, with corresponding control sequences.

Eukaryotic hosts include mammalian and yeast cells in culture systems. Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers (1978), Nature 273:113), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art. Vectors suitable for replication in mammalian cells may include viral replicons, or sequences which insure integration of the appropriate sequences encoding NANBV epitopes into the host genome.

The vaccinia virus system can also be used to express foreign DNA in mammalian cells. To express heterologous genes, the foreign DNA is usually inserted into the thymidine kinase gene of the vaccinia virus and then infected cells can be selected. This procedure is known in the art and further information can be found in these references (Mackett et al. J. Virol. 49: 857–864 (1984) and Chapter 7 in DNA Cloning, Vol. 2, IRL Press).

Yeast expression systems are also known to one of ordinary skill in the art. A yeast promoter is any DNA sequence capable of binding yeast RNA polymerase and initiating the downstream (3') transcription of a coding sequence (e.g., structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences (Myanohara et al. (1983) *Proc. Natl. Acad. Sci. USA* 80:1).

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, (Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109).

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EP-A-0 196 056. Another example is a ubiquitin fusion protein. Such a fusion protein is made with the ubiquitin region that preferably retains a site for a processing enzyme (e.g., ubiquitin-specific processing protease) to cleave the ubiquitin from the foreign protein. Through this method, therefore, native foreign protein can be isolated (e.g., WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (e.g., see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 (Botstein et al. (1979) *Gene* 8:17–24), pC1/1 (Brake et al. (1984) *Proc. Natl. Acad. Sci USA* 81:4642–4646), and YRp17 (Stinchcomb et al. (1982) *J. Mol. Biol.* 158:157). In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome (Orr-Weaver et al. (1983) *Methods in Enzymol.* 101:228–245). An integrating vector may be directed to a specific locus in yeast by selecting the appropriate homologous sequence for inclusion in the vector. See Orr-Weaver et al., supra. One or more expression construct may integrate, possibly affecting levels of recombinant protein produced (Rine et al. (1983) *Proc. Natl. Acad. Sci. USA* 80:6750). The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions (Butt et al. (1987) *Microbiol, Rev.* 51:351).

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* (Kurtz, et al. (1986) *Mol. Cell. Biol.* 6:142), *Candida maltosa* (Kunze, et al. (1985)*J. Basic Microbiol.* 25:141). *Hansenula polymorpha* (Gleeson, et al. (1986) *J. Gen. Microbiol.* 132:3459; Roggenkamp et al. (1986) *Mol. Gen. Genet.* 202:302), *Kluyveromyces fragilis* (Das, et al. (1984) *J. Bacteriol.* 158:1165), *Kluyveromyces lactis* (De Louvencourt et al. (1983) *J. Bacteriol.* 154:737; Van den Berg et al. (1990) *Bio/Technology* 8:135), *Pichia guillerimondii* (Kunze et al. (1985) *J. Basic Microbiol.* 25:141), *Pichia pastoris* (Cregg, et al. (1985) *Mol. Cell. Biol.* 5:3376; U.S. Pat. Nos. 4,837,148 and 4,929,555), *Saccharomyces cerevisiae* (Hinnen et al. (1978) *Proc. Natl. Acad. Sci. USA* 75:1929; Ito et al. (1983) *J. Bacteriol.* 153:163), *Schizosaccharomyces pombe* (Beach and Nurse (1981) Nature 300:706), and *Yarrowia lipolytica* (Davidow, et al. (1985) *Curr. Genet.* 10:380471 Gaillardin, et al. (1985) *Curr. Genet.* 10:49).

Methods of introducing exogenous DNA into yeast hosts are well-known in the art, and usually include either the transformation of spheroplasts or of intact yeast cells treated with alkali cations. Transformation procedures usually vary with the yeast species to be transformed. (See e.g., Kurtz et al. (1986) *Mol. Cell. Biol.* 6:142; Kunze et al. (1985) J *Basic Microbiol.* 25:141; *Candida*; Gleeson et al. (1986) *J. Gen. Microbiol.* 132:3459; Roggenkamp et al. (1986) *Mol. Gen. Genet.* 202:302; *Hansenula*; Das et al. (1984) *J. Bacteriol.* 158:1165;De Louvencourt et al. (1983) *J. Bacteriol.* 154: 1165; Van den Berg et al. (1990) *Bio/Technology* 8:135; *Kluyveromyces*; Cregg et al. (1985) *Mol. Cell. Biol.* 5:3376; Kunze et al. (1985)*J. Basic Microbiol.* 25:141; U.S. Pat. Nos. 4,837,148 and 4,929,555; *Pichia*; Hinnen et al. (1978) *Proc. Natl. Acad. Sci. USA* 75;1929; Ito et al. (1983) *J. Bacteriol.* 153:163 *Saccharomyces*; Beach and Nurse (1981) *Nature* 300:706; *Schizosaccharomyces*; Davidow et al. (1985) *Curr. Genet.* 10:39; Gaillardin et al. (1985) *Curr. Genet.* 10:49; *Yarrowia*).

Bacterial expression techniques are known in the art. A bacterial promoter is any DNA sequence capable of binding bacterial RNA polymerase and initiating the downstream (3') transcription of a coding sequence (e.g., structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) (Raibaud et al. (1984) *Annu. Rev. Genet.* 18:173). Regulated expression may therefore be either positive or negative, thereby either enhancing or reducing transcription.

Expression and transformation vectors, either extra-chromosomal replicons or integrating vectors, have been developed for transformation into many bacteria. For example, expression vectors have been developed for, inter alia, the following bacteria: *Bacillus subtilis* (Palva et al. (1982) *Proc. Natl. Acad. Sci. USA* 79:5582; EP-A-0 036 259 and EP-A-0 063 953; WO 84/04541), *Escherichia coli* (Shimatake et al. (1981) *Nature* 292:128; Amann et al. (1985) *Gene* 40:183; Studier et al. (1986) *J. Mol. Biol.* 189:113; EP-A-0 036 776,EP-A-0 136 829 and EP-A-0 136 907), *Streptococcus cremoris* (Powell et al. (1988) *Appl. Environ. Microbiol.* 54:655); *Streptococcus lividans* (Powell et al. (1988) *Appl. Environ. Microbiol.* 54:655), *Streptomyces lividans* (U.S. Pat. No. 4,745,056).

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. (See e.g., Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*, Miller et al. (1988) *Proc. Natl. Acad. Sci.* 85:856; Wang et al. (1990) *J. Bacteriol.* 172:949; *Campylobacter*, Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. *In Genetic Engineering: Proceedings of the International Symposium on Genetic Engineering* (eds. H. W. Boyer and *S. Nicosia*); Mandel et al. (1970) *J. Mol. Biol.* 53:159; Taketo (1988) *Biochim. Biophys. Acta* 949:318; *Escherichia*; Chassy et al. (1987) *FEMS Microbiol. Lett.* 44:173 *Lactobacillus*; Fiedler et al. (1988) *Anal. Biochem* 170:38, *Pseudomonas*; Augustin et al. (1990) *FEMS Microbiol. Lett.* 66:203, *Staphylococcus*, Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) Infect. Immun. 32:1295; Powell et al. (1988) *Appl. Environ. Microbiol.* 54:655; Somkuti et al. (1987) *Proc. 4th Evr. Cong. Biotechnology* 1:412, *Streptococcus*).

In addition, viral antigens can be expressed in insect cells by the Baculovirus system. A general guide to Baculovirus expression by Summer and Smith is A Manual of Methods for Baculovirus Vectors and Insect Cell Culture Procedures (Texas Agricultural Experiment Station Bulletin No. 1555). To incorporate the heterologous gene into the Baculovirus genome the gene is first cloned into a transfer vector containing some Baculovirus sequences. This transfer vector, when it is cotransfected with wild-type virus into insect cells, will recombine with the wild-type virus. Usually, the transfer vector will be engineered so that the heterologous gene will disrupt the wild-type Baculovirus polyhedron gene. This disruption enables easy selection of the recombinant virus since the cells infected with the recombinant virus will appear phenotypically different from the cells infected with the wild-type virus. The purified recombinant virus can be used to infect cells to express the heterologous gene. The foreign protein can be secreted into the medium if a signal peptide is linked in frame to the heterologous gene; otherwise, the protein will be bound in the cell lysates. For further information, see Smith et al Mol. & Cell. Biol. 3:2156–2165 (1983) or Luckow and Summers in Virology 17: 31–39 (1989).

Baculovirus expression can also be affected in plant cells. There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861–3863 (1991). Descriptions of plant protein signal peptides may be found in addition to the references described above in Vaulcombe et al., *Mol. Gen. Genet.* 209:33–40 (1987); Chandler et al., *Plant Molecular Biology* 3:407–418 (1984); Rogers, *J. Biol. Chem.* 260:3731–3738 (1985); Rothstein et al., *Gene* 55:353–356 (1987); Whittier et al., Nucleic Acids Research 15:2515–2535 (1987); Wirsel et al., *Molecular Microbiology* 3:3–14 (1989); Yu et al., *Gene* 122:247–253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology*,. Malcolm B. Wilkins, ed., 1984 Pitman Publishing Limited, London, pp. 21–52. References that describe other metabolically-regulated genes: Sheen, *Plant Cell,* 2:1027–1038 (1990); Maas et al., *EMBO J.* 9:3447–3452 (1990); Benkel and Hickey, *Proc. Natl. Acad. Sci.* 84:1337–1339 (1987).

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Transformation can be by any method for introducing polynucleotides into a host cell, including, for example packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (Cohen (1972), Proc. Natl. Acad. Sci. U.S.A. 69:2110; Maniatis et al. (1982), MOLECULAR CLONING; A LABORATORY MANUAL (Cold Spring Harbor Press, Cold Spring Harbor, N.Y.). Yeast transformation by direct uptake may be carried out using the method of Hinnen et al. (1978) Proc. Natl. Acad. Sci. U.S.A. 75: 1929. Mammalian transformations by direct uptake may be conducted using the calcium phosphate precipitation method of Graham and Van der Eb (1978), Virology 52:546 or the various known modifications thereof.

Vector construction employs techniques which are known in the art. Site-specific DNA cleavage is performed by treating with suitable restriction enzymes under conditions which generally are specified by the manufacturer of these commercially available enzymes. The cleaved fragments may be separated using polyacrylamide or agarose gel electrophoresis techniques, according to the general procedures found in Methods in Enzymology (1980) 65:499–560. Sticky ended cleavage fragments may be blunt ended using *E. coli* DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation. Ligation mixtures are transformed into suitable cloning hosts, such as *E. coli*, and successful transformants selected by, for example, antibiotic resistance, and screened for the correct construction.

Synthetic oligonucleotides may be prepared using an automated oligonucleotide synthesizer as described by Warner (1984), DNA 3:401. If desired, the synthetic strands may be labeled with $^{32}P$ by treatment with polynucleotide kinase in the presence of $^{32}P$-ATP, using standard conditions for the reaction. DNA sequences, including those isolated from cDNA libraries, may be modified by known techniques, including, for example site directed mutagenesis, as described by Zoller (1982), Nucleic Acids Res. 10:6487.

The expression constructs of the present invention, including the desired fusion, or individual expression constructs comprising the individual components of these fusions, may be used for nucleic acid immunization, to activate HCV-specific T cells, using standard gene delivery protocols. Methods for gene delivery are known in the art. See, e.g., U.S. Pat. Nos. 5,399,346, 5,580,859, 5,589,466, incorporated by reference herein in their entireties. Genes can be delivered either directly to the vertebrate subject or, alternatively, delivered ex vivo, to cells derived from the subject and the cells reimplanted in the subject. For example, the constructs can be delivered as plasmid DNA, e.g., contained within a plasmid, such as pBR322, pUC, or ColE1

Additionally, the expression constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta*. (1991) 1097:1–17; Straubinger et al., in *Methods of Enzymology* (1983), Vol. 101, pp. 512–527.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413–7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art. See, e.g., Straubinger et al., in METHODS OF IMMUNOLOGY (1983), Vol. 101, pp. 512–527; Szoka et al., *Proc. Natl. Acad. Sci. USA* (1978) 75:4194–4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta*. (1975) 394:483–491. See, also, U.S. Pat. Nos. 4,663,161 and 4,871,488.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980–990; Miller, A. D., *Human Gene Therapy* (1990) 1:5–14; Scarpa et al., *Virology* (1991) 180:849–852; Burns et al., *Proc. Natl. Acad. Sci. USA* (1993) 90:8033–8037; and Boris-Lawrie and Temin, *Cur. Opin. Genet. Develop.* (1993) 3:102–109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110-2209), or isolated from known sources using commonly available techniques.

A number of adenovirus vectors have also been described, such as adenovirus Type 2 and Type 5 vectors. Unlike retroviruses which integrate into the host genome, adenoviruses persist extrachromosomally thus minimizing the risks associated with insertional mutagenesis (Haj-Ahmad and Graham, *J. Virol.* (1986) 57:267–274; Bett et al., *J. Virol.* (1993) 67:5911–5921; Mittereder et al., *Human Gene Therapy* (1994) 5:717–729; Seth et al., *J. Virol.* (1994) 68:933–940; Barr et al., *Gene Therapy* (1994) 1:51–58; Berkner, K. L. *BioTechniques* (1988) 6:616–629; and Rich et al., *Human Gene Therapy* (1993) 4:461–476).

Molecular conjugate vectors, such as the adenovirus chimeric vectors described in Michael et al., *J. Biol. Chem.* (1993) 268:6866–6869 and Wagner et al., *Proc. Natl. Acad. Sci. USA* (1992) 89:6099–6103, can also be used for gene delivery.

Members of the Alphavirus genus, such as but not limited to vectors derived from the Sindbis and Semliki Forest viruses, VEE, will also find use as viral vectors for delivering the gene of interest. For a description of Sindbis-virus derived vectors useful for the practice of the instant methods, see, Dubensky et al., *J. Virol.* (1996) 70:508–519; and International Publication Nos. WO 95/07995 and WO 96/17072.

Other vectors can be used, including but not limited to simian virus 40, cytomegalovirus. Bacterial vectors, such as *Salmonella* ssp. *Yersinia enterocolitica, Shigella* spp., *Vibrio cholerae, Mycobacterium* strain BCG, and *Listeria monocytogenes* can be used. Minichromosomes such as MC and MC1, bacteriophages, cosmids (plasmids into which phage lambda cos sites have been inserted) and replicons (genetic elements that are capable of replication under their own control in a cell) can also be used.

The expression constructs may also be encapsulated, adsorbed to, or associated with, particulate carriers. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362–368; and McGee et al., *J. Microencap.* (1996).

A wide variety of other methods can be used to deliver the expression constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest; and Felgner, P. L., *Advanced Drug Delivery Reviews* (1990) 5:163–187, for a review of delivery systems useful for gene transfer. One particularly effective method of delivering DNA using electroporation is described in International Publication No. WO/0045823.

Additionally, biolistic delivery systems employing particulate carriers such as gold and tungsten, are especially useful for delivering the expression constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

Compositions

The invention also provides compositions comprising the HCV polypeptides or polynucleotides described herein. Such compositions are useful as diagnostics, for example, using the mutant polypeptides (or polynucleotides encoding these polypeptides) in diagnostic reagents. Diagnostics using polypeptides and polynucleotides are known to those of skill in the art.

In addition, immunogenic compounds can be prepared from one or more immunogenic polypeptides derived from the polypeptides described herein, for example the ΔNS35 polypeptide. The preparation of immunogenic compounds which contain immunogenic polypeptide(s) as active ingredients is known to one skilled in the art. Typically, such immunogenic compounds are prepared as injectables, either as liquid solutions or suspensions; solid forms suitable for solution in, or suspension in, liquid prior to injection can also be prepared. The preparation can also be emulsified, or the protein encapsulated in liposomes.

Immunogenic and diagnostic compositions of the invention preferably comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, and inactive virus particles.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, ethanol, or the like, singly or in combination, as well as substances such as wetting agents, emulsifying agents, or pH buffering agents. Liposomes can also be used as a carrier for a composition of the invention, such liposomes are described above.

If desired, co-stimulatory molecules which improve immunogen presentation to lymphocytes, such as B7-1 or B7-2, or cytokines such as GM-CSF, IL-2, and IL-12, can be included in a composition of the invention. Optionally, adjuvants can also be included in a composition. Adjuvants which can be used include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE), formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) detoxified mutants of a bacterial ADP-ribosylating toxin such as a cholera toxin (CT), a pertussis toxin (PT), or an *E. coli* heat-labile toxin (LT), particularly LT-K63, LT-R 72, CT-S109, PT-K9/G129; see, e.g., WO 93/13302 and WO 92/19265; (7) other substances that act as immunostimulating agents to enhance the effectiveness of the composition; and (8) microparticles with adsorbed macromolecules, as described in copending U.S. patent application Ser. No. 09/285,855 (filed Apr. 2, 1999) and international Patent Application Serial No. PCT/US99/17308 (filed Jul. 29, 1999). Alum and MF59 are preferred. The effectiveness of an adjuvant can be determined by measuring the amount of antibodies directed against an immunogenic polypeptide containing an HCV antigenic sequence resulting from administration of this polypeptide in immunogenic compounds which are also comprised of the various adjuvants.

As mentioned above, muramyl peptides include, but are not limited to, N-acetyl- muramyl-L-threonyl-D-isoglutamine (thr-MDP), -acetyl-normuramyl-L-alanyl-D- isoglutamine (CGP 11637, referred to nor-MDP), N-acetylmuramyl-L-alanyl-D- isoglutaminyl-L-alanine-2-(1'-2'-dipalmitoyl-sn-glycero-3-hydroxyphosphoryloxy)-ethylamine (CGP 19835A, referred to as MTP-PE), etc.

Thus, such recombinant or synthetic HCV polypeptides can be used in vaccines and as diagnostics. Further, antibodies raised against these polypeptides can also be used as diagnostics, or for passive immunotherapy. In addition, antibodies to these polypeptides are useful for isolating and identifying HCV particles.

Native HCV antigens can also be isolated from HCV virions. The virions can be grown in HCV infected cells in tissue culture, or in an infected host.

Administration and Delivery

The polynucleotide and polypeptide compositions described herein (e.g., immunogenic compounds) may be administered to a subject using any suitable delivery means. Methods of delivering nucleic acids into host cells are discussed above. Further, HCV polynucleotides and/or polypeptides can be administered parenterally, by injection, usually, subcutaneously, intramuscularly, transdermally or transcutaneously. Certain adjuvants, e.g. LTK63, LTR72 or PLG formulations, can be administered intranasally or orally. Additional formulations which are suitable for other modes of administration include suppositories. For suppositories, traditional binders and carriers can include, for example, polyalkylene glycols or triglycerides; such suppositories can be formed from mixtures containing the active ingredient in the range of 0.5% to 10%, preferably 1%-2%. Other oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

The polypeptides of the present invention can be formulated into the immunogenic compound as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The immunogenic compounds are administered in a manner compatible with the dosage formulation, and in such amount as will be prophylactically and/or therapeutically effective. The quantity to be administered, which is generally in the range of 5 micrograms to 250 micrograms of polypeptide per dose, depends on the subject to be treated, capacity of the subject's immune system to synthesize antibodies, and the degree of protection desired. Precise amounts of active ingredient required to be administered may depend on the judgment of the practitioner and can be peculiar to each subject.

The immunogenic compound can be given in a single dose schedule, or preferably in a multiple dose schedule. A multiple dose schedule is one in which a primary course of vaccination can be with 1–10 separate doses, followed by other doses given at subsequent time intervals required to maintain and or reenforce the immune response, for example, at 1–4 months for a second dose, and if needed, a subsequent dose(s) after several months. Further, the course of administration may include polynucleotides and polypeptides, together or sequentially (for example, priming with a polynucleotide composition and boosting with a polypeptide composition). The dosage regimen will also, at least in part, be determined by the need of the individual and be dependent upon the judgment of the practitioner.

In certain embodiments, administration of the polynucleotides and polypeptides described herein is used to activate T cells. In addition to the practical advantages of simplicity of construction and modification, administration of polynucleotides encoding mutant NS polypeptides results in the synthesis of a mutant NS polypeptide in the host. Thus, these immunogens are presented to the host immune system with native post-translational modifications, structure, and conformation. The polynucleotides are preferably injected intramuscularly to a large mammal, such as a human, at a dose of 0.5, 0.75, 1.0, 1.5, 2.0, 2.5, 5 or 10 mg/kg.

The proteins and/or polynucleotides can be administered either to a mammal which is not infected with an HCV or can be administered to an HCV-infected mammal. The particular dosages of the polynucleotides or fusion proteins in a composition or will depend on many factors including, but not limited to the species, age, and general condition of the mammal to which the composition is administered, and the mode of administration of the composition. An effective amount of the composition of the invention can be readily determined using only routine experimentation. In vitro and in vivo models can be employed to identify appropriate doses. Generally, 0.5, 0.75, 1.0, 1.5, 2.0, 2.5, 5 or 10 mg will be administered to a large mammal, such as a baboon, chimpanzee, or human. If desired, co-stimulatory molecules or adjuvants can also be provided before, after, or together with the compositions.

Antibodies and Diagnostics

Antibodies, both monoclonal and polyclonal, which are directed against HCV epitopes are particularly useful in diagnosis, and those which are neutralizing are useful in passive immunotherapy. Monoclonal antibodies, in particular, may be used to raise anti- idiotype antibodies.

Anti-idiotype antibodies are immunoglobulins which carry an "internal image" of the antigen of the infectious agent against which protection is desired. Techniques for raising anti-idiotype antibodies are known in the art. See, e.g., Grzych (1985), Nature 316:74; MacNamara et al. (1984), Science 226:1325, Uytdehaag et al (1985), J. Immunol. 134:1225. These anti-idiotype antibodies may also be useful for treatment and/or diagnosis of NANBH, as well as for an elucidation of the immunogenic regions of HCV antigens.

An immunoassay for viral antigen may use, for example, a monoclonal antibody directed towards a viral epitope, a combination of monoclonal antibodies directed towards epitopes of one viral polypeptide, monoclonal antibodies directed towards epitopes of different viral polypeptides, polyclonal antibodies directed towards the same viral antigen, polyclonal antibodies directed towards different viral antigens or a combination of monoclonal and polyclonal antibodies.

Immunoassay protocols may be based, for example, upon competition, or direct reaction, or sandwich type assays. Protocols may also, for example, use solid supports, or may be by immunoprecipitation. Most assays involve the use of labeled antibody or polypeptide. The labels may be, for example, fluorescent, chemiluminescent, radioactive, or dye molecules. Assays which amplify the signals from the probe are also known. Examples of which are assays which utilize biotin and avidin, and enzyme-labeled and mediated immunoassays, such as ELISA assays.

An enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microplate or plastic cup), incubated with test serum dilutions, washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization colorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is estimated calorimetrically, and related to antigen concentration.

The HCV fusion proteins, such as NS3 mutant and core fusion proteins, can also be used to produce HCV-specific polyclonal and monoclonal antibodies. HCV-specific polyclonal and monoclonal antibodies specifically bind to HCV antigens.

Polyclonal antibodies can be produced by administering the fusion protein to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against HCV-specific epitopes present in the fusion proteins can also be readily produced. Normal B cells from a mammal, such as a mouse, immunized with, e.g., a mutant NS3 polypeptide or NS-core fusion protein can be fused with, for example, HAT-sensitive mouse myeloma cells to produce hybridomas. Hybridomas producing HCV-specific antibodies can be identified using RIA or ELISA and isolated by cloning in semi-solid agar or by limiting dilution. Clones producing HCV-specific antibodies are isolated by another round of screening.

Antibodies, either monoclonal and polyclonal, which are directed against HCV epitopes, are particularly useful for detecting the presence of HCV or HCV antigens in a sample, such as a serum sample from an HCV-infected human. An immunoassay for an HCV antigen may utilize one antibody or several antibodies. An immunoassay for an HCV antigen may use, for example, a monoclonal antibody directed towards an HCV epitope, a combination of monoclonal antibodies directed towards epitopes of one HCV polypeptide, monoclonal antibodies directed towards epitopes of different HCV polypeptides, polyclonal antibodies directed towards the same HCV antigen, polyclonal antibodies directed towards different HCV antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate HCV particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind HCV particles or antigens from a biological sample, such as blood or plasma. The bound HCV particles or antigens are recovered from the column matrix by, for example, a change in pH.

Methods of Eliciting Immune Responses

HCV-specific T cells that are activated by the above-described polypeptides, expressed in vivo or in vitro preferably recognize an epitope of an HCV polypeptide such as a mutant NS3 polypeptide, including an epitope of a mutant HCV polypeptide. HCV-specific T cells can be $CD8^+$ or $CD4^+$.

HCV-specific $CD8^+$ T cells preferably are cytotoxic T lymphocytes (CTL) which can kill HCV-infected cells that display NS3, NS4, NS5a, NS5b epitopes complexed with an MHC class I molecule. HCV-specific $CD8^+$ T cells may also express interferon-γ (IFN-γ). HCV-specific $CD8^+$ T cells can be detected by, for example, $^{51}$Cr release assays. $^{51}$Cr release assays measure the ability of HCV-specific $CD8^+$ T cells to lyse target cells displaying an nonstructural (e.g., mutant NS) epitope. HCV-specific $CD8^+$ T cells which express IFN-γ can also be detected by immunological methods, preferably by intracellular staining for IFN-γ after in vitro stimulation with a mutant NS polypeptide.

HCV-specific $CD4^+$ cells activated by the above-described polypeptides, expressed in vivo or in vitro, and combinations of the individual components of these proteins, preferably recognize an epitope of a mutant nonstructural polypeptide, including an epitope of a mutant protein, that is bound to an MHC class II molecule on an HCV-infected cell and proliferate in response to stimulating mutant peptides.

HCV-specific $CD4^+$ T cells can be detected by a lymphoproliferation assay. Lymphoproliferation assays measure the ability of HCV-specific $CD4^+$ T cells to proliferate in response to an epitope.

Mutant NS (or fusions thereof with core, envelope or other viral polypeptides) can be used to activate HCV-specific T cells either in vitro or in vivo. Activation of HCV-specific T cells can be used, inter alia, to provide model systems to optimize CTL responses to HCV and to provide prophylactic or therapeutic treatment against HCV infection. For in vitro activation, proteins are preferably supplied to T cells via a plasmid or a viral vector, such as an adenovirus vector, as described above.

Polyclonal populations of T cells can be derived from the blood, and preferably from peripheral lymphoid organs, such as lymph nodes, spleen, or thymus, of mammals that have been infected with an HCV. Preferred mammals include mice, chimpanzees, baboons, and humans. The HCV serves to expand the number of activated HCV-specific T cells in the mammal. The HCV-specific T cells derived from the mammal can then be restimulated in vitro by adding HCV epitopic peptides to the T cells. The HCV-specific T cells can then be tested for, inter alia, proliferation (e.g., lymphoproliferation assays known in the art), the production of IFN-γ, and the ability to lyse target cells displaying HCV NS epitopes in vitro.

The following examples are meant to illustrate the invention and are not meant to limit it in any way. Those of ordinary skill in the art will recognize modifications within the spirit and scope of the invention as set forth herein.

EXAMPLES

Example 1

Figure 10:
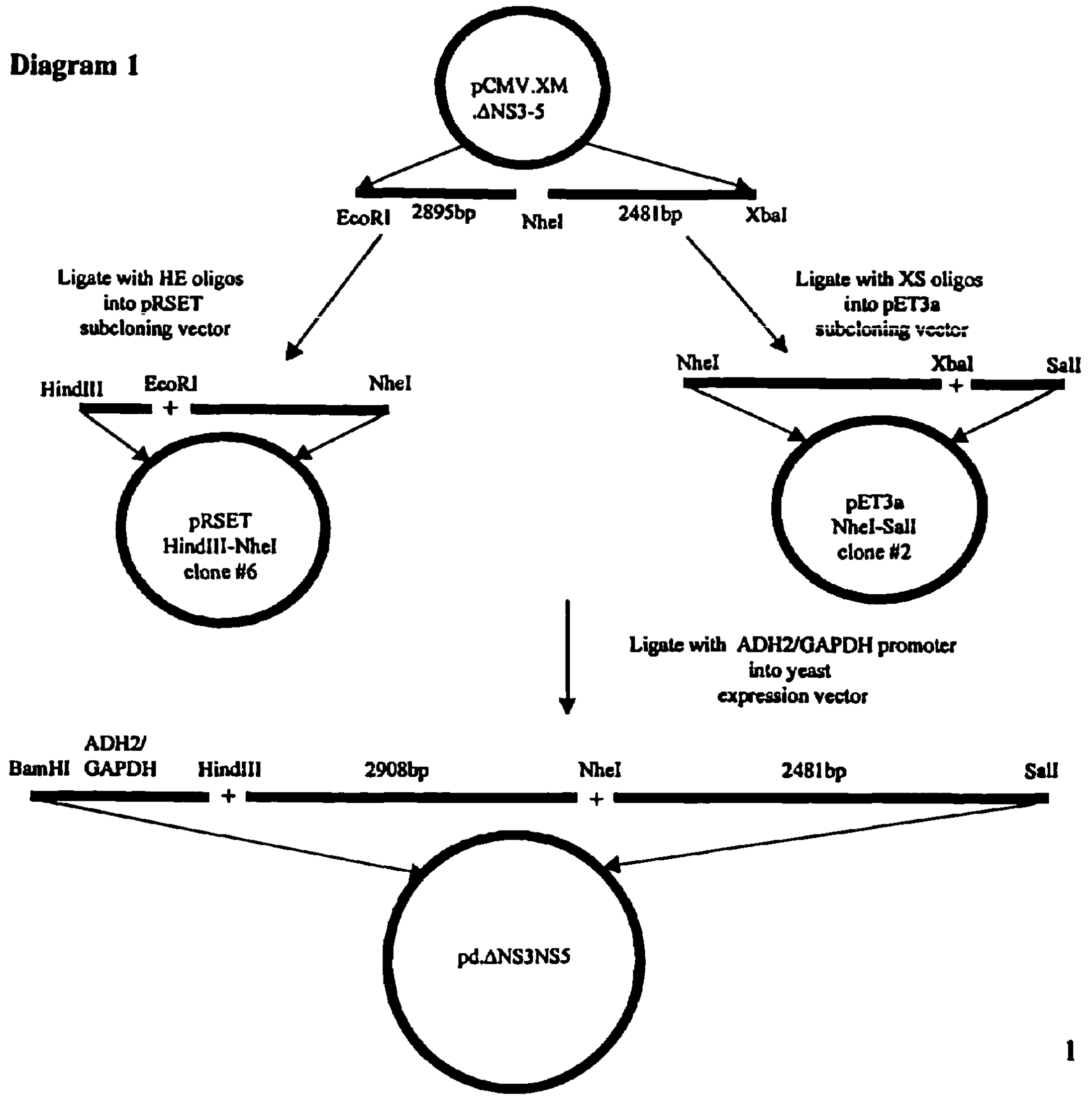
FIG. 10 shows the cloning scheme for generating pd.ΔNS3NS5.
Figure 13:
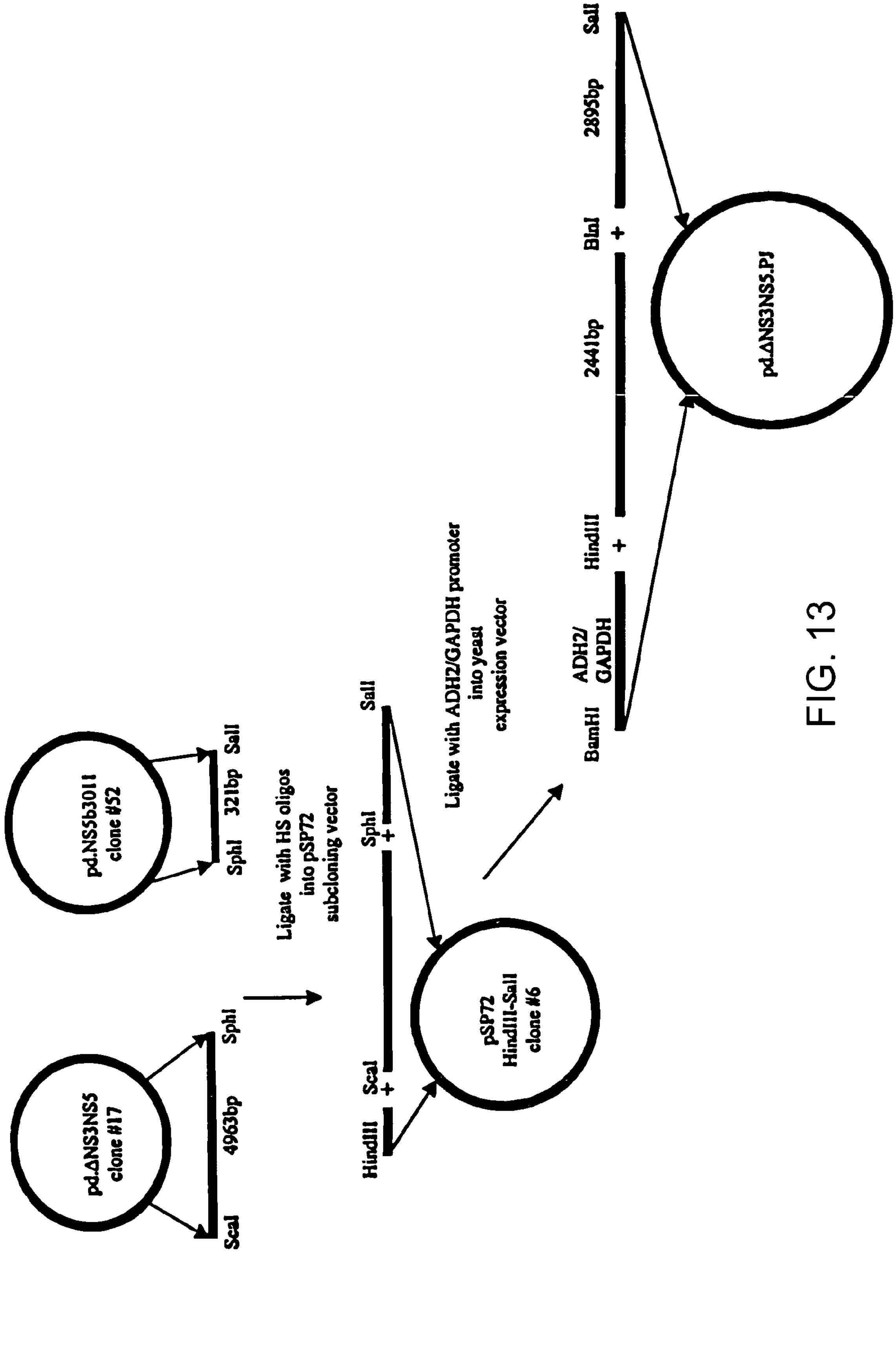
FIG. 13 shows the cloning scheme for generating pd.ΔNS3NS5.pj.

Constructs pCMV-II: pCMV-II (FIG. 7, SEQ ID NO:5) was created to contain the human CMV promoter, enhancer, intron A, polylinker and the bovine growth hormone terminator in a deleted-pUC backbone (Life Technologies).

pT7-HCV: pT7-HCV was created in a polylinker-modified pUC vector to contain full-length HCV cDNA preceded by a synthetic T7 promoter. pT7-HCV also contains the complete 5' UTR and the poly A version of the 3' UTR.

pCMV.ΔNS35: To generate pCMV.ΔNS35 (FIG. 5, SEQ ID NO:3), a two step procedure was undertaken. First, a PCR product was generated from pT7-HCV that corresponded to the following: a 5' EcoRI site, followed by the Kozak sequence of ACCATGG; the initiator ATG followed by amino acid #1242 and continuing to the StuI site. Second, the StuI to XbaI fragment from a full-length genomic clone was isolated. The genomic clone consisted of the T7 promoter fused to the full-length HCV cDNA with the poly A version of the 3' end, in a pUC vector. Finally, the EcoRI-StuI and StuI-XbaI fragments were ligated into the pCMV-II expression vector, transformed into HB 101 competent cells and plated onto ampicillin (100 μg/ml). Miniprep analyses led to the identification of the desired clone which was amplified on a larger scale using a Quigen Gigaprep kit following the manufacturer's specifications. The resulting clone was named pCMV.ΔNS35 (FIG. 5, SEQ ID NO:3).

pd.ΔNS3NS5: As shown schematically in FIG. 10, the yeast expression plasmid pd.ΔNS3NS5 (SEQ ID NO:8) was constructed using restriction fragments obtained from the mammalian expression plasmid pCMV.KM.ΔNS35. pCMV.KM.ΔNS35 is identical to pCMV.ΔNS35 (FIG. 5, SEQ ID NO:3) except that it contains a kanamycin resistance gene in the viral backbone. pCMV.KM.ΔNS35 was digested with EcoRI and NheI to obtain 2895 bp EcoRI-NheI fragment. EcoRI-NheI fragment was ligated into pRSET HindIII-NheI subcloning vector with oligos (HE) from HindIII to EcoRI. After sequence verification, pRSETHindIII-NheI #6 was digested with HindIII and NheI to obtain a 2908 bp HindIII-NheI fragment.

pCMV.KM.ΔNS35 was linearized with XbaI and ligated with synthetic oligos (XS) from XbaI-SalI. The ligation was digested with NheI and SalI to obtain 2481 bp NheI-SalI fragment. The fragment was ligated into pET3a NheI-SalI subcloning vector. After sequence verification, pET3a NheI-SalI #2 was digested with NheI and SalI to obtain a 2481 bp NheI-SalI fragment. BamHI-HindIII ADH2/GAPDH promoter fragment was then ligated with HindIII-NheI and NheI-SalI fragments into pBS24.1 BamHI-SalI yeast expression vector.

pd.ΔNS3NS5.PJ: pd.ΔNS3NS5.PJ (FIGS. 13 and 14; SEQ ID NO:10) was generated to create a "perfect junction" at the 5' and 3' end of the HCV coding region. At the 5' end of pd.ΔNS3NS5, there were 6 extra bases between the yeast ADH2/GAPDH promoter and the ATG of the polypeptide. At the 3' end, there were 52 bases of untranslated sequence between the stop codon of the polypeptide and the α-factor terminator in the yeast expression vector. pd.ΔNS3NS5.PJ was created by digesting pd.ΔNS3NS5 #17 with ScaI and SphI to obtain 4963 bp ScaI-SphI fragment. pd.NS5b3011 was digested with SphI and SalI to obtain a 321 bp SphI-SalI fragment which gave the "perfect junction" at the 3' end of the polypeptide. The ScaI-SphI and SphI-SalI fragments were ligated into pSP72 HindIII-SalI subcloning vector with synthetic oligos from HindIII-ScaI(HS) for the "perfect junction" at the 5' end.

Figure 16A:
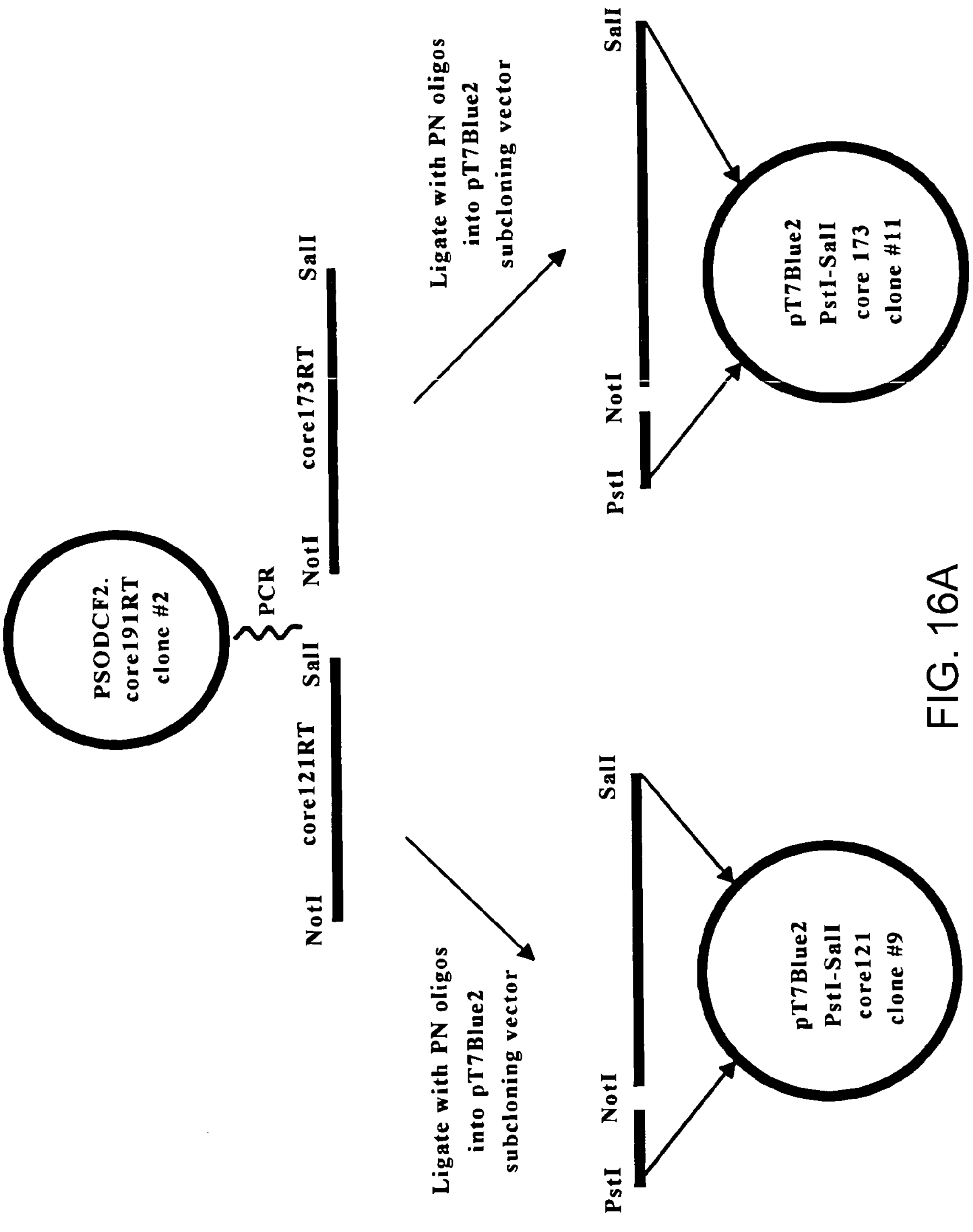
FIG. 16 shows the cloning scheme for generating pdΔNS3NS5.pj.core121RT and pdΔNS3NS5.pj.core173RT.
Figure 16B:
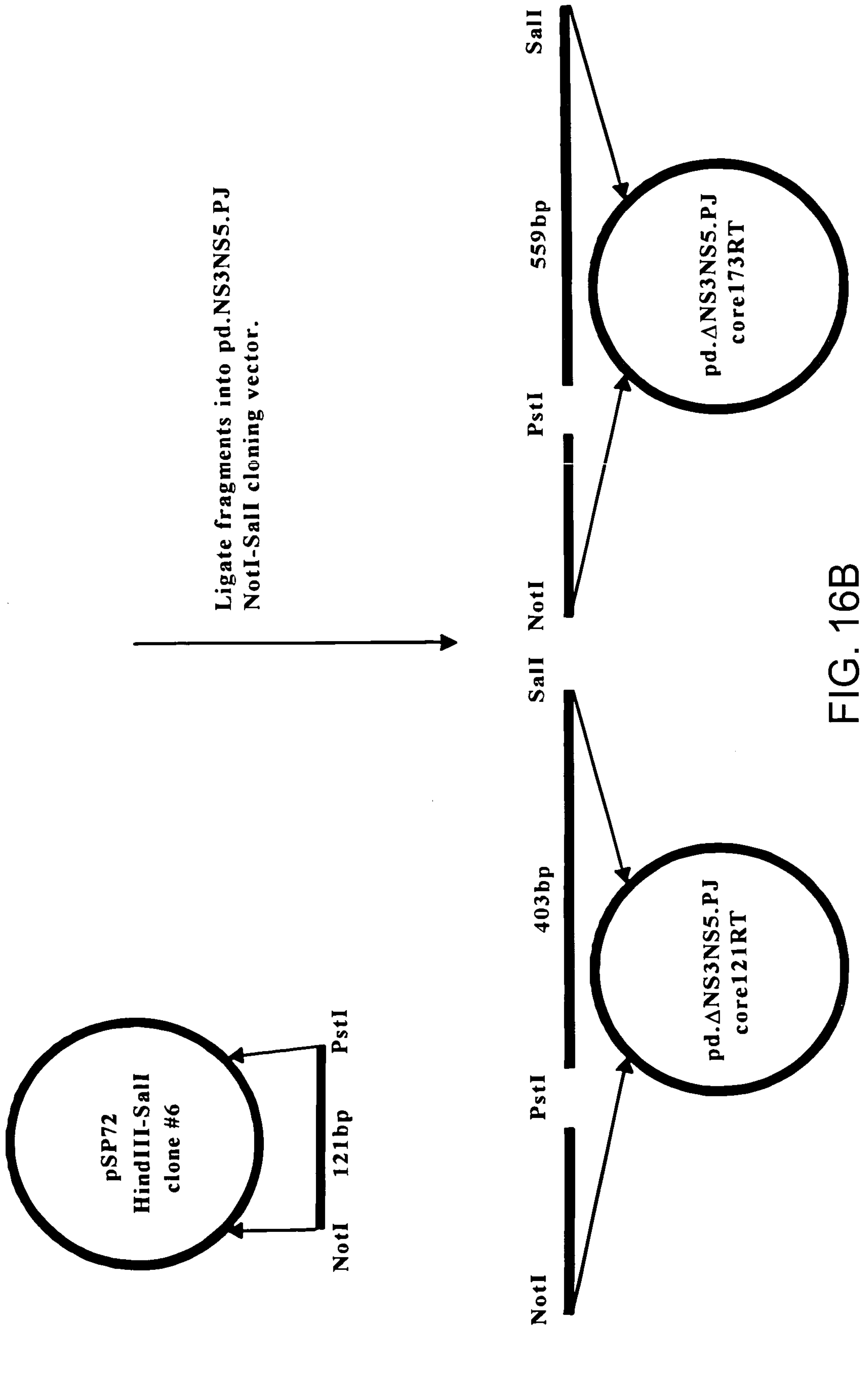

The region of synthetic sequence in pSP72 HindIII-SalI clone# 6 was verified. pSP72 HindIII-SalI clone#6 was digested with HindIII and BlnI or with BlnI and SalI to obtain 2441 bp HindIII-BlnI and 2895 bp BlnI-SalI fragments, respectively. The BamHI-HindIII ADH2/GAPDH promoter fragment was ligated to HindIII-BlnI and BlnI-SalI fragments into pBS24.1 BamHI-SalI yeast expression vector.

pd.ΔNS3NS5.PJ.core121RT and pd.ΔNS3NS5.PJ.core173RT were generated and encode HCV core aa 1-121 at the C-terminus of the ΔNS3NS5 polypeptide (designated pd.ΔNS3NS5.PJ.core121RT, SEQ ID NO:12) and core aa 1–173 at the C-terminus of the ΔNS3NS5 polypeptide (designated pd.ΔNS3NS5.PJ.core173RT, SEQ ID NO:14). The core sequence had aa 9 mutated from Lys to Arg and aa 11 mutated from Asn to Thr, designated as core 121RT or 173RT.

pd.ΔNS3NS5.PJ.core121RT and pd.ΔNS3NS5.PJ.core173RT: To generate pd.ΔNS3NS5.PJ.core121RT (FIG. 17, SEQ ID NO:12) and pd.ΔNS3NS5.PJ.core173RT (FIG. 18, SEQ ID NO:14). As shown in FIG. 16, a NotI-Sal HCVcore121RT and HCVcore173RT were amplified by PCR, from an *E. coli* expression plasmid, pSODCF2.HCVcore191RT #2. Either the core 121RT Not-SalI PCR product or the core 173RT Not-SalI PCR product were ligated into a pT7Blue2 PstI-SalI subcloning vector with synthetic oligos (PN) from PstI to NotI. After sequence confirmation, pT7Blue2core121RT clone#9 and pT7Blue2core173RT clone#11 was digested with PstI and SalI to obtain 403 bp and 559 bp PstI-SalI fragments, respectively, for further cloning.

A 121 bp NotI-PstI fragment from pSP72 HindIII-SalI clone #6 was isolated as described above during the cloning of pd.ΔNS3NS5.PJ. NotI-PstI and PstI-SalI fragments were assembled into a vector made by digesting pd.NS3NS5.PJ clone#5 (described above) with NotI and SalI.

Figure 20A:
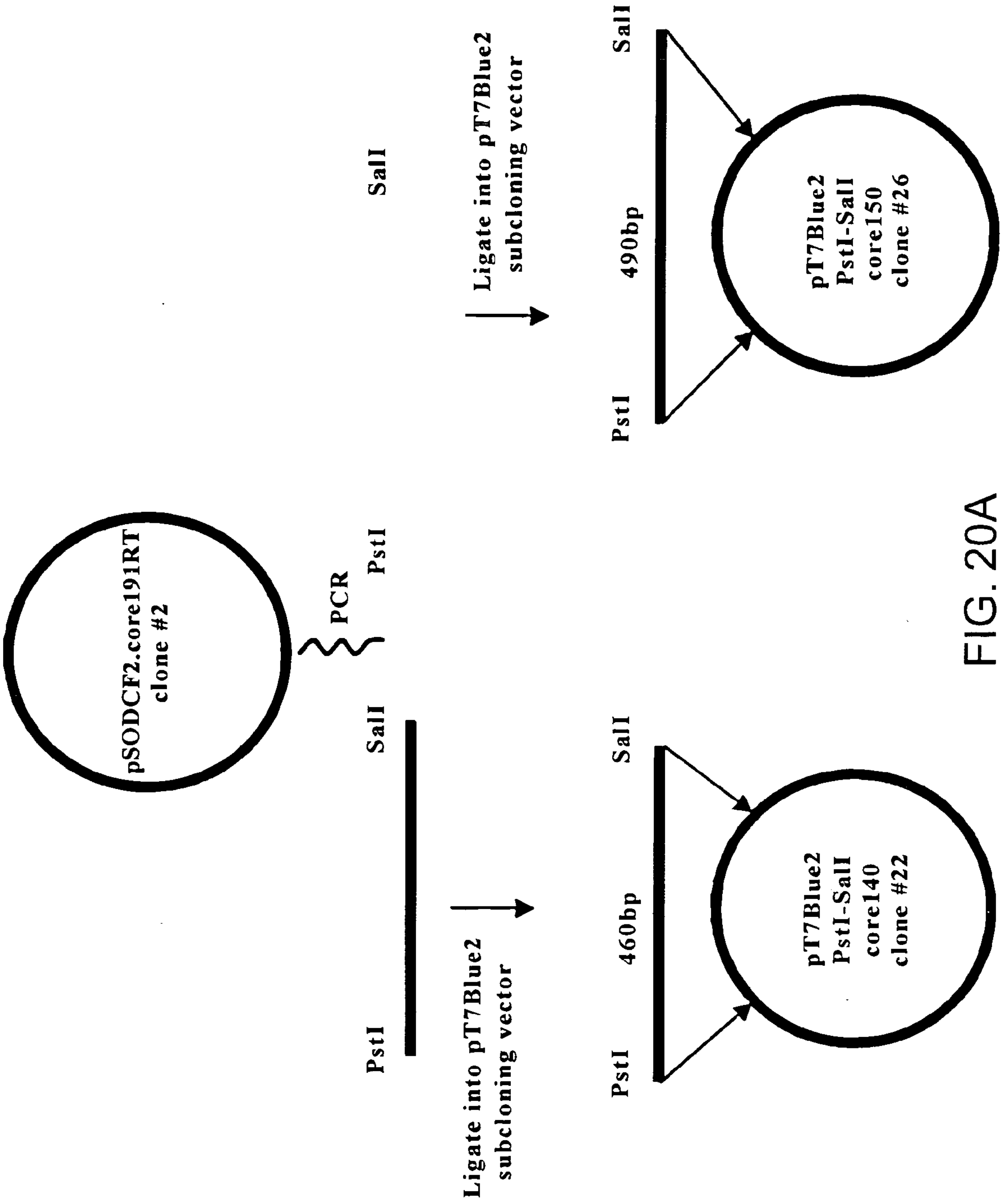
FIG. 20 shows the cloning scheme for generating pdΔNS3NS5.pj.core140RT and pdΔNS3NS5.pj.core150RT.
Figure 20B:
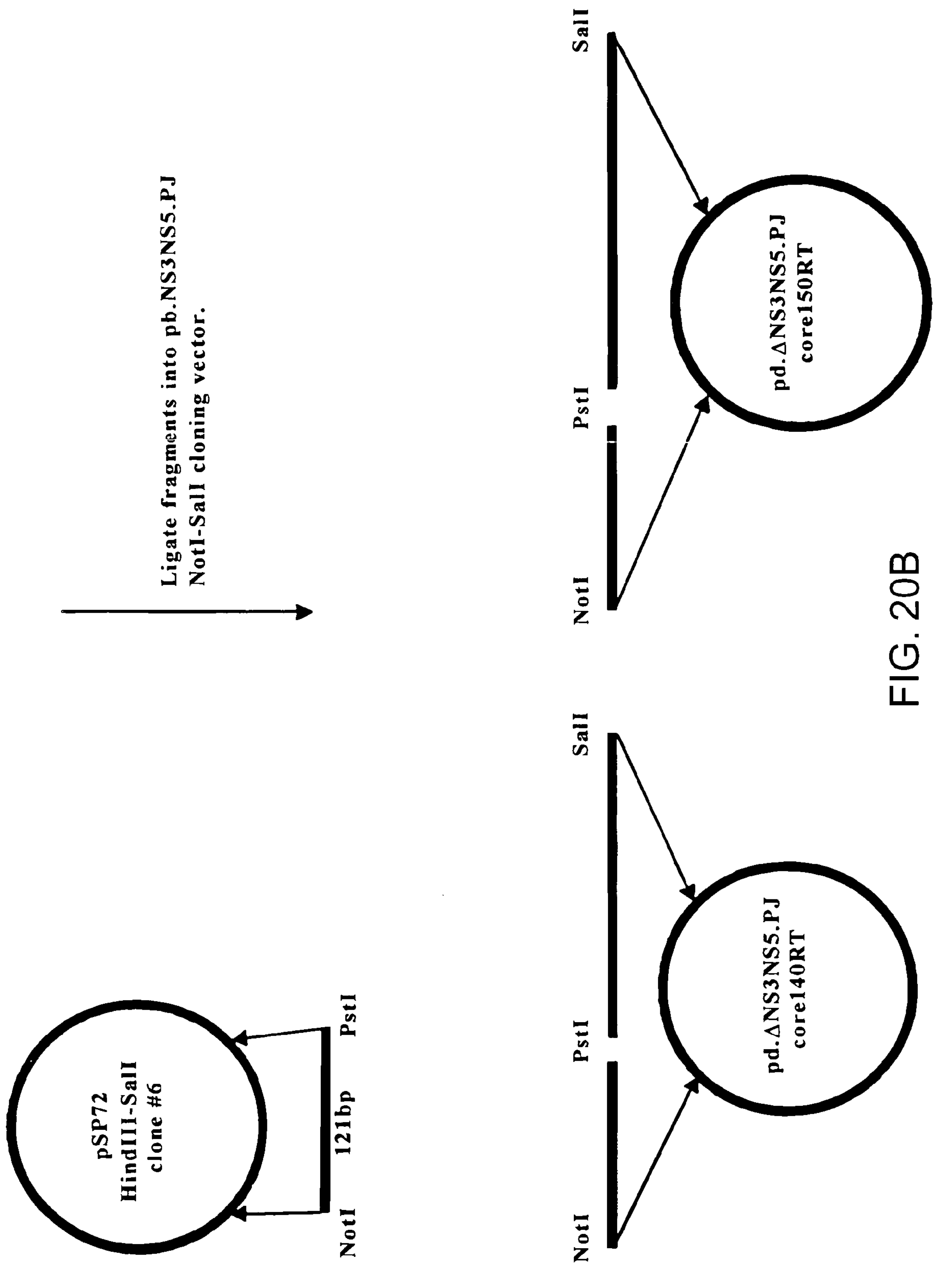

ΔNS3NS5 and Core 140 and Core 150: An HCV core epitope was found which elicits CTLs in baboons (HCV core aa 121–135). Since pd.ΔNS3NS5.PJ.core121RT ends right before this potentially important epitope and was expressed better than the longer pd.ΔNS3NS5.PJ.core173RT construct (Example 2), two intermediate constructs were made which include this epitope, possibly giving intermediate expression levels. The two new constructs fused HCV core aa 1–140 or HCV core aa1–150 to the *C terminus* of ΔNS3NS5.PJ.

pd.ΔNS3NS5.PJ.core140RT (FIG. 21. SEQ ID NO:16) and pd.ΔNS3NS5.PJ.core150RT (FIG. 22, SEQ ID NO:18): As shown in FIG. 20, a PstI-SalI HCVcore140RT and a PstI-SalIHCVcore150RT fragment were amplified by PCR from pd.ΔNS3NS5.PJ.core173RT clone #16. Ligate either HCV core PstI-SalI PCR products into pT7Blue2 PstI-SalI subcloning vector. After sequence confirmation, pT7Blue2core140RT clone#22 and pT7Blue2core150RT clone#26 were digested with PstI-SalI to obtain 460 bp and 490 bp PstI-SalI fragments, respectively, for further cloning.

A 121 bp NotI-PstI fragment was isolated from pSP72 HindIII-SalI clone #6 (as described above during the cloning of pd.ΔNS3NS5.PJ. NotI-PstI and PstI-SalI fragments were assembled into a vector made by digesting pd.ΔNS3NS5.PJ clone#5 (described above) with NotI and SalI.

Example 2

Protein Expression

Figure 12:
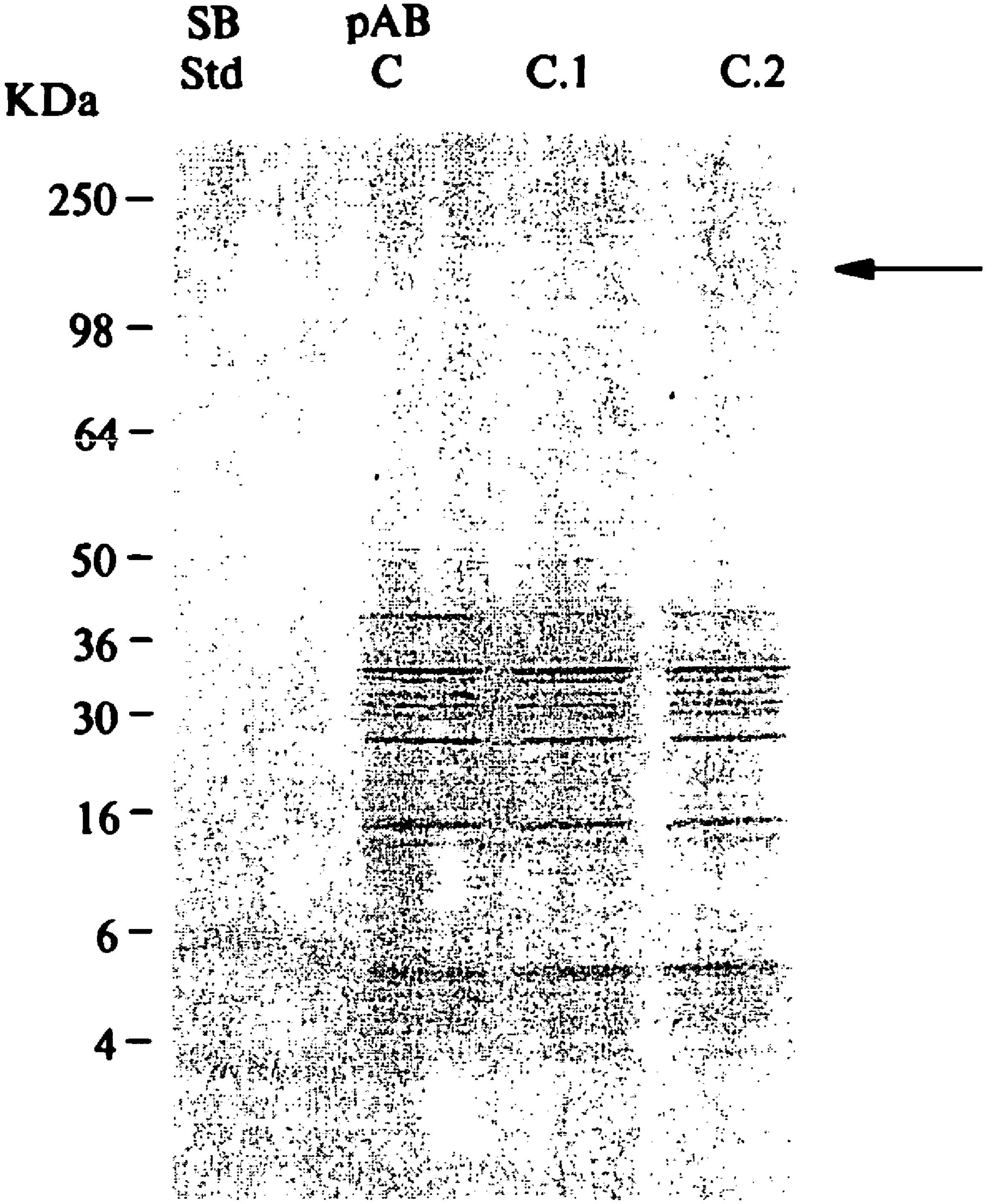
FIG. 12 shows the Western blot of proteins expressed by *S. cerevisiae* strain AD3 transformed with pd.ΔNS3NS5.
Figure 15:
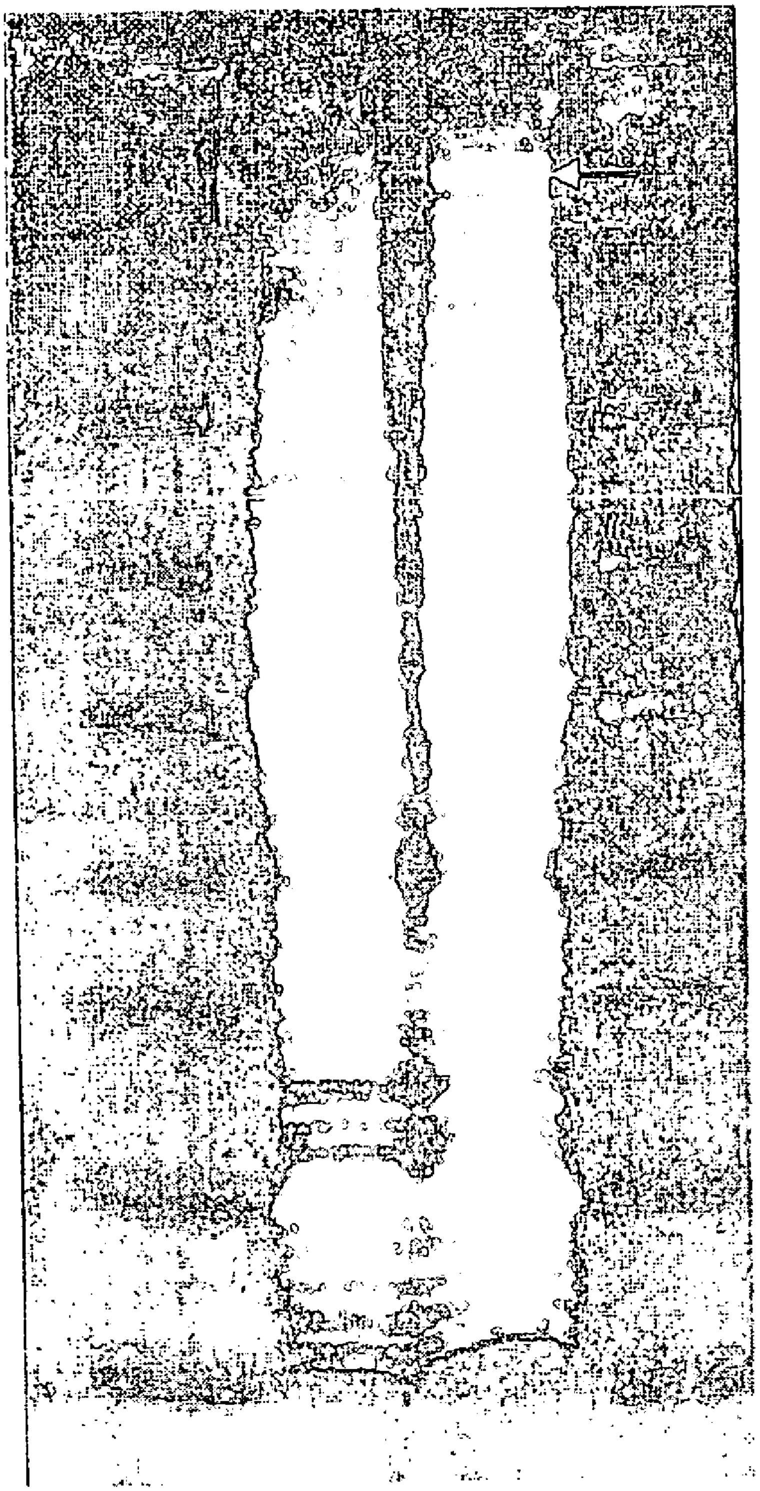
FIG. 15 shows the Western blot of proteins expressed by *S. cerevisiae* strain AD3 transformed with pd.ΔNS3NS5.pj, specifically demonstrating the expression of ΔNS3NS5 polypeptide.
Figure 19:
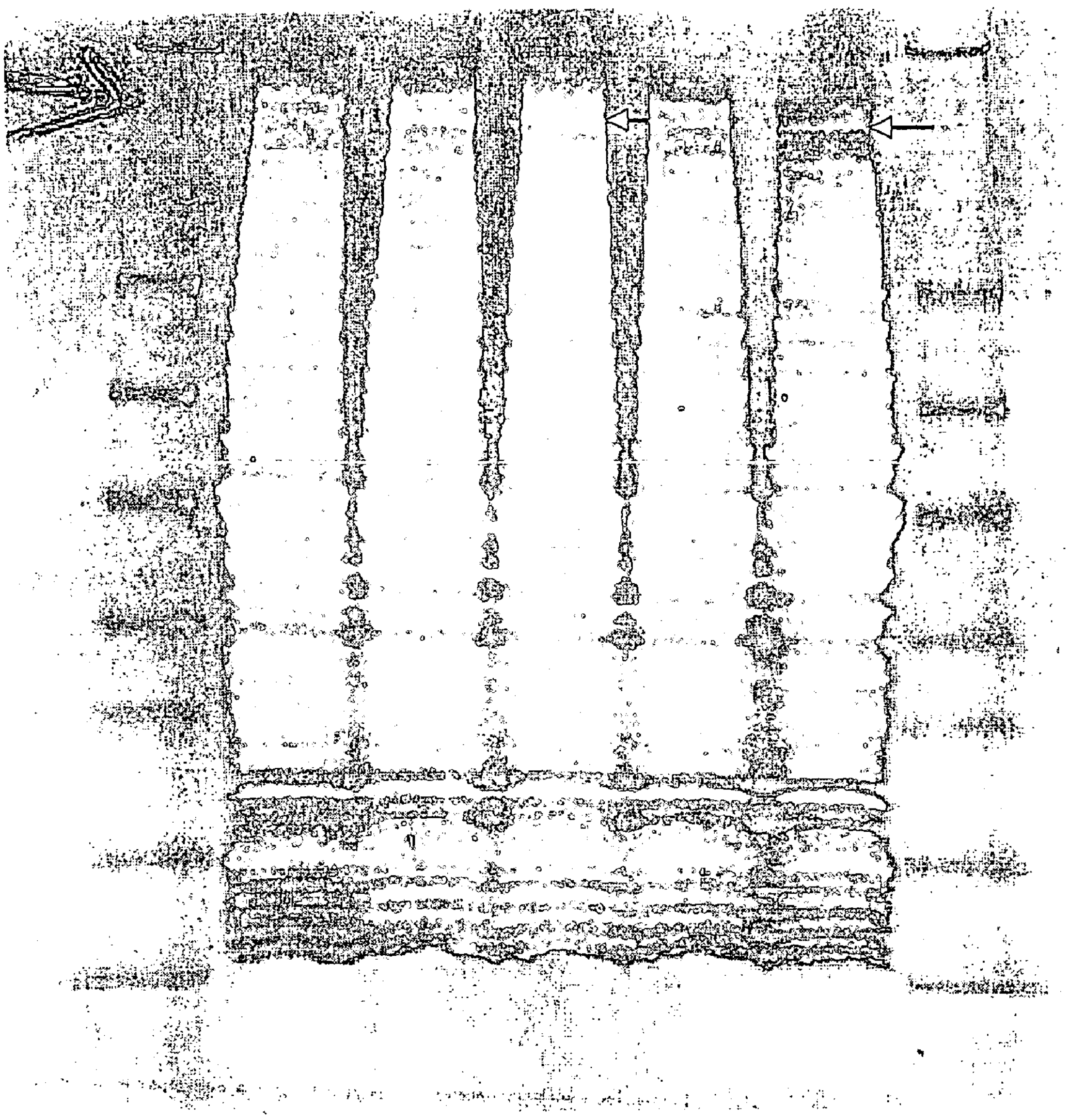
FIG. 19 shows the Western blot of proteins expressed by *S. cerevisiae* strain AD3 transformed with pd.ΔNS3NS5.pj, specifically demonstrating the expression of ΔNS3NS5.core121 and ΔNS3NS5.core173 polypeptides. Lanes 1 and 7 show See Blue Standards. Lane 2 shows control yeast plasmid. Lanes 3 and 4 show ΔNS3NS5.core121RT polypeptide, colonies 1 and 2. Lanes 5 and 6 show ΔNS3NS5.core173RT polypeptide, colonies 3 and 4.

Various of the constructs described herein, encoding HCV-1 ΔNS3 to NS5 antigen (aa 1242–3011), were expressed in yeast. *S. cerevisiae* strain AD3 was transformed with pd.ΔNS3NS5 and checked for expression. A stained protein band at the expected molecular weight of 194 kD was not observed (FIG. 12). Strain AD3 was also transformed with pd.ΔNS3NS5.PJ clone #5 and checked for expression. A protein band of the expected molecular weight of 194 kD was detected (FIG. 15). Strain AD3 was transformed with pd.ΔNS3NS5.PJ.core121RT clone #6 and pd.ΔNS3NS5.PJ.core173RT clone# 15 and checked for expression. Protein bands of the expected molecular weight of 206 kD and 210 kD, respectively, were observed. Expression levels of the pd.ΔNS3NS5.PJ.core173RT construct were much less than that of the pd.ΔNS3NS5.PJ.core121RT construct. (See FIG. 19). Thus, there is a correlation of protein expression levels and the length of HCV core.

Figure 23:
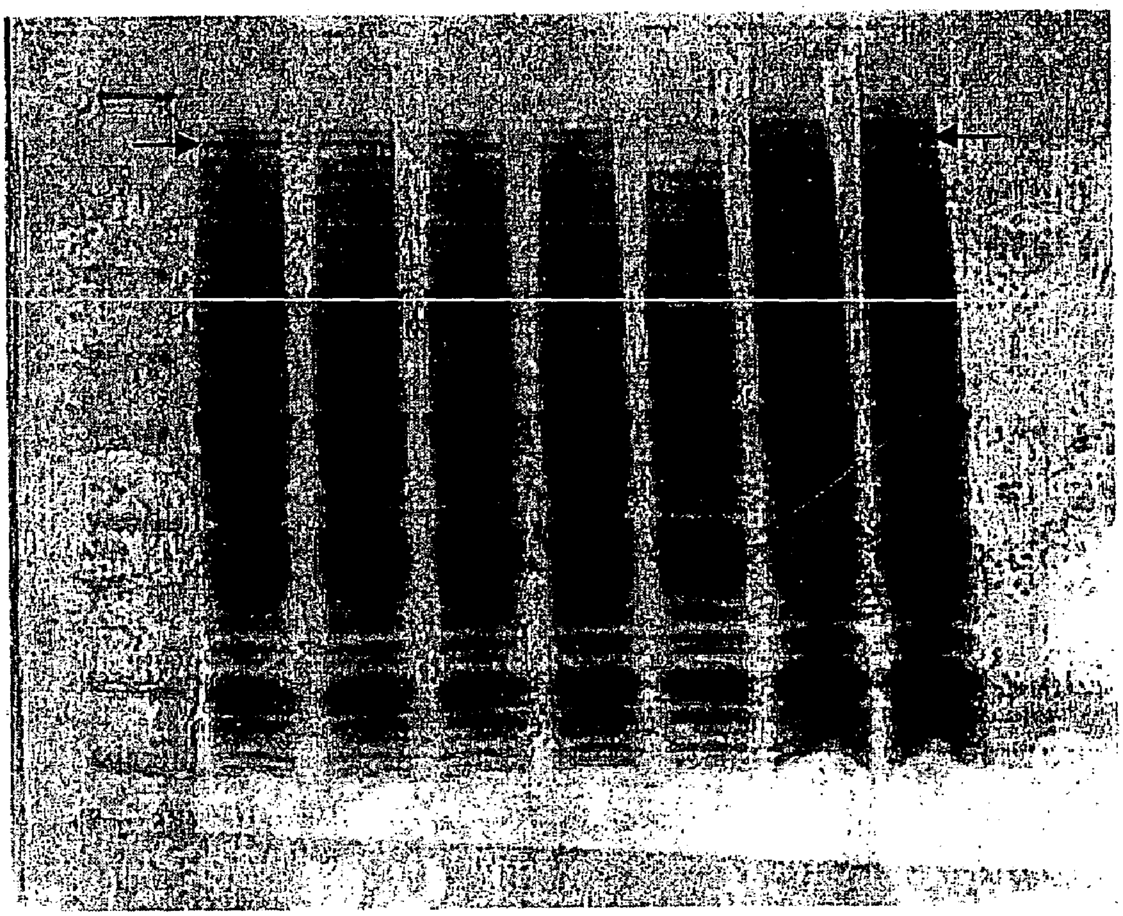
FIG. 23 shows the Western blot of proteins expressed by *S. cerevisiae* strain AD3 transformed with pd.ΔNS3NS5.pj, specifically demonstrating the expression of ΔNS3NS5core140 and ΔNS3NS5core150 polypeptides. Lane 1 shows See Blue Standards. Lanes 2 and 3 show ΔNS3NS55core140RT polypeptide, colonies 5 and 6. Lanes 4 and 5 show ΔNS3NS5core150RT polypeptide, colonies 7 and 8. Lane 6 shows control yeast plasmid. Lane 7 shows ΔNS3NS5core121RT polypeptide, colony 1. Lane 8 shows ΔNS3NS5core173RT polypeptide, colony 5.

Strain AD3 were transformed with pd.ΔNS3NS5.PJ.core140RT clone# 29 and pd.ΔNS3NS5.PJ.core150RT clone#35 and checked for expression. Bands of the expected molecular weights of 208 kD and 209 kD were seen by stain at levels close to those of pd.ΔNS3NS5core173RT (FIG. 23).

Example 3

Eliciting Immune Responses

A. Immunization

To evaluate the immunogenicity of the mutant NS polypeptides, studies using guinea pigs, rabbits, mice, rhesus macaques and/or baboons are performed. The studies are structured as follows: DNA immunization alone (single or multiple); DNA immunization followed by protein immunization (boost); DNA immunization followed by protein immunization; immunization by PLG particles. Immunization is intramuscular or mucosally.

B. Humoral Immune Response

The humoral immune response is checked in serum specimens from immunized animals with anti-NS antibody ELISAs (enzyme-linked immunosorbent assays) at various times post-immunization. Briefly, serum from immunized animals is screened for antibodies directed against the NS or mutant NS proteins. Wells of ELISA microtiter plates are coated overnight with the selected HCV protein and washed four times; subsequently, blocking is done with PBS-0.2% Tween (Sigma). After removal of the blocking solution, diluted mouse serum is added. Sera are tested at various dilutions. Microtiter plates are washed and incubated with a secondary, peroxidase-coupled anti- mouse IgG antibody (Pierce, Rockford, Ill.). ELISA plates are washed and 3, 3', 5,5'-tetramethyl benzidine (TMB; Pierce) is added per well. The optical density of each well is measured. Titers are typically reported as the reciprocal of the dilution of serum that gave a half-maximum optical density (O.D.). Similarly, generation of neutralization of binding (NOB) antibodies can be measured by methods known in the art.

C. Cellular Immune Response The frequency of specific cytotoxic T-lymphocytes (CTL) is evaluated by a standard chromium release assay of peptide pulsed Balb/c mouse CD4 cells. Briefly, spleen cells (Effector cells, E) are obtained from the BALB/c mice immunized, cultured, restimulated, and assayed for CTL activity against HCV peptide-pulsed target cells. Cytotoxic activity is measured in a standard $^{51}Cr$ release assay.

Example 4

Immunization with PLG-delivered DNA

The polylactide-co-glycolide (PLG) polymers are obtained from Boehringer Ingelheim, U.S.A. The PLG polymer is RG505, which has a copolymer ratio of 50/50 and a molecular weight of 65 kDa (manufacturers data). Cationic microparticles with adsorbed DNA are prepared using a modified solvent evaporation process, essentially as described in Singh et al., *Proc. Natl. Acad. Sci. USA* (2000) 97:811–816. Briefly, the microparticles are prepared by emulsifying a 5% w/v polymer solution in methylene chloride with PBS at high speed using an IKA homogenizer. The primary emulsion is then added to distilled water containing cetyl trimethyl ammonium bromide (CTAB) (0.5% w/v). This results in the formation of a w/o/w emulsion which was stirred at room temperature, allowing the methylene chloride to evaporate. The resulting microparticles are washed in distilled water by centrifugation and freeze dried. Following preparation, washing and collection, DNA is adsorbed onto the microparticles by incubating cationic microparticles in a solution of DNA. The microparticles are then separated by centrifugation, the pellet washed with TE buffer and the microparticles are freeze dried, resuspended and administered to animals. Antibody titers are measured by ELISA assays.

All patents, patent applications, and other publications mentioned herein, are hereby incorporated herein by reference in their entireties.

What is claimed is:

1. An isolated, immunogenic, mutant non-structural ("NS") HCV polypeptide comprising a mutant NS3 polypeptide, an NS4 polypeptide and an NS5 polypeptide, wherein the mutant NS3 polypeptide has an N-terminal deletion that functionally disrupts the catalytic domain of NS3 and further wherein said mutant NS3 polypeptide has an N-terminus at an amino acid corresponding to amino acid 1242 of HCV-1 and comprises an amino acid sequence corresponding to amino acids 1242–1657 of HCV-1.

2. The polypeptide of claim 1, wherein said NS polypeptide consists of said mutant NS3 polypeptide, NS4 and NS5.

3. The polypeptide of claim 1, wherein said NS5 polypeptide consists of NS5a.

4. The polypeptide of claim 1, wherein said NS5 polypeptide consists of NS5b.

5. The polypeptide of claim 1, wherein said NS4 polypeptide consists of NS4a.

6. The polypeptide of claim 1, wherein said NS4 polypeptide consists of NS4b.

7. The polypeptide of claim 1, further comprising a second viral polypeptide that is not NS3, NS4 or NS5 of HCV.

8. The polypeptide of claim 7, wherein the second viral polypeptide comprises an HCV Core polypeptide ("C") or immunogenic fragment thereof.

9. The polypeptide of claim 8, wherein the C polypeptide is truncated.

10. The polypeptide of claim 9, wherein the truncation is at amino acid 121.

11. The polypeptide of claim 7, wherein the polypeptide further comprises an HCV envelope protein ("E").

12. The polypeptide of claim 11, wherein the E is E1.

13. The polypeptide of claim 11, wherein the E is E2.

14. A composition comprising (a) the polypeptide of claim 1; and (b) a pharmaceutically acceptable excipient.

15. The polypeptide of claim 1, wherein the polypeptide comprises the sequence of amino acids of SEQ ID NO:9.

16. The polypeptide of claim 1, wherein the polypeptide consists of the sequence of amino acids of SEQ ID NO:9.

17. A composition comprising (a) the polypeptide of claim 7; and (b) a pharmaceutically acceptable excipient.

18. A composition comprising (a) the polypeptide of claim 15; and (b) a pharmaceutically acceptable excipient.

19. A composition comprising (a) the polypeptide of claim 16; and (b) a pharmaceutically acceptable excipient.

* * * * *